US012264314B1

(12) United States Patent
Doudna et al.

(10) Patent No.: US 12,264,314 B1
(45) Date of Patent: Apr. 1, 2025

(54) CasZ COMPOSITIONS AND METHODS OF USE

(71) Applicant: The Regents of the University of California, Oakland, CA (US)

(72) Inventors: Jennifer A. Doudna, Berkeley, CA (US); David Burstein, Berkeley, CA (US); Janice S. Chen, Berkeley, CA (US); Lucas B. Harrington, Berkeley, CA (US); David Paez-Espino, Walnut Creek, CA (US); Jillian F. Banfield, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 18/392,905

(22) Filed: Dec. 21, 2023

Related U.S. Application Data

(63) Continuation of application No. 17/935,521, filed on Sep. 26, 2022, now abandoned, which is a continuation of application No. 16/896,711, filed on Jun. 9, 2020, now Pat. No. 11,453,866, which is a continuation of application No. 16/694,720, filed on Nov. 25, 2019, now abandoned, which is a continuation of application No. PCT/US2018/058545, filed on Oct. 31, 2018.

(60) Provisional application No. 62/580,395, filed on Nov. 1, 2017.

(51) Int. Cl.
*C12N 15/10* (2006.01)
*C12N 9/10* (2006.01)
*C12N 15/86* (2006.01)

(52) U.S. Cl.
CPC ......... *C12N 15/102* (2013.01); *C12N 9/1007* (2013.01); *C12N 15/86* (2013.01); *C12N 2750/14143* (2013.01)

(58) Field of Classification Search
CPC .... C12N 15/102; C12N 9/1007; C12N 15/86; C12N 2750/14143
See application file for complete search history.

(56) References Cited

U.S. PATENT DOCUMENTS

| | | |
|---|---|---|
| 6,773,885 B1 | 8/2004 | Walder et al. |
| 8,597,886 B2 | 12/2013 | Smith et al. |
| 8,815,782 B2 | 8/2014 | Zeiner et al. |
| 9,730,967 B2 | 6/2017 | Kovarik et al. |
| 9,790,490 B2 | 10/2017 | Zhang et al. |
| 10,253,365 B1 | 4/2019 | Doudna et al. |
| 10,266,886 B2 | 4/2019 | Abudayyeh et al. |
| 10,316,324 B2 | 6/2019 | Begemann et al. |
| 10,337,051 B2 | 7/2019 | Doudna et al. |
| 10,494,664 B2 | 12/2019 | Doudna et al. |
| 10,570,415 B2 | 2/2020 | Doudna et al. |
| 11,180,743 B2 | 11/2021 | Doudna et al. |
| 11,371,031 B2 | 6/2022 | Doudna et al. |
| 11,441,137 B2 | 9/2022 | Doudna et al. |
| 11,453,866 B2 | 9/2022 | Doudna et al. |
| 2013/0261196 A1 | 10/2013 | Diamond et al. |
| 2014/0068797 A1 | 3/2014 | Doudna et al. |
| 2014/0093883 A1 | 4/2014 | Maples et al. |
| 2014/0273226 A1 | 9/2014 | Wu |
| 2015/0211058 A1 | 7/2015 | Carstens |
| 2016/0017366 A1 | 1/2016 | Chen et al. |
| 2016/0138008 A1 | 5/2016 | Charpentier et al. |
| 2016/0201089 A1* | 7/2016 | Gersbach ............... C12N 15/85 |
| 2016/0208243 A1 | 7/2016 | Zhang et al. |
| 2016/0289659 A1 | 10/2016 | Doudna et al. |
| 2017/0037432 A1 | 2/2017 | Donohoue et al. |
| 2017/0051276 A1 | 2/2017 | May et al. |
| 2017/0175104 A1 | 6/2017 | Doudna et al. |
| 2017/0198277 A1 | 7/2017 | Kmiec et al. |
| 2017/0211142 A1 | 7/2017 | Smargon et al. |
| 2017/0233756 A1 | 8/2017 | Begemann et al. |
| 2017/0306335 A1 | 10/2017 | Zhang et al. |
| 2017/0321198 A1 | 11/2017 | Severinov et al. |
| 2017/0321214 A1 | 11/2017 | Zhang et al. |

(Continued)

FOREIGN PATENT DOCUMENTS

| CN | 1886512 A | 12/2006 |
|---|---|---|
| CN | 101283089 A | 10/2008 |

(Continued)

OTHER PUBLICATIONS

Yamano (Molecular cell 67.4 (2017): 633-645) (Year: 2017).*
Stepper (Nucleic acids research 45.4 (2017): 1703-1713) (Year: 2017).*
Nishimasu (Cell 156.5 (2014): 935-949) (Year: 2014).*
Jiang (Cell research 27.3 (2017): 440-443) (Year: 2017).*
Richardson (Nature biotechnology 34.3 (2016): 339-344) (Year: 2016).*
Abudayyeh, et al.; "C2c2 is a single-component programmable RNA-guided RNA-targeting CRISPR effector; Supplementary Information"; Science; vol. 353, vol. 6299, 31 pages (Aug. 5, 2016).

(Continued)

*Primary Examiner* — Nancy J Leith
*Assistant Examiner* — Kyle T Rega
(74) *Attorney, Agent, or Firm* — Bozicevic, Field & Francis LLP; Shweta Chandra

(57) ABSTRACT

Provided are compositions and methods that include one or more of: (1) a "CasZ" protein (also referred to as a CasZ polypeptide), a nucleic acid encoding the CasZ protein, and/or a modified host cell comprising the CasZ protein (and/or a nucleic acid encoding the same); (2) a CasZ guide RNA that binds to and provides sequence specificity to the CasZ protein, a nucleic acid encoding the CasZ guide RNA, and/or a modified host cell comprising the CasZ guide RNA (and/or a nucleic acid encoding the same); and (3) a CasZ transactivating noncoding RNA (trancRNA) (referred to herein as a "CasZ trancRNA"), a nucleic acid encoding the CasZ trancRNA, and/or a modified host cell comprising the CasZ trancRNA (and/or a nucleic acid encoding the same).

30 Claims, 108 Drawing Sheets

Specification includes a Sequence Listing.

(56) References Cited

U.S. PATENT DOCUMENTS

| | | |
|---|---|---|
| 2017/0369870 A1 | 12/2017 | Gill et al. |
| 2018/0320163 A1 | 11/2018 | Koonin et al. |
| 2018/0340218 A1 | 11/2018 | Abudayyeh et al. |
| 2019/0276842 A1 | 9/2019 | Doudna et al. |
| 2019/0300908 A1 | 10/2019 | Doudna et al. |
| 2020/0017879 A1 | 1/2020 | Doudna et al. |
| 2020/0087640 A1 | 3/2020 | Doudna et al. |
| 2020/0172886 A1 | 6/2020 | Doudna et al. |
| 2020/0255858 A1 | 8/2020 | Doudna et al. |
| 2020/0299660 A1 | 9/2020 | Doudna et al. |
| 2020/0370028 A1 | 11/2020 | Doudna et al. |
| 2021/0017508 A1 | 1/2021 | Doudna et al. |
| 2021/0166783 A1 | 6/2021 | Shmakov et al. |
| 2022/0396812 A1 | 12/2022 | Doudna et al. |
| 2023/0323319 A1 | 10/2023 | Doudna et al. |
| 2024/0200105 A1* | 6/2024 | Kim .................... C12N 15/907 |

FOREIGN PATENT DOCUMENTS

| | | |
|---|---|---|
| CN | 106701830 A | 5/2017 |
| EP | 1580273 A1 | 9/2005 |
| EP | 3009511 A2 | 4/2016 |
| EP | 2825654 B1 | 4/2017 |
| EP | 3546573 A1 | 10/2019 |
| EP | 3283625 B1 | 12/2019 |
| EP | 3665279 A1 | 6/2020 |
| JP | 2004521606 A | 7/2004 |
| WO | WO 2015/071474 | 5/2015 |
| WO | WO 2015/139139 | 9/2015 |
| WO | WO 2015/191693 | 12/2015 |
| WO | WO 2016/094872 | 12/2015 |
| WO | WO 2016/106236 | 12/2015 |
| WO | WO 2016/028843 | 2/2016 |
| WO | WO 2016/094867 | 6/2016 |
| WO | WO 2016/205711 | 6/2016 |
| WO | WO 2016/123243 | 8/2016 |
| WO | WO 2016166340 A1 | 10/2016 |
| WO | WO 2016/205613 | 12/2016 |
| WO | WO 2016/205749 | 12/2016 |
| WO | WO 2016/205764 | 12/2016 |
| WO | WO 2017/070605 | 4/2017 |
| WO | WO 2017/205668 | 5/2017 |
| WO | WO 2017/120410 | 7/2017 |
| WO | WO 2017/147345 | 8/2017 |
| WO | WO 2017/176529 | 10/2017 |
| WO | WO 2017/218573 | 12/2017 |
| WO | WO 2017/219027 | 12/2017 |
| WO | WO 2017/223538 | 12/2017 |
| WO | WO 2018035250 A1 | 2/2018 |
| WO | WO 2018/064352 | 4/2018 |
| WO | WO 2018/064371 | 4/2018 |
| WO | WO 2018/107129 | 6/2018 |
| WO | WO 2018/172556 | 9/2018 |
| WO | WO 2018/195545 | 10/2018 |
| WO | WO 2019/030695 | 2/2019 |
| WO | WO 2019/089796 | 5/2019 |
| WO | WO 2019/089804 | 5/2019 |
| WO | WO 2019/089808 | 5/2019 |
| WO | WO 2019/089820 | 5/2019 |
| WO | WO 2019/126577 | 6/2019 |

OTHER PUBLICATIONS

Abudayyeh, et al.; "C2c2 is a single-component programmable RNA-guided RNA-targeting CRISPR effector"; Science; vol. 353, No. 6299, 23 pages (Aug. 5, 2016).
Abudayyeh, et al.; "RNA targeting with CRISPR-Cas13"; Nature; vol. 550, 18 pages (Oct. 12, 2017).
Ambion; "RnaseAlert Lab Test Kit v2, User Guide"; 12 pages (Mar. 1, 2013).
Anantharaman, et al.; "Thousands of microbial genomes shed light on interconnected biogeochemical processes in an aquifer system"; Nature Communications; vol. 7, No. 13210, 11 pages (Oct. 24, 2016).
Applied Biosystems/Ambion; "RNaseAlert Lab Test Kit"; 12 pages (2008).
Armitage, et al.; "Hairpin-Forming Peptide Nucleic Acid Oligomers"; Biochemistry; vol. 37, No. 26, pp. 9417-9425 (1998).
Baker, et al.; "Enigmatic, ultrasmall, uncultivated Archaea"; PNAS; vol. 107, No. 19, pp. 8806-8811 (May 11, 2010).
Barrangou, et al.; "Expanding the CRISPR Toolbox: Targeting RNA with Cas13b"; Molecular Cell; vol. 65, No. 4, pp. 582-584 (Feb. 16, 2017).
Bautista, et al.; "Virus-Induced Dormancy in the Archaeon Sulfolobus islandicus"; mBio; vol. 6, No. 2, 8 pages (2015).
Burstein, et al.; "New CRISPR-Cas systems from uncultivated microbes"; Nature; vol. 542, No. 7640, pp. 237-241 (Feb. 9, 2017).
Chen, et al.; "CRISPR-Cas12a target binding unleashes indiscriminate single-stranded DNase activity"; Science; vol. 360, pp. 436-439 (2018).
Choudhury, et al.; "CRISPR-dCas9 mediated TET1 targeting for selective DNA demethylation at BRCA1 promoter"; Oncotarget; vol. 7, No. 29, pp. 46545-46556 (2016).
Chylinski, et al.; "Classification and evolution of type II CRISPR-Cas systems"; Nucleic Acids Research; vol. 42, No. 10, pp. 6091-6105 (2014).
Clustl; "Omega Multiple Sequence Alignment. https://www.ebi.ac.uk/Tools/msa/clustalo/" [Retrieved from internet Feb. 2, 2022]. Alignment and Percent identity matrix. (Year: 2022).
Cong, et al.; "Multiplex Genome Engineering Using CRISPR/Cas Systems"; Science; vol. 339, No. 6121, pp. 819-823 (Feb. 15, 2013).
Cox, et al.; "RNA editing with CRISPR-Cas13"; Science; vol. 358, No. 6366, 15 pages (Nov. 24, 2017).
CRZ3554.1 (hypothetical protein HHT344_2368 [Herbinix hemicellulosilytica], Gen Bank Accession sequence, priority to Jul. 24, 2015, 1 page) (Year: 2015).
Deltcheva, et al.; "CRISPR RNA maturation by trans-encoded small RNA and host factor RNase III"; Nature; vol. 471, pp. 1-19 (Mar. 31, 2011).
East-Seletsky, et al.; "RNA Targeting by Functionally Orthogonal Type VI-A CRISPR-Cas Enzymes"; Molecular Cell; vol. 66, pp. 373-383 (May 4, 2017).
East-Seletsky, et al.; "Two distinct Rnase activities of CRISPR-C2c2 enable guide-RNA processing and RNA detection"; Nature; vol. 538, Issue 7624, pp. 270-273 (Oct. 13, 2016).
Fonfara, et al.; "Phylogeny of Cas9 determines functional exchangeability of dual-RNA and Cas9 among orthologous type II CRISPR-Cas systems"; Nucleic Acids Research; vol. 42, No. 4, pp. 2577-2590 (2014).
GenBank CRL33181.1; Hypothetical protein T1815_05231 [[Eubacterium] rectale], priority to Apr. 6, 2016, 2 pages (Year: 2016).
GenBank CRZ35554 1; "Hypothetical protein HHT355_2368 [Herbinix hemicellulosilytica]"; 1 page (Oct. 11, 2018).
GenBank OHA03494.1 (hypothetical protein A3J58_03210 [*Candidatus sung* bacteria bacterium RIFCSPH IGHO2_02_Full_52_23], NCBI Reference Sequence, priority to Oct. 21, 2016, 2 pages) (Year: 2016).
Gootenberg, et al.; "Multiplexed and portable nucleic acid detection platform with Cas13, Cas12a, and Csm6"; Science; vol. 360, pp. 439-444 (2018).
Gootenberg, et al.; "Nucleic acid detection with CRISPR-Cas13a/C2c2"; Science; 9 pages (Apr. 13, 2017).
Hale, et al.; "RNA-Guided RNA Cleavage by a CRISPR RNA-Cas Protein Complex"; Cell; vol. 139, No. 5, pp. 945-956 (Nov. 25, 2009).
Hale, et al.; "Target RNA capture and cleavage by the Cmr type III-B CRISPR-Cas effector complex"; Genes & Development; vol. 28, No. 21, pp. 2432-2443 (Nov. 1, 2014).
Harrington, et al.; "Programmed DNA destruction by miniature CRISPR-Cas14 enzymes"; Science; vol. 362, pp. 839-842 (Nov. 16, 2018).
Hooton et al. "The Bacteriophage Carrier State of Campylobacter jejuni Features Changes in Host Non-coding RNAs and the Acqui-

(56) References Cited

OTHER PUBLICATIONS sition of New Host-derived CRISPR Spacer Sequences," Frontiers in Microbiology; vol. 7, Article 355, pp. 1-8 (Mar. 23, 2016).
Hyun, et al.; "Site-directed mutagenesis in *Arabidopsis thaliana* using dividing tissue-targeted RGEN of the CRISPR/Cas system to generate heritable null alleles"; Planta; vol. 241, pp. 271-284 (Jan. 2015).
Karvelis, et al.; "PAM recognition by miniature CRISPR-Cas12f nucleases triggers programmable double-stranded DNA target cleavage"; Nucleic Acids Research; pp. 1-8 (2020).
Kelemen, et al.; "Hypersensitive substrate for ribonucleases"; Nucleic Acids Research; vol. 27, No. 18, pp. 3696-3701 (1999).
Kim, et al.; "Specific and sensitive detection of nucleic acids and RNases using gold nanoparticle-RNA-fluorescent dye conjugates"; Chemical Communications; vol. 14, No. 42, pp. 4342-4344 (Sep. 19, 2007).
Knott, et al.; "Guide-bound structures of an RNA-targeting A-cleaving CRISPR-Cas13a enzyme"; Nature Structural & Molecular Biology; vol. 24, No. 10, 13 pages (Oct. 2017).
Kodak (Gel Logic 100 System User's Guide, 2005, 98 pages) (Year: 2005).
Koonin, et al.; "CRISPR-Cas: an adaptive immunity system in prokaryotes"; F1000 Biology Reports; vol. 1, No. 95, 6 pages (Dec. 9, 2009).
Koonin, et al.; "Diversity, classification and evolution of CRISPR-Cas systems"; Current Opinion in Microbiology; vol. 37, pp. 67-78 (2017).
Koonin, et al.; "Origins and evolution of CRISPR-Cas systems"; Phil. Trans. R. Soc. B.; vol. 374, No. 1772, 6 pages (Mar. 25, 2019).
Le Cong, et al.; "Multiplex Genome Engineering Using CRISPR/Cas Systems"; Science; vol. 339, pp. 819-823 (Feb. 15, 2013).
Li, et al.; "Using molecular beacons as a sensitive fluorescence assay for enzymatic cleavage of single-stranded DNA"; Nucleic Acids Research; vol. 28, No. 11, 6 pages (2000).
Liu, et al.; "CasX enzymes comprise a distinct family of RNA-guided genome editors"; Nature; vol. 566, pp. 23 pages (Feb. 14, 2019).
Liu, et al.; "Delivery strategies of the CRISPR-Cas9 gene-editing system for therapeutic applications"; Journal of Controlled Release; vol. 266, pp. 17-26 (2017).
Liu, et al.; "The Molecular Architecture for RNA-Guided RNA Cleavage by Cas13a"; Cell; vol. 170, pp. 714-126 (Aug. 10, 2017).
Liu, et al.; "Two Distant Catalytic Sites Are Responsible for C2c2 RNase Activities"; Cell; vol. 168, pp. 121-134 (Jan. 12, 2017).
Makarova, et al.; "An updated evolutionary classification of CRISPR-Cas systems"; Nat. Rev. Microbiol.; vol. 13, No. 11, pp. 722-736 (Nov. 2015).
Makarova, et al.; "Evolutionary classification of CRISPR-Cas systems: a burst of class 2 and derived variants"; Nature Reviews Microbiology; vol. 18, pp. 67-83 (Feb. 2020).
Makarova, et al.; "SnapShot: Class 2 CRISPR-Cas Systems"; Cell; vol. 168, 2 pages (Jan. 12, 2017).
Mohanraju, et al.; "Diverse evolutionary roots and mechanistic variations of the CRISPR-Cas systems"; Science; vol. 353, No. 6299, 14 pages (Aug. 5, 2016).
NCBI Reference Sequence: WP_012985477.1 (May 18, 2013).
NCBI Reference Sequence: WP_015770004.1 (May 20, 2013).
NCBI Reference Sequence: WP_021746003.1 (Sep. 24, 2013).
NCBI Reference Sequence: WP_021746774.1 (Sep. 24, 2013).
NCBI Reference Sequence: WP_021747205.1 (Sep. 24, 2013).
NCBI Reference Sequence: WP_023911507.1 (Oct. 23, 2013).
NCBI Accession No. KZX85786 (May 2, 2016).
NCBI Reference Sequence: WP_034560163.1 (Oct. 22, 2015).
Ngo, et al.; "Computational Complexity, Protein Structure Prediction, and the Levinthal Paradox"; The Protein Folding Problem and Tertiary Structure Prediction; pp. 433 and 492-495 (1994).
O'Connell; "Molecular Mechanisms of RNA Targeting by Cas13-containing Type VI CRISPR-Cas Systems"; J Mol Biol; vol. 431, pp. 66-87 (2019).
OHA03494.1 (hypothetical protein A3J58_03210 [*Candidatus sung* bacteria bacterium RIFCSPH IGHO2_02_Full_52_23], NCBI Reference Sequence, priority to Oct. 21, 2016, 2 pages) (Year: 2016).
Price, et al.; "Cas9-mediated targeting of viral RNA in eukaryotic cells"; PNAS; vol. 112, No. 19, pp. 6164-6169 (May 12, 2015).
RNaseAlert Lab Test Kit (Applied Biosystems, Fluorometric RNase Detection Assay, 2008, 12 pages). (Year: 2008).
Sampson, et al.; "A CRISPR/Cas system mediates bacterial innate immune evasion and virulence"; Nature; vol. 497, No. 7448; pp. 254-257 (May 9, 2013).
Sato, et al.; "Highly Sensitive Nuclease Assays Based on Chemically Modified DNA or RNA"; Sensors; vol. 14, No. 7, pp. 12437-12450 (2014).
Shmakov, et al.; "Discovery and functional characterization of diverse Class 2 CRISPR-Cas systems"; Mol. Cell.; vol. 60, No. 3, pp. 385-397 (Nov. 5, 2015).
Shmakov, et al.; "Diversity and evolution of class 2 CRISPR-Cas systems"; Nature Reviews Microbiology; vol. 15, pp. 169-182 (2017).
Smargon, et al.; "Cas13b is a Type VI-B CRISPR-associated RNA-Guided RNAse differentially regulated by accessory proteins Csx27 and Csx28"; Molecular Cell; vol. 65, No. 4, pp. 618-630 (Feb. 16, 2017).
Stella, et al.; "Class 2 CRISPR-Cas RNA-guided endonucleases: Swiss Army knives of genome editing"; Nature Structural & Molecular Biology; vol. 24, No. 11, pp. 882-892 (Nov. 2017).
Stephen Floor; "CV"; 6 pages (Jun. 11, 2018).
Stephen Floor; "Tweets cited in third party observation filed on Oct. 15, 2018"; 1 page (date of tweets are May 21, 2016).
Strauß, et al.; "Zinc Fingers, TAL Effectors, or Cas9-Based DNA Binding Proteins: What's Best for Targeting Desired Genome Loci?"; Molecular Plant; vol. 6, No. 5, pp. 1384-1387 (Sep. 2013).
Third Party Observations filed on Oct. 15, 2018 in UK patent application No. GB 1804822.3 (18 pages).
Wright, et al.; "Biology and Applications of CRISPR Systems: Harnessing Nature's Toolbox for Genome Engineering"; Cell; vol. 164, pp. 29-44 (2016).
Xie et al. (2013) " RNA-Guided Genome Editing in Plants Using a CRISPR-Cas System." Molecular Plant, vol. 6, No. 6 , pp. 1975-1983.
Yamano, et al.; "Crystal Structure of Cpf1 in Complex with Guide RNA and Target DNA"; Cell; vol. 165, pp. 949-962 (2016).
Yan, et al.; "Cas13d Is a Compact RNA-Targeting Type VI CRISPR Effector Positively Modulated by a WYL-Domain-Containing Accessory Protein"; Molecular Cell; vol. 70, pp. 327-339 (2018).
Yang, et al.; "Using Molecular Beacons for Sensitive Fluorescence Assays of the Enzymatic Cleavage of Nucleic Acids"; Methods in Molecular Biology, Fluorescent Energy Transfer Nucleic Acid Probes: Designs and Protocols; vol. 335, pp. 71-81 (2006).
Yang, et al.; "New CRISPR-Cas systems discovered"; Cell Res.; vol. 27, pp. 313-314 (Feb. 21, 2017).
Zetsche, et al.; "Cpf1 Is a Single RNA-Guided Endonuclease of a Class 2 CRISPR-Cas System"; Cell; vol. 163, pp. 759-771 (Oct. 22, 2015).
Zhang, et al.; "Design of a Molecular Beacon DNA Probe with Two Fluorophores"; Angew. Chem.; vol. 113, No. 2, pp. 416-419 (2001).
Burstein, et al.; "Major bacterial lineages are essentially devoid of CRISPR-Cas viral defence systems"; Nature Communications; vol. 7, No. 10613, 8 pages (Feb. 3, 2016).
GenBank KU516197.1; "Uncultured bacterium GWB1_scaffold_10668 CRISPR-Cas system-like gene, complete sequence"; 4 pages (2016).
Lander et al.; "Genome Editing by CRISPR/Cas9: a Game Change in the Genetic Manipulation of Protists"; J Eukaryot Microbial.; vol. 63, No. 5, pp. 679-690 (Sep. 2016).
Transposase, JGI Accession No. 3300025142.a:Ga0210019_10421012, Sep. 1, 2021, 2 pages.
Transposase, JGI Accession No. 3300025308.a:Ga0209211_100536734, Nov. 9, 2021, 2 pages.
Transposase, JGI Accession No. 3300025317.a:Ga0209541_100096836, Nov. 9, 2021, 2 pages.
Transposase, JGI Accession No. 3300025323.a:Ga0209542_1000010711, Nov. 9, 2021, 2 pages.

(56) References Cited

OTHER PUBLICATIONS

Transposase, JGI Accession No. 3300025323.a:Ga0209542_10000107204, Nov. 9, 2021, 2 pages.
Transposase, JGI Accession No. (Taxon ID:Gene ID) 3300013125.a:Ga0172369_100104642, Nov. 5, 2021, 2 pages.
Transposase, JGI Accession No. (Taxon ID:Gene ID) 3300013130.a:Ga0172363, Nov. 5, 2021, 2 pages.
Transposase, JGI Accession No. (Taxon ID:Gene ID) 3300025317.a:Ga0209541_100217848, Nov. 5, 2021, 2 pages.
Transposase, JGI Accession No. (Taxon ID:Gene ID) 3300025323.a:Ga0209542_100271699, Nov. 5, 2021, 2 pages.
Transposase, JGI Accession No. (Taxon ID:Gene ID) 3300013127.a:Ga0172365_100044211, Nov. 5, 202, 2 pages.
Transposase, JGI Accession No. (Taxon ID:Gene ID) 3300013123.a:Ga0172368_100090142, Nov. 5, 2021, 2 pages.
Transposase, JGI Accession No. (Taxon ID:Gene ID) 3300025317.a:Ga0209541_1000016152, Nov. 5, 2021, 2 pages.
Transposase, JGI Accession No. (Taxon ID:Gene ID) 3300025317.a:Ga0209541_1000046133, Nov. 5, 2021, 1 pages.
Transposase and inactivated derivatives, JGI Accession No. (Taxon ID:Gene ID) 3300005573.a:Ga0078972_100101520, Nov. 5, 2021, 1 pages.
Transposase and inactivated derivatives, JGI Accession No. 3300002502.a:C687J35174_100538264, Sep. 1, 2021, 2 pages.
Transposase and inactivated derivatives, JGI Accession No. (Taxon ID:Gene ID) 3300002966.a:JG|24721J44947_100297402, Nov. 5, 2021, 2 pages.
Transposase and inactivated derivatives, JGI Accession No. (Taxon ID:Gene ID) 3300002502.a:C687J35174_100502431, Nov. 5, 2021, 2 pages.
Transposase and inactivated derivatives, JGI Accession No. (Taxon ID:Gene ID) 3300001245.a:JG|12048J13642_102012859, Nov. 5, 2021, 2 pages.
Transposase and inactivated derivatives, JGI Accession No. (Taxon ID:Gene ID) 3300001245.a:JG|12048J13642_102012865, Nov. 5, 2021, 2 pages.
Transposase and inactivated derivatives, JGI Accession No. (Taxon ID:Gene ID) 3300001256.a:JG|12210J13797_103875826, Nov. 5, 2021, 2 pages.
Transposase and inactivated derivatives, JGI Accession No. (Taxon ID:Gene ID) 3300001256.a:JG|12210J13797_103875833, Nov. 5, 2021, 2 pages.
Transposase and inactivated derivatives, JGI Accession No. (Taxon ID: Gene ID) 3300000353.a:ElkS_mat_MD6ADRAFT_10068983, Nov. 5, 2021, 2 pages.
Transposase and inactivated derivatives, JGI Accession No. 3300002105.a:C687J26635_100228363, Nov. 9, 2021, 2 pages.
Sawamura, et al., "Generation of biallelic F0 mutants in medaka using the CRISPR/Cas9 system", Genes Cells, Aug. 2017, 22(8):756-763.
Wright, et al., "Rational design of a split-Cas9 enzyme complex", PNAS, Mar. 10, 2015, 112(10):2984-2989.
Harrington et al., (2020) "A scoutRNA Is Required for Some Type V CRISPRCas Systems." Molecular Cell, vol. 79, pp. 416-424.

* cited by examiner

FIG. 1A

>CasZa.1|rifcsphigho2_02_scaffold_2167_39 \N id=61050970
partial=0 scaf=rifcsphigho2_02_scaffold_2167
bin=RIFCSPHIGHO2_02_FULL_Archaea_Woesearchaeota_57_22
sample=Archaea-Rifle02 proj=Rifle Groundwater Metagenome
mEVQKTVMKTLSLRILRPLYSQEIEKEIKEEKERRKQAGGTGELDGGFYKKLEKKHSEMFSFDR
LNLLLNQLQREIAKVYNHAISELYIATIAQGNKSNKHYISSIVYNRAYGYFNAYIALGICSKV
EANFRSNELLTQQSALPTAKSDNFPIVLHQKGAEGEDGGFRISTEGSDLIFEIPIPFYEYNGE
NRKEPYKWVKKGGQKPVLKLILSTFRRQRNKGWAKDEGTDAEIRKVTEGKYQVSQIEINRGKKL
GEHQKWFANFSIEQPIYERKPNRSIVGGLDVGIRSPLVCAINNSFSRYSVDSNDVFKFSKQVFA
FRRRLLSKNSLKRKGHGAAHKLEPITEMTEKNDKFRKKIIERWAKEVTNFFVKNQVGIVQIEDL
STMKDREDHFFNQYLRGFWPYYQMQTLIENKLKEYGIEVKRVQAKYTSQLCSNPNCRYWNNYFN
FEYRKVNKFPKFKCEKCNLEISADYNAARNLSTPDIEKFVAKATKGINLPEK
    (SEQ ID NO: 1)

>CasZa.2|gwa2_scaffold_18027_12 Putative transposase DNA-binding
domain family id=2625699 partial=0 scaf=gwa2_scaffold_18027
bin=GWA2_Unbinned sample=GWA2 proj=Rifle Groundwater Metagenome
mEEAKTVSKTLSLRILRPLYSAEIEKEIKEEKERRKQGGKSGELDSGFYKKLEKKHTQMFGWDK
LNLMLSQLQRQIARVFNQSISELYIETVIQGKKSNKHYTSKIVYNRAYSVFYNAYLALGITSKV
EANFRSTELLMQKSSLPTAKSDNFPILLHQKGVEGEEGGFKISADGNDLIFEIPIPFYEYDSA
NKKEPFKWIKKGGQKPTIKLILSTFRRQRNKGWAKDEGTDAEIRKVIEGKYQVSHIEINRGKKL
GDHQKWFVNFTIEQPIYERKLDKNIIGGIDVGIKSPLVCAVNNSFARYSVDSNDVLKFSKQAFA
FRRRLLSKNSLKRSGHGSKNKLDPITRMTEKNDRFRKKIIERWAKEVTNFFIKNQVGTVQIEDL
STMKDRQDNFFNQYLRGFWPYYQMQNLIENKLKEYGIETKRIKARYTSQLCSNPSCRHWNSYFS
FDHRKTNNFPKFKCEKCALEISADYNAARNISTPDIEKFVAKATKGINLPDKNENVILE
    (SEQ ID NO: 2)

>CasZa.3|gwa1_scaffold_1795_31 Transposase, IS605 OrfB family
id=2784443 partial=0 scaf=gwa1_scaffold_1795
bin=GWA1_Archaeon_57_19 sample=GWA1 proj=Rifle Groundwater
Metagenome
mAKNTITKTLKLRIVRPYNSAEVEKIVADEKNNREKIALEKNKDKVKEACSKHLKVAAYCTTQV
ERNACLFCKARKLDDKFYQKLRGQFPDAVFWQEISEIFRQLQKQAAEIYNQSLIELYYEIFIKG
KGIANASSVEHYLSDVCYTRAAELFKNAAIASGLRSKIKSNFRLKELKNMKSGLPTTKSDNFPI
PLVKQKGGQYTGFEISNHNSDFIIKIPFGRWQVKKEIDKYRPWEKFDFEQVQKSPKPISLLLST
QRRKRNKGWSKDEGTEAEIKKVMNGDYQTSYIEVKRGSKIGEKSAWMLNLSIDVPKIDKGVDPS
IIGGIDVGVKSPLVCAINNAFSRYSISDNDLFHFNKKMFARRRILLKKNRHKRAGHGAKNKLKP
ITILTEKSERFRKKLIERWACEIADFFIKNKVGTVQmENLESMKRKEDSYFNIRLRGFWPYAEM
QNKIEFKLKQYGIEIRKVAPNNTSKTCSKCGHLNNYFNFEYRKKNKFPHFKCEKCNFKENADYN
AALNISNPKLKSTKEEP (SEQ ID NO: 3)

FIG. 1B

\>CasZa.4|CG10_big_fil_rev_8_21_14_0.10_scaffold_20906_2 \N
id=132542232 partial=0
scaf=CG10_big_fil_rev_8_21_14_0.10_scaffold_20906
bin=CG10_big_fil_rev_8_21_14_0_10_UNK
sample=CG10_big_fil_rev_8_21_14_0_10 proj=Crystal Geyser
mERQKVPQIRKIVRVVPLRILRPKYSDVIENALKKFKEKGDDTNTNDFWRAIRDRDTEFFRKEL
NFSEDEINQLERDTLFRVGLDNRVLFSYFDFLQEKLMKDYNKIISKLFINRQSKSSFENDLTDE
EVEELIEKDVTPFYGAYIGKGIKSVIKSNLGGKFIKSVKIDRETKKVTKLTAINIGLMGLPVAK
SDTFPIKIIKTNPDYITFQKSTKENLQKIEDYETGIEYGDLLVQITIPWFKNENKDFSLIKTKE
AIEYYKLNGVGKKDLLNINLVLTTYHIRKKKSWQIDGSSQSLVREMANGELEEKWKSFFDTFIK
KYGDEGKSALVKRRVNKKSRAKGEKGRELNLDERIKRLYDSIKAKSFPSEINLIPENYKWKLHF
SIEIPPMVNDIDSNLYGGIDFGEQNIATLCVKNIEKDDYDFLTIYGNDLLKHAQASYARRRIMR
VQDEYKARGHGKSRKTKAQEDYSERMQKLRQKITERLVKQISDFFLWRNKFHMAVCSLRYEDLN
TLYKGESVKAKRMRQFINKQQLFNGIERKLKDYNSEIYVNSRYPHYTSRLCSKCGKLNLYFDFL
KFRTKNIIIRKNPDGSEIKYMPFFICEFCGWKQAGDKNASANIADKDYQDKLNKEKEFCNIRKP
KSKKEDIGEENEEERDYSRRFNRNSFIYNSLKKDNKLNQEKLFDEWKNQLKRKIDGRNKFEPKE
YKDRFSYLFAYYQEIIKNESES (SEQ ID NO: 4)

\>CasZa.5|rifcsplowo2_01_scaffold_34461_9 \N id=58382281
partial=0 scaf=rifcsplowo2_01_scaffold_34461
bin=RifCSPlowO2_01_full_UNK sample=RIFCSPLOWO2_01_FULL
proj=RifleCSP2_LowO2
mVPTELITKTLQLRVIRPLYFEEIEKELAELKEQKEKEFEETNSLLLESKKIDAKSLKKLKRKA
RSSAAVEFWKIAKEKYPDILTKPEMEFIFSEMQKMMARFYNKSMTNIFIEMNNDEKVNPLSLIS
KASTEANQVIKCSSISSGLNRKIAGSINKTKFQVRDGLISLPTARTETFPISFYKSTANKDEI
PISKINLPSEEEADLTITLPFPFFEIKKEKKGQKAYSYFNIIEKSGRSNNKIDLLLSTHRRQRR
KGWKEEGGTSAEIRRLMEGEFDKEWEIYLGEAEKSEKAKNDLIKNMTRGKLSKDIKEQLEDIQV
KYFSDNNVESWNDLSKEQKQELSKLRKKKVEELKDWKHVKEILKTRAKIGWVELKRGKRQRDRN
KWFVNITITRPPFINKELDDTKFGGIDLGVKVPFVCAVHGSPARLIIKENEILQFNKMVSARNR
QITKDSEQRKGRGKKNKFIKKEIFNERNELFRKKIIERWANQIVKFFEDQKCATVQIENLESFD
RTSYK (SEQ ID NO: 5)

\>CasZa.6|037|3300012359.a:Ga0137385_10000156_01776
Zr6.cluA_1a.mostc10like protein
MKSDTKDKKIIIHQTKTLSLRIVKPQSIPMEEFTDLVRYHQMIIFPVYNNGAIDLYKKLFKAKI
QKGNEARAIKYFMNKIVYAPIANTVKNSYIALGYSTKMQSSFSGKRLWDLRFGEATPPTIKADF
PLPFYNQSGFKVSSENGEFIIGIPFGQYTKKTVSDIEKKTSFAWDKFTLEDTTKKTLIELLLST
KTRKMNEGWKNNEGTEAEIKRVMDGTYQVTSLEILQRDDSWFVNFNIAYDSLKKQPDRDKIAGI
HMGITRPLTAVIYNNKYRALSIYPNTVMHLTQKQLARIKEQRTNSKYATGGHGRNAKVTGTDTL
SEAYRQRRKKIIEDWIASIVKFAINNEIGTIYLEDISNTNSFFAAREQKLIYLEDISNTNSFLS
TYKYPISAISDTLQHKLEEKAIQVIRKKAYYVNQICSLCGHYNKGFTYQFRRKNKFPKMKCQGC
LEATSTEFNAAANVANPDYEKLLIKHGLLQLKK (SEQ ID NO: 6)

FIG. 1C

>CasZa.7|127|3300009029.a:Ga0066793_10010091_01298
Zr6.cluA_1.c10.inclusive
MSTITRQVRLSPTPEQSRLLMAHCQQYISTVNVLVAAFDSEVLTGKVSTKDFRAALPSAVKNQA
LRDAQSVFKRSVELGCLPVLKKPHCQWNNQNWRVEGDQLILPICKDGKTQQERFRCAAVALEGK
AGILRIKKKRGKWIADLTVTQEDAPESSGSAIMGVDLGIKVPAVAHIGGKGTRFFGNGRSQRSM
RRRFYARRKTLQKAKKLRAVRKSKGKEARWMKTINHQLSRQIVNHAHALGVGTIKIEALQGIRK
GTTRKSRGAAARKNNRMTNTWSFSQLTLFITYKAQRQGITVEQVDPAYTSQDCPACRARNGAQD
RTYVCSECGWRGHRDTVGAINISRRAGLSGHRRGATGA (SEQ ID NO: 7)

>CasZb.1|bjp_ig2599_sub10_scaffold_488_2 transposase id=60827220
partial=0 scaf=bjp_ig2599_sub10_scaffold_488
bin=BJP_IG2599_SUB10_Micrarchaeota_NOVEL_41_24
sample=BJP_IG2599_SUB10 proj=Borehole JP
mIAQKTIKIKLNPTKEQIIKLNSIIEEYIKVSNFTAKKIAEIQESFTDSGLTQGTCSECGKEKT
YRKYHLLKKDNKLFCITCYKRKYSQFTLQKVEFQNKTGLRNVAKLPKTYYTNAIRFASDTFSGF
DEIIKKKQNRLNSIQNRLNFWKELLYNPSNRNEIKIKVVKYAPKTDTREHPHYYSEAEIKGRIK
RLEKQLKKFKMPKYPEFTSETISLQRELYSWKNPDELKISSITDKNESmNYYGKEYLKRYIDLI
NSQTPQILLEKENNSFYLCFPITKNIEMPKIDDTFEPVGIDWGITRNIAVVSILDSKTKKPKFV
KFYSAGYILGKRKHYKSLRKHFGQKKRQDKINKLGTKEDRFIDSNIHKLAFLIVKEIRNHSNKP
IILMENITDNREEAEKSMRQNILLHSVKSRLQNYIAYKALWNNIPTNLVKPEHTSQICNRCGHQ
DRENRPKGSKLFKCVKCNYMSNADFNASINIARKFYIGEYEPFYKDNEKMKSGVNSISM (SEQ
ID NO: 8)

>CasZb.2|rifcsplowo2_01_scaffold_239_52 IS605 OrfB family
transposase id=57672634 partial=0
scaf=rifcsplowo2_01_scaffold_239 bin=RifCSPlowO2_01_full_UNK
sample=RIFCSPLOWO2_01_FULL proj=RifleCSP2_LowO2
LKLSEQENITTGVKFKLKLDKETSEGLNDYFDEYGKAINFAIKVIQKELAEDRFAGKVRLDENK
KPLLNEDGKKIWDFPNEFCSCGKQVNRYVNGKSLCQECYKNKFTEYGIRKRMYSAKGRKAEQDI
NIKNSTNKISKTHFNYAIREAFILDKSIKKQRKERFRRLREMKKKLQEFIEIRDGNKILCPKIE
KQRVERYIHPSWINKEKKLEDFRGYSMSNVLGKIKILDRNIKREEKSLKEKGQINFKARRLMLD
KSVKFLNDNKISFTISKNLPKEYELDLPEKEKRLNWLKEKIKIIKNQKPKYAYLLRKDDNFYLQ
YTLETEFNLKEDYSGIVGIDRGVSHIAVYTFVHNNGKNERPLFLNSSEILRLKNLQKERDRFLR
RKHNKKRKKSNMRNIEKKIQLILHNYSKQIVDFAKNKNAFIVFEKLEKPKKNRSKMSKKSQYKL
SQFTFKKLSDLVDYKAKREGIKVLYISPEYTSKECSHCGEKVNTQRPFNGNSSLFKCNKCGVEL
NADYNASINIAKKGLNILNSTN
(SEQ ID NO: 9)

FIG. 1D

>CasZb.3|rifcsplowo2_01_scaffold_282_93 IS605 OrfB family transposase id=57678680 partial=0 scaf=rifcsplowo2_01_scaffold_282 bin=RifCSPlowO2_01_full_UNK sample=RIFCSPLOWO2_01_FULL proj=RifleCSP2_LowO2
mEESIITGVKFKLRIDKETTKKLNEYFDEYGKAINFAVKIIQKELADDRFAGKAKLDQNKNPIL
DENGKKIYEFPDEFCSCGKQVNKYVNNKPFCQECYKIRFTENGIRKRMYSAKGRKAEHKINILN
STNKISKTHFNYAIREAFILDKSIKKQRKKRNERLRESKKRLQQFIDMRDGKREICPTIKGQKV
DRFIHPSWITKDKKLEDFRGYTLSIINSKIKILDRNIKREEKSLKEKGQIIFKAKRLMLDKSIR
FVGDRKVLFTISKTLPKEYELDLPSKEKRLNWLKEKIEIIKNQKPKYAYLLRKNIESEKKPNYE
YYLQYTLEIKPELKDFYDGAIGIDRGINHIAVCTFISNDGKVTPPKFFSSGEILRLKNLQKERD
RFLLRKHNKNRKKGNMRVIENKINLILHRYSKQIVDmAKKLNASIVFEELGRIGKSRTKMKKSQ
RYKLSLFIFKKLSDLVDYKSRREGIRVTYVPPEYTSKECSHCGEKVNTQRPFNGNYSLFKCNKC
GIQLNSDYNASINIAKKGLKIPNST
    (SEQ ID NO: 10)

>CasZb.4|rifcsphigho2_01_scaffold_36781_5 transposase, IS605 OrfB family id=55842010 partial=0 scaf=rifcsphigho2_01_scaffold_36781 bin=RifCSPhighO2_01_full_UNK sample=RIFCSPHIGHO2_01_FULL proj=RifleCSP2_HighO2
LWTIVIGDFIEMPKQDLVTTGIKFKLDVDKETRKKLDDYFDEYGKAINFAVKIIQKNLKEDRFA
GKIALGEDKKPLLDKDGKKIYNYPNESCSCGNQVRRYVNAKPFCVDCYKLKFTENGIRKRMYSA
RGRKADSDINIKNSTNKISKTHFNYAIREGFILDKSLKKQRSKRIKKLLELKRKLQEFIDIRQG
QMVLCPKIKNQRVDKFIHPSWLKRDKKLEEFRGYSLSVVEGKIKIFNRNILREEDSLRQRGHVN
FKANRIMLDKSVRFLDGGKVNFNLNKGLPKEYLLDLPKKENKLSWLNEKISLIKLQKPKYAYLL
RREGSFFIQYTIENVPKTFSDYLGAIGIDRGISHIAVCTFVSKNGVNKAPVFFSSGEILKLKSL
QKQRDLFLRGKHNKIRKKSNMRNIDNKINLILHKYSRNIVNLAKSEKAFIVFEKLEKIKKSRFK
MSKSLQYKLSQFTFKKLSDLVEYKAKIEGIKVDYVPPEYTSKECSHCGEKVDTQRPFNGNSSLF

KCNKCRVQLNADYNASINIAKKSLNISNN (SEQ ID NO: 11)

>CasZb.5|cg1_0.2_scaffold_785_c_37 transposase, IS605 OrfB family id=91826491 partial=0 scaf=cg1_0.2_scaffold_785_c bin=CG1_02_FULL_Micrarchaeota_47_40_curated sample=CG1_02_FULL proj=Crystal Geyser
mSKTTISVKLKIIDLSSEKKEFLDNYFNEYAKATTFCQLRIRRLLRNTHWLGKKEKSSKKWIFE
SGICDLCGENKELVNEDRNSGEPAKICKRCYNGRYGNQMIRKLFVSTKKREVQENMDIRRVAKL
NNTHYHRIPEEAFDMIKAADTAEKRRKKNVEYDKKRQMEFIEMFNDEKKRAARPKKPNERETRY
VHISKLESPSKGYTLNGIKRKIDGMGKKIERAEKGLSRKKIFGYQGNRIKLDSNWVRFDLAESE
ITIPSLFKEMKLRITGPTNVHSKSGQIYFAEWFERINKQPNNYCYLIRKTSSNGKYEYYLQYTY
EAEVEANKEYAGCLGVDIGCSKLAAAVYYDSKNKKAQKPIEIFTNPIKKIKMRREKLIKLLSRV
KVRHRRRKLMQLSKTEPIIDYTCHKTARKIVEMANTAKAFISMENLETGIKQKQQARETKKQKF
YRNMFLFRKLSKLIEYKALLKGIKIVYVKPDYTSQTCSSCGADKEKTERPSQAIFRCLNPTCRY

YQRDINADFNAAVNIAKKALNNTEVVTTLL   (SEQ ID NO: 12)

FIG. 1E

>CasZb.6|rifcsphigho2_02_scaffold_55589_5 transposase, IS605
OrfB family id=61682131 partial=0
scaf=rifcsphigho2_02_scaffold_55589 bin=RifCSPhighO2_02_full_UNK
sample=RIFCSPHIGHO2_02_FULL proj=RifleCSP2_HighO2
mARAKNQPYQKLTTTTGIKFKLDLSEEEGKRFDEYFSEYAKAVNFCAKVIYQLRKNLKFAGKKE
LAAKEWKFEISNCDFCNKQKEIYYKNIANGQKVCKGCHRTNFSDNAIRKKMIPVKGRKVESKFN
IHNTTKKISGTHRHWAFEDAADIIESMDKQRKEKQKRLRREKRKLSYFFELFGDPAKRYELPKV
GKQRVPRYLHKIIDKDSLTKKRGYSLSYIKNKIKISERNIERDEKSLRKASPIAFGARKIKMSK
LDPKRAFDLENNVFKIPGKVIKGQYKFFGTNVANEHGKKFYKDRISKILAGKPKYFYLLRKKVA
ESDGNPIFEYYVQWSIDTETPAITSYDNILGIDAGITNLATTVLIPKNLSAEHCSHCGNNHVKP
IFTKFFSGKELKAIKIKSRKQKYFLRGKHNKLVKIKRIRPIEQKVDGYCHVVSKQIVEMAKERN
SCIALEKLEKPKKSKFRQRRREKYAVSMFVFKKLATFIKYKAAREGIEIIPVEPEGTSYTCSHC
KNAQNNQRPYFKPNSKKSWTSMFKCGKCGIELNSDYNAAFNIAQKALNMTSA
    (SEQ ID NO: 13)

>CasZb.7|CG03_land_8_20_14_0.80_scaffold_2214_9 transposase,
IS605 OrfB family id=135165146 partial=0
scaf=CG03_land_8_20_14_0.80_scaffold_2214
bin=CG03_land_8_20_14_0_80_cor_UNK
sample=CG03_land_8_20_14_0_80_cor proj=Crystal Geyser
mDEKHFFCSYCNKELKISKNLINKISKGSIREDEAVSKAISIHNKKEHSLILGIKFKLFIENKL
DKKKLNEYFDNYSKAVTFAARIFDKIRSPYKFIGLKDKNTKKWTFPKAKCVFCLEEKEVAYANE
KDNSKICTECYLKEFGENGIRKKIYSTRGRKVEPKYNIFNSTKELSSTHYNYAIRDAFQLLDAL
KKQRQKKLKSIFNQKLRLKEFEDIFSDPQKRIELSLKPHQREKRYIHLSKSGQESINRGYTLRF
VRGKIKSLTRNIEREEKSLRKKTPIHFKGNRLMIFPAGIKFDFASNKVKISISKNLPNEFNFSG
TNVKNEHGKSFFKSRIELIKTQKPKYAYVLRKIKREYSKLRNYEIEKIRLENPNADLCDFYLQY
TIETESRNNEEINGIIGIDRGITNLACLVLLKKGDKKPSGVKFYKGNKILGMKIAYRKHLYLLK
GKRNKLRKQRQIRAIEPKINLILHQISKDIVKIAKEKNFAIALEQLEKPKKARFAQRKKEKYKL
ALFTFKNLSTLIEYKSKREGIPVIYVPPEKTSQMCSHCAINGDEHVDTQRPYKKPNAQKPSYSL
FKCNKCGIELNADYNAAFNIAQKGLKTLMLNHSH   (SEQ ID NO: 14)

>CasZb.8|058|3300002172.a:JGI24730J26740_1002785_01697
Zr6.newTrpA
MLQTLLVKLDPSKEQYKMLYETMERFNEACNQIAETVFAIHSANKIEVQKTVYYPIREKFGLSA
QLTILAIRKVCEAYKRDKSIKPEFRLDGALVYDQRVLSWKGLDKVSLVTLQGRQIIPIKFGDYQ
KARMDRIRGQADLILVKGVFYLCVVVESEESPYDPKGVLGVDLGIKNLAVDSDGEVHSGEQTT
NTRERLDSLKARLQSKGTKSAKRHLKKLSGRMAKFSKDVNHCISKKLVAKAKGTLMSIALEDLQ
GIRDRVTVRKAQRRNLHTWNFGLLRMFVDYKAKIAGVPLVFVDPRNTSRTCPSCGHVAKANRPT
RDEFRCVSCGFAGAADHIAAMNIAFRAEVSQPIVTRFFVQSQAPSFRVG
    (SEQ ID NO: 15)

FIG. 1F

>CasZb.9|114|3300013125.a:Ga0172369_10000737_00842
Zr6.cluA_2b.c10_like protein
MDEEPDSAEPNLAPISVKLKLVKLDGEKLAALNDYFNEYAKAVNFCELKMQKIRKNLVNIRGTY
LKEKKAWINQTGECCICKKIDELRCEDKNPDINGKICKKCYNGRYGNQMIRKLFVSTNKRAVPK
SLDIRKVARLHNTHYHRIPPEAADIIKAIETAERKRRNRILFDERRYNELKDALENEEKRVARP
KKPKEREVRYVPISKKDTPSKGYTMNALVRKVSGMAKKIERAKRNLNKRKKIEYLGRRILLDKN
WVRFDFDKSEISIPTMKEFFGEMRFEITGPSNVMSPNGREYFTKWFDRIKAQPDNYCYLLRKES
EDETDFYLQYTWRPDAHPKKDYTGCLGIDIGGSKLASAVYFDADKNRAKQPIQIFSNPIGKWKT
KRQKVIKVLSKAAVRHKTKKLESLRNIEPRIDVHCHRIARKIVGMALAANAFISMENLEGGIRE
KQKAKETKKQKFSRNMFVFRKLSKLIEYKALMEGVKVVYIVPDYTSQLCSSCGTNNTKRPKQAI

FMCQNTECRYFGKNINADFNAAINIAKKALNRKDIVRELS (SEQ ID NO: 16)

>CasZb.10|115|3300013125.a:Ga0172369_10010464_01540
Zr6.cluA_2b.c10_like protein
MEKNNSEQTSITTGIKFKLKLDKETKEKLNNYFDEYGKAINFAVRIIQMQLNDDRLAGKYKRDE
KGKPILGEDGKKILEIPNDFCSCGNQVNHYVNGVSFCQECYKKRFSENGIRKRMYSAKGRKAEQ
DINIKNSTNKISKTHFNYAIREAFNLDKSIKKQREKRFKKLKDMKRKLQEFLEIRDGKRVICPK
IEKQKVERYIHPSWINKEKKLEEFRGYSLSIVNSKIKSFDRNIQREEKSLKEKGQINFKAQRLM
LDKSVKFLKDNKVSFTISKELPKTFELDLPKKEKKLNWLNEKLEIIKNQKPKYAYLLRKENNIF
LQYTLDSIPEIHSEYSGAVGIDRGVSHIAVYTFLDKDGKNERPFFLSSSGILRLKNLQKERDKF
LRKKHNKIRKKGNMRNIEQKINLILHEYSKQIVNFAKDKNAFIVFELLEKPKKSRERMSKKIQY
KLSQFTFKKLSDLVDYKAKREGIKVIYVEPAYTSKDCSHCGERVNTQRPFNGNFSLFKCNKCGI

VLNSDYNASLNIARKGLNISAN (SEQ ID NO: 17)

>CasZb.11|134|3300013127.a:Ga0172365_10004421_00828
Zr6.cluA_2b.c10_like protein
MAEEKFFFCEKCNKDIKIPKNYINKQGAEEKARAKHEHRVHALILGIKFKIYPKKEDISKLNDY
FDEYAKAVTFTAKIVDKLKAPFLFAGKRDKDTSKKKWVFPVDKCSFCKEKTEINYRTKQGKNIC
NSCYLTEFGEQGLLEKIYATKGRKVSSSFNLFNSTKKLTGTHNNYVVKESLQLLDALKKQRSKR
LKKLSNTRRKLKQFEEMFEKEDKRFQLPLKEKQRELRFIHVSQKDRATEFKGYTMNKIKSKIKV
LRRNIEREQRSLNRKSPVFFRGTRIRLSPSVQFDDKDNKIKLTLSKELPKEYSFSGLNVANEHG
RKFFAEKLKLIKENKSKYAYLLRRQVNKNNKKPIYDYYLQYTVEFLPNIITNYNGILGIDRGIN
TLACIVLLENKKEKPSFVKFFSGKGILNLKNKRRKQLYFLKGVHNKYRKQQKIRPIEPRIDQIL
HDISKQIIDLAKEKRVAISLEQLEKPQKPKFRQSRKAKYKLSQFNFKTLSNYIDYKAKKEGIRV
IYIAPEMTSQNCSRCAMKNDLHVNTQRPYKNTSSLFKCNKCGVELNADYNAAFNIAQKGLKILN

S (SEQ ID NO: 18)

FIG. 1G

>CasZc.1|CG08_land_8_20_14_0.20_scaffold_1609_10 Tax=CG_Micra_03
id=133381002 partial=0 scaf=CG08_land_8_20_14_0.20_scaffold_1609
bin=CG08_land_8_20_14_0_20_UNK sample=CG08_land_8_20_14_0_20
proj=Crystal Geyser
mISLKLKLLPDEEQKKLLDEMFWKWASICTRVGFGRADKEDLKPPKDAEGVWFSLTQLNQANTD
INDLREAMKHQKHRLEYEKNRLEAQRDDTQDALKNPDRREISTKRKDLFRPKASVEKGFLKLKY
HQERYWVRRLKEINKLIERKTKTLIKIEKGRIKFKATRITLHQGSFKIRFGDKPAFLIKALSGK
NQIDAPFVVVPEQPICGSVVNSKKYLDEITTNFLAYSVNAMLFGLSRSEEMLLKAKRPEKIKKK
EEKLAKKQSAFENKKKELQKLLGRELTQQEEAIIEETRNQFFQDFEVKITKQYSELLSKIANEL
KQKNDFLKVNKYPILLRKPLKKAKSKKINNLSPSEWKYYLQFGVKPLLKQKSRRKSRNVLGIDR
GLKHLLAVTVLEPDKKTFVWNKLYPNPITGWKWRRRKLLRSLKRLKRRIKSQKHETIHENQTRK
KLKSLQGRIDDLLHNISRKIVETAKEYDAVIVVEDLQSMRQHGRSKGNRLKTLNYALSLFDYAN
VMQLIKYKAGIEGIQIYDVKPAGTSQNCAYCLLAQRDSHEYKRSQENSKIGVCLNPNCQNHKKQ

IDADLNAARVIASCYALKINDSQPFGTRKRFKKRTTN (SEQ ID NO: 19)

>CasZc.2|CG_4_10_14_0.8_um_filter_scaffold_20762_4
Tax=CG_Micra_03 id=144037526 partial=0
scaf=CG_4_10_14_0.8_um_filter_scaffold_20762
bin=CG_4_10_14_0_8_um_filter_cor_UNK
sample=CG_4_10_14_0_8_um_filter_cor proj=Crystal Geyser
mETLSLKLKLNPSKEQLLVLDKMFWKWASICTRLGLKKAEMSDLEPPKDAEGVWFSKTQLNQAN
TDVNDLRKAMQHQGKRIEYELDKVENRRNEIQEMLEKPDRRDISPNRKDLFRPKAAVEKGYLKL
KYHKLGYWSKELKTANKLIERKRKTLAKIDAGKMFKPTRISLHTNSFRIKFGEEPKIALSTTS
KHEKIELPLITSLQRPLKTSCAKKSKTYLDAAILNFLAYSTNAALFGLSRSEEMLLKAKKPEKI
EKRDRKLATKRESFDKKLKTLEKLLERKLSEKEKSVFKRKQTEFFDKFCITLDETYVEALHRIA
EELVSKNKYLEIKKYPVLLRKPESRLRSKKLKNLKPEDWTYYIQFGFQPLLDTPKPIKTKTVLG
IDRGVRHLLAVSIFDPRTKTFTFNRLYSNPIVDWKWRRRKLLRSIKRLKRRLKSEKHVHLHENQ
FKAKLRSLEGRIEDHFHNLSKEIVDLAKENNSVIVVENLGGMRQHGRGRGKWLKALNYAISHFD
YAKVMQLIKYKAELAGVFVYDVAPAGTSINCAYCLLNDKDASNYTRGKVINGKKNTKIGECKTC

KKEFDADLNAARVIALCYEKRLNDPQPFGTRKQFKPKKP (SEQ ID NO: 20)

FIG. 1H

>CasZc.3|CG22_combo_CG10-13_8_21_14_all_scaffold_2003_2 IS605
OrfB family transposase id=130740989 partial=0
scaf=CG22_combo_CG10-13_8_21_14_all_scaffold_2003
bin=CG22_combo_CG10-13_8_21_14_all_UNK sample=CG22_combo_CG10-
13_8_21_14_all proj=Crystal Geyser
mKALKLQLIPTRKQYKILDEMFWKWASLANRVSQKGESKETLAPKKDIQKIQFNATQLNQIEKD
IKDLRGAMKEQQKQKERLLLQIQERRSTISEMLNDDNNKERDPHRPLNFRPKGWRKFHTSKHWV
GELSKILRQEDRVKKTIERIVAGKISFKPKRIGIWSSNYKINFFKRKISINPLNSKGFELTLMT
EPTQDLIGKNGGKSVLNNKRYLDDSIKSLLMFALHSRFFGLNNTDTYLLGGKINPSLVKYYKKN
QDMGEFGREIVEKFERKLKQEINEQQKKIIMSQIKEQYSNRDSAFNKDYLGLINEFSEVFNQRK
SERAEYLLDSFEDKIKQIKQEIGESLNISDWDFLIDEAKKAYGYEEGFTEYVYSKRYLEILNKI
VKAVLITDIYFDLRKYPILLRKPLDKIKKISNLKPDEWSYYIQFGYDSINPVQLMSTDKFLGID
RGLTHLLAYSVFDKEKKEFTINQLEPNPIMGWKWLRKVKRSLQHLERRIRAQKMVKLPENQMK
KKLKSIEPKIEVHYHNISRKIVNLAKDYNASIVVESLEGGGLKQHGRKKNARNRSLNYALSLFD
YGKIASLIKYKADLEGVPMYEVLPAYTSQQCAKCVLEKGSFVDPEIIGYVEDIGIKGSLLDSLF
EGTELSSIQVLKKIKNKIELSARDNHNKEINLILKYNFKGLVIVRGQDKEEIAEHPIKEINGKF
AILDFVYKRGKEKVGKKGNQKVRYTGNKKVGYCSKHGQVDADLNASRVIALCKYLDINDPILFG
EQRKSFK (SEQ ID NO: 21)

>CasZc.4|rifcsphigho2_01_scaffold_82367_2 Tax=CG_Micra_03
id=56177664 partial=0 scaf=rifcsphigho2_01_scaffold_82367
bin=RifCSPhighO2_01_full_UNK sample=RIFCSPHIGHO2_01_FULL
proj=RifleCSP2_HighO2
mVTRAIKLKLDPTKNQYKLLNEMFWKWASLANRFSQKGASKETLAPKDGTQKIQFNATQLNQIK
KDVDDLRGAMEKQGKQKERLLIQIQERLLTISEILRDDSKKEKDPHRPQNFRPFGWRRFHTSAY
WSSEASKLTRQVDRVRRTIERIKAGKINFKPKRIGLWSSTYKINFLKKKINISPLKSKSFELDL
ITEPQQKIIGKEGGKSVANSKKYLDDSIKSLLIFAIKSRLFGLNNKDKPLFENIITPNLVRYHK
KGQEQENFKKEVIKKFENKLKKEISQKQKEIIFSQIERQYENRDATFSEDYLRAISEFSEIFNQ
RKKERAKELLNSFNEKIRQLKKEVNGNISEEDLKILEVAEKAYNYENGFIEWEYSEQFLGVLE
KIARAVLISDNYFDLKKYPILIRKPTNKSKKITNLKPEEWDYYIQFGYGLINSPMKIETKNFMG
IDRGLTHLLAYSIFDRDSEKFTINQLELNPIKGWKWLRKVKRSLQHLERRMRAQKGVKLPENQ
MKKRLKSIEPKIESYYHNLSRKIVNLAKANNASIVVESLEGGGLKQHGRKKNSRHRALNYALSL
FDYGKIASLIKYKSDLEGVPMYEVLPAYTSQQCAKCVLKKGSFVEPEIIGYIEEIGFKENLLTL
LFEDTGLSSVQVLKKSKNKMTLSARDKEGKMVDLVLKYNFKGLVISQEKKKEEIVEFPIKEIDG
KFAVLDSAYKRGKERISKKGNQKLVYTGNKKVGYCSVHGQVDADLNASRVIALCKYLGINEPIV
FGEQRKSFK       (SEQ ID NO: 22)

FIG. 1I

\>CasZc.5|gwc1_scaffold_8732_6 Transposase, IS605 OrfB family
id=3520800 partial=0 scaf=gwc1_scaffold_8732 bin=GWC1 Unbinned
sample=GWC1 proj=Rifle Groundwater Metagenome
LDLITEPIQPHKSSSLRSKEFLEYQISDFLNFSLHSLFFGLASNEGPLVDFKIYDKIVIPKPEE
RFPKKESEEGKKLDSFDKRVEEYYSDKLEKKIERKLNTEEKNVIDREKTRIWGEVNKLEEIRSI
IDEINEIKKQKHISEKSKLLGEKWKKVNNIQETLLSQEYVSLISNLSDELTNKKKELLAKKYSK
FDDKIKKIKEDYGLEFDENTIKKEGEKAFLNPDKFSKYQFSSSYLKLIGEIARSLITYKGFLDL
NKYPIIFRKPINKVKKIHNLEPDEWKYYIQFGYEQINNPKLETENILGIDRGLTHILAYSVFEP
RSSKFILNKLEPNPIEGWKWKLRKLRRSIQNLERRWRAQDNVKLPENQMKKNLRSIEDKVENLY
HNLSRKIVDLAKEKNACIVFEKLEGQGMKQHGRKKSDRLRGLNYKLSLFDYGKIAKLIKYKAEI
EGIPIYRIDSAYTSQNCAKCVLESRRFAQPEEISCLDDFKEGDNLDKRILEGTGLVEAKIYKKL
LKEKKEDFEIEEDIAMFDTKKVIKENKEKTVILDYVYTRRKEIIGTNHKKNIKGIAKYTGNTKI
GYCMKHGQVDADLNASRTIALCKNFDINNPEIWK  (SEQ ID NO: 23)

\>CasZc.6|109|3300010293.a:Ga0116204_1008574_00822
Zr6.cluA_2a.c10_like protein
MSDESLVSSEDKLAIKIKIVPNAEQAKMLDEMFKKWSSICNRISRGKEDIETLRPDEGKELQFN
STQLNSATMDVSDLKKAMARQGERLEAEVSKLRGRYETIDASLRDPSRRHTNPQKPSSFYPSDW
DISGRLTPRFHTARHYSTELRKLKAKEDKMLKTINKIKNGKIVFKPKRITLWPSSVNMAFKGSR
LLLKPFANGFEMELPIVISPQKTADGKSQKASAEYMRNALLGLAGYSINQLLFGMNRSQKMLAN
AKKPEKVEKFLEQMKNKDANFDKKIKALEGKWLLDRKLKESEKSSIAVVRTKFFKSGKVELNED
YLKLLKHMANEILERDGFVNLNKYPILSRKPMKRYKQKNIDNLKPNMWKYYIQFGYEPIFERKA
SGKPKNIMGIDRGLTHLLAVAVFSPDQQKFLFNHLESNPIMHWKWKLRKIRRSIQHMERRIRAE
KNKHIHEAQLKKRLGSIEEKTEQHYHIVSSKIINWAIEYEAAIVLESLSHMKQRGGKKSVRTRA
LNYALSLFDYEKVARLITYKARIRGIPVYDVLPGMTSKTCATCLLNGSQGAYVRGLETTKAAGK
ATKRKNMKIGKCMVCNSSENSMIDADLNAARVIAICKYKNLNDPQPAGSRKVFKRF
  (SEQ ID NO: 24)

\>CasZc.7|126|3300005573.a:Ga0078972_1001015_00056
Zr6.cluA_2a.c10_like protein
MLALKLKIMPTEKQAEILDAMFWKWASICSRIAKMKKKVSVKENKKELSKKIPSNSDIWFSKTQ
LCQAEVDVGDHKKALKNFEKRQESLLDELKYVKAINEVINDESKREIDPNNPSKFRIKDSTKK
GNLNSPKFFTLKKWQKILQENEKRIKKKESTIEKLKRGNIFFNPTKISLHEEEYSINFGSSKLL
LNCFYKYNKKSGINSDQLENKFNEFQNGLNIICSPLQPIRGSSKRSFEFIRNSIINFLMYSLYA
KLFGIPRSVKALMKSNKDENKLKLEEKLKKKKSSFNKTVKEFEKMIGRKLSDNESKILNDESKK
FFEIIKSNNKYIPSEEYLKLLKDISEEIYNSNIDFKPYKYSILIRKPLSKFKSKKLYNLKPTDY
KYYLQLSYEPFSKQLIATKTILGIDRGLKHLLAVSVFDPSQNKFVYNKLIKNPVFKWKKRYHDL
KRSIRNRERRIRALTGVHIHENQLIKKLKSMKNKINVLYHNVSKNIVDLAKKYESTIVLERLEN
LKQHGRSKGKRYKKLNYVLSNFDYKKIESLISYKAKKEGVPVSNINPKYTSKTCAKCLLEVNQL
SELKNEYNRDSKNSKIGICNIHGQIDADLNAARVIALCYSKNLNEPHFK
  (SEQ ID NO: 25)

FIG. 1J

>CasZd.1|CG10_big_fil_rev_8_21_14_0.10_scaffold_4477_25 IS605
OrfB family transposase id=132383911 partial=0
scaf=CG10_big_fil_rev_8_21_14_0.10_scaffold_4477
bin=CG10_big_fil_rev_8_21_14_0_10_test2
sample=CG10_big_fil_rev_8_21_14_0_10 proj=Crystal Geyser
VINLFGYKFALYPNKTQEELLNKHLGECGWLYNKAIEQNEYYKADSNIEEAQKKFELLPDKNSD
EAKVLRGNISKDNYVYRTLVKKKKSEINVQIRKAVVLRPAETIRNLAKVKKKGLSVGRLKFIPI
REWDVLPFKQSDQIRLEENYLILEPYGRLKFKMHRPLLGKPKTFCIKRTATDRWTISFSTEYDD
SNMRKNDGGQVGIDVGLKTHLRLSNENPDEDPRYPNPKIWKRYDRRLTILQRRISKSKKLGKNR
TRLRLRLSRLWEKIRNSRADLIQNETYEILSENKLIAIEDLNVKGMQEKKDKKGRKGRTRAQEK
GLHRSISDAAFSEFRRVLEYKAKRFGSEVKPVSAIDSSKECHNCGNKKGMPLESRIYECPKCGL
KIDRDLNSAKVILARATGVRPGSNARADTKISATAGASVQTEGTVSEDFRQQMETSDQKPMQGE
GSKEPPMNPEHKSSGRGSKHVNIGCKNKVGLYNEDENSRSTEKQIMDENRSTTEDMVEIGALHS
PVLTT (SEQ ID NO: 26)

>CasZd.2|053|3300001245.a:JGI12048J13642_10201286_01511
Zr6.c9.inclusive
MIASIDYEAVSQALIVFEFKAKGKDSQYQAIDEAIRSYRFIRNSCLRYWMDNKKVGKYDLNKYC
KVLAKQYPFANKLNSQARQSAAECSWSAISRFYDNCKRKVSGKKGFPKFKKHARSVEYKTSGWK
LSENRKAITFTDKNGIGKLKLKGTYDLHFSQLEDMKRVRLVRRADGYYVQFCISVDVKVETEPT
GKAIGLDVGIKYFLADSSGNTIENPQFYRKAEKKLNRANRRKSKKYIRGVKPQSKNYHKARCRY
ARKHLRVSRQRKEYCKRVAYCVIHSNDVVAYEDLNVKGMVKNRHLAKSISDVAWSTFRHWLEYF
AIKYGKLTIPVAPHNTSQNCSNCDKKVPKSLSTRTHICHHCGYSEDRDVNAAKNILKKALSTVG
QTGSLKLGEIEPLLVLEQSCTRKFDL (SEQ ID NO: 27)

>CasZe.1|19ft_2_nophage_noknown_scaffold_0_545 \N id=8269792
partial=0 scaf=19ft_2_nophage_noknown_scaffold_0 bin=19ft_2_UNK
sample=19FT_2_THINNED proj=Rifle Sediment CSP1
LAEENTLHLTLAMSLPLNDLPENRTRSELWRRQWLPQKKLSLLLGVNQSVRKAAADCLRWFEPY
QELLWWEPTDPDGKKLLDKEGRPIKRTAGHMRVLRKLEEIAPFRGYQLGSAVKNGLRHKVADLL
LSYAKRKLDPQFTDKTSYPSIGDQFPIVWTGAFVCYEQSITGQLYLYLPLFPRGSHQEDITNNY
DPDRGPALQVFGEKEIARLSRSTSGLLLPLQFDKWGEATFIRGENNPPTWKATHRRSDKKWLSE
VLLREKDFQPKRVELLVRNGRIFVNVACEIPTKPLLEVENFMGVSFGLEHLVTVVVINRDGNVV
HQRQEPARRYEKTYFARLERLRRRGGPFSQELETFHYRQVAQIVEEALRFKSVPAVEQVGNIPK
GRYNPRLNLRLSYWPFGKLADLTSYKAVKEGLPKPYSVYSATAKMLCSTCGAANKEGDQPISLK
GPTVYCGNCGTRHNTGFNTALNLARRAQELFVKGVVAR (SEQ ID NO: 28)

FIG. 1K

>CasZe.2|RIFCSPHIGHO2_01_FULL_CPR_46_36_rifcsphigho2_01_scaffold
_646_49 Tax=RIFCSPHIGHO2_01_FULL_RIF_OD1_04_46_36_curated
id=87353177 partial=0
scaf=RIFCSPHIGHO2_01_FULL_CPR_46_36_rifcsphigho2_01_scaffold_646
bin=RIFCSPHIGHO2_01_FULL_OD1_Andersenbacteria_46_36_curated
sample=2500-curated-genomes-non-redundant proj=2500_Genomes
mSQSLLKWHDMAGRDKDASRSLQKSAVEGVLLHLTASHRVALEMLEKSVSQTVAVTMEAAQQRL
VIVLEDDPTKATSRKRVISADLQFTREEFGSLPNWAQKLASTCPEIATKYADKHINSIRIAWGV
AKESTNGDAVEQKLQWQIRLLDVTMFLQQLVLQLADKALLEQIPSSIRGGIGQEVAQQVTSHIQ
LLDSGTVLKAELPTISDRNSELARKQWEDAIQTVCTYALPFSRERARILDPGKYAAEDPRGDRL
INIDPMWARVLKGPTVKSLPLLFVSGSSIRIVKLTLPRKHAAGHKHTFTATYLVLPVSREWINS
LPGTVQEKVQWWKKPDVLATQELLVGKGALKKSANTLVIPISAGKKRFFNHILPALQRGFPLQW
QRIVGRSYRRPATHRKWFAQLTIGYTNPSSLPEMALGIHFGMKDILWWALADKQGNILKDGSIP
GNSILDFSLQEKGKIERQQKAGKNVAGKKYGKSLLNATYRVVNGVLEFSKGISAEHASQPIGLG
LETIRFVDKASGSSPVNARHSNWNYGQLSGIFANKAGPAGFSVTEITLKKAQRDLSDAEQARVL
AIEATKRFASRIKRLATKRKDDTLFV (SEQ ID NO: 29)

>CasZe.3|rifcsphigho2_01_scaffold_10981_6
Tax=RIFCSPHIGHO2_01_FULL_OD1_47_10b curated id=55513311
partial=0 scaf=rifcsphigho2_01_scaffold_10981
bin=RIFCSPHIGHO2_01_FULL_OD1_47_10b sample=2500-genomes
proj=2500_Genomes
VEPVEKERFYYRTYTFRLDGQPRTQNLTTQSGWGLLTKAVLDNTKHYWEIVHHARIANQPIVFE
NPVIDEQGNPKLNKLGQPRFWKRPISDIVNQLRALFENQNPYQLGSSLIQGTYWDVAENLASWY
ALNKEYLAGTATWGEPSFPEPHPLTEINQWMPLTFSSGKVVRLLKNASGRYFIGLPILGENNPC
YRMRTIEKLIPCDGKGRVTSGSLILFPLVGIYAQQHRRMTDICESIRTEKGKLAWAQVSIDYVR
EVDKRRRMRRTRKSQGWIQGPWQEVFILRLVLAHKAPKLYKPRCFAGISLGPKTLASCVILDQD
ERVVEKQQWSGSELLSLIHQGEERLRSLREQSKPTWNAAYRKQLKSLINTQVFTIVTFLRERGA
AVRLESIARVRKSTPAPPVNFLLSHWAYRQITERLKDLAIRNGMPLTHSNGSYGVRFTCSQCGA
TNQGIKDPTKYKVDIESETFLCSICSHREIAAVNTATNLAKQLLDE (SEQ ID NO: 30)

>CasZe.4b|rifcsplowo2_02_scaffold_57876_2 hypothetical protein
Tax=GWA2_OD1_56_11 id=66016044 partial=0
scaf=rifcsplowo2_02_scaffold_57876 bin=RifCSPlowO2_02_full_UNK
sample=RIFCSPLOWO2_02_FULL proj=RifleCSP2_LowO2
mNDTETSETLTSHRTVCAHLHVVGETGSLPRLVEAALAELITLNGRATQALLSLAKNGLVLRRD
KEENLIAAELTLPCRKNKYADVAAKAGEPILATRINNKGKLVTKKWYGEGNSYHIVRFTPETGM
FTVRVFDRYAFDEELLHLHSEVVFGSDLPKGIKAKTDSLPANFLQAVFTSFLELPFQGFPDIVV
KPAMKQAAEQLLSYVQLEAGENQQAEYPDTNERDPELRLVEWQKSLHELSVRTEPFEFVRARDI
DYYAETDRRGNRFVNITPEWTKFAESPFARRLPLKIPPEFCILLRRKTEGHAKIPNRIYLGLQI
FDGVTPDSTLGVLATAEDGKLFWWHDHLDEFSNLEGKPEPKLKNKPQLLMVSLEYDREQRFEES
VGGDRKICLVTLKETRNFRRGWNGRILGIHFQHNPVITWALMDHDAEVLEKGFIEGNAFLGKAL
DKQALNEYLQKGGKWVGDRSFGNLKGITHTLASLIVRLAREKDAWIALEEISWVQKQSADSVA
NHEIVEQPHHSLTR (SEQ ID NO: 31)

FIG. 1L

>CasZe.4|RIFCSPLOWO2_01_FULL_OD1_45_34b_rifcsplowo2_01_scaffold_
3495_33 hypothetical_protein Tax=GWA2_OD1_56_11 id=88324948
partial=0
scaf=RIFCSPLOWO2_01_FULL_OD1_45_34b_rifcsplowo2_01_scaffold_3495
bin=RIFCSPLOWO2_01_FULL_OD1_Taylorbacteria_45_34b_curated
sample=2500-curated-genomes proj=2500 Genomes
mNDTETSETLTSHRTVCAHLHVVGETGSLPRLVEAALAELITLNGRATQALLSLAKNGLVLRRD
KEENLIAAELTLPCRKNKYADVAAKAGEPILATRINNKGKLVTKKWYGEGNSYHIVRFTPETGM
FTVRVFDRYAFDEELLHLHSEVVFGSDLPKGIKAKTDSLPANFLQAVFTSFLELPFQGFPDIVV
KPAMKQAAEQLLSYVQLEAGENQQAEYPDTNERDPELRLVEWQKSLHELSVRTEPFEFVRARDI
DYYAETDRRGNRFVNITPEWTKFAESPFARRLPLKIPPEFCILLRRKTEGHAKIPNRIYLGLQI
FDGVTPDSTLGVLATAEDGKLFWWHDHLDEFSNLEGKPEPKLKNKPQLLMVSLEYDREQRFEES
VGGDRKICLVTLKETRNFRRGRHGHTRTDRLPAGNTLWRADFATSAEVAAPKWNGRILGIHFQH
NPVITWALMDHDAEVLEKGFIEGNAFLGKALDKQALNEYLQKGGKWVGDRSFGNKLKGITHTLA
SLIVRLAREKDAWIALEEISWVQKQSADSVANRRFSMWNYSRLATLIEWLGTDIATRDCGTAAP
LAHKVSDYLTHFTCPECGACRKAGQKKEIADTVRAGDILTCRKCGFSGPIPDNFIAEFVAKKAL
ERMLKKKPV (SEQ ID NO: 32)

>CasZf.1|rifcsphigho2_01_scaffold_566_121
Tax=RIFCSPHIGHO2_01_FULL_RIF_OD1_10_44_22b curated id=55167017
partial=0 scaf=rifcsphigho2_01_scaffold_566
bin=RifCSPhighO2_01_full_UNK sample=RIFCSPHIGHO2_01_FULL
proj=RifleCSP2_HighO2
mAKRNFGEKSEALYRAVRFEVRPSKEELSILLAVSEVLRMLFNSALAERQQVFTEFIASLYAEL
KSASVPEEISEIRKKLREAYKEHSISLFDQINALTARRVEDEAFASVTRNWQEETLDALDGAYK
SFLSLRRKGDYDAHSPRSRDSGFFQKIPGRSGFKIGEGRIALSCGAGRKLSFPIPDYQQGRLAE
TTKLKKFELYRDQPNLAKSGRFWISVVYELPKEATTCQSEQVAFVALGASSIGVVSQRGEEVI
ALWRSDKHWVPKIEAVEERMKRRVKGSRGWLRLLNSGKRRMHMISSRQHVQDEREIVDYLVRNH
GSHFVVTELVVRSKEGKLADSSKPERGGSLGLNWAAQNTGSLSRLVRQLEEKVKEHGGSVRKHK
LTLTEAPPARGAENKLWMARKLRESFLKEV (SEQ ID NO: 33)

>CasZf.2|rifcsplowo2_01_scaffold_81231_1 transposase, IS605 OrfB
family, central region id=58737995 partial=0
scaf=rifcsplowo2_01_scaffold_81231 bin=RifCSPlowO2_01_full_UNK
sample=RIFCSPLOWO2_01_FULL proj=RifleCSP2_LowO2
LAKNDEKELLYQSVKFEIYPDESKIRVLTRVSNILVLWNSALGERRARFELYIAPLYEELKKF
PRKSAESNALRQKIREGYKEHIPTFFDQLKKLLTPMRKEDPALLGSVPRAYQEETLNTLNGSFV
SFMTLRRNNDMDAKPPKGRAEDRFHEISGRSGFKIDGSEFVLSTKEQKLRFPIPNYQLEKLKEA
KQIKKFTLYQSRDRRFWISIAYEIELPDQRPFNPEEVIYIAFGASSIGVISPEGEKVIDFWRPD
KHWKPKIKEVENRMRSCKKGSRAWKKRAAARRKMYAMTQRQQKLNHREIVASLLRLGFHFVVTE
YTVRSKPGKLADGSNPKRGGAPQGFNWSAQNTGSFGEFILWLKQKVKEQGGTVQTFRLVLGQSE
RPEKRGRDNKIEMVRLLREKYLESQTIVV (SEQ ID NO: 34)

FIG. 1M

>CasZf.3|rifcsphigho2_01_scaffold_4702_81 IS605 OrfB family transposase id=55366684 partial=0 scaf=rifcsphigho2_01_scaffold_4702 bin=RifCSPhighO2_01_full_UNK sample=RIFCSPHIGHO2_01_FULL proj=RifleCSP2_HighO2
mAKGKKKEGKPLYRAVRFEIFPTSDQITLFLRVSKNLQQVWNEAWQERQSCYEQFFGSIYERIG
QAKKRAQEAGFSEVWENEAKKGLNKKLRQQEISMQLVSEKESLLQELSIAFQEHGVTLYDQING
LTARRIIGEFALIPRNWQEETLDSLDGSFKSFLALRKNGDPDAKPPRQRVSENSFYKIPGRSGF
KVSNGQIYLSFGKIGQTLTSVIPEFQLKRLETAIKLKKFELCRDERDMAKPGRFWISVAYEIPK
PEKVPVVSKQITYLAIGASRLGVVSPKGEFCLNLPRSDYHWKPQINALQERLEGVVKGSRKWKK
RMAACTRMFAKLGHQQKQHGQYEVVKKLLRHGVHFVVTELKVRSKPGALADASKSDRKGSPTGP
NWSAQNTGNIARLIQKLTDKASEHGGTVIKRNPPLLSLEERQLPDAQRKIFIAKKLREEFLADQ
K (SEQ ID NO: 35)

>CasZg.1|rifcsp13_1_sub10_scaffold_3_54 \N id=12787801 partial=0 scaf=rifcsp13_1_sub10_scaffold_3 bin=RifCSP13_1_UNK sample=RIFCSP13_1 proj=Rifle Sediment CSP2
mAKREKKDDVVLRGTKMRIYPTDRQVTLMDMWRRRCISLWNLLLNLETAAYGAKNTRSKLGWRS
IWARVVEENHAKALIVYQHGKCKKDGSFVLKRDGTVKHPPRERFPGDRKILLGLFDALRHTLDK
GAKCKCNVNQPYALTRAWLDETGHGARTADIIAWLKDFKGECDCTAISTAAKYCPAPPTAELLT
KIKRAAPADDLPVDQAILLDLFGALRGGLKQKECDHTHARTVAYFEKHELAGRAEDILAWLIAH
GGTCDCKIVEEAANHCPGPRLFIWEHELAMIMARLKAEPRTEWIGDLPSHAAQTVVKDLVKALQ
TMLKERAKAAAGDESARKTGFPKFKKQAYAAGSVYFPNTTmFFDVAAGRVQLPNGCGSMRCEIP
RQLVAELLERNLKPGLVIGAQLGLLGGRIWRQGDRWYLSCQWERPQPTLLPKTGRTAGVKIAAS
IVFTTYDNRGQTKEYPMPPADKKLTAVHLVAGKQNSRALEAQKEKEKKLKARKERLRLGKLEKG
HDPNALKPLKRPRVRRSKLFYKSAARLAACEAIERDRRDGFLHRVTNEIVHKFDAVSVQKMSVA
PMMRRQKQKEKQIESKKNEAKKEDNGAAKKPRNLKPVRKLLRHVAMARGRQFLEYKYNDLRGPG
SVLIADRLEPEVQECSRCGTKNPQMKDGRRLLRCIGVLPDGTDCDAVLPRNRNAARNAEKRLRK
HREAHNA (SEQ ID NO: 36)

>CasZg.2|033|3300009991.a:Ga0105042_100140_01533 Zr6.c9.inclusive
MNEVLPIPAVGEDAADTIMRGSKMRIYPSVRQAATMDLWRRRCIQLWNLLLELEQAAYSGENRR
TQIGWRSIWATVVEDSHAEAVRVAREGKKRKDGTFRKAPSGKEIPPLDPAMLAKIQRQMNGAVD
VDPKTGEVTPAQPRLFMWEHELQKIMARLKQAPRTHWIDDLPSHAAQSVVKDLIKALQAMLRER
KKRASGIGGRDTGFPKFKKNRYAAGSVYFANTQLRFEAKRGKAGDPDAVRGEFARVKLPNGVGW
MECRMPRHINAAHAYAQATLMGGRIWRQGENWYLSCQWKMPKPAPLPRAGRTAAIKIAAAIPIT
TVDNRGQTREYAMPPIDRERIAAHAAAGRAQSRALEARKRRAKKREAYAKKRHAKKLERGIAAK
PPGRARIKLSPGFYAAAAKLAKLEAEDANAREAWLHEITTQIVRNFDVIAVPRMEVAKLMKKPE
PPEEKEEQVKAPWQGKRRSLKAARVMMRRTAMALIQTTLKYKAVDLRGPQAYEEIAPLDVTAAA
CSGCGVLKPEWKMARAKGREIMRCQEPLPGGKTCNTVLTYTRNSARVIGRELAVRLAERQKA
(SEQ ID NO: 37)

FIG. 1N

>CasZh.1|rifcsp2_19_4_full_scaffold_168_120 transposase
id=102318404 partial=0 scaf=rifcsp2_19_4_full_scaffold_168
bin=RifCSP19_4_full_UNK sample=RIFCSP19_4_FULL proj=Rifle
Sediment CSP1
mTTQKTYNFCFYDQRFFELSKEAGEVYSRSLEEFWKIYDETGVWLSKFDLQKHMRNKLERKLLH
SDSFLGAMQQVHANLASWKQAKKVVPDACPPRKPKFLQAILFKKSQIKYKNGFLRLTLGTEKEF
LYLKWDINIPLPIYGSVTYSKTRGWKINLCLETEVEQKNLSENKYLSIDLGVKRVATIFDGENT
ITLSGKKFMGLMHYRNKLNGKTQSRLSHKKKGSNNYKKIQRAKRKTTDRLLNIQKEMLHKYSSF
IVNYAIRNDIGNIIIGDNSSTHDSPNMRGKTNQKISQNPEQKLKNYIKYKFESISGRVDIVPEP
YTSRKCPHCKNIKKSSPKGRTYKCKKCGFIFDRDGVGAINIYNENVSFGQIISPGRIRSLTEPI
GMKFHNEIYFKSYVAA  (SEQ ID NO: 38)

>CasZi.1|RBG_13_scaffold_1401_19
Tax=RBG_13_Planctomycetes_46_10_curated id=16386779 partial=0
scaf=RBG_13_scaffold_1401 bin=RBG_13_Planctomycetes_46_10
sample=2500-genomes proj=2500 Genomes
mSVRSFQARVECDKQTMEHLWRTHKVFNERLPEIIKILFKMKRGECGQNDKQKSLYKSISQSIL
EANAQNADYLLNSVSIKGWKPGTAKKYRNASFTWADDAAKLSSQGIHVYDKKQVLGDLPGMMSQ
MVCRQSVEAISGHIELTKKWEKEHNEWLKEKEKWESEDEHKKYLDLREKFEQFEQSIGGKITKR
RGRWHLYLKWLSDNPDFAAWRGNKAVINPLSEKAQIRINKAKPNKKNSVERDEFFKANPEMKAL
DNLHGYYERNFVRRRKTKKNPDGFDHKPTFTLPHPTIHPRWFVFNKPKTNPEGYRKLILPKKAG
DLGSLEMRLLTGEKNKGNYPDDWISVKFKADPRLSLIRPVKGRRVVRKGKEQGQTKETDSYEFF
DKHLKKWRPAKLSGVKLIFPDKTPKAAYLYFTCDIPDEPLTETAKKIQWLETGDVTKKGKKRKK
KVLPHGLVSCAVDLSMRRGTTGFATLCRYENGKIHILRSRNLWVGYKEGKGCHPYRWTEGPDLG
HIAKHKREIRILRSKRGKPVKGEESHIDLQKHIDYMGEDRFKKAARTIVNFALNTENAASKNGF
YPRADVLLLENLEGLIPDAEKERGINRALAGWNRRHLVERVIEMAKDAGFKRRVFEIPPYGTSQ
VCSKCGALGRRYSIIRENNRREIRFGYVEKLFACPNCGYCANADHNASVNLNRRFLIEDSFKSY
YDWKRLSEKKQKEEIETIESKLMDKLCAMHKISRGSISK  (SEQ ID NO: 39)

FIG. 1O

>CasZi.2|026|3300009652.a:Ga0123330_1010394_01528
Zr6.c2c1.inclusive
MHLWRTHCVFNQRLPALLKRLFAMRRGEVGGNEAQRQVYQRVAQFVLARDAKDSVDLLNAVSLR
KRSANSAFKKKATISCNGQAREVTGEEVFAEAVALASKGVFAYDKDDMRAGLPDSLFQPLTRDA
VACMRSHEELVATWKKEYREWRDRKSEWEAEPEHALYLNLRPKFEEGEAARGGRFRKRAERDHA
YLDWLEANPQLAAWRRKAPPAVVPIDEAGKRRIARAKAWKQASVRAEEFWKRNPELHALHKIHV
QYLREFVRPRRTRRNKRREGFKQRPTFTMPDPVRHPRWCLFNAPQTSPQGYRLLRLPQSRRTVG
SVELRLLTGPSDGAGFPDAWVNVRFKADPRLAQLRPVKVPRTVTRGKNKGAKVEADGFRYYDDQ
LLIERDAQVSGVKLLFRDIRMAPFADKPIEDRLLSATPYLVFAVEIKDEARTERAKAIRFDETS
ELTKSGKKRKTLPAGLVSVAVDLDTRGVGFLTRAVIGVPEIQQTHHGVRLLQSRYVAVGQVEAR
ASGEAEWSPGPDLAHIARHKREIRRLRQLRGKPVKGERSHVRLQAHIDRMGEDRFKKAARKIVN
EALRGSNPAAGDPYTRADVLLYESLETLLPDAERERGINRALLRWNRAKLIEHLKRMCDDAGIR
HFPVSPFGTSQVCSKCGALGRRYSLARENGRAVIRFGWVERLFACPNPECPGRRPDRPDRPFTC
NSDHNASVNLHRVFALGDQAVAAFRALAPRDSPARTLAVKRVEDTLRPQLMRVHKLADAGVDSP
F (SEQ ID NO: 40)

>CasZj.1|130|3300012532.a:Ga0137373_10000316_00700 c2c4
MATLVYRYGVRAHGSARQQDAVVSDPAMLEQLRLGHELRNALVGVQHRYEDGKRAVWSGFASVA
AADHRVTTGETAVAELEKQARAEHSADRTAATRQGTAESLKAARAAVKQARADRKAAMAAVAEQ
AKPKIQALGDDRDAEIKDLYRRFCQDGVLLPRCGRCAGDLRSDGDCTDCGAAHEPRKLYWATYN
AIREDHQTAVKLVEAKRKAGQPARLRFRRWTGDGTLTVQLQRMHGPACRCVTCAEKLTRRARKT
DPQAPAVAADPAYPPTDPPRDPALLASGQGKWRNVLQLGTWIPPGEWSAMSRAERRRVGRSHIG
WQLGGGRQLTLPVQLHRQMPADADVAMAQLTRVRVGGRHRMSVALTAKLPDPPQVQGLPPVALH
LGWRQRPDGSLRVATWACPQPLDLPPAVADVVVSHGGRWGEVIMPARWLADAEVPPRLLGRRDK
AMEPVLEALADWLEAHTEACTARMTPALVRRWRSQGRLAGLTNRWRGQPPTGSAEILTYLEAWR
IQDKLLWERESHLRRRLAARRDDAWRRVASWLARHAGVLVVDDADIAELRRRDDPADTDPTMPA
SAAQAARARAALAAPGRLRHLATITATRDGLVHTVASAGLTRLHRKCGHQAPDPRYAASAVV
TCPGCGNGYDQDYNAAMLMLDRQQQP (SEQ ID NO: 41)

>CasZk.1|012|3300005602.a:Ga0070762_10001740_01506
Zr6.c9.inclusive
MSRVELHRAYKFRLYPTPAQVAELAEWERQLRRLYNLAHSQRLAAMQRHVRPKSPGVLKSECLS
CGAVAVAEIGTDGKAKKTVKHAVGCSVLECRSCGGSPDAEGRTAHTAACSFVDYYRQGREMTQL
LEEDDQLARVVCSARQETLRDLEKAWQRWHKMPGFGKPHFKKRIDSCRIYFSTPKSWAVDLGYL
SFTGVASSVGRIKIRQDRVWPGDAKFSSCHVVRDVDEWYAVFPLTFTKEIEKPKGGAVGINRGA
VHAIADSTGRVVDSPKFYARSLGVIRHRARLLDRKVPFGRAVKPSPTKYHGLPKADIDAAAARV
NASPGRLVYEARARGSIAAAEAHLAALVLPAPRQTSQLPSEGRNRERARRFLALAHQRVRRQRE
WFLHNESAHYAQSYTKIAIEDWSTKEMTSSEPRDAEEMKRVTRARNRSILDVGWYELGRQIAYK
SEATGAEFAKVDPGLRETETHVPEAIVRERDVDVSGMLRGEAGISGTCSRCGGLLRASASGHAD
AECEVCLHVEVGDVNAAVNVLKRAMFPGAAPPSKEKAKVTIGIKGRKKKRAA
(SEQ ID NO: 42)

FIG. 1P

>CasZk.2|016|3300005921.a:Ga0070766_10011912_01491
Zr6.c9.inclusive
MSRVELHRAYKFRLYPTPVQVAELSEWERQLRRLYNLGHEQRLLTLTRHLRPKSPGVLKGECLS
CDSTQVQEVGADGRPKTTVRHAEQCPTLACRSCGALRDAEGRTAHTVACAFVDYYRQGREMTEL
LAADDQLARVVCSARQEVLRDLDKAWQRWRKMPGFGKPRFKRRTDSCRIYFSTPKAWKLEGGHL
SFTGAATTVGAIKMRQDRNWPASVQFSSCHVVRDVDEWYAVFPLTFVAEVARPKGGAVGINRGA
VHAIADSTGRVVDSPRYYARALGVIRHRARLFDRKVPSGHAVKPSPTKYRGLSAIEVDRVARAT
GFTPGRVVTEALNRGGVAYAECALAAIAVLGHGPERPLTSDGRNREKARKFLALAHQRVRRQRE
WFLHNESAHYARTYSKIAIEDWSTKEMTASEPQGEETRRVTRSRNRSILDVGWYELGRQLAYKT
EATGAEFAQVDPGLKETETNVPKAIADARDVDVSGMLRGEAGISGTCSKCGGLLRAPASGHADA
ECEICLNVEVGDVNAAVNVLKRAMFPGDAPPASGEKPKVSIGIKGRQKKKAA
    (SEQ ID NO: 43)

>CasZk.3|106|3300009698.a:Ga0116216_10000905_01565 c2c9
MEAIATGMSPERRVELGILPGSVELKRAYKFRLYPMKVQQAELSEWERQLRRLYNLAHEQRLAA
LLRYRDWDFQKGACPSCRVAVPGVHTAACDHVDYFRQAREMTQLLEVDAQLSRVICCARQEVLR
DLDKAWQRWRKKLGGRPRFKRRTDSCRIYLSTPKHWEIAGRYLRLSGLASSVGEIRIEQDRAFP
EGALLSSCSIVRDVDEWYACLPLTFTQPIERAPHRSVGLNRGVVHALADSDGRVVDSPKFFERA
LATVQKRSRDLARKVSGSRNAHKARIKLAKAHQRVRRQRAAFLHQESAYYSKGFDLVALEDMSV
RKMTATAGEAPEMGRGAQRDLNRGILDVGWYELARQIDYKRLAHGGELLRVDPGQTTPLACVTE
EQPARGISSACAVCGIPLARPASGNARMRCTACGSSQVGDVNAAENVLTRALSSAPSGPKSPKA
SIKIKGRQKRLGTPANRAGEASGGDPPVRGPVEGGTLAYVVEPVSESQSDT
    (SEQ ID NO: 44)

>CasZk.4|072|3300006028.a:Ga0070717_10000077_00263
Zr6.c9.inclusive
MTVRTYKYRAYPTPEQAEALTSWLRFASQLYNAALEHRKNAWGRHDAHGRGFRFWDGDAAPRKK
SDPPGRWVYRGGGGAHISKNDQGKLLTEFRREHAELLPPGMPALVQHEVLARLERSMAAFFQRA
TKGQKAGYPRWRSEHRYDSLTFGLTSPSKERFDPETGESLGRGKTVGAGTYHNGDLRLTGLGEL
RILEHRRIPMGAIPKSVIVRRSGKRWFVSIAMEMPSVEPAASGRPAVGLDMGVVTWGTAFTADT
SAAAALVADLRRMATDPSDCRRLEELEREAAQLSEVLAHCRARGLDPARPRRCPKELTKLYRRS
LHRLGELDRACARIRRRLQAAHDIAEPVPDEAGSAVLIEGSNAGMRHARRVARTQRRVARRTRA
GHAHSNRRKKAVQAYARAKERERSARGDHRHKVSRALVRQFEEISVEALDIKQLTVAPEHNPDP
QPDLPAHVQRRRNRGELDAAWGAFFAALDYKAADAGGRVARKPAPHTTQECARCGTLVPKPISL
RVHRCPACGYTAPRTVNSARNVLQRPLEEPGRAGPSGANGRGVPHAVA (SEQ ID NO: 45)

FIG. 1Q

>CasZ1.1|004|3300001256.a:JGI12210J13797_10004690_01983 c2c9
MNCRYRYRIYPTPGQRQSLARLFGCVRVVWNDALFLCRQSEKLPKNSELQKLCITQAKKTEARG
WLGQVSAIPLQQSVADLGVAFKNFFQSRSGKRKGKKVNPPRVKRRNNRQGARFTRGGFKVKTSK
VYLARIGDIKIKWSRPLPSEPSSVTVIKDCAGQYFLSFVVEVKPEIKPPKNPSIGIDLGLKTFA
SCSNGEKIDSPDYSRLYRKLKRCQRRLAKRQRGSKRRERMRVKVAKLNAQIRDKRKDFLHKLST
KVVNENQVIALEDLNVGGMLKNRKLSRAISQAGWYEFRSLCEGKAEKHNRDFRVISRWEPTSQV
CSECGYRWGKIDLSVRSIVCINCGVEHDRDDNASVNIEQAGLKVGVGHTHDSKRTGSACKTSNG

AVCVEPSTHREYVQLTLFDW    (SEQ ID NO: 46)

>CasZ1.2|014|3300005660.a:Ga0073904_10021651_01988 c2c9
MKSRWTFRCYPTPEQEQHLARTFGCVRFVWNWALRARTDAFRAGERIGYPATDKALTLLKQQPE
TVWLNEVSSVCLQQALRDLQVAFSNFFDKRAAHPSFKRKEARQSANYTERGFSFDHERRILKLA
KIGAIKVKWSRKAIPHPSSIRLIRTASGKYFVSLVVETQPAPMPETGESVGVDFGVARLATLSN
GERISNPKHGAKWQRRLAFYQKRLARATKGSKRRMRIKRHVARIHEKIGNSRSDTLHKLSTDLV
TRFDLICVEDLNLRGMVKNHSLARSLHDASIGSAIRMIEEKAERYGKNVVKIDRWFPSSKTCSD
CGHIVEQLPLNVREWTCPECGTTHDRDANAAANILAVGQTVSAHGGTVRRSRAKASERKSQRSA

NRQGVNRA    (SEQ ID NO: 47)

FIG. 2

| | # | Cas1 | Organism | Locus example |
|---|---|---|---|---|
| Za | 5 | I-B | DPANN | Cas1–2–4–CasZa (508aa) –▮–◆– |
| Zb | 7 | I-B | DPANN | Cas1–2–4–CasZb (538aa) –▮◆– |
| Zc | 5 | I-B | DPANN | CasZc (614aa) –▮–◆–Cas1–2–4– |
| Zd | 1 | I-B | DPANN | Cas1–2–4–CasZd (518aa) –▮◆– |
| Ze | 4 | III-D* | CPR | CasZe (650aa) –Cas1–◆–▮– |
| Zf | 3 | III-D | CPR | CasZf (415aa) –Cas1–▮–◆– |
| Zg | 1 | I-E | Phage? | CasZg (712aa) –Cas1–2–▮–◆– |
| Zh | 1 | II-C | MGE | CasZh (401aa) –Tnsp–Cas1–2–◆–▮– |
| Zi | 1 | I-U | Plancto | Cas4+1–2–CasZi (744aa) –▮–◆– |

FIG. 7A

>Cas14a.1|gwa1_scaffold_1795_curated|25635..27224|revcom
PEEKTSKLKPNSINLAANYDANEKFNCKECKFHPFKNKKRYEFNFYNNLHGCKSCTKST
NNPAVKRIEIGYQKLKFEIKNQMEAYPWFGRLRINFYSDEKRKMSELNEMQVTGVKNKI
FFDAIECAWREILKKRFRESKETLITIPKLKNKAGHGARKHRNKKLLIRRRAFMKKNFH
FLDNDSISYRSFANNIACVLPSKVGVDIGGIISPDVGKDIKPVDISLNLMWASKEGIKS
GRKVEIYSTQYDGNMVKKIEAETGEDKSWGKNRKRRQTSLLLSIPKPSKQVQEFDFKEW
PRYKDIEKKVQWRGFPIKIIFDSNHNSIEFGTYQGGKQKVLPIPFNDSKTTPLGSKMNK
LEKLRFNSKIKSRLGSAIAANKFLEAARTYCVDSLYHEVSSANAIGKGKIFIEYYLEIL
SQNYIEAAQKQLQRFIESIEQWFVADPFQGRLKQYFKDDLKRAKCFLCANREVQTTCYA
AVKLHKSCAEKVKDKNKELAIKERNNKEDAVIKEVEASNYPRVIRLKLTKTITNKAM
(SEQ ID NO:306)

>Cas14a.2|gwa2_scaffold_18027_curated|7105..8628
ELIVNENKDPLNIGKTAKAVFKEIDPTSINRAANYDASIELACKECKFKPFNNTKRHDF
SFYSNWHRCSPNSCLQSTYRAKIRKTEIGYEKLKNEILNQMQYYPWFGRLYQNFFNDQR
DKMTSLDEIQVTGVQNKIFFNTVEKAWREIIKKRFRDNKETMRTIPDLKNKSGHGSRKL
SNKSLLRRRFAFAQKSFKLVDNSDVSYRAFSNNVACVLPSKIGVDIGGIINKDLKREYI
PQEITFNVFWKQHDGLKKGRNIEIHSVQYKGEIVKRIEADTGEDKAWGKNRQRRFTSLI
LKITPKQGGKKIWKFPEKKNASDYEYFPIPIEFILDNGDASIKFGGEEGEVGKQKHLLI
PFNDSKATPLSSKQMLLETSRFNAEVKSTIGLALYANYFVSYARNYVIKSTYHKNSKKG
QIVTEIYLESISQNFVRAIQRQLQSLMLNLKDWGFMQTHKKELKKYFGSDLEGSKGGQK
RREKEEKIEKEIEASYLPRLIRLSLTKSVTKAEEM (SEQ ID NO:305)

>Cas14a.3|rifcsphigho2_02_scaffold_2167_curated|30296..31798|revcom
KEPLNIGKTAKAVFKEIDPTSLNRAANYDASIELNCKECKFKPFKNVKRYEFNFYNNWY
RCNPNSCLQSTYKAQVRKVEIGYEKLKNEILTQMQYYPWFGRLYQNFFHDERDKMTSLD
EIQVIGVQNKVFFNTVEKAWREIIKKRFKDNKETMETIPELKHAAGHGKRKLSNKSLLR
RRFAFVQKSFKFVDNSDVSYRSFSNNIACVLPSRIGVDLGGVISRNPKREYIPQEISFN
AFWKQHEGLKKGRNIEIQSVQYKGETVKRIEADTGEDKAWGKNRQRRFTSLILKLVPKQ
GGKKVWKYPEKRNEGNYEYFPIPIEFILDSGETSIRFGGDEGEAGKQKHLVIPFNDSKA
TPLASQQTLLENSRFNAEVKSCIGLAIYANYFYGYARNYVISSIYHKNSKNGQAITAIY
LESIAHNYVKAIERQLQNLLLNLRDFSFMESHKKELKKYFGDLEGTGGAQKRREKEEK
IEKEIEQSYLPRLIRLSLTKMVTKQVEM (SEQ ID NO:304)

FIG. 7B

>Cas14a.4|CG10_big_fil_rev_8_21_14_0.10_scaffold_20906_cura
ted|649..2829
SESENKIIEQYYAFLYSFRDKYEKPEFKNRGDIKRKLQNKWEDFLKEQNLKNDKKLSNY
IFSNRNFRRSYDREEENEEGIDEKKSKPKRINCFEKEKNLKDQYDKDAINASANKDGAQ
KWGCFECIFFPMYKIESGDPNKRIIINKTRFKLFDFYLNLKGCKSCLRSTYHPYRSNVY
IESNYDKLKREIGNFLQQKNIFQRMRKAKVSEGKYLTNLDEYRLSCVAMHFKNRWLFFD
SIQKVLRETIKQRLKQMRESYDEQAKTKRSKGHGRAKYEDQVRMIRRRAYSAQAHKLLD
NGYITLFDYDDKEINKVCLTAINQEGFDIGGYLNSDIDNVMPPIEISFHLKWKYNEPIL
NIESPFSKAKISDYLRKIREDLNLERGKEGKARSKKNVRRKVLASKGEDGYKKIFTDFF
SKWKEELEGNAMERVLSQSSGDIQWSKKKRIHYTTLVLNINLLDKKGVGNLKYYEIAEK
TKILSFDKNENKFWPITIQVLLDGYEIGTEYDEIKQLNEKTSKQFTIYDPNTKIIKIPF
TDSKAVPLGMLGINIATLKTVKKTERDIKVSKIFKGGLNSKIVSKIGKGIYAGYFPTVD
KEILEEVEEDTLDNEFSSKSQRNIFLKSIIKNYDKMLKEQLFDFYSFLVRNDLGVRFLT
DRELQNIEDESFNLEKRFFETDRDRIARWFDNTNTDDGKEKFKKLANEIVDSYKPRLIR
LPVVRVIKRIQPVKQREM (SEQ ID NO:178)

>Cas14a.5|rifcsplowo2_01_scaffold_34461_curated|4968..6521
KYSTRDFSELNEIQVTACKQDEFFKVIQNAWREIIKKRFLENRENFIEKKIFKNKKGRG
KRQESDKTIQRNRASVMKNFQLIENEKIILRAPSGHVACVFPVKVGLDIGGFKTDDLEK
NIFPPRTITINVFWKNRDRQRKGRKLEVWGIKARTKLIEKVHKWDKLEEVKKKRLKSLE
QKQEKSLDNWSEVNNDSFYKVQIDELQEKIDKSLKGRTMNKILDNKAKESKEAEGLYIE
WEKDFEGEMLRRIEASTGGEEKWGKRRQRRHTSLLLDIKNNSRGSKEIINFYSYAKQGK
KEKKIEFFPFPLTITLDAEEESPLNIKSIPIEDKNATSKYFSIPFTETRATPLSILGDR
VQKFKTKNISGAIKRNLGSSISSCKIVQNAETSAKSILSLPNVKEDNNMEIFINTMSKN
YFRAMMKQMESFIFEMEPKTLIDPYKEKAIKWFEVAASSRAKRKLKKLSKADIKKSELL
LSNTEEFEKEKQEKLEALEKEIEEFYLPRIVRLQLTKTILETPVM (SEQ ID
NO:179)

>Cas14a.6|3300012359.a|Ga0137385_10000156|41289..42734
KKLQLLGHKILLKEYDPNAVNAAANFETSTAELCGQCKMKPFKNKRRFQYTFGKNYHGC
LSCIQNVYYAKKRIVQIAKEELKHQLTDSIASIPYKYTSLFSNTNSIDELYILKQERAA
FFSNTNSIDELYITGIENNIAFKVISAIWDEIIKKRRQRYAESLTDTGTVKANRGHGGT
AYKSNTRQEKIRALQKQTLHMVTNPYISLARYKNNYIVATLPRTIGMHIGAIKDRDPQK
KLSDYAINFNVFWSDDRQLIELSTVQYTGDMVRKIEAETGENNKWGENMKRTKTSLLLE
ILTKKTTDELTFKDWAFSTKKEIDSVTKKTYQGFPIGIIFEGNESSVKFGSQNYFPLPF
DAKITPPTAEGFRLDWLRKGSFSSQMKTSYGLAIYSNKVTNAIPAYVIKNMFYKIARAE
NGKQIKAKFLKKYLDIAGNNYVPFIIMQHYRVLDTFEEMPISQPKVIRLSLTKTQHIII
KKDKTDSKM (SEQ ID NO:180)

FIG. 7C

>Cas14b.1|rifcsplowo2_01_scaffold_239_curated|54653..56257
NTSNLINLGKKAINISANYDANLEVGCKNCKFLSSNGNFPRQTNVKEGCHSCEKSTYEP
SIYLVKIGERKAKYDVLDSLKKFTFQSLKYQSKKSMKSRNKKPKELKEFVIFANKNKAF
DVIQKSYNHLILQIKKEINRMNSKKRKKNHKRRLFRDREKQLNKLRLIESSNLFLPREN
KGNNHVFTYVAIHSVGRDIGVIGSYDEKLNFETELTYQLYFNDDKRLLYAYKPKQNKII
KIKEKLWNLRKEKEPLDLEYEKPLNKSITFSIKNDNLFKVSKDLMLRRAKFNIQGKEKL
SKEERKINRDLIKIKGLVNSMSYGRFDELKKEKNIWSPHIYREVRQKEIKPCLIKNGDR
IEIFEQLKKKMERLRRFREKRQKKISKDLIFAERIAYNFHTKSIKNTSNKINIDQEAKR
GKASYMRKRIGYETFKNKYCEQCLSKGNVYRNVQKGCSCFENPFDWIKKGDENLLPKKN
EDLRVKGAFRDEALEKQIVKIAFNIAKGYEDFYDNLGESTEKDLKLKFKVGTTINEQES
LKL (SEQ ID NO:181)

>Cas14b.2|rifcsplowo2_01_scaffold_282_curated|77370..78983
TSNPIKLGKKAINISANYDSNLQIGCKNCKFLSYNGNFPRQTNVKEGCHSCEKSTYEPP
VYTVRIGERRSKYDVLDSLKKFIFLSLKYRQSKKMKTRSKGIRGLEEFVISANLKKAMD
VIQKSYRHLILNIKNEIVRMNGKKRNKNHKRLLFRDREKQLNKLRLIEGSSFFKPPTVK
GDNSIFTCVAIHNIGRDIGIAGDYFDKLEPKIELTYQLYYEYNPKKESEINKRLLYAYK
PKQNKIIEIKEKLWNLRKEKSPLDLEYEKPLTKSITFLVKRDGVFRISKDLMLRKAKFI
IQGKEKLSKEERKINRDLIKIKSNIISLTYGRFDELKKDKTIWSPHIFRDVKQGKITPC
IERKGDRMDIFQQLRKKSERLRENRKKRQKKISKDLIFAERIAYNFHTKSIKNTSNLIN
IKHEAKRGKASYMRKRIGNETFRIKYCEQCFPKNNVYKNVQKGCSCFEDPFEYIKKGNE
DLIPNKNQDLKAKGAFRDDALEKQIIKVAFNIAKGYEDFYENLKKTTEKDIRLKFKVGT
IISEEM (SEQ ID NO:182)

>Cas14b.3|rifcsphigho2_01_scaffold_36781_curated|2592..4217
NNSINLSKKAINISANYDANLQVRCKNCKFLSSNGNFPRQTDVKEGCHSCEKSTYEPPV
YDVKIGEIKAKYEVLDSLKKFTFQSLKYQLSKSMKFRSKKIKELKEFVIFAKESKALNV
INRSYKHLILNIKNDINRMNSKKRIKNHKGRLFLDRQKQLSKLKLIEGSSFFVPAKNVG
NKSVFTCVAIHSIGRDIGIAGLYDSFTKPVNEITYQIFFSGERRLLYAYKPKQLKILSI
KENLWSLKNEKKPLDLLYEKPLGKNLNFNVKGGDLFRVSKDLMIRNAKFNVHGRQRLSD
EERLINRNFIKIKGEVVSLSYGRFEELKKDRKLWSPHIFKDVRQNKIKPCLVMGQQRID
IFEQLKRKLELLKKIRKSRQKKLSKDLIFGERIAYNFHTKSIKNTSNKINIDSDAKRGR
ASYMRKRIGNETFKLKYCDVCFPKANVYRRVQNGCSCSENPYNYIKKGDKDLLPKKDEG
LAIKGAFRDEKLNKQIIKVAFNIAKGYEDFYDDLKKRTEKDVDLKFKIGTTVLDQKPME
IFDGIVITWL (SEQ ID NO:183)

FIG. 7D

>Cas14b.4|cg1_0.2_scaffold_785_c_curated|32521..34155
LLTTVVETNNLAKKAINVAANFDANIDRQYYRCTPNLCRFIAQSPRETKEKDAGCSSCT
QSTYDPKVYVIKIGKLLAKYEILKSLKRFLFMNRYFKQKKTERAQQKQKIGTELNEMSI
FAKATNAMEVIKRATKHCTYDIIPETKSLQMLKRRRHRVKVRSLLKILKERRMKIKKIP
NTFIEIPKQAKKNKSDYYVAAALKSCGIDVGLCGAYEKNAEVEAEYTYQLYYEYKGNSS
TKRILYCYNNPQKNIREFWEAFYIQGSKSHVNTPGTIRLKMEKFLSPITIESEALDFRV
WNSDLKIRNGQYGFIKKRSLGKEAREIKKGMGDIKRKIGNLTYGKSPSELKSIHVYRTE
RENPKKPRAARKKEDNFMEIFEMQRKKDYEVNKKRRKEATDAAKIMDFAEEPIRHYHTN
NLKAVRRIDMNEQVERKKTSVFLKRIMQNGYRGNYCRKCIKAPEGSNRDENVLEKNEGC
LDCIGSEFIWKKSSKEKKGLWHTNRLLRRIRLQCFTTAKAYENFYNDLFEKKESSLDII
KLKVSITTKSM (SEQ ID NO:184)

>Cas14b.5|rifcsphigho2_02_scaffold_55589_curated|1904..3598
ASTMNLAKQAINFAANYDSNLEIGCKGCKFMSTWSKKSNPKFYPRQNNQANKCHSCTYS
TGEPEVPIIEIGERAAKYKIFTALKKFVFMSVAYKERRRQRFKSKKPKELKELAICSNR
EKAMEVIQKSVVHCYGDVKQEIPRIRKIKVLKNHKGRLFYKQKRSKIKIAKLEKGSFFK
TFIPKVHNNGCHSCHEASLNKPILVTTALNTIGADIGLINDYSTIAPTETDISWQVYYE
FIPNGDSEAVKKRLLYFYKPKGALIKSIRDKYFKKGHENAVNTGFFKYQGKIVKGPIKF
VNNELDFARKPDLKSMKIKRAGFAIPSAKRLSKEDREINRESIKIKNKIYSLSYGRKKT
LSDKDIIKHLYRPVRQKGVKPLEYRKAPDGFLEFFYSLKRKERRLRKQKEKRQKDMSEI
IDAADEFAWHRHTGSIKKTTNHINFKSEVKRGKVPIMKKRIANDSFNTRHCGKCVKQGN
AINKYYIEKQKNCFDCNSIEFKWEKAALEKKGAFKLNKRLQYIVKACFNVAKAYESFYE
DFRKGEEESLDLKFKIGTTTTLKQYPQNKARAM (SEQ ID NO:185)

>Cas14b.6|CG03_land_8_20_14_0.80_scaffold_2214_curated|6634
..8466|revcom
HSHNLMLTKLGKQAINFAANYDANLEIGCKNCKFLSYSPKQANPKKYPRQTDVHEDGNI
ACHSCMQSTKEPPVYIVPIGERKSKYEILTSLNKFTFLALKYKEKKRQAFRAKKPKELQ
ELAIAFNKEKAIKVIDKSIQHLILNIKPEIARIQRQKRLKNRKGKLLYLHKRYAIKMGL
IKNGKYFKVGSPKKDGKKLLVLCALNTIGRDIGIIGNIEENNRSETEITYQLYFDCLDA
NPNELRIKEIEYNRLKSYERKIKRLVYAYKPKQTKILEIRSKFFSKGHENKVNTGSFNF
ENPLNKSISIKVKNSAFDFKIGAPFIMLRNGKFHIPTKKRLSKEEREINRTLSKIKGRV
FRLTYGRNISEQGSKSLHIYRKERQHPKLSLEIRKQPDSFIDEFEKLRLKQNFISKLKK
QRQKKLADLLQFADRIAYNYHTSSLEKTSNFINYKPEVKRGRTSYIKKRIGNEGFEKLY
CETCIKSNDKENAYAVEKEELCFVCKAKPFTWKKTNKDLGIFKYPSRIKDFIRAAFTV
AKSYNDFYENLKKKDLKNEIFLKFKIGLILSHEKKNHISIAKSVAEDERISGKSIKNIL
NKSIKLEKNCYSCFFHKEDM (SEQ ID NO:186)

FIG. 7E

>Cas14b.7|3300013125.a|Ga0172369_10000737|994..2652|revcom
SLERVIDKRNLAKKAINIAANFDANINKGFYRCETNQCMFIAQKPRKTNNTGCSSCLQS
TYDPVIYVVKVGEMLAKYEILKSLKRFVFMNRSFKQKKTEKAKQKERIGGELNEMSIFA
NAALAMGVIKRAIRHCVDIRPEINRLSELKKTHRVAAKSLVKIVQRKTKWKGIPNS
FIQIPQKARNKDADFYVASALKSGGIDIGLCGTYDKKPHADPRWTYQLYFDTEDESEKR
LLYCYNDPQAKIRDFWKTFYERGNPSMVNSPGTIEFRMEGFFEKMTPISIESKDFDFRV
WNKDLLIRRGLYEIKKRKNLNRKAREIKKAMGSVKRVLANMTYGKSPTDKKSIPVYRVE
REKPKKPRAVRKEENELADKLENYRREDFLIRNRRKREATEIAKIIDAAEPPIRHYHTN
HLRAVKRIDLSKPVARKNTSVFLKRIMQNGYRGNYCKKCIKGNIDPNKDECRLEDIKKC
ICCEGTQNIWAKKEKLYTGRINVLNKRIKQMKLECFNVAKAYENFYDNLAALKEGDLKV
LKLKVSIPALNPEASDPEEDM (SEQ ID NO:187)

>Cas14b.8|3300013125.a|Ga0172369_10010464|885..2489|revcom
NASINLGKRAINLSANYDSNLVIGCKNCKFLSFNGNFPRQTNVREGCHSCDKSTYAPEV
YIVKIGERKAKYDVLDSLKKFTFQSLKYQIKKSMRERSKKPKELLEFVIFANKDKAFNV
IQKSYEHLILNIKQEINRMNGKKRIKNHKKRLFKDREKQLNKLRLIGSSSLFFPRENKG
DKDLFTYVAIHSVGRDIGVAGSYESHIEPISDLTYQLFINNEKRLLYAYKPKQNKIIEL
KENLWNLKKEKKPLDLEFTKPLEKSITFSVKNDKLFKVSKDLMLRQAKFNIQGKEKLSK
EERQINRDFSKIKSNVISLSYGRFEELKKEKNIWSPHIYREVKQKEIKPCIVRKGDRIE
LFEQLKRKMDKLKKFRKERQKKISKDLNFAERIAYNFHTKSIKNTSNKINIDQEAKRGK
ASYMRKRIGNESFRKKYCEQCFSVGNVYHNVQNGCSCFDNPIELIKKGDEGLIPKGKED
RKYKGALRDDNLQMQIIRVAFNIAKGYEDFYNNLKEKTEKDLKLKFKIGTTISTQESNN
KEM (SEQ ID NO:188)

>Cas14b.9|3300013127.a|Ga0172365_10004421|633..2366|revcom
SNLIKLGKQAINFAANYDANLEVGCKNCKFLSSTNKYPRQTNVHLDNKMACRSCNQSTM
EPAIYIVRIGEKKAKYDIYNSLTKFNFQSLKYAKRSQRFKPKQPKELQELSIAVRKEK
ALDIIQKSIDHLIQDIRPEIPRIKQQKRYKNHVGKLFYLQKRRKNKLNLIGKGSFFKVF
SPKEKKNELLVICALTNIGRDIGLIGNYNTIINPLFEVTYQLYYDYIPKKNNKNVQRRL
LYAYKSKNEKILKLKEAFFKRGHENAVNLGSFSYEKPLEKSLTLKIKNDKDDFQVSPSL
RIRTGRFFVPSKRNLSRQEREINRRLVKIKSKIKNMTYGKFETARDKQSVHIFRLERQK
EKLPLQFRKDEKEFMEEFQKLKRRTNSLKKLRKSRQKKLADLLQLSEKVVYNNHTGTLK
KTSNFLNFSSSVKRGKTAYIKELLGQEGFETLYCSNCINKGQKTRYNIETKEKCFSCKD
VPFVWKKKSTDKDRKGAFLFPAKLKDVIKATFTVAKAYEDFYDNLKSIDEKKPYIKFKI
GLILAHVRHEHKARAKEEAGQKNIYNKPIKIDKNCKECFFFKEEAM (SEQ ID NO:189
)

FIG. 7F

>Cas14b.10|CG08_land_8_20_14_0.20_scaffold_1609_curated|613
4..7975
NTTRKKFRKRTGFPQSDNIKLAYCSAIVRAANLDADIQKKHNQCNPNLCVGIKSNEQSR
KYEHSDRQALLCYACNQSTGAPKVDYIQIGEIGAKYKILQMVNAYDFLSLAYNLTKLRN
GKSRGHQRMSQLDEVVIVADYEKATEVIKRSINHLLDDIRGQLSKLKKRTQNEHITEHK
QSKIRRKLRKLSRLLKRRRWKWGTIPNPYLKNVVFTKKDPELVTVALLHKLGRDIGLVN
RSKRRSKQKLLPKVGFQLYYKWESPSLNNIKKSKAKKLPKRLLIPYKNVKLFDNKQKLE
NAIKSLLESYQKTIKVEFDQFFQNRTEEIIAEEQQTLERGLLKQLEKKKNEFASQKKAL
KEEKKKIKEPRKAKLLMEESRSLGFLMANVSYALFNTTIEDLYKKSNVVSGCIPQEPVV
VFPADIQNKGSLAKILFAPKDGFRIKFSGQHLTIRTAKFKIRGKEIKILTKTKREILKN
IEKLRRVWYREQHYKLKLFGKEVSAKPRFLDKRKTSIERRDPNKLADQTDDRQAELRNK
EYELRHKQHKMAERLDNIDTNAQNLQTLSFWVGEADKPPKLDEKDARGFGVRTCISAWK
WFMEDLLKKQEEDPLLKLKLSIM (SEQ ID NO:190)

>Cas14b.11|CG_4_10_14_0.8_um_filter_scaffold_20762_curated|
1372..3219
PKKPKFQKRTGFPQPDNLRKEYCLAIVRAANLDADFEKKCTKCEGIKTNKKGNIVKGRT
YNSADKDNLLCYACNISTGAPAVDYVFVGALEAKYKILQMVKAYDFHSLAYNLAKLWKG
RGRGHQRMGGLNEVVIVSNNEKALDVIEKSLNHFHDEIRGELSRLKAKFQNEHLHVHKE
SKLRRKLRKISRLLKRRRWKWDVIPNSYLRNFTFTKTRPDFISVALLHRVGRDIGLVTK
TKIPKPTDLLPQFGFQIYYTWDEPKLNKLKKSRLRSEPKRLLVPYKKIELYKNKSVLEE
AIRHLAEVYTEDLTICFKDFFETQKRKFVSKEKESLKRELLKELTKLKKDFSERKTALK
RDRKEIKEPKKAKLLMEESRSLGFLAANTSYALFNLIAADLYTKSKKACSTKLPRQLST
ILPLEIKEHKSTTSLAIKPEEGFKIRFSNTHLSIRTPKFKMKGADIKALTKRKREILKN
ATKLEKSWYGLKHYKLKLYGKEVAAKPRFLDKRNPSIDRRDPKELMEQIENRRNEVKDL
EYEIRKGQHQMAKRLDNVDTNAQNLQTKSFWVGEADKPPELDSMEAKKLGLRTCISAWK
WFMKDLVLLQEKSPNLKLKLSLTEM (SEQ ID NO:191)

>Cas14b.12|CG22_combo_CG10-
13_8_21_14_all_scaffold_2003_curated|553..2880|revcom
KFSKRQEGFLIPDNIDLYKCLAIVRSANLDADVQGHKSCYGVKKNGTYRVKQNGKKGVK
EKGRKYVFDLIAFKGNIEKIPHEAIEEKDQGRVIVLGKFNYKLILNIEKNHNDRASLEI
KNKIKKLVQISSLETGEFLSDLLSGKIGIDEVYGIIEPDVFSGKELVCKACQQSTYAPL
VEYMPVGELDAKYKILSAIKGYDFLSLAYNLSRNRANKKRGHQKLGGGELSEVVISANY
DKALNVIKRSINHYHVEIKPEISKLKKKMQNEPLKVMKQARIRRELHQLSRKVKRLKWK
WGMIPNPELQNIIFEKKEKDFVSYALLHTLGRDIGLFKDTSMLQVPNISDYGFQIYYSW
EDPKLNSIKKIKDLPKRLLIPYKRLDFYIDTILVAKVIKNLIELYRKSYVYETFGEEYG
YAKKAEDILFDWDSINLSEGIEQKIQKIKDEFSDLLYEARESKRQNFVESFENILGLYD
KNFASDRNSYQEKIQSMIIKKQQENIEQKLKREFKEVIERGFEGMDQNKKYYKVLSPNI
KGGLLYTDTNNLGFFRSHLAFMLLSKISDDLYRKNNLVSKGGNKGILDQTPETMLTLEF
GKSNLPNISIKRKFFNIKYNSSWIGIRKPKFSIKGAVIREITKKVRDEQRLIKSLEGVW
HKSTHFKRWGKPRFNLPRHPDREKNNDDNLMESITSRREQIQLLLREKQKQQEKMAGRL
DKIDKEIQNLQTANFQIKQIDKKPALTEKSEGKQSVRNALSAWKWFMEDLIKYQKRTPI
LQLKLAKM (SEQ ID NO: 192)

FIG. 7G

\>Cas14b.13|rifcsphigho2_01_scaffold_82367_curated|1523..3856|revcom
KFSKRQEGFVIPENIGLYKCLAIVRSANLDADVQGHVSCYGVKKNGTYVLKQNGKKSIR
EKGRKYASDLVAFKGDIEKIPFEVIEEKKKEQSIVLGKFNYKLVLDVMKGEKDRASLTM
KNKSKKLVQVSSLGTDEFLLTLLNEKFGIEEIYGIIEPEVFSGKKLVCKACQQSTYAPL
VEYMPVGELDSKYKILSAIKGYDFLSLAYNLARHRSNKKRGHQKLGGGELSEVVISANN
AKALNVIKRSLNHYYSEIKPEISKLRKKMQNEPLKVGKQARMRRELHQLSRKVKRLKWK
WGKIPNLELQNITFKESDRDFISYALLHTLGRDIGMFNKTEIKMPSNILGYGFQIYYDW
EEPKLNTIKKSKNTPKRILIPYKKLDFYNDSILVARAIKELVGLFQESYEWEIFGNEYN
YAKEAEVELIKLDEESINGNVEKKLQRIKENFSNLLEKAREKKRQNFIESFESIARLYD
ESFTADRNEYQREIQSFIIEKQKQSIEKKLKNEFKKIVEKKFNEQEQGKKHYRVLNPTI
INEFLPKDKNNLGFLRSKIAFILLSKISDDLYKKSNAVSKGGEKGIIKQQPETILDLEF
SKSKLPSINIKKKLFNIKYTSSWLGIRKPKFNIKGAKIREITRRVRDVQRTLKSAESSW
YASTHFRRWGFPRFNQPRHPDKEKKSDDRLIESITLLREQIQILLREKQKGQKEMAGRL
DDVDKKIQNLQTANFQIKQTGDKPALTEKSAGKQSFRNALSAWKWFMENLLKYQNKTPD
LKLKIARTVM (SEQ ID NO: 193)

\>Cas14b.14|gwc1_scaffold_8732_curated|2705..4537
KWIEPNNIDFNKCLAITRSANLDADVQGHKMCYGIKTNGTYKAIGKINKKHNTGIIEKR
RTYVYDLIVTKEKNEKIVKKTDFMAIDEEIEFDEKKEKLLKKYIKAEVLGTGELIRKDL
NDGEKFDDLCSIEEPQAFRRSELVCKACNQSTYASDIRYIPIGEIEAKYKILKAIKGYD
FLSLKYNLGRLRDSKKRGHQKMGQGELKEFVICANKEKALDVIKRSLNHYLNEVKDEIS
RLNKKMQNEPLKVNDQARWRRELNQISRRLKRLKWKWGEIPNPELKNLIFKSSRPEFVS
YALIHTLGRDIGLINETELKPNNIQEYGFQIYYKWEDPELNHIKKVKNIPKRFIIPYKN
LDLFGKYTILSRAIEGILKLYSSSFQYKSFKDPNLFAKEGEKKITNEDFELGYDEKIKK
IKDDFKSYKKALLEKKKNTLEDSLNSILSVYEQSLLTEQINNVKKWKEGLLKSKESIHK
QKKIENIEDIISRIEELKNVEGWIRTKERDIVNKEETNLKREIKKELKDSYYEEVRKDF
SDLKKGEESEKKPFREEPKPIVIKDYIKFDVLPGENSALGFFLSHLSFNLFDSIQYELF
EKSRLSSSKHPQIPETILDL (SEQ ID NO: 194)

\>Cas14b.15|3300010293.a|Ga0116204_1008574|2134..4032
FRKFVKRSGAPQPDNLNKYKCIAIVRAANLDADIMSNESSNCVMCKGIKMNKRKTAKGA
AKTTELGRVYAGQSGNLLCTACTKSTMGPLVDYVPIGRIRAKYTILRAVKEYDFLSLAY
NLARTRVSKKGGRQKMHSLSELVIAAEYEIAWNIIKSSVIHYHQETKEEISGLRKKLQA
EHIHKNKEARIRREMHQISRRIKRLKWKWHMIPNSELHNFLFKQQDPSFVAVALLHTLG
RDIGMINKPKGSAKREFIPEYGFQIYYKWMNPKLNDINKQKYRKMPKRSLIPYKNLNVF
GDRELIENAMHKLLKLYDENLEVKGSKFFKTRVVAISSKESEKLKRDLLWKGELAKIKK
DFNADKNKMQELFKEVKEPKKANALMKQSRNMGFLLQNISYGALGLLANRMYEASAKQS
KGDATKQPSIVIPLEMEFGNAFPKLLLRSGKFAMNVSSPWLTIRKPKFVIKGNKIKNIT
KLMKDEKAKLKRLETSYHRATHFRPTLRGSIDWDSPYFSSPKQPNTHRRSPDRLSADIT
EYRGRLKSVEAELREGQRAMAKKLDSVDMTASNLQTSNFQLEKGEDPRLTEIDEKGRSI
RNCISSWKKFMEDLMKAQEANPVIKIKIALKDESSVLSEDSM (SEQ ID NO: 195)

FIG. 7H

>Cas14b.16|3300005573.a|Ga0078972_1001015a|33750..35627
KFHPENLNKSYCLAIVRAANLDADIQGHINCIGIKSNKSDRNYENKLESLQNVELLCKA
CTKSTYKPNINSVPVGEKKAKYSILSEIKKYDFNSLVYNLKKYRKGKSRGHQKLNELRE
LVITSEYKKALDVINKSVNHYLVNIKNKMSKLKKILQNEHIHVGTLARIRRERNRISRK
LDHYRKKWKFVPNKILKNYVFKNQSPDFVSVALLHKLGRDIGLITKTAILQKSFPEYSL
QLYYKYDTPKLNYLKKSKFKSLPKRILISYKYPKFDINSNYIEESIDKLLKLYEESPIY
KNNSKIIEFFKKSEDNLIKSENDSLRGIMKEFEKVTKNFSSKKKKLKEELKLKNEDKN
SKMLAKVSRPIGFLKAYLSYMLFNIISNRIFEFSRKSSGRIPQLPSCIINLGNQFENFK
NELQDSNIGSKKNYKYFCNLLLKSSGFNISYEEEHLSIKTPNFFINGRKLKEITSEKKK
IRKENEQLIKQWKKLTFFKPSNLNGKKTSDKIRFKSPNNPDIERKSEDNIVENIAKVKY
KLEDLLSEQRKEFNKLAKKHDGVDVEAQCLQTKSFWIDSNSPIKKSLEKKNEKVSVKKK
MKAIRSCISAWKWFMADLIEAQKETPMIKLKLALM (SEQ ID NO: 196)

>Cas14c.1|CG10_big_fil_rev_8_21_14_0.10_scaffold_4477_curat
ed|19327..20880|revcom
TTLVPSHLAGIEVMDETTSRNEDMIQKETSRSNEDENYLGVKNKCGINVHKSGRGSSKH
EPNMPPEKSGEGQMPKQDSTEMQQRFDESVTGETQVSAGATASIKTDARANSGPRVGTA
RALIVKASNLDRDIKLGCKPCEYIRSELPMGKKNGCNHCEKSSDIASVPKVESGFRKAK
YELVRRFESFAADSISRHLGKEQARTRGKRGKKDKKEQMGKVNLDEIAILKNESLIEYT
ENQILDARSNRIKEWLRSLRLRLRTRNKGLKKSKSIRRQLITLRRDYRKWIKPNPYRPD
EDPNENSLRLHTKLGVDIGVQGGDNKRMNSDDYETSFSITWRDTATRKICFTKPKGLLP
RHMKFKLRGYPELILYNEELRIQDSQKFPLVDWERIPIFKLRGVSLGKKKVKALNRITE
APRLVVAKRIQVNIESKKKKVLTRYVYNDKSINGRLVKAEDSNKDPLLEFKKQAEEINS
DAKYYENQEIAKNYLWGCEGLHKNLLEEQTKNPYLAFKYGFLNIV (SEQ ID
NO:197)

>Cas14c.2|3300001245.a|JGI12048J13642_10201286|4257..5489|r
evcom
LDFKRTCSQELVLLPEIEGLKLSGTQGVTSLAKKLINKAANVDRDESYGCHHCIHTRTS
LSKPVKKDCNSCNQSTNHPAVPITLKGYKIAFYELWHRFTSWAVDSISKALHRNKVMGK
VNLDEYAVVDNSHIVCYAVRKCYEKRQRSVRLHKRAYRCRAKHYNKSQPKVGRIYKKSK
RRNARNLKKEAKRYFQPNEITNGSSDALFYKIGVDLGIAKGTPETEVKVDVSICFQVYY
GDARRVLRVRKMDELQSFHLDYTGKLKLKGIGNKDTFTIAKRNESLKWGSTKYEVSRAH
KKFKPFGKKGSVKRKCNDYFRSIASWSCEAASQRAQSNLKNAFPYQKALVKCYKNLDYK
GVKKNDMWYRLCSNRIFRYSRIAEDIAQYQSDKGKAKFEFVILAQSVAEYDISAIM
(SEQ ID NO: 198)

FIG. 71

>Cas14d.1|RIFCSPHIGHO2_01_FULL_CPR_46_36_rifcsphigho2_01_sc
affold_646_curated|49808..51616|revcom
VFLTDDKRKTALRKIRSAFRKTAEIALVRAQEADSLDRQAKKLTIETVSFGAPGAKNAF
IGSLQGYNWNSHRANVPSSGSAKDVFRITELGLGIPQSAHEASIGKSFELVGNVVRYTA
NLLSKGYKKGAVNKGAKQQREIKGKEQLSFDLISNGPISGDKLINGQKDALAWWLIDKM
GFHIGLAMEPLSSPNTYGITLQAFWKRHTAPRRYSRGVIRQWQLPFGRQLAPLIHNFFR
KKGASIPIVLTNASKKLAGKGVLLEQTALVDPKKWWQVKEQVTGPLSNIWERSVPLVLY
TATFTHKHGAAHKRPLTLKVIRISSGSVFLLPLSKVTPGKLVRAWMPDINILRDGRPDE
AAYKGPDLIRARERSFPLAYTCVTQIADEWQKRALESNRDSITPLEAKLVTGSDLLQIH
STVQQAVEQGIGGRISSPIQELLAKDALQLVLQQLFMTVDLLRIQWQLKQEVADGNTSE
KAVGWAIRISNIHKDAYKTAIEPCTSALKQAWNPLSGFEERTFQLDASIVRKRSTAKTP
DDELVIVLRQQAAEMTVAVTQSVSKELMELAVRHSATLHLLVGEVASKQLSRSADKDRG
AMDHWKLLSQSM (SEQ ID NO: 199)

>Cas14d.2|rifcsphigho2_01_scaffold_10981_curated|5762..7246
|revcom
EDLLQKALNTATNVAAIERHSCISCLFTESEIDVKYKTPDKIGQNTAGCQSCTFRVGYS
GNSHTLPMGNRIALDKLRETIQRYAWHSLLFNVPPAPTSKRVRAISELRVAAGRERLFT
VITFVQTNILSKLQKRYAANWTPKSQERLSRLREEGQHILSLLESGSWQQKEVVREDQD
LIVCSALTKPGLSIGAFCRPKYLKPAKHALVLRLIFVEQWPGQIWGQSKRTRRMRRRKD
VERVYDISVQAWALKGKETRISECIDTMRRHQQAYIGVLPFLILSGSTVRGKGDCPILK
EITRMRYCPNNEGLIPLGIFYRGSANKLLRVVKGSSFTLPMWQNIETLPHPEPFSPEGW
TATGALYEKNLAYWSALNEAVDWYTGQILSSGLQYPNQNEFLARLQNVIDSIPRKWFRP
QGLKNLKPNGQEDIVPNEFVIPQNAIRAHHVIEWYHKTNDLVAKTLLGWGSQTTLNQTR
PQGDLRFTYTRYYFREKEVPEV (SEQ ID NO: 200)

>Cas14d.3|RIFCSPLOWO2_01_FULL_OD1_45_34b_rifcsplowo2_01_sca
ffold_3495_curated|25656..27605|revcom
VPKKKLMRELAKKAVFEAIFNDPIPGSFGCKRCTLIDGARVTDAIEKKQGAKRCAGCEP
CTFHTLYDSVKHALPAATGCDRTAIDTGLWEILTALRSYNWMSFRRNAVSDASQKQVWS
IEELAIWADKERALRVILSALTHTIGKLKNGFSRDGVWKGGKQLYENLAQKDLAKGLFA
NGEIFGKELVEADHDMLAWTIVPNHQFHIGLIRGNWKPAAVEASTAFDARWLTNGAPLR
DTRTHGHRGRRFNRTEKLTVLCIKRDGGVSEEFRQERDYELSVMLLQPKNKLKPEPKGE
LNSFEDLHDHWWFLKGDEATALVGLTSDPTVGDFIQLGLYIRNPIKAHGETKRRLLICF
EPPIKLPLRRAFPSEAFKTWEPTINVFRNGRRDTEAYYDIDRARVFEFPETRVSLEHLS
KQWEVLRLEPDRENTDPYEAQQNEGAELQVYSLLQEAAQKMAPKVVIDPFGQFPLELFS
TFVAQLFNAPLSDTKAKIGKPLDSGFVVESHLHLLEEDFAYRDFVRVTFMGTEPTFRVI
HYSNGEGYWKKTVLKGKNNIRTALIPEGAKAAVDAYKNKRCPLTLEAAILNEEKDRRLV
LGNKALSLLAQTARGNLTILEALAAEVLRPLSGTEGVVHLHACVTRHSTLTESTETDNM
(SEQ ID NO: 201)

FIG. 7J

>Cas14e.1|rifcsphigho2_01_scaffold_566_curated|113069..1143
13
VEKLFSERLKRAMWLKNEAGRAPPAETLTLKHKRVSGGHEKVKEELQRVLRSLSGTNQA
AWNLGLSGGREPKSSDALKGEKSRVVLETVVFHSGHNRVLYDVIEREDQVHQRSSIMHM
RRKGSNLLRLWGRSGKVRRKMREEVAEIKPVWHKDSRWLAIVEEGRQSVVGISSAGLAV
FAVQESQCTTAEPKPLEYVVSIWFRGSKALNPQDRYLEFKKLKTTEALRGQQYDPIPFS
LKRGAGCSLAIRGEGIKFGSRGPIKQFFGSDRSRPSHADYDGKRRLSLFSKYAGDLADL
TEEQWNRTVSAFAEDEVRRATLANIQDFLSISHEKYAERLKKRIESIEEPVSASKLEAY
LSAIFETFVQQREALASNFLMRLVESVALLISLEEKSPRVEFRVARYLAESKEGFNRKA
M (SEQ ID NO: 202)

>Cas14e.2|rifcsplowo2_01_scaffold_81231_curated|976..2217
VVITQSELYKERLLRVMEIKNDRGRKEPRESQGLVLRFTQVTGGQEKVQKLWLIFEGF
SGTNQASWNFGQPAGGRKPNSGDALKGPKSRVTYETVVFHFGLRLLSAVIERHNLKQQR
QTMAYMKRRAAARKKWARSGKKCSRMRNEVEKIKPKWHKDPRWFDIVKEGEPSIVGISS
AGFAIYIVEEPNFPRQDPLEIEYAISIWFRRDRSQYLTFKKIQKAEKLKELQYNPIPFR
LKQEKTSLVFESGDIKFGSRGSIEHFRDEARGKPPKADMDNNRRLTMFSVFSGNLTNLT
EEQYARPVSGLLAPDEKRMPTLLKKLQDFFTPIHEKYGERIKQRLANSEASKRPFKKLE
EYLPAIYLEFRARREGLASNWLVLINSVRTLVRIKSEDPYIEFKVSQYLLEKEDNKAL
(SEQ ID NO: 203)

>Cas14e.3|rifcsphigho2_01_scaffold_4702_curated|82881..8423
0|revcom
KQDALFEERLKKAIFIKRQADPLQREELSLLPPNRKIVTGGHESAKDTLKQILRAINGT
NQASWNPGTPSGKRDSKSADALAGPKSRVKLETVVFHVGHRLLKKVVEYQGHQKQQHGL
KAFMRTCAAMRKKWKRSGKVVGELREQLANIQPKWHYDSRPLNLCFEGKPSVVGLRSAG
IALYTIQKSVVPVKEPKPIEYAVSIWFRGPKAMDREDRCLEFKKLKIATELRKLQFEPI
VSTLTQGIKGFSLYIQGNSVKFGSRGPIKYFSNESVRQRPPKADPDGNKRLALFSKFSG
DLSDLTEEQWNRPILAFEGIIRRATLGNIQDYLTVGHEQFAISLEQLLSEKESVLQMSI
EQQRLKKNLGKKAENEWVESFGAEQARKKAQGIREYISGFFQEYCSQREQWAENWVQQL
NKSVRLFLTIQDSTPFIEFRVARYLPKGEKKKGKAM (SEQ ID NO: 204)

>Cas14f.1|rifcsp13_1_sub10_scaffold_3_curated|38906..41041
ANHAERHKRLRKEANRAANRNRPLVADCDTGDPLVGICRLLRRGDKMQPNKTGCRSCEQ
VEPELRDAILVSGPGRLDNYKYELFQRGRAMAVHRLLKRVPKLNRPKKAAGNDEKKAEN
KKSEIQKEKQQRRMMPAVSMKQVSVADFKHVIENTVRHLFGDRRDREIAECAALRAAS
KYFLKSRRVRPRKLPKLANPDHGKELKGLRLREKRAKLKKEKEKQAELARSNQKGAVLH
VATLKKDAPPMPYEKTQGRNDYTTFVISAAIKVGATRGTKPLLTPQPREWQCSLYWRDG
QRWIRGGLLGLQAGIVLGPKLNRELLEAVLQRPIECRMSGCGNPLQVRGAAVDFFMTTN
PFYVSGAAYAQKKFKPFGTKRASEDGAAAKAREKLMTQLAKVLDKVVTQAAHSPLDGIW
ETRPEAKLRAMIMALEHEWIFLRPGPCHNAAEEVIKCDCTGGHAILWALIDEARGALEH
KEFYAVTRAHTHDCEKQKLGGRLAGFLDLLIAQDVPLDDAPAARKIKTLLEATPPAPCY
KAATSIATCDCEGKFDKLWAIIDATRAGHGTEDLWARTLAYPQNVNCKCKAGKDLTHRL
ADFLGLLIKRDGPFRERPPHKVTGDRKLVFSGDKKCKGHQYVILAKAHNEEVVRAWISR
WGLKSRTNKAGYAATELNLLLNWLSICRRRWMDMLTVQRDTPYIRMKTGRLVVDDKKER
KAM (SEQ ID NO: 205)

FIG. 7K

>Cas14f.2|3300009991.a|Ga0105042_100140|1624..3348
AKQREALRVALERGIVRASNRTYTLVTNCTKGGPLPEQCRMIERGKARAMKWEPKLVGC
GSCAAATVDLPAIEEYAQPGRLDVAKYKLTTQILAMATRRMMVRAAKLSRRKGQWPAKV
QEEKEEPPEPKKMLKAVEMRPVAIVDFNRVIQTTIEHLWAERANADEAELKALKAAAAY
FGPSLKIRARGPPKAAIGRELKKAHRKKAYAERKKARRKRAELARSQARGAAAHAAIRE
RDIPPMAYERTQGRNDVTTIPIAAAIKIAATRGARPLPAPKPMKWQCSLYWNEGQRWIR
GGMLTAQAYAHAANIHRPMRCEMWGVGNPLKVRAFEGRVADPDGAKGRKAEFRLQTNAF
YVSGAAYRNKKFKPFGTDRGGIGSARKKRERLMAQLAKILDKVVSQAAHSPLDDIWHTR
PAQKLRAMIKQLEHEWMFLRPQAPTVEGTKPDVDVAGNMQRQIKALMAPDLPPIEKGSP
AKRFTGDKRKKGERAVRVAEAHSDEVVTAWISRWGIQTRRNEGSYAAQELELLLNWLQI
CRRRWLDMTAAQRVSPYIRMKSGRMITDAADEGVAPIPLVENM (SEQ ID NO: 206
)

>Cas14g.1|RBG_13_scaffold_1401_curated|15949..18180
KSISGRSIKHMACLKDMLKSEITEIEEKQKKESLRKWDYYSKFSDEILFRRNLNVSANH
DANACYGCNPCAFLKEVYGFRIERRNNERIISYRRGLAGCKSCVQSTGYPPIEFVRRKF
GADKAMEIVREVLHRRNWGALARNIGREKEADPILGELNELLLVDARPYFGNKSAANET
NLAFNVITRAAKKFRDEGMYDIHKQLDIHSEEGKVPKGRKSRLIRIERKHKAIHGLDPG
ETWRYPHCGKGEKYGVWLNRSRLIHIKGNEYRCLTAFGTTGRRMSLDVACSVLGHPLVK
KKRKKGKKTVDGTELWQIKKATETLPEDPIDCTFLYAAKPTKDPFILKVGSLKAPRWK
KLHKDFFEYSDTEKTQGQEKGKRVVRRGKVPRILSLRPDAKFKVSIWDDPYNGKNKEGT
LLRMELSGLDGAKKPLILKRYGEPNTKPKNFVFWRPHITPHPLTFTPKHDFGDPNKKTK
RRRVFNREYYGHLNDLAKMEPNAKFFEDREVSNKKNPKAKNIRIQAKESLPNIVAKNGR
WAAFDPNDSLWKLYLHWRGRRKTIKGGISQEFQEFKERLDLYKKHEDESEWKEKEKLWE
NHEKEWKKTLEIHGSIAEVSQRCVMQSMMGPLDGLVQKKDYVHIGQSSLKAADDAWTFS
ANRYKKATGPKWGKISVSNLLYDANQANAELISQSISKYLSKQKDNQGCEGRKMKFLIK
IIEPLRENFVKHTRWLHEMTQKDCEVRAQFSRVSM (SEQ ID NO:207)

>Cas14g.2|3300009652.a|Ga0123330_1010394|2814..5123
FPSDVGADALKHVRMLQPRLTDEVRKVALTRAPSDRPALARFAAVAQDGLAFVRHLNVS
ANHDSNCTFPRDPRDPRRGPCEPNPCAFLREVWGFRIVARGNERALSYRRGLAGCKSCV
QSTGFPSVPFHRIGADDCMRKLHEILKARNWRLLARNIGREREADPLLTELSEYLLVDA
RTYPDGAAPNSGRLAENVIKRAAKKFRDEGMRDIHAQLRVHSREGKVPKGRLQRLRRIE
RKHRAIHALDPGPSWEAEGSARAEVQGVAVYRSQLLRVGHHTQQIEPVGIVARTLFGVG
RTDLDVAVSVLGAPLTKRKKGSKTLESTEDFRIAKARETRAEDKIEVAFVLYPTASLLR
DEIPKDAFPAMRIDRFLLKVGSVQADREILLQDDYYRFGDAEVKAGKNKGRTVTRPVKV
PRLQALRPDAKFRVNVWADPFGAGDSPGTLLRLEVSGVTRRSQPLRLLRYGQPSTQPAN
FLCWRPHRVPDPMTFTPRQKFGERRKNRRTRRPRVFERLYQVHIKHLAHLEPNRKWFEE
ARVSAQKWAKARAIRRKGAEDIPVVAPPAKRRWAALQPNAELWDLYAHDREARKRFGG
RAAEGEEFKPRLNLYLAHEPEAEWESKRDRWERYEKKWTAVLEEHSRMCAVADRTLPQF
LSDPLGARMDDKDYAFVGKSALAVAEAFVEEGTVERAGGNCSITAKKKFASNASRKRLS
VANLLDVSDKADRALVFQAVRQYVQRQAENGGVEGRRMAFLRKLLAPLRQNFVCHTRWL
HM (SEQ ID NO: 208)

FIG. 7L

>Cas14h.1|3300005602.a|Ga0070762_10001740|7377..9071|revcom
AARKKKRGKIGITVKAKEKSPPAAGPFMARKLVNVAANVDGVEVHLCVECEADAHGSAS
ARLLGGCRSCTGSIGAEGRLMGSVDVDRERVIAEPVHTETERLGPDVKAFEAGTAESKY
AIQRGLEYWGVDLISRNRARTVRKMEEADRPESSTMEKTSWDEIAIKTYSQAYHASENH
LFWERQRRVRQHALALFRRARERNRGESPLQSTQRPAPLVLAALHAEAAAISGRARAEY
VLRGPSANVRAAAADIDAKPLGHYKTPSPKVARGFPVKRDLLRARHRIVGLSRAYFKPS
DVVRGTSDAIAHVAGRNIGVAGGKPKEIEKTFTLPFVAYWEDVDRVVHCSSFKADGPWV
RDQRIKIRGVSSAVGTFSLYGLDVAWSKPTSFYIRCSDIRKKFHPKGFGPMKHWRQWAK
ELDRLTEQRASCVVRALQDDEELLQTMERGQRYYDVFSCAATHATRGEADPSGGCSRCE
LVSCGVAHKVTKKAKGDTGIEAVAVAGCSLCESKLVGPSKPRVHRQMAALRQSHALNYL
RRLQREWEALEAVQAPTPYLRFKYARHLEVRSM (SEQ ID NO: 209)

>Cas14h.2|3300005921.a|Ga0070766_10011912|384..2081
AAKKKQRGKIGISVKPKEGSAPPADGPFMARKLVNVAANVDGVEVNLCIECEADAHGS
APARLLGGCKSCTGSIGAEGRLMGSVDVDRADAIAKPVNTETEKLGPDVQAFEAGTAET
KYALQRGLEYWGVDLISRNRSRTVRRTEEGQPESATMEKTSWDEIAIKSYTRAYHASEN
HLFWERQRRVRQHALALFKRAKERNRGDSTLPREPGHGLVAIAALCEAYAVGGRNLAE
TVVRGPTFGTARAVRDVEIASLGRYKTPSPKVAHGSPVKRDFLRARHRIVGLARAYYRP
SDVVRGTSDAIAHVAGRNIGVAGGKPRAVEAVFTLPFVAYWEDVDRVVHCSSFQVSAPW
NRDQRMKIAGVTTAAGTFSLHGGELKWAKPTSFYIRCSDTRRKFRPKGFGPMKRWRQWA
KDLDRLVEQRASCVVRALQDDAALLETMERGQRYYDVFACAVTHATRGEADRLAGCSRC
ALTPCQEAHRVTTKPRGDAGVEQVQTSDCSLCEGKLVGPSKPRLHRTLTLLRQEHGLNY
LRRLQREWESLEAVQVPTPYLRFKYARHLEVRSM (SEQ ID NO: 210)

>Cas14h.3|3300009698.a|Ga0116216_10000905|8005..9504
TDSQSESVPEVVYALTGGEVPGRVPPDGGSAEGARNAPTGLRKQRGKIKISAKPSKPGS
PASSLARTLVNEAANVDGVQSSGCATCRMRANGSAPRALPIGCVACASSIGRAPQEETV
CALPTTQGPDVRLLEGGHALRKYDIQRALEYWGVDLIGRNLDRQAGRGMEPAEGATATM
KRVSMDELAVLDFGKSYYASEQHLFAARQRRVRQHAKALKIRAKHANRSGSVKRALDRS
RKQVTALAREFFKPSDVVRGDSDALAHVVGRNLGVSRHPAREIPQTFTLPLCAYWEDVD
RVISCSSLLAGEPFARDQEIRIEGVSSALGSLRLYRGAIEWHKPTSLYIRCSDTRRKFR
PRGGLKKRWRQWAKDLDRLVEQRACCIVRSLQADVELLQTMERAQRFYDVHDCAATHVG
PVAVRCSPCAGKQFDWDRYRLLAALRQEHALNYLRRLQREWESLEAQQVKMPYLRFKYA
RKLEVSGPLIGLEVRREPSMGTAIAEM (SEQ ID NO: 211)

>Cas14u.1|3300009029.a|Ga0066793_10010091|37..1113|revcom
AGTAGRRHGSLGARRSINIAGVTDRHGRWGCESCVYTRDQAGNRARCAPCDQSTYAPDV
QEVTIGQRQAKYTIFLTQSFSWTNTMRNNKRAAAGRSKRTTGKRIGQLAEIKITGVGL
AHAHNVIQRSLQHNITKMWRAEKGKSKRVARLKKAKQLTKRRAYFRRRMSRQSRGNGFF
RTGKGGIHAVAPVKIGLDVGMIASGSSEPADEQTVTLDAIWKGRKKKIRLIGAKGELAV
AACRFREQQTKGDKCIPLILQDGEVRWNQNNWQCHPKKLVPLCGLEVSRKFVSQADRLA
QNKVASPLAARFDKTSVKGTLVESDFAAVLVNVTSIYQQCHAMLLRSQEPTPSLRVQRT
ITSM (SEQ ID NO: 212)

FIG. 7M

>Cas14u.2|3300002172.a|JGI24730J26740_1002785|496..1605|rev
com
GVRFSPAQSQVFFRTVIPQSVEARFAINMAAIHDAAGAFGCSVCRFEDRTPRNAKAVHG
CSPCTRSTNRPDVFVLPVGAIKAKYDVFMRLLGFNWTHLNRRQAKRVTVRDRIGQLDEL
AISMLTGKAKAVLKKSICHNVDKSFKAMRGSLKKLHRKASKTGKSQLRAKLSDLRERTN
TTQEGSHVEGDSDVALNKIGLDVGLVGKPDYPSEESVEVVVCLYFVGKVLILDAQGRIR
DMRAKQYDGFKIPIIQRGQLTVLSVKDLGKWSLVRQDYVLAGDLRFEPKISKDRKYAEC
VKRIALITLQASLGFKERIPYYVTKQVEIKNASHIAFVTEAIQNCAENFREMTEYLMKY
QEKSPDLKVLLTQLM (SEQ ID NO: 213)

>Cas14u.3|19ft_2_nophage_noknown_scaffold_0_curated|508188.
.509648
RAVVGKVFLEQARRALNLATNFGTNHRTGCNGCYVTPGKLSIPQDGEKNAAGCTSCLMK
ATASYVSYPKPLGEKVAKYSTLDALKGFPWYSLRLNLRPNYRGKPINGVQEVAPVSKFR
LAEEVIQAVQRYHFTELEQSFPGGRRRLRELRAFYTKEYRRAPEQRQHVVNGDRNIVVV
TVLHELGFSVGMFNEVELLPKTPIECAVNVFIRGNRVLLEVRKPQFDKERLLVESLWKK
DSRRHTAKWTPPNNEGRIFTAEGWKDFQLPLLLGSTSRSLRAIEKEGFVQLAPGRDPDY
NNTIDEQHSGRPFLPLYLYLQGTISQEYCVFAGTWVIPFQDGISPYSTKDFQPDLKRK
AYSLLLDAVKHRLGNKVASGLQYGRFPAIEELKRLVRMHGATRKIPRGEKDLLKKGDPD
TPEWWLLEQYPEFWRLCDAAAKRVSQNVGLLLSLKKQPLWQRRWLESRTRNEPLDNLPL
SMALTLHLTNEEAL (SEQ ID NO: 214)

>Cas14u.4|rifcsp2_19_4_full_scaffold_168_curated|84455..856
57
AAVYSKFYIENHFKMGIPETLSRIRGPSIIQGFSVNENYINIAGVGDRDFIFGCKKCKY
TRGKPSSKKINKCHPCKRSTYPEPVIDVRGSISEFKYKIYNKLKQEPNQSIKQNTKGRM
NPSDHTSSNDGIIINGIDNRIAYNVIFSSYKHLMEKQINLLRDTTKRKARQIKKYNNSG
KKKHSLRSQTKGNLKNRYHMLGMFKKGSLTITNEGDFITAVRKVGLDISLYKNESLNKQ
EVETELCLNIKWGRTKSYTVSGYIPLPINIDWKLYLFEKETGLTLRLFGNYKIQSKKF
LIAQLFKPKRPPCADPVVKKAQKWSALNAHVQQMAGLFSDSHLLKRELKNRMHKQLDFK
SLWVGTEDYIKWFEELSRSYVEGAEKSLEFFRQDYFCFNYTKQTTM (SEQ ID NO: 215
)

>Cas14u.5|3300012532.a|Ga0137373_10000316|3286..5286
PQQQRDLMLMAANYDQDYGNGCGPCTVVASAAYRPDPQAQHGCKRHLRTLGASAVTHVG
LGDRTATITALHRLRGPAALAARARAAQAASAPMTPDTDAPDDRRRLEAIDADDVVLVG
AHRALWSAVRRWADDRRAALRRRLHSEREWLLKDQIRWAELYTLIEASGTPPQGRWRNT
LGALRGQSRWRRVLAPTMRATCAETHAELWDALAELVPEMAKDRRGLLRPPVEADALWR
APMIVEGWRGGHSVVVDAVAPPLDLPQPCAWTAVRLSGDPRQRWGLHLAVPPLGQVQPP
DPLKATLAVSMRHGGVRVRTLQAMAVDADAPMQRHLQVPLTLQRGGGLQWGIHSRGVR
RREARSMASWEGPPIWTGLQLVNRWKGQGSALLAPDRPPDTPPYAPDAAVAPAQPDTKR
ARRTLKEACTVCRCAPGHMRQLQVTLTGDGTWRRFRLRAPQGAKRKAEVLKVATQHDER
IANYTAWYLKRPEHAAGCDTCDGDSRLDGACRGCRPLLVGDQCFRRYLDKIEADRDDGL
AQIKPKAQEAVAAMAAKRDARAQKVAARAAKLSEATGQRTAATRDASHEARAQKELEAV
ATEGTTVRHDAAAVSAFGSWVARKGDEYRHQVGVLANRLEHGLRLQELMAPDSVVADQQ
RASGHARVGYRYVLTAM (SEQ ID NO:216)

FIG. 7N

>Cas14u.6|3300006028.a|Ga0070717_10000077|54519..56201|revc
om
AVAHPVGRGNAGSPGARGPEELPRQLVNRASNVTRPATYGCAPCRHVRLSIPKPVLTGC
RACEQTTHPAPKRAVRGGADAAKYDLAAFFAGWAADLEGRNRRRQVHAPLDPQPDPNHE
PAVTLQKIDLAEVSIEEFQRVLARSVKHRHDGRASREREKARAYAQVAKKRRNSHAHGA
RTRRAVRRQTRAVRRAHRMGANSGEILVASGAEDVPEAIDHAAQLRRRIRACARDLEG
LRHLSRRYLKTLEKPCRRPRAPDLGRARCHALVESLQAAERELEELRRCDSPDTAMRRL
DAVLAAAASTDATFATGWTVVGMDLGVAPRGSAAPEVSPMEMAISVFWRKGSRRVIVSK
PIAGMPIRRHELIRLEGLGTLRLDGNHYTGAGVTKGRGLSEGTEPDFREKSPSTLGFTL
SDYRHESRWRPYGAKQGKTARQFFAAMSRELRALVEHQVLAPMGPPLLEAHERRFETLL
KGQDNKSIHAGGGGRYVWRGPPDSKKRPAADGDWFRFGRGHADHRGWANKRHELAANYL
QSAFRLWSTLAEAQEPTPYARYKYTRVTM (SEQ ID NO:217)

>Cas14u.7|3300001256.a|JGI12210J13797_10004690|5792..7006
WDFLTLQVYERHTSPEVCVAGNSTKCASGTRKSDHTHGVGVKLGAQEINVSANDDRDHE
VGCNICVISRVSLDIKGWRYGCESCVQSTPEWRSIVRFDRNHKEAKGECLSRFEYWGAQ
SIARSLKRNKLMGGVNLDELAIVQNENVVKTSLKHLFDKRKDRIQANLKAVKVRMRERR
KSGRQRKALRRQCRKLKRYLRSYDPSDIKEGNSCSAFTKLGLDIGISPNKPPKIEPKVE
VVFSLFYQGACDKIVTVSSPESPLPRSWKIKIDGIRALYVKSTKVKFGGRTFRAGQRNN
RRKVRPPNVKKGKRKGSRSQFFNKFAVGLDAVSQQLPIASVQGLWGRAETKKAQTICLK
QLESNKPLKESQRCLFLADNWVVRVCGFLRALSQRQGPTPYIRYRYRCNM (SEQ ID
NO:218)

>Cas14u.8|3300005660.a|Ga0073904_10021651|765..1943
ARNVGQRNASRQSKRESAKARSRRVTGGHASVTQGVALINAAANADRDHTTGCEPCTWE
RVNLPLQEVIHGCDSCTKSSPFWRDIKVVNKGYREAKEEIMRIASGISADHLSRALSHN
KVMGRLNLDEVCILDFRTVLDTSLKHLTDSRSNGIKEHIRAVHRKIRMRRKSGKTARAL
RKQYFALRRQWKAGHKPNSIREGNSLTALRAVGFDVGVSEGTEPMPAPQTEVVLSVFYK
GSATRILRISSPHPIAKRSWKVKIAGIKALKLIRREHDFSFGRETYNASQRAEKRKFSP
HAARKDFFNSFAVQLDRLAQQLCVSSVENLWVTEPQQKLLTLAKDTAPYGIREGARFAD
TRARLAWNWVFRVCGFTRALHQEQEPTPYCRFTWRSKM (SEQ ID NO:219)

FIG. 10
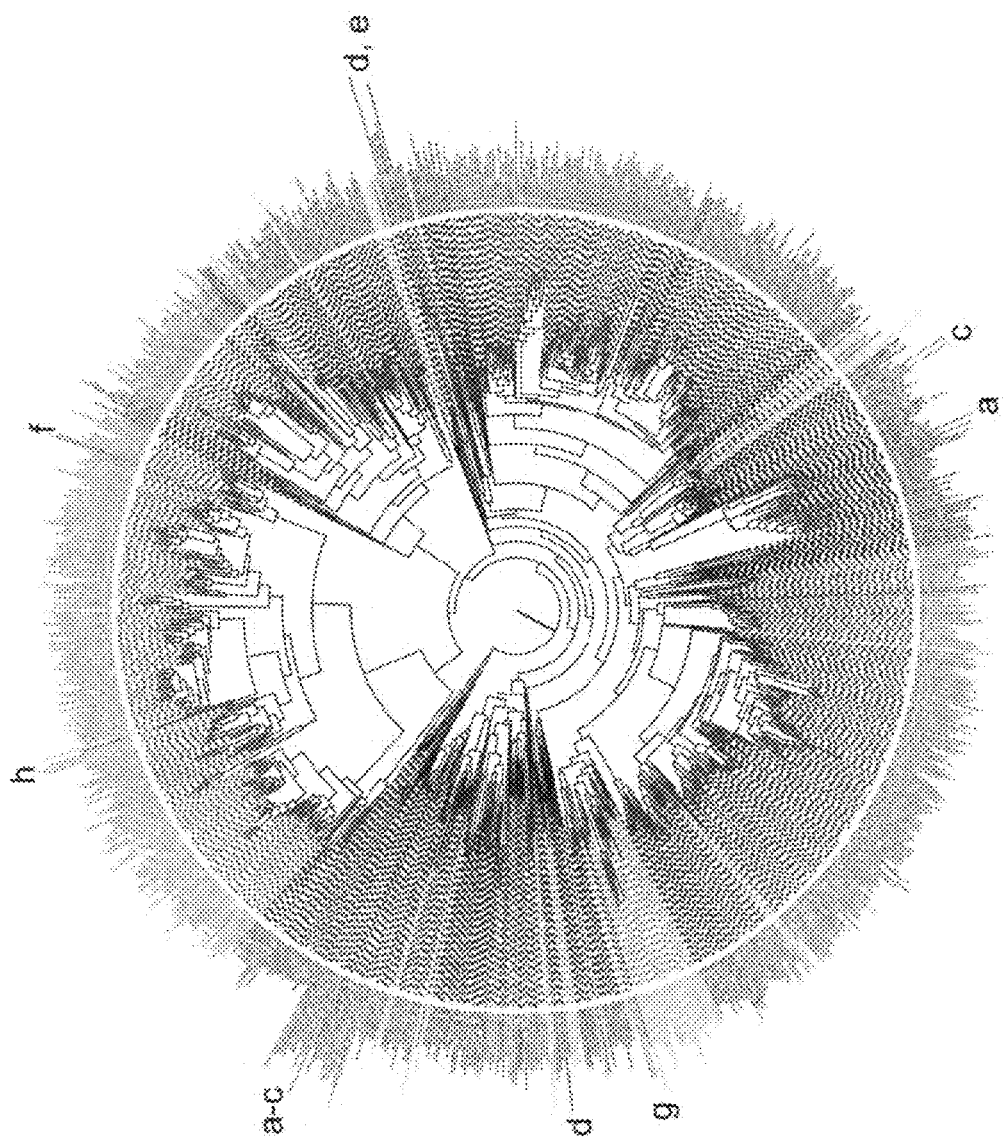
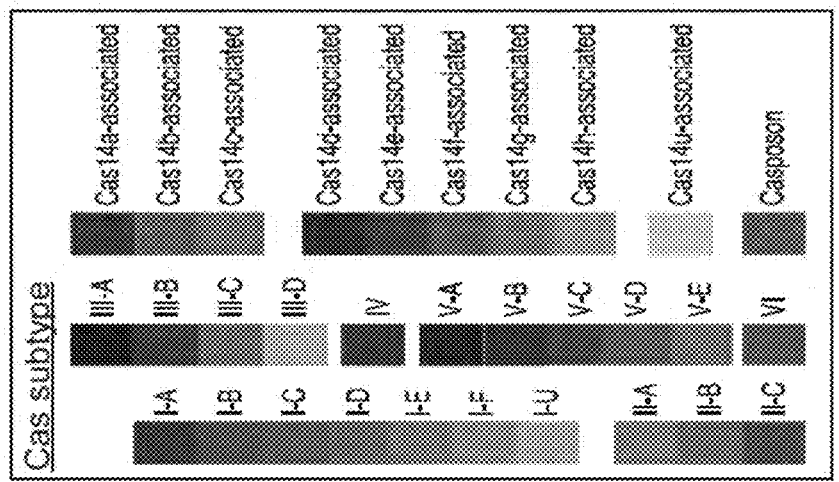

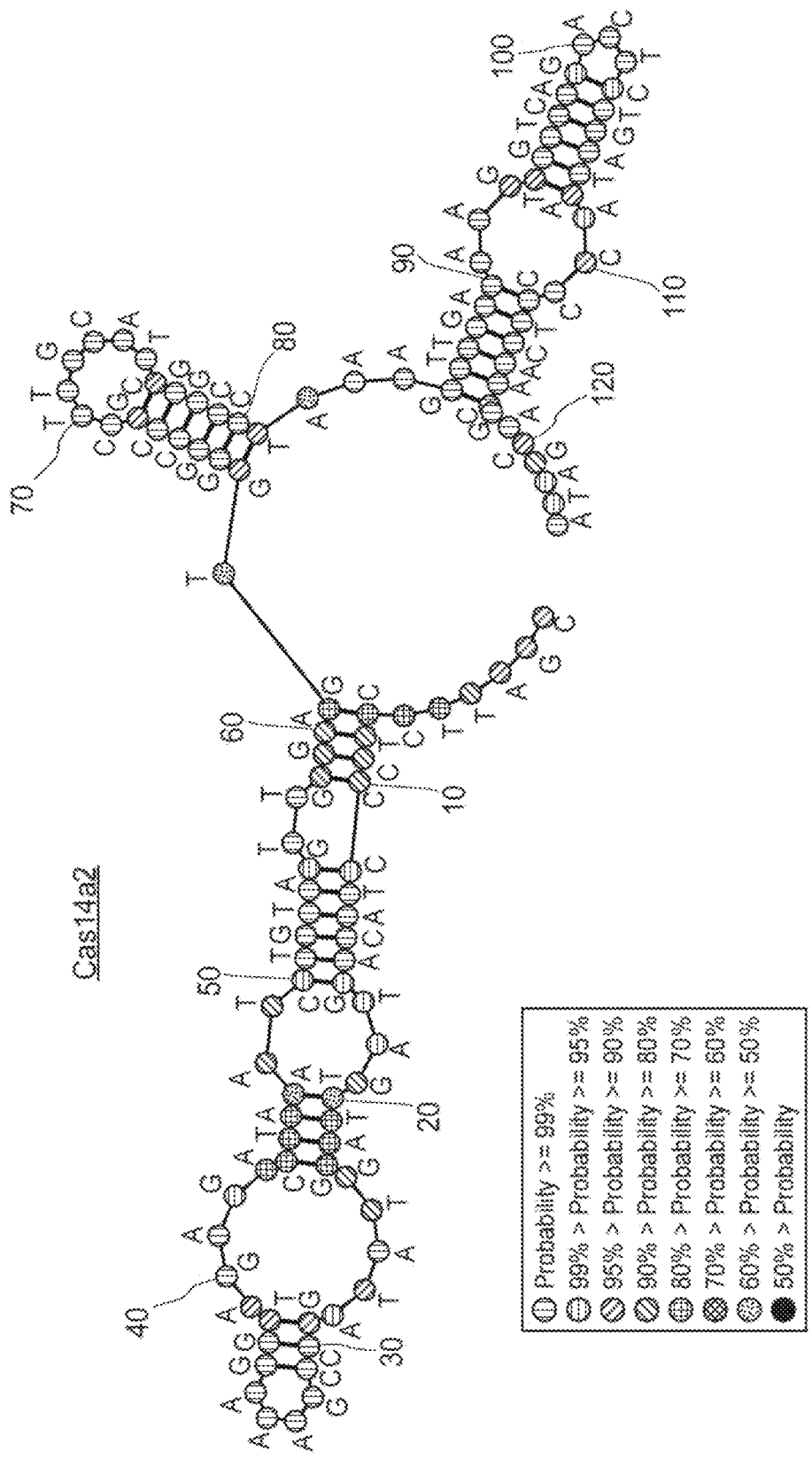

FIG. 15B
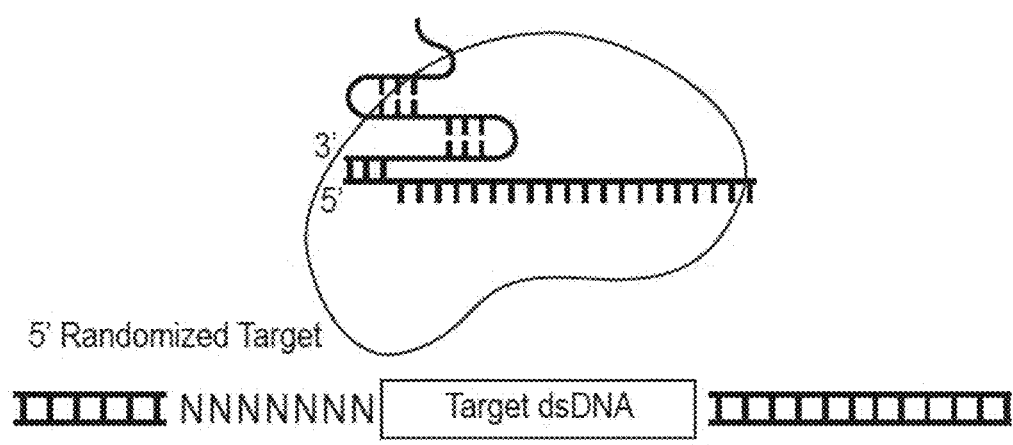
PDVT
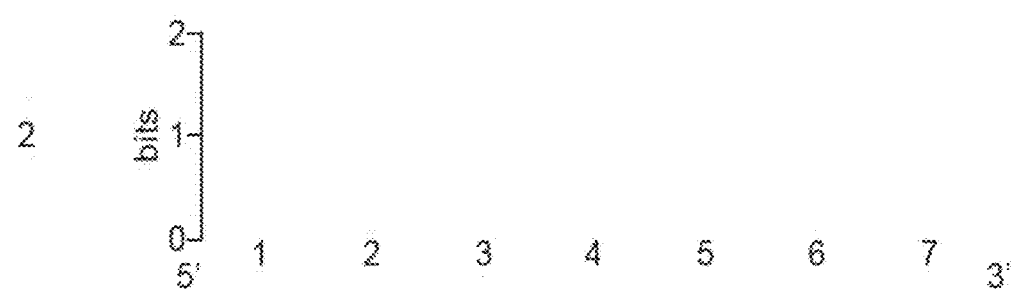
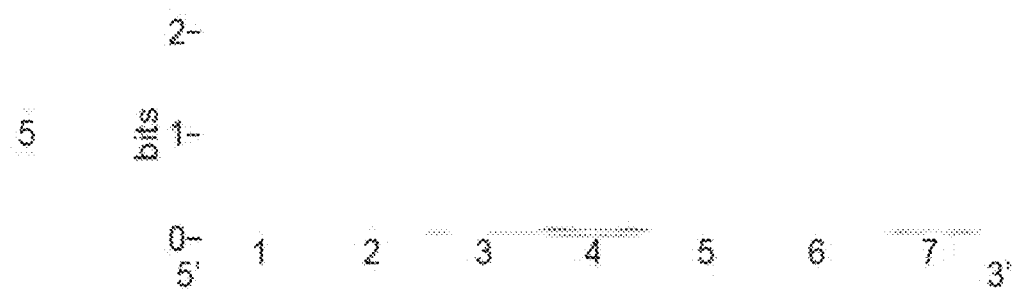

FIG. 15C
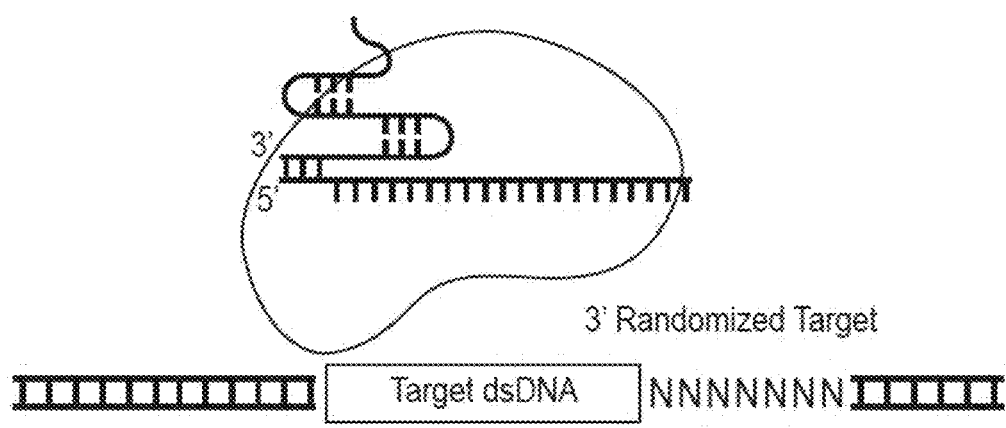
PDVT
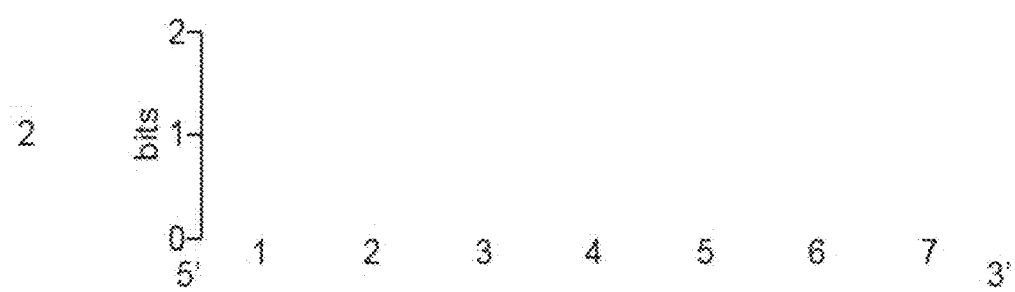
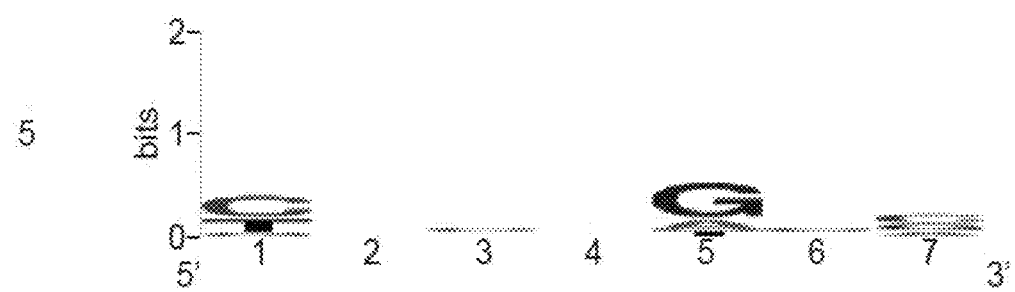

FIG. 16B
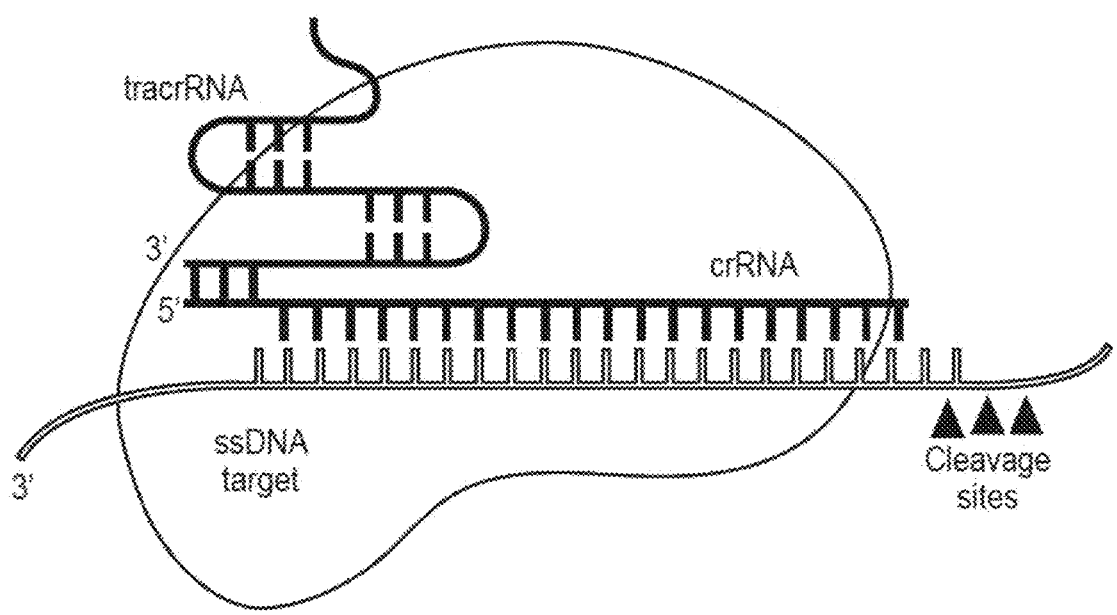
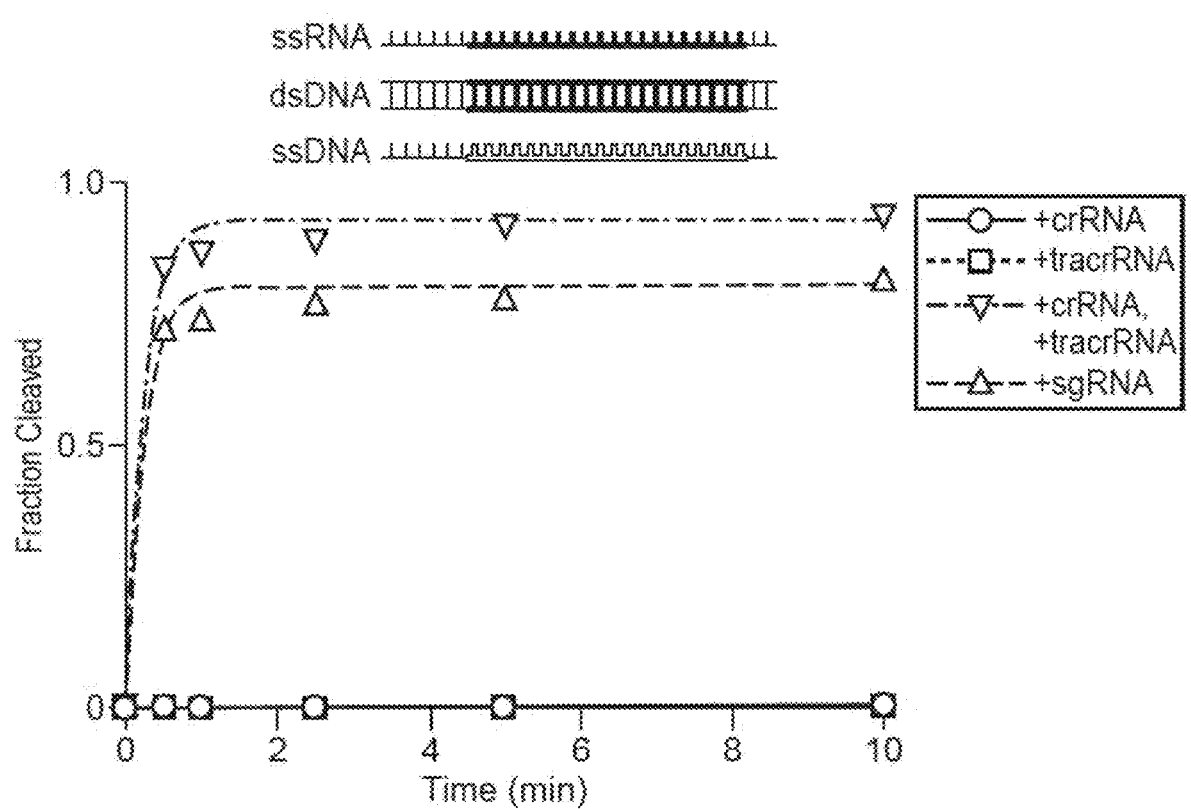

FIG. 17E

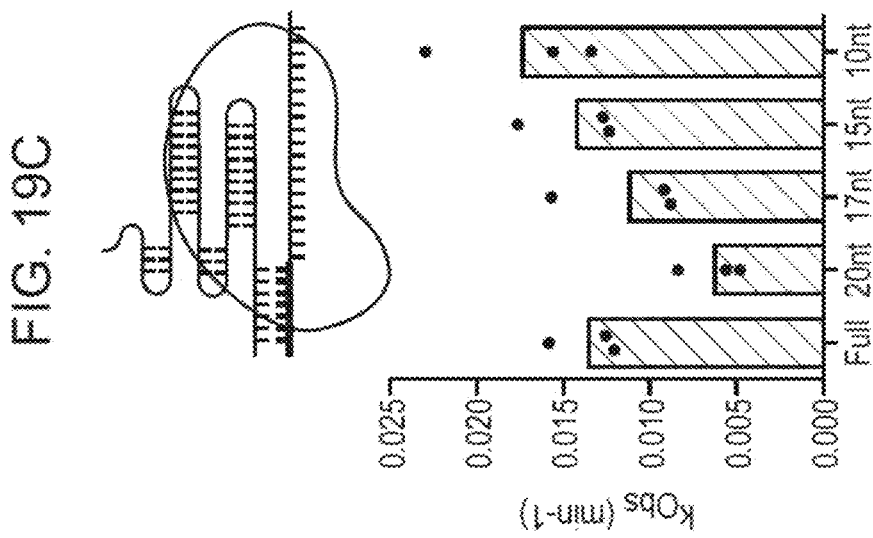
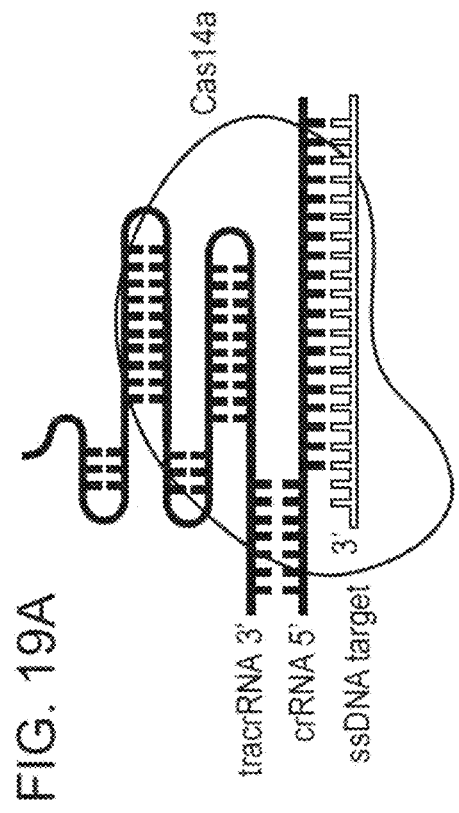
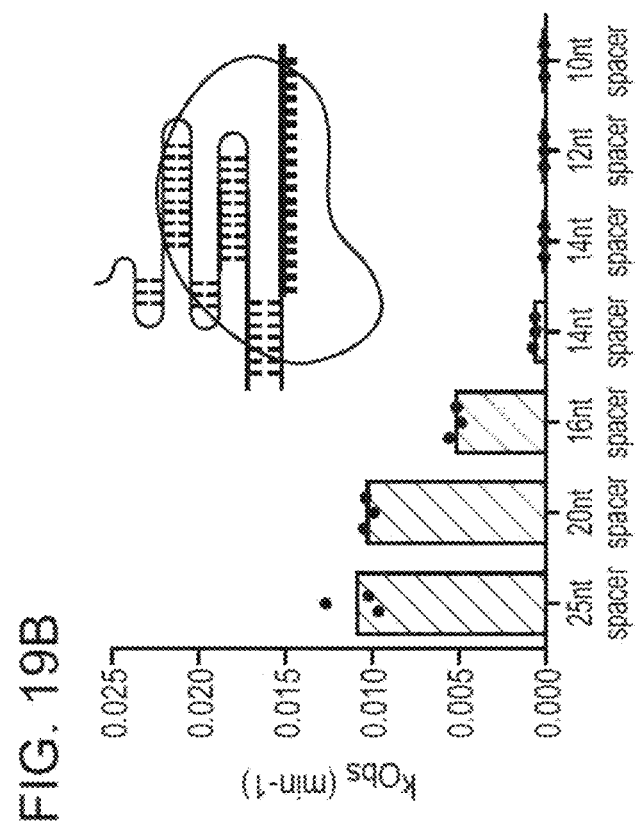

FIG. 19F
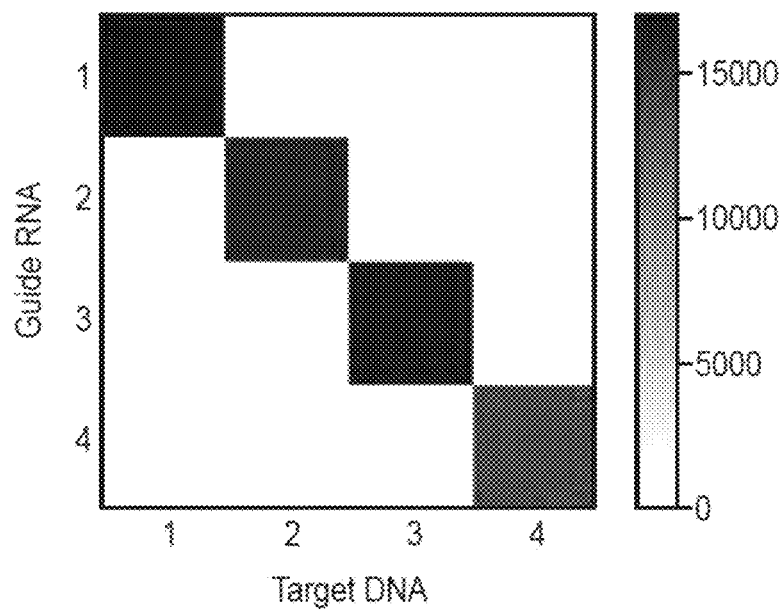
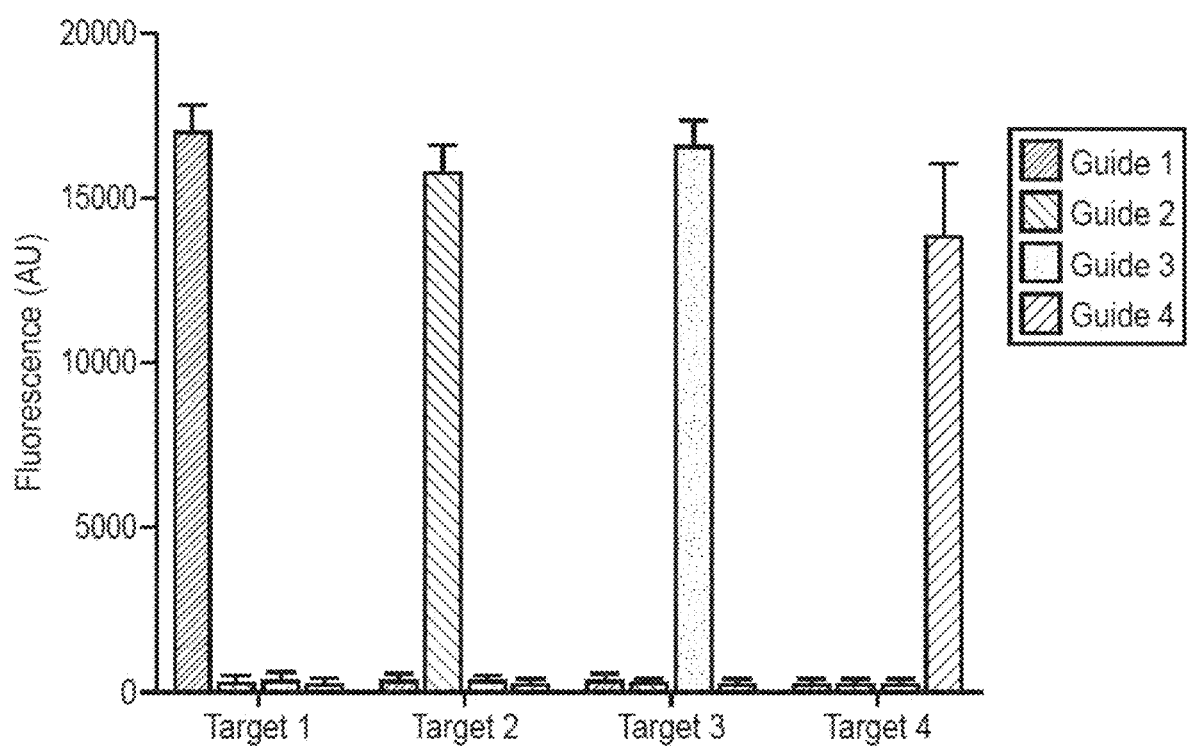

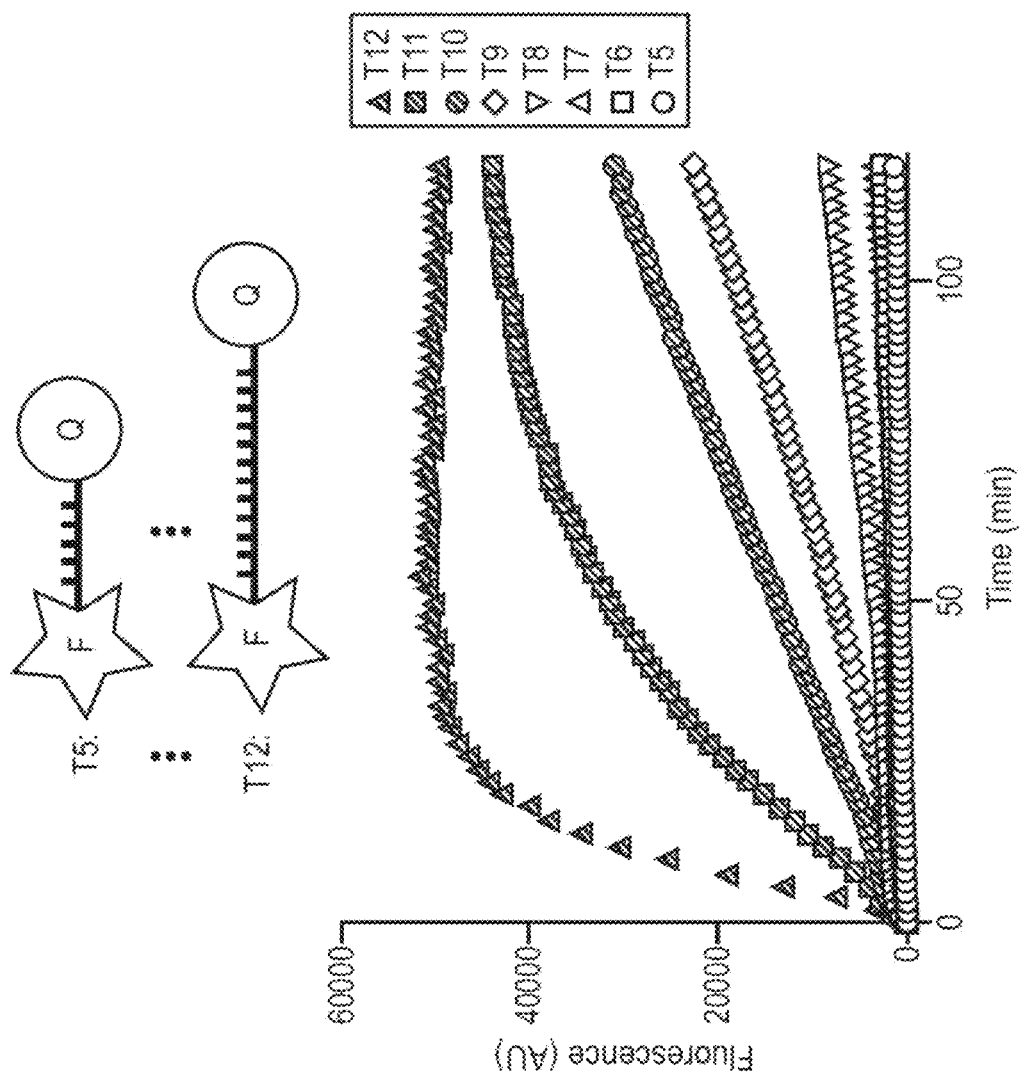
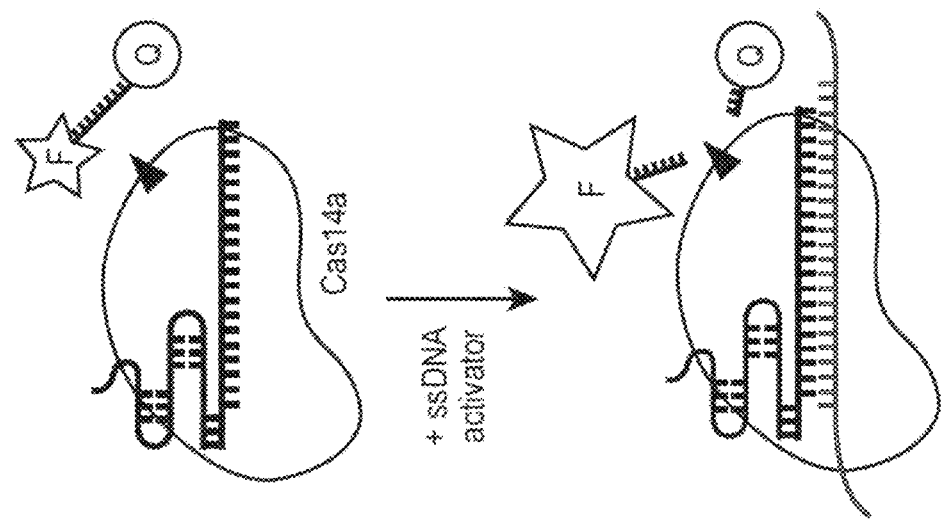
FIG. 20A

FIG. 21A
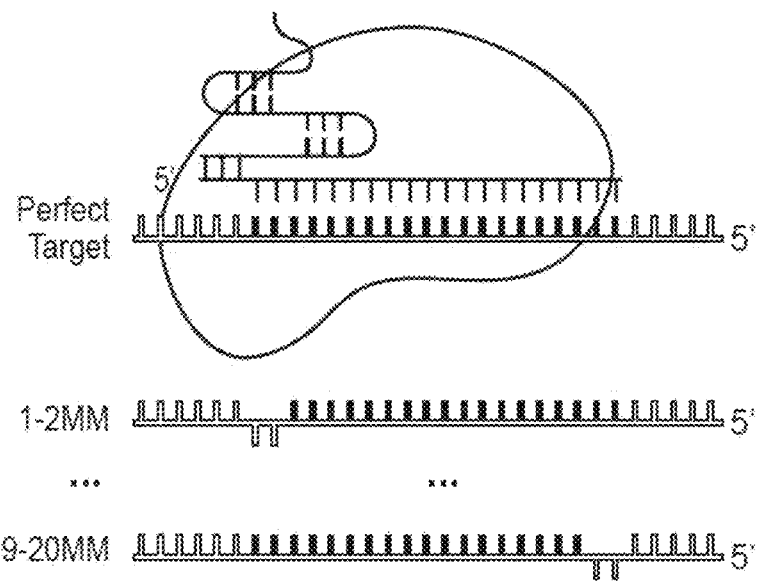
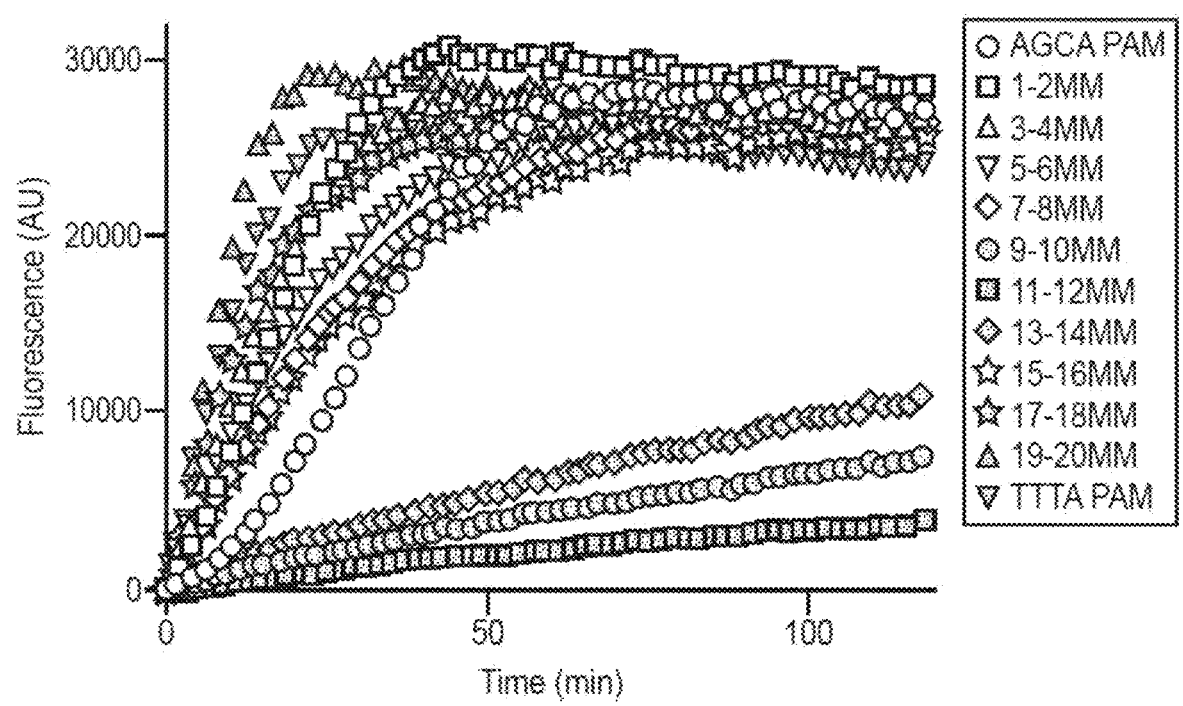

FIG. 24A

Plasmid pLBH533_MBP-Cas14b2 expression (Addgene Plasmid Number 112506)

GCAACCCGCCACCTGTGGCGCCGGTGATGCCGGCCACGATGCGTCCGGCGTAGAGGATGAGATCGATCC
CGGCGAATTAATACGACTCACTATAGGGAGACCACAACGGTTCCTCTAGTGCCGGCTCCGGAGAGCTC
TTAATTAAGCGGCCGCCCTGCAGGACTCGAGTTCTAGAAATAATTTGTTTAACTTTAAGAAGGAGATA
TACATATGAAATCTCTCACCATCACCATCACCATCACCACTGGTTCTTCTATGAAAATCGAAGA
AGGTAAAACTGGTAATCTGATTAACGGCGATAAAGGCTATAACGGTCTCGCTGAAGTCGGTAAGAATTC
GAGAAAGATACCGGAATTAAAGTCACGGTTGAGCATCGGATAAACTGGAAGAGAAATTCCACAGGTTG
CGGCAACTGCCGATGCCCCTGACATTATCTTCTGGCACCACGACCCTTTGGTGGCTACCGCTCAATCTGG
CCTGTTGGCTGAAATCACCCCGGACAATTAACCCGGACAAGCGGTTCCAGGACAAGCTGTATCCGTTTACTCGGATGCCGTA
CGTTACAACGGCAAGCTGATGCCTTACCGACGTGTTGAAGCGGTATCGTGATTTATAACAAGATC
TGCTGCCGAACCCGCAAAAACCTGGGAAGAGAATCCCGGGCTGATAAGAACTGAAAGGAAAGGTAA
GAGCGCGCTGATGTTCAACCTGCAAGAACCGTACTTCACCTGCCCCTGATTGCTGCTGACGGGTTAT
GGCGTTCAAGTATGAAAACGGCAAGTACGACATTAAAGACGTGGGGTGGATAACGCTGGGCGAAAGCGG
GTCTGACCTTCCTGGTTGACCTGATTAAAACAACGATCGAATGCAGACAAGATCCAACATGCAGA
AGCTGCTCTTTAATAAGGCGAAACAGCAGTCGAACATGCCGACCTCAAGGGTCAACATCCAACCGTTCGTTGCCG
AGCAAGGAATTATGGGTGTAACGCCGCCCCAGTACTGCCGACCTCAGGGGTCAACATCCAACATCGACACC
TGCTTGAGCGGCAGGTATTAACGCGCGACGTCTGAAGCGTTAATAACGCGGTAATAAGAGAGTGCCGTAAGCTGAAACTATCT
GAGGAAGAGTTGGCGAAAGATATCCACGTATTGCGCGCACTGTAATTCGAGCTGAACATAGCCCAGAAGGTGAAATCATGC
CGAACATCCCGCAGATGTCCGCTTTCGGTCCGTCCATGACCGAAGACGATGATCGCAACGCGCCAGCGTCG
TCAGACTGTGCATGAAGCCTGCAGAGACCGCAGATTCGAAGAGAGCGCAGACTTCCAATGCAATGGAGATCGAGTAAGCA
AACAACAACTCGGGATCGAGGAGAACCGATCATTCAGAAGAAAGACTGGCAGATGATCGTTTGCAGGTAAAGCA
GGTGAAATTCAAACTGCGCATCGATAAGACCGATAAAGAAAAAATTCATGAATTCCCGATGAAT
CAAAGGACCAGATAAACCCGCGTGGTAAACAGGTTAACAAGTACGTTAACAACAAAACCGTTTGCCAAGAGTCGTAAAAT
TTTGCAGCTGTGTTACCGAAATGGTATTGCAAAGTACGTATGCCAAGGTCGTAAAGCCGAACATAAATC
CGGCTTTACGCAACAACAGACAGCAATCAGCAAAACCATTTAACTATGCCATTCGCGAAGCCTTCATTC
AATATCCTGAACAGCAGCAGCAATCAGCAAAACCATTTAACTATGCCATTCGCGAAGCCTTCATTC
TGGATAAAAAGCATCAAAAGCAGGCAAAACGTAATGAAACGTCGCGTCAAGAACGTAAAAAAACGTCTGCA
GCAGTTTATCGATATGCGTGATGGTAAACGTGAAATTTGCCGACCATTAAAAGGTCAGAAGTGGATCGT
TTATTCATCCGAGCTGAATCACCAAAGATAAAAAGCTGGAAGATTTCGGGGTTATACCTGAGCATTA

TGCCCGAGATGCGGCGCGTGCGGCTGCTGGAGATGGGGACGCGATGGATATGTTCTGCCAAGGGTTGGT
TTGCGCATTCACAGTTCTCCGCAAGATTGATTGGCTCCAATTCTTGGAGTGGTGAATCCGTTAGCGAGG
TGCCGCGGCTTCCATTCAGGTCGAGGTGGCCCGGCTCCATGCACCGGACGCAACGCGGGGAGGCAGAC
AAGTATAGGCGCGCCTACAATCCATGCCAACCGTTCTGCTCGCCGAGGCGGCATAAATCGCC
GTGACGATCAGCGGTCCAATGATCGAAGTAGGCTGGTAAGAGCCGGAGGATCCTTGAAGCTGTCCCT
GATGGTCGTCATCTACCTGCCTGGACAGCATGCCGCCTGCAACGCGGACATCCGATCCGCCGAAGCGAG
AAGAATCATAATGGGGAAGGCCATCCAGCCTCGCGTCGCGAAGCCAGCAAGACGTAGCCAGCGCGTCG
GCCGCCATGCCGGCGATAATGCCTGCTTCTCCGGAAACGTTGGTGGCGGGACCAGTGACGAAGGTT
GAGCGAGGGCGTGCAAGATTCCGAATACCGCAAGCGACAGGCGATCATCGTCGCTCCAGCGAAAGCG
GTCCTGCCGAAAATGACCCAGAGCGCTGCGGCACCTGTCCTAGAGTTGCATGATAAAGAAGACAGTC
ATAAGTGGCGGACGATAGTCATGCCCCGCCCACCGAAGGAGCTGACTGGGTTGAAGGTCTCAAGG
GCATCGGTCGACGCTCTCCCTTATGCGACTCCTGCATTAGGAAGCAGCCACAGTCCCCGGCCCCGTT
GAGCACCGCCGCCAAGGAATGGTGCATGCAAGGAGATGGCGCCAACAGTCCCCGGCCACGGGCCT
GCCACCATACCAGCGAAACAAGGCGTCATGACCCGAAGTGGCGAGCCCGATCTTCCCCATCGGTGA
TGTCGGCGATATAGGGCGCCA (SEQ ID NO: 493)

FIG. 24E

Plasmid pLBH547_Tet-Cas14b2Locus (AddGene Plasmid Number: 112504)

```
ATGGTTGATAGAGTTATTTTACCACTCCCTATCCAGTGATAGAGAAAAGAATTCAAAGATCTAAAGAGGA
GAAGGATCTATGGAAGAAAGCATTATTACCGGTGTGAAATTCAACTGCCATCGCCATGATAAGAACCACC
AAAAACTGAACGAGTACTTCGATGAATATGGCAAAGCAATTAACTTCGCCGTGAAGATCATTCAGAAG
AACTGGCAGATGATCGTTTTGCAGGTAAAGCAAAACTGGACCAGAATAAAACCGATCCTGATGAAAA
CGGCAAAAAAATCTATGAAAATTCCCGGATGAATTTGCAGCTGTGGTAAACAGGTTAACAAGTACGTTAAC
AACAAACCGTTTGCCAGAGTGTATAAATCCGTTTACGGAAAATGGTATTGCGAAACGTATGTATA
GCGCCAAGGTCGTAAAGCCGAACATAAATCAATATCCTGAACAGCACCAACAGATCAGCAAAACCA
TTTAACTATGCCGCGAAGCCTTCATTCTGGATAAAACGCAGCGCAAAAACGTAAT
GAACGTCGCGTGAAGTAAAAACGTCTGCAGCCAGTTTATCGATATGCGTGATGGTAAACGTGAAATTT
GCCGACCATTAAAGGTCAGAAGTGGATGTTTATTCATCGAGCTGGATCACCAAAGATAAAAGCT
GGAAGATTTTGCGGTTATACCCTGAGCATTATCACAGCAAATTAAGATTCTGGATGCCAACATCAA
CGTCGAAGAAAACCTGAAAGAAAAAGCCAGATCATCTTAAAGCCAAACCTGCGAAGTCTGATGCTGATAAAT
CCATTCGTTTGTTGGTGATCCGCAAGTGCTGTTTACAATTAGTAAACCCTGCCGAAAGAGTATGAACT
GGATCTGCCGAGCAAAGAAAACGGCTGAATTGGCTGAAAGAAGAAGATGGAGATTATCAAGAACCAGAAA
CCGAAATATGCCTATCTGCTGCGCAAAAACATTGAGAGCGAAAAAACCAACTATGAGTACTATCTGC
AGTACACCCTGGAAATTAAACCGGAACTGAAAGATTTTATGATGGTGCCATTGGTATTGACCGTGGCAT
TAATCATTATGCCGTTTGCACCTTTGCAAAATCTATTAGCACGATGTAAGTTACCGTAAGTGTAAACACAACAGC
GGTGAAATTCTGCGTCTGAAAAATGCGCGTGAACAGGCAACAAAATCAATCTGATTCCTGCGTTATACCAAGCA
ATGCAAAAAGGCAACATGCCGATGAAAGCTGAAATCAATTGTTTTGAAGAACTGGGTCGTATTGGTAAAGC
GATTGTTGATATGGCCAAAAAAAGCAGCGTTATAAACTGAGCCTGTTCATCTTCCGCCTGAATTACCAGCAAGCA
GCACCAAAATGAAAAAGCCGTCGTGAAGTTATTCGTGTTACCTATGTTCCGCCTGAATATACCAGCAAGAATG
TTGATTACAAAGCCGTGAAAGCTGAAATGAACAGCAGCGTTATAATGCCGGATTATCACCAGGATATAATATCGCAAC
TAGCCATTGCGGGTGAAAAGTAATACCCAGCTGAACAGCAGCGATTATAATGCCGGATTATCACCAGGATAT
AATGTGGCATCAGCTGAAACAGCAGCGATTATAATGCCAGCATCAACATGAAAAGGCCTGAAATTC
CGAATAGCACTAATCTCAAGTCCGGAAGATTTGGCGTTGTGTTAAGCAATAAAGGGGTAACCCTGAA
ATTAATAATCTTCGAAGGCTATATAAACCTAGTTTGTTAATTGAGTTTATTGAGCTCAATAAAGTGAACAGACCAATTTT
AAGGTTGAAATCATATAAAACCTAGTTTATTTGAGTCCATCTTTATTATAAGTATATAACAAAAGTGTACATTCCAAAT
AATTCCGTTCTGATTAAAATCAGAATCTCTTTATAATAGTATAACAAAAGTGTACATTCCAAAT
```

FIG. 24F

```
CCGAAAGCAGAATTGACCTTTTTAAGCCTAAAAAGCCAAATTTCAAGCTCTTTCATACTCAGAACAAA
GGGATTAAGGAATGCAACTACCTTACACCGCTTGCGAAAGTTGTCAGAAGATAATCTTTCATACTCAGAA
CAAAGGGATTAAGATGCAACTATCTTATCCATTTCTTGACATCAAATTTCTTGCAGCATCTGAATTG
CTTAATTGCTTTCCTTGCTTGCTGTGTAGATTTTGTTCTTCAGGACCTTCTTTTCCATGCTAGAGTCAAGCA
CGGGGATTTGCTTGCTGTGTAGATTTTGTTCTTCAGGACCTTCTTTTCCATGCTAGAGTCACACTGC
TCACCTTCGGGTGGGCCTTTCTGGTTTATACCTAGGGATATATCCGCTTCCTGCTCACTGACTCGCT
ACGCTCGGTCGTTCGACTGCCGCGGCGAGCGGAAATGCTTACGAACGGGCGGAGATTCCTGAAGATGCC
AGGAAGATACTTAACAGGGAAGTGAGAGGGCGCGGCAAAGCCGTTTTCCATAGCCTCGCCCCCCTGA
CAAGCATCACGAAATCGACGTCAAATCAGTGGTGGCGAAACCCGACAGAGACTATAAAGATACCAGGCG
TTTCCCCCTGCGCTCCCTGCGCCTCGTGCCGTCTGCCTTTCGGTTACCGTGTCATTCCGCTGT
TATGGCCGCGGTTTGTCTCCACGCTCAGTCGCCCTTATCCGGTAACTATCGTCTGAGTCCAACC
GTATGCACGAACCCCGTTCAGTCGACCTGCGCTTATCCGGTAACTATCGTCTGAGTCCAACC
GAAAGACATGCAAAAGCACCAGTGGCAGCACCAAGTTTTGGTGACTGCGCTCCAAGCCAGTTACCTCG
ATGCCGCCGTTAAGGCTAAACTGAAAGGACAAGTTTTGGTGACTGCGCTCCAAGCCAGTTACCTCG
TTCAAAGATTGGTAGCTCAGTTAATGAAAACCGCCGTTCGTTTTCGTTTTCGTTTTCAGAGC
AAGAATTACGGCAGACCAAAACGATCTCAAGAAGATCATCTTATTAATCAGATAAATATTCTAGAT
TCAGTGCAATTACTCTCAATATGTAGCACCTGAAGTCACCGAGCCCATAGAGATATAAGTTGTACTAGTG
CTTGGATTCTCACCAATAAAAAACCGCCGGGGTCAAGCGAGTCGTTCTGAACAATCCAGATGGAGTTCTG
AGGTCATTACTGGATCTATCAACAGGAGTCCAAGCGAGCTCGATATCAATTACGCCCCGCCTGCCACT
CATCGCAGTACTGTTGTAATTCAGCCATTCTGCCGACATGGAAGCCATCACAAACGGCATGATGAAC
CTGAATGCGCCAGCGCATCAGCACCTTGTCGCCTTGCCGTATAATATTGGCCATGGTGAAAAACGGGCG
AAGAAGTTGTCCATATTGGCCACGTTAAATCAAACTCAAGCTGAACTCACCGGATTGGCTGAGACGA
AAACATATTCTCAATAAAACCTTTTAGGGAAATAGGCCAGTTTCACCGTAACACGCCACATCTTGCGA
ATATATTGTAGAACTGCCGGAAATCGTCGTGGTATTCACTCCAGACCGCTGAAACGTTCAGTTTGC
TCATGGAAAACGGTGTAACAAGGGTTGAACACTACTTTACCCCATATCACCAGCTCACCGTCTTCATTGCCATAC
GAAATTCGGATGAGCATTCATCAGCGCGGCAAGATGGAGGCCGATAAAGGCCGATATAAGGTCCGATA
TTTCTCTTTACGCGCTTCCTTAGCTCCTAGAAATCTGATAACTCGATAATCCGTAATACGCCCGGTTATAGGTCAACT
GACTGAAATGCCTCAAAATGTTCTTTACGATGCCATTGGGATATACTGCGTGTATCCAGTGATTT
TTTTCATTATGTGAAGTTGAAGCTTCTTCACATTTAAGTTGTTTTCTAATCCGCATATGATCAATTCAAGGCGAATAAGA
TATTTCATTATGTGAAGTTGAAGCTTGATCAATAATTCGATAGCTTGCTGTAATAATGGCGCGATACTATCAGT
AGGCTGGCTCTGCACCTTGGGTGATCAAATAATTCGATAGCTTGCTGTAATAATGGCGCGATACTATCAGT
```

FIG. 24G

AGTAGGTGTTTCCCTTCTTCTTAGGGACTTGATGCTCTTGATCTTCCAATACGCAACCTAAAGTAAAA
TGCCCCACAGGCTGAGTGCATATAATGCATTCTCTAGTGAAAAACCTTGTTGGCATAAAAGGCTAATT
GATTTCGAGAGTTTCATACTGTTTTCTGTAGGCCGTGTACCTAAATGTACTTTGCTCCATGCGATG
ACTTAGTAAAGCACATCTAAAACTTTTAGGGTTATTACGTAAAAAATCTGCCAGCTTCCCTTCTAAA
GGGCAAAAGTGAGTATGGTGCCTATCTAACATCTCAATGGCTAAGGCGTCGAGCAAGCCCGCTATTTT
TTACATGCCAATACAATGTAGGCTGCTCTACACCTAGCTTCTGGCGAGTTTACGGGTTGTTAAACCTTC
GATTCCGACCTCATTAAGCAGCTCTAATGCGCTGTTAATCACTTTACTTTTATCTAATCTAGACATCATT
AATTCCTAATTTTTGTGACACTCT (SEQ ID NO: 494)

FIG. 24H

Plasmid pLBH559_Tet-HisCas14a1Locus (AddGene Plasmid Number: 112502)

```
TAATTCCTAATTTTGTTGACACTCTATCGTTGATAGAGTTATTTACCACTCCCTATCAGTGATAGAGA
AAAGAATTCAAAAGATCTAAAGAGGAGAAAGGATCTATGAAATCTACCATCACCATGAAAACC
TGTACTTCCAATATTGGAAGTGGCCAAAAATGGCCAAAAACACCATTACCAAACACTGAAACTGCGTAT
TGTGGGTCCGTATAATAGCGCAGAAGTGGAAAAATTGTTGCCGACGAAAAACAACCCGAAAAATC
GCACTGGAAGAACAAAGAACAAAGAAGAGCCTGCAGCAAACATCTGAAGTTGCAGCATATTGTA
CCACACAGGTTGAACGTAATGCATGCCTGTTTTGTAAAGCACGTAAACTGGATGACAAATTCTACCAAA
ACTGCGTGGTCAGTTCCGGATGCAGTTTTTGGCAAGAAATCAGGAAATTTTCGCCAGCTGCAGAAA
CAGGCAGCAGAAATCTATAATCAGAGACCTGATCGAACTGTACTACGAGAATTTTATCAAGGCAAGGTA
TTGCAAATGCAGCAGCGGTTGAAATTCGAACATTATCGAGTGTTGTTATACCGTGCAGCAGCTGTTAA
AAACGCAGCAATTGCAAGCGGTCTGGTAGCAAATCAAAAGCAATTTTCGTCTGAAGAACTGAAAAAC
ATGAAAAAGTGTCTGCCGACCACCAAAAGCGATAATTTTCCGATTCCGGTTAAACAGAAAGGTGGTC
AGTATACCGGTTTTGAAATTAGCAATCATATAGCGACTTCATCATCAAGATTCCGTTTGGTGTTGGCA
GGTCAAAAAGAGATTGATAAATATCGTCCGTGGGAGAAATTTGACTTTGAACAGTTTGAGAAAAGCCCG
AAACCGATTAGCCTGCTGCTGAAAACCAGCAGGTGCTGTAAATAAAGTTGGAGCAAAGATGAAGGCA
CCGAAGCCGAAATCAAAAAATGGATTATGAAGGATGCTGAAATCTGAGCATTGATGTTCCGAAATGATAAGGTG
CAAATCGGTGAAAAAGCGCATGTGGTATTGATGTGGTGATTCACCGCTGGTTTGCGCAATTAACAATGCAT
GATCCGAGCATTATTGGGTAATTCAGCGATAACGACCTGTTTGCACTTCAACAAGAAAATGTTTGCACGTCGTCGTAT
TTAGCCCGTTATAGCATCAGCGATAACGACCTGTTTGCACTTCAACAAGAAAAACAAACTGAAACCGATCACCATT
CCTGCTGCTGAAAAAAACCGTCATAAACGTGCAGGTCAGGTCATGGTGCAAAAAAACAAACTGAAACCGATCACCATT
CTGACCGAAAAAGTGAACGTTTCCAAAAGTGATTGAACGTTGGCATGTGAATCGCGGATTTCT
TCATTAAAAACAAAGTTGGCACCGTCAGATGGAAAATCTGGAAAGCATGAAACGTAAAGAGGACAGTA
TTTAACATTCGCCTGCCGTGGCTTTGGCCGTATGCCCGTATGCAGAACAATCGAATTCAAACTGAAG
CAGTATGGCATCGAAATTCGTAAAGTTGCACCGAAGCCCTGAAATAATACCAGCAAAACCTGTAGCAAATGTGGCCATC
TTCAAAGAAAAACGCCGATTATATACTTCGAGTCAGCCCCGAATATTTCAAACCGACACTTAAATGCGAAAATGCAA
CTTCAAAGAAAAACGCCGATTATATACTTTATCCTTCATTGACAAAATGAGAATGTTATCCCAGATAACATTTG
GAACCGTAAATATTTATTATCCTTCATTGACAAAATGAGAATGTTATCCCAGATAACATTTG
ATGTACACAGATTCACACTTCACTGATAAAGTTGGAGAACCGTTCACCAAAAGTCCTCCCTTAGGGATT
AGAACTGAGTGAAGTGGTGCTTGCATCAGCCTAATGTCGAGAAGTGCTTTTCTCGAAAGTAACCC
TCGAAACAAATTCATTTTCCTCTCCAATTCTGCACAAAAAGGTGAGTCCTTATAACCGGCGTGCAG
```

FIG. 24I

CATATAATGCATTCTCTAGTGAAAAACCCTTGTTGGCATAAAAAGGCTAATTGATTTTCGAGAGTTTCATA
CTGTTTTCTGTAGGCCGTGTACCTAAATGTACTTTTGATCCATCGCGATGACTTAGTAAAGCACATCTA
AAACTTTAGCGGTTATTACGTAAAAATCTGCCAGCTTCCCCTCTAAAGGGCAAAGTGAGTATGGT
GCCTATCTAACATCTCAATGGCTAAGGCGTCGAGCAAAGCCCGCTTATTTTTACATGCCAATACAATGT
AGGCTGCTCTACACCTAGCTTCTGGGCGAGTTTACGGGTTGTTAAACCTTGATTCCGACCTCATTAAGC
AGCTCTAATGCGCTGTTAATCACTTTTATCTAATCTAGACATCAT (SEQ ID NO: 495)

Plasmid pLBH545_Tet-Cas14a1_Locus (Addgene Plasmid Number: 112501)

```
TTACTTTTATCTAATCTAGACATCATTAATTCCTAATTTTTGTTGACACTCTATCGTTGATAGAGTTATT
TTACCACTCCCTATCCAGTGATAGAGAAAAGAATTCAAAAGATCTAAAGAGGAGAAAGGATCTATGGCCAA
AACACCATTACCAAACACTGAAACTGCGTATTGTGCGTCCGTATAATAGCGCAGAAGTGCAAGTGGAAAAATT
GTTGCCGACGAAAAAACAACCGCGAAAAAATGCACTGGAAAGAACAAAGACAAAGTGAAGTGAAGAAGCCT
GCAGCAAACATTGAAGTTGCAGACAAATTCTACCACACAGGTTGAACGTAATGCATGCCTGTTTTTGTAA
AGCACGTAAACTGATGACAAATTCTACCAAAAACTGGCTGGTTCAGTTCCGGATGCAGTTTTTGGCAA
GAAATCAGCGAAATTTTGCCCAGCAGCTGCAGAAACAGGCAGCAGAATCTATAATCGAGACCTGATCGAAC
TGTACTACGAGATTTTTATCAAAGGCAAAGTATTGCAAAGGTCCAGCAGGTTGAAACATTATCTGAGTGA
TGTTTGTTATACCGTGCAGCAGCAAACTGTTAAAACGCAGCAATTGCAAGGTCTGCGTAGCAAATC
AAAAGCAATTTTCGTCTGAAAGAACTGAAAACATGAAAAGTGGTCTGCCGACCACCAAAAGCGATAATT
TCCGATTCCGCTGGTTAAACAGAGAAGGTGGTCAGTATACCGGTTTGAAATTAGCAATCATAATAGCGA
CTTCATCATCAAGATTCCGTTTGGTCGTTGGCAGGTCAAGGCACCGAAATGACGGATAAATATCGTCGTGGAG
AAATTTGACTTTGAACAGGTTCAGAACGCCGAAAGCCTGAGCCTGCAAAAATCAAAAAGTTATGCGATTA
ACGTAATAAAGGTTGGAGCAAAGATGAAGGCACCGAAGCCGAAATCAAAAGTTGTGAAAAAGCGATTATGCCATTA
TCAGACCAGTCACATTGAAGTTAAACGTGGCAGCATTATTGGCGTTATAGCCGGATACAGGATAATCTG
AGCATTGATGTTCGAAATTGATAAAGGCTACACGGATTTCTTTTAACAATGCATTTAGCCGTTATAGCCGTTA
AATCACGCTGGTTTGCGCAATGTTTGCACGTCGTCGTATCCGAGCATTAGCCGTTATCTCTGCTGAAA
CTTCAACAAGATATGTTTAAACTGAAATCGAAATCGAACACCGATCACCATTCTGACCGAAAAAAACAAGATGAACGTCAGGTCAT
GGTGCAAAAACTGAAACCGAAAATCGAAATGTGGCATCTGAACAATATTTCAACTTCGAGTACCGGCAAGATCA
TGAAACGTTGGCATGAAAGCATGAAACGTAAACTTCAACGTATGGCATCTGAACAACTATTTCAACTTCGAGTACCGGCAAGAAATA
TCTGGAAAAGCAGCATGAAACGTAAAGAGGACAGCTATTTTTAACATTGCCTGCGTGGCTTTGGCCGTATCGA
GAAATGCAGAACAAATCGAAATCAAACTGCAAACTTGGCATGCAGTATGGCATCTGAACTAGTAACCGATA
ATACCAGCAAAACCTGTAGCAAATGTGGCCATCTGAACAACTATTTCAACTTCGAGTACCGCAAGAAAAA
CAATTCCCGCACTTTAAATGCGAAAACTGAAAGCACCAAAGAGGAACGTAAATATTTATACTTTATATCCTTCATTGA
ATTCAAACCGCACTTAATGTTATCCCAGATAACATTGATGTAGAACTTGAGTGAGTTGAAGTGAGTTAAGTGGAGA
CAAAATGAGAATGTTATCCCAGATAACATTAGGGGGATTAGAACTTGAGTGAGTTGAAGTGAGTTAAGTGGAGA
ACCGCTTCACCAAAGCTGTCCCTTAGGGGATTAGAACCTGAAGTGATTGGTGGGCTGCTTGCATCAGCTA
ATGTCGAGAAGTGCTTCTTCGAAGTAACCCTCGAAACAAATTCATTTTTCCTCCAATTCATTCGCACA
```

FIG. 24L

```
AAAAAAGGTGAGTCCTTATAAACCGGCGTGCAGAACGCCGGCTCACCTTTTTCTTCATCGATTTATG
CTTAAAGCCGTAAAACGCGGAATTCGGCCCGTTGCAGAACCCGACAGAACCGAATAGACGAATGAAGGAATGCAAC
TACCTTACACCGCTTGCGAAAGTTGTCAGAAGATAATCTTGCAGAACCCGAATAGACGAATGAAGGAATG
CAATCTGACAGAGCCCGATTGCGTTATCCGTTATCCAGGAGAAACATATAAAGCATCACCGCTGATCGGACT
AGAGTCACACTGGCTCACCTTCGGGGTGGGCTTTCTGCGTTTATACCTAGGGATATATTCCGCTCCTCG
CTCACTGACTGCTACGCTCGGTCGTTGCAGTGCGGCGAGCGAGGTTACGAACGGGGCGGAGATT
TCCTGGAAGATGCCAGGAAGATACTTAACAGGAAGTGAGAGGGCGGGCAAAGCCGTTTTCCATAGG
CTCCGCCCCTGACAAGCATCACGAAATCTGACGTCAAATCAGTGGTGGCGAAACCGACAGACTAT
AAAGATACCAGGCGTTTCCCCTGGCGTCCCGTGGCCTCTCCTGTTCCTGCCTTTCGGTTTACCGG
TGTCATTCCGCTGTTATGGCGGCGTTTGTCATTCCACGCCTGACACTCAGTTCCGGGTAGCAGTTCG
CTCCAAGCTGACTGTATGCACGAACCCCCGTTCAGTCAGCCCCTTATCCGGTAACTATCGT
CTTGAGTCCAACCCGAAAGACATGCAAAAGCACCACTGCCAGCAGCCACTGGTAATTGATTTAGAGGAG
TTAGTCTTGAAGTCATCGCCCGGTTAAGGCTAAACTGAAGACAAGTTTGGTGACTGCGCTCTCCAA
GCCAGTTACCTCGGTTCAAGAGTTGGTAGCTCAGAGCCAGACCAAACGCCCTGAAAAAACGCCCTGCAAGGCGGTTTT
TCGTTTCAGAGCAAGAGATTACGGCCAGACCAAACGATCTCAAGAAGATCATCTTATTAATCAGATA
AAATATTCTAGATTCAGTGCAATTTATCTCTCAAAATGTAGCACCTGAAGTCAGCCCATCAGCCCATACGATATA
AGTTGTTACTAGTGCTTGGATTCTCACCAATAAAAAACGCCCGGCCGCAACCGAGCGGTTCTGAACAATC
CAGATGGAGTTCTGAGGTCATTACTGGATAACTACTGTGTATCGCAGTACATTCATTAAGCATTCTGCCGACATGAGCCATACGC
CCGCCCTGCCACTCATCGCCAGTACTGTGTATCGCCAGTACATTCATTAAGCATTCTGCCGACATGAGAAGCCATCACAA
ACGGCATGATGAACCTGAATCGCCAGCGGCATCAGCACCTTGTGCCTTGGCTATATATTGCCATGG
TGAAACGGGCGGAAGAAGAAGTTGTCCATATTGGCCACGTTTAAATCAAACTGGTGAAACTCACCCAGGG
ATTGGCTGAGACGAAGAAACATATTCTCAATAAACCCTTTAGGAAATAGGCCAGTTTCACCGTAACAC
GCCACATCTTGCGAATATATGTAGAAACTGCCAAAGGGTGAACACTATCCACCAGCTACCGCTC
ACGTTCAGTTTGCTCATGGAAAACGGTGTAACAAGGGTGAACACTATCCACCAGCTACCGCTC
TTTCATTGCCATACGAAATTCCGATGAGCATTCATCAGCGGGCAAGAATGTGAATAAGGCCGGATAA
AACTTGTGCTTATTTTTCTTTACGGTCTTAAAAGCCGTAATATCCAGCTGAACGGTCGGTTATAGG
TACATTGAGCAACTGACTGAAATGCCTCAAAAGTTCTTTACGATGCCATTGGGATATCAAGGTGGT
ATATCCAGTGATTTTTCTCCATTTTAGCTTCCTTAGCTCCTGAAAATCTGATAACTCAAAAATACG
CCCGGTAGTAGTCGGTCTTAAGACCACTTCACATTAAGTTGAACCTCTTACGTGCCGATCAACGTCTCATTTC
GCCAGATATCGACGTCTTAAGACCCACTTCACATTTAAGTGTTTTCTAATCCGCATATGATCAATTC
AAGGCCGAATAAGAAGGCTGGCTCGCACCTGGTCTGCAACCTTGTGTATCGATAGCTTGTCGTAATAATGGC
GGCATACTATCAGTAGTAGGTTGTTCCCTTTCTCTTAGGACTTGAGCTCTTGAGATCCTTGATCTTCCAATACGC
```

FIG. 24M

AACCTAAAGTAAATGCCCCACAGCGCTGAGTGCATATAATGCATTCTCTAGTGAAAAACCTTGTTGGCA
TAAAAGGCTAAATTGATTTCGAGAGTTCATACTGTTTTCTGTTAGGCCGTGTACCTAAATGTACTTTT
GCTCCATGCGATGACTTAGTAAAGCACATCTAAAACTTTAGCGTTATTACGTAAAAATCTTGCCAGC
TTTCCCCTTCTAAAGGGCAAAAGTGAGTATGGTGCCTATCTAACATCTCAATGGCTAAGGCGTCGAGCAA
AGCCCGGCTTATTTTTACATGCCAATACAATGTAGGCTGCTCTACACCTAGCTTCTGGGCGAGTTACGG
GTTGTTAAACCTTCGATTCCGACCTCATTAAGCAGCTCTAATGCGCTGTTAATCACT (SEQ ID NO: 496)

FIG. 24N

Plasmid_pLBH531_MBP-Cas14a1 expression (Addgene Plasmid Number: 112500)

```
ACCCACGCCGAAACAAGGCTCATGAGCCGAAGTGGCGAGCCCGATCTTCCCCATCGGTGATGTCGGCG
ATATAGGCGCCAGCAACCGCTGTGGCGGTGATGCCGGCCACGATGCGTCCGCGTAGAGGATCG
AGATCTCGATCCCGGGAAATTAATACGACTCACTATAGGGAGACCACAACGGTTTCCCTCTAGTGCCGGC
TCCGGAGAGCTCTTTAATTAAGCGGCCGCCCTGCCAGACTCGAGTTCTAGAAATAATTTGTTTAACTTT
AAGAAGGAGATATACATATGAAAATCTTCTCACCATCACCATCACCATCACCATGGTTCTTCTAT
GAAATCGAAGAAGGTAAACTGGTAATCTGATTAACGGGATAAAGGCTATAACGGTCTGCTGAAGTC
GGTAAGAAATTCGAGAAAGATACCGGAATTAAAGTCACCGTTGAGCATCCGGATAAAGTCACTGGAAGAGAAAT
TCCACAGGTTGCGCAACTGGCGATGCCCAACGTTCCAGGACGCACAGCCCGCTTGGTGGCTA
CGCTCAATCTGGCCTGTTGGCTGAAATCACCCCGGACAAAGGTTCCAGGACAAGCTGAAGCTGAAGCGTTACC
TGGGATGCCGTACGTTACAACGGCAAGCTGATTGCTTACCGCTGTGAAGCTGTTATCGCTGATTT
ATAACAAAGATCTGCTGCCGAACCGCCAAACCTGGAAGTCCGGAAGAGATCCGGCTGGATAAGAACTGAA
AGCGAAAGTAAGAGGCGCTGAIGTTCAAGTTGAAAACCGTACTCACCTGCCGCTGATTGCTGCT
GACGGGGTTATGCGTCAAGTATGATGAAAACGGCAAGTACGACATTAAAGACGTGGGCCTGGATAACGCTG
GCGCGAAAGCGGGTCTGAACCTTCCTGGTTGACCTGAATTAAAACACAACATGAATGCAGACACGATTA
CTCCATGCCAGAAGCTGCTCTTTAATAAGCGAACAGCGATGACCATCAACGGCCCGTGGGCATGGTCC
AACATCGACACCAGCAAAGTGAATTATGGTGTAACGGTACTGCCGACCTTCAAGGGGTCAACCATCCAAAC
CGTTCGTTGCGTTGAGCGCAGGCAGTATTAACGCCGCCAGTCGAACAAGAGCTGGCAAAGAGTTCCT
CGAAAACTATCTGCTGACTGATGAGGTCTGGAAGGGTTAATAAGACAAACCGCTGGGTGCCGTAGCG
CTGAAGTCTTACGAGAAGAGTTGGCGAAAGATCCAAGCTACCACGTTTTCTGGTATGCCGCCACTATTGCCCCCACTATGAAAACGCCAGAAAG
GTGAAATCATGCCGAACATCCGCAGATGTCCGTTGCGGAAGACCGTATGCCGGTACTGCGGGTGATCAACGC
CGCCAGCGTCGTCAGATGACTGTGGAGCCTGGATGAAGCGCCAGACTAATTGGCCAGCTCGAACAACAAC
AACAATAACAATAAACAACAACTCGGAAGATCGAGGAAAACCTGTACTTCCAATCCATGGCCAAA
ACCATTACCAAACCCGGAAAAAATGCACTGCGTATTGTGCGTCCGTATATAGAAGAACAAAGACAAGTGAAGAGCCTGC
TGCCGACGAAAAAAAACACCGGAAACAGGCCAGCAGAACAGGCAGCATATGTACCACCAGGTTGAAGTAATGCATGCCTGTTTGTAAAG
AGCAAGCATCTGAAAGTTGCAGCATATGTACCACCAGGTTGAAGTAATGCATGCCTGTTTGTAAAG
CACGTAAACTGGATGACAAATTCTACCAAAAACTGGTGGTCAGTTTCCGGATGCAGTTTTTGGCAAGA
AATCAGCGAAATTTTCGCCAGCTGCAGAACAGGCAGCAGAAATCTATAATCAGAGCCTGATCGAACTG
```

FIG. 240

```
TACTACGAGATTTTATCAAAGGCAAACTGTATTGCAAATGCCAGCAGCGTTGAACATTATCTGAGTGATG
TTGTTATACCCGTGCAGCAGCAGAACTGTTTAAAAACGCAGCAATTGCAAGCGGTCTGCTAGCAAATCAA
AGCAATTTCGTCGAAAGAACTGAAAAACATGAAAAAGTGGTCTGCGACCACCAAAAGCGATAATTTT
CCGATTCCGCTGGTTAAACAGAAGTGGTCAGTATACCGGTTTTGAAATTAGCAATCATATAGCGACT
TCATCATCAAGATTCCGTTGGTCGTTGGCAGGTCAAAAAAGAGATTGATAAATATGTCCGTGGGAGAA
ATTGACTTTGAACAGGTTCAGAAAGCCGAAAAGCCGATTAGCCTGCTGAGCACCCAGCGTCGTAA
CGTAATAAAGTTGGAGCAAAGATGAAGGCACCGAAGCCGAAATCAAAAAGTTATGAATGGCGATTATC
AGACCAGTACATTGAAGTTAAACGTGGCAGCAAATCTGTGAAAAAAGCATGGATGCTGAATCTGAG
CATTGATGTTCCGAAAATTGATAAAGGTGTGATTCCGAGCATTAGCCGTGTATTGGTGGTGTTAAA
TCACCGCTGGTTGCCGCAATTAACAATGCCGTCGTATCCTGCTGAAAAAAAACCGTCATAAACGTTCAGGTCATGG
TCAACAAGAAATGTTTGCACGTGTCGTATCCTGCTGAAAAAAACCGTCATAAACGTCAGGTCATGG
TGCAAAAAACAACTGAAACTGAATCAGTATGGCATCGAAATTCGTAAAGTTGCACCGAATAAT
GAACGTTGGGCATGTGAAATCGCGGATTTCTTCATTAAAACAAGTTGGCACCGTGCAGATGGAAATC
TGGAAGCATGAAAGTAAGAGGACAGTATTTAACATTGCCTGCCGTGGCTTTGCGTAATCGCGAGA
AATGCAGAACAAACTGAATTCAAACTGAATGGCATCGAAATTCGTAAAGTGTACCGAATAAT
ACCAGCAAAACTGTAGCAAATGTGGCCATCTGAACAACTATTCACTTCGAGTACCGCAAGAAAAACA
AATTCCCGCACTTTAAATGCGAAAATGCAAACTTCAAAGAAACGCCGATTATAATGCAGCCCTGAATAT
TCAAACCCGAAACTGAAACTGAAAAAGCACCAAGAGAACCGTAATAACATTGGAATGGAATCCGGA
TCCGGCGGCCGCCACCTGGTGCCGCCGCCGGAACTGGCGCCGCTGAGCCGTGATCGCGTACTGCTACAAGCCCGA
AAGGAAGCTGAGTTGGCTGCTGCCAGGAGAACTAGCATAATCCGGATATCCACAGGACGGGTGTGTGCCATGA
TCTTGAGGGTTTTTGCTGAAAGGAGCTCCAAGTAGAAATTGCATCAACGCATCAACGCTAGCAGCCAGCACATGGAAAGCACCTATGCCTA
TCGGGTAGTGAAGCGGCTCGATGGGTGCATAGAGGCCTCCAAGTAGAAATTGCATCAACGCATCAACGCTAGCAGCCAGCACGTGGACAG
TGCTCCGAGAACGGCACTTTGCGGGAAGAATGGCCATAGAGGCCCGGCAGTAGCGCAGTACCGGCATAACAAGCCTAGCCTAGCCTA
GGGATGCTGTCCAGGGACGATGCCGAGATCCGCAAGAGGCCCGGCAGTAGCGCAGTACCGGCATAACAAGCCTAGCCTAGCCTA
CAGCCATCCAGGGGTGCCGAGCATCGACATGACGATGAGCGCATTGTTAGATTCATACACGGTCCCTGACT
GCGTTAGCAATTAACTGTGATAACCTGGTGAAAATCGCGATTAAGCTTATCGATGATAAGCTTATCGATGATAAGCTTATCGATGAAAGTGATAAGCTTATCGATGATAAGCTTATCGATGATAAGCTTATCGATGAAA
TTCTTGAGACGAAAGGCCTCGTGATACCCTATTTTATAGGTAATGTCATGATAATAATGTTCT
TAGAGGTCAGGTGGCACTTTCGGGGAACATGTGCGGGAACCCTGTTTCGGCATTTGTTATTTTCTAAATACATT
CAATATGTATCCGCTCATGAGACAATAACCCTGATAAATGCTTCAATAACATTGAAAAGGAAGAGTAT
GAGTATTCAACATTTCCGTGTCGCCCTTATTCCCTTTTTTGCGCATTTTGCCTTCCTGTTTTTGCTCAC
CCAGAAACGCTGGTGAAAGTAAAAGATGCTGAAGATCAGTTGGGTGCACGAGTGGGTTACATCGAACTGG
```

GCGGCGGGACCAGAGAAAAATCACTCAGGGTCAATGCCAGGCCTTCGTTAATACAGATGTAGGTGTTCCA
CAGGGTAGCCAGCAGCATCCTGCGATGCAGATCCCGGAACATAATGGTCAGGGCCTGACTTCCGCGTTT
CCAGACTTTACGAAACACGGAAACCGAAGACCATTCATGTTGCTCAGGTCGCAGACGTTTGCAGCA
GCAGTCGCTTCGCTTCCGTCGCGTATCGCGTATCGCGTAATTCATTCGCTAACCAGTAAGCAACCCGCCAGCCT
AGCCGGGTCCTCAACGACAGGAGCACGATCATGCGCACCCGTGGCCAGGACGCCCAACGCTGCCCGAGATGC
GCCGCGTGCCGCTGTCTGAGATGGCGGACGCGATGGATATGTTCTGCCAAGGGTTGGTTTGCATTCAC
AGTTCTCCGCAAGAATTGATTGGCTCCAATTCTTGGAGTTGGTGAATCCGTTAGCGAGGTGCCGCGGCTT
CCATTCAGTCAGGTGCAGGTCGAGGTGCCCGGCTCCATGCACCGGCAACGCGGAGCAACGGGAGCAGACAAGTAGGC
GGCGCCTACAATCCATGCCAACCCGTTCCATGTGCTCGTCGCCGAGGCGGGCATAATCGCCGTGACGATCAGC
GGTTCCAATGATGAAGTTAGGCTGGTAAGAGCCGGAGGCGATCTTGAAGCTGTCCCTGATGGTCGTCAT
CTACCTGCCTGGACAGCAGCCATGGCCTGCGTCGCGAACGCCGGGCATCCGATGCGAAGCGAGAAGCCGGTCCAGCCGCGCCATGCCG
GGGAAGGCCATCCAGCCTTCTCGCCGAAACGTTTGGGCGGGACCAGTAGCGACGAAGGCTTGAGCGAGGGGT
GCGATAATGGCCCTGCTTCTCGCCGAAACGTTTGGGCGGGACCAGTAGCGACGAAGGCTTGAGCGAGGGGT
GCAAGATTCCGAATACCGCAAGCGACAGGCCGATCATCGTCGCTCGCCGCTCCAGGAAAGCGTCCTCGCGAA
AATGACCCAGAGCGCTGCCGGCACCTGTCCTACGAGTTGCATGATGAAAGAAAGACAGTCATAAGTGCGGCG
ACGATAGTCATGCCCCGCCCCAACAGTCGCCCAACAGTCGCCCAACAGTGACTGGGGTTGAAGCAGTCTCAAGGCATCGGTGAC
GCTCTCCCTTATGCGACTCCTGCATTAGGAAGCCAGCAGCAGCCCAGTAGTAGTTGAGGCGTTGAGCACCGCCGAC
CGCAAGGAATGGTGCAATGCAAGGAGATGGCGCCCAACAGTCGCCCACGGCCCACGGGCCACGGGCCCTGCCACCAT (SEQ ID NO: 497)

SEQUENCE LISTING

```
Sequence total quantity: 373
SEQ ID NO: 1           moltype = AA  length = 500
FEATURE                Location/Qualifiers
REGION                 1..500
                       note = Synthetic sequence
source                 1..500
                       mol_type = protein
                       organism = synthetic construct
SEQUENCE: 1
MEVQKTVMKT LSLRILRPLY SQEIEKEIKE EKERRKQAGG TGELDGGFYK KLEKKHSEMF   60
SFDRLNLLLN QLQREIAKVY NHAISELYIA TIAQGNKSNK HYISSIVYNR AYGYFYNAYI  120
ALGICSKVEA NFRSNELLTQ QSALPTAKSD NFPIVLHKQK GAEGEDGGFR ISTEGSDLIF  180
EIPIPFYEYN GENRKEPYKW VKKGGQKPVL KLILSTFRRQ RNKGWAKDEG TDAEIRKVTE  240
GKYQVSQIEI NRGKKLGEHQ KWFANFSIEQ PIYERKPNRS IVGGLDVGIR SPLVCAINNS  300
FSRYSVDSND VFKFSKQVFA FRRRLLSKNS LKRKGHGAAH KLEPITEMTE KNDKFRKKII  360
ERWAKEVTNF FVKNQVGIVQ IEDLSTMKDR EDHFFNQYLR GFWPYYQMQT LIENKLKEYG  420
IEVKRVQAKY TSQLCSNPNC RYWNNYFNFE YRKVNKFPKF KCEKCNLEIS ADYNAARNLS  480
TPDIEKFVAK ATKGINLPEK                                              500

SEQ ID NO: 2           moltype = AA  length = 507
```

```
FEATURE                 Location/Qualifiers
REGION                  1..507
                        note = Synthetic sequence
source                  1..507
                        mol_type = protein
                        organism = synthetic construct
SEQUENCE: 2
MEEAKTVSKT LSLRILRPLY SAEIEKEIKE EKERRKQGGK SGELDSGFYK KLEKKHTQMF    60
GWDKLNLMLS QLQRQIARVF NQSISELYIE TVIQGKKSNK HYTSKIVYNR AYSVFYNAYL   120
ALGITSKVEA NFRSTELLMQ KSSLPTAKSD NFPILLHKQK GVEGEEGGFK ISADGNDLIF   180
EIPIPPFYEYD SANKKEPFKW IKKGGQKPTI KLILSTFRRQ RNKGWAKDEG TDAEIRKVIE   240
GKYQVSHIEI NRGKKLGDHQ KWFVNFTIEQ PIYERKLDKN IIGGIDVGIK SPLVCAVNNS   300
FARYSVDSND VLKFSKQAFA FRRRLLSKNS LKRSGHGSKN KLDPITRMTE KNDRFRKKII   360
ERWAKEVTNF FIKNQVGTVQ IEDLSTMKDR QDNFFNQYLR GFWPYYQMQN LIENKLKEYG   420
IETKRIKARY TSQLCSNPSC RHWNSYFSFD HRKTNNFPKF KCEKCALEIS ADYNAARNIS   480
TPDIEKFVAK ATKGINLPDK NENVILE                                      507

SEQ ID NO: 3            moltype = AA   length = 529
FEATURE                 Location/Qualifiers
REGION                  1..529
                        note = Synthetic sequence
source                  1..529
                        mol_type = protein
                        organism = synthetic construct
SEQUENCE: 3
MAKNTITKTL KLRIVRPYNS AEVEKIVADE KNNREKIALE KNKDKVKEAC SKHLKVAAYC    60
TTQVERNACL FCKARKLDDK FYQKLRGQFP DAVFWQEISE IFRQLQKQAA EIYNQSLIEL   120
YYEIFIKGKG IANASSVEHY LSDVCYTRAA ELFKNAAIAS GLRSKIKSNF RLKELKNMKS   180
GLPTTKSDNF PIPLVKQKGG QYTGFEISNH NSDFIIKIPF GRWQVKKEID KYRPWEKFDF   240
EQVQKSPKPI SLLLSTQRRK RNKGWSKDEG TEAEIKKVMN GDYQTSYIEV KRGSKIGEKS   300
AWMLNLSIDV PKIDKGVDPS IIGGIDVGVK SPLVCAINNA FSRYSISDND LFHFNKKMFA   360
RRRILLKKNR HKRAGHGAKN KLKPITILTE KSERFRKKLI ERWACEIADF FIKNKVGTVQ   420
MENLESMKRK EDSYFNIRLR GFWPYAEMQN KIEFKLKQYG IEIRKVAPNN TSKTCSKCGH   480
LNNYFNFEYR KKNKFPHFKC EKCNFKENAD YNAALNISNP KLKSTKEEP              529

SEQ ID NO: 4            moltype = AA   length = 726
FEATURE                 Location/Qualifiers
REGION                  1..726
                        note = Synthetic sequence
source                  1..726
                        mol_type = protein
                        organism = synthetic construct
SEQUENCE: 4
MERQKVPQIR KIVRVVPLRI LRPKYSDVIE NALKKFKEKG DDTNTNDFWR AIRDRDTEFF    60
RKELNFSEDE INQLERDTLF RVGLDNRVLF SYFDFLQEKL MKDYNKIISK LFINRQSKSS   120
FENDLTDEEV EELIEKDVTP FYGAYIGKGI KSVIKSNLGG KFIKSVKIDR ETKKVTKLTA   180
INIGLMGLPV AKSDTFPIKI IKTNPDYITF QKSTKENLGK IEDYETGIEY GDLLVQITIP   240
WFKNENKDFS LIKTKEAIEY YKLNGVGKKD LLNINLVLTT YHIRKKKSWQ IDGSSQSLVR   300
EMANGELEEK WKSFFDTFIK KYGDEGKSAL VKRRVNKKSR AKGEKGRELN LDERIKRLYD   360
SIKAKSFPSE INLIPENYKW KLHFSIEIPP MVNDIDSNLY GGIDFGEQNI ATLCVKNIEK   420
DDYDFLTIYG NDLLKHAQAS YARRRIMRVQ DEYKARGHGK SRKTKAQEDY SERMQKLRQK   480
ITERLVKQIS DFFLWRNKFH MAVCSLRYED LNTLYKGESV KAKRMRQFIN KQQLFNGIER   540
KLKDYNSEIY VNSRYPHYTS RLCSKCGKLN LYFDFLKFRT KNIIIRKNPD GSEIKYMPFF   600
ICEFCGWKQA GDKNASANIA DKDYQDKLNK EKEFCNIRKP KSKKEDIGEE NEEERDYSRR   660
FNRNSFIYNS LKKDNKLNQE KLFDEWKNQL KRKIDGRNKF EPKEYKDRFS YLFAYYQEII   720
KNESES                                                             726

SEQ ID NO: 5            moltype = AA   length = 517
FEATURE                 Location/Qualifiers
REGION                  1..517
                        note = Synthetic sequence
source                  1..517
                        mol_type = protein
                        organism = synthetic construct
SEQUENCE: 5
MVPTELITKT LQLRVIRPLY FEEIEKELAE LKEQKEKEFE ETNSLLLESK KIDAKSLKKL    60
KRKARSSAAV EFWKIAKEKY PDILTKPEME FIFSEMQKMM ARFYNKSMTN IFIEMNNDEK   120
VNPLSLISKA STEANQVIKC SSISSGLNRK IAGSINKTKF KQVRDGLISL PTARTETFPI   180
SFYKSTANKD EIPISKINLP SEEEADLTIT LPFPPFEIKK EKKGQKAYSY FNIIEKSGRS   240
NNKIDLLLST HRRQRRKGWK EEGGTSAEIR RLMEGEFDKE WEIYLGEAEK SEKAKNDLIK   300
NMTRGKLSKD IKEQLEDIQV KYFSDNNVES WNDLSKEQKQ ELSKLRKKKV EELKDWKHVK   360
EILKTRAKIG WVELKRGKRQ RDRNKWFVNI TITRPPFINK ELDDTKFGGI DLGVKVPFVC   420
AVHGSPARLI IKENEILQFN KMVSARNRQI TKDSEQRKGR GKKNKFIKKE IFNERNELFR   480
KKIIERWANQ IVKFFEDQKC ATVQIENLES FDRTSYK                           517

SEQ ID NO: 6            moltype = AA   length = 481
FEATURE                 Location/Qualifiers
REGION                  1..481
                        note = Synthetic sequence
```

```
source                    1..481
                          mol_type = protein
                          organism = synthetic construct
SEQUENCE: 6
MKSDTKDKKI IIHQTKTLSL RIVKPQSIPM EEFTDLVRYH QMIIFPVYNN GAIDLYKKLF    60
KAKIQKGNEA RAIKYFMNKI VYAPIANTVK NSYIALGYST KMQSSFSGKR LWDLRFGEAT   120
PPTIKADFPL PFYNQSGFKV SSENGEFIIG IPFGQYTKKT VSDIEKKTSF AWDKFTLEDT   180
TKKTLIELLL STKTRKMNEG WKNNEGTEAE IKRVMDGTYQ VTSLEILQRD DSWFVNFNIA   240
YDSLKKQPDR DKIAGIHMGI TRPLTAVIYN NKYRALSIYP NTVMHLTQKQ LARIKEQRTN   300
SKYATGGHGR NAKVTGTDTL SEAYRQRRKK IIEDWIASIV KFAINNEIGT IYLEDISNTN   360
SFFAAREQKL IYLEDISNTN SFLSTYKYPI SAISDTLQHK LEEKAIQVIR KKAYYVNQIC   420
SLCGHYNKGF TYQFRRKNKF PKMKCQGCLE ATSEFNAAA NVANPDYEKL LIKHGLLQLK   480
K                                                                  481

SEQ ID NO: 7              moltype = AA  length = 358
FEATURE                   Location/Qualifiers
REGION                    1..358
                          note = Synthetic sequence
source                    1..358
                          mol_type = protein
                          organism = synthetic construct
SEQUENCE: 7
MSTITRQVRL SPTPEQSRLL MAHCQQYIST VNVLVAAFDS EVLTGKVSTK DFRAALPSAV    60
KNQALRDAQS VFKRSVELGC LPVLKKPHCQ WNNQNWRVEG DQLILPICKD GKTQQERFRC   120
AAVALEGKAG ILRIKKKRGK WIADLTVTQE DAPESSGSAI MGVDLGIKVP AVAHIGGKGT   180
RFFGNGRSQR SMRRRFYARR KTLQKAKKLR AVRKSKGKEA RWMKTINHQL SRQIVNHAHA   240
LGVGTIKIEA LQGIRKGTTR KSRGAAARKN NRMTNTWSFS QLTLFITYKA QRQGITVEQV   300
DPAYTSQDCP ACRARNGAQD RTYVCSECGW RGHRDTVGAI NISRRAGLSG HRRGATGA    358

SEQ ID NO: 8              moltype = AA  length = 507
FEATURE                   Location/Qualifiers
REGION                    1..507
                          note = Synthetic sequence
source                    1..507
                          mol_type = protein
                          organism = synthetic construct
SEQUENCE: 8
MIAQKTIKIK LNPTKEQIIK LNSIIEEYIK VSNFTAKKIA EIQESFTDSG LTQGTCSECG    60
KEKTYRKYHL LKKDNKLFCI TCYKRKYSQF TLQKVEFQNK TGLRNVAKLP KTYYTNAIRF   120
ASDTFSGFDE IIKKKQNRLN SIQNRLNFWK ELLYNPSNRN EIKIKVVKYA PKTDTREHPH   180
YYSEAEIKGR IKRLEKQLKK FKMPKYPEFT SETISLQREL YSWKNPDELK ISSITDKNES   240
MNYYGKEYLK RYIDLINSQT PQILLEKENN SFYLCFPITK NIEMPKIDDT FEPVGIDWGI   300
TRNIAVVSIL DSKTKKPKFV KFYSAGYILG KRKHYKSLRK HFGQKKRQDK INKLGTKEDR   360
FIDSNIHKLA FLIVKEIRNH SNKPIILMEN ITDNREEAEK SMRQNILLHS VKSRLQNYIA   420
YKALWNNIPT NLVKPEHTSQ ICNRCGHQDR ENRPKGSKLF KCVKCNYMSN ADFNASINIA   480
RKFYIGEYEP FYKDNEKMKS GVNSISM                                      507

SEQ ID NO: 9              moltype = AA  length = 534
FEATURE                   Location/Qualifiers
REGION                    1..534
                          note = Synthetic sequence
source                    1..534
                          mol_type = protein
                          organism = synthetic construct
SEQUENCE: 9
LKLSEQENIT TGVKFKLKLD KETSEGLNDY FDEYGKAINF AIKVIQKELA EDRFAGKVRL    60
DENKKPLLNE DGKKIWDFPN EFCSCGKQVN RYVNGKSLCQ ECYKNKFTEY GIRKRMYSAK   120
GRKAEQDINI KNSTNKISKT HFNYAIREAF ILDKSIKKQR KERFRRLREM KKKLQEFIEI   180
RDGNKILCPK IEKQRVERYI HPSWINKEKK LEDFRGYSMS NVLGKIKILD RNIKREEKSL   240
KEKGQINFKA RRLMLDKSVK FLNDNKISFT ISKNLPKEYE LDLPEKEKRL NWLKEKIKII   300
KNQKPKYAYL LRKDDNFYLQ YTLETEFNLK EDYSGIVGID RGVSHIAVYT FVHNNGKNER   360
PLFLNSSEIL RLKNLQKERD RFLRRKHNKK RKKSNMRNIE KKIQLILHNY SKQIVDFAKN   420
KNAFIVFEKL EKPKKNRSKM SKKSQYKLSQ FTFKKLSDLV DYKAKREGIK VLYISPEYTS   480
KECSHCGEKV NTQRPFNGNS SLFKCNKCGV ELNADYNASI NIAKKGLNIL NSTN         534

SEQ ID NO: 10             moltype = AA  length = 537
FEATURE                   Location/Qualifiers
REGION                    1..537
                          note = Synthetic sequence
source                    1..537
                          mol_type = protein
                          organism = synthetic construct
SEQUENCE: 10
MEESIITGVK FKLRIDKETT KKLNEYFDEY GKAINFAVKI IQKELADDRF AGKAKLDQNK    60
NPILDENGKK IYEFPDEFCS CGKQVNKYVN NKPFCQECYK IRFTENGIRK RMYSAKGRKA   120
EHKINILNST NKISKTHFNY AIREAFILDK SIKKQRKKRN ERLRESKKRL QQFIDMRDGK   180
REICPTIKGQ KVDRFIHPSW ITKDKKLEDF RGYTLSIINS KIKILDRNIK REEKSLKEKG   240
QIIFKAKRLM LDKSIRFVGD RKVLFTISKT LPKEYELDLP SKEKRLNWLK EKIEIIKNQK   300
PKYAYLLRKN IESEKKPNYE YYLQYTLEIK PELKDFYDGA IGIDRGINHI AVCTFISNDG   360
```

```
KVTPPKFFSS GEILRLKNLQ KERDRFLLRK HNKNRKKGNM RVIENKINLI LHRYSKQIVD    420
MAKKLNASIV FEELGRIGKS RTKMKKSQRY KLSLFIFKKL SDLVDYKSRR EGIRVTYVPP    480
EYTSKECSHC GEKVNTQRPF NGNYSLFKCN KCGIQLNSDY NASINIAKKG LKIPNST      537

SEQ ID NO: 11            moltype = AA   length = 540
FEATURE                  Location/Qualifiers
REGION                   1..540
                         note = Synthetic sequence
source                   1..540
                         mol_type = protein
                         organism = synthetic construct
SEQUENCE: 11
LWTIVIGDFI EMPKQDLVTT GIKFKLDVDK ETRKKLDDYF DEYGKAINFA VKIIQKNLKE    60
DRFAGKIALG EDKKPLLDKD GKKIYNYPNE SCSCGNQVRR YVNAKPFCVD CYKLKFTENG   120
IRKRMYSARG RKADSDINIK NSTNKISKTH FNYAIREGFI LDKSLKKQRS KRIKKLLELK   180
RKLQEFIDIR QGQMVLCPKI KNQRVDKFIH PSWLKRDKKL EEFRGYSLSV VEGKIKIFNR   240
NILREEDSLR QRGHVNFKAN RIMLDKSVRF LDGGKVNFNL NKGLPKEYLL DLPKKENKLS   300
WLNEKISLIK LQKPKYAYLL RREGSFFIQY TIENVPKTFS DYLGAIGIDR GISHIAVCTF   360
VSKNGVNKAP VFFSSGEILK LKSLQKQRDL FLRGKHNKIR KKSNMRNIDN KINLILHKYS   420
RNIVNLAKSE KAFIVPEKLE KIKKSRFKMS KSLQYKLSQF TFKKLSDLVE YKAKIEGIKV   480
DYVPPEYTSK ECSHCGEKVD TQRPFNGNSS LFKCNKCRVQ LNADYNASIN IAKKSLNISN   540

SEQ ID NO: 12            moltype = AA   length = 542
FEATURE                  Location/Qualifiers
REGION                   1..542
                         note = Synthetic sequence
source                   1..542
                         mol_type = protein
                         organism = synthetic construct
SEQUENCE: 12
MSKTTISVKL KIIDLSSEKK EFLDNYFNEY AKATTFCQLR IRRLLRNTHW LGKKEKSSKK    60
WIFESGICDL CGENKELVNE DRNSGEPAKI CKRCYNGRYG NQMIRKLFVS TKKREVQENM   120
DIRRVAKLNN THYHRIPEEA FDMIKAADTA EKRRKKNVEY DKKRQMEFIE MFNDEKKRAA   180
RPKKPNERET RYVHISKLES PSKGYTLNGI KRKIDGMGKK IERAEKGLSR KKIFGYQGNR   240
IKLDSNWVRF DLAESEITIP SLFKEMKLRI TGPTNVHSKS GQIYFAEWFE RINKQPNNYC   300
YLIRKTSSNG KYEYYLQYTY EAEVEANKEY AGCLGVDIGC SKLAAAVYYD SKNKKAQKPI   360
EIFTNPIKKI KMRREKLIKL LSRVKVRHRR RKLMQLSKTE PIIDYTCHKT ARKIVEMANT   420
AKAFISMENL ETGIKQKQQA RETKKQKFYR NMFLFRKLSK LIEYKALLKG IKIVYVKPDY   480
TSQTCSSCGA DKEKTERPSQ AIFRCLNPTC RYYQRDINAD FNAAVNIAKK ALNNTEVVTT   540
LL                                                                 542

SEQ ID NO: 13            moltype = AA   length = 564
FEATURE                  Location/Qualifiers
REGION                   1..564
                         note = Synthetic sequence
source                   1..564
                         mol_type = protein
                         organism = synthetic construct
SEQUENCE: 13
MARAKNQPYQ KLTTTTGIKF KLDLSEEEGK RFDEYFSEYA KAVNFCAKVI YQLRKNLKFA    60
GKKELAAKEW KFEISNCDFC NKQKEIYYKN IANGQKVCKG CHRTNFSDNA IRKKMIPVKG   120
RKVESKFNIH NTTKKISGTH RHWAFEDAAD IIESMDKQRK EKQKRLRREK RKLSYFFELF   180
GDPAKRYELP KVGKQRVPRY LHKIIDKDSL TKKRGYSLSY IKNKIKISER NIERDEKSLR   240
KASPIAFGAR KIKMSKLDPK RAFDLENNVF KIPGKVIKGQ YKFFGTNVAN EHGKKFYKDR   300
ISKILAGKPK YFYLLRKKVA ESDGNPIFEY YVQWSIDTET PAITSYDNIL GIDAGITNLA   360
TTVLIPKNLS AEHCSHCGNN HVKPIFTKFF SGKELKAIKI KSRQKYFLR GKHNKLVKIK   420
RIRPIEQKVD GYCHVVSKQI VEMAKERNSC IALEKLEKPK KSKFRQRRRE KYAVSMFVFK   480
KLATFIKYKA AREGIEIIPV EPEGTSYTCS HCKNAQNNQR PYFKPNSKKS WTSMFKCGKC   540
GIELNSDYNA AFNIAQKALN MTSA                                         564

SEQ ID NO: 14            moltype = AA   length = 610
FEATURE                  Location/Qualifiers
REGION                   1..610
                         note = Synthetic sequence
source                   1..610
                         mol_type = protein
                         organism = synthetic construct
SEQUENCE: 14
MDEKHFFCSY CNKELKISKN LINKISKGSI REDEAVSKAI SIHNKKEHSL ILGIKFKLFI    60
ENKLDKKKLN EYFDNYSKAV TFAARIFDKI RSPYKFIGLK DKNTKKWTFP KAKCVFCLEE   120
KEVAYANEKD NSKICTECYL KEFGENGIRK KIYSTRGRKV EPKYNIFNST KELSSTHYNY   180
AIRDAFQLLD ALKKQRQKKL KSIFNQKLRL KEFEDIFSDP QKRIELSLKP HQREKRYIHL   240
SKSGQESINR GYTLRFVRGK IKSLTRNIER EEKSLRKRTP IHFKGNRLMI FPAGIKPDFA   300
SNKVKISISK NLPNEFNFSG TNVKNEHGKS FFKSRIELIK TQKPKYAYVL RKIKREYSKL   360
RNYEIEKIRL ENPNADLCDF YLQYTIETES RNNEEINGII GIDRGITNLA CLVLLKKGDK   420
KPSGVKFYKG NKILGMKIAY RKHLYLLKGK RNKLRKQRQI RAIEPKINLI LHQISKDIVK   480
IAKEKNFAIA LEQLEKPKKA RFAQRKKEKY KLALFTFKNL STLIEYKSKR EGIPVIYVPP   540
EKTSQMCSHC AINGDEHVDT QRPYKKPNAQ KPSYSLFKCN KCGIELNADY NAAFNIAQKG   600
LKTLMLNHSH                                                         610
```

```
SEQ ID NO: 15              moltype = AA  length = 369
FEATURE                    Location/Qualifiers
REGION                     1..369
                           note = Synthetic sequence
source                     1..369
                           mol_type = protein
                           organism = synthetic construct
SEQUENCE: 15
MLQTLLVKLD PSKEQYKMLY ETMERFNEAC NQIAETVFAI HSANKIEVQK TVYYPIREKF   60
GLSAQLTILA IRKVCEAYKR DKSIKPEFRL DGALVYDQRV LSWKGLDKVS LVTLQGRQII  120
PIKFGDYQKA RMDIRGQAD LILVKGVFYL CVVVEVSEES PYDPKGVLGV DLGIKNLAVD   180
SDGEVHSGEQ TTNTRERLDS LKARLQSKGT KSAKRHLKKL SGRMAKFSKD VNHCISKKLV  240
AKAKGTLMSI ALEDLQGIRD RVTVRKAQRR NLHTWNFGLL RMFVDYKAKI AGVPLVFVDP  300
RNTSRTCPSC GHVAKANRPT RDEFRCVSCG FAGAADHIAA MNIAFRAEVS QPIVTRFFVQ  360
SQAPSFRVG                                                          369

SEQ ID NO: 16              moltype = AA  length = 552
FEATURE                    Location/Qualifiers
REGION                     1..552
                           note = Synthetic sequence
source                     1..552
                           mol_type = protein
                           organism = synthetic construct
SEQUENCE: 16
MDEEPDSAEP NLAPISVKLK LVKLDGEKLA ALNDYFNEYA KAVNFCELKM QKIRKNLVNI   60
RGTYLKEKKA WINQTGECCI CKKIDELRCE DKNPDINGKI CKKCYNGRYG NQMIRKLFVS  120
TNKRAVPKSL DIRKVARLHN THYHRIPPEA ADIIKAIETA ERKRRNRILF DERRYNELKD  180
ALENEEKRVA RPKKPKEREV RYVPISKKDT PSKGYTMNAL VRKVSGMAKK IERAKRNLNK  240
RKKIEYLGRR ILLDKNWVRF DFDKSEISIP TMKEFFGEMR FEITGPSNVM SPNGREYFTK  300
WFDRIKAQPD NYCYLLRKES EDETDFYLQY TWRPDAHPKK DYTGCLGIDI GGSKLASAVY  360
FDADKNRAKQ PIQIFSNPIG KWKTKRQKVI KVLSKAAVRH KTKKLESLRN IEPRIDVHCH  420
RIARKIVGMA LAANAFISME NLEGGIREKQ KAKETKKQKF SRNMFVFRKL SKLIEYKALM  480
EGVKVVYIVP DYTSQLCSSC GTNNTKRPKQ AIFMCQNTEC RYFGKNINAD FNAAINIAKK  540
ALNRKDIVRE LS                                                      552

SEQ ID NO: 17              moltype = AA  length = 534
FEATURE                    Location/Qualifiers
REGION                     1..534
                           note = Synthetic sequence
source                     1..534
                           mol_type = protein
                           organism = synthetic construct
SEQUENCE: 17
MEKNNSEQTS ITTGIKFKLK LDKETKEKLN NYFDEYGKAI NFAVRIIQMQ LNDDRLAGKY   60
KRDEKGKPIL GEDGKKILEI PNDFCSCGNQ VNHYVNGVSF CQECYKKRFS ENGIRKRMYS  120
AKGRKAEQDI NIKNSTNKIS KTHFNYAIRE AFNLDKSIKS QREKRFKKLK DMKRKLQEFL  180
EIRDGKRVIC PKIEKQKVER YIHPSWINKE KKLEEFRGYS LSIVNSKIKS FDRNIQREEK  240
SLKEKGQINF KAQRLMLDKS VKFLKDNKVS FTISKELPKT FELDLPKKEK KLNWLNEKLE  300
IIKNQKPKYA YLLRKENNIF LQYTLDSIPE IHSEYSGAVG IDRGVSHIAV YTFLDKDGKN  360
ERPFFLSSSG ILRLKNLQKE RDKFLRKKHN KIRKKGNMRN IEQKINLILH EYSKQIVNFA  420
KDKNAFIVFE LLEKPKKSRE RMSKKIQYKL SQFTFKKLSD LVDYKAKREG IKVIYVEPAY  480
TSKDCSHCGE RVNTQRPFNG NFSLFKCNKC GIVLNSDYNA SLNIARKGLN ISAN        534

SEQ ID NO: 18              moltype = AA  length = 577
FEATURE                    Location/Qualifiers
REGION                     1..577
                           note = Synthetic sequence
source                     1..577
                           mol_type = protein
                           organism = synthetic construct
SEQUENCE: 18
MAEEKFFFCE KCNKDIKIPK NYINKQGAEE KARAKHEHRV HALILGIKFK IYPKKEDISK   60
LNDYFDEYAK AVTFTAKIVD KLKAPFLFAG KRDKDTSKKK WVFPVDKCSF CKEKTEINYR  120
TKQGKNICNS CYLTEFGEQG LLEKIYATKG RKVSSSFNLF NSTKKLTGTH NNYVVKESLQ  180
LLDALKKQRS KRLKKLSNTR RKLKQFEEMF EKEDKRFQLP LKEKQRELRF IHVSQKDRAT  240
EFKGYTMNKI KSKIKVLRRN IEREQRSLNR KSPVFFRGTR IRLSPSVQFD DKDNKIKLTL  300
SKELPKEYSF SGLNVANEHG RKFFAEKLKL IKENKSKYAY LRRQVNKNN KKPIYDYYLQ   360
YTVEFLPNII TNYNGILGID RGINTLACIV LLENKKEKPS FVKFFSGKGI LNLKNKRRKQ  420
LYFLKGVHNK YRKQQKIRPI EPRIDQILHD ISKQIIDLAK EKRVAISLEQ LEKPQKPKFR  480
QSRKAKYKLS QFNFKTLSNY IDYKAKKEGI RVIYIAPEMT SQNCSRCAMK NDLHVNTQRP  540
YKNTSSLFKC NKCGVELNAD YNAAFNIAQK GLKILNS                           577

SEQ ID NO: 19              moltype = AA  length = 613
FEATURE                    Location/Qualifiers
REGION                     1..613
                           note = Synthetic sequence
source                     1..613
                           mol_type = protein
```

```
                        organism = synthetic construct
SEQUENCE: 19
MISLKLKLLP DEEQKKLLDE MFWKWASICT RVGFGRADKE DLKPPKDAEG VWFSLTQLNQ    60
ANTDINDLRE AMKHQKHRLE YEKNRLEAQR DDTQDALKNP DRREISTKRK DLFRPKASVE   120
KGFLKLKYHQ ERYWVRRLKE INKLIERKTK TLIKIEKGRI KPFKATRITLH QGSFKIRFGD  180
KPAFLIKALS GKNQIDAPFV VVPEQPICGS VVNSKKYLDE ITTNFLAYSV NAMLFGLSRS   240
EEMLLKAKRP EKIKKKEEKL AKKQSAFENK KKELQKLLGR ELTQQEEAII EETRNQFFQD   300
FEVKITKQYS ELLSKIANEL KQKNDFLKVN KYPILLRKPL KKAKSKKINN LSPSEWKYYL   360
QFGVKPLLKQ KSRRKSRNVL GIDRGLKHLL AVTVLEPDKK TFVWNKLYPN PITGWKWRRR   420
KLLRSLKRLK RRIKSQKHET IHENQTRKKL KSLQGRIDDL LHNISRKIVE TAKEYDAVIV   480
VEDLQSMRQH GRSKGNRLKT LNYALSLFDY ANVMQLIKYK AGIEGIQIYD VKPAGTSQNC   540
AYCLLAQRDS HEYKRSQENS KIGVCLNPNC QNHKKQIDAD LNAARVIASC YALKINDSQP   600
FGTRKRFKKR TTN                                                     613

SEQ ID NO: 20         moltype = AA length = 615
FEATURE               Location/Qualifiers
REGION                1..615
                      note = Synthetic sequence
source                1..615
                      mol_type = protein
                      organism = synthetic construct
SEQUENCE: 20
METLSLKLKL NPSKEQLLVL DKMFWKWASI CTRLGLKKAE MSDLEPPKDA EGVWFSKTQL    60
NQANTDVNDL RKAMQHQGKR IEYELDKVEN RRNEIQEMLE KPDRRDISPN RKDLFRPKAA   120
VEKGYLKLKY HKLGYWSKEL KTANKLIERK RKTLAKIDAG KMKFKPTRIS LHTNSFRIKF   180
GEEPKIALST TSKHEKIELP LITSLQRPLK TSCAKKSKTY LDAAILNFLA YSTNAALFGL   240
SRSEEMLLKA KKPEKIEKRD RKLATKRESF DKKLKTLEKL LERKLSEKEK SVFKRKQTEF   300
FDKFCITLDE TYVEALHRIA EELVSKNKYL EIKKYPVLLR KPESRLRSKK LKNLKPEDWT   360
YYIQFGFQPL LDTPKPIKTK TVLGIDRGVR HLLAVSIFDP RTKTFTFNRL YSNPIVDWKW   420
RRRKLLRSIK RLKRRLKSEK HVHLHENQFK AKLRSLEGHL EDHFHNLSKE IVDLAKENNS   480
VIVVENLGGM RQHGRGRGKW LKALNYALSH FDYAKVMQLI KYKAELAGVF VYDVAPAGTS   540
INCAYCLLND KDASNYTRGK VINGKKNTKI GECKTCKKEF DADLNAARVI ALCYEKRLND   600
PQPFGTRKQF KPKKP                                                   615

SEQ ID NO: 21         moltype = AA length = 775
FEATURE               Location/Qualifiers
REGION                1..775
                      note = Synthetic sequence
source                1..775
                      mol_type = protein
                      organism = synthetic construct
SEQUENCE: 21
MKALKLQLIP TRKQYKILDE MFWKWASLAN RVSQKGESKE TLAPKKDIQK IQFNATQLNQ    60
IEKDIKDLRG AMKEQQKQE RLLLQIQERR STISEMLNDD NNKERDPHRP LNFRPKGWRK   120
FHTSKHWVGE LSKILRQEDR VKKTIERIVA GKISFKPKRI GIWSSNYKIN FFKRKISINP   180
LNSKGFELTL MTEPTQDLIG KNGGKSVLNN KRYLDDSIKS LLMFAHSRF FGLNNTDTYL    240
LGGKINPSLV KYYKKNQDMG EFGREIVEKF ERKLKQEENE QQKKIIMSQI KEQYSNRDSA   300
FNKDYLGLIN EFSEVFNQRK SERAEYLLDS FEDKIKQIKQ EIGESLNISD WDFLIDEAKK   360
AYGYEEGFTE YVYSKRYLEI LNKIVKAVLI TDIYFDLRKY PILLRKPLDK IKKISNLKPD   420
EWSYYIQFGY DSINPVQLMS TDKFLGIDRG LTHLLAYSVF DKEKKEFIIN QLEPNPIMGW   480
KWKLRKVKRS LQHLERRIRA QKMVKLPENQ MKKKLKSIEP KIEVHYHNIS RKIVNLAKDY   540
NASIVVESLE GGGLKQHGRK KNARNRSLNY ALSLFDYGKI ASLIKYKADL EGVPMYEVLP   600
AYTSQQCAKC VLEKGSFVDP EIIGYVEDIG IKGSLLDSLF EGTELSSIQV LKKIKNKIEL   660
SARDNHNKEI NLILKYNFKG LVIVRGQDKE EIAEHPIKEI NGKFAILDFV YKRGKEKVGK   720
KGNQKVRYTG NKKVGYCSKH GQVDADLNAS RVIALCKYLD INDPILFGEQ RKSFK        775

SEQ ID NO: 22         moltype = AA length = 777
FEATURE               Location/Qualifiers
REGION                1..777
                      note = Synthetic sequence
source                1..777
                      mol_type = protein
                      organism = synthetic construct
SEQUENCE: 22
MVTRAIKLKL DPTKNQYKLL NEMFWKWASL ANRFSQKGAS KETLAPKDGT QKIQFNATQL    60
NQIKKDVDDL RGAMEKQGKQ KERLLIQIQE RLLTISEILR DDSKKEKDPH RPQNFRPFGW   120
RRFHTSAYWS SEASKLTRQV DRVRRTIERI KAGKINFKPK RIGLWSSTYK INFLKKKINI   180
SPLKSKSFEL DLITEPQQKI IGKEGGKSVA NSKKYLDDSI KSLLIFAIKS RLFGLNNKDK   240
PLFENIITPN LVRYHKKGQE QENFKKEVIK KFENKLKKEI SQKQKEIIFS QIERQYENRD   300
ATFSEDYLRA ISEFSEIFNQ RKKERAKELL NSFNEKIRQL KKEVNGNISE EDLKILEVEA   360
EKAYNYENGF IEWEYSEQFL GVLEKIARAV LISDNYFDLK KYPILIRKPT NKSKKITNLK   420
PEEWDYYIQF GYGLINSPMK IETKNFMGID RGLTHLLAYS IFDRDSEKFT INQLELNPIK   480
GWKWKLRKVK RSLQHLERRM RAQKGVKLPE NQMKKRLKSI EPKIESYYHN LSRKIVNLAK   540
ANNASIVVES LEGGGLKQHG RKKNSRHRAL NYALSLFDYG KIASLIKYKS DLEGVPMYEV   600
LPAYTSQQCA KCVLKKGSFV EPEIIGYIEE IGFKENLLTL LFEDTGLSSV QVLKKSKNKM   660
TLSARDKEGK MVDLVLKYNF KGLVISQEKK KEEIVEFPIK EIDGKFAVLD SAYKRGKERI   720
SKKGNQKLVY TGNKKVGYCS VHGQVDADLN ASRVIALCKY LGINEPIVFG EQRKSFK     777

SEQ ID NO: 23         moltype = AA length = 610
```

```
FEATURE                 Location/Qualifiers
REGION                  1..610
                        note = Synthetic sequence
source                  1..610
                        mol_type = protein
                        organism = synthetic construct
SEQUENCE: 23
LDLITEPIQP HKSSSLRSKE FLEYQISDFL NFSLHSLFFG LASNEGPLVD FKIYDKIVIP   60
KPEERFPKKE SEEGKKLDSF DKRVEEYYSD KLEKKIERKL NTEEKNVIDR EKTRIWGEVN  120
KLEEIRSIID EINEIKKQKH ISEKSKLLGE KWKKVNNIQE TLLSQEYVSL ISNLSDELTN  180
KKKELLAKKY SKFDDKIKKI KEDYGLEFDE NTIKKEGEKA FLNPDKFSKY QFSSSYLKLI  240
GEIARSLITY KGFLDLNKYP IIFRKPINKV KKIHNLEPDE WKYYIQFGYE QINNPKLETE  300
NILGIDRGLT HILAYSVFEP RSSKFILNKL EPNPIEGWKW KLRKLRRSIQ NLERRWRAQD  360
NVKLPENQMK KNLRSIEDKV ENLYHNLSRK IVDLAKEKNA CIVFEKLEGQ GMKQHGRKKS  420
DRLRGLNYKL SLFDYGKIAK LIKYKAEIEG IPIYRIDSAY TSQNCAKCVL ESRRFAQPEE  480
ISCLDDFKEG DNLDKRILEG TGLVEAKIYK KLLKEKKEDF EIEEDIAMFD TKKVIKENKE  540
KTVILDYVYT RRKEIIGTNH KKNIKGIAKY TGNTKIGYCM KHGQVDADLN ASRTIALCKN  600
FDINNPEIWK                                                         610

SEQ ID NO: 24           moltype = AA  length = 632
FEATURE                 Location/Qualifiers
REGION                  1..632
                        note = Synthetic sequence
source                  1..632
                        mol_type = protein
                        organism = synthetic construct
SEQUENCE: 24
MSDESLVSSE DKLAIKIKIV PNAEQAKMLD EMFKKWSSIC NRISRGKEDI ETLRPDEGKE   60
LQFNSTQLNS ATMDVSDLKK AMARQGERLE AEVSKLRGRY ETIDASLRDP SRRHTNPQKP  120
SSFYPSDWDI SGRLTPRFHT ARHYSTELRK LKAKEDKMLK TINKIKNGKI VPKPKRITLW  180
PSSVNMAFKG SRLLLKPFAN GFEMELPIVI SPQKTADGKS QKASAEYMRN ALLGLAGYSI  240
NQLLFGMNRS QKMLANAKKP EKVEKFLEQM KNKDANFDKK IKALEGKWLL DRKLKESEKS  300
SIAVVRTKFF KSGKVELNED YLKLLKHMAN EILERDGFVN LNKYPILSRK PMKRYKQKNI  360
DNLKPNMWKY YIQFGYEPIF ERKASGKPKN IMGIDRGLTH LLAAVAFSPD QQKFLFNHLE  420
SNPIMHWKWK LRKIRRSIQH MERRIRAEKN KHIHEAQLKK RLGSIEEKTE QHYHIVSSKI  480
INWAIEYEAA IVLESLSHMK QRGGKKSVRT RALNYALSLF DYEKVARLIT YKARIRGIPV  540
YDVLPGMTSK TCATCLLNGS QGAYVRGLET TKAAGKATKR KNMKIGKCMV CNSSENSMID  600
ADLNAARVIA ICKYKNLNDP QPAGSRKVFK RF                                632

SEQ ID NO: 25           moltype = AA  length = 625
FEATURE                 Location/Qualifiers
REGION                  1..625
                        note = Synthetic sequence
source                  1..625
                        mol_type = protein
                        organism = synthetic construct
SEQUENCE: 25
MLALKLKIMP TEKQAEILDA MFWKWASICS RIAKMKKKVS VKENKKELSK KIPSNSDIWF   60
SKTQLCQAEV DVGDHKKALK NFEKRQESLL DELKYKVKAI NEVINDESKR EIDPNNPSKF  120
RIKDSTKKGN LNSPKFFTLK KWQKILQENE KRIKKKESTI EKLKRGNIFF NPTKISLHEE  180
EYSINFGSSK LLLNCFYKYN KKSGINSDQL ENKFNEFQNG LNIICSPLQP IRGSSKRSFW  240
FIRNSIINFL MYSLYAKLFG IPRSVKALMK SNKDENKLKL EEKLKKKKSS FNKTVKEFEK  300
MIGRKLSDNE SKILNDESKK FFEIIKSNNK YIPSEEYLKL LKDISEEIYN SNIDFKPYKY  360
SILIRKPLSK FKSKKLYNLK PTDYKYYLQL SYEPFSKQLI ATKTILGIDR GLKHLLAVSV  420
FDPSQNKFVY NKLIKNPVFK WKKRYHDLKR SIRNRERRIR ALTGVHIHEN QLIKKLKSMK  480
NKINVLYHNV SKNIVDLAKK YESTIVLERL ENLKQHGRSK GKRYKKLNYV LSNFDYKKIE  540
SLISYKAKKE GVPVSNINPK YTSKTCAKCL LEVNQLSELK NEYNRDSKNS KIGICNIHGQ  600
IDADLNAARV IALCYSKNLN EPHFK                                        625

SEQ ID NO: 26           moltype = AA  length = 517
FEATURE                 Location/Qualifiers
REGION                  1..517
                        note = Synthetic sequence
source                  1..517
                        mol_type = protein
                        organism = synthetic construct
SEQUENCE: 26
VINLFGYKFA LYPNKTQEEL LNKHLGECGW LYNKAIEQNE YYKADSNIEE AQKKFELLPD   60
KNSDEAKVLR GNISKDNYVY RTLVKKKKSE INVQIRKAVV LRPAETIRNL AKVKKKGLSV  120
GRLKFIPIRE WDVLPFKQSD QIRLEENYLI LEPYGRLKFK MHRPLLGKPK TFCIKRTATD  180
RWTISFSTEY DDSNMRKNDG GQVGIDVGLK THLRLSNENP DEDPRYPNPK IWKRYDRRLT  240
ILQRRISKSK KLGNRTRLR LRLSRLWEKI RNSRADLIQN ETYEILSENK LIAIEDLNVK  300
GMQEKKDKKG RKGRTRAQEK GLHRSISDAA FSEFRRVLEY KAKRFGSEVK PVSAIDSSKE  360
CHNCGNKKGM PLESRIYECP KCGLKIDRDL NSAKVILARA TGVRPGSNAR ADTKISATAG  420
ASVQTEGTVS EDFRQQMETS DQKPMQGEGS KEPPMNPEHK SSGRGSKHVN IGCKNKVGLY  480
NEDENSRSTE KQIMDENRST TEDMVEIGAL HSPVLTT                           517

SEQ ID NO: 27           moltype = AA  length = 410
FEATURE                 Location/Qualifiers
```

```
REGION                      1..410
                            note = Synthetic sequence
source                      1..410
                            mol_type = protein
                            organism = synthetic construct
SEQUENCE: 27
MIASIDYEAV SQALIVFEFK AKGKDSQYQA IDEAIRSYRF IRNSCLRYWM DNKKVGKYDL   60
NKYCKVLAKQ YPFANKLNSQ ARQSAAECSW SAISRFYDNC KRKVSGKKGF PKFKKHARSV  120
EYKTSGWKLS ENRKAITFTD KNGIGKLKLK GTYDLHFSQL EDMKRVRLVR RADGYYVQFC  180
ISVDVKVETE PTGKAIGLDV GIKYFLADSS GNTIENPQFY RKAEKKLNRA NRRKSKKYIR  240
GVKPQSKNYH KARCRYARKH LRVSRQRKEY CKRVAYCVIH SNDVVAYEDL NVKGMVKNRH  300
LAKSISDVAW STFRHWLEYF AIKYGKLTIP VAPHNTSQNC SNCDKKVPKS LSTRTHICHH  360
CGYSEDRDVN AAKNILKKAL STVGQTGSLK LGEIEPLLVL EQSCTRKFDL            410

SEQ ID NO: 28               moltype = AA  length = 486
FEATURE                     Location/Qualifiers
REGION                      1..486
                            note = Synthetic sequence
source                      1..486
                            mol_type = protein
                            organism = synthetic construct
SEQUENCE: 28
LAEENTLHLT LAMSLPLNDL PENRTRSELW RRQWLPQKKL SLLLGVNQSV RKAAADCLRW   60
FEPYQELLWW EPTDPDGKKL LDKEGRPIKR TAGHMRVLRK LEEIAPFRGY QLGSAVKNGL  120
RHKVADLLLS YAKRKLDPQF TDKTSYPSIG DQFPIVWTGA FVCYEQSITG QLYLYLPLFP  180
RGSHQEDITN NYDPDRGPAL QVFGEKEIAR LSRSTSGLLL PLQFDKWGEA TFIRGENNPP  240
TWKATHRRSD KKWLSEVLLR EKDFQPKRVE LLVRNGRIFV NVACEIPTKP LLEVENFMGV  300
SFGLEHLVTV VVINRDGNVV HQRQEPARRY EKTYFARLER LRRRGGPFSQ ELETFHYRQV  360
AQIVEEALRF KSVPAVEQVG NIPKGRYNPR LNLRLSYWPF GKLADLTSYK AVKEGLPKPY  420
SVYSATAKML CSTCGAANKE GDQPISLKGP TVYCGNCGTR HNTGFNTALN LARRAQELFV  480
KGVVAR                                                            486

SEQ ID NO: 29               moltype = AA  length = 602
FEATURE                     Location/Qualifiers
REGION                      1..602
                            note = Synthetic sequence
source                      1..602
                            mol_type = protein
                            organism = synthetic construct
SEQUENCE: 29
MSQSLLKWHD MAGRDKDASR SLQKSAVEGV LLHLTASHRV ALEMLEKSVS QTVAVTMEAA   60
QQRLVIVLED DPTKATSRKR VISADLQFTR EEFGSLPNWA QKLASTCPEI ATKYADKHIN  120
SIRIAWGVAK ESTNGDAVEQ KLQWQIRLLD VTMFLQQLVL QLADKALLEQ IPSSIRGGIG  180
QEVAQQVTSH IQLLDSGTVL KAELPTISDR NSELARKQWE DAIQTVCTYA LPFSRERARI  240
LDPGKYAAED PRGDRLINID PMWARVLKGP TVKSLPLLFV SGSSIRIVKL TLPRKHAAGH  300
KHTFTATYLV LPVSREWINS LPGTVQEKVQ WWKKPDVLAT QELLVGKGAL KKSANTLVIP  360
ISAGKKRFFN HILPALQRGF PLQWQRIVGR SYRRPATHRK WFAQLTIGYT NPSSLPEMAL  420
GIHFGMKDIL WWALADKQGN ILKDGSIPGN SILDFSLQEK GKIERQQKAG KNVAGKKYGK  480
SLLNATYRVV NGVLEFSKGI SAEHASQPIG LGLETIRFVD KASGSSPVNA RHSNWNYGQL  540
SGIFANKAGP AGFSVTEITL KKAQRDLSDA EQARVLAIEA TKRFASRIKR LATKRKDDTL  600
FV                                                                602

SEQ ID NO: 30               moltype = AA  length = 494
FEATURE                     Location/Qualifiers
REGION                      1..494
                            note = Synthetic sequence
source                      1..494
                            mol_type = protein
                            organism = synthetic construct
SEQUENCE: 30
VEPVEKERFY YRTYTFRLDG QPRTQNLTTQ SGWGLLTKAV LDNTKHYWEI VHHARIANQP   60
IVFENPVIDE QGNPKLNKLG QPRFWKRPIS DIVNQLRALF ENQNPYQLGS SLIQGTYWDV  120
AENLASWYAL NKEYLAGTAT WGEPSFPEPH PLTEINQWMP LTFSSGKVVR LLKNASGRYF  180
IGLPILGENN PCYRMRTIEK LIPCDGKGRV TSGSLILFPL VGIYAQQHRR MTDICESIRT  240
EKGKLAWAQV SIDYVREVDK RRRMRRTRKS QGWIQGPWQE VFILRLVLAH KAPKLYKPRC  300
FAGISLGPKT LASCVILDQD ERVVEKQQWS GSELLSLIHQ GEERLRSLRE QSKPTWNAAY  360
RKQLKSLINT QVFTIVTFLR ERGAAVRLES IARVRKSTPA PPVNFLLSHW AYRQITERLK  420
DLAIRNGMPL THSNGSYGVR FTCSQCGATN QGIKDPTKYK VDIESETFLC SICSHREIAA  480
VNTATNLAKQ LLDE                                                   494

SEQ ID NO: 31               moltype = AA  length = 526
FEATURE                     Location/Qualifiers
REGION                      1..526
                            note = Synthetic sequence
source                      1..526
                            mol_type = protein
                            organism = synthetic construct
SEQUENCE: 31
MNDTETSETL TSHRTVCAHL HVVGETGSLP RLVEAALAEL ITLNGRATQA LLSLAKNGLV   60
```

```
LRRDKEENLI AAELTLPCRK NKYADVAAKA GEPILATRIN NKGKLVTKKW YGEGNSYHIV    120
RFTPETGMFT VRVFDRYAFD EELLHLHSEV VFGSDLPKGI KAKTDSLPAN FLQAVFTSFL    180
ELPFQGFPDI VVKPAMKQAA EQLLSYVQLE AGENQQAEYP DTNERDPELR LVEWQKSLHE    240
LSVRTEPFEF VRARDIDYYA ETDRRGNRFV NITPEWTKFA ESPFARRLPL KIPPEFCILL    300
RRKTEGHAKI PNRIYLGLQI FDGVTPDSTL GVLATAEDGK LFWWHDHLDE FSNLEGKPEP    360
KLKNKPQLLM VSLEYDREQR FEESVGGDRK ICLVTLKETR NFRRGWNGRI LGIHFQHNPV    420
ITWALMDHDA EVLEKGFIEG NAFLGKALDK QALNEYLQKG GKWVGDRSFG NKLKGITHTL    480
ASLIVRLARE KDAWIALEEI SWVQKQSADS VANHEIVEQP HHSLTR                  526

SEQ ID NO: 32           moltype = AA  length = 649
FEATURE                 Location/Qualifiers
REGION                  1..649
                        note = Synthetic sequence
source                  1..649
                        mol_type = protein
                        organism = synthetic construct
SEQUENCE: 32
MNDTETSETL TSHRTVCAHL HVVGETGSLP RLVEAALAEL ITLNGRATQA LLSLAKNGLV     60
LRRDKEENLI AAELTLPCRK NKYADVAAKA GEPILATRIN NKGKLVTKKW YGEGNSYHIV    120
RFTPETGMFT VRVFDRYAFD EELLHLHSEV VFGSDLPKGI KAKTDSLPAN FLQAVFTSFL    180
ELPFQGFPDI VVKPAMKQAA EQLLSYVQLE AGENQQAEYP DTNERDPELR LVEWQKSLHE    240
LSVRTEPFEF VRARDIDYYA ETDRRGNRFV NITPEWTKFA ESPFARRLPL KIPPEFCILL    300
RRKTEGHAKI PNRIYLGLQI FDGVTPDSTL GVLATAEDGK LFWWHDHLDE FSNLEGKPEP    360
KLKNKPQLLM VSLEYDREQR FEESVGGDRK ICLVTLKETR NFRRGRHGHT RTDRLPAGNT    420
LWRADFATSA EVAAPKWNGR ILGIHFQHNP VITWALMDHD AEVLEKGFIE GNAFLGKALD    480
KQALNEYLQK GGKWVGDRSF GNKLKGITHT LASLIVRLAR EKDAWIALEE ISWVQKQSAD    540
SVANRRFSMW NYSRLATLIE WLGTDIATRD CGTAAPLAHK VSDYLTHFTC PECGACRKAG    600
QKKEIADTVR AGDILTCRKC GFSGPIPDNF IAEFVAKKAL ERMLKKKPV                649

SEQ ID NO: 33           moltype = AA  length = 414
FEATURE                 Location/Qualifiers
REGION                  1..414
                        note = Synthetic sequence
source                  1..414
                        mol_type = protein
                        organism = synthetic construct
SEQUENCE: 33
MAKRNFGEKS EALYRAVRFE VRPSKEELSI LLAVSEVLRM LFNSALAERQ QVFTEFIASL     60
YAELKSASVP EEISEIRKKL REAYKEHSIS LFDQINALTA RRVEDEAFAS VTRNWQEETL    120
DALDGAYKSF LSLRRKGDYD AHSPRSRDSG FFQKIPGRSG FKIGEGRIAL SCGAGRKLSF    180
PIPDYQQGRL AETTKLKKFE LYRDQPNLAK SGRFWISVVY ELPKPEATTC QSEQVAFVAL    240
GASSIGVVSQ RGEEVIALWR SDKHWVPKIE AVEERMKRRV KGSRGWLRLL NSGKRRMHMI    300
SSRQHVQDER EIVDYLVRNH GSHFVVTELV VRSKEGKLAD SSKPERGGSL GLNWAAQNTG    360
SLSRLVRQLE EKVKEHGGSV RKHKLTLTEA PPARGAENKL WMARKLRESF LKEV           414

SEQ ID NO: 34           moltype = AA  length = 413
FEATURE                 Location/Qualifiers
REGION                  1..413
                        note = Synthetic sequence
source                  1..413
                        mol_type = protein
                        organism = synthetic construct
SEQUENCE: 34
LAKNDEKELL YQSVKFEIYP DESKIRVLTR VSNILVLVWN SALGERRARF ELYIAPLYEE     60
LKKFPRKSAE SNALRQKIRE GYKEHIPTFF DQLKKLLTPM RKEDPALLGS VPRAYQEETL    120
NTLNGSFVSF MTLRRNNDMD AKPPKGRAED RFHEISGRSG FKIDGSEFVL STKEQKLRFP    180
IPNYQLEKLK EAKQIKKFTL YQSRDRRFWI SIAYEIELPD QRPFNPEEVI YIAFGASSIG    240
VISPEGEKVI DFWRPDKHWK PKIKEVENRM RSCKKGSRAW KKRAAARRKM YAMTQRQQKL    300
NHREIVASLL RLGFHFVVTE YTVRSKPGKL ADGSNPKRGG APQGFNWSAQ NTGSFGEFIL    360
WLKQKVKEQG GTVQTFRLVL GQSERPEKRG RDNKIEMVRL LREKYLESQT IVV            413

SEQ ID NO: 35           moltype = AA  length = 449
FEATURE                 Location/Qualifiers
REGION                  1..449
                        note = Synthetic sequence
source                  1..449
                        mol_type = protein
                        organism = synthetic construct
SEQUENCE: 35
MAKGKKKEGK PLYRAVRFEI FPTSDQITLF LRVSKNLQQV WNEAWQERQS CYEQFFGSIY     60
ERIGGQAKKRA QEAGFSEVWE NEAKKGLNKK LRQQEISMQL VSEKESLLQE LSIAFQEHGV   120
TLYDQINGLT ARRIIGEFAL IPRNWQEETL DSLDGSFKSF LALRKNGDPD AKPPRQRVSE    180
NSFYKIPGRS GFKVSNGQIY LSFGKIGQTL TSVIPEFQLK RLETAIKLKK FELCRDERDM    240
AKPGRFWISV AYEIPKPEKV PVVSKQITYL AIGASRLGVV SPKGEFCLNL PRSDYHWKPQ    300
INALQERLEG VVKGSRKWKK RMAACTRMFA KLGHQQKQHG QYEVVKKLLR HGVHFVVTEL    360
KVRSKPGALA DASKSDRKGS PTGPNWSAQN TGNIARLIQK LTDKASEHGG TVIKRNPPLL    420
SLEERQLPDA QRKIFIAKKL REEFLADQK                                     449

SEQ ID NO: 36           moltype = AA  length = 711
```

```
FEATURE              Location/Qualifiers
REGION               1..711
                     note = Synthetic sequence
source               1..711
                     mol_type = protein
                     organism = synthetic construct
SEQUENCE: 36
MAKREKKDDV  VLRGTKMRIY  PTDRQVTLMD  MWRRRCISLW  NLLLNLETAA  YGAKNTRSKL   60
GWRSIWARVV  EENHAKALIV  YQHGKCKKDG  SFVLKRDGTV  KHPPRERFPG  DRKILLGLFD  120
ALRHTLDKGA  KCKCNVNQPY  ALTRAWLDET  GHGARTADII  AWLKDFKGEC  DCTAISTAAK  180
YCPAPPTAEL  LTKIKRAAPA  DDLPVDQAIL  LDLFGALRGG  LKQKECDHTH  ARTVAYFEKH  240
ELAGRAEDIL  AWLIAHGGTC  DCKIVEEAAN  HCPGPRLFIW  EHELAMIMAR  LKAEPRTEWI  300
GDLPSHAAQT  VVKDLVKALQ  TMLKERAKAA  AGDESARKTG  FPKFKKQAYA  AGSVYFPNTT  360
MFFDVAAGRV  QLPNGCGSMR  CEIPRQLVAE  LLERNLKPGL  VIGAQLGLLG  GRIWRQGDRW  420
YLSCQWERPQ  PTLLPKTGRT  AGVKIAASIV  FTTYDNRGQT  KEYPMPPADK  KLTAVHLVAG  480
KQNSRALEAQ  KEKEKKLKAR  KERLRLGKLE  KGHDPNALKP  LKRPRVRRSK  LFYKSAARLA  540
ACEAIERDRR  DGFLHRVTNE  IVHKFDAVSV  QKMSVAPMMR  RQKQKEKQIE  SKKNEAKKED  600
NGAAKKPRNL  KPVRKLLRHV  AMARGRQFLE  YKYNDLRGPG  SVLIADRLEP  EVQECSRCGT  660
KNPQMKDGRR  LLRCIGVLPD  GTDCDAVLPR  NRNAARNAEK  RLRKHREAHN  A           711

SEQ ID NO: 37        moltype = AA  length = 574
FEATURE              Location/Qualifiers
REGION               1..574
                     note = Synthetic sequence
source               1..574
                     mol_type = protein
                     organism = synthetic construct
SEQUENCE: 37
MNEVLPIPAV  GEDAADTIMR  GSKMRIYPSV  RQAATMDLWR  RRCIQLWNLL  LELEQAAYSG   60
ENRRTQIGWR  SIWATVVEDS  HAEAVRVARE  GKKRKDGTFR  KAPSGKEIPP  LDPAMLAKIQ  120
RQMNGAVDVD  PKTGEVTPAQ  PRLFMWEHEL  QKIMARLKQA  PRTHWIDDLP  SHAAQSVVKD  180
LIKALQAMLR  ERKKRASGIG  GRDTGFPKPK  KNRYAAGSVY  FANTQLRFEA  KRGKAGDPDA  240
VRGEFARVKL  PNGVGWMECR  MPRHINAAHA  YAQATLMGGR  IWRQGENWYL  SCQWKMPKPA  300
PLPRAGRTAA  IKIAAAIPIT  TVDNRGQTRE  YAMPPIDRER  IAAHAAAGRA  QSRALEARKR  360
RAKKREAYAK  KRHAKKLERG  IAAKPPGRAR  IKLSPGFYAA  AAKLAKLEAE  DANAREAWLH  420
EITTQIVRNF  DVIAVPRMEV  AKLMKKPEPP  EEKEEQVKAP  WQGKRRSLKA  ARVMMRRTAM  480
ALIQTTLKYK  AVDLRGPQAY  EEIAPLDVTA  AACSGCGVLK  PEWKMARAKG  REIMRCQEPL  540
PGGKTCNTVL  TYTRNSARVI  GRELAVRLAE  RQKA                                574

SEQ ID NO: 38        moltype = AA  length = 400
FEATURE              Location/Qualifiers
REGION               1..400
                     note = Synthetic sequence
source               1..400
                     mol_type = protein
                     organism = synthetic construct
SEQUENCE: 38
MTTQKTYNFC  FYDQRFFELS  KEAGEVYSRS  LEEFWKIYDE  TGVWLSKFDL  QKHMRNKLER   60
KLLHSDSFLG  AMQQVHANLA  SWKQAKKVVP  DACPPRKPKF  LQAILFKKSQ  IKYKNGFLRL  120
TLGTEKEFLY  LKWDINIPLP  IYGSVTYSKT  RGWKINLCLE  TEVEQKNLSE  NKYLSIDLGV  180
KRVATIFDGE  NTITLSGKKF  MGLMHYRNKL  NGKTQSRLSH  KKKGSNNYKK  IQRAKRKTTD  240
RLLNIQKEML  HKYSSFIVNY  AIRNDIGNII  IGDNSSTHDS  PNMRGKTNQK  ISQNPEQKLK  300
NYIKYKFESI  SGRVDIVPEP  YTSRKCPHCK  NIKKSSPKGR  TYKCKKCGFI  FDRDGVGAIN  360
IYNENVSFGQ  IISPGRIRSL  TEPIGMKFHN  EIYFKSYVAA                          400

SEQ ID NO: 39        moltype = AA  length = 743
FEATURE              Location/Qualifiers
REGION               1..743
                     note = Synthetic sequence
source               1..743
                     mol_type = protein
                     organism = synthetic construct
SEQUENCE: 39
MSVRSFQARV  ECDKQTMEHL  WRTHKVFNER  LPEIIKILFK  MKRGECGQND  KQKSLYKSIS   60
QSILEANAQN  ADYLLNSVSI  KGWKPGTAKK  YRNASFTWAD  DAAKLSSQGI  HVYDKKQVLG  120
DLPGMMSQMV  CRQSVEAISG  HIELTKKWEK  EHNEWLKEKE  KWESEDEHKK  YLDLREKFEQ  180
FEQSIGGKIT  KRRGRWHLYL  KWLSDNPDFA  AWRGNKAVIN  PLSEKAQIRI  NKAKPNKKNS  240
VERDEFFKAN  PEMKALDNLH  GYYERNFVRR  RKTKKNPDGF  DHKPTFTLPH  PTIHPRWFVF  300
NKPKTNPEGY  RKLILPKKAG  DLGSLEMRLL  TGEKNKGNYP  DDWISVKFKA  DPRLSLIRPV  360
KGRRVVRKGK  EQGQTKETDS  YEFFDKHLKK  WRPAKLSGVK  LIFPDKTPKA  AYLYFTCDIP  420
DEPLTETAKK  IQWLETGDVT  KKGKKRKKKV  LPHGLVSCAV  DLSMRRGTTG  FATLCRYENG  480
KIHILRSRNL  WVGYKEGKGC  HPYRWTEGPD  LGHIAKHKRE  IRILRSKRGK  PVKGEESHID  540
LQKHIDYMGE  DRFKKAARTI  VNFALNTENA  ASKNGFYPRA  DVLLLENLEG  LIPDAEKERG  600
INRALAGWNR  RHLVERVIEM  AKDAGFKRRY  FEIPPYGTSQ  VCSKCGALGR  RYSIIRENNR  660
REIRFGYVEK  LFACPNCGYC  ANADHNASVN  LNRRFLIEDS  FKSYYDWKRL  SEKKQKEEIE  720
TIESKLMDKL  CAMHKISRGS  ISK                                             743

SEQ ID NO: 40        moltype = AA  length = 769
FEATURE              Location/Qualifiers
```

```
REGION                        1..769
                              note = Synthetic sequence
source                        1..769
                              mol_type = protein
                              organism = synthetic construct
SEQUENCE: 40
MHLWRTHCVF NQRLPALLKR LFAMRRGEVG GNEAQRQVYQ RVAQFVLARD AKDSVDLLNA    60
VSLRKRSANS AFKKKATISC NGQAREVTGE EVFAEAVALA SKGVFAYDKD DMRAGLPDSL   120
FQPLTRDAVA CMRSHEELVA TWKKEYREWR DRKSEWEAEP EHALYLNLRP KFEEGEAARG   180
GRFRKRAERD HAYLDWLEAN PQLAAWRRKA PPAVVPIDEA GKRRIARAKA WKQASVRAEE   240
FWKRNPELHA LHKIHVQYLR EFVRPRRTRR NKRREGFKQR PTFTMPDPVR HPRWCLFNAP   300
QTSPQGYRLL RLPQSRRTVG SVELRLLTGP SDGAGFPDAW VNVRFKADPR LAQLRPVKVP   360
RTVTRGKNKG AKVEADGFRY YDDQLLIERD AQVSGVKLLF RDIRMAPFAD KPIEDRLLSA   420
TPYLVFAVEI KDEARTERAK AIRFDETSEL TKSGKKRKTL PAGLVSVAVD LDTRGVGFLT   480
RAVIGVPEIQ QTHHGVRLLQ SRYVAVGQVE ARASGEAEWS PGPDLAHIAR HKREIRRLRQ   540
LRGKPVKGER SHVRLQAHID RMGEDRFKKA ARKIVNEALR GSNPAAGDPY TRADVLLYES   600
LETLLPDAER ERGINRALLR WNRAKLIEHL KRMCDDAGIR HFPVSPFGTS QVCSKCGALG   660
RRYSLARENG RAVIRFGWVE RLFACPNPEC PGRRPDRPDR PFTCNSDHNA SVNLHRVFAL   720
GDQAVAAFRA LAPRDSPART LAVKRVEDTL RPQLMRVHKL ADAGVDSPF              769

SEQ ID NO: 41                 moltype = AA  length = 666
FEATURE                       Location/Qualifiers
REGION                        1..666
                              note = Synthetic sequence
source                        1..666
                              mol_type = protein
                              organism = synthetic construct
SEQUENCE: 41
MATLVYRYGV RAHGSARQQD AVVSDPAMLE QLRLGHELRN ALVGVQHRYE DGKRAVWSGF    60
ASVAAADHRV TTGETAVAEL EKQARAEHSA DRTAATRQGT AESLKAARAA VKQARADRKA   120
AMAAVAEQAK PKIQALGDDR DAEIKDLYRR FCQDGVLLPR CGRCAGDLRS DGDCTDCGAA   180
HEPRKLYWAT YNAIREDHQT AVKLVEAKRK AGQPARLRFR RWTGDGTLTV QLQRMHGPAC   240
RCVTCAEKLT RRARKTDPQA PAVAADPAYP PTDPPRDPAL LASGQGKWRN VLQLGTWIPP   300
GEWSAMSRAE RRRVGRSHIG WQLGGGRQLT LPVQLHRQMP ADADVAMAQL TRVRVGGRHR   360
MSVALTAKLP DPPQVQGLPP VALHLGWRQR PDGSLRVATW ACPQPLDLPP AVADVVVSHG   420
GRWGEVIMPA RWLADAEVPP RLLGRRDKAM EPVLEALADW LEAHTEACTA RMTPALVRRW   480
RSQGRLAGLT NRWRGQPPTG SAEILTYLEA WRIQDKLLWE RESHLRRRLA ARRDDAWRRV   540
ASWLARHAGV LVVDDADIAE LRRRDDPADT DPTMPASAAQ AARARAALAA PGRLRHLATI   600
TATRDGLGVH TVASAGLTRL HRKCGHQAQP DPRYAASAVV TCPGCGNGYD QDYNAAMLML   660
DRQQQP                                                             666

SEQ ID NO: 42                 moltype = AA  length = 564
FEATURE                       Location/Qualifiers
REGION                        1..564
                              note = Synthetic sequence
source                        1..564
                              mol_type = protein
                              organism = synthetic construct
SEQUENCE: 42
MSRVELHRAY KFRLYPTPAQ VAELAEWERQ LRRLYNLAHS QRLAAMQRHV RPKSPGVLKS    60
ECLSCGAVAV AEIGTDGKAK KTVKHAVGCS VLECRSCGAS PDAEGRTAHT AACSFVDYYR   120
QGREMTQLLE EDDQLARVVC SARQETLRDL EKAWQRWHKM PGFGKPHFKK RIDSCRIYFS   180
TPKSWAVDLG YLSFTGVASS VGRIKIRQDR VWPGDAKFSS CHVVRDVDEW YAVFPLTFTK   240
EIEKPKGGAV GINRGAVHAI ADSTGRVVDS PKFYARSLGV IRHRARLLDR KVPFGRAVKP   300
SPTKYHGLPK ADIDAAAARV NASPGRLVYE ARARGSIAAA EAHLAALVLP APRQTSQLPS   360
EGRNRERARR FLALAHQRVR RQREWFLHNE SAHYAQSYTK IAIEDWSTKE MTSSEPRDAE   420
EMKRVTRARN RSILDVGWYE LGRQIAYKSE ATGAEFAKVD PGLRETETHV PEAIVRERDV   480
DVSGMLRGEA GISGTCSRCG GLLRASASGH ADAECEVCLH VEVGDVNAAV NVLKRAMFPG   540
AAPPSKEKAK VTIGIKGRKK KRAA                                         564

SEQ ID NO: 43                 moltype = AA  length = 565
FEATURE                       Location/Qualifiers
REGION                        1..565
                              note = Synthetic sequence
source                        1..565
                              mol_type = protein
                              organism = synthetic construct
SEQUENCE: 43
MSRVELHRAY KFRLYPTPVQ VAELSEWERQ LRRLYNLGHE QRLLTLTRHL RPKSPGVLKG    60
ECLSCDSTQV QEVGADGRPK TTVRHAEQCP TLACRSCGAL RDAEGRTAHT VACAFVDYYR   120
QGREMTELLA ADDQLARVVC SARQEVLRDL DKAWQRWRKM PGFGKPRFKR RTDSCRIYFS   180
TPKAWKLEGG HLSFTGAATT VGAIKMRQDR NWPASVQFSS CHVVRDVDEW YAVFPLTFVA   240
EVARPKGGAV GINRGAVHAI ADSTGRVVDS PRYYARALGV IRHRARLFDR KVPSGHAVKP   300
SPTKYRGLSA IEVDRVARAT GFTPGRVVTE ALNRGGVAYA ECALAAIAVL GHGPERPLTS   360
DGRNREKARK FLALAHQRVR RQREWFLHNE SAHYARTYSK IAIEDWSTKE MTASEPQGEE   420
TRRVTRSRNR SILDVGWYEL GRQLAYKTEA TGAEFAQVDP GLKETETNVP KAIADARDVD   480
VSGMLREAG ISGTCSKCGG LLRAPASGHA DAECEICLNV EVGDVNAAVN VLKRAMFPGD   540
APPASGEKPK VSIGIKGRQK KKKAA                                        565
```

```
SEQ ID NO: 44            moltype = AA  length = 499
FEATURE                  Location/Qualifiers
REGION                   1..499
                         note = Synthetic sequence
source                   1..499
                         mol_type = protein
                         organism = synthetic construct
SEQUENCE: 44
MEAIATGMSP ERRVELGILP GSVELKRAYK FRLYPMKVQQ AELSEWERQL RRLYNLAHEQ    60
RLAALLRYRD WDFQKGACPS CRVAVPGVHT AACDHVDYFR QAREMTQLLE VDAQLSRVIC   120
CARQEVLRDL DKAWQRWRKK LGGRPRFKRR TDSCRIYLST PKHWEIAGRY LRLSGLASSV   180
GEIRIEQDRA FPEGALLSSC SIVRDVDEWY ACLPLTFTQP IERAPHRSVG LNRGVVHALA   240
DSDGRVVDSP KFFERALATV QKRSRDLARK VSGSRNAHKA RIKLAKAHQR VRRQRAAFLH   300
QESAYYSKGF DLVALEDMSV RKMTATAGEA PEMGRGAQRD LNRGILDVGW YELARQIDYK   360
RLAHGGELLR VDPGQTTPLA CVTEEQPARG ISSACAVCGI PLARPASGNA RMRCTACGSS   420
QVGDVNAAEN VLTRALSSAP SGPKSPKASI KIKGRQKRLG TPANRAGEAS GGDPPVRGPV   480
EGGTLAYVVE PVSESQSDT                                                499

SEQ ID NO: 45            moltype = AA  length = 560
FEATURE                  Location/Qualifiers
REGION                   1..560
                         note = Synthetic sequence
source                   1..560
                         mol_type = protein
                         organism = synthetic construct
SEQUENCE: 45
MTVRTYKYRA YPTPEQAEAL TSWLRFASQL YNAALEHRKN AWGRHDAHGR GFRFWDGDAA    60
PRKKSDPPGR WVYRGGGGAH ISKNDQGKLL TEFRREHAEL LPPGMPALVQ HEVLARLERS   120
MAAFFQRATK GQKAGYPRWR SEHRYDSLTF GLTSPSKERF DPETGESLGR GKTVGAGTYH   180
NGDLRLTGLG ELRILEHRRI PMGAIPKSVI VRRSGKRWFV SIAMEMPSVE PAASGRPAVG   240
LDMGVVTWGT AFTADTSAAA ALVADLRRMA TDPSDCRRLE ELEREAAQLS EVLAHCRARG   300
LDPARPRRCP KELTKLYRRS LHRLGELDRA CARIRRRLQA AHDIAEPVPD EAGSAVLIEG   360
SNAGMRHARR VARTQRRVAR RTRAGHAHSN RRKKAVQAYA RAKERERSAR GDHRHKVSRA   420
LVRQFEEISV EALDIKQLTV APEHNPDPQP DLPAHVQRRR NRGELDAAWG AFFAALDYKA   480
ADAGGRVARK PAPHTTQECA RCGTLVPKPI SLRVHRCPAC GYTAPRTVNS ARNVLQRPLE   540
EPGRAGPSGA NGRGVPHAVA                                               560

SEQ ID NO: 46            moltype = AA  length = 404
FEATURE                  Location/Qualifiers
REGION                   1..404
                         note = Synthetic sequence
source                   1..404
                         mol_type = protein
                         organism = synthetic construct
SEQUENCE: 46
MNCRYRYRIY PTPGQRQSLA RLFGCVRVVW NDALFLCRQS EKLPKNSELQ KLCITQAKKT    60
EARGWLGQVS AIPLQQSVAD LGVAFKNFFQ SRSGKRKGKK VNPPRVKRRN NRQGARFTRG   120
GFKVKTSKVY LARIGDIKIK WSRPLPSEPS SVTVIKDCAG QYFLSFVVEV KPEIKPPKNP   180
SIGIDLGLKT FASCSNGEKI DSPDYSRLYR KLKRCQRRLA KRQRGSKRRE RMRVKVAKLN   240
AQIRDKRKDF LHKLSTKVVN ENQVIALEDL NVGGMLKNRK LSRAISQAGW YEFRSLCEGK   300
AEKHNRDFRV ISRWEPTSQV CSECGYRWGK IDLSVRSIVC INCGVEHDRD DNASVNIEQA   360
GLKVGVGHTH DSKRTGSACK TSNGAVCVEP STHREYVQLT LFDW                    404

SEQ ID NO: 47            moltype = AA  length = 392
FEATURE                  Location/Qualifiers
REGION                   1..392
                         note = Synthetic sequence
source                   1..392
                         mol_type = protein
                         organism = synthetic construct
SEQUENCE: 47
MKSRWTFRCY PTPEQEQHLA RTFGCVRFVW NWALRARTDA FRAGERIGYP ATDKALTLLK    60
QQPETVWLNE VSSVCLQQAL RDLQVAFSNF FDKRAAHPSF KRKEARQSAN YTERGFSFDH   120
ERRILKLAKI GAIKVKWSRK AIPHPSSIRL IRTASGKYFV SLVVETQPAP MPETGESVGV   180
DFGVARLATL SNGERISNPK HGAKWQRRLA FYQKRLARAT KGSKRRMRIK RHVARIHEKI   240
GNSRSDTLHK LSTDLVTRFD LICVEDLNLR GMVKNHSLAR SLHDASIGSA IRMIEEKAER   300
YGKNVVKIDR WFPSSKTCSD CGHIVEQLPL NVREWTCPEC GTTHDRDANA AANILAVGQT   360
VSAHGGTVRR SRAKASERKS QRSANRQGVN RA                                 392

SEQ ID NO: 48            moltype = AA  length = 10
FEATURE                  Location/Qualifiers
REGION                   1..10
                         note = Synthetic sequence
source                   1..10
                         mol_type = protein
                         organism = synthetic construct
SEQUENCE: 48
AAAAAAAAAA                                                           10
```

```
SEQ ID NO: 49          moltype = AA   length = 10
FEATURE                Location/Qualifiers
REGION                 1..10
                       note = Synthetic sequence
source                 1..10
                       mol_type = protein
                       organism = synthetic construct
SEQUENCE: 49
AAAAAAAAAA                                                              10

SEQ ID NO: 50          moltype = AA   length = 10
FEATURE                Location/Qualifiers
REGION                 1..10
                       note = Synthetic sequence
source                 1..10
                       mol_type = protein
                       organism = synthetic construct
SEQUENCE: 50
AAAAAAAAAA                                                              10

SEQ ID NO: 51          moltype = DNA   length = 37
FEATURE                Location/Qualifiers
misc_feature           1..37
                       note = Synthetic sequence
source                 1..37
                       mol_type = other DNA
                       organism = synthetic construct
SEQUENCE: 51
gttgcattcc ttcattcgtc tattcgggtt ctgcaac                                37

SEQ ID NO: 52          moltype = DNA   length = 37
FEATURE                Location/Qualifiers
misc_feature           1..37
                       note = Synthetic sequence
source                 1..37
                       mol_type = other DNA
                       organism = synthetic construct
SEQUENCE: 52
gttgcattcc ttcattcgtc tatccgggtt ctgcaag                                37

SEQ ID NO: 53          moltype = DNA   length = 37
FEATURE                Location/Qualifiers
misc_feature           1..37
                       note = Synthetic sequence
source                 1..37
                       mol_type = other DNA
                       organism = synthetic construct
SEQUENCE: 53
gttgcagaac ccgaatagac gaatgaagga atgcaac                                37

SEQ ID NO: 54          moltype = DNA   length = 37
FEATURE                Location/Qualifiers
misc_feature           1..37
                       note = Synthetic sequence
source                 1..37
                       mol_type = other DNA
                       organism = synthetic construct
SEQUENCE: 54
ctatcatatt cagaacaaag ggattaagga atgcaac                                37

SEQ ID NO: 55          moltype = DNA   length = 37
FEATURE                Location/Qualifiers
misc_feature           1..37
                       note = Synthetic sequence
source                 1..37
                       mol_type = other DNA
                       organism = synthetic construct
SEQUENCE: 55
ctttcatact cagaacaaag ggattaagga atgcaac                                37

SEQ ID NO: 56          moltype = DNA   length = 37
FEATURE                Location/Qualifiers
misc_feature           1..37
                       note = Synthetic sequence
source                 1..37
                       mol_type = other DNA
                       organism = synthetic construct
SEQUENCE: 56
gtctacaact cattgataga aatcaatgag ttagaca                                37
```

```
SEQ ID NO: 57            moltype = DNA  length = 37
FEATURE                  Location/Qualifiers
misc_feature             1..37
                         note = Synthetic sequence
source                   1..37
                         mol_type = other DNA
                         organism = synthetic construct
SEQUENCE: 57
gttataaagg cggggatcgc gaccgagcga ttgaaag                                   37

SEQ ID NO: 58            moltype = DNA  length = 37
FEATURE                  Location/Qualifiers
misc_feature             1..37
                         note = Synthetic sequence
source                   1..37
                         mol_type = other DNA
                         organism = synthetic construct
SEQUENCE: 58
gttgcattcc ttaattcatt ttctcaatat cggaaac                                   37

SEQ ID NO: 59            moltype = DNA  length = 37
FEATURE                  Location/Qualifiers
misc_feature             1..37
                         note = Synthetic sequence
source                   1..37
                         mol_type = other DNA
                         organism = synthetic construct
SEQUENCE: 59
gttgcagaaa tagaataaag gaattaagga atgcaac                                   37

SEQ ID NO: 60            moltype = DNA  length = 37
FEATURE                  Location/Qualifiers
misc_feature             1..37
                         note = Synthetic sequence
source                   1..37
                         mol_type = other DNA
                         organism = synthetic construct
SEQUENCE: 60
ctttcatact cagaacaaag ggattaagga atgcaac                                   37

SEQ ID NO: 61            moltype = DNA  length = 37
FEATURE                  Location/Qualifiers
misc_feature             1..37
                         note = Synthetic sequence
source                   1..37
                         mol_type = other DNA
                         organism = synthetic construct
SEQUENCE: 61
atttcatact cagaacaaag ggattaagga atgcaac                                   37

SEQ ID NO: 62            moltype = DNA  length = 38
FEATURE                  Location/Qualifiers
misc_feature             1..38
                         note = Synthetic sequence
source                   1..38
                         mol_type = other DNA
                         organism = synthetic construct
SEQUENCE: 62
gtttcagcgc acgaattaac gagatgagag atgcaact                                  38

SEQ ID NO: 63            moltype = DNA  length = 37
FEATURE                  Location/Qualifiers
misc_feature             1..37
                         note = Synthetic sequence
source                   1..37
                         mol_type = other DNA
                         organism = synthetic construct
SEQUENCE: 63
cttgcagaag ctgaatagac gaatcaagga atgcaac                                   37

SEQ ID NO: 64            moltype = DNA  length = 39
FEATURE                  Location/Qualifiers
misc_feature             1..39
                         note = Synthetic sequence
source                   1..39
                         mol_type = other DNA
                         organism = synthetic construct
SEQUENCE: 64
```

```
cacttgcagg ccttgaatag aggagttaag gaatgcaac                          39

SEQ ID NO: 65           moltype = DNA  length = 36
FEATURE                 Location/Qualifiers
misc_feature            1..36
                        note = Synthetic sequence
source                  1..36
                        mol_type = other DNA
                        organism = synthetic construct
SEQUENCE: 65
gtctccatga ctgaaaagtc gtggccgaat tgaaac                             36

SEQ ID NO: 66           moltype = DNA  length = 37
FEATURE                 Location/Qualifiers
misc_feature            1..37
                        note = Synthetic sequence
source                  1..37
                        mol_type = other DNA
                        organism = synthetic construct
SEQUENCE: 66
gttgcagcgc ccgaactgac gagacgagag atgcaac                            37

SEQ ID NO: 67           moltype = DNA  length = 37
FEATURE                 Location/Qualifiers
misc_feature            1..37
                        note = Synthetic sequence
source                  1..37
                        mol_type = other DNA
                        organism = synthetic construct
SEQUENCE: 67
gttgcgcgaa tagaataaag gaattaagga atgcaac                            37

SEQ ID NO: 68           moltype = DNA  length = 38
FEATURE                 Location/Qualifiers
misc_feature            1..38
                        note = Synthetic sequence
source                  1..38
                        mol_type = other DNA
                        organism = synthetic construct
SEQUENCE: 68
agttgcattc cttaatccct ctgttcagtt tgtgcaat                           38

SEQ ID NO: 69           moltype = DNA  length = 37
FEATURE                 Location/Qualifiers
misc_feature            1..37
                        note = Synthetic sequence
source                  1..37
                        mol_type = other DNA
                        organism = synthetic construct
SEQUENCE: 69
gttgcattcc tagtttctct aattagcact gtgcaac                            37

SEQ ID NO: 70           moltype = DNA  length = 37
FEATURE                 Location/Qualifiers
misc_feature            1..37
                        note = Synthetic sequence
source                  1..37
                        mol_type = other DNA
                        organism = synthetic construct
SEQUENCE: 70
gttgcggcgc gcgaataaac gagactagga atgcaac                            37

SEQ ID NO: 71           moltype = DNA  length = 41
FEATURE                 Location/Qualifiers
misc_feature            1..41
                        note = Synthetic sequence
source                  1..41
                        mol_type = other DNA
                        organism = synthetic construct
SEQUENCE: 71
actagttgca ttccttaatc cctttgttct gaatatgcta g                       41

SEQ ID NO: 72           moltype = DNA  length = 37
FEATURE                 Location/Qualifiers
misc_feature            1..37
                        note = Synthetic sequence
source                  1..37
                        mol_type = other DNA
                        organism = synthetic construct
```

-continued

```
SEQUENCE: 72
ctttcatatt cagaacaaag ggattaagga atgcaac                              37

SEQ ID NO: 73            moltype = DNA   length = 39
FEATURE                  Location/Qualifiers
misc_feature             1..39
                         note = Synthetic sequence
source                   1..39
                         mol_type = other DNA
                         organism = synthetic construct
SEQUENCE: 73
gttgcagtcc ttaacccta gtttctgaat atgaaagat                             39

SEQ ID NO: 74            moltype = DNA   length = 37
FEATURE                  Location/Qualifiers
misc_feature             1..37
                         note = Synthetic sequence
source                   1..37
                         mol_type = other DNA
                         organism = synthetic construct
SEQUENCE: 74
gttgcagccc ccgaactaac gagatgagag atgcaac                              37

SEQ ID NO: 75            moltype = DNA   length = 38
FEATURE                  Location/Qualifiers
misc_feature             1..38
                         note = Synthetic sequence
source                   1..38
                         mol_type = other DNA
                         organism = synthetic construct
SEQUENCE: 75
cttgcagaac aatcatatat gactaatcag actgcaac                             38

SEQ ID NO: 76            moltype = DNA   length = 37
FEATURE                  Location/Qualifiers
misc_feature             1..37
                         note = Synthetic sequence
source                   1..37
                         mol_type = other DNA
                         organism = synthetic construct
SEQUENCE: 76
gttgcactca ccggtgctca cgacgtaggg atgcaac                              37

SEQ ID NO: 77            moltype = DNA   length = 36
FEATURE                  Location/Qualifiers
misc_feature             1..36
                         note = Synthetic sequence
source                   1..36
                         mol_type = other DNA
                         organism = synthetic construct
SEQUENCE: 77
gtccctactc gctagggaaa ctaattgaat ggaaac                               36

SEQ ID NO: 78            moltype = DNA   length = 37
FEATURE                  Location/Qualifiers
misc_feature             1..37
                         note = Synthetic sequence
source                   1..37
                         mol_type = other DNA
                         organism = synthetic construct
SEQUENCE: 78
gttgcattcg ggtgcaaaac agggagtaga gtgtaac                              37

SEQ ID NO: 79            moltype = DNA   length = 35
FEATURE                  Location/Qualifiers
misc_feature             1..35
                         note = Synthetic sequence
source                   1..35
                         mol_type = other DNA
                         organism = synthetic construct
SEQUENCE: 79
cttccaaact cgagccagtg gggagagaag tggca                                35

SEQ ID NO: 80            moltype = DNA   length = 38
FEATURE                  Location/Qualifiers
misc_feature             1..38
                         note = Synthetic sequence
source                   1..38
                         mol_type = other DNA
```

```
                        organism = synthetic construct
SEQUENCE: 80
cctgtagacc ggtctcattc tgagagggt atgcaact                              38

SEQ ID NO: 81           moltype = DNA  length = 37
FEATURE                 Location/Qualifiers
misc_feature            1..37
                        note = Synthetic sequence
source                  1..37
                        mol_type = other DNA
                        organism = synthetic construct
SEQUENCE: 81
gtctcgagac cctacagatt ttggagaggg gtgggac                              37

SEQ ID NO: 82           moltype = DNA  length = 37
FEATURE                 Location/Qualifiers
misc_feature            1..37
                        note = Synthetic sequence
source                  1..37
                        mol_type = other DNA
                        organism = synthetic construct
SEQUENCE: 82
gtcccacccc tctccaaaat ctgtagggtc tcgagac                              37

SEQ ID NO: 83           moltype = DNA  length = 37
FEATURE                 Location/Qualifiers
misc_feature            1..37
                        note = Synthetic sequence
source                  1..37
                        mol_type = other DNA
                        organism = synthetic construct
SEQUENCE: 83
gtagcaggac tctcctcgag agaaacaggg gtatgct                              37

SEQ ID NO: 84           moltype = DNA  length = 40
FEATURE                 Location/Qualifiers
misc_feature            1..40
                        note = Synthetic sequence
source                  1..40
                        mol_type = other DNA
                        organism = synthetic construct
SEQUENCE: 84
gtacaatacc tctcctttaa gagagggagg ggtacgctac                           40

SEQ ID NO: 85           moltype = DNA  length = 31
FEATURE                 Location/Qualifiers
misc_feature            1..31
                        note = Synthetic sequence
source                  1..31
                        mol_type = other DNA
                        organism = synthetic construct
SEQUENCE: 85
cccctcgtt tccttcaggg gattcctttc c                                     31

SEQ ID NO: 86           moltype = DNA  length = 28
FEATURE                 Location/Qualifiers
misc_feature            1..28
                        note = Synthetic sequence
source                  1..28
                        mol_type = other DNA
                        organism = synthetic construct
SEQUENCE: 86
ggttcccccg ggcgcgggtg gggtggcg                                        28

SEQ ID NO: 87           moltype = DNA  length = 28
FEATURE                 Location/Qualifiers
misc_feature            1..28
                        note = Synthetic sequence
source                  1..28
                        mol_type = other DNA
                        organism = synthetic construct
SEQUENCE: 87
ggctgctccg ggtgcgcgtg gagcgagg                                        28

SEQ ID NO: 88           moltype = DNA  length = 35
FEATURE                 Location/Qualifiers
misc_feature            1..35
                        note = Synthetic sequence
source                  1..35
```

```
                        mol_type = other DNA
                        organism = synthetic construct
SEQUENCE: 88
gttttatacc ctttagaatt taaactgtct aaaag                              35

SEQ ID NO: 89           moltype = DNA   length = 36
FEATURE                 Location/Qualifiers
misc_feature            1..36
                        note = Synthetic sequence
source                  1..36
                        mol_type = other DNA
                        organism = synthetic construct
SEQUENCE: 89
attgcaccgg ccaacgcaaa tctgattgat ggacac                             36

SEQ ID NO: 90           moltype = DNA   length = 36
FEATURE                 Location/Qualifiers
misc_feature            1..36
                        note = Synthetic sequence
source                  1..36
                        mol_type = other DNA
                        organism = synthetic construct
SEQUENCE: 90
gccgcagcgg ccgacgcggc cctgatcgat ggacac                             36

SEQ ID NO: 91           moltype = DNA   length = 36
FEATURE                 Location/Qualifiers
misc_feature            1..36
                        note = Synthetic sequence
source                  1..36
                        mol_type = other DNA
                        organism = synthetic construct
SEQUENCE: 91
gtcgaaatgc ccgcgcgggg gcgtcgtacc cgcgac                             36

SEQ ID NO: 92           moltype = DNA   length = 29
FEATURE                 Location/Qualifiers
misc_feature            1..29
                        note = Synthetic sequence
source                  1..29
                        mol_type = other DNA
                        organism = synthetic construct
SEQUENCE: 92
ggctagcccg tgcgcgcagg gacgagtgg                                     29

SEQ ID NO: 93           moltype = DNA   length = 24
FEATURE                 Location/Qualifiers
misc_feature            1..24
                        note = Synthetic sequence
source                  1..24
                        mol_type = other DNA
                        organism = synthetic construct
SEQUENCE: 93
gcccgtgcgc gcagggacga gtgg                                          24

SEQ ID NO: 94           moltype = DNA   length = 37
FEATURE                 Location/Qualifiers
misc_feature            1..37
                        note = Synthetic sequence
source                  1..37
                        mol_type = other DNA
                        organism = synthetic construct
SEQUENCE: 94
gttgcagcgg ccgacggagc gcgagcgtgg atgccac                            37

SEQ ID NO: 95           moltype = DNA   length = 29
FEATURE                 Location/Qualifiers
misc_feature            1..29
                        note = Synthetic sequence
source                  1..29
                        mol_type = other DNA
                        organism = synthetic construct
SEQUENCE: 95
ccatcgcccc gcgcgcacgt ggatgagcc                                     29

SEQ ID NO: 96           moltype = DNA   length = 35
FEATURE                 Location/Qualifiers
misc_feature            1..35
                        note = Synthetic sequence
```

```
source                  1..35
                        mol_type = other DNA
                        organism = synthetic construct
SEQUENCE: 96
ctttagactt ctccggaagt cgaattaatg gaaac                              35

SEQ ID NO: 97           moltype = DNA   length = 28
FEATURE                 Location/Qualifiers
misc_feature            1..28
                        note = Synthetic sequence
source                  1..28
                        mol_type = other DNA
                        organism = synthetic construct
SEQUENCE: 97
gggcgccccg cgcgagcggg ggttgaag                                      28

SEQ ID NO: 98           moltype = AA   length = 10
FEATURE                 Location/Qualifiers
REGION                  1..10
                        note = Synthetic sequence
source                  1..10
                        mol_type = protein
                        organism = synthetic construct
SEQUENCE: 98
AAAAAAAAAA                                                          10

SEQ ID NO: 99           moltype = AA   length = 10
FEATURE                 Location/Qualifiers
REGION                  1..10
                        note = Synthetic sequence
source                  1..10
                        mol_type = protein
                        organism = synthetic construct
SEQUENCE: 99
AAAAAAAAAA                                                          10

SEQ ID NO: 100          moltype = AA   length = 10
FEATURE                 Location/Qualifiers
REGION                  1..10
                        note = Synthetic sequence
source                  1..10
                        mol_type = protein
                        organism = synthetic construct
SEQUENCE: 100
AAAAAAAAAA                                                          10

SEQ ID NO: 101          moltype = AA   length = 84
FEATURE                 Location/Qualifiers
REGION                  1..84
                        note = Synthetic sequence
source                  1..84
                        mol_type = protein
                        organism = synthetic construct
SEQUENCE: 101
MASMISSSAV TTVSRASRGQ SAAMAPFGGL KSMTGFPVRK VNTDITSITS NGGRVKCMQV   60
WPPIGKKKFE TLSYLPPLTR DSRA                                          84

SEQ ID NO: 102          moltype = AA   length = 57
FEATURE                 Location/Qualifiers
REGION                  1..57
                        note = Synthetic sequence
source                  1..57
                        mol_type = protein
                        organism = synthetic construct
SEQUENCE: 102
MASMISSSAV TTVSRASRGQ SAAMAPFGGL KSMTGFPVRK VNTDITSITS NGGRVKS      57

SEQ ID NO: 103          moltype = AA   length = 85
FEATURE                 Location/Qualifiers
REGION                  1..85
                        note = Synthetic sequence
source                  1..85
                        mol_type = protein
                        organism = synthetic construct
SEQUENCE: 103
MASSMLSSAT MVASPAQATM VAPFNGLKSS AAFPATRKAN NDITSITSNG GRVNCMQVWP   60
PIEKKKFETL SYLPDLTDSG GRVNC                                         85

SEQ ID NO: 104          moltype = AA   length = 76
```

```
FEATURE                 Location/Qualifiers
REGION                  1..76
                        note = Synthetic sequence
source                  1..76
                        mol_type = protein
                        organism = synthetic construct
SEQUENCE: 104
MAQVSRICNG VQNPSLISNL SKSSQRKSPL SVSLKTQQHP RAYPISSSWG LKKSGMTLIG    60
SELRPLKVMS SVSTAC                                                    76

SEQ ID NO: 105          moltype = AA  length = 76
FEATURE                 Location/Qualifiers
REGION                  1..76
                        note = Synthetic sequence
source                  1..76
                        mol_type = protein
                        organism = synthetic construct
SEQUENCE: 105
MAQVSRICNG VWNPSLISNL SKSSQRKSPL SVSLKTQQHP RAYPISSSWG LKKSGMTLIG    60
SELRPLKVMS SVSTAC                                                    76

SEQ ID NO: 106          moltype = AA  length = 72
FEATURE                 Location/Qualifiers
REGION                  1..72
                        note = Synthetic sequence
source                  1..72
                        mol_type = protein
                        organism = synthetic construct
SEQUENCE: 106
MAQINNMAQG IQTLNPNSNF HKPQVPKSSS FLVFGSKKLK NSANSMLVLK KDSIFMQLFC    60
SFRISASVAT AC                                                        72

SEQ ID NO: 107          moltype = AA  length = 69
FEATURE                 Location/Qualifiers
REGION                  1..69
                        note = Synthetic sequence
source                  1..69
                        mol_type = protein
                        organism = synthetic construct
SEQUENCE: 107
MAALVTSQLA TSGTVLSVTD RFRRPGFQGL RPRNPADAAL GMRTVGASAA PKQSRKPHRF    60
DRRCLSMVV                                                            69

SEQ ID NO: 108          moltype = AA  length = 77
FEATURE                 Location/Qualifiers
REGION                  1..77
                        note = Synthetic sequence
source                  1..77
                        mol_type = protein
                        organism = synthetic construct
SEQUENCE: 108
MAALTTSQLA TSATGFGIAD RSAPSSLLRH GFQGLKPRSP AGGDATSLSV TTSARATPKQ    60
QRSVQRGSRR FPSVVVC                                                   77

SEQ ID NO: 109          moltype = AA  length = 57
FEATURE                 Location/Qualifiers
REGION                  1..57
                        note = Synthetic sequence
source                  1..57
                        mol_type = protein
                        organism = synthetic construct
SEQUENCE: 109
MASSVLSSAA VATRSNVAQA NMVAPFTGLK SAASFPVSRK QNLDITSIAS NGGRVQC       57

SEQ ID NO: 110          moltype = AA  length = 65
FEATURE                 Location/Qualifiers
REGION                  1..65
                        note = Synthetic sequence
source                  1..65
                        mol_type = protein
                        organism = synthetic construct
SEQUENCE: 110
MESLAATSVF APSRVAVPAA RALVRAGTVV PTRRTSSTSG TSGVKCSAAV TPQASPVISR    60
SAAAA                                                                65

SEQ ID NO: 111          moltype = AA  length = 72
FEATURE                 Location/Qualifiers
REGION                  1..72
                        note = Synthetic sequence
```

```
source                      1..72
                            mol_type = protein
                            organism = synthetic construct
SEQUENCE: 111
MGAAATSMQS LKFSNRLVPP SRRLSPVPNN VTCNNLPKSA APVRTVKCCA SSWNSTINGA     60
AATTNGASAA SS                                                         72

SEQ ID NO: 112              moltype = AA  length = 20
FEATURE                     Location/Qualifiers
REGION                      1..20
                            note = Synthetic sequence
SITE                        4
                            note = misc_feature - Xaa can be any naturally occurring
                             amino acid
SITE                        8
                            note = misc_feature - Xaa can be any naturally occurring
                             amino acid
SITE                        11
                            note = misc_feature - Xaa can be any naturally occurring
                             amino acid
SITE                        15
                            note = misc_feature - Xaa can be any naturally occurring
                             amino acid
SITE                        19
                            note = misc_feature - Xaa can be any naturally occurring
                             amino acid
source                      1..20
                            mol_type = protein
                            organism = synthetic construct
SEQUENCE: 112
GLFXALLXLL XSLWXLLLXA                                                 20

SEQ ID NO: 113              moltype = AA  length = 20
FEATURE                     Location/Qualifiers
REGION                      1..20
                            note = Synthetic sequence
source                      1..20
                            mol_type = protein
                            organism = synthetic construct
SEQUENCE: 113
GLFHALLHLL HSLWHLLLHA                                                 20

SEQ ID NO: 114              moltype = AA  length = 7
FEATURE                     Location/Qualifiers
REGION                      1..7
                            note = Synthetic sequence
source                      1..7
                            mol_type = protein
                            organism = synthetic construct
SEQUENCE: 114
PKKKRKV                                                                7

SEQ ID NO: 115              moltype = AA  length = 16
FEATURE                     Location/Qualifiers
REGION                      1..16
                            note = Synthetic sequence
source                      1..16
                            mol_type = protein
                            organism = synthetic construct
SEQUENCE: 115
KRPAATKKAG QAKKKK                                                     16

SEQ ID NO: 116              moltype = AA  length = 9
FEATURE                     Location/Qualifiers
REGION                      1..9
                            note = Synthetic sequence
source                      1..9
                            mol_type = protein
                            organism = synthetic construct
SEQUENCE: 116
PAAKRVKLD                                                              9

SEQ ID NO: 117              moltype = AA  length = 11
FEATURE                     Location/Qualifiers
REGION                      1..11
                            note = Synthetic sequence
source                      1..11
                            mol_type = protein
                            organism = synthetic construct
```

```
SEQUENCE: 117
RQRRNELKRS P                                                                    11

SEQ ID NO: 118          moltype = AA   length = 38
FEATURE                 Location/Qualifiers
REGION                  1..38
                        note = Synthetic sequence
source                  1..38
                        mol_type = protein
                        organism = synthetic construct
SEQUENCE: 118
NQSSNFGPMK GGNFGGRSSG PYGGGGQYFA KPRNQGGY                                        38

SEQ ID NO: 119          moltype = AA   length = 42
FEATURE                 Location/Qualifiers
REGION                  1..42
                        note = Synthetic sequence
source                  1..42
                        mol_type = protein
                        organism = synthetic construct
SEQUENCE: 119
RMRIZFKNKG KDTAELRRRR VEVSVELRKA KKDEQILKRR NV                                   42

SEQ ID NO: 120          moltype = AA   length = 8
FEATURE                 Location/Qualifiers
REGION                  1..8
                        note = Synthetic sequence
source                  1..8
                        mol_type = protein
                        organism = synthetic construct
SEQUENCE: 120
VSRKRPRP                                                                         8

SEQ ID NO: 121          moltype = AA   length = 8
FEATURE                 Location/Qualifiers
REGION                  1..8
                        note = Synthetic sequence
source                  1..8
                        mol_type = protein
                        organism = synthetic construct
SEQUENCE: 121
PPKKARED                                                                         8

SEQ ID NO: 122          moltype = AA   length = 8
FEATURE                 Location/Qualifiers
REGION                  1..8
                        note = Synthetic sequence
source                  1..8
                        mol_type = protein
                        organism = synthetic construct
SEQUENCE: 122
PQPKKKPL                                                                         8

SEQ ID NO: 123          moltype = AA   length = 12
FEATURE                 Location/Qualifiers
REGION                  1..12
                        note = Synthetic sequence
source                  1..12
                        mol_type = protein
                        organism = synthetic construct
SEQUENCE: 123
SALIKKKKM AP                                                                    12

SEQ ID NO: 124          moltype = AA   length = 5
FEATURE                 Location/Qualifiers
REGION                  1..5
                        note = Synthetic sequence
source                  1..5
                        mol_type = protein
                        organism = synthetic construct
SEQUENCE: 124
DRLRR                                                                            5

SEQ ID NO: 125          moltype = AA   length = 7
FEATURE                 Location/Qualifiers
REGION                  1..7
                        note = Synthetic sequence
source                  1..7
                        mol_type = protein
```

```
                          organism = synthetic construct
SEQUENCE: 125
PKQKKRK                                                                  7

SEQ ID NO: 126            moltype = AA  length = 10
FEATURE                   Location/Qualifiers
REGION                    1..10
                          note = Synthetic sequence
source                    1..10
                          mol_type = protein
                          organism = synthetic construct
SEQUENCE: 126
RKLKKKIKKL                                                              10

SEQ ID NO: 127            moltype = AA  length = 10
FEATURE                   Location/Qualifiers
REGION                    1..10
                          note = Synthetic sequence
source                    1..10
                          mol_type = protein
                          organism = synthetic construct
SEQUENCE: 127
REKKKFLKRR                                                              10

SEQ ID NO: 128            moltype = AA  length = 20
FEATURE                   Location/Qualifiers
REGION                    1..20
                          note = Synthetic sequence
source                    1..20
                          mol_type = protein
                          organism = synthetic construct
SEQUENCE: 128
KRKGDEVDGV DEVAKKKSKK                                                   20

SEQ ID NO: 129            moltype = AA  length = 17
FEATURE                   Location/Qualifiers
REGION                    1..17
                          note = Synthetic sequence
source                    1..17
                          mol_type = protein
                          organism = synthetic construct
SEQUENCE: 129
RKCLQAGMNL EARKTKK                                                      17

SEQ ID NO: 130            moltype = AA  length = 11
FEATURE                   Location/Qualifiers
REGION                    1..11
                          note = Synthetic sequence
source                    1..11
                          mol_type = protein
                          organism = synthetic construct
SEQUENCE: 130
YGRKKRRQRR R                                                            11

SEQ ID NO: 131            moltype = AA  length = 12
FEATURE                   Location/Qualifiers
REGION                    1..12
                          note = Synthetic sequence
source                    1..12
                          mol_type = protein
                          organism = synthetic construct
SEQUENCE: 131
RRQRRTSKLM KR                                                           12

SEQ ID NO: 132            moltype = AA  length = 27
FEATURE                   Location/Qualifiers
REGION                    1..27
                          note = Synthetic sequence
source                    1..27
                          mol_type = protein
                          organism = synthetic construct
SEQUENCE: 132
GWTLNSAGYL LGKINLKALA ALAKKIL                                           27

SEQ ID NO: 133            moltype = AA  length = 33
FEATURE                   Location/Qualifiers
REGION                    1..33
                          note = Synthetic sequence
source                    1..33
```

```
                        mol_type = protein
                        organism = synthetic construct
SEQUENCE: 133
KALAWEAKLA KALAKALAKH LAKALAKALK CEA                                    33

SEQ ID NO: 134          moltype = AA   length = 16
FEATURE                 Location/Qualifiers
REGION                  1..16
                        note = Synthetic sequence
source                  1..16
                        mol_type = protein
                        organism = synthetic construct
SEQUENCE: 134
RQIKIWFQNR RMKWKK                                                       16

SEQ ID NO: 135          moltype = AA   length = 9
FEATURE                 Location/Qualifiers
REGION                  1..9
                        note = Synthetic sequence
source                  1..9
                        mol_type = protein
                        organism = synthetic construct
SEQUENCE: 135
RKKRRQRRR                                                                9

SEQ ID NO: 136          moltype = AA   length = 8
FEATURE                 Location/Qualifiers
REGION                  1..8
                        note = Synthetic sequence
source                  1..8
                        mol_type = protein
                        organism = synthetic construct
SEQUENCE: 136
RKKRRQRR                                                                 8

SEQ ID NO: 137          moltype = AA   length = 11
FEATURE                 Location/Qualifiers
REGION                  1..11
                        note = Synthetic sequence
source                  1..11
                        mol_type = protein
                        organism = synthetic construct
SEQUENCE: 137
YARAAARQAR A                                                            11

SEQ ID NO: 138          moltype = AA   length = 11
FEATURE                 Location/Qualifiers
REGION                  1..11
                        note = Synthetic sequence
source                  1..11
                        mol_type = protein
                        organism = synthetic construct
SEQUENCE: 138
THRLPRRRRR R                                                            11

SEQ ID NO: 139          moltype = AA   length = 11
FEATURE                 Location/Qualifiers
REGION                  1..11
                        note = Synthetic sequence
source                  1..11
                        mol_type = protein
                        organism = synthetic construct
SEQUENCE: 139
GGRRARRRRR R                                                            11

SEQ ID NO: 140          moltype = AA   length = 5
FEATURE                 Location/Qualifiers
REGION                  1..5
                        note = Synthetic sequence
source                  1..5
                        mol_type = protein
                        organism = synthetic construct
SEQUENCE: 140
GSGGS                                                                    5

SEQ ID NO: 141          moltype = AA   length = 6
FEATURE                 Location/Qualifiers
REGION                  1..6
                        note = Synthetic sequence
```

```
source                      1..6
                            mol_type = protein
                            organism = synthetic construct
SEQUENCE: 141
GGSGGS                                                                  6

SEQ ID NO: 142              moltype = AA  length = 4
FEATURE                     Location/Qualifiers
REGION                      1..4
                            note = Synthetic sequence
source                      1..4
                            mol_type = protein
                            organism = synthetic construct
SEQUENCE: 142
GGGS                                                                    4

SEQ ID NO: 143              moltype = AA  length = 4
FEATURE                     Location/Qualifiers
REGION                      1..4
                            note = Synthetic sequence
source                      1..4
                            mol_type = protein
                            organism = synthetic construct
SEQUENCE: 143
GGSG                                                                    4

SEQ ID NO: 144              moltype = AA  length = 5
FEATURE                     Location/Qualifiers
REGION                      1..5
                            note = Synthetic sequence
source                      1..5
                            mol_type = protein
                            organism = synthetic construct
SEQUENCE: 144
GGSGG                                                                   5

SEQ ID NO: 145              moltype = AA  length = 5
FEATURE                     Location/Qualifiers
REGION                      1..5
                            note = Synthetic sequence
source                      1..5
                            mol_type = protein
                            organism = synthetic construct
SEQUENCE: 145
GSGSG                                                                   5

SEQ ID NO: 146              moltype = AA  length = 5
FEATURE                     Location/Qualifiers
REGION                      1..5
                            note = Synthetic sequence
source                      1..5
                            mol_type = protein
                            organism = synthetic construct
SEQUENCE: 146
GSGGG                                                                   5

SEQ ID NO: 147              moltype = AA  length = 5
FEATURE                     Location/Qualifiers
REGION                      1..5
                            note = Synthetic sequence
source                      1..5
                            mol_type = protein
                            organism = synthetic construct
SEQUENCE: 147
GGGSG                                                                   5

SEQ ID NO: 148              moltype = AA  length = 5
FEATURE                     Location/Qualifiers
REGION                      1..5
                            note = Synthetic sequence
source                      1..5
                            mol_type = protein
                            organism = synthetic construct
SEQUENCE: 148
GSSSG                                                                   5

SEQ ID NO: 149              moltype = AA  length = 4
FEATURE                     Location/Qualifiers
REGION                      1..4
```

```
                        note = Synthetic sequence
source                  1..4
                        mol_type = protein
                        organism = synthetic construct
SEQUENCE: 149
AAAA                                                                             4

SEQ ID NO: 150          moltype = AA   length = 4
FEATURE                 Location/Qualifiers
REGION                  1..4
                        note = Synthetic sequence
source                  1..4
                        mol_type = protein
                        organism = synthetic construct
SEQUENCE: 150
AAAA                                                                             4

SEQ ID NO: 151          moltype = DNA   length = 80
FEATURE                 Location/Qualifiers
misc_feature            1..80
                        note = Synthetic sequence
source                  1..80
                        mol_type = other DNA
                        organism = synthetic construct
SEQUENCE: 151
cgattcctcc ctacagtagt taggtatagc cgaaaggtag agactaaatc tgtagttgga              60
gtgggccgct tgcatcggcc                                                          80

SEQ ID NO: 152          moltype = DNA   length = 122
FEATURE                 Location/Qualifiers
misc_feature            1..122
                        note = Synthetic sequence
source                  1..122
                        mol_type = other DNA
                        organism = synthetic construct
SEQUENCE: 152
tcgtctcgag ggttaccaaa attggcactt ctcgacttta ggccgatgca agcggcccac              60
tccactacag atttagtctc taccttgcgg ctataccaa cttactgtag ggaggaatcg              120
tg                                                                             122

SEQ ID NO: 153          moltype = DNA   length = 91
FEATURE                 Location/Qualifiers
misc_feature            1..91
                        note = Synthetic sequence
source                  1..91
                        mol_type = other DNA
                        organism = synthetic construct
SEQUENCE: 153
cttcactgat aaagtggaga accgcttcac caaaagctgt cccttagggg attagaactt              60
gagtgaaggt gggctgcttg catcagccta a                                             91

SEQ ID NO: 154          moltype = DNA   length = 114
FEATURE                 Location/Qualifiers
misc_feature            1..114
                        note = Synthetic sequence
source                  1..114
                        mol_type = other DNA
                        organism = synthetic construct
SEQUENCE: 154
cagaataata ctgacttact aagatatctt gagggtatac ccgaaaagat tggcgttgtt              60
gcaacgcaat aagatgtaaa tctgaaaagg tttggaatca tataataat ttta                    114

SEQ ID NO: 155          moltype = DNA   length = 104
FEATURE                 Location/Qualifiers
misc_feature            1..104
                        note = Synthetic sequence
source                  1..104
                        mol_type = other DNA
                        organism = synthetic construct
SEQUENCE: 155
aagccaagat atggaatgcc attgtaatat tatggtgttg acttagttta gatttaaaca              60
atcttcgatg gctatatgcg gaaggtttgg cgtcgttgta acgc                              104

SEQ ID NO: 156          moltype = DNA   length = 213
FEATURE                 Location/Qualifiers
misc_feature            1..213
                        note = Synthetic sequence
source                  1..213
                        mol_type = other DNA
```

```
                        organism = synthetic construct
SEQUENCE: 156
cagtgtgcat agctataaca ctacgcaaag actgctaaag agcgatgtgc tctatcgcag    60
tctcaccttt aatggactta cggatctttt ggagcactaa gctccgctgc ggtgcaacac   120
cgcccttttc ttgcctctgc ttgccctttc cggttattat agcccgggaga gtgcggaaga  180
ttaccgctct agctcgcagc atgttactga gtc                                213

SEQ ID NO: 157          moltype = DNA   length = 94
FEATURE                 Location/Qualifiers
misc_feature            1..94
                        note = Synthetic sequence
source                  1..94
                        mol_type = other DNA
                        organism = synthetic construct
SEQUENCE: 157
gcaagtcatt cggggacact ttttgttatt taaagtgttt tagataaatc agtgtcatgc    60
tgaataacga cccgacctat aaataacata atcc                                94

SEQ ID NO: 158          moltype = DNA   length = 252
FEATURE                 Location/Qualifiers
misc_feature            1..252
                        note = Synthetic sequence
source                  1..252
                        mol_type = other DNA
                        organism = synthetic construct
SEQUENCE: 158
gtccttaagg tactacacat tacatgtgaa cgtggagcta ataatagaaa tattattaga    60
ctacacctta ttaataacgg taggagatct atatggtctt gaatggaata gtaattgtga   120
aattataatt tctgttctta gctacttaag atggctcgtt gcaagccact cggggggctc   180
cttgaagtca aagagcttta gacaaatcag tgtcaaactg aataacgacc cgaccatgac   240
ttcataatcc cg                                                       252

SEQ ID NO: 159          moltype = DNA   length = 152
FEATURE                 Location/Qualifiers
misc_feature            1..152
                        note = Synthetic sequence
source                  1..152
                        mol_type = other DNA
                        organism = synthetic construct
SEQUENCE: 159
ctcgaggcta tttcatactc agaacaaagg gattaaggaa tgcaacccat ttcaaaatct    60
gtggaattat cacaaccatt aacatttcat actcagaaca aagggattaa ggaatgcaac   120
ggacaccttg ctatgtcctt ttgatgtatg tg                                 152

SEQ ID NO: 160          moltype = DNA   length = 61
FEATURE                 Location/Qualifiers
misc_feature            1..61
                        note = Synthetic sequence
source                  1..61
                        mol_type = other DNA
                        organism = synthetic construct
SEQUENCE: 160
ctcgaggcta tttcatactc agaacaaagc tcagaacaaa gggaataagg aatgcaacgg    60
a                                                                    61

SEQ ID NO: 161          moltype = DNA   length = 101
FEATURE                 Location/Qualifiers
misc_feature            1..101
                        note = Synthetic sequence
source                  1..101
                        mol_type = other DNA
                        organism = synthetic construct
SEQUENCE: 161
ctcagaaaca aagggattaa ggaatgcaac ccatttcaaa atctgtggaa actcagaaca    60
aagggattaa ggaatgcaac ggacaccttg ctatgtcctt c                       101

SEQ ID NO: 162          moltype = DNA   length = 86
FEATURE                 Location/Qualifiers
misc_feature            1..86
                        note = Synthetic sequence
source                  1..86
                        mol_type = other DNA
                        organism = synthetic construct
SEQUENCE: 162
ctcagaacaa agggattaag gaatgcaacc catttcctca gaacaaaggg attaaggaat    60
gcaacggaca ccttgctatg tccttc                                         86

SEQ ID NO: 163          moltype = DNA   length = 76
FEATURE                 Location/Qualifiers
```

```
misc_feature            1..76
                        note = Synthetic sequence
source                  1..76
                        mol_type = other DNA
                        organism = synthetic construct
SEQUENCE: 163
ctcagaacaa agggattaag gaatgcaacc catttctcag aacaaaggga ttaaggaatg    60
caacggacac cttgct                                                   76

SEQ ID NO: 164          moltype = DNA  length = 82
FEATURE                 Location/Qualifiers
misc_feature            1..82
                        note = Synthetic sequence
source                  1..82
                        mol_type = other DNA
                        organism = synthetic construct
SEQUENCE: 164
ctcagaacaa agggattaag gaatgcaacc catttcaaaa ctcagaacaa agggattaag    60
gaatgcaacg gacaccttgc ta                                            82

SEQ ID NO: 165          moltype = DNA  length = 72
FEATURE                 Location/Qualifiers
misc_feature            1..72
                        note = Synthetic sequence
source                  1..72
                        mol_type = other DNA
                        organism = synthetic construct
SEQUENCE: 165
ctcagaacaa agggattaag gaatgcaacc catttcctca gaacaaaggg attaaggaat    60
gcaacggaca cc                                                       72

SEQ ID NO: 166          moltype = DNA  length = 59
FEATURE                 Location/Qualifiers
misc_feature            1..59
                        note = Synthetic sequence
source                  1..59
                        mol_type = other DNA
                        organism = synthetic construct
SEQUENCE: 166
ctcagaacaa agggattaag gaatgcaacc cgggattaag gaatgcaacg gacaccttg    59

SEQ ID NO: 167          moltype = DNA  length = 50
FEATURE                 Location/Qualifiers
misc_feature            1..50
                        note = Synthetic sequence
source                  1..50
                        mol_type = other DNA
                        organism = synthetic construct
SEQUENCE: 167
ctcagaacaa agggattaag gaatgcaacc aacggacacc ttgctatgtc              50

SEQ ID NO: 168          moltype = DNA  length = 45
FEATURE                 Location/Qualifiers
misc_feature            1..45
                        note = Synthetic sequence
source                  1..45
                        mol_type = other DNA
                        organism = synthetic construct
SEQUENCE: 168
ctcagaacaa agggattaag gaatgcaacc catttcaaaa tctgt                   45

SEQ ID NO: 169          moltype = DNA  length = 41
FEATURE                 Location/Qualifiers
misc_feature            1..41
                        note = Synthetic sequence
source                  1..41
                        mol_type = other DNA
                        organism = synthetic construct
SEQUENCE: 169
ctcagaacaa agggattaag gaatgcaacc catttcaaaa t                       41

SEQ ID NO: 170          moltype = DNA  length = 36
FEATURE                 Location/Qualifiers
misc_feature            1..36
                        note = Synthetic sequence
source                  1..36
                        mol_type = other DNA
                        organism = synthetic construct
SEQUENCE: 170
```

```
ctcagaacaa agggattaag gaatgcaacc catttc                                36

SEQ ID NO: 171          moltype = DNA  length = 36
FEATURE                 Location/Qualifiers
misc_feature            1..36
                        note = Synthetic sequence
source                  1..36
                        mol_type = other DNA
                        organism = synthetic construct
SEQUENCE: 171
ctcagaacaa agggattaag gaatgcaacc catttc                                36

SEQ ID NO: 172          moltype = DNA  length = 36
FEATURE                 Location/Qualifiers
misc_feature            1..36
                        note = Synthetic sequence
source                  1..36
                        mol_type = other DNA
                        organism = synthetic construct
SEQUENCE: 172
ctcagaacaa agggattaag gaatgcaacc catttc                                36

SEQ ID NO: 173          moltype = DNA  length = 37
FEATURE                 Location/Qualifiers
misc_feature            1..37
                        note = Synthetic sequence
source                  1..37
                        mol_type = other DNA
                        organism = synthetic construct
SEQUENCE: 173
ctcagaacaa agggattaag gaatgcaacc catttca                               37

SEQ ID NO: 174          moltype = DNA  length = 38
FEATURE                 Location/Qualifiers
misc_feature            1..38
                        note = Synthetic sequence
source                  1..38
                        mol_type = other DNA
                        organism = synthetic construct
SEQUENCE: 174
ctcagaacaa agggattaag gaatgcaacc catttcaa                              38

SEQ ID NO: 175          moltype = DNA  length = 46
FEATURE                 Location/Qualifiers
misc_feature            1..46
                        note = Synthetic sequence
source                  1..46
                        mol_type = other DNA
                        organism = synthetic construct
SEQUENCE: 175
ctcagaacaa agggattaag gaatgcaacc catttcaaaa tctgtg                     46

SEQ ID NO: 176          moltype = DNA  length = 46
FEATURE                 Location/Qualifiers
misc_feature            1..46
                        note = Synthetic sequence
source                  1..46
                        mol_type = other DNA
                        organism = synthetic construct
SEQUENCE: 176
ctcagaacaa agggattaag gaatgcaacc catttcaaaa tctgtg                     46

SEQ ID NO: 177          moltype = DNA  length = 44
FEATURE                 Location/Qualifiers
misc_feature            1..44
                        note = Synthetic sequence
source                  1..44
                        mol_type = other DNA
                        organism = synthetic construct
SEQUENCE: 177
ctcagaacaa agggattaag gaatgcaacc catttcaaaa tctg                       44

SEQ ID NO: 178          moltype = AA   length = 726
FEATURE                 Location/Qualifiers
REGION                  1..726
                        note = Synthetic sequence
source                  1..726
                        mol_type = protein
                        organism = synthetic construct
```

```
SEQUENCE: 178
SESENKIIEQ YYAFLYSFRD KYEKPEFKNR GDIKRKLQNK WEDFLKEQNL KNDKKLSNYI    60
FSNRNFRRSY DREEENEEGI DEKKSKPKRI NCFEKEKNLK DQYDKDAINA SANKDGAQKW   120
GCFECIFFPM YKIESGDPNK RIIINKTRFK LFDFYLNLKG CKSCLRSTYH PYRSNVYIES   180
NYDKLKREIG NFLQQKNIFQ RMRKAKVSEG KYLTNLDEYR LSCVAMHFKN RWLFFDSIQK   240
VLRETIKQRL KQMRESYDEQ AKTKRSKGHG RAKYEDQVRM IRRAYSAQA HKLLDNGYIT    300
LFDYDDKEIN KVCLTAINQE GFDIGGYLNS DIDNVMPPIE ISFHLKWKYN EPILNIESPF   360
SKAKISDYLR KIREDLNLER GKEGKARSKK NVRRKVLASK GEDGYKKIFT DFFSKWKEEL   420
EGNAMERVLS QSSGDIQWSK KKRIHYTTLV LNINLLLDKKG VGNLKYYEIA EKTKILSFDK  480
NENKFWPITI QVLLDGYEIG TEYDEIKQLN EKTSKQFTIY DPNTKIIKIP FTDSKAVPLG   540
MLGINIATLK TVKKTERDIK VSKIFKGGLN SKIVSKIGKG IYAGYFPTVD KEILEEVEED   600
TLDNEFSSKS QRNIFLKSII KNYDKMLKEQ LFDFYSFLVR NDLGVRFLTD RELQNIEDES   660
FNLEKRFFET DRDRIARWFD NTNTDDGKEK FKKLANEIVD SYKPRLIRLP VVRVIKRIQP   720
VKQREM                                                              726

SEQ ID NO: 179          moltype = AA  length = 517
FEATURE                 Location/Qualifiers
REGION                  1..517
                        note = Synthetic sequence
source                  1..517
                        mol_type = protein
                        organism = synthetic construct
SEQUENCE: 179
KYSTRDFSEL NEIQVTACKQ DEFFKVIQNA WREIIKKRFL ENRENFIEKK IFKNKKGRGK    60
RQESDKTIQR NRASVMKNFQ LIENEKIILR APSGHVACVF PVKVGLDIGG FKTDDLEKNI   120
FPPRTITINV FWKNRDRQRK GRKLEVWGIK ARTKLIEKVH KWDKLEEVKK KRLKSLEQKQ   180
EKSLDNWSEV NNDSFYKVQI DELQEKIDKS LKGRTMNKIL DNKAKESKEA EGLYIEWEKD   240
FEGEMLRRIE ASTGGEEKWG KRRQRRHTSL LLDIKNNSRG SKEIINFYSY AKQGKKEKKI   300
EFFPFPLTIT LDAEEESPLN IKSIPIEDKN ATSKYFSIPF TETRATPLSI LGDRVQKFKT   360
KNISGAIKRN LGSSISSCKI VQNAETSAKS ILSLPNVKED NNMEIFINTM SKNYFRAMMK   420
QMESFIFEME PKTLIDPYKE KAIKWFEVAA SSRAKRKLKK LSKADIKKSE LLLSNTEEFE   480
KEKQEKLEAL EKEIEEFYLP RIVRLQLTKT ILETPVM                            517

SEQ ID NO: 180          moltype = AA  length = 481
FEATURE                 Location/Qualifiers
REGION                  1..481
                        note = Synthetic sequence
source                  1..481
                        mol_type = protein
                        organism = synthetic construct
SEQUENCE: 180
KKLQLLGHKI LLKEYDPNAV NAAANFETST AELCGQCKMK PFKNKRRFQY TFGKNYHGCL    60
SCIQNVYYAK KRIVQIAKEE LKHQLTDSIA SIPYKYTSLF SNTNSIDELY ILKQERAAFF   120
SNTNSIDELY ITGIENNIAF KVISAIWDEI IKKRRQRYAE SLTDTGTVKA NRGHGGTAYK   180
SNTRQEKIRA LQKQTLHMVT NPYISLARYK NNYIVATLPR TIGMHIGAIK DRDPQKKLSD   240
YAINFNVFWS DDRQLIELST VQYTGDMVRK IEAETGENNK WGENMKRTKT SLLLEILTKK   300
TTDELTFKDW AFSTKKEIDS VTKKTYQGFP IGIIFEGNES SVKFGSQNYF PLPFDAKITP   360
PTAEGFRLDW LRKGSFSSQM KTSYGLAIYS NKVTNAIPAY VIKNMFYKIA RAENGKQIKA   420
KPFLKKYLDIA GNNYVPFIIM QHYRVLDTFE EMPISQPKVI RLSLTKTQHI IKKDKTDSK   480
M                                                                   481

SEQ ID NO: 181          moltype = AA  length = 534
FEATURE                 Location/Qualifiers
REGION                  1..534
                        note = Synthetic sequence
source                  1..534
                        mol_type = protein
                        organism = synthetic construct
SEQUENCE: 181
NTSNLINLGK KAINISANYD ANLEVGCKNC KFLSSNGNFP RQTNVKEGCH SCEKSTYEPS    60
IYLVKIGERK AKYDVLDSLK KFTFQSLKYQ SKKSMKSRNK KPKELKEFVI FANKNKAFDV   120
IQKSYNHLIL QIKKEINRMN SKKRKKNHKR RLFRDREKQL NKLRLIESSN LFLPRENKGN   180
NHVFTYVAIH SVGRDIGVIG SYDEKLNFET ELTYQLFYND DKRLLYAYKP KQNKIIKDE    240
KLWNLRKEKE PLDLEYEKPL NKSITFSIKN DNLFKVSKDL MLRRAKFNIQ GKEKLSKEER   300
KINRDLIKIK GLVNSMSYGR FDELKKEKNI WSPHIYREVR QKEIKPCLIK NGDRIEIFEQ   360
LKKKMERLRR FREKRQKKIS KDLIFAERIA YNFHTKSIKN TSNKINIDQE AKRGKASYMR   420
KRIGYETFKN KYCEQCLSKG NVYRNVQKGC SCFENPFDWI KKGDENLLPK KNEDLRVKGA   480
FRDEALEKQI VKIAFNIAKG YEDFYDNLGE STEKDLKLKF KVGTTINEQE SLKL         534

SEQ ID NO: 182          moltype = AA  length = 537
FEATURE                 Location/Qualifiers
REGION                  1..537
                        note = Synthetic sequence
source                  1..537
                        mol_type = protein
                        organism = synthetic construct
SEQUENCE: 182
TSNPIKLGKK AINISANYDS NLQIGCKNCK FLSYNGNFPR QTNVKEGCHS CEKSTYEPPV    60
YTVRIGERRS KYDVLDSLKK FIFLSLKYRQ SKKMKTRSKG IRGLEEFVIS ANLKKAMDVI   120
```

```
QKSYRHLILN IKNEIVRMNG KKRNKNHKRL LFRDREKQLN KLRLIEGSSF FKPPTVKGDN   180
SIFTCVAIHN IGRDIGIAGD YFDKLEPKIE LTYQLYYEYN PKKESEINKR LLYAYKPKQN   240
KIIEIKEKLW NLRKEKSPLD LEYEKPLTKS ITFLVKRDGV FRISKDLMLR KAKFIIQGKE   300
KLSKEERKIN RDLIKIKSNI ISLTYGRFDE LKKDKTIWSP HIFRDVKQGK ITPCIERKGD   360
RMDIFQQLRK KSERLRENRK KRQKKISKDL IFAERIAYNF HTKSIKNTSN LINIKHEAKR   420
GKASYMRKRI GNETFRIKYC EQCFPKNNVY KNVQKGCSCF EDPFEYIKKG NEDLIPNKNQ   480
DLKAKGAFRD DALEKQIIKV AFNIAKGYED FYENLKKTTE KDIRLKFKVG TIISEEM      537

SEQ ID NO: 183           moltype = AA  length = 541
FEATURE                  Location/Qualifiers
REGION                   1..541
                         note = Synthetic sequence
source                   1..541
                         mol_type = protein
                         organism = synthetic construct
SEQUENCE: 183
NNSINLSKKA ININSANYDAN LQVRCKNCKF LSSNGNFPRQ TDVKEGCHSC EKSTYEPPVY    60
DVKIGEIKAK YEVLDSLKKF TFQSLKYQLS KSMKFRSKKI KELKEFVIFA KESKALNVIN   120
RSYKHLILNI KNDINRMNSK KRIKNHKGRL FLDRQKQLSK LKLIEGSSFF VPAKNVGNKS   180
VFTCVAIHSI GRDIGIAGLY DSFTKPVNEI TYQIFFSGER RLLYAYKPKQ LKILSIKENL   240
WSLKNEKKPL DLLYEKPLGK NLNFNVKGGD LFRVSKDLMI RNAKFNVHGR QRLSDEERLI   300
NRNFIKIKGE VVSLSYGRFE ELKKDRKLWS PHIFKDVRQN KIKPCLVMQG QRIDIFEQLK   360
RKLELLKKIR KSRQKKLSKD LIFGERIAYN FHTKSIKNTS NKINIDSDAK RGRASYMRKR   420
IGNETFKLKY CDVCFPKANV YRRVQNGCSC SENPYNYIKK GDKDLLPKKD EGLAIKGAFR   480
DEKLNKQIIK VAFNIAKGYE DFYDDLKKRT EKDVDLKFKI GTTVLDQKPM EIFDGIVITW   540
L                                                                  541

SEQ ID NO: 184           moltype = AA  length = 542
FEATURE                  Location/Qualifiers
REGION                   1..542
                         note = Synthetic sequence
source                   1..542
                         mol_type = protein
                         organism = synthetic construct
SEQUENCE: 184
LLTTVVETNN LAKKAINVAA NFDANIDRQY YRCTPNLCRF IAQSPRETKE KDAGCSSCTQ    60
STYDPKVYVI KIGKLLAKYE ILKSLKRFLF MNRYFKQKKT ERAQQKQKIG TELNEMSIFA   120
KATNAMEVIK RATKHCTYDI IPETKSLQML KRRRHRVKVR SLLKILKERR MKIKKIPNTF   180
IEIPKQAKKN KSDYYVAAAL KSCGIDVGLC GAYEKNAEVE AEYTYQLYYE YKGNSSTKRI   240
LYCYNNPQKN IREFWEAFYI QGSKSHVNTP GTIRLKMEKF LSPITIESEA LDFRVWNSDL   300
KIRNGQYGFI KKRSLGKEAR EIKKGMGDIK RKIGNLTYGK SPSELKSIHV YRTERENPKK   360
PRAARKKEDN FMEIFEMQRK KDYEVNKKRR KEATDAAKIM DFAEEPIRHY HTNNLKAVRR   420
IDMNEQVERK KTSVFLKRIM QNGYRGNYCR KCIKAPEGSN RDENVLEKNE GCLDCIGSEF   480
IWKKSSKEKK GLWHTNRLLR RIRLQCFTTA KAYENFYNDL FEKKESSLDI IKLKVSITTK   540
SM                                                                 542

SEQ ID NO: 185           moltype = AA  length = 564
FEATURE                  Location/Qualifiers
REGION                   1..564
                         note = Synthetic sequence
source                   1..564
                         mol_type = protein
                         organism = synthetic construct
SEQUENCE: 185
ASTMNLAKQA INFAANYDSN LEIGCKGCKF MSTWSKKSNP KFYPRQNNQA NKCHSCTYST    60
GEPEPVPIIEI GERAAKYKIF TALKKFVFMS VAYKERRRQR FKSKKPKELK ELAICSNREK   120
AMEVIQKSVV HCYGDVKQEI PRIRKIKVLK NHKGRLFYKQ KRSKIKIAKL EKGSFFKTFI   180
PKVHNNGCHS CHEASLNKPI LVTTALNTIG ADIGLINDYS TIAPTETDIS WQVYYEFIPN   240
GDSEAVKKRL LYFYKPKGAL IKSIRDKYPK KGHENAVNTG PFKYQGKIVK GPIKFVNNEL   300
DFARKPDLKS MKIKRAGFAI PSAKRLSKED REINRESIKI KNKIYSLSYG RKKTLSDKDI   360
IKHLYRPVRQ KGVKPLEYRK APDGFLEFFY SLRKKERRLR KQKEKRQKDM SEIIDAADEF   420
AWHRHTGSIK KTTNHINFKS EVKRGKVPIM KKRIANDSFN TRHCGKCVKQ GNAINKYYIE   480
KQKNCFDCNS IEFKWEKAAL EKKGAFKLNK RLQYIVKACF NVAKAYESPY EDFRKGEEES   540
LDLKFKIGTT TTLKQYPQNK ARAM                                         564

SEQ ID NO: 186           moltype = AA  length = 610
FEATURE                  Location/Qualifiers
REGION                   1..610
                         note = Synthetic sequence
source                   1..610
                         mol_type = protein
                         organism = synthetic construct
SEQUENCE: 186
HSHNLMLTKL GKQAINFAAN YDANLEIGCK NCKFLSYSPK QANPKKYPRQ TDVHEDGNIA    60
CHSCMQSTKE PPVYIVPIGE RKSKYEILTS LNKFTFLALK YKEKKRQAFR AKKPKELQEL   120
AIAFNKEKAI KVIDKSIQHL ILNIKPEIAR IQRQKRLKNR KGKLLYLHKR YAIKMGLIKN   180
GKYFKVGSPK KDGKKLLVLC ALNTIGRDIG IIGNIEENNR SETEITYQLY FDCLDANPNE   240
LRIKEIEYNR LKSYERKIKR LVYAYKPKQT KILEIRSKFF SKGHENKVNT GSFNFENPLN   300
KSISIKVKNS AFDFKIGAPF IMLRNGKFHI PTKKRLSKEE REINRTLSKI KGRVFRLTYG   360
```

```
RNISEQGSKS LHIYRKERQH PKLSLEIRKQ PDSFIDEFEK LRLKQNFISK LKKQRQKKLA   420
DLLQFADRIA YNYHTSSLEK TSNFINYKPE VKRGRTSYIK KRIGNEGFEK LYCETCIKSN   480
DKENAYAVEK EELCFVCKAK PFTWKKTNKD KLGIFKYPSR IKDFIRAAFT VAKSYNDFYE   540
NLKKKDLKNE IFLKFKIGLI LSHEKKNHIS IAKSVAEDER ISGKSIKNIL NKSIKLEKNC   600
YSCFFHKEDM                                                        610

SEQ ID NO: 187          moltype = AA   length = 552
FEATURE                 Location/Qualifiers
REGION                  1..552
                        note = Synthetic sequence
source                  1..552
                        mol_type = protein
                        organism = synthetic construct
SEQUENCE: 187
SLERVIDKRN LAKKAINIAA NFDANINKGF YRCETNQCMF IAQKPRKTNN TGCSSCLQST   60
YDPVIYVVKV GEMLAKYEIL KSLKRFVFMN RSFKQKKTEK AKQKERIGGE LNEMSIFANA   120
ALAMGVIKRA IRHCHVDIRP EINRLSELKK TKHRVAAKSL VKIVKQRKTK WKGIPNSFIQ   180
IPQKARNKDA DFYVASALKS GGIDIGLCGT YDKKPHADPR WTYQLYFDTE DESEKRLLYC   240
YNDPQAKIRD FWKTFYERGN PSMVNSPGTI EFRMEGFFEK MTPISIESKD FDFRVWNKDL   300
LIRRGLYEIK KRKNLNRKAR EIKKAMGSVK RVLANMTYGK SPTDKKSIPV YRVEREKPKK   360
PRAVRKEENE LADKLENYRR EDFLIRNRRK REATEIAKII DAAEPPIRHY HTNHLRAVKR   420
IDLSKPVARK NTSVFLKRIM QNGYRGNYCK KCIKGNIDPN KDECRLEDIK KCICCEGTQN   480
IWAKKEKLYT GRINVLNKRI KQMKLECFNV AKAYENFYDN LAALKEGDLK VLKLKVSIPA   540
LNPEASDPEE DM                                                     552

SEQ ID NO: 188          moltype = AA   length = 534
FEATURE                 Location/Qualifiers
REGION                  1..534
                        note = Synthetic sequence
source                  1..534
                        mol_type = protein
                        organism = synthetic construct
SEQUENCE: 188
NASINLGKRA INLSANYDSN LVIGCKNCKF LSFNGNFPRQ TNVREGCHSC DKSTYAPEVY   60
IVKIGERKAK YDVLDSLKKF TFQSLKYQIK KSMRERSKKP KELLEFVIFA NKDKAFNVIQ   120
KSYEHLILNI KQEINRMNGK KRIKNHKKRL FKDREKQLNK LRLIGSSSLF FPRENKGDKD   180
LFTYVAIHSV GRDIGVAGSY ESHIEPISDL TYQLFINNEK RLLYAYKPKQ NKIIELKENL   240
WNLKKEKKPL DLEFTKPLEK SITFSVKNDK LFKVSKDLML RQAKFNIQGK EKLSKEERQI   300
NRDFSKIKSN VISLSYGRFE ELKKEKNIWS PHIYREVKQK EIKPCIVRKG DRIELFEQLK   360
RKMDKLKKFR KERQKKISKD LNFAERIAYN FHTKSIKNTS NKINIDQEAK RGKASYMRKR   420
IGNESFRKKY CEQCFSVGNV YHNVQNGCSC FDNPIELIKK GDEGLIPKGK EDRKYKGALR   480
DDNLQMQIIR VAFNIAKGYE DFYNNLKEKT EKDLKLKFKI GTTISTQESN NKEM        534

SEQ ID NO: 189          moltype = AA   length = 577
FEATURE                 Location/Qualifiers
REGION                  1..577
                        note = Synthetic sequence
source                  1..577
                        mol_type = protein
                        organism = synthetic construct
SEQUENCE: 189
SNLIKLGKQA INFAANYDAN LEVGCKNCKF LSSTNKYPRQ TNVHLDNKMA CRSCNQSTME   60
PAIYIVRIGE KKAKYDIYNS LTKFNFQSLK YKAKRSQRFK PKQPKELQEL SIAVRKEKAL   120
DIIQKSIDHL IQDIRPEIPR IKQQKRYKNH VGKLFYLQKR RKNKLNLIGK GSFFKVFSPK   180
EKKNELLVIC ALTNIGRDIG LIGNYNTIIN PLFEVTYQLY YDYIPKKNNK NVQRRLLYAY   240
KSKNEKILKL KEAFFKRGHE NAVNLGSFSY EKPLEKSLTL KIKNDKDDFQ VSPSLRIRTG   300
RPFFVPSKRNL SRQEREINRR LVKIKSKIKN MTYGKFETAR DKQSVHIFRL ERQKEKLPLQ   360
FRKDEKEFME EFQKLKRRTN SLKKLRKSRQ KKLADLLQLS EKVVYNNHTG TLKKTSNFLN   420
FSSSVKRGKT AYIKELLGQE GFETLYCSNC INKGQKTRYN IETKEKCFSC KDVPFVWKKK   480
STDKDRKGAF LFPAKLKDVI KATFTVAKAY EDFYDNLKSI DEKKPYIKFK IGLILAHVRH   540
EHKARAKEEA GQKNIYNKPI KIDKNCKECF FFKEEAM                           577

SEQ ID NO: 190          moltype = AA   length = 613
FEATURE                 Location/Qualifiers
REGION                  1..613
                        note = Synthetic sequence
source                  1..613
                        mol_type = protein
                        organism = synthetic construct
SEQUENCE: 190
NTTRKKFRKR TGFPQSDNIK LAYCSAIVRA ANLDADIQKK HNQCNPNLCV GIKSNEQSRK   60
YEHSDRQALL CYACNQSTGA PKVDYIQIGE IGAKYKILQM VNAYDFLSLA YNLTKLRNGK   120
SRGHQRMSQL DEVVIVADYE KATEVIKRSI NHLLDDIRGQ LSKLKKRTQN EHITEHKQSK   180
IRRKLRSR LLKRRRWKWG TIPNPYLKNW VFTKKDPELV TVALLHKRIN DIGLVNRSKR   240
RSKQKLLPKV GFQLYYKWES PSLNIKKSK AKKLPKRLLI PYKNVKLFDN KQKLENAIKS   300
LLESYQKTIK VEFDQFFQNR TEEIIAEEQQ TLERGLLKQL EKKKNEFASQ KKALKEEKKK   360
IKEPRKAKLL MEESRSLGFL MANVSYALFN TTIEDLYKKS NVVSGCIPQE PVVVFPADIQ   420
NKGSLAKILF APKDGFRIKF SGQHLTIRTA KFKIRGKEIK ILTKTKREIL KNIEKLRRVW   480
YREQHYKLKL FGKEVSAKPR FLDKRKTSIE RRDPNKLADQ TDDRQAELRN KEYELRHKQH   540
```

```
KMAERLDNID TNAQNLQTLS FWVGEADKPP KLDEKDARGF GVRTCISAWK WFMEDLLKKQ 600
EEDPLLKLKL SIM                                                  613

SEQ ID NO: 191          moltype = AA  length = 615
FEATURE                 Location/Qualifiers
REGION                  1..615
                        note = Synthetic sequence
source                  1..615
                        mol_type = protein
                        organism = synthetic construct
SEQUENCE: 191
PKKPKFQKRT GFPQPDNLRK EYCLAIVRAA NLDADFEKKC TKCEGIKTNK KGNIVKGRTY  60
NSADKDNLLC YACNISTGAP AVDYVFVGAL EAKYKILQMV KAYDFHSLAY NLAKLWKGRG 120
RGHQRMGGLN EVVIVSNNEK ALDVIEKSLN HFHDEIRGEL SRLKAKFQNE HLHVHKESKL 180
RRKLRKISRL LKRRRWKWDV IPNSYLRNFT FTKTRPDFIS VALLHRVGRD IGLVTKTKIP 240
KPTDLLPQFG FQIYYTWDEP KLNKLKKSRL RSEPKRLLVP YKKIELYKNK SVLEEAIRHL 300
AEVYTEDLTI CFKDFFETQK RKFVSKEKES LKRELLKELT KLKKDFSERK TALKRDRKEI 360
KEPKKAKLLM EESRSLGFLA ANTSYALFNL IAADLYTKSK KACSTKLPRQ LSTILPLEIK 420
EHKSTTSLAI KPEEGFKIRF SNTHLSIRTP KFKMKGADIK ALTKRKREIL KNATKLEKSW 480
YGLKHYKLKL YGKEVAAKPR FLDKRNPSID RRDPKELMEQ IENRRNEVKD LEYEIRKGQH 540
QMAKRLDNVD TNAQNLQTKS FWVGEADKPP ELDSMEAKKL GLRTCISAWK WFMKDLVLLQ 600
EKSPNLKLKL SLTEM                                                615

SEQ ID NO: 192          moltype = AA  length = 775
FEATURE                 Location/Qualifiers
REGION                  1..775
                        note = Synthetic sequence
source                  1..775
                        mol_type = protein
                        organism = synthetic construct
SEQUENCE: 192
KFSKRQEGFL IPDNIDLYKC LAIVRSANLD ADVQGHKSCY GVKKNGTYRV KQNGKKGVKE  60
KGRKYVFDLI AFKGNIEKIP HEAIEEKDQG RVIVLGKFNY KLILNIEKNH NDRASLEIKN 120
KIKKLVQISS LETGEFLSDL LSGKIGIDEV YGIIEPDVFS GKKLVCKACQ QSTYAPLVEY 180
MPVGELDAKY KILSAIKGYD FLSLAYNLSR NRANKKRGHQ KLGGGELSEV VISANYDKAL 240
NVIKRSINHY HVEIKPEISK LKKKMQNEPL KVMKQARIRR ELHQLSRKVK RLKWKWGMIP 300
NPELQNIIFE KKEKDFVSYA LLHTLGRDIG LFKDTSMLQV PNISDYGFQI YYSWEDPKLN 360
SIKKIKDLPK RLLIPYKRLD FYIDTILVAK VIKNLIELYT KSYVYETFGE EYGYAKKAED 420
ILFDWDSINL SEGIEQKIQK IKDEFSDLLY EARESKRQNF VESFENILGL YDKNFASDRN 480
SYQEKIQSMI IKKQQENIEQ KLKREFKEVI ERGFEGMDQN KKYYKVLSPN IKGGLLYTDT 540
NNLGFFRSHL AFMLLSKISD DLYRKNNLVS KGGNKGILDQ TPETMLTLEF GKSNLPNISI 600
KRKFFNIKYN SSWIGIRKPK FSIKGAVIRE ITKKVRDEQR LIKSLEGVWH KSTHFKRWGK 660
PRFNLPRHPD REKNNDDNLM ESITSRREQI QLLLREKQKQ QEKMAGRLDK IDKEIQNLQT 720
ANFQIKQIDK KPALTEKSEG KQSVRNALSA WKWFMEDLIK YQKRTPILQL KLAKM      775

SEQ ID NO: 193          moltype = AA  length = 777
FEATURE                 Location/Qualifiers
REGION                  1..777
                        note = Synthetic sequence
source                  1..777
                        mol_type = protein
                        organism = synthetic construct
SEQUENCE: 193
KFSKRQEGFV IPENIGLYKC LAIVRSANLD ADVQGHVSCY GVKKNGTYVL KQNGKKSIRE  60
KGRKYASDLV AFKGDIEKIP FEVIEEKKKE QSIVLGKFNY KLVLDVMKGE KDRASLTMKN 120
KSKKLVQVSS LGTDEFLLTL LNEKFGIEEI YGIIEPEVFS GKKLVCKACQ QSTYAPLVEY 180
MPVGELDSKY KILSDEFAIKGYD FLSLAYNLAR HRSNKKRGHQ KLGGGELSEV VISANNAKAL 240
NVIKRSLNHY YSEIKPEISK LRKKMQNEPL KVGKQARMRR ELHQLSRKVK RLKWKWGKIP 300
NLELQNITFK ESDRDFISYA LLHTLGRDIG MFNKTEIKMP SNILGYGFQI YYDWEEPKLN 360
TIKKSKNTPK RILIPYKKLD FYNDSILVAR AIKELVGLFQ ESYEWEIFGN EYNYAKEAEV 420
ELIKLDEESI NGNVEKKLQR IKENFSNLLE KAREKKRQNF IESFESIARL YDESFTADRN 480
EYQREIQSFI IEKQKQSIEK KLKNEFKKIV EKKFNEQEQG KKHYRVLNPT IINEFLPKDK 540
NNLGFLRSKI AFILLSKISD DLYKKSNAVS KGGEKGIIKQ QPETILDLEF SKSKLPSINI 600
KKKLFNIKYT SSWLGIRKPK FNIKGAKIRE ITRRVRDVQR TLKSAESSWY ASTHFRRWGF 660
PRFNQPRHPD KEKKSDDRLI ESITLLREQI QILLREKQKG QKEMAGRLDD VDKKIQNLQT 720
ANFQIKQTGD KPALTEKSAG KQSFRNALSA WKWFMENLLK YQNKTPDLKL KIARTVM    777

SEQ ID NO: 194          moltype = AA  length = 610
FEATURE                 Location/Qualifiers
REGION                  1..610
                        note = Synthetic sequence
source                  1..610
                        mol_type = protein
                        organism = synthetic construct
SEQUENCE: 194
KWIEPNNIDF NKCLAITRSA NLDADVQGHK MCYGIKTNGT YKAIGKINKK HNTGIIEKRR  60
TYVYDLIVTK EKNEKIVKKT DFMAIDEEIE FDEKKEKLLK KYIKAEVLGT GELIRKDLND 120
GEKFDDLCSI EEPQAFRRSE LVCKACNQST YASDIRYIPI GEIEAKYKIL KAIKGYDFLS 180
LKYNLGRLRD SKKRGHQKMG QGELKEFVIC ANKEKALDVI KRSLNHYLNE VKDEISRLNK 240
```

```
KMQNEPLKVN DQARWRRELN QISRRLKRLK WKWGEIPNPE LKNLIFKSSR PEFVSYALIH    300
TLGRDIGLIN ETELKPNNIQ EYGFQIYYKW EDPELNHIKK VKNIPKRFII PYKNLDLFGK    360
YTILSRAIEG ILKLYSSSFQ YKSFKDPNLF AKEGEKKITN EDFELGYDEK IKKIKDDFKS    420
YKKALLEKKK NTLEDSLNSI LSVYEQSLLT EQINNVKKWK EGLLKSKESI HKQKKIENIE    480
DIISRIEELK NVEGWIRTKE RDIVNKEETN LKREIKKELK DSYYEEVRKD FSDLKKGEES    540
EKKPFREEPK PIVIKDYIKF DVLPGENSAL GFFLSHLSFN LFDSIQYELF EKSRLSSSKH    600
PQIPETILDL                                                         610

SEQ ID NO: 195           moltype = AA   length = 632
FEATURE                  Location/Qualifiers
REGION                   1..632
                         note = Synthetic sequence
source                   1..632
                         mol_type = protein
                         organism = synthetic construct
SEQUENCE: 195
FRKFVKRSGA PQPDNLNKYK CIAIVRAANL DADIMSNESS NCVMCKGIKM NKRKTAKGAA     60
KTTELGRVYA GQSGNLLCTA CTKSTMGPLV DYVPIGRIRA KYTILRAVKE YDFLSLAYNL    120
ARTRVSKKGG RQKMHSLSEL VIAAEYEIAW NIIKSSVIHY HQETKEEISG LRKKLQAEHI    180
HKNKEARIRR EMHQISRRIK RLKWKWHMIP NSELHNFLFK QQDPSFVAVA LLHTLGRDIG    240
MINKPKGSAK REFIPEYGFQ IYYKWMNPKL NDINKQKYRK MPKRSLIPYK NLNVFGDREL    300
IENAMHKLLK LYDENLEVKG SKFFKTRVVA ISSKESEKLK RDLLWKGELA KIKKDFNADK    360
NKMQELFKEV KEPKKANALM KQSRNMGFLL QNISYGALGL LANRMYEASA KQSKGDATKQ    420
PSIVIPLEME FGNAFPKLLL RSGKFAMNVS SPWLTIRKPK FVIKGNKIKN ITKLMKDEKA    480
KLKRLETSYH RATHFRPTLR GSIDWDSPYF SSPKQPNTHR RSPDRLSADI TEYRGRLKSV    540
EAELREGQRA MAKKLDSVDM TASNLQTSNF QLEKGEDPRL TEIDEKGRSI RNCISSWKKF    600
MEDLMKAQEA NPVIKIKIAL KDESSVLSED SM                                  632

SEQ ID NO: 196           moltype = AA   length = 625
FEATURE                  Location/Qualifiers
REGION                   1..625
                         note = Synthetic sequence
source                   1..625
                         mol_type = protein
                         organism = synthetic construct
SEQUENCE: 196
KFHPENLNKS YCLAIVRAAN LDADIQGHIN CIGIKSNKSD RNYENKLESL QNVELLCKAC     60
TKSTYKPNIN SVPVGEKKAK YSILSEIKKY DFNSLVYNLK KYRKGKSRGH QKLNELRELV    120
ITSEYKKALD VINKSVNHYL VNIKNKMSKL KKILQNEHIH VGTLARIRRE RNRISRKLDH    180
YRKKWKFVPN KILKNYVFKN QSPDFVSVAL LHKLGRDIGL ITKTAILQKS FPEYSLQLYY    240
KYDTPKLNYL KKSKFKSLPK RILISYKYPK FDINSNYIEE SIDKLLKLYE ESPIYKNNSK    300
IIEFFKKSED NLIKSENDSL KRGIMKEFEK VTKNFSSSKK KLKEELKLKN EDKNSKMLAK    360
VSRPIGFLKA YLSYMLFNII SNRIFEFSRK SSGRIPQLPS CIINLGNQFE NFKNELQDSN    420
IGSKKNYKYF CNLLLKSSGF NISYEEEHLS IKTPNFFING RKLKEITSEK KKIRKENEQL    480
IKQWKKLTFF KPSNLNGKKT SDKIRFKSPN NPDIERKSED NIVENIAKVK YKLEDLLSEQ    540
RKEFNKLAKK HDGVDVEAQC LQTKSFWIDS NSPIKKSLEK KNEKVSVKKK MKAIRSCISA    600
WKWFMADLIE AQKETPMIKL KLALM                                         625

SEQ ID NO: 197           moltype = AA   length = 517
FEATURE                  Location/Qualifiers
REGION                   1..517
                         note = Synthetic sequence
source                   1..517
                         mol_type = protein
                         organism = synthetic construct
SEQUENCE: 197
TTLVPSHLAG IEVMDETTSR NEDMIQKETS RSNEDENYLG VKNKCGINVH KSGRGSSKHE     60
PNMPPEKSGE GQMPKQDSTE MQQRFDESVT GETQVSAGAT ASIKTDARAN SGPRVGTARA    120
LIVKASNLDR DIKLGCKPCE YIRSELPMGK KNGCNHCEKS SDIASVPKVE SGFRKAKYEL    180
VRRFESFAAD SISRHLGKEQ ARTRGKRGKK DKKEQMGKVN LDEIAILKNE SLIEYTENQI    240
LDARSNRIKE WLRSLRLRLR TRNKGLKKSK SIRRQLITLR RDYRKWIKPN PYRPDEDPNE    300
NSLRLHTKLG VDIGVQGGDN KRMNSDDYET SFSITWRDTA TRKICFTKPK GLLPRHMKFK    360
LRGYPELILY NEELRIQDSQ KFPLVDWERI PIFKLRGVSL GKKKVKALNR ITEAPRLVVA    420
KRIQVNIESK KKKVLTRYVY NDKSINGRLV KAEDSNKDPL LEFKKQAEEI NSDAKYYENQ    480
EIAKNYLWGC EGLHKNLLEE QTKNPYLAFK YGFLNIV                            517

SEQ ID NO: 198           moltype = AA   length = 410
FEATURE                  Location/Qualifiers
REGION                   1..410
                         note = Synthetic sequence
source                   1..410
                         mol_type = protein
                         organism = synthetic construct
SEQUENCE: 198
LDFKRTCSQE LVLLPEIEGL KLSGTQGVTS LAKKLINKAA NVDRDESYGC HHCIHTRTSL     60
SKPVKKDCNS CNQSTNHPAV PITLKGYKIA FYELWHRFTS WAVDSISKAL HRNKVMGKVN    120
LDEYAVVDNS HIVCYAVRKC YEKRQRSVRL HKRAYRCRAK HYNKSQPKVG RIYKKSKRRN    180
ARNLKKEAKR YFQPNEITNG SSDALFYKIG VDLGIAKGTP ETEVKVDVSI CFQVYYGDAR    240
RVLRVRKMDE LQSFHLDYTG KLKLKGIGNK DTFTIAKRNE SLKWGSTKYE VSRAHKKFKP    300
```

```
FGKKGSVKRK CNDYFRSIAS WSCEAASQRA QSNLKNAFPY QKALVKCYKN LDYKGVKKND  360
MWYRLCSNRI FRYSRIAEDI AQYQSDKGKA KFEFVILAQS VAEYDISAIM             410

SEQ ID NO: 199          moltype = AA   length = 602
FEATURE                 Location/Qualifiers
REGION                  1..602
                        note = Synthetic sequence
source                  1..602
                        mol_type = protein
                        organism = synthetic construct
SEQUENCE: 199
VFLTDDKRKT ALRKIRSAFR KTAEIALVRA QEADSLDRQA KKLTIETVSF GAPGAKNAFI  60
GSLQGYNWNS HRANVPSSGS AKDVFRITEL GLGIPQSAHE ASIGKSFELV GNVVRYTANL  120
LSKGYKKGAV NKGAKQQREI KGKEQLSFDL ISNGPISGDK LINGQKDALA WWLIDKMGFH  180
IGLAMEPLSS PNTYGITLQA FWKRHTAPRR YSRGVIRQWQ LPFGRQLAPL IHNFFRKKGA  240
SIPIVLTNAS KKLAGKGVLL EQTALVDPKK WWQVKEQVTG PLSNIWERSV PLVLYTATFT  300
HKHGAAHKRP LTLKVIRISS GSVFLLPLSK VTPGKLVRAW MPDINILRDG RPDEAAYKGP  360
DLIRARERSF PLAYTCVTQI ADEWQKRALE SNRDSITPLE AKLVTGSDLL QIHSTVQQAV  420
EQGIGGRISS PIQELLAKDA LQLVLQQLFM TVDLLRIQWQ LKQEVADGNT SEKAVGWAIR  480
ISNIHKDAYK TAIEPCTSAL KQAWNPLSGF EERTFQLDAS IVRKRSTAKT PDDELVIVLR  540
QQAAEMTVAV TQSVSKELME LAVRHSATLH LLVGEVASKQ LSRSADKDRG AMDHWKLLSQ  600
SM                                                                602

SEQ ID NO: 200          moltype = AA   length = 494
FEATURE                 Location/Qualifiers
REGION                  1..494
                        note = Synthetic sequence
source                  1..494
                        mol_type = protein
                        organism = synthetic construct
SEQUENCE: 200
EDLLQKALNT ATNVAAIERH SCISCLFTES EIDVKYKTPD KIGQNTAGCQ SCTFRVGYSG  60
NSHTLPMGNR IALDKLRETI QRYAWHSLLF NVPPAPTSKR VRAISELRVA AGRERLFTVI  120
TFVQTNILSK LQKRYAANWT PKSQERLSRL REEGQHILSL LESGSWQQKE VVREDQDLIV  180
CSALTKPGLS IGAFCRPKYL KPAKHALVLR LIFVEQWPGQ IWGQSKRTRR MRRRKDVERV  240
YDISVQAWAL KGKETRISEC IDTMRRHQQA YIGVLPFLIL SGSTVRGKGD CPILKEITRM  300
RYCPNNEGLI PLGIFYRGSA NKLLRVVKGS SFTLPMWQNI ETLPHPEPFS PEGWTATGAL  360
YEKNLAYWSA LNEAVDWYTG QILSSGLQYP NQNEFLARLQ NVIDSIPRKW FRPQGLKNLK  420
PNGQEDIVPN EFVIPQNAIR AHHVIEWYHK TNDLVAKTLL GWGSQTTLNQ TRPQGDLRFT  480
YTRYYFREKE VPEV                                                   494

SEQ ID NO: 201          moltype = AA   length = 649
FEATURE                 Location/Qualifiers
REGION                  1..649
                        note = Synthetic sequence
source                  1..649
                        mol_type = protein
                        organism = synthetic construct
SEQUENCE: 201
VPKKKLMREL AKKAVFEAIF NDPIPGSFGC KRCTLIDGAR VTDAIEKKQG AKRCAGCEPC  60
TFHTLYDSVK HALPAATGCD RTAIDTGLWE ILTALRSFRN MSFRRNAVSD ASQKQVWSIE  120
ELAIWADKER ALRVILSALT HTIGKLKNGF SRDGVWKGGK QLYENLAQKD LAKGLFANGE  180
IFGKELVEAD HDMLAWTIVP NHQFHIGLIR GNWKPAAVEA STAFDARWLT NGAPLRDTRT  240
HGHRGRRFNR TEKLTVLCIK RDGGVSEEFR QERDYELSVM LLQPKNKLKP EPKGELNSFE  300
DLHDHWWFLK GDEATALVGL TSDPTVGDFI QLGLYIRNPI KAHGETKRRL LICFEPPIKL  360
PLRRAFPSEA FKTWEPTINV FRNGRRDTEA YYDIDRARVF EFPETRVSLE HLSKQWEVLR  420
LEPDRENTDP YEAQQNEGAE LQVYSLLQEA AQKMAPKVVI DPPGQFPLEL FSTFVAQLFN  480
APLSDTKAKI GKPLDSGFVV ESHLHLLEED FAYRDFVRVT FMGTEPTFRV IHYSNGEGYW  540
KKTVLKGKNN IRTALIPEGA KAAVDAYKNK RCPLTLEAAI LNEEKDRRLV LGNKALSLLA  600
QTARGNLTIL EALAAEVLRP LSGTEGVVHL HACVTRHSTL TESTETDNM             649

SEQ ID NO: 202          moltype = AA   length = 414
FEATURE                 Location/Qualifiers
REGION                  1..414
                        note = Synthetic sequence
source                  1..414
                        mol_type = protein
                        organism = synthetic construct
SEQUENCE: 202
VEKLFSERLK RAMWLKNEAG RAPPAETLTL KHKRVSGGHE KVKEELQRVL RSLSGTNQAA  60
WNLGLSGGRE PKSSDALKGE KSRVVLETVV FHSGHNRVLY DVIEREDQVH QRSSIMHMRR  120
KGSNLLRLWG RSGKVRRKMR EEVAEIKPVW HKDSRWLAIV EEGRQSVVGI SSAGLAVFAV  180
QESQCTTAEP KPLEYVVSIW FRGSKALNPQ DRYLEFKKLK TTEALRGQQY DPIPFSLKRG  240
AGCSLAIRGE GIKFGSRGPI KQFFGSDRSR PSHADYDGKR RLSLFSKYAG DLADLTEEQW  300
NRTVSAFAED EVRRATLANI QDFLSISHEK YAERLKKRIE SIEEPVSASK LEAYLSAIFE  360
TFVQQREALA SNFLMRLVES VALLISLEEK SPRVEFRVAR YLAESKEGFN RKAM        414

SEQ ID NO: 203          moltype = AA   length = 413
FEATURE                 Location/Qualifiers
```

```
REGION                        1..413
                              note = Synthetic sequence
source                        1..413
                              mol_type = protein
                              organism = synthetic construct
SEQUENCE: 203
VVITQSELYK ERLLRVMEIK NDRGRKEPRE SQGLVLRFTQ VTGGQEKVKQ KLWLIFEGFS    60
GTNQASWNFG QPAGGRKPNS GDALKGPKSR VTYETVVFHF GLRLLSAVIE RHNLKQQRQT   120
MAYMKRRAAA RKKWARSGKK CSRMRNEVEK IKPKWHKDPR WFDIVKEGEP SIVGISSAGF   180
AIYIVEEPNF PRQDPLEIEY AISIWFRRDR SQYLTFKKIQ KAEKLKELQY NPIPFRLKQE   240
KTSLVFESGD IKFGSRGSIE HFRDEARGKP PKADMDNNRR LTMFSVFSGN LTNLTEEQYA   300
RPVSGLLAPD EKRMPTLLKK LQDFFTPIHE KYGERIKQRL ANSEASKRPF KKLEEYLPAI   360
YLEFRARREG LASNWVLVLI NSVRTLVRIK SEDPYIEFKV SQYLLEKEDN KAL          413

SEQ ID NO: 204                moltype = AA  length = 449
FEATURE                       Location/Qualifiers
REGION                        1..449
                              note = Synthetic sequence
source                        1..449
                              mol_type = protein
                              organism = synthetic construct
SEQUENCE: 204
KQDALFEERL KKAIFIKRQA DPLQREELSL LPPNRKIVTG GHESAKDTLK QILRAINGTN    60
QASWNPGTPS GKRDSKSADA LAGPKSRVKL ETVVFHVGHR LLKKVVEYQG HQKQQHGLKA   120
FMRTCAAMRK KWKRSGKVVG ELREQLANIQ PKWHYDSRPL NLCFEGKPSV VGLRSAGIAL   180
YTIQKSVVPV KEPKPIEYAV SIWFRGPKAM DREDRCLEFK KLKIATELRK LQFEPIVSTL   240
TQGIKGFSLY IQGNSVKFGS RGPIKYFSNE SVRQRPPKAD PDGNKRLALF SKFSGDLSDL   300
TEEQWNRPIL AFEGIIRRAT LGNIQDYLTV GHEQFAISLE QLLSEKESVL QMSIEQQRLK   360
KNLGKKAENE WVESFGAEQA RKKAQGIREY ISGFFQEYCS QREQWAENWV QQLNKSVRLF   420
LTIQDSTPFI EFRVARYLPK GEKKKGKAM                                    449

SEQ ID NO: 205                moltype = AA  length = 711
FEATURE                       Location/Qualifiers
REGION                        1..711
                              note = Synthetic sequence
source                        1..711
                              mol_type = protein
                              organism = synthetic construct
SEQUENCE: 205
ANHAERHKRL RKEANRAANR NRPLVADCDT GDPLVGICRL LRRGDKMQPN KTGCRSCEQV    60
EPELRDAILV SGPGRLDNYK YELFQRGRAM AVHRLLKRVP KLNRPKKAAG NDEKKAENKK   120
SEIQKEKQKQ RRMMPAVSMK QVSVADFKHV IENTVRHLFG DRRDREIAEC AALRAASKYF   180
LKSRRVRPRK LPKLANPDHG KELKGLRLRE KRAKLKKEKE KQAELARSNQ KGAVLHVATL   240
KKDAPPMPYE KTQGRNDYTT FVISAAIKVG ATRGTKPLLT PQPREWQCSL YWRDGQRWIR   300
GGLLGLQAGI VLGPKLNREL LEAVLQRPIE CRMSGCGNPL QVRGAAVDFF MTTNPFYVSG   360
AAYAQKKFKP FGTKRASEDG AAAKAREKLM TQLAKVLDKV VTQAAHSPLD GIWETRPEAK   420
LRAMIMALEH EWIFLRPGPC HNAAEEVIKC DCTGGHAILW ALIDEARGAL EHKEFYAVTR   480
AHTHDCEKQK LGGRLAGFLD LLIAQDVPLD DAPAARKIKT LLEATPPAPC YKAATSIATC   540
DCEGKFDKLW AIIDATRAGH GTEDLWARTL AYPQNVNCKC KAGKDLTHRL ADFLGLLIKR   600
DGPFRERPPH KVTGDRKLVF SGDKKCKGHQ YVILAKAHNE EVVRAWISRW GLKSRTNKAG   660
YAATELNLLL NWLSICRRRW MDMLTVQRDT PYIRMKTGRL VVDDKKERKA M            711

SEQ ID NO: 206                moltype = AA  length = 574
FEATURE                       Location/Qualifiers
REGION                        1..574
                              note = Synthetic sequence
source                        1..574
                              mol_type = protein
                              organism = synthetic construct
SEQUENCE: 206
AKQREALRVA LERGIVRASN RTYTLVTNCT KGGPLPEQCR MIERGKARAM KWEPKLVGCG    60
SCAAATVDLP AIEEYAQPGR LDVAKYKLTT QILAMATRRM MVRAAKLSRR KGQWPAKVQE   120
EKEEPPEPKK MLKAVEMRPV AIVDFNRVIQ TTIEHLWAER ANADEAELKA LKAAAAYFGP   180
SLKIRARGPP KAAIGRELKK AHRKKAYAER KKARRKRAEL ARSQARGAAA HAAIRERDIP   240
PMAYERTQGR NDVTTIPIAA AIKIAATRGA RPLPAPKPMK WQCSLYWNEG QRWIRGGMLT   300
AQAYAHAANI HRPMRCEMWG VGNPLKVRAF EGRVADPDGA KGRKAEFRLQ TNAFYVSGAA   360
YRNKKFKPFG TDRGGIGSAR KKRERLMAQL AKILDKVVSQ AAHSPLDDIW HTRPAQKLRA   420
MIKQLEHEWM FLRPQAPTVE GTKPDVDVAG NMQRQIKALM APDLPPIEKG SPAKRFTGDK   480
RKKGERAVRV AEAHSPDEVVT AWISRWGIQT RRNEGSYAAQ ELELLLNWLQ ICRRRWLDMT   540
AAQRVSPYIR MKSGRMITDA ADEGVAPIPL VENM                               574

SEQ ID NO: 207                moltype = AA  length = 743
FEATURE                       Location/Qualifiers
REGION                        1..743
                              note = Synthetic sequence
source                        1..743
                              mol_type = protein
                              organism = synthetic construct
SEQUENCE: 207
```

```
KSISGRSIKH MACLKDMLKS EITEIEEKQK KESLRKWDYY SKFSDEILFR RNLNVSANHD    60
ANACYGCNPC AFLKEVYGFR IERRNNERII SYRRGLAGCK SCVQSTGYPP IEFVRRKFGA   120
DKAMEIVREV LHRRNWGALA RNIGREKEAD PILGELNELL LVDARPYFGN KSAANETNLA   180
FNVITRAAKK FRDEGMYDIH KQLDIHSEEG KVPKGRKSRL IRIERKHKAI HGLDPGETWR   240
YPHCGKGEKY GVWLNRSRLI HIKGNEYRCL TAFGTTGRRM SLDVACSVLG HPLVKKKRKK   300
GKKTVDGTEL WQIKKATETL PEDPIDCTFY LYAAKPTKDP FILKVGSLKA PRWKKLHKDF   360
FEYSDTEKTQ GQEKGKRVVR RGKVPRILSL RPDAKFKVSI WDDPYNGKNK EGTLLRMELS   420
GLDGAKKPLI LKRYGEPNTK PKNFVFWRPH ITPHPLTFTP KHDFGDPNKK TKRRRVFNRE   480
YYGHLNDLAK MEPNAKFFED REVSNKKNPK AKNIRIQAKE SLPNIVAKNG RWAAFDPNDS   540
LWKLYLHWRG RRKTIKGGIS QEFQEFKERL DLYKKHEDES EWKEKEKLWE NHEKEWKKTL   600
EIHGSIAEVS QRCVMQSMMG PLDGLVQKKD YVHIGQSSLK AADDAWTFSA NRYKKATGPK   660
WGKISVSNLL YDANQANAEL ISQSISKYLS KQKDNQGCEG RKMKFLIKII EPLRENFVKH   720
TRWLHEMTQK DCEVRAQFSR VSM                                          743

SEQ ID NO: 208         moltype = AA   length = 769
FEATURE                Location/Qualifiers
REGION                 1..769
                       note = Synthetic sequence
source                 1..769
                       mol_type = protein
                       organism = synthetic construct
SEQUENCE: 208
FPSDVGADAL KHVRMLQPRL TDEVRKVALT RAPSDRPALA RFAAVAQDGL AFVRHLNVSA    60
NHDSNCTFPR DPRDPRRGPC EPNPCAFLRE VWGFRIVARG NERALSYRRG LAGCKSCVQS   120
TGFPSVPFHR IGADDCMRKL HEILKARNWR LLARNIGRER EADPLLTELS EYLLVDARTY   180
PDGAAPNSGR LAENVIKRAA KKFRDEGMYD IHAQLRVHSR EGKVPKGRLQ RLRRIERKHR   240
AIHALDPGPS WEAEGSARAE VQGVAVYRSQ LLRVGHHTQQ IEPVGIVART LFGVGRTDLD   300
VAVSVLGAPL TKRKKGSKTL ESTEDFRIAK ARETRAEDKI EVAFVLYPTA SLLRDEIPKD   360
AFPAMRIDRF LLKVGSVQAD REILLQDDYY RFGDAEVKAG KNKGRTVTRP VKVPRLQALR   420
PDAKFRVNVW ADPFGAGDSP GTLLRLEVSG VTRRSQPLRL LRYGQPSTQP ANFLCWRPHR   480
VPDPMTFTPR QKFGERRKNR RTRRPRVFER LYQVHIKHLA HLEPNRKWFE EARVSAQKWA   540
KARAIRRKGA EDIPVVAPPA KRRWAALQPN AELWDLYAHD REARKRFGG RAAEGEEFKP    600
RLNLYLAHEP EAEWESKRDR WERYEKKWTA VLEEHSRMCA VADRTLPQFL SDPLGARMDD   660
KDYAFVGKSA LAVAEAFVEE GTVERAQGNC SITAKKKFAS NASRKRLSVA NLLDVSDKAD   720
RALVFQAVRQ YVQRQAENGG VEGRRMAFLR KLLAPLRQNF VCHTRWLHM              769

SEQ ID NO: 209         moltype = AA   length = 564
FEATURE                Location/Qualifiers
REGION                 1..564
                       note = Synthetic sequence
source                 1..564
                       mol_type = protein
                       organism = synthetic construct
SEQUENCE: 209
AARKKKRGKI GITVKAKEKS PPAAGPFMAR KLVNVAANVD GVEVHLCVEC EADAHGSASA    60
RLLGGCRSCT GSIGAEGRLM GSVDVDRERV IAEPVHTETE RLGPDVKAFE AGTAESKYAI   120
QRGLEYWGVD LISRNRARTV RKMEEADRPE SSTMEKTSWD EIAIKTYSQA YHASENHLFW   180
ERQRRVRQHA LALFRRARER NRGESPLQST QRPAPLVLAA LHAEAAAISG RARAEYVLRG   240
PSANVRAAAA DIDAKPLGHY KTPSPKVARG FPVKRDLLRA RHRIVGLSRA YFKPSDVVRG   300
TSDAIAHVAG RNIGVAGGKP KEIEKTFTLP FVAYWEDVDR VVHCSSFKAD GPWVRDQRIK   360
IRGVSSAVGT FSLYGLDVAW SKPTSFYIRC SDIRKKFHPK GFGPMKHWRQ WAKELDRLTE   420
QRASCVVRAL QDDEELLQTM ERGQRYYDVF SCAATHATRG EADPSGGCSR CELVSCGVAH   480
KVTKKAKGDT GIEAVAVAGC SLCESKLVGP SKPRVHRQMA ALRQSHALNY LRRLQREWEA   540
LEAVQAPTPY LRFKYARHLE VRSM                                         564

SEQ ID NO: 210         moltype = AA   length = 565
FEATURE                Location/Qualifiers
REGION                 1..565
                       note = Synthetic sequence
source                 1..565
                       mol_type = protein
                       organism = synthetic construct
SEQUENCE: 210
AAKKKKQRGK IGISVKPKEG SAPPADGPFM ARKLVNVAAN VDGVEVNLCI ECEADAHGSA    60
PARLLGGCKS CTGSIGAEGR LMGSVDVDRA DAIAKPVNTE TEKLGPDVQA FEAGTAETKY   120
ALQRGLEYWG VDLISRNRSR TVRRTEEGQP ESATMEKTSW DEIAIKSYTR AYHASENHLF   180
WERQRRVRQH ALALFKRAKE RNRGDSTLPR EPGHGLVAIA ALACEAYAVG GRNLAETVVR   240
GPTFGTARAV RDVEIASLGR YKTPSPKVAH GSPVKRDFLR ARHRIVGLAR AYYRPSDVVR   300
GTSDAIAHVA GRNIGVAGGK PRAVEAVFTL PFVAYWEDVD RVVHCSSFQV SAPWNRDQRM   360
KIAGVTTAAG TFSLHGGELK WAKPTSFYIR CSDTRRKFRP KGFGPMKRWR QWAKDLDRLV   420
EQRASCVVRA LQDDAALLET MERGQRYYDV FACAVTHATR GEADRLAGCS RCALTPCQEA   480
HRVTTKPRGD AGVEQVQTSD CSLCEGKLVG PSKPRLHRTL TLLRQEHGLN YLRRLQREWE   540
SLEAVQPTP YLRFKYARHL EVRSM                                         565

SEQ ID NO: 211         moltype = AA   length = 499
FEATURE                Location/Qualifiers
REGION                 1..499
                       note = Synthetic sequence
source                 1..499
```

```
                            mol_type = protein
                            organism = synthetic construct
SEQUENCE: 211
TDSQSESVPE VVYALTGGEV PGRVPPDGGS AEGARNAPTG LRKQRGKIKI SAKPSKPGSP    60
ASSLARTLVN EAANVDGVQS SGCATCRMRA NGSAPRALPI GCVACASSIG RAPQEETVCA   120
LPTTQGPDVR LLEGGHALRK YDIQRALEYW GVDLIGRNLD RQAGRGMEPA EGATATMKRV   180
SMDELAVLDF GKSYYASEQH LFAARQRRVR QHAKALKIRA KHANRSGSVK RALDRSRKQV   240
TALAREFFKP SDVVRGDSDA LAHVVGRNLG VSRHPAREIP QTFTLPLCAY WEDVDRVISC   300
SSLLAGEPFA RDQEIRIEGV SSALGSLRLY RGAIEWHKPT SLYIRCSDTR RKFRPRGGLK   360
KRWRQWAKDL DRLVEQRACC IVRSLQADVE LLQTMERAQR FYDVHDCAAT HVGPVAVRCS   420
PCAGKQFDWD RYRLLAALRQ EHALNYLRRL QREWESLEAQ QVKMPYLRFK YARKLEVSGP   480
LIGLEVRREP SMGTAIAEM                                                499

SEQ ID NO: 212           moltype = AA  length = 358
FEATURE                  Location/Qualifiers
REGION                   1..358
                         note = Synthetic sequence
source                   1..358
                         mol_type = protein
                         organism = synthetic construct
SEQUENCE: 212
AGTAGRRHGS LGARRSINIA GVTDRHGRWG CESCVYTRDQ AGNRARCAPC DQSTYAPDVQ    60
EVTIGQRQAK YTIFLTLQSF SWTNTMRNNK RAAAGRSKRT TGKRIGQLAE IKITGVGLAH   120
AHNVIQRSLQ HNITKMWRAE KGKSKRVARL KKAKQLTKRR AYFRRRMSRQ SRGNGFFRTG   180
KGGIHAVAPV KIGLDVGMIA SGSSEPADEQ TVTLDAIWKG RKKKIRLIGA KGELAVAACR   240
FREQQTKGDK CIPLILQDGE VRWNQNNWQC HPKKLVPLCG LEVSRKFVSQ ADRLAQNKVA   300
SPLAARFDKT SVKGTLVESD FAAVLVNVTS IYQQCHAMLL RSQEPTPSLR VQRTITSM    358

SEQ ID NO: 213           moltype = AA  length = 369
FEATURE                  Location/Qualifiers
REGION                   1..369
                         note = Synthetic sequence
source                   1..369
                         mol_type = protein
                         organism = synthetic construct
SEQUENCE: 213
GVRFSPAQSQ VFFRTVIPQS VEARFAINMA AIHDAAGAFG CSVCRFEDRT PRNAKAVHGC    60
SPCTRSTNRP DVFVLPVGAI KAKYDVFMRL LGFNWTHLNR RQAKRVTVRD RIGQLDELAI   120
SMLTGKAKAV LKKSICHNVD KSFKAMRGSL KKLHRKASKT GKSQLRAKLS DLRERTNTTQ   180
EGSHVEGDSD VALNKIGLDV GLVGKPDYPS EESVEVVVCL YFVGKVLILD AQGRIRDMRA   240
KQYDGFKIPI IQRGQLTVLS VKDLGKWSLV RQDYVLAGDL RFEPKISKDR KYAECVKRIA   300
LITLQASLGF KERIPYYVTK QVEIKNASHI AFVTEAIQNC AENFREMTEY LMKYQEKSPD   360
LKVLLTQLM                                                           369

SEQ ID NO: 214           moltype = AA  length = 486
FEATURE                  Location/Qualifiers
REGION                   1..486
                         note = Synthetic sequence
source                   1..486
                         mol_type = protein
                         organism = synthetic construct
SEQUENCE: 214
RAVVGKVFLE QARRALNLAT NFGTNHRTGC NGCYVTPGKL SIPQDGEKNA AGCTSCLMKA    60
TASYVSYPKP LGEKVAKYST LDALKGFPWY SRLRNLRPNY RGKPINGVQE VAPVSKFRLA   120
EEVIQAVQRY HFTELEQSFP GGRRRLRELR AFYTKEYRRA PEQRQHVVNG DRNIVVVTVL   180
HELGFSVGMF NEVELLPKTP IECAVNVFIR GNRVLLEVRK PQFDKERLLV ESLWKKDSRR   240
HTAKWTPPNN EGRIFTAEGW KDFQLPLLLG STSRSLRAIE KEGFVQLAPG RDPDYNNTID   300
EQHSGRPFLP LYLYLQGTIS QEYCVFAGTW VIPFQDGISP YSTKDTFQPD LKRKAYSLLL   360
DAVKHRLGNK VASGLQYGRF PAIEELKRLV RMHGATRKIP RGEKDLLKKG DPDTPEWWLL   420
EQYPEFWRLC DAAAKRVSQN VGLLLSLKKQ PLWQRRWLES RTRNEPLDNL PLSMALTLHL   480
TNEEAL                                                              486

SEQ ID NO: 215           moltype = AA  length = 400
FEATURE                  Location/Qualifiers
REGION                   1..400
                         note = Synthetic sequence
source                   1..400
                         mol_type = protein
                         organism = synthetic construct
SEQUENCE: 215
AAVYSKFYIE NHFKMGIPET LSRIRGPSII QGFSVNENYI NIAGVGDRDF IFGCKKCKYT    60
RGKPSSKKIN KCHPCKRSTY PEPVIDVRGS ISEFKYKIYN KLKQEPNQSI KQNTKGRMNP   120
SDHTSSNDGI IINGIDNRIA YNVIFSSYKH LMEKQINLLR DTTKRKARQI KKYNNSGKKK   180
HSLRSQTKGN LKNRYHMLGM FKKGSLTITN EGDFITAVRK VGLDISLYKN ESLNKQEVET   240
ELCLNIKWGR TKSYTVSGYI PLPINIDWKL YLFEKETGLT LRLFGNKYKI QSKKFLIAQL   300
FKPKRPPCAD PVVKKAQKWS ALNAHVQQMA GLFSDSHLLK RELKNRMHKQ LDFKSLWVGT   360
EDYIKWFEEL SRSYVEGAEK SLEFFRQDYF CFNYTKQTTM                         400

SEQ ID NO: 216           moltype = AA  length = 666
```

```
FEATURE                 Location/Qualifiers
REGION                  1..666
                        note = Synthetic sequence
source                  1..666
                        mol_type = protein
                        organism = synthetic construct
SEQUENCE: 216
PQQQRDLMLM AANYDQDYGN GCGPCTVVAS AAYRPDPQAQ HGCKRHLRTL GASAVTHVGL    60
GDRTATITAL HRLRGPAALA ARARAAQAAS APMTPDTDAP DDRRRLEAID ADDVVLVGAH   120
RALWSAVRRW ADDRRAALRR RLHSEREWLL KDQIRWAELY TLIEASGTPP QGRWRNTLGA   180
LRGQSRWRRV LAPTMRATCA ETHAELWDAL AELVPEMAKD RRGLLRPPVE ADALWRAPMI   240
VEGWRGGHSV VVDAVAPPLD LPQPCAWTAV RLSGDPRQRW GLHLAVPPLG QVQPPDPLKA   300
TLAVSMRHRG GVRVRTLQAM AVDADAPMQR HLQVPLTLQR GGGLQWGIHS RGVRRREARS   360
MASWEGPPIW TGLQLVNRWK GQGSALLAPD RPPDTPPYAP DAAVAPAQPD TKRARRTLKE   420
ACTVCRCAPG HMRQLQVTLT GDGTWRRFRL RAPQGAKRKA EVLKVATQHD ERIANYTAWY   480
LKRPEHAAGC DTCDGDSRLD GACRGCRPLL VGDQCFRRYL DKIEADRDDG LAQIKPKAQE   540
AVAAMAAKRD ARAQKVAARA AKLSEATGQR TAATRDASHE ARAQKELEAV ATEGTTVRHD   600
AAAVSAFGSW VARKGDEYRH QVGVLANRLE HGLRLQELMA PDSVVADQQR ASGHARVGYR   660
YVLTAM                                                             666

SEQ ID NO: 217          moltype = AA  length = 560
FEATURE                 Location/Qualifiers
REGION                  1..560
                        note = Synthetic sequence
source                  1..560
                        mol_type = protein
                        organism = synthetic construct
SEQUENCE: 217
AVAHPVGRGN AGSPGARGPE ELPRQLVNRA SNVTRPATYG CAPCRHVRLS IPKPVLTGCR    60
ACEQTTHPAP KRAVRGGADA AKYDLAAFFA GWAADLEGRN RRRQVHAPLD PQPDPNHEPA   120
VTLQKIDLAE VSIEEFQRVL ARSVKHRHDG RASREREKAR AYAQVAKKRR NSHAHGARTR   180
RAVRRQTRAV RRAHRMGANS GEILVASGAE DPVPEAIDHA AQLRRRIRAC ARDLEGLRHL   240
SRRYLKTLEK PCRRPRAPDL GRARCHALVE SLQAAERELE ELRRCDSPDT AMRRLDAVLA   300
AAASTDATFA TGWTVVGMDL GVAPRGSAAP EVSPMEMAIS VFWRKGSRRV IVSKPIAGMP   360
IRRHELIRLE GLGTLRLDGN HYTGAGVTKG RGLSEGTEPD FREKSPSTLG FTLSDYRHES   420
RWRPYGAKQG KTARQFFAAM SRELRALVEH QVLAPMGPPL LEAHERRFET LLKGQDNKSI   480
HAGGGGRYVW RGPPDSKKRP AADGDWRFRG RGHADHRGWA NKRHELAANY LQSAFRLWST   540
LAEAQEPTPY ARYKYTRVTM                                              560

SEQ ID NO: 218          moltype = AA  length = 404
FEATURE                 Location/Qualifiers
REGION                  1..404
                        note = Synthetic sequence
source                  1..404
                        mol_type = protein
                        organism = synthetic construct
SEQUENCE: 218
WDFLTLQVYE RHTSPEVCVA GNSTKCASGT RKSDHTHGVG VKLGAQEINV SANDDRDHEV    60
GCNICVISRV SLDIKGWRYG CESCVQSTPE WRSIVRFDRN HKEAKGECLS RFEYWGAQSI   120
ARSLKRNKLM GGVNLDELAI VQNENVVKTS LKHLFDKRKD RIQANLKAVK VRMRERRKSG   180
RQRKALRRQC RKLKRYLRSY DPSDIKEGNS CSAFTKLGLD IGISPNKPPK IEPKVEVVFS   240
LFYQGACDKI VTVSSPESPL PRSWKIKIDG IRALYVKSTK VKFGGRTFRA GQRNNRRKVR   300
PPNVKKGKRK GSRSQFFNKF AVGLDAVSQQ LPIASVQGLW GRAETKKAQT ICLKQLESNK   360
PLKESQRCLF LADNWVVRVC GFLRALSQRQ GPTPYIRYRY RCNM                    404

SEQ ID NO: 219          moltype = AA  length = 392
FEATURE                 Location/Qualifiers
REGION                  1..392
                        note = Synthetic sequence
source                  1..392
                        mol_type = protein
                        organism = synthetic construct
SEQUENCE: 219
ARNVGQRNAS RQSKRESAKA RSRRVTGGHA SVTQGVALIN AAANADRDHT TGCEPCTWER    60
VNLPLQEVIH GCDSCTKSSP FWRDIKVVNK GYREAKEEIM RIASGISADH LSRALSHNKV   120
MGRLNLDEVC ILDFRTVLDT SLKHLTDSRS NGIKEHIRAV HRKIRMRRKS GKTARALRKQ   180
YFALRRQWKA GHKPNSIREG NSLTALRAVG FDVGVSEGTE PMPAPQTEVV LSVFYKGSAT   240
RILRISSPHP IAKRSWKVKI AGIKALKLIR REHDFSFGRE TYNASQRAEK RKFSPHAARK   300
DFFNSFAVQL DRLAQQLCVS SVENLWVTEP QQKLLTLAKD TAPYGIREGA RFADTRARLA   360
WNWVFRVCGF TRALHQEQEP TPYCRFTWRS KM                                 392

SEQ ID NO: 220          moltype = DNA  length = 59
FEATURE                 Location/Qualifiers
misc_feature            1..59
                        note = Synthetic sequence
source                  1..59
                        mol_type = other DNA
                        organism = synthetic construct
SEQUENCE: 220
```

```
ctacgccgat tatcttctga caactttcgc aagcggtgta aggtaaaaaa tgcgggcac        59

SEQ ID NO: 221           moltype = DNA   length = 59
FEATURE                  Location/Qualifiers
misc_feature             1..59
                         note = Synthetic sequence
source                   1..59
                         mol_type = other DNA
                         organism = synthetic construct
SEQUENCE: 221
gtgcccgcat tttttacctt acaccgcttg cgaaagttgt cagaagataa tcggcgtag        59

SEQ ID NO: 222           moltype = DNA   length = 90
FEATURE                  Location/Qualifiers
misc_feature             1..90
                         note = Synthetic sequence
source                   1..90
                         mol_type = other DNA
                         organism = synthetic construct
SEQUENCE: 222
tttatatgtt tctcctggag ataacgcaat cgtgacaact ttcgcaagcg gtgtaaggta        60
gcaggcttcc gaattccgcg tttttacggc                                        90

SEQ ID NO: 223           moltype = DNA   length = 90
FEATURE                  Location/Qualifiers
misc_feature             1..90
                         note = Synthetic sequence
source                   1..90
                         mol_type = other DNA
                         organism = synthetic construct
SEQUENCE: 223
gccgtaaaaa cgcggaattc ggaagcctgc taccttacac cgcttgcgaa agttgtcacg        60
attgcgttat ctccaggaga aacatataaa                                        90

SEQ ID NO: 224           moltype = DNA   length = 56
FEATURE                  Location/Qualifiers
misc_feature             1..56
                         note = Synthetic sequence
source                   1..56
                         mol_type = other DNA
                         organism = synthetic construct
SEQUENCE: 224
gatcttcagc tatacattat tgcaccaaca ctaaggcaga gtatgtttac ctggac           56

SEQ ID NO: 225           moltype = DNA   length = 56
FEATURE                  Location/Qualifiers
misc_feature             1..56
                         note = Synthetic sequence
source                   1..56
                         mol_type = other DNA
                         organism = synthetic construct
SEQUENCE: 225
gatcttcagc tttgtattac tggaaggatg cttgcttgag gtgtaaaaac ctggac           56

SEQ ID NO: 226           moltype =    length =
SEQUENCE: 226
000

SEQ ID NO: 227           moltype =    length =
SEQUENCE: 227
000

SEQ ID NO: 228           moltype =    length =
SEQUENCE: 228
000

SEQ ID NO: 229           moltype =    length =
SEQUENCE: 229
000

SEQ ID NO: 230           moltype =    length =
SEQUENCE: 230
000

SEQ ID NO: 231           moltype = DNA   length = 10
FEATURE                  Location/Qualifiers
misc_feature             1..10
                         note = Synthetic sequence
source                   1..10
```

```
                        mol_type = other DNA
                        organism = synthetic construct
SEQUENCE: 231
tttttttttt                                                              10

SEQ ID NO: 232          moltype = DNA   length = 11
FEATURE                 Location/Qualifiers
misc_feature            1..11
                        note = Synthetic sequence
source                  1..11
                        mol_type = other DNA
                        organism = synthetic construct
SEQUENCE: 232
tttttttttt t                                                            11

SEQ ID NO: 233          moltype = DNA   length = 12
FEATURE                 Location/Qualifiers
misc_feature            1..12
                        note = Synthetic sequence
source                  1..12
                        mol_type = other DNA
                        organism = synthetic construct
SEQUENCE: 233
tttttttttt tt                                                           12

SEQ ID NO: 234          moltype = DNA   length = 55
FEATURE                 Location/Qualifiers
misc_feature            1..55
                        note = Synthetic sequence
source                  1..55
                        mol_type = other DNA
                        organism = synthetic construct
SEQUENCE: 234
gccggggtgg tgcccatcct ggtcgagctg gacggcgacg taaacggcca caagc            55

SEQ ID NO: 235          moltype = DNA   length = 55
FEATURE                 Location/Qualifiers
misc_feature            1..55
                        note = Synthetic sequence
source                  1..55
                        mol_type = other DNA
                        organism = synthetic construct
SEQUENCE: 235
gccggggtgg tgcccatcct ggtcgagctg gacggcgacg tgctcggcca caagc            55

SEQ ID NO: 236          moltype = DNA   length = 55
FEATURE                 Location/Qualifiers
misc_feature            1..55
                        note = Synthetic sequence
source                  1..55
                        mol_type = other DNA
                        organism = synthetic construct
SEQUENCE: 236
gccggggtgg tgcccatcct ggtcgagctg gacggcgagc taaacggcca caagc            55

SEQ ID NO: 237          moltype = DNA   length = 55
FEATURE                 Location/Qualifiers
misc_feature            1..55
                        note = Synthetic sequence
source                  1..55
                        mol_type = other DNA
                        organism = synthetic construct
SEQUENCE: 237
gccggggtgg tgcccatcct ggtcgagctg gacggcctcg taaacggcca caagc            55

SEQ ID NO: 238          moltype = DNA   length = 55
FEATURE                 Location/Qualifiers
misc_feature            1..55
                        note = Synthetic sequence
source                  1..55
                        mol_type = other DNA
                        organism = synthetic construct
SEQUENCE: 238
gccggggtgg tgcccatcct ggtcgagctg gacgcggacg taaacggcca caagc            55

SEQ ID NO: 239          moltype = DNA   length = 55
FEATURE                 Location/Qualifiers
misc_feature            1..55
                        note = Synthetic sequence
```

```
                          source              1..55
                                              mol_type = other DNA
                                              organism = synthetic construct
                          SEQUENCE: 239
                          gccggggtgg tgcccatcct ggtcgagctg gagcgcgacg taaacggcca caagc        55

SEQ ID NO: 240      moltype = DNA  length = 55
                          FEATURE             Location/Qualifiers
                          misc_feature        1..55
                                              note = Synthetic sequence
                          source              1..55
                                              mol_type = other DNA
                                              organism = synthetic construct
                          SEQUENCE: 240
                          gccggggtgg tgcccatcct ggtcgagctg ctcggcgacg taaacggcca caagc        55

SEQ ID NO: 241      moltype = DNA  length = 55
                          FEATURE             Location/Qualifiers
                          misc_feature        1..55
                                              note = Synthetic sequence
                          source              1..55
                                              mol_type = other DNA
                                              organism = synthetic construct
                          SEQUENCE: 241
                          gccggggtgg tgcccatcct ggtcgagcac gacggcgacg taaacggcca caagc        55

SEQ ID NO: 242      moltype = DNA  length = 55
                          FEATURE             Location/Qualifiers
                          misc_feature        1..55
                                              note = Synthetic sequence
                          source              1..55
                                              mol_type = other DNA
                                              organism = synthetic construct
                          SEQUENCE: 242
                          gccggggtgg tgcccatcct ggtcgacgtg gacggcgacg taaacggcca caagc        55

SEQ ID NO: 243      moltype = DNA  length = 55
                          FEATURE             Location/Qualifiers
                          misc_feature        1..55
                                              note = Synthetic sequence
                          source              1..55
                                              mol_type = other DNA
                                              organism = synthetic construct
                          SEQUENCE: 243
                          gccggggtgg tgcccatcct ggtcctgctg gacggcgacg taaacggcca caagc        55

SEQ ID NO: 244      moltype = DNA  length = 55
                          FEATURE             Location/Qualifiers
                          misc_feature        1..55
                                              note = Synthetic sequence
                          source              1..55
                                              mol_type = other DNA
                                              organism = synthetic construct
                          SEQUENCE: 244
                          gccggggtgg tgcccatcct ggaggagctg gacggcgacg taaacggcca caagc        55

SEQ ID NO: 245      moltype = DNA  length = 55
                          FEATURE             Location/Qualifiers
                          misc_feature        1..55
                                              note = Synthetic sequence
                          source              1..55
                                              mol_type = other DNA
                                              organism = synthetic construct
                          SEQUENCE: 245
                          gccggggtgg tgcccatcct cctcgagctg gacggcgacg taaacggcca caagc        55

SEQ ID NO: 246      moltype = DNA  length = 34
                          FEATURE             Location/Qualifiers
                          misc_feature        1..34
                                              note = Synthetic sequence
                          source              1..34
                                              mol_type = other DNA
                                              organism = synthetic construct
                          SEQUENCE: 246
                          gtgttaatac aaaggtacag gaacaaagaa tttg                               34

SEQ ID NO: 247      moltype = DNA  length = 18
                          FEATURE             Location/Qualifiers
                          misc_feature        1..18
```

```
                        note = Synthetic sequence
source                  1..18
                        mol_type = other DNA
                        organism = synthetic construct
SEQUENCE: 247
caaagagaag cctcggcc                                                       18

SEQ ID NO: 248          moltype = DNA  length = 55
FEATURE                 Location/Qualifiers
misc_feature            1..55
                        note = Synthetic sequence
source                  1..55
                        mol_type = other DNA
                        organism = synthetic construct
SEQUENCE: 248
tttattcaag gcaatcacta tcagctgtgg aacacccagg taaactaaca caact            55

SEQ ID NO: 249          moltype = DNA  length = 55
FEATURE                 Location/Qualifiers
misc_feature            1..55
                        note = Synthetic sequence
source                  1..55
                        mol_type = other DNA
                        organism = synthetic construct
SEQUENCE: 249
tttattcaag gcaatcacta tcagctgtgg aacacccagg tgctctaaca caact            55

SEQ ID NO: 250          moltype = DNA  length = 55
FEATURE                 Location/Qualifiers
misc_feature            1..55
                        note = Synthetic sequence
source                  1..55
                        mol_type = other DNA
                        organism = synthetic construct
SEQUENCE: 250
tttattcaag gcaatcacta tcagctgtgg aacacccacc taaactaaca caact            55

SEQ ID NO: 251          moltype = DNA  length = 55
FEATURE                 Location/Qualifiers
misc_feature            1..55
                        note = Synthetic sequence
source                  1..55
                        mol_type = other DNA
                        organism = synthetic construct
SEQUENCE: 251
tttattcaag gcaatcacta tcagctgtgg aacaccgtgg taaactaaca caact            55

SEQ ID NO: 252          moltype = DNA  length = 55
FEATURE                 Location/Qualifiers
misc_feature            1..55
                        note = Synthetic sequence
source                  1..55
                        mol_type = other DNA
                        organism = synthetic construct
SEQUENCE: 252
tttattcaag gcaatcacta tcagctgtgg aacaggcagg taaactaaca caact            55

SEQ ID NO: 253          moltype = DNA  length = 55
FEATURE                 Location/Qualifiers
misc_feature            1..55
                        note = Synthetic sequence
source                  1..55
                        mol_type = other DNA
                        organism = synthetic construct
SEQUENCE: 253
tttattcaag gcaatcacta tcagctgtgg aagtcccagg taaactaaca caact            55

SEQ ID NO: 254          moltype = DNA  length = 55
FEATURE                 Location/Qualifiers
misc_feature            1..55
                        note = Synthetic sequence
source                  1..55
                        mol_type = other DNA
                        organism = synthetic construct
SEQUENCE: 254
tttattcaag gcaatcacta tcagctgtgg ttcacccagg taaactaaca caact            55

SEQ ID NO: 255          moltype = DNA  length = 55
FEATURE                 Location/Qualifiers
```

```
misc_feature             1..55
                         note = Synthetic sequence
source                   1..55
                         mol_type = other DNA
                         organism = synthetic construct
SEQUENCE: 255
tttattcaag gcaatcacta tcagctgtcc aacacccagg taaactaaca caact         55

SEQ ID NO: 256           moltype = DNA  length = 55
FEATURE                  Location/Qualifiers
misc_feature             1..55
                         note = Synthetic sequence
source                   1..55
                         mol_type = other DNA
                         organism = synthetic construct
SEQUENCE: 256
tttattcaag gcaatcacta tcagctcagg aacacccagg taaactaaca caact         55

SEQ ID NO: 257           moltype = DNA  length = 55
FEATURE                  Location/Qualifiers
misc_feature             1..55
                         note = Synthetic sequence
source                   1..55
                         mol_type = other DNA
                         organism = synthetic construct
SEQUENCE: 257
tttattcaag gcaatcacta tcaggagtgg aacacccagg taaactaaca caact         55

SEQ ID NO: 258           moltype = DNA  length = 55
FEATURE                  Location/Qualifiers
misc_feature             1..55
                         note = Synthetic sequence
source                   1..55
                         mol_type = other DNA
                         organism = synthetic construct
SEQUENCE: 258
tttattcaag gcaatcacta tctcctgtgg aacacccagg taaactaaca caact         55

SEQ ID NO: 259           moltype = DNA  length = 55
FEATURE                  Location/Qualifiers
misc_feature             1..55
                         note = Synthetic sequence
source                   1..55
                         mol_type = other DNA
                         organism = synthetic construct
SEQUENCE: 259
tttattcaag gcaatcacta agagctgtgg aacacccagg taaactaaca caact         55

SEQ ID NO: 260           moltype = DNA  length = 59
FEATURE                  Location/Qualifiers
misc_feature             1..59
                         note = Synthetic sequence
source                   1..59
                         mol_type = other DNA
                         organism = synthetic construct
SEQUENCE: 260
ctacgccgat tatcttctga caactttcgc aagcggtgta aggcgaaaaa tgcgggcac    59

SEQ ID NO: 261           moltype = DNA  length = 59
FEATURE                  Location/Qualifiers
misc_feature             1..59
                         note = Synthetic sequence
source                   1..59
                         mol_type = other DNA
                         organism = synthetic construct
SEQUENCE: 261
ctacgccgat tatcttctga caactttcgc aagcggtgta aaataaaaaa tgcgggcac    59

SEQ ID NO: 262           moltype = DNA  length = 59
FEATURE                  Location/Qualifiers
misc_feature             1..59
                         note = Synthetic sequence
source                   1..59
                         mol_type = other DNA
                         organism = synthetic construct
SEQUENCE: 262
ctacgccgat tatcttctga caactttcgc aagcggtgtg gggtaaaaaa tgcgggcac    59

SEQ ID NO: 263           moltype = DNA  length = 59
```

```
FEATURE                 Location/Qualifiers
misc_feature            1..59
                        note = Synthetic sequence
source                  1..59
                        mol_type = other DNA
                        organism = synthetic construct
SEQUENCE: 263
ctacgccgat tatcttctga caactttcgc aagcggtaca aggtaaaaaa tgcgggcac    59

SEQ ID NO: 264          moltype = DNA   length = 59
FEATURE                 Location/Qualifiers
misc_feature            1..59
                        note = Synthetic sequence
source                  1..59
                        mol_type = other DNA
                        organism = synthetic construct
SEQUENCE: 264
ctacgccgat tatcttctga caactttcgc aagcgacgta aggtaaaaaa tgcgggcac    59

SEQ ID NO: 265          moltype = DNA   length = 59
FEATURE                 Location/Qualifiers
misc_feature            1..59
                        note = Synthetic sequence
source                  1..59
                        mol_type = other DNA
                        organism = synthetic construct
SEQUENCE: 265
ctacgccgat tatcttctga caactttcgc aagtagtgta aggtaaaaaa tgcgggcac    59

SEQ ID NO: 266          moltype = DNA   length = 59
FEATURE                 Location/Qualifiers
misc_feature            1..59
                        note = Synthetic sequence
source                  1..59
                        mol_type = other DNA
                        organism = synthetic construct
SEQUENCE: 266
ctacgccgat tatcttctga caactttcgc agacggtgta aggtaaaaaa tgcgggcac    59

SEQ ID NO: 267          moltype = DNA   length = 59
FEATURE                 Location/Qualifiers
misc_feature            1..59
                        note = Synthetic sequence
source                  1..59
                        mol_type = other DNA
                        organism = synthetic construct
SEQUENCE: 267
ctacgccgat tatcttctga caactttcgt gagcggtgta aggtaaaaaa tgcgggcac    59

SEQ ID NO: 268          moltype = DNA   length = 59
FEATURE                 Location/Qualifiers
misc_feature            1..59
                        note = Synthetic sequence
source                  1..59
                        mol_type = other DNA
                        organism = synthetic construct
SEQUENCE: 268
ctacgccgat tatcttctga caacttttac aagcggtgta aggtaaaaaa tgcgggcac    59

SEQ ID NO: 269          moltype = DNA   length = 59
FEATURE                 Location/Qualifiers
misc_feature            1..59
                        note = Synthetic sequence
source                  1..59
                        mol_type = other DNA
                        organism = synthetic construct
SEQUENCE: 269
ctacgccgat tatcttctga caactcccgc aagcggtgta aggtaaaaaa tgcgggcac    59

SEQ ID NO: 270          moltype = DNA   length = 59
FEATURE                 Location/Qualifiers
misc_feature            1..59
                        note = Synthetic sequence
source                  1..59
                        mol_type = other DNA
                        organism = synthetic construct
SEQUENCE: 270
ctacgccgat tatcttctga caatcttcgc aagcggtgta aggtaaaaaa tgcgggcac    59
```

```
SEQ ID NO: 271          moltype = DNA    length = 59
FEATURE                 Location/Qualifiers
misc_feature            1..59
                        note = Synthetic sequence
source                  1..59
                        mol_type = other DNA
                        organism = synthetic construct
SEQUENCE: 271
ctacgccgat tatcttctga cggctttcgc aagcggtgta aggtaaaaaa tgcgggcac        59

SEQ ID NO: 272          moltype = DNA    length = 59
FEATURE                 Location/Qualifiers
misc_feature            1..59
                        note = Synthetic sequence
source                  1..59
                        mol_type = other DNA
                        organism = synthetic construct
SEQUENCE: 272
ctacgccgat tatcttctgg taactttcgc aagcggtgta aggtaaaaaa tgcgggcac        59

SEQ ID NO: 273          moltype = DNA    length = 49
FEATURE                 Location/Qualifiers
misc_feature            1..49
                        note = Synthetic sequence
source                  1..49
                        mol_type = other DNA
                        organism = synthetic construct
SEQUENCE: 273
tatcttctga caactttcgc aagcggtgta aggtaaaaaa tgcgggcac                   49

SEQ ID NO: 274          moltype = DNA    length = 44
FEATURE                 Location/Qualifiers
misc_feature            1..44
                        note = Synthetic sequence
source                  1..44
                        mol_type = other DNA
                        organism = synthetic construct
SEQUENCE: 274
tctgacaact ttcgcaagcg gtgtaaggta aaaatgcgg gcac                         44

SEQ ID NO: 275          moltype = DNA    length = 39
FEATURE                 Location/Qualifiers
misc_feature            1..39
                        note = Synthetic sequence
source                  1..39
                        mol_type = other DNA
                        organism = synthetic construct
SEQUENCE: 275
caactttcgc aagcggtgta aggtaaaaaa tgcgggcac                              39

SEQ ID NO: 276          moltype = DNA    length = 34
FEATURE                 Location/Qualifiers
misc_feature            1..34
                        note = Synthetic sequence
source                  1..34
                        mol_type = other DNA
                        organism = synthetic construct
SEQUENCE: 276
ttcgcaagcg gtgtaaggta aaaatgcgg gcac                                    34

SEQ ID NO: 277          moltype = DNA    length = 54
FEATURE                 Location/Qualifiers
misc_feature            1..54
                        note = Synthetic sequence
source                  1..54
                        mol_type = other DNA
                        organism = synthetic construct
SEQUENCE: 277
ctacgccgat tatcttctga caactttcgc aagcggtgta aggtaaaaaa tgcg             54

SEQ ID NO: 278          moltype = DNA    length = 49
FEATURE                 Location/Qualifiers
misc_feature            1..49
                        note = Synthetic sequence
source                  1..49
                        mol_type = other DNA
                        organism = synthetic construct
SEQUENCE: 278
ctacgccgat tatcttctga caactttcgc aagcggtgta aggtaaaaa                   49
```

```
SEQ ID NO: 279          moltype = DNA  length = 40
FEATURE                 Location/Qualifiers
misc_feature            1..40
                        note = Synthetic sequence
source                  1..40
                        mol_type = other DNA
                        organism = synthetic construct
SEQUENCE: 279
ctacgccgat tatcttctga caactttcgc aagcggtgta                              40

SEQ ID NO: 280          moltype = DNA  length = 35
FEATURE                 Location/Qualifiers
misc_feature            1..35
                        note = Synthetic sequence
source                  1..35
                        mol_type = other DNA
                        organism = synthetic construct
SEQUENCE: 280
ctacgccgat tatcttctga caactttcgc aagcg                                   35

SEQ ID NO: 281          moltype = DNA  length = 30
FEATURE                 Location/Qualifiers
misc_feature            1..30
                        note = Synthetic sequence
source                  1..30
                        mol_type = other DNA
                        organism = synthetic construct
SEQUENCE: 281
ctacgccgat tatcttctga caactttcgc                                         30

SEQ ID NO: 282          moltype = DNA  length = 25
FEATURE                 Location/Qualifiers
misc_feature            1..25
                        note = Synthetic sequence
source                  1..25
                        mol_type = other DNA
                        organism = synthetic construct
SEQUENCE: 282
ctacgccgat tatcttctga caact                                              25

SEQ ID NO: 283          moltype = DNA  length = 20
FEATURE                 Location/Qualifiers
misc_feature            1..20
                        note = Synthetic sequence
source                  1..20
                        mol_type = other DNA
                        organism = synthetic construct
SEQUENCE: 283
ctacgccgat tatcttctga                                                    20

SEQ ID NO: 284          moltype = DNA  length = 34
FEATURE                 Location/Qualifiers
misc_feature            1..34
                        note = Synthetic sequence
source                  1..34
                        mol_type = other DNA
                        organism = synthetic construct
SEQUENCE: 284
caactttcgc aagcggtgta aggtaaaaaa tgcg                                    34

SEQ ID NO: 285          moltype = DNA  length = 63
FEATURE                 Location/Qualifiers
misc_feature            1..63
                        note = Synthetic sequence
source                  1..63
                        mol_type = other DNA
                        organism = synthetic construct
SEQUENCE: 285
atggaatgtg gcgaacgctt tcaacgaaac aactttcgca agcggtgtaa ggtaaaaaat        60
gcg                                                                     63

SEQ ID NO: 286          moltype = DNA  length = 63
FEATURE                 Location/Qualifiers
misc_feature            1..63
                        note = Synthetic sequence
source                  1..63
                        mol_type = other DNA
                        organism = synthetic construct
```

```
SEQUENCE: 286
atggaatgtg gcgaacgctt agttggaaac aactttcgca agcggtgtaa ggtaaaaaat    60
gcg                                                                  63

SEQ ID NO: 287          moltype = DNA   length = 63
FEATURE                 Location/Qualifiers
misc_feature            1..63
                        note = Synthetic sequence
source                  1..63
                        mol_type = other DNA
                        organism = synthetic construct
SEQUENCE: 287
atggaatgtg gcgaagcgaa agttggaaac aactttcgca agcggtgtaa ggtaaaaaat    60
gcg                                                                  63

SEQ ID NO: 288          moltype = DNA   length = 63
FEATURE                 Location/Qualifiers
misc_feature            1..63
                        note = Synthetic sequence
source                  1..63
                        mol_type = other DNA
                        organism = synthetic construct
SEQUENCE: 288
atggaatgtg cgcttgcgaa agttggaaac aactttcgca agcggtgtaa ggtaaaaaat    60
gcg                                                                  63

SEQ ID NO: 289          moltype = DNA   length = 63
FEATURE                 Location/Qualifiers
misc_feature            1..63
                        note = Synthetic sequence
source                  1..63
                        mol_type = other DNA
                        organism = synthetic construct
SEQUENCE: 289
atggatacac cgcttgcgaa agttggaaac aactttcgca agcggtgtaa ggtaaaaaat    60
gcg                                                                  63

SEQ ID NO: 290          moltype = DNA   length = 63
FEATURE                 Location/Qualifiers
misc_feature            1..63
                        note = Synthetic sequence
source                  1..63
                        mol_type = other DNA
                        organism = synthetic construct
SEQUENCE: 290
taccttacac cgcttgcgaa agttggaaac aactttcgca agcggtgtaa ggtaaaaaat    60
gcg                                                                  63

SEQ ID NO: 291          moltype = DNA   length = 40
FEATURE                 Location/Qualifiers
misc_feature            1..40
                        note = Synthetic sequence
source                  1..40
                        mol_type = other DNA
                        organism = synthetic construct
SEQUENCE: 291
gttttatctt ctgctggtgg ttcgttcggt atttttaatg                          40

SEQ ID NO: 292          moltype = DNA   length = 40
FEATURE                 Location/Qualifiers
misc_feature            1..40
                        note = Synthetic sequence
source                  1..40
                        mol_type = other DNA
                        organism = synthetic construct
SEQUENCE: 292
cattaaaaat accgaacgaa ccaccagcag aagataaaac                          40

SEQ ID NO: 293          moltype = DNA   length = 43
FEATURE                 Location/Qualifiers
misc_feature            1..43
                        note = Synthetic sequence
source                  1..43
                        mol_type = other DNA
                        organism = synthetic construct
SEQUENCE: 293
gaccatttgc gaaatgtatc taatggtcaa actaaatcta ctc                      43

SEQ ID NO: 294          moltype = DNA   length = 43
```

```
FEATURE                 Location/Qualifiers
misc_feature            1..43
                        note = Synthetic sequence
source                  1..43
                        mol_type = other DNA
                        organism = synthetic construct
SEQUENCE: 294
gagtagattt agtttgacca ttagatacat ttcgcaaatg gtc                             43

SEQ ID NO: 295          moltype = DNA  length = 37
FEATURE                 Location/Qualifiers
misc_feature            1..37
                        note = Synthetic sequence
source                  1..37
                        mol_type = other DNA
                        organism = synthetic construct
SEQUENCE: 295
cttgcagaac ccggatagac gaatgaagga atgcaac                                    37

SEQ ID NO: 296          moltype = DNA  length = 37
FEATURE                 Location/Qualifiers
misc_feature            1..37
                        note = Synthetic sequence
source                  1..37
                        mol_type = other DNA
                        organism = synthetic construct
SEQUENCE: 296
cttgcaggcc ttgaatagag gagttaagga atgcaac                                    37

SEQ ID NO: 297          moltype = DNA  length = 37
FEATURE                 Location/Qualifiers
misc_feature            1..37
                        note = Synthetic sequence
source                  1..37
                        mol_type = other DNA
                        organism = synthetic construct
SEQUENCE: 297
gttgcacagt gctaattaga gaaactagga atgcaac                                    37

SEQ ID NO: 298          moltype = DNA  length = 37
FEATURE                 Location/Qualifiers
misc_feature            1..37
                        note = Synthetic sequence
source                  1..37
                        mol_type = other DNA
                        organism = synthetic construct
SEQUENCE: 298
ctagcatatt cagaacaaag ggattaagga atgcaac                                    37

SEQ ID NO: 299          moltype = DNA  length = 37
FEATURE                 Location/Qualifiers
misc_feature            1..37
                        note = Synthetic sequence
source                  1..37
                        mol_type = other DNA
                        organism = synthetic construct
SEQUENCE: 299
ctttcatatt cagaaactag gggttaagga ctgcaac                                    37

SEQ ID NO: 300          moltype = DNA  length = 37
FEATURE                 Location/Qualifiers
misc_feature            1..37
                        note = Synthetic sequence
source                  1..37
                        mol_type = other DNA
                        organism = synthetic construct
SEQUENCE: 300
gttgcatccc tacgtcgtga gcaccggtga gtgcaac                                    37

SEQ ID NO: 301          moltype = DNA  length = 31
FEATURE                 Location/Qualifiers
misc_feature            1..31
                        note = Synthetic sequence
source                  1..31
                        mol_type = other DNA
                        organism = synthetic construct
SEQUENCE: 301
ggaaaggaat cccctgaagg aaacgagggg g                                          31
```

```
SEQ ID NO: 302          moltype = DNA  length = 36
FEATURE                 Location/Qualifiers
misc_feature            1..36
                        note = Synthetic sequence
source                  1..36
                        mol_type = other DNA
                        organism = synthetic construct
SEQUENCE: 302
gtgtccatca atcagatttg cgttggccgg tgcaat                                    36

SEQ ID NO: 303          moltype = DNA  length = 37
FEATURE                 Location/Qualifiers
misc_feature            1..37
                        note = Synthetic sequence
source                  1..37
                        mol_type = other DNA
                        organism = synthetic construct
SEQUENCE: 303
gtttcagcgc acgaattaac gagatgagag atgcaac                                   37

SEQ ID NO: 304          moltype = AA  length = 500
FEATURE                 Location/Qualifiers
REGION                  1..500
                        note = Synthetic sequence
source                  1..500
                        mol_type = protein
                        organism = synthetic construct
SEQUENCE: 304
KEPLNIGKTA KAVFKEIDPT SLNRAANYDA SIELNCKECK FKPFKNVKRY EFNFYNNWYR    60
CNPNSCLQST YKAQVRKVEI GYEKLKNEIL TQMQYYPWFG RLYQNFFHDE RDKMTSLDEI   120
QVIGVQNKVF FNTVEKAWRE IIKKRFKDNK ETMETIPELK HAAGHGKRKL SNKSLLRRRF   180
AFVQKSFKFV DNSDVSYRSF SNNIACVLPS RIGVDLGGVI SRNPKREYIP QEISFNAFWK   240
QHEGLKKGRN IEIQSVQYKG ETVKRIEADT GEDKAWGKNR QRRFTSLILK LVPKQGGKKV   300
WKYPEKRNEG NYEYFPIPIE FILDSGETSI RFGGDEGEAG KQKHLVIPFN DSKATPLASQ   360
QTLLENSRFN AEVKSCIGLA IYANYFYGYA RNYVISSIYH KNSKNGQAIT AIYLESIAHN   420
YVKAIERQLQ NLLLNLRDFS FMESHKKELK KYFGGDLEGT GGAQKRREKE EKIEKEIEQS   480
YLPRLIRLSL TKMVTKQVEM                                              500

SEQ ID NO: 305          moltype = AA  length = 507
FEATURE                 Location/Qualifiers
REGION                  1..507
                        note = Synthetic sequence
source                  1..507
                        mol_type = protein
                        organism = synthetic construct
SEQUENCE: 305
ELIVNENKDP LNIGKTAKAV FKEIDPTSIN RAANYDASIE LACKECKFKP FNNTKRHDFS    60
FYSNWHRCSP NSCLQSTYRA KIRKTEIGYE KLKNEILNQM QYYPWFGRLY QNFFNDQRDK   120
MTSLDEIQVT GVQNKIFFNT VEKAWREIIK KRFRDNKETM RTIPDLKNKS GHGSRKLSNK   180
SLLRRRFAFA QKSFKLVDNS DVSYRAFSNN VACVLPSKIG VDIGGIINKD LKREYIPQEI   240
TFNVFWKQHD GLKKGRNIEI HSVQYKGEIV KRIEADTGED KAWGKNRQRR FTSLILKITP   300
KQGGKKIWKF PEKKNASDYE YFPIPIEFIL DNGDASIKFG GEEGEVGKQK HLLIPFNDSK   360
ATPLSSKQML LETSRFNAEV KSTIGLALYA NYFVSYARNY VIKSTYHKNS KKGQIVTEIY   420
LESISQNFVR AIQRQLQSLM LNLKDWGFMQ THKKELKKYF GSDLEGSKGG QKRREKEEKI   480
EKEIEASYLP RLIRLSLTKS VTKAEEM                                      507

SEQ ID NO: 306          moltype = AA  length = 529
FEATURE                 Location/Qualifiers
REGION                  1..529
                        note = Synthetic sequence
source                  1..529
                        mol_type = protein
                        organism = synthetic construct
SEQUENCE: 306
PEEKTSKLKP NSINLAANYD ANEKFNCKEC KFHPFKNKKR YEFNFYNNLH GCKSCTKSTN    60
NPAVKRIEIG YQKLKFEIKN QMEAYPWFGR LRINFYSDEK RKMSELNEMQ VTGVKNKIFF   120
DAIECAWREI LKKRFRESKE TLITIPKLKN KAGHGARKHN NKKLLIRRRA FMKKNFHFLD   180
NDSISYRSFA NNIACVLPSK VGVDIGGIIS PDVGKDIKPV DISLNLMWAS KEGIKSGRKV   240
EIYSTQYDGN MVKKIEAETG EDKSWGKNRK RRQTSLLLSI PKPSKQVQEF DFKEWPRYKD   300
IEKKVQWRGF PIKIIFDSNH NSIEFGTYQG GKQKVLPIPF NDSKTTPLGS KMNKLEKLRF   360
NSKIKSRLGS AIAANKFLEA ARTYCVDSLY HEVSSANAIG KGKIFIEYYL EILSQNYIEA   420
AQKQLQRFIE SIEQWFVADP FQGRLKQYFK DDLKRAKCFL CANREVQTTC YAAVKLHKSC   480
AEKVKDKNKE LAIKERNNKE DAVIKEVEAS NYPRVIRLKL TKTITNKAM               529

SEQ ID NO: 307          moltype = DNA  length = 35
FEATURE                 Location/Qualifiers
misc_feature            1..35
                        note = Synthetic sequence
source                  1..35
```

```
                          mol_type = other DNA
                          organism = synthetic construct
SEQUENCE: 307
cttttagaca gtttaaattc taaagggtat aaaac                               35

SEQ ID NO: 308            moltype = DNA   length = 36
FEATURE                   Location/Qualifiers
misc_feature              1..36
                          note = Synthetic sequence
source                    1..36
                          mol_type = other DNA
                          organism = synthetic construct
SEQUENCE: 308
gtcgaaatgc ccgcgcgggg gcgtcgtacc cgcgac                              36

SEQ ID NO: 309            moltype = DNA   length = 37
FEATURE                   Location/Qualifiers
misc_feature              1..37
                          note = Synthetic sequence
source                    1..37
                          mol_type = other DNA
                          organism = synthetic construct
SEQUENCE: 309
gttgcagcgg ccgacggagc gcgagcgtgg atgccac                             37

SEQ ID NO: 310            moltype = DNA   length = 35
FEATURE                   Location/Qualifiers
misc_feature              1..35
                          note = Synthetic sequence
source                    1..35
                          mol_type = other DNA
                          organism = synthetic construct
SEQUENCE: 310
ctttagactt ctccggaagt cgaattaatg gaaac                               35

SEQ ID NO: 311            moltype = DNA   length = 28
FEATURE                   Location/Qualifiers
misc_feature              1..28
                          note = Synthetic sequence
source                    1..28
                          mol_type = other DNA
                          organism = synthetic construct
SEQUENCE: 311
gggcgccccg cgcgagcggg ggttgaag                                       28

SEQ ID NO: 312            moltype = DNA   length = 136
FEATURE                   Location/Qualifiers
misc_feature              1..136
                          note = Synthetic sequence
source                    1..136
                          mol_type = other DNA
                          organism = synthetic construct
SEQUENCE: 312
gaaggatgct tgcttgaggt gtagttgtca ttccttcatt cgtctattcg ggttctgcaa    60
ctatacatta ttgcaccaac actaaggcag agtatggttg cattccttca ttcgtctatt   120
cgggttctgc aacggg                                                   136

SEQ ID NO: 313            moltype = DNA   length = 102
FEATURE                   Location/Qualifiers
misc_feature              1..102
                          note = Synthetic sequence
source                    1..102
                          mol_type = other DNA
                          organism = synthetic construct
SEQUENCE: 313
agaatgcttg cttgaggtgt agttgcattc cttcattcgt ctattcgggt aattgcacca    60
acactaaggc agagtatggt tgcattcctt cattcgtcta gg                      102

SEQ ID NO: 314            moltype = DNA   length = 75
FEATURE                   Location/Qualifiers
misc_feature              1..75
                          note = Synthetic sequence
source                    1..75
                          mol_type = other DNA
                          organism = synthetic construct
SEQUENCE: 314
cgatgcttgc ttgaggtgta gttgcattgc accaacacta aggcagagta tggttgcatt    60
ccttcattcg tctag                                                    75
```

```
SEQ ID NO: 315            moltype = DNA  length = 90
FEATURE                   Location/Qualifiers
misc_feature              1..90
                          note = Synthetic sequence
source                    1..90
                          mol_type = other DNA
                          organism = synthetic construct
SEQUENCE: 315
gatgcttgct tgaggtgtag ttgcattcct tcattctgca ccaacactaa ggcagagtat    60
ggttgcattc cttttcgggt tctgcaacgg                                     90

SEQ ID NO: 316            moltype = DNA  length = 73
FEATURE                   Location/Qualifiers
misc_feature              1..73
                          note = Synthetic sequence
source                    1..73
                          mol_type = other DNA
                          organism = synthetic construct
SEQUENCE: 316
gcttgcttga ggtgtagttg cattccttca ttccacctac actaaggcag agtatggttg    60
cattccttca ttc                                                       73

SEQ ID NO: 317            moltype = DNA  length = 73
FEATURE                   Location/Qualifiers
misc_feature              1..73
                          note = Synthetic sequence
source                    1..73
                          mol_type = other DNA
                          organism = synthetic construct
SEQUENCE: 317
gcttgcttga ggtgtagttg cattccttca ttccacctac actaaggcag agtatggttg    60
cattccttca ttc                                                       73

SEQ ID NO: 318            moltype = DNA  length = 63
FEATURE                   Location/Qualifiers
misc_feature              1..63
                          note = Synthetic sequence
source                    1..63
                          mol_type = other DNA
                          organism = synthetic construct
SEQUENCE: 318
gcttgcttga ggtgtagttg cattcgcaac actaaggcag agtatggttg cattccttca    60
ttc                                                                  63

SEQ ID NO: 319            moltype = DNA  length = 66
FEATURE                   Location/Qualifiers
misc_feature              1..66
                          note = Synthetic sequence
source                    1..66
                          mol_type = other DNA
                          organism = synthetic construct
SEQUENCE: 319
cttgcttgag gtgtagttgc cgacactaag gcagagtatg gttgcattat tcgggttctg    60
caacgg                                                               66

SEQ ID NO: 320            moltype = DNA  length = 69
FEATURE                   Location/Qualifiers
misc_feature              1..69
                          note = Synthetic sequence
source                    1..69
                          mol_type = other DNA
                          organism = synthetic construct
SEQUENCE: 320
cttgcttgag gtgtagttgc attccttcat tcaaacacta aggcagagta tggttgcatt    60
ccttcattc                                                            69

SEQ ID NO: 321            moltype = DNA  length = 73
FEATURE                   Location/Qualifiers
misc_feature              1..73
                          note = Synthetic sequence
source                    1..73
                          mol_type = other DNA
                          organism = synthetic construct
SEQUENCE: 321
ttgcttgagg tgtagttgca ttccttcatt ctaacactaa ggcagagtat ggttgcattc    60
cttcattcgt cta                                                       73

SEQ ID NO: 322            moltype = DNA  length = 58
FEATURE                   Location/Qualifiers
```

```
misc_feature            1..58
                        note = Synthetic sequence
source                  1..58
                        mol_type = other DNA
                        organism = synthetic construct
SEQUENCE: 322
ttgcttgagg tgtagttgca tccacactaa ggcagagtat ggttgcattc cttcattc      58

SEQ ID NO: 323          moltype = DNA   length = 67
FEATURE                 Location/Qualifiers
misc_feature            1..67
                        note = Synthetic sequence
source                  1..67
                        mol_type = other DNA
                        organism = synthetic construct
SEQUENCE: 323
tgcttaaggt gtagttgcat tccttcattc aacactaagg cagagtatgg ttgcattcc     60
ttcattc                                                              67

SEQ ID NO: 324          moltype = DNA   length = 66
FEATURE                 Location/Qualifiers
misc_feature            1..66
                        note = Synthetic sequence
source                  1..66
                        mol_type = other DNA
                        organism = synthetic construct
SEQUENCE: 324
tgcttgaggt gtagttgcat tccttcattc cacactaagg cagagtatgg ttgcattcct    60
tcattc                                                               66

SEQ ID NO: 325          moltype = DNA   length = 72
FEATURE                 Location/Qualifiers
misc_feature            1..72
                        note = Synthetic sequence
source                  1..72
                        mol_type = other DNA
                        organism = synthetic construct
SEQUENCE: 325
tgcttgaggt gtagttgcat tccttcattc aacactaagg cagagtatgg ttgcattcct    60
tcattcgtct at                                                        72

SEQ ID NO: 326          moltype = DNA   length = 64
FEATURE                 Location/Qualifiers
misc_feature            1..64
                        note = Synthetic sequence
source                  1..64
                        mol_type = other DNA
                        organism = synthetic construct
SEQUENCE: 326
cttgaggtgt agttgcattc cttcattcaa cactaaggca gagtatggtt gcattccttc    60
attc                                                                 64

SEQ ID NO: 327          moltype = DNA   length = 59
FEATURE                 Location/Qualifiers
misc_feature            1..59
                        note = Synthetic sequence
source                  1..59
                        mol_type = other DNA
                        organism = synthetic construct
SEQUENCE: 327
cttgaggtgt agttgcattc cttaacacta aggcagagta tggttgcatt ccttcattc     59

SEQ ID NO: 328          moltype = DNA   length = 63
FEATURE                 Location/Qualifiers
misc_feature            1..63
                        note = Synthetic sequence
source                  1..63
                        mol_type = other DNA
                        organism = synthetic construct
SEQUENCE: 328
ttgaggtgta gttgcattcc ttcattcaac actaaggcag agtatggttg cattccttca    60
ttc                                                                  63

SEQ ID NO: 329          moltype = DNA   length = 62
FEATURE                 Location/Qualifiers
misc_feature            1..62
                        note = Synthetic sequence
source                  1..62
                        mol_type = other DNA
```

```
                        organism = synthetic construct
SEQUENCE: 329
tgaggtgtag ttgcattcct tcattcaaca ctaaggcaga gtatggttgc attccttcat    60
tc                                                                   62

SEQ ID NO: 330          moltype = DNA  length = 61
FEATURE                 Location/Qualifiers
misc_feature            1..61
                        note = Synthetic sequence
source                  1..61
                        mol_type = other DNA
                        organism = synthetic construct
SEQUENCE: 330
tgaggtgtag ttgcattcct tcgttcacac taaggcagag tatggttgca ttccttcatt    60
c                                                                    61

SEQ ID NO: 331          moltype = DNA  length = 61
FEATURE                 Location/Qualifiers
misc_feature            1..61
                        note = Synthetic sequence
source                  1..61
                        mol_type = other DNA
                        organism = synthetic construct
SEQUENCE: 331
tgaggtgtag ttgcattcct tcattcacac taaggcagag tatggttgca ttccttcatt    60
c                                                                    61

SEQ ID NO: 332          moltype = DNA  length = 61
FEATURE                 Location/Qualifiers
misc_feature            1..61
                        note = Synthetic sequence
source                  1..61
                        mol_type = other DNA
                        organism = synthetic construct
SEQUENCE: 332
ctacgccgat tatcttctga caactttcgc aagcggtgta aggtaaaaaa tgcgggcacc    60
c                                                                    61

SEQ ID NO: 333          moltype = DNA  length = 30
FEATURE                 Location/Qualifiers
misc_feature            1..30
                        note = Synthetic sequence
source                  1..30
                        mol_type = other DNA
                        organism = synthetic construct
SEQUENCE: 333
ggaatgcaac taccttacac cgcttgcgaa                                     30

SEQ ID NO: 334          moltype = DNA  length = 140
FEATURE                 Location/Qualifiers
misc_feature            1..140
                        note = Synthetic sequence
source                  1..140
                        mol_type = other DNA
                        organism = synthetic construct
SEQUENCE: 334
cttcactgat aaagtggaga accgcttcac caaaagctgt cccttagggg attagaactt    60
gagtgaaggt gggctgcttg catcagccta atgtcgagaa gtgctttctt cggaaagtaa   120
ccctcgaaac aaattcattt                                               140

SEQ ID NO: 335          moltype = DNA  length = 40
FEATURE                 Location/Qualifiers
misc_feature            1..40
                        note = Synthetic sequence
source                  1..40
                        mol_type = other DNA
                        organism = synthetic construct
SEQUENCE: 335
gacgaatgaa ggaatgcaac taccttacac cgcttgcgaa                          40

SEQ ID NO: 336          moltype = DNA  length = 40
FEATURE                 Location/Qualifiers
misc_feature            1..40
                        note = Synthetic sequence
source                  1..40
                        mol_type = other DNA
                        organism = synthetic construct
SEQUENCE: 336
gacgaatgaa ggaatgcaac ccttacaccg cttgcgaaag                          40
```

```
SEQ ID NO: 337        moltype = DNA  length = 40
FEATURE               Location/Qualifiers
misc_feature          1..40
                      note = Synthetic sequence
source                1..40
                      mol_type = other DNA
                      organism = synthetic construct
SEQUENCE: 337
gacgaatgaa ggaatgcaac ttacaccgct tgcgaaagtt                              40

SEQ ID NO: 338        moltype = DNA  length = 40
FEATURE               Location/Qualifiers
misc_feature          1..40
                      note = Synthetic sequence
source                1..40
                      mol_type = other DNA
                      organism = synthetic construct
SEQUENCE: 338
gacgaatgaa ggaatgcaac acaccgcttg cgaaagttgt                              40

SEQ ID NO: 339        moltype = DNA  length = 41
FEATURE               Location/Qualifiers
misc_feature          1..41
                      note = Synthetic sequence
source                1..41
                      mol_type = other DNA
                      organism = synthetic construct
SEQUENCE: 339
gacgaatgaa ggaatgcaac cgtcgccgtc cagctcgacc a                            41

SEQ ID NO: 340        moltype = DNA  length = 40
FEATURE               Location/Qualifiers
misc_feature          1..40
                      note = Synthetic sequence
source                1..40
                      mol_type = other DNA
                      organism = synthetic construct
SEQUENCE: 340
gacgaatgaa ggaatgcaac gatcgttacg ctaactatga                              40

SEQ ID NO: 341        moltype = DNA  length = 180
FEATURE               Location/Qualifiers
misc_feature          1..180
                      note = Synthetic sequence
source                1..180
                      mol_type = other DNA
                      organism = synthetic construct
SEQUENCE: 341
ttcactgata aagtggagaa ccgcttcacc aaaagctgtc ccttaggggga ttagaacttg       60
agtgaaggtg ggctgcttgc atcagcctaa tgtcgagaag tgctttcttc ggaaagtaac       120
cctcgaaaca aattcatttg aaagaatgaa ggaatgcaac acttgacact taatgctcaa       180

SEQ ID NO: 342        moltype = DNA  length = 44
FEATURE               Location/Qualifiers
misc_feature          1..44
                      note = Synthetic sequence
source                1..44
                      mol_type = other DNA
                      organism = synthetic construct
SEQUENCE: 342
gggtaatttc tactaagtgt agatacttga cacttaatgc tcaa                         44

SEQ ID NO: 343        moltype = DNA  length = 45
FEATURE               Location/Qualifiers
misc_feature          1..45
                      note = Synthetic sequence
source                1..45
                      mol_type = other DNA
                      organism = synthetic construct
SEQUENCE: 343
gacgaatgaa ggaatgcaac taccttacac cgcttgcgaa agttg                        45

SEQ ID NO: 344        moltype = DNA  length = 38
FEATURE               Location/Qualifiers
misc_feature          1..38
                      note = Synthetic sequence
source                1..38
                      mol_type = other DNA
```

```
                        organism = synthetic construct
SEQUENCE: 344
gacgaatgaa ggaatgcaac taccttacac cgcttgcg                              38

SEQ ID NO: 345          moltype = DNA   length = 36
FEATURE                 Location/Qualifiers
misc_feature            1..36
                        note = Synthetic sequence
source                  1..36
                        mol_type = other DNA
                        organism = synthetic construct
SEQUENCE: 345
gacgaatgaa ggaatgcaac taccttacac cgcttg                                36

SEQ ID NO: 346          moltype = DNA   length = 34
FEATURE                 Location/Qualifiers
misc_feature            1..34
                        note = Synthetic sequence
source                  1..34
                        mol_type = other DNA
                        organism = synthetic construct
SEQUENCE: 346
gacgaatgaa ggaatgcaac taccttacac cgct                                  34

SEQ ID NO: 347          moltype = DNA   length = 32
FEATURE                 Location/Qualifiers
misc_feature            1..32
                        note = Synthetic sequence
source                  1..32
                        mol_type = other DNA
                        organism = synthetic construct
SEQUENCE: 347
gacgaatgaa ggaatgcaac taccttacac cg                                    32

SEQ ID NO: 348          moltype = DNA   length = 30
FEATURE                 Location/Qualifiers
misc_feature            1..30
                        note = Synthetic sequence
source                  1..30
                        mol_type = other DNA
                        organism = synthetic construct
SEQUENCE: 348
gacgaatgaa ggaatgcaac taccttacac                                       30

SEQ ID NO: 349          moltype = DNA   length = 57
FEATURE                 Location/Qualifiers
misc_feature            1..57
                        note = Synthetic sequence
source                  1..57
                        mol_type = other DNA
                        organism = synthetic construct
SEQUENCE: 349
gttgcagaac ccgaatagac gaatgaagga atgcaactac cttacaccgc ttgcgaa         57

SEQ ID NO: 350          moltype = DNA   length = 37
FEATURE                 Location/Qualifiers
misc_feature            1..37
                        note = Synthetic sequence
source                  1..37
                        mol_type = other DNA
                        organism = synthetic construct
SEQUENCE: 350
gaatgaagga atgcaactac cttacaccgc ttgcgaa                               37

SEQ ID NO: 351          moltype = DNA   length = 35
FEATURE                 Location/Qualifiers
misc_feature            1..35
                        note = Synthetic sequence
source                  1..35
                        mol_type = other DNA
                        organism = synthetic construct
SEQUENCE: 351
atgaaggaat gcaactacct tacaccgctt gcgaa                                 35

SEQ ID NO: 352          moltype = DNA   length = 179
FEATURE                 Location/Qualifiers
misc_feature            1..179
                        note = Synthetic sequence
source                  1..179
```

```
                    mol_type = other DNA
                    organism = synthetic construct
SEQUENCE: 352
cttcactgat aaagtggaga accgcttcac caaaagctgt cccttagggg attagaactt    60
gagtgaaggt gggctgcttg catcagccta atgtcgagaa gtgctttctt cggaaagtaa   120
ccctcgaaac aaattcattt ttcctctcca attctgcaca aaaaaggtg agtccttat     179

SEQ ID NO: 353          moltype = DNA   length = 110
FEATURE                 Location/Qualifiers
misc_feature            1..110
                        note = Synthetic sequence
source                  1..110
                        mol_type = other DNA
                        organism = synthetic construct
SEQUENCE: 353
cttcactgat aaagtggaga accgcttcac caaaagctgt cccttagggg attagaactt    60
gagtgaaggt gggctgcttg catcagccta atgtcgagaa gtgctttctt                110

SEQ ID NO: 354          moltype = DNA   length = 72
FEATURE                 Location/Qualifiers
misc_feature            1..72
                        note = Synthetic sequence
source                  1..72
                        mol_type = other DNA
                        organism = synthetic construct
SEQUENCE: 354
cttcactgat aaagtggaga accgcttcac caaaagctgt cccttagggg attagaactt    60
gagtgaaggt gg                                                         72

SEQ ID NO: 355          moltype = DNA   length = 136
FEATURE                 Location/Qualifiers
misc_feature            1..136
                        note = Synthetic sequence
source                  1..136
                        mol_type = other DNA
                        organism = synthetic construct
SEQUENCE: 355
ttcactgata aagtggagaa ccgcttcacc aaaagctgtc ccttagggga ttagaacttg    60
agtgaaggtg ggctgcttgc atcagcctaa tgtcgagaag tgctttcttc ggaaagtaac   120
cctcgaaaca aattca                                                    136

SEQ ID NO: 356          moltype = DNA   length = 234
FEATURE                 Location/Qualifiers
misc_feature            1..234
                        note = Synthetic sequence
source                  1..234
                        mol_type = other DNA
                        organism = synthetic construct
SEQUENCE: 356
ttcacacttc actgataaag tggagaaccg cttcaccaaa agctgtccct taggggatta    60
gaacttgagt gaaggtgggc tgcttgcatc agcctaatgt cgagaagtgc tttcttcgga   120
aagtaaccct cgaaacaaat tcattttttcc tctccaattc tgcacaaaaa aaggtgagtc  180
cttataaacc ggcgtgcaga acgccggctc acctttttc ttcattcgat ttta           234

SEQ ID NO: 357          moltype = DNA   length = 181
FEATURE                 Location/Qualifiers
misc_feature            1..181
                        note = Synthetic sequence
source                  1..181
                        mol_type = other DNA
                        organism = synthetic construct
SEQUENCE: 357
cttcactgat aaagtggaga accgcttcac caaaagctgt cccttagggg attagaactt    60
gagtgaaggt gggctgcttg catcagccta atgtcgagaa gtgctttctt cggaaagtaa   120
ccctcgaaac aaattcattt gaaagaatga aggaatgcaa ctaccttaca ccgcttgcga   180
a                                                                    181

SEQ ID NO: 358          moltype = DNA   length = 222
FEATURE                 Location/Qualifiers
misc_feature            1..222
                        note = Synthetic sequence
source                  1..222
                        mol_type = other DNA
                        organism = synthetic construct
SEQUENCE: 358
cttcactgat aaagtggaga accgcttcac caaaagctgt cccttagggg attagaactt    60
gagtgaaggt gggctgcttg catcagccta atgtcgagaa gtgctttctt cggaaagtaa   120
ccctcgaaac aaattcattt ttcctctcca attctgcaca agaaagttgc agaacccgaa   180
tagacgaatg aaggaatgca actaccttac accgcttgcg aa                      222
```

-continued

```
SEQ ID NO: 359           moltype = DNA   length = 45
FEATURE                  Location/Qualifiers
misc_feature             1..45
                         note = Synthetic sequence
source                   1..45
                         mol_type = other DNA
                         organism = synthetic construct
SEQUENCE: 359
gacgaatgaa ggaatgcaac taccgaacga accaccagca gaaga             45

SEQ ID NO: 360           moltype = DNA   length = 45
FEATURE                  Location/Qualifiers
misc_feature             1..45
                         note = Synthetic sequence
source                   1..45
                         mol_type = other DNA
                         organism = synthetic construct
SEQUENCE: 360
gacgaatgaa ggaatgcaac tcttctgctg gtggttcgtt cggta             45

SEQ ID NO: 361           moltype = DNA   length = 43
FEATURE                  Location/Qualifiers
misc_feature             1..43
                         note = Synthetic sequence
source                   1..43
                         mol_type = other DNA
                         organism = synthetic construct
SEQUENCE: 361
gacgaatgaa ggaatgcaac gtttgaccat tagatacatt tcg               43

SEQ ID NO: 362           moltype = DNA   length = 43
FEATURE                  Location/Qualifiers
misc_feature             1..43
                         note = Synthetic sequence
source                   1..43
                         mol_type = other DNA
                         organism = synthetic construct
SEQUENCE: 362
gacgaatgaa ggaatgcaac cgaaatgtat ctaatggtca aac               43

SEQ ID NO: 363           moltype = DNA   length = 7580
FEATURE                  Location/Qualifiers
misc_feature             1..7580
                         note = Synthetic sequence
source                   1..7580
                         mol_type = other DNA
                         organism = synthetic construct
SEQUENCE: 363
gcaaccgcac ctgtggcgcc ggtgatgccg gccacgatgc gtccggcgta gaggatcgag    60
atctcgatcc cgcgaaatta atacgactca ctatagggag accacaacgg tttccctcta   120
gtgccggctc cggagagctc tttaattaag cggccgccct gcaggactcg agttctagaa   180
ataattttgt ttaactttaa gaaggagata tacatatgaa atcttctcac catcaccatc   240
accatcacca tcaccatggt tcttctatga aaatcgaaga aggtaaactg gtaatctgga   300
ttaacggcga taaaggctat aacggtctcg ctgaagtcgg taagaaattc gagaaagata   360
ccggaattaa agtcaccgtt gagcatccgg ataaactgga agagaaattc ccacaggttg   420
cggcaactgg cgatggccct gacattatct tctgggcaca cgaccgcttt ggtggctacg   480
ctcaatctgg cctgttggct gaaatcaccc cggacaaagc gttccaggac aagctgtatc   540
cgtttacctg ggatgccgta cgttacaacg gcaagctgat tgcttacccg atcgctgttg   600
aagcgttatc gctgatttat aacaaagatc tgctgccgaa cccgccaaaa acctgggaag   660
agatcccggc gctggataaa gaactgaaag cgaaaggtaa gagcgcgctg atgttcaacc   720
tgcaagaacc gtacttcacc tggccgctga ttgctgctga cggggggtat gcgttcaagt   780
atgaaaacgg caagtacgac attaaagacg tgggcgtgga taacgctggc gcgaaagcgg   840
gtctgacctt cctggttgac ctgattaaaa acaaaccatg accgattact   900
ccatcgcaga agctgccttt aataaaggcg aaacagcgat gaccatcaac ggcccgtggg   960
catggtccaa catcgacacc agcaaagtga attatggtgt aacggtactg ccgaccttca  1020
agggtcaacc atccaaaccg ttcgttggcg tgctgagcgc aggtattaac gccgccagtc  1080
cgaacaaaga gctggcaaaa gagttcctcg aaaactatct gctgactgat gaaggtctgg  1140
aagcggttaa taaagacaaa ccgctgggtg ccgtagcgct gaagtcttac gaggaagagt  1200
tggcgaaaga tccacgtatt gccgccacta tggaaacgc ccagaaaggt gaaatcatgc  1260
cgaacatccc gcagatgtcc gctttctggt atgccgtgcg tactgcggtg atcaacgccg  1320
ccagcggtcg tcagactgtc gatgaagccc tgaaagacgc gcagactaat tcgagctcga  1380
acaacaacaa caataacaat aacaacaacc tcgggatcga ggaaacctg tacttccaat  1440
ccaatgcaat ggaagaaagc attattaccg gtgtgaaatt caaactgcgc atcgataaag  1500
aaaccaccaa aaaactgaac gagtacttcg atgaatatgg caaagcaatt aacttcgccg  1560
tgaagatcat tcagaaagaa ctggcagatg atcgttttgc aggtaaagca aaactggacc  1620
agaataaaaa cccgatcctg gatgaaaacg gcaaaaaaat ctatgaattc ccggatgaat  1680
tttgcagctg tggtaaacag gttaacaagt acgttaacaa caaaccgttt tgccaagagt  1740
gctataaaat ccgctttacc gaaatggta ttcgcaaacg tatgtatagc gccaaaggtc  1800
```

```
gtaaagccga acataaaatc aatatcctga acagcaccaa caagatcagc aaaacccatt   1860
ttaactatgc cattcgcgaa gccttcattc tggataaaag catcaaaaag cagcgcaaaa   1920
aacgtaatga acgtctgcgt gaaagtaaaa acgtctgca gcagtttatc gatatgcgtg    1980
atggtaaacg tgaaatttgc ccgaccatta aaggtcagaa agtggatcgt tttattcatc   2040
cgagctggat caccaaagat aaaaagctgg aagattttcg cggttatacc ctgagcatta   2100
tcaacagcaa aattaagatt ctggatcgca acatcaaacg cgaagaaaaa agcctgaaag   2160
aaaaaggcca gatcatcttt aaagccaaac gtctgatgct ggataaatcc attcgttttg   2220
ttggtgatcg caaagtgctg tttacaatta gtaaaaccct gccgaaagag tatgaactgg   2280
atctgccgag caaagaaaaa cggctgaatt ggctgaaaga gaagatcgag attatcaaga   2340
accagaaacc gaaatatgcc tatctgctgc gcaaaaacat tgagagcgaa aaaaaaccga   2400
actatgagta ctatctgcag tacaccctgg aaattaaacc ggaactgaaa gattttttatg  2460
atggtgccat tggtattgac cgtggcatta atcatattgc cgtttgcacc tttattagca   2520
acgatggtaa agttacccct ccgaaatttt tcagcagcgg tgaaattctg cgtctgaaaa   2580
atctgcagaa agagcgtgat cgcttttctgc tgcgtaaaca caacaaaaat cgcaaaaaag   2640
gcaacatgcg cgtgatcgaa aacaaaatca atctgatcct gcaccgttat agcaagcaga   2700
ttgttgatat ggccaaaaag ctgaatgcca gcattgtttt tgaagaactg ggtcgtattg   2760
gtaaaagccg caccaaaatg aaaaaaagcc agcgttataa actgagcctg ttcatcttca   2820
agaaactgag cgatctggtt gattacaaaa gccgtcgtga aggtattcgt gttacctatg   2880
ttccgcctga atataccagc aaagaatgta gccattgcgg tgaaaaagtt aatacccagc   2940
gtccgtttaa tggcaactat agcctgttta aatgcaacaa atgtggcatc cagctgaaca   3000
gcgattataa tgcaagcatc aacattgcga aaaagggcct gaaaattccg aatagccacct  3060
aataacattg gaagtggata acggatccgc gatcgcgccg tgccacctgg tggccggccg   3120
gtaccacgcg tgcgcgctga tccggctgct aacaaagccc gaaaggaagc tgagttggct   3180
gctgccaccg ctgagcaata actagcataa ccccttgggg cctctaaacg ggtcttgagg   3240
ggttttttgc tgaaaggagg aactatacc ggatatccac aggacgggtg tggtcgccat    3300
gatcgcgtag tcgatagtgg ctccaagtag cgaagcgagc gaagcgagc ggcggccaaa    3360
gcggtcggac agtgctccga gaacgggtgc gcatagaaat tgcatcaacg catatagcgc   3420
tagcagcacg ccatagtgac tggcgatgct gtcggaatgg acgatatccc gcaagaggcc   3480
cggcagtacc ggcataacca agcctatgcc tacagcatcc agggtgacgg tgccgaggat   3540
gacgatgagc gcattgttag atttcataca cggtgcctga ctgcgttagc aatttaactg   3600
tgataaacta ccgcattaaa gcttatcgat gataagctgt caaacatgag aattcttgaa   3660
gacgaaaggg cctcgtgata cgcctatttt tataggttaa tgtcatgata ataatggttt    3720
cttagacgtc aggtggcact tttcgggaa atgtgcgcgg aacccctatt tgtttatttt     3780
tctaaataca ttcaaatatg tatccgctca tgagacaata accctgataa atgcttcaat   3840
aacattgaaa aaggaagagt atgagtattc aacatttccg tgtcgccctt attccctttt   3900
ttgcggcatt ttgccttcct gttttgctc acccagaaac gctggtgaaa gtaaaagatg     3960
ctgaagatca gttgggtgca cgagtgggtt acatcgaact ggatctcaac agcggtaaga   4020
tccttgagag ttttcgcccc gaagaacgtt ttccaatgat gagcactttt aaagttctgc   4080
tatgtggcgc ggtattatcc cgtgttgacg ccgggcaaga gcaactcggt cgccgcatac   4140
actattctca gaatgacttg gttgagtact caccagtcac agaaaagcat cttacgggatg  4200
gcatgacagt aagagaatta tgcagtgctg ccataaccat gagtgataac actgcggcca   4260
acttacttct gacaacgatc ggaggaccga aggagctaac cgcttttttg cacaacatgg    4320
gggatcatgt aactcgcctt gatcgttggg aaccggagct gaatgaagcc ataccaaacg   4380
acgagcgtga ccacacgatg cctgcagcaa tggcaacaac gttgcgcaaa ctattaactg   4440
gcgaactact tactctagct tcccggcaac aattaataga ctggatggag gcggataaag   4500
ttgcaggacc acttctgcgc tcggcccttc cggctggctg gtttattgct gataaatctg   4560
gagccggtga gcgtgggtct cgcggtatca ttgcagcact ggggccagat ggtaagccct    4620
cccgtatcgt agttatctac acgacgggga gtcaggcaac tatggatgaa cgaaatagac   4680
agatcgctga gataggtgcc tcactgatta gcattggta actgtcagac caagtttact    4740
catatatact ttagattgat ttaaaacttc atttttaatt taaaaggatc taggtgaaga   4800
tcctttttga taatctcatg accaaaatcc cttaacgtga gttttcgttc cactgagcgt   4860
cagaccccgt agaaaagatc aaaggatctt cttgagatcc ttttttttctg cgcgtaatct   4920
gctgcttgca acaaaaaaa ccaccgctac cagcggtggt ttgtttgccg gatcaagagc    4980
taccaactct ttttccgaag gtaactggct tcagcagagc gcagatacca aatactgtcc   5040
ttctagtgta gccgtagtta ggccaccact tcaagaactc tgtagcaccg cctacatacc   5100
tcgctctgct aatcctgtta ccagtggctg ctgccagtgg cgataagtcg tgtcttaccg   5160
ggttggactc aagacgatag ttaccggata aggcgcagcg gtcgggctga acggggggtt   5220
cgtgcacaca gcccagcttg gagcgaacga cctacaccga actgagatac ctacagcgtg   5280
agctatgaga aagcgccacg cttcccgaag ggagaaaggc ggacaggtat ccggtaagcg   5340
gcagggtcgg aacaggagag cgcacgaggg agcttccagg gggaaacgcc tggtatcttt   5400
atagtcctgt cgggtttcgc cacctctgac ttgagcgtcg attttgtga tgctcgtcag    5460
gggggcggag cctatggaaa aacgccagca acgcggcctt tttacggttc ctggccttt    5520
gctggccttt tgctcacatg ttctttcctg cgttatcccc tgattctgtg ataaccgta    5580
ttaccgcctt tgagtgagct gataccgctc gccgcagccg aacgaccgag cgcagcgagt   5640
cagtgagcga ggaagcggaa gagcgcctga tgcggtattt tctccttacg catctgtgcg   5700
gtatttcaca ccgcaatggt gcactctcag tacaatctgc tctgatgccg catagttaag   5760
ccagtataca ctccgctatc gctacgtgac tgggtcatgg ctgcgccccg acacccgcca   5820
acacccgctg acgcgccctg acgggcttgt ctgctcccgg catccgctta cagacaagct   5880
gtgaccgtct ccgggagctg catgtgtcag aggttttcac cgtcatcacc gaaacgcgcg   5940
aggcagctgc ggtaaagctc atcagcgtgg tcgtgaagcg attcacagat gtctgcctgt   6000
tcatccgcgt ccagctcgtt gagtttctcc agaagcgtta atgtctggct tctgataaag   6060
cgggccatgt taagggcggt tttttcctgt ttggtcactg atgcctccgt gtaagggga    6120
tttctgttca tgggggtaat gataccgatg aaacgagaga ggatgctcac gatacgggtt   6180
actgatgatg aacatgcccg gttactggaa cgttgtgagg gtaaacaact ggcggtatgg   6240
atgcggcggg accagagaaa aatcactcag ggtcaatgcc agcgcttcgt taatacagat   6300
gtaggtgttc cacagggtag ccagcagcat cctgcgatgc agatccggaa cataatggtg   6360
cagggcgctg acttccgcgt ttccagactt tacgaaacac ggaaaccgaa gaccattcat   6420
gttgttgctc aggtcgcaga cgttttgcag cagcagtcgc ttcacgttcg ctcgcgtatc   6480
ggtgattcat tctgctaacc agtaaggcaa ccccgccagc ctagccgggt cctcaacgac   6540
```

| | | | | |
|---|---|---|---|---|
| aggagcacga | tcatgcgcac | ccgtggccag | gacccaacgc | tgcccgagat | gcgccgcgtg | 6600 |
| cggctgctgg | agatggcgga | cgcgatggat | atgttctgcc | aagggttggt | ttgcgcattc | 6660 |
| acagttctcc | gcaagaattg | attggctcca | attcttggag | tggtgaatcc | gttagcgagg | 6720 |
| tgccgccggc | ttccattcag | gtcgaggtgg | cccggctcca | tgcaccgcga | cgcaacgcgg | 6780 |
| ggaggcagac | aaggtatagg | gcggcgccta | caatccatgc | caacccgttc | catgtgctcg | 6840 |
| ccgaggcggc | ataaatcgcc | gtgacgatca | gcggtccaat | gatcgaagtt | aggctggtaa | 6900 |
| gagccgcgag | cgatccttga | agctgtccct | gatggtcgtc | atctacctgc | ctggacagca | 6960 |
| tggcctgcaa | cgcgggcatc | ccgatgccgc | cggaagcgag | aagaatcata | atggggaagg | 7020 |
| ccatccagcc | tcgcgtcgcg | aacgccagca | agacgtagcc | cagcgcgtcg | gccgccatgc | 7080 |
| cggcgataat | ggcctgcttc | tcgccgaaac | gtttggtggc | gggaccagtg | acgaaggctt | 7140 |
| gagcgagggc | gtgcaagatt | ccgaataccg | caagcgacag | gccgatcatc | gtcgcgctcc | 7200 |
| agcgaaagcg | gtcctcgccg | aaaatgaccc | agagcgctgc | cggcacctgt | cctacgagtt | 7260 |
| gcatgataaa | gaagacagtc | ataagtgcgg | cgacgatagt | catgccccgc | gcccaccgga | 7320 |
| aggagctgac | tgggttgaag | gctctcaagg | gcatcggtcg | acgctctccc | ttatgcgact | 7380 |
| cctgcattag | gaagcagccc | agtagtaggg | tgaggccgtt | gagcaccgcc | gccgcaagga | 7440 |
| atggtgcatg | caaggagatg | gcgcccaaca | gtcccccggc | cacggggcct | gccaccatac | 7500 |
| ccacgccgaa | acaagcgctc | atgagcccga | agtggcgagc | ccgatcttcc | ccatcggtga | 7560 |
| tgtcggcgat | ataggcgcca | | | | | 7580 |

```
SEQ ID NO: 364         moltype = DNA  length = 4715
FEATURE                Location/Qualifiers
misc_feature           1..4715
                       note = Synthetic sequence
source                 1..4715
                       mol_type = other DNA
                       organism = synthetic construct
SEQUENCE: 364
```

| | | | | | | |
|---|---|---|---|---|---|---|
| atcgttgata | gagttatttt | accactccct | atcagtgata | gagaaaagaa | ttcaaaagat | 60 |
| ctaaagagga | gaaaggatct | atggaagaaa | gcattattac | cggtgtgaaa | ttcaaactgc | 120 |
| gcatcgataa | agaaaccacc | aaaaaactga | acgagtactt | cggcaaagcaa | | 180 |
| ttaacttcgc | cgtgaagatc | attcagaaag | aactggcaga | tgatcgtttt | gcaggtaaag | 240 |
| caaaactgga | ccagaataaa | aacccgatcc | tggatgaaaa | cggcaaaaaa | atctatgaat | 300 |
| tcccggatga | attttgcagc | tgtggtaaac | aggttaacaa | gtacgttaac | aacaaaccgt | 360 |
| tttgccaaga | gtgctataaa | atccgcttta | ccgaaaatgg | tattcgcaaa | cgtatgtata | 420 |
| gcgccaaagg | tcgtaaagcc | gaacataaaa | tcaatatcct | gaacagcacc | aacaagatca | 480 |
| gcaaaaccca | tttaactat | gccattcgcg | aagccttcat | tctggataaa | agcatcaaaa | 540 |
| agcagcgcaa | aaaacgtaat | gaacgtctgc | gtgaaagtaa | aaaacgtctg | cagcagttta | 600 |
| tcgatatgcg | tgatggtaaa | cgtgaaattt | gcccgaccat | taaaggtcag | aaagtggatc | 660 |
| gttttattca | tccgagctgg | atcaccaaag | ataaaaagct | ggaagatttt | cgcggttata | 720 |
| ccctgagcat | tatcaacagc | aaaattaaga | ttctggatcg | caacatcaaa | cgcgaagaaa | 780 |
| aaagcctgaa | agaaaaaggc | cagatcatct | ttaaagccaa | acgtctgatg | ctggataaat | 840 |
| ccattcgttt | tgttggtgat | cgcaaagtgc | tgtttacaat | tagtaaaacc | ctgccgaaag | 900 |
| agtatgaact | ggatctgccg | agcaagaaa | aacggctgga | ttggctgaaa | gagaagatca | 960 |
| agattatcaa | gaaccagaaa | ccgaaatatg | cctatctgct | gcgcaaaaac | attgagagcg | 1020 |
| aaaaaaaacc | gaactatgag | tactatctgc | agtacaccct | ggaaattaaa | ccggaactga | 1080 |
| aagatttta | tgatggtgcc | attggtattg | accgtgcat | taatcatatt | gccgtttgca | 1140 |
| cctttattag | caacgatggt | aaagttaccc | ctccgaaatt | tttcagcagc | ggtgaaattc | 1200 |
| tgcgtctgaa | aaatctgcag | aaagagcgtg | atcgctttct | gctgcgtaaa | cacaacaaaa | 1260 |
| atcgcaaaaa | aggcaacatg | cgcgtgatcg | aaaacaaaat | caatctgatc | ctgcaccgtt | 1320 |
| atagcaagca | gattgttgat | atggccaaaa | agctgaatgc | cagcattgtt | tttgaagaac | 1380 |
| tgggtcgtat | tggtaaaagc | cgcaccaaaa | tgaaaaaacg | ccagcgttat | aaactgagcc | 1440 |
| tgttcatctt | caagaaactg | agcgatctgg | ttgattacaa | aagccgtcgt | gaaggtattc | 1500 |
| gtgttaccta | tgttccgcct | gaatatacca | gcaaagaatg | tagccattgc | ggtgaaaaag | 1560 |
| ttaatacccca | gcgtccgttt | aatggcaact | atagcctgtt | taaatgcaac | aaatgtggca | 1620 |
| tccagctgaa | cagcgattat | aatgcaagca | tcaacattgc | gaaaaaggcc | ctgaaaattc | 1680 |
| cgaatagcac | ctaataatgt | tggttaagcc | acaatatgga | atattgttct | tatgcacagt | 1740 |
| attgacttaa | attaataatc | ttcgaaggct | atatgcggaa | gatttggcgt | tgttgtaacg | 1800 |
| caataagggg | taaccctgaa | aaggtttgaa | atcatataaa | cctagtttta | tttgagttta | 1860 |
| ggctcagata | aatgaacag | accaatcttt | aattccgttc | tgatttaaaa | aatcagaatc | 1920 |
| tcttaataaa | tagtattaca | aaaagtgtac | attccaaaat | ccgaaagcag | aattgaccttt | 1980 |
| tttaagccta | aaaaagccaa | atttcaaggc | tctttcatac | tcagaacaaa | gggattaagg | 2040 |
| aatgcaacta | ccttacaccg | cttgcgaaag | ttgtcagaag | ataatctttc | atactcagaa | 2100 |
| caaagggatt | aaggaatgca | actatcttat | ccatttcttg | acatcaaatt | ttcttgcagc | 2160 |
| atctgaattg | cttaattgct | ttccttgctt | cagcaggaaa | tagccaagat | tttccagttc | 2220 |
| tgctggcgtt | attgcaagca | cggggatttt | gtgcttgctg | tagattttgt | tcttcaggac | 2280 |
| cttctttttc | catgctagag | tcacactggc | tcaccttcgg | gtgggccttt | ctgcgtttat | 2340 |
| acctaggat | atattccgct | tcctcgctca | ctgactcgct | acgctcggtc | gttcgactgc | 2400 |
| ggcgagcgga | aatggcttac | gaacggggcg | gagatttcct | ggaagatgcc | aggaagatac | 2460 |
| ttaacaggga | agtgagaggg | ccgcggcaaa | gccgtttttc | cataggctcc | gcccccctga | 2520 |
| caagcatcac | gaaatctgac | gctcaaatca | gtggtggcga | aacccgacag | gactataaag | 2580 |
| ataccaggcg | tttccccctg | gcggctccct | cgtgcgctct | cctgttcctg | cctttcggtt | 2640 |
| taccggtgtc | attccgctgt | tatggccgcg | tttgtctcat | tccacgcctg | acactcagtt | 2700 |
| ccgggtaggc | agttcgctcc | aagctggact | gtatgcacga | accccccgtt | cagtccgacc | 2760 |
| gctgcgcctt | atccggtaac | tatcgtcttg | agtccaaccc | ggaaagacat | gcaaaagcac | 2820 |
| cactggcagc | agccactggt | aattgattta | gaggagttag | tcttgaagtc | atgcgccggt | 2880 |
| taaggctaaa | ctgaaaggac | aagttttggt | gactgcgctc | ctccaagcca | gttacctcgg | 2940 |
| ttcaaagagt | tggtagctca | gagaaccttc | gaaaaaccgc | cctgcaaggc | ggttttttcg | 3000 |
| ttttcagagc | aagagattac | gcgcagacca | aaacgatctc | aagaagatca | tcttattaat | 3060 |
| cagataaaat | atttctagat | ttcagtgcaa | tttatctctt | caaatgtagc | acctgaagtc | 3120 |

```
agccccatac gatataagtt gttactagtg cttggattct caccaataaa aaacgcccgg  3180
cggcaaccga gcgttctgaa caaatccaga tggagttctg aggtcattac tggatctatc  3240
aacaggagtc caagcgagct cgatatcaaa ttacgcccgc cctgccact  catcgcagta  3300
ctgttgtaat tcattaagca ttctgccgac atggaagcca tcacaaacgg catgatgaac  3360
ctgaatcgcc agcggcatca gcaccttgtc gccttgcgta taatatttgc ccatggtgaa  3420
aacgggggcg aagaagttgt ccatattggc cacgtttaaa tcaaaactgg tgaaactcac  3480
ccagggattg gctgagacga aaaacatatt ctcaataaac cctttaggga aataggccag  3540
gttttcaccg taacacgcca catcttgcga atatatgtgt agaaactgcc ggaaatcgtc  3600
gtggtattca ctccagagcg atgaaaacgt ttcagtttgc tcatggaaaa cggtgtaaca  3660
agggtgaaca ctatcccata tcaccagctc accgtcttc  attgccatac gaaattccgg  3720
atgagcattc atcaggcggg caagaatgtg aataaaggcc ggataaaact tgtgcttatt  3780
tttctttacg gtctttaaaa aggccgtaat atccagctga acgtctggt  tataggtaca  3840
ttgagcaact gactgaaatg cctcaaaatg ttctttacga tgccattggg atatatcaac  3900
ggtggtatat ccagtgattt ttttctccat tttagcttcc ttagctcctg aaaatctcag  3960
taactcaaaa aatacgcccg gtagtgatct tatttcatta tggtgaaagt tggaacctct  4020
tacgtgccga tcaacgtctc attttcgcca gatatcgacg tcttaagacc cactttcaca  4080
tttaagttgt ttttctaatc cgcatatgat caattcaagg ccgaataaga aggctggctc  4140
tgcaccttgg tgatcaaata attcgatagc ttgtcgtaat aatggcggca tactatcagt  4200
agtaggtgtt tcccttttctt ctttagcgac ttgatgctct tgatcttcca atacgcaacc  4260
taaagtaaaa tgcccacag  cgctgagtgc atataatgca ttctctagtg aaaaaccttg  4320
ttggcataaa aaggctaatt gattttcgag agtttcatac tgtttttctg taggccgtgt  4380
acctaaatgt acttttgctc catcgcgatg acttagtaaa gcacatctaa aactttttagc  4440
gttattacgt aaaaaatctt gccagctttc cccttctaaa gggcaaaagt gagtatggtg  4500
cctatctaac atctcaatgg ctaaggcgtg agcaaagcc  cgcttatttt ttacatgcca  4560
atacaatgta ggctgctcta cacctagctt ctgggcgagt ttacggttg  ttaaaccttc  4620
gattccgacc tcattaagca gctctaatgc gctgttaatc actttacttt tatctaatct  4680
agacatcatt aattcctaat ttttgttgac actct                             4715

SEQ ID NO: 365           moltype = DNA  length = 4670
FEATURE                  Location/Qualifiers
misc_feature             1..4670
                         note = Synthetic sequence
source                   1..4670
                         mol_type = other DNA
                         organism = synthetic construct
SEQUENCE: 365
taattcctaa tttttgttga cactctatcg ttgatagagt tatttaccca ctccctatca  60
gtgatagaga aagaattca  aaagatctaa agaggagaaa ggatctatga aatctcacca  120
tcaccatcac catgaaaacc tgtacttcca atccaatatt ggaagtggaa tggccaaaaa  180
caccattacc aaaacactga aactgcgtat tgtgcgtccg tataatagcg cagaagtgga  240
aaaaattgtt gccgacgaaa aaaacaaccg cgaaaaaatc gcactggaaa agaacaaaga  300
caaagtgaaa gaagcctgca gcaaacatct gaaagttgca gcatattgta ccacacaggt  360
tgaacgtaat gcatgcctgt tttgtaaagc acgtaaactg gatgacaaat tctaccaaaa  420
actgcgtggt cagttttccgg atgcagtttt ttggcaagaa atcagcgaaa ttttttcgcca  480
gctgcagaaa caggcagcag aaatctataa tcagagcctg atcgaactgt actacgagat  540
ttttatcaaa ggcaaaggta ttgcaaatgc cagcagcgtt gaacattatc tgagtgatgt  600
ttgttatacc cgtgcagcag aactgtttaa aaacgcaagcg gtctgcgtag  660
caaaatcaaa agcaatttc  gtctgaaaga actgaaaaac atgaaaagtg gtctgccgac  720
caccaaaagc gataatttc  cgattccgct ggttaaacag aaaggtggtc agtataccgg  780
ttttgaaatt agcaatcata atagcgactt catcatcaag attccgtttg gtcgttggca  840
ggtcaaaaaa gagattgata aatatcgtcc gtgggagaaa tttgactttg aacaggttca  900
gaaaagcccg aaaccgatta gcctgctgct gagcaccag  cgtcgtaaac gtaataaagg  960
ttggagcaaa gatgaaggca ccgaagccga aatcaaaaaa gttatgaatg gcgattatca  1020
gaccagctac attgaagtta acgtggcag  caaaatcggt gaaaaagcg  catggatgct  1080
gaatctgagc attgatgttc cgaaaattga taaaggtgtg gatcgagca  ttattggtgg  1140
tattgatgtt ggtgttaaat caccgctggt ttgcgcaatt aacaatgcat ttagccgtta  1200
tagcatcagc gataacgacc tgtttcactt caacaagaaa atgttgcac  gtcgtcgtat  1260
cctgctgaaa aaaaccgtc  ataaacgtgc aggtcatggt gcaaaaaca  aactgaaacc  1320
gatcaccatt ctgaccgaaa aaagtgaacg ttttcgcaaa aagctgattg aacgttggg   1380
atgtgaaatc gcggatttct tcattaaaaa caaagttggc accgtgcaga tggaaaatct  1440
ggaaagcatg aaacgtaaag aggacagcta ttttaacatt cgcctgcgtg gcttttggcc  1500
gtatgcagaa atgcagaaca aaatcgaatt caaactgaag cagtatggca tcgaaattcg  1560
taaagttgca ccgaataata ccagcaaaac ctgtagcaaa tgtggccatc tgaacaacta  1620
tttcaacttc gagtaccgca agaaaaacaa attcccgcac tttaaatgcg aaaaatgcaa  1680
cttcaaagaa aacgccgatt ataatgcagc cctgaatatt tcaaacccga actgaaaag   1740
caccaaagag gaaccgtaaa tatttatact ttattatcct tcattgacaa aaatgagaat  1800
gttatcccag ataacatttg atgtacacag attcacactt cactgataaa gtggagaacc  1860
gcttcaccaa aagctgtccc ttaggggatt agaacttgag tgaaggtggg ctgcttgcat  1920
cagcctaatg tcgagaagtg cttcttcgg  aaagtactc  tcgaaacaaa ttcatttttc  1980
ctctccaatt ctgcacaaaa aaaggtgagt cctataaaac cggcgtgcag aacgccggct  2040
caccttttttt cttcattcga ttttatgctt aaaagccgta aaaacgcgga attcggcgcc  2100
gttgcagaac ccgaatagac gaatgaagga atgcaactac cttacccgc  ttgcgaaagt  2160
tgtcagaaga taatcttgca gaacccgaat agacgaatga aggaatgcaa tcttgacaga  2220
gcccgattgc gttatctcca ggagaaacat ataaagcat  caaccgctga tcggactaga  2280
gtcacactgg ctcaccttcg ggtgggcctt tctgcgtta  acctaggga  tatattccgc  2340
ttcctcgctc actgactcgc tacgctcggt cgttcgactg cggcgagcgg aaatggctta  2400
cgaacgggc  ggagatttcc tggaagatgc aggaagata  cttaacaggg aagtgagagg  2460
gccgcggcaa agccgttttt ccataggctc cgccccctg  acaagcatca cgaaatctga  2520
cgctcaaatc agtggtggcg aaacccgaca ggactataaa gataccaggc gtttccccct  2580
```

```
ggcggctccc tcgtgcgctc tcctgttcct gcctttcggt ttaccggtgt cattccgctg   2640
ttatggccgc gtttgtctca ttccacgcct gacactcagt tccgggtagg cagttcgctc   2700
caagctggac tgtatgcacg aaccccccgt tcagtccgac cgctgcgcct tatccggtaa   2760
ctatcgtctt gagtccaacc cggaaagaca tgcaaaagca ccactggcag cagccactgg   2820
taattgattt agaggagtta gtcttgaagt catgcgccgg ttaaggctaa actgaaagga   2880
caagttttgg tgactgcgct cctccaagcc agttacctcg gttcaaagag ttggtagctc   2940
agagaaacctt cgaaaaaccg ccctgcaagg cggtttttc gttttcagag caagagatta   3000
cgcgcagacc aaaacgatct caagaagatc atcttattaa tcagataaaa tatttctaga   3060
tttcagtgca atttatctct tcaaatgtag cacctgaagt cagccccata cgatataagt   3120
tgttactagt gcttggattc tcaccaataa aaaacgcccg gcggcaaccg agcgttctga   3180
acaaatccag atggagttct gaggtcatta ctggatctat caacaggagt ccaagcgagc   3240
tcgatatcaa attcgccccc gccctgccac tcatcgcagt actgttgtaa ttcattaagc   3300
attctgccga catggaagcc atcacaaacg gcatgatgaa cctgaatcgc cagcggcatc   3360
agcaccttgt cgccttgcgt ataatatttg cccatggtga aacgggggc gaagaagtta   3420
tccatattgg ccacgtttaa atcaaaactg gtgaaactca cccagggatt ggctgagacg   3480
aaaaacatat tctcaataaa ccctttaggg aaataggcca ggttttcacc gtaacacgcc   3540
acatcttgcg aatatatgtg tagaaactgc cggaaatcgt cgtggtattc actccagagc   3600
gatgaaaacg tttcagtttg tcatggaaa acggtgtaac aagggtgaac actatcccat   3660
atcaccagct caccgtcttt cattgccata cgaaattccg gatgagcatt catcaggcgg   3720
gcaagaatgt gaataaaggc cggataaaac ttgtgcttat ttttcttac ggtctttaaa   3780
aaggccgtaa tatccagctg aacggtctgg ttataggtac attgagcaac tgactgaaat   3840
gcctcaaaat gttcttacg atgccattgg gatatatcaa cggtggtata tccagtgatt   3900
tttttctcca ttttagcttc cttagctcct gaaaatctcg ataactcaaa aaatacgccc   3960
ggtagtgatc ttatttcatt atggtgaaag ttggaacctc ttacgtgccg atcaacgtct   4020
catttttcgcc agatatcgac gtcttaagac ccacttccac atttaagttg ttttctaat   4080
ccgcatatga tcaattcaag gccgaataag aaggctggct ctgcaccttg gtgatcaaat   4140
aattcgatag cttgtcgtaa taatggcggc atactatcag tagtaggtgt ttccctttct   4200
tctttagcga cttgatgctc ttgatcttcc aatacgcaac ctaaagtaaa atgccccaca   4260
gcgctgagtg catataatgc attctctagt gaaaaacctt gttggcataa aaaggctaat   4320
tgattttcga gagtttcata ctgtttttct gtaggccggta tacctaaatg tactttttgat   4380
ccatcgcgat gacttagtaa agcacatcta aaacttttag cgttattacg taaaaaaatct   4440
tgccagcttt ccccttctaa agggcaaaag tgagtatggt gcctatctaa catctcaatg   4500
gctaaggcgt cgagcaaagc ccgcttattt tttacatgcc aatacaatgt aggctgctct   4560
acacctagct tctgggcgag tttacgggtt gttaaacctt cgattccgac ctcattaagc   4620
agctctaatg cgctgttaat cactttactt ttatctaatc tagacatcat             4670
```

| SEQ ID NO: 366 | moltype = DNA length = 4607 |
|---|---|
| FEATURE | Location/Qualifiers |
| misc_feature | 1..4607 |
| | note = Synthetic sequence |
| source | 1..4607 |
| | mol_type = other DNA |
| | organism = synthetic construct |

SEQUENCE: 366
```
ttacttttat ctaatctaga catcattaat tcctaatttt tgttgacact ctatcgttga     60
tagagttatt ttaccactcc ctatcagtga tagagaaaag aattcaaaag atctaaagag    120
gagaaaggat ctatggccaa aaacaccatt accaaaacac tgaaactgcg tattgtgcgt    180
ccgtataata gcgcagaagt ggaaaaaatt gttgccgacg aaaaaaacaa ccgcgaaaaa    240
atcgcactgg aaaagaacaa agacaaagtg aagaagcct gcagcaaaca tctgaaagtt    300
gcagcatatt gtaccacaca ggttgaacgt aatgcatgcc tgtttgtaa agcacgtaaa    360
ctggatgaca aattctacca aaaactgcgt ggtcagtttc cggatgcagt ttttggcgaa    420
gaaatcagcg aaattttcg ccagctgcag aaacaggcag cagaaatcta taatcagagc    480
ctgatcgaac tgtactacga gatttttatc aaaggcaaag gtattgcaaa tgccagcagc    540
gttgaacatt atctgagtga tgtttgttat acccgtgcag cagaactgtt taaaaacgca    600
gcaattgcaa gcggtctgcg tagcaaaatc aaaagcaatt ttcgtctgaa agaactgaaa    660
aacatgaaaa gtggtctgcc gaccaccaaa agcgataatt ttccgattcc gctggttaaa    720
cagaaaggtg gtcagtatac cggttttgaa attagcaatc ataatagcga cttcatcatc    780
aagattccgt ttggtcgttg gcaggtcaaa aagagattg ataaatatcg tccgtgggag    840
aaatttgact ttgaacaggt tcagaaaagc ccgaaaccga ttagcctgct gctgagcacc    900
cagcgtcgta aacgtaataa aggttggagc aaagatgaag gcaccgaagc cgaaatcaaa    960
aaagttatga atggcgatta tcagaccagc tacattgaag ttaaacgtgg cagcaaaatc   1020
ggtgaaaaaa gcgcatggat gctgaatctg agcattgatg ttccgaaaat tgataaaggt   1080
gtggatccga gcattattgg tggtattgat gttggtgtta aatcaccgct ggtttgcgca   1140
attaacaatg catttagccg ttatagcatc agcgataacg acctgttca cttcaacaag   1200
aaaatgtttg cacgtcgtcg tatcctgctg aaaaaaaacc gtcataaacg tgcaggtcat   1260
ggtgcaaaaa acaaactgaa accgatcacc attctgaccg aaaaaagtga acgttttcgc   1320
aaaaagctga ttgaacgttg gcatgtgaa atcgcggatt tcttcattaa aaacaaagtt   1380
ggcaccgtgc agatggaaaa tctggaaagc atgaaacgta agaggacga ctattttaac   1440
attcgcctgc gtggctttg gccgtatgca gaatgcaga acaaaatcga attcaaactg   1500
aagcagtatg gcatcgaaat tcgtaaagtt gcaccgaata ataccagcaa acctgtagc   1560
aaatgtggcc atctgaacaa ctatttcaac ttcgagtacc gcaagaaaaa caaattcccg   1620
cactttaaat gcgaaaatg caacttcaaa gaaacgccg attataatgc agccctgaat   1680
atttcaaacc cgaaactgaa aagcaccaaa gaggaaccgt aaatatttat actttattat   1740
cctttattga caaaatgag aatgttatcc cagataaca ttgatgtaca cagattcaca   1800
cttcactgat aaagtggaga accgcttcac caaaagctgt cccttaggg attagaactt   1860
gagtgaaggt gggctgcttg catcagccta atgtcgagaa gtgcttttctt cggaaagtaa   1920
ccctcgaaac aaattcattt ttcctctcca attctgcaca aaaaaggtg agtccttata   1980
aaccggcgtg cagaacgccg gctcaccttt tttcttcatt cgattttatg cttaaaagcc   2040
gtaaaaacgc ggaattcggc gccgttgcag aacccgaata gacgaatgaa ggaatgcaac   2100
```

```
taccttacac cgcttgcgaa agttgtcaga agataatctt gcagaacccg aatagacgaa    2160
tgaaggaatg caatcttgac agagcccgat tgcgttatct ccaggagaaa catataaaag    2220
catcaaccgc tgatcggact agagtcacac tggctcacct tcgggtgggc ctttctgcgt    2280
ttatacctag ggatatattc cgcttcctcg ctcactgact cgctacgctc ggtcgttcga    2340
ctgcggcgag cggaaatggc ttacgaacgg ggcggagatt tcctgaaaga tgccaggaag    2400
atacttaaca gggaagtgag agggccgcgg caaagccgtt tttccatagg ctccgccccc    2460
ctgacaagca tcacgaaatc tgacgctcaa atcagtggtg gcgaacccg acaggactat     2520
aaagatacca ggcgtttccc cctggcggct ccctcgtgcg ctctcctgtt cctgcctttc    2580
ggttaccgg tgtcattccg ctgttatggc cgcgtttgtc tcattccacg cctgacactc     2640
agttccgggt aggcagttcg ctccaagctg gactgtatgc acgaaccccc cgttcagtcc    2700
gaccgctgcg ccttatccgg taactatcgt cttgagtcca acccggaaag acatgcaaaa    2760
gcaccactgg cagcagccac tggtaattga tttagaggag ttagtcttga agtcatgcgc    2820
cggttaaggc taaactgaaa ggacaagttt tggtgactgc gctcctccaa gccagttacc    2880
tcggttcaaa gagttggtag ctcagagaac cttcgaaaaa ccgccctgca aggcggtttc    2940
ttcgttttca gagcaagaga ttacgcgcag accaaaacga tctcaagaag atcatcttat    3000
taatcagata aatatttct agatttcagt gcaatttatc tcttcaaatg tagcacctga     3060
agtcagcccc atacgatata agttgttact agtgcttgga ttctcaccaa taaaaaacgc    3120
ccggcggcaa ccgagcgttc tgaacaaatc cagatggagt tctgaggtca ttactggatc    3180
tatcaacagg agtccaagcg agctcgatat caaattacgc cccgccctgc cactcatcgc    3240
agtactgttg taattcatta agcattctgc cgacatggaa gccatcacaa acggcatgat    3300
gaacctgaat cgccagcggc atcagcacct tgtcgcttg cgtataatat ttgcccatgg     3360
tgaaaacggg ggcgaagaag ttgtccatat tggccacgtt taaatcaaaa ctggtgaaac    3420
tcacccaggg attggctgag acgaaaaaca tattctcaat aaaccctttta gggaaatagg   3480
ccaggttttc accgtaacac gccacatctt gcgaatatat gtgtagaaac tgccggaaat    3540
cgtcgtggta ttcactccag agcgatgaaa acgtttcagt ttgctcatgg aaaacggtgt    3600
aacaagggtg aacactatcc catatcacca gctcaccgtc tttcattgcc atacgaaatt    3660
ccggatgagc attcatcagg cgggcaagaa tgtgaataaa ggccggataa aacttgtgct    3720
tattttctt tacggtcttt aaaaaggccg taatatccag ctgaacggtc tggttatagg     3780
tacattgagc aactgactga aatgcctcaa aatgttcttt acgatgccat gggatatat    3840
caacggtggt atatccagtg attttttttct ccatttttagc ttccttagct cctgaaaatc   3900
tcgataactc aaaaaatacg cccggtagtg atcttatttc attatggtga aagttggaac    3960
ctcttacgtg ccgatcaacg tctcattttc gccagatatc gacgtcttaa gacccacttt    4020
cacatttaag ttgttttttct aatccgcata tgatcaattc aaggccgaat aagaaggctg    4080
gctctgcacc ttggtgatca aataattcga tagctgtcg taataatggc ggctactat     4140
cagtagtagg tgtttccctt tcttctttag cgacttgagt ctcttgatct tccaatacgc    4200
aacctaaagt aaaatgcccc acagcgctga gtgcatataa tgcattctct agtgaaaaac    4260
cttgttggca taaaaggct aattgatttt cgagagtttc atactgtttt tctgtaggcc     4320
gtgtacctaa atgtacttttt gctccatcgc gatgacttag taaagcacat ctaaaacttt   4380
tagcgttatt acgtaaaaaa tcttgccagc tttcccctcc taaagggcaa aagtgagtat    4440
ggtgcctatc taacatctca atggctaagg cgtcgagcaa agcccgctta ttttttacat    4500
gccaatacaa tgtaggctgc tctacaccta gcttctgggc gagtttacgg gttgttaaac    4560
cttcgattcc gacctcatta agcagctcta atgcgctgtt aatcact                  4607
```

SEQ ID NO: 367        moltype = DNA   length = 7556
FEATURE                Location/Qualifiers
misc_feature        1..7556
                        note = Synthetic sequence
source                 1..7556
                        mol_type = other DNA
                        organism = synthetic construct
SEQUENCE: 367

```
acccacgccg aaacaagcgc tcatgagccc gaagtggcga gcccgatctt ccccatcggt    60
gatgtcggcg atataggcgc cagcaaccgc acctgtggcg ccggtgatgc cggccacgat    120
gcgtccggcg tagaggatcg agatctcgat cccgcgaaat taatacgact cactataggg    180
agaccacaac ggtttccctc tagtgccggc tccggagacg tctttaatta agcggccgcc    240
ctgcaggact cgagttctag aaataatttt gtttaactt aagaaggaga tatacatatg      300
aaatcttctc accatcacca tcaccatcac catgttcttt ctat gaaaatcgaa           360
gaaggtaaac tggtaatctg gattaacggc gataaaggct ataacggtct cgctgaagtc    420
ggtaagaaat tcgagaaaga taccggaatt aaagtcaccg ttgagcatcc ggataaactg    480
gaagagaaat tcccacaggt tgcggcaact ggcgatgagc ctgacattat cttctgggca    540
cacgaccgct ttggtggcta cgctcaatct ggcctgttgg ctgaaatcac cccggacaaa    600
gcgttccagg acaagctgta tccgtttacc tgggatgccg tacgttacaa cggcaagctg    660
attgcttacc cgatcgctgt tgaagcgtta tcgctgattt ataacaaaga tctgctgccg    720
aacccgccaa aaacctggga agagatcccg gcgctggata aagaactgaa agcgaaagtt    780
aagagcgcgc tgatgttcaa cctgcaagaa ccgtacttca cctggccgct gattgctgct    840
gacgggggtt atgcgttcaa gtatgaaaac ggcaagtacg acattaaaga cgtgggcgtg    900
gataacgctg gcgcgaaagc gggtctgacc ttcctggttg acctgattaa aaacaaacac    960
atgaatgcag acaccgatta ctccatcgca gaagctgcct ttaataaagg cgaaacagcg    1020
atgaccatca acggcccgtg ggcatggtcc aacatcgata ccagcaaagt gaattatgtc    1080
gtaacggtac tgccgacctt caagggtcaa ccatccaaac cgttcgttgg cgtgctgagc    1140
gcaggtatta acgccgccag tccgaacaaa gagctggcaa agagttcct gaaaactat     1200
ctgctgactg atgaaggtct ggaagcggtt aataaagaca aaccgctggg tgccgtagcg    1260
ctgaagtctt acgaggaaga gttggcgaaa gatccacgta ttgccgccac tatggaaaac    1320
gcccgaaag gtgaaatcat gccgaacatc ccgcagatgt ccgtttctg gtatgccgtg     1380
cgtactgcgc tgatcaacgc cgccagcggt cgtcagactg tcgatgaagc cctgaaagac    1440
gcgcagacta ttcgagctc gaacaacaac aacaataaca ataacaacaa cctcgggatc    1500
gaggaaaacc tgtacttcca atccaatgca atggccaaaa acaccattac caaaacactg    1560
aaactgcgta ttgtgcgtcc gtataatagc gcagaagtgg aaaaaattgt tgccgacgaa    1620
aaaaacaacc gcgaaaaaat cgcactggaa aagaacaaag acaagtgaa agaagcctgc     1680
```

```
agcaaacatc tgaaagttgc agcatattgt accacacagg ttgaacgtaa tgcatgcctg  1740
ttttgtaaag cacgtaaact ggatgacaaa ttctaccaaa aactgcgtgg tcagtttccg  1800
gatgcagttt tttggcaaga aatcagcgaa attttcgcc agctgcagaa acaggcagca  1860
gaaatctata atcagagcct gatcgaactg tactacgaga ttttatcaa aggcaaaggt  1920
attgcaaatg ccagcagcgt tgaacattat ctgagtgatg tttgttatac ccgtgcagca  1980
gaactgttta aaaacgcagc aattgcaagc ggtctgcgta gcaaaatcaa aagcaatttt  2040
cgtctgaaag aactgaaaaa catgaaaagt ggtctgccga ccaccaaaag cgataatttt  2100
ccgattccgc tggttaaaca gaaaggtggt cagtataccg gttttgaaat tagcaatcat  2160
aatagcgact tcatcatcaa gattccgttt ggtcgttggc aggtcaaaaa agagattgat  2220
aaatatcgtc cgtgggagaa atttgacttt gaacaggttc agaaaagccc gaaaccgatt  2280
agcctgctgc tgagcaccca gcgtcgtaaa cgtaataaag gttggagcaa agatgaaggc  2340
accgaagccg aaatcaaaaa agttatgaat ggcgattatc agaccagcta cattgaagtt  2400
aaacgtggca gcaaaatctg tgaaaaaagc gcatggatgc tgaatctgag cattgatgtt  2460
ccgaaaattg ataaaggtgt ggatccgagc attattggtg gtattgatgt tggtgttaaa  2520
tcaccgctgg tttgcgcaat taacaatgca tttagccgtt atagcatcag cgataacgac  2580
ctgtttcact tcaacaagaa aatgtttgca cgtcgtcgta tcctgctgaa aaaaaaccgt  2640
cataaacgtg caggtcatgg tgcaaaaaac aaactgaaac cgatcaccat tctgaccgaa  2700
aaaagtgaac gttttcgcaa aaagctgatt gaacgttggg catgtgaaat cgcggatttc  2760
ttcattaaaa acaaagttgg caccgtgcag atggaaaatc tggaaagcat gaaacgtaaa  2820
gaggacagct atttaacat tcgcctgcgt ggcttttggc cgtatgcaga aatgcagaac  2880
aaaatcgaat tcaaactgaa gcagtatggc atcgaaattc gtaaagttgc accgaataat  2940
accagcaaaa cctgtagcaa atgtggccat ctgaacaact atttcaactt cgagtaccgc  3000
aagaaaaaca aattcccgca ctttaaatgc gaaaaatgca acttcaaaga aaacgccgat  3060
tataatgcag ccctgaatat ttcaaacccg aaactgaaaa gcaccaaaga ggaacgtaa  3120
taacattgga agtggataac ggatccgcga tcgcggcgcg ccacctggtg gccggccggt  3180
accacgcgtg cgcgctgatc cggctgctaa caaagcccga aaggaagctg agttggctgc  3240
tgccaccgct gagcaataac tagcataacc ccttgggggcc tctaaacggg tcttgagggg  3300
tttttttgctg aaaggaggaa ctatatccgg atatccacag gacgggtgtg gtcgccatga  3360
tcgcgtagtc gatagtggct ccaagtagcg aagcgagcag gactgggcgg cggccaaagc  3420
ggtcggacag tgctccgaga acgggtgcgc atagaaattg catcaacgca tatagcgcta  3480
gcagcacgcc atagtgactg gcgatgctgt cggaatggac gatatcccgc aagaggcccg  3540
gcagtaccgg cataaccaag cctatgccta cagcatccag ggtgacggtg ccgaggatga  3600
cgatgagcgc attgttagat ttcatacacg gtgcctgact gcgttagcaa tttaactgtg  3660
ataaactacc gcattaaagc ttatcgatga taagctgtca aacatgagaa ttcttgaaga  3720
cgaaagggcc tcgtgatacg cctatttta taggttaatg tcatgataat aatgtttct  3780
tagacgtcag gtgcactttt cggggaaat gtgcgcggaa cccctatttg ttatttttc  3840
taaatacatt caaatatgta tccgctcatg agacaataac cctgataaat gcttcaataa  3900
cattgaaaaa ggaagagtat gagtattcaa catttccgtg tcgcccttat tcccttttt  3960
gcggcatttt gccttcctgt ttttgctcac ccagaaacgc tggtgaaagt aaaagatgct  4020
gaagatcagt tgggtgcacg agtgggttac atcgaactgg atctcaacag cggtaagatc  4080
cttgagagtt ttcgccccga agaacgtttt ccaatgatga gcacttttaa agttctgcta  4140
tgtggcgcgg tattatcccg tgttgacgcc gggcaagagc aactcggtcg ccgcatacac  4200
tattctcaga atgacttggt tgagtactca ccagtcacag aaaagcatct tacggatggc  4260
atgacagtaa gagaattatg cagtgctgcc ataaccatga gtgataacac tgcggccaac  4320
ttacttctga caacgatcgg aggaccgaag gagctaaccg cttttttgca caacatgggg  4380
gatcatgtaa ctcgccttga tcgttgggaa ccggagctga tgaagccat accaaacgac  4440
gagcgtgaca ccacgatgcc tgcagcaatg gcaacaact tgcgcaaact attaactggc  4500
gaactactta ctctagcttc ccggcaacaa ttaatagact ggatggaggc ggataaagtt  4560
gcaggaccac ttctgcgctc ggcccttccg gctggctggt ttattgctga taaatctgga  4620
gccggtgagc gtgggtctcg cggtatcatt gcagcactgg ggccagatgg taagccctcc  4680
cgtatcgtag ttatctacac gacggggagt caggcaacta tggatgaacg aaatagacag  4740
atcgctgaga taggtgcctc actgattaag cattggtaac tgtcagacca gttactca  4800
tatatacttt agattgattt aaaacttcat ttttaattta aaaggatcta ggtgaagatc  4860
cttttttgata atctcatgac caaaatccct taacgtgagt tttcgttcca ctgagcgtca  4920
gacccgtag aaaagatcaa aggatcttct tgagatcctt tttttctgcg cgtaatctgc  4980
tgcttgcaaa caaaaaaacc accgctacca gcggtggttt gtttgccagt tcaagagcta  5040
ccaactcttt ttccgaaggt aactggcttc agcagagcgc agataccaaa tactgtcctt  5100
ctagtgtagc cgtagttagg ccaccacttc aagaactctg tagcaccgcc tacatacctc  5160
gctctgctaa tcctgttacc agtggctgct gccagtggcg ataagtcgtg tcttaccggg  5220
ttggactcaa gacgatagtt accggataag gcgcagcggt cgggctgaac ggggggttcg  5280
tgcacacagc ccagcttgga gcgaacgacc tacaccgaac tgagatacct acagcgtgag  5340
ctatgagaaa gcgccacgct tcccgaaggg agaaaggcgg acaggtatcc ggtaagcggc  5400
agggtcggaa caggagagcg cacgagggag cttccagggg gaaacgcctg gtatctttat  5460
agtcctgtcg ggtttcgcca cctctgactt gagcgtcgat ttttgtgatg ctcgtcaggg  5520
gggcggagcc tatggaaaaa cgccagcaac gcggcctttt tacggttcct ggccttttgc  5580
tggcctttg ctcacatgtt ctttcctgcg ttatccctg attctgtgga taaccgtatt  5640
accgcctttg agtgagctga taccgctcgc cgcagccgaa cgaccgagcg cagcgagtca  5700
gtgagcgagg aagcggaaga gcgcctgatg cggtattttc tccttacgca tctgtgcggt  5760
atttcacacc gcaatggtgc actctcagta caatctgctc tgatgccgca tagttaagcc  5820
agtatacact ccgctatcgc tacgtgactg gtcatggct gcgccccgac acccgccaac  5880
acccgctgac gcgccctgac gggcttgtct gctcccggca tccgcttaca gacaagctgt  5940
gaccgtctcc gggagctgca tgtgtcagag gttttcaccg tcatcaccga aacgcgcgag  6000
gcagctgcgg taaagctcat cagcgtggtc gtgaagcgat tcacagatgt ctgcctgttc  6060
atccgcgtcc agctcgttga gtttctccag aagcgttaat gtctggcttc tgataaagcg  6120
ggccatgtta agggcggttt ttcctgtttt ggtcactgat gcctccgtgt aagggggatt  6180
tctgttcatg ggggtaatga taccgatgaa acgagagagg atgctcacga tacgggttac  6240
tgatgatgaa catgcccggt tactggaacg ttgtgagggt aaacaactgg cggtatggat  6300
gcggcggac cagagaaaaa tcactcaggg tcaatgccac cgcttcgtta atacagatgt  6360
aggtgttcca caggggtagcc agcagcatcc tgcgatgcag atccggaaca taatggtgca  6420
```

```
gggcgctgac ttccgcgttt ccagacttta cgaaacacgg aaaccgaaga ccattcatgt  6480
tgttgctcag gtcgcagacg ttttgcagca gcagtcgctt cacgttcgct cgcgtatcgg  6540
tgattcattc tgctaaccag taaggcaacc ccgccagcct agccgggtcc tcaacgacag  6600
gagcacgatc atgcgcaccc gtggccagga cccaacgctg cccgagatgc gccgcgtgcg  6660
gctgctggag atggcggacg cgatggatat gttctgcaa gggttggttt gcgcattcac  6720
agttctccgc aagaattgat tggctccaat tcttggagtg gtgaatccgt tagcgaggtg  6780
ccgccggctt ccattcaggt cgaggtggcc cggctccatg caccgcgacg caacgcgggg  6840
aggcagacaa ggtatagggc ggcgcctaca atccatgcca acccgttcca tgtgctcgcc  6900
gaggcggcat aaatcgccgt gacgatcagc ggtccaatga tcgaagttag gctggtaaga  6960
gccgcgagcg atccttgaag ctgtccctga tggtcgtcat ctacctgcct ggacagcatg  7020
gcctgcaacg cgggcatccc gatgccgccg gaagcgagaa gaatcataat ggggaaggcc  7080
atccagcctc gcgtcgcgaa cgccagcaag acgtagccca gcgcgtcggc cgccatgccg  7140
gcgataatgg cctgcttctc gccgaaacgt ttggtggcgg gaccagtgac gaaggcttga  7200
gcgagggcgt gcaagattcc gaataccgca agcgacaggc cgatcatcgt cgcgctccag  7260
cgaaagcggt cctcgccgaa aatgacccag agcgctgccg gcacctgtcc tacgagttgc  7320
atgataaaga agacagtcat aagtgcggcg acgatagtca tgccccgcgc ccaccggaag  7380
gagctgactg ggttgaaggc tctcaagggc atcggtcgac gctctccctt atgcgactcc  7440
tgcattagga agcagcccag tagtaggttg aggccgttga gcaccgccgc cgcaaggaat  7500
ggtgcatgca aggagatggc gcccaacagt cccccggcca cggggcctgc caccat     7556

SEQ ID NO: 368         moltype = DNA  length = 30
FEATURE                Location/Qualifiers
misc_feature           1..30
                       note = Synthetic sequence
source                 1..30
                       mol_type = other DNA
                       organism = synthetic construct
SEQUENCE: 368
ttcatttgag cattaaatgt caagttctgc                                    30

SEQ ID NO: 369         moltype = DNA  length = 30
FEATURE                Location/Qualifiers
misc_feature           1..30
                       note = Synthetic sequence
source                 1..30
                       mol_type = other DNA
                       organism = synthetic construct
SEQUENCE: 369
ttcatttgag cattaagtgt caagttctgc                                    30

SEQ ID NO: 370         moltype = DNA  length = 21
FEATURE                Location/Qualifiers
misc_feature           1..21
                       note = Synthetic sequence
source                 1..21
                       mol_type = other DNA
                       organism = synthetic construct
SEQUENCE: 370
aaactcgtaa ttcacagttc a                                             21

SEQ ID NO: 371         moltype = DNA  length = 10
FEATURE                Location/Qualifiers
misc_feature           1..10
                       note = Synthetic sequence
source                 1..10
                       mol_type = other DNA
                       organism = synthetic construct
SEQUENCE: 371
tatatatata                                                          10

SEQ ID NO: 372         moltype =      length =
SEQUENCE: 372
000

SEQ ID NO: 373         moltype =      length =
SEQUENCE: 373
000
```

CasZ COMPOSITIONS AND METHODS OF USE

CROSS REFERENCE

This application is a continuation of U.S. application Ser. No. 17/935,521, filed on Sep. 26, 2022,now abandoned, which is a continuation of U.S. application Ser. No. 16/896, 711 filed on Jun. 9, 2020, now U.S. Pat. No. 11,453,866; which is a continuation of U.S. application Ser. No. 16/694, 720 filed on Nov. 25,2019, now abandoned, which is a continuation of PCT/US2018/058545 filed on Oct. 31, 2018; which claims the benefit of U.S. Provisional Patent Application No. 62/580,395, filed Nov. 1, 2017,which applications are incorporated herein by reference in their entirety.

A Sequence Listing is provided herewith as a Sequence Listing XML, "BERK 374CON7_SEQ_LIST.xml" created on Dec. 18, 2023 and having a size of 552,160 bytes. The contents of the Sequence Listing XML are incorporated herein by reference in their entirety.

INTRODUCTION

The CRISPR-Cas system, an example of a pathway that was unknown to science prior to the DNA sequencing era, is now understood to confer bacteria and archaea with acquired immunity against phage and viruses. Intensive research has uncovered the biochemistry of this system. CRISPR-Cas systems consist of Cas proteins, which are involved in acquisition, targeting and cleavage of foreign DNA or RNA, and a CRISPR array, which includes direct repeats flanking short spacer sequences that guide Cas proteins to their targets. Class 2 CRISPR-Cas are streamlined versions in which a single Cas protein bound to RNA is responsible for binding to and cleavage of a targeted sequence. The programmable nature of these minimal systems has facilitated their use as a versatile technology that is revolutionizing the field of genome manipulation.

SUMMARY

The present disclosure provides compositions and methods that include one or more of: (1) a "CasZ" protein (also referred to as a CasZ polypeptide), a nucleic acid encoding the CasZ protein, and/or a modified host cell comprising the CasZ protein (and/or a nucleic acid encoding the same); (2) a CasZ guide RNA that binds to and provides sequence specificity to the CasZ protein, a nucleic acid encoding the CasZ guide RNA, and/or a modified host cell comprising the CasZ guide RNA (and/or a nucleic acid encoding the same); and (3) a CasZ transactivating noncoding RNA (trancRNA) (referred to herein as a "CasZ trancRNA"), a nucleic acid encoding the CasZ trancRNA, and/or a modified host cell comprising the CasZ trancRNA (and/or a nucleic acid encoding the same).

BRIEF DESCRIPTION OF THE DRAWINGS

FIGS. 1A-1Q depict examples of naturally occurring CasZ protein sequences.

FIG. 2 depicts schematic representations of CasZ loci, which include a Cas1 protein in addition to the CasZ protein.

FIGS. 5A-5I depict transcriptomic RNA mapping data demonstrating expression of trancRNA from CasZ loci. The trancRNAs are adjacent to the CasZ repeat array, but do not include the repeat sequence and are not complementary to the repeat sequence. Shown are RNA mapping data for the following loci: CasZa3, CasZb4, CasZc5, CasZd1, and CasZe3. Small repeating aligned arrows represent the repeats of the CRISPR array (indicating the presence of guide RNA-encoding sequence); The peaks outside and adjacent to the repeat arrays represent highly transcribed trancRNAs.

FIGS. 7A-7N depict the sequences of Cas14 proteins described herein.

FIG. 10 depicts a maximum likelihood tree for Cas1 from known CRISPR systems.

FIGS. 13A-13E depict metatranscriptomics for CRISPR-Cas14 loci.

FIGS. 15A-15D depict plasmid depletion by Cas14a1 and SpCas9.

FIGS. 16A-16D depict CRISPR-Cas14a is an RNA-guided DNA-endonuclease.

FIGS. 17A-17F depict degradation of ssDNA by Cas14a1.

FIGS. 19A-19F depict optimization of Cas14a1 guide RNA components.

FIGS. 20A-20E depict high fidelity ssDNA DNP detection by CRISPR-Cas14a.

FIGS. 21A-21F depict the impact of various activators on Cas14a1 cleavage rate.

Figure 24I:
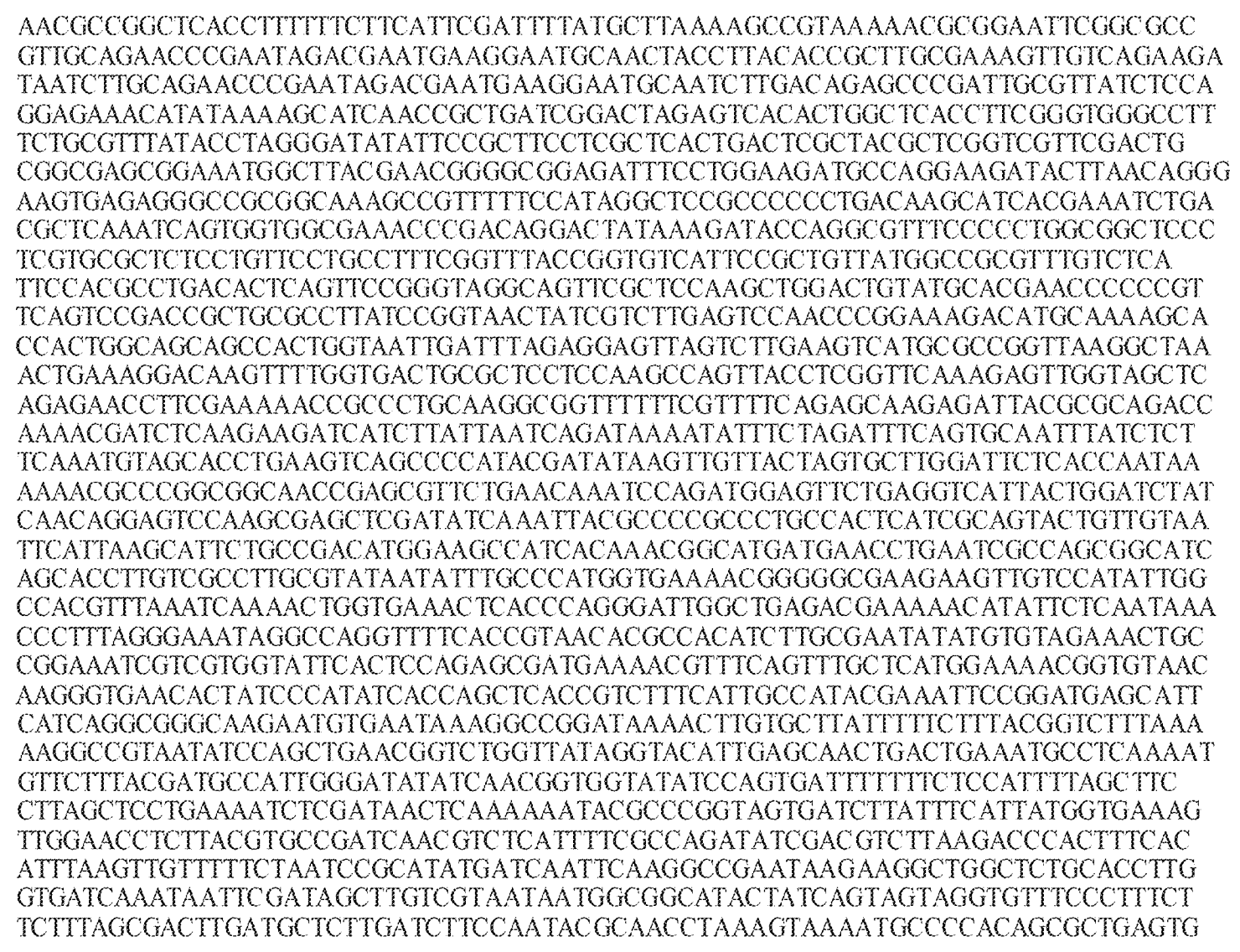
Figure 24P:
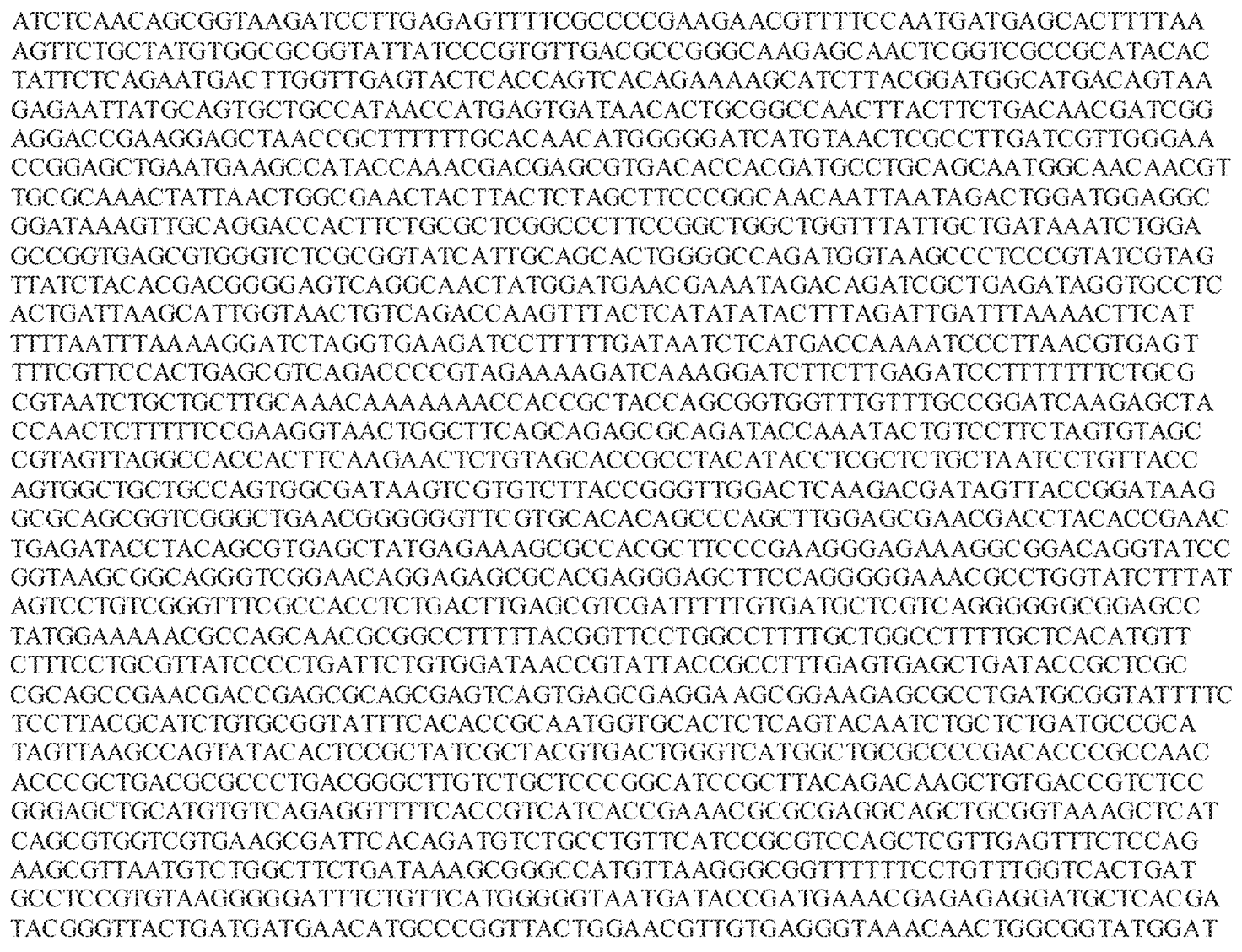

FIGS. 24A-24Q depict Cas14 nucleotide sequences of plasmids used in the present invention.

DEFINITIONS

Figure 3:
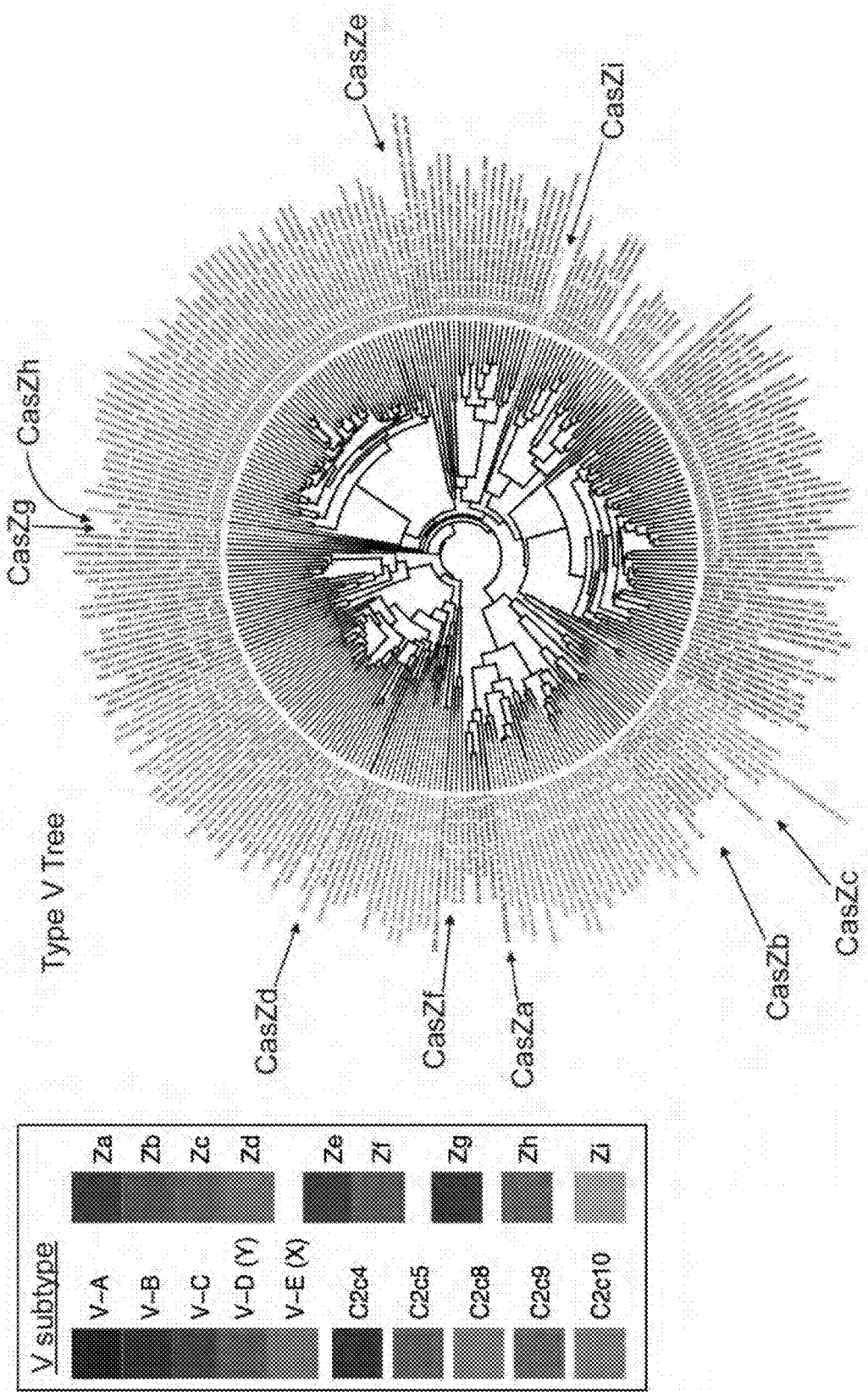
FIG. 3 depicts a phylogenetic tree of CasZ sequences in relation to other Class 2 CRISPR/Cas effector protein sequences.

"Heterologous," as used herein, means a nucleotide or polypeptide sequence that is not found in the native nucleic acid or protein, respectively. For example, relative to a CasZ polypeptide, a heterologous polypeptide comprises an amino acid sequence from a protein other than the CasZ polypeptide. In some cases, a portion of a CasZ protein from one species is fused to a portion of a CasZ protein from a different species. The CasZ sequence from each species could therefore be considered heterologous relative to one another. As another example, a CasZ protein (e.g., a dCasZ protein) can be fused to an active domain from a non-CasZ protein (e.g., a histone deacetylase), and the sequence of the active domain could be considered a heterologous polypeptide (it is heterologous to the CasZ protein).

The terms "polynucleotide" and "nucleic acid," used interchangeably herein, refer to a polymeric form of nucleotides of any length, either ribonucleotides or deoxynucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. The terms "polynucleotide" and "nucleic acid" should be understood to include, as applicable to the embodiment being described, single-stranded (such as sense or antisense) and double-stranded polynucleotides.

The terms "polypeptide," "peptide," and "protein", are used interchangeably herein, refer to a polymeric form of amino acids of any length, which can include genetically coded and non-genetically coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like.

The term "naturally-occurring" as used herein as applied to a nucleic acid, a protein, a cell, or an organism, refers to a nucleic acid, cell, protein, or organism that is found in nature.

As used herein the term "isolated" is meant to describe a polynucleotide, a polypeptide, or a cell that is in an environment different from that in which the polynucleotide, the polypeptide, or the cell naturally occurs. An isolated genetically modified host cell may be present in a mixed population of genetically modified host cells.

As used herein, the term "exogenous nucleic acid" refers to a nucleic acid that is not normally or naturally found in and/or produced by a given bacterium, organism, or cell in nature. As used herein, the term "endogenous nucleic acid" refers to a nucleic acid that is normally found in and/or produced by a given bacterium, organism, or cell in nature. An "endogenous nucleic acid" is also referred to as a "native nucleic acid" or a nucleic acid that is "native" to a given bacterium, organism, or cell.

"Recombinant," as used herein, means that a particular nucleic acid (DNA or RNA) is the product of various combinations of cloning, restriction, and/or ligation steps resulting in a construct having a structural coding or noncoding sequence distinguishable from endogenous nucleic acids found in natural systems. Generally, DNA sequences encoding the structural coding sequence can be assembled from cDNA fragments and short oligonucleotide linkers, or from a series of synthetic oligonucleotides, to provide a synthetic nucleic acid which is capable of being expressed from a recombinant transcriptional unit contained in a cell or in a cell-free transcription and translation system. Such sequences can be provided in the form of an open reading frame uninterrupted by internal non-translated sequences, or introns, which are typically present in eukaryotic genes. Genomic DNA comprising the relevant sequences can also be used in the formation of a recombinant gene or transcriptional unit. Sequences of non-translated DNA may be present 5' or 3' from the open reading frame, where such sequences do not interfere with manipulation or expression of the coding regions, and may indeed act to modulate production of a desired product by various mechanisms (see "DNA regulatory sequences", below).

Thus, e.g., the term "recombinant" polynucleotide or "recombinant" nucleic acid refers to one which is not naturally occurring, e.g., is made by the artificial combination of two otherwise separated segments of sequence through human intervention. This artificial combination is often accomplished by either chemical synthesis means, or by the artificial manipulation of isolated segments of nucleic acids, e.g., by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a desired combination of functions. This artificial combination is often accomplished by either chemical synthesis means, or by the artificial manipulation of isolated segments of nucleic acids, e.g., by genetic engineering techniques.

Similarly, the term "recombinant" polypeptide refers to a polypeptide which is not naturally occurring, e.g., is made by the artificial combination of two otherwise separated segments of amino acid sequence through human intervention. Thus, e.g., a polypeptide that comprises a heterologous amino acid sequence is recombinant.

By "construct" or "vector" is meant a recombinant nucleic acid, generally recombinant DNA, which has been generated for the purpose of the expression and/or propagation of a specific nucleotide sequence(s), or is to be used in the construction of other recombinant nucleotide sequences.

The terms "DNA regulatory sequences," "control elements," and "regulatory elements," used interchangeably herein, refer to transcriptional and translational control sequences, such as promoters, enhancers, polyadenylation signals, terminators, protein degradation signals, and the like, that provide for and/or regulate expression of a coding sequence and/or production of an encoded polypeptide in a host cell.

The term "transformation" is used interchangeably herein with "genetic modification" and refers to a permanent or transient genetic change induced in a cell following introduction of new nucleic acid (e.g., DNA exogenous to the cell) into the cell. Genetic change ("modification") can be accomplished either by incorporation of the new nucleic acid into the genome of the host cell, or by transient or stable maintenance of the new nucleic acid as an episomal element. Where the cell is a eukaryotic cell, a permanent genetic change is generally achieved by introduction of new DNA into the genome of the cell. In prokaryotic cells, permanent changes can be introduced into the chromosome or via extrachromosomal elements such as plasmids and expression vectors, which may contain one or more selectable markers to aid in their maintenance in the recombinant host cell. Suitable methods of genetic modification include viral infection, transfection, conjugation, protoplast fusion, electroporation, particle gun technology, calcium phosphate precipitation, direct microinjection, and the like. The choice of method is generally dependent on the type of cell being transformed and the circumstances under which the transformation is taking place (i.e. in vitro, ex vivo, or in vivo). A general discussion of these methods can be found in Ausubel, et al, Short Protocols in Molecular Biology, 3rd ed., Wiley & Sons, 1995.

"Operably linked" refers to a juxtaposition wherein the components so described are in a relationship permitting them to function in their intended manner. For instance, a promoter is operably linked to a coding sequence if the promoter affects its transcription or expression. As used herein, the terms "heterologous promoter" and "heterologous control regions" refer to promoters and other control regions that are not normally associated with a particular nucleic acid in nature. For example, a "transcriptional control region heterologous to a coding region" is a transcriptional control region that is not normally associated with the coding region in nature.

A "host cell," as used herein, denotes an in vivo or in vitro eukaryotic cell, a prokaryotic cell, or a cell from a multicellular organism (e.g., a cell line) cultured as a unicellular entity, which eukaryotic or prokaryotic cells can be, or have been, used as recipients for a nucleic acid (e.g., an expression vector), and include the progeny of the original cell which has been genetically modified by the nucleic acid. It is understood that the progeny of a single cell may not necessarily be completely identical in morphology or in genomic or total DNA complement as the original parent, due to natural, accidental, or deliberate mutation. A "recombinant host cell" (also referred to as a "genetically modified host cell") is a host cell into which has been introduced a heterologous nucleic acid, e.g., an expression vector. For example, a subject prokaryotic host cell is a genetically modified prokaryotic host cell (e.g., a bacterium), by virtue of introduction into a suitable prokaryotic host cell of a heterologous nucleic acid, e.g., an exogenous nucleic acid that is foreign to (not normally found in nature in) the prokaryotic host cell, or a recombinant nucleic acid that is not normally found in the prokaryotic host cell; and a subject eukaryotic host cell is a genetically modified eukaryotic host cell, by virtue of introduction into a suitable eukaryotic host cell of a heterologous nucleic acid, e.g., an exogenous nucleic acid that is foreign to the eukaryotic host cell, or a recombinant nucleic acid that is not normally found in the eukaryotic host cell.

The term "conservative amino acid substitution" refers to the interchangeability in proteins of amino acid residues having similar side chains. For example, a group of amino acids having aliphatic side chains consists of glycine, alanine, valine, leucine, and isoleucine; a group of amino acids having aliphatic-hydroxyl side chains consists of serine and threonine; a group of amino acids having amide-containing side chains consists of asparagine and glutamine; a group of amino acids having aromatic side chains consists of phenylalanine, tyrosine, and tryptophan; a group of amino acids having basic side chains consists of lysine, arginine, and histidine; and a group of amino acids having sulfur-containing side chains consists of cysteine and methionine. Exemplary conservative amino acid substitution groups are: valine-leucine-isoleucine, phenylalanine-tyrosine, lysine-arginine, alanine-valine, and asparagine-glutamine.

A polynucleotide or polypeptide has a certain percent "sequence identity" to another polynucleotide or polypeptide, meaning that, when aligned, that percentage of bases or amino acids are the same, and in the same relative position, when comparing the two sequences. Sequence similarity can be determined in a number of different manners. To determine sequence identity, sequences can be aligned using the methods and computer programs, including BLAST, available over the world wide web at ncbi.nlm.nih.gov/BLAST. See, e.g., Altschul et al. (1990), *J. Mol. Biol.* 215:403-10. Another alignment algorithm is FASTA, available in the Genetics Computing Group (GCG) package, from Madison, Wisconsin, USA, a wholly owned subsidiary of Oxford Molecular Group, Inc. Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, California, USA. Of particular interest are alignment programs that permit gaps in the sequence. The Smith-Waterman is one type of algorithm that permits gaps in sequence alignments. See *Meth. Mol. Biol.* 70: 173-187 (1997). Also, the GAP program using the Needleman and Wunsch alignment method can be utilized to align sequences. See *J. Mol. Biol.* 48: 443-453 (1970).

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a mammal, e.g., in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

The terms "individual," "subject," "host," and "patient," used interchangeably herein, refer to an individual organism, e.g., a mammal, including, but not limited to, murines, simians, non-human primates, humans, mammalian farm animals, mammalian sport animals, and mammalian pets.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a CasZ polypeptide" includes a plurality of such polypeptides and reference to "the guide RNA" includes reference to one or more guide RNAs and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides compositions and methods that include one or more of: (1) a "CasZ" protein (also referred to as a CasZ polypeptide), a nucleic acid encoding the CasZ protein, and/or a modified host cell comprising the CasZ protein (and/or a nucleic acid encoding the same); (2) a CasZ guide RNA that binds to and provides sequence specificity to the CasZ protein, a nucleic acid encoding the CasZ guide RNA, and/or a modified host cell comprising the CasZ guide RNA (and/or a nucleic acid encoding the same); and (3) a CasZ transactivating noncoding RNA (trancRNA) (referred to herein as a "CasZ trancRNA"), a nucleic acid encoding the CasZ trancRNA, and/or a modified host cell comprising the CasZ trancRNA (and/or a nucleic acid encoding the same).

Compositions

Crispr/CasZ Proteins, Guide RNAs, and TrancRNAs

Class 2 CRISPR-Cas systems are characterized by effector modules that include a single multidomain protein. In the CasZ system, a CRISPR/Cas endonuclease (e.g., a CasZ protein) interacts with (binds to) a corresponding guide RNA (e.g., a CasZ guide RNA) to form a ribonucleoprotein (RNP) complex that is targeted to a particular site in a target nucleic acid via base pairing between the guide RNA and a target sequence within the target nucleic acid molecule. A guide RNA includes a nucleotide sequence (a guide sequence) that is complementary to a sequence (the target site) of a target nucleic acid. Thus, a CasZ protein forms a complex with a CasZ guide RNA and the guide RNA provides sequence specificity to the RNP complex via the guide sequence. The CasZ protein of the complex provides the site-specific activity. In other words, the CasZ protein is guided to a target site (e.g., stabilized at a target site) within a target nucleic acid (e.g. a target nucleotide sequence within a target chromosomal nucleic acid; or a target nucleotide sequence within a target extrachromosomal nucleic acid, e.g., an episomal nucleic acid, a minicircle nucleic acid, a mitochondrial nucleic acid, a chloroplast nucleic acid, etc.) by virtue of its association with the guide RNA.

The present disclosure provides compositions comprising a CasZ polypeptide (and/or a nucleic acid encoding the CasZ polypeptide) (e.g., where the CasZ polypeptide can be a naturally existing CasZ protein, a nickase CasZ protein, a dCasZ protein, a chimeric CasZ protein, etc.)(a CasZa, CasZb, CasZc, CasZd, CasZe, CasZf, CasZg, CasZh, CasZi, CasZj, CasZK, or CasZl protein). The present disclosure provides compositions comprising a CasZ guide RNA (and/or a nucleic acid encoding the CasZ guide RNA). For example, the present disclosure provides compositions comprising (a) a CasZ polypeptide (and/or a nucleic acid encoding the CasZ polypeptide) and (b) a CasZ guide RNA (and/or a nucleic acid encoding the CasZ guide RNA). The present disclosure provides a nucleic acid/protein complex (RNP complex) comprising: (a) a CasZ polypeptide; and (b) a CasZ guide RNA. The present disclosure provides compositions comprising a CasZ trancRNA. The present disclosure provides compositions comprising a CasZ trancRNA and one or more of: (a) a CasZ protein, and (b) a CasZ guide RNA (e.g., comprising a CasZ trancRNA and a CasZ protein, a CasZ trancRNA and a CasZ guide RNA, or a CasZ trancRNA and a CasZ protein and a CasZ guide RNA. The present disclosure provides a nucleic acid/protein complex (RNP complex) comprising: (a) a CasZ polypeptide; (b) a CasZ guide RNA; and (c) a CasZ trancRNA. The present disclosure provides compositions comprising a CasZ protein and one or more of: (a) a CasZ trancRNA, and (b) a CasZ guide RNA.

CasZ Protein

A CasZ polypeptide (this term is used interchangeably with the term "CasZ protein", "Cas14", "Cas14 polypeptide", or "Cas14 protein") can bind and/or modify (e.g., cleave, nick, methylate, demethylate, etc.) a target nucleic acid and/or a polypeptide associated with target nucleic acid (e.g., methylation or acetylation of a histone tail) (e.g., in some cases the CasZ protein includes a fusion partner with an activity, and in some cases the CasZ protein provides nuclease activity). In some cases, the CasZ protein is a naturally-occurring protein (e.g., naturally occurs in prokaryotic cells). In other cases, the CasZ protein is not a naturally-occurring polypeptide (e.g., the CasZ protein is a variant CasZ protein, a chimeric protein, and the like). A CasZ protein includes 3 partial RuvC domains (RuvC-I, RuvC-II, and RuvC-III, also referred to herein as subdomains) that are not contiguous with respect to the primary amino acid sequence of the CasZ protein, but form a RuvC domain once the protein is produced and folds. A naturally occurring CasZ protein functions as an endonuclease that catalyzes cleavage at a specific sequence in a targeted nucleic acid (e.g., a double stranded DNA (dsDNA)). The sequence specificity is provided by the associated guide RNA, which hybridizes to a target sequence within the target DNA. The naturally occurring CasZ guide RNA is a crRNA, where the crRNA includes (i) a guide sequence that hybridizes to a target sequence in the target DNA and (ii) a protein binding segment that binds to the CasZ protein.

In some embodiments, the CasZ protein of the subject methods and/or compositions is (or is derived from) a naturally occurring (wild type) protein. Examples of naturally occurring CasZ proteins (e.g., CasZa, CasZb, CasZc, CasZd, CasZe, CasZf, CasZg, CasZh, CasZi, CasZj, CasZk, CasZl) are depicted in FIG. 1. In some cases, a subject CasZ protein is a CasZa protein. In some cases, a subject CasZ protein is a CasZb protein. In some cases, a subject CasZ protein is a CasZc protein. In some cases, a subject CasZ protein is a CasZd protein. In some cases, a subject CasZ protein is a CasZe protein. In some cases, a subject CasZ protein is a CasZf protein. In some cases, a subject CasZ protein is a CasZg protein. In some cases, a subject CasZ protein is a CasZh protein. In some cases, a subject CasZ protein is a CasZi protein. In some cases, a subject CasZ protein is a CasZj protein. In some cases, a subject CasZ protein is a CasZk protein. In some cases, a subject CasZ protein is a CasZl protein. In some cases, a subject CasZ protein is a CasZe, CasZf, CasZg, or CasZh protein. In some cases, a subject CasZ protein is a CasZj, CasZk, or CasZl protein.

It is important to note that this newly discovered protein (CasZ) is short compared to previously identified CRISPR-Cas endonucleases, and thus use of this protein as an alternative provides the advantage that the nucleotide sequence encoding the protein is relatively short. This is useful, for example, in cases where a nucleic acid encoding the CasZ protein is desirable, e.g., in situations that employ a viral vector (e.g., an AAV vector), for delivery to a cell such as a eukaryotic cell (e.g., mammalian cell, human cell, mouse cell, in vitro, ex vivo, in vivo) for research and/or clinical applications. In addition, in their natural context, the CasZ-encoding DNA sequences are present in loci that also have a Cas1 protein.

In some cases, a subject CasZ protein has a length of 900 amino acids or less (e.g., 850 amino acids or less, 800 amino acids or less, 750 amino acids or less, or 700 amino acids or less). In some cases, a subject CasZ protein has a length of 850 amino acids or less (e.g., 850 amino acids or less). In some cases, a subject CasZ protein length of 800 amino acids or less (e.g., 750 amino acids or less). In some cases, a subject CasZ protein has a length of 700 amino acids or less. In some cases, a subject CasZ protein has a length of 650 amino acids or less.

In some cases, a subject CasZ protein has a length in a range of from 350-900 amino acids (e.g., 350-850, 350-800, 350-750, 350-700, 400-900, 400-850, 400-800, 400-750, or 400-700 amino acids).

In some cases, a subject CasZ protein (e.g., CasZa) has a length in a range of from 350-750 amino acids (e.g., 350-700, 350-550, 450-550, 450-750, 450-650, or 450-550 amino acids). In some cases, a subject CasZ protein (e.g., CasZa) has a length in a range of from 450-750 amino acids (e.g., 500-700 amino acids). In some cases, a subject CasZ protein (e.g., CasZa) has a length in a range of from 350-700 amino acids (e.g., 350-650, 350-600, or 350-550 amino acids). In some cases, a subject CasZ protein (e.g., CasZa) has a length in a range of from 500-700 amino acids. In some cases, a subject CasZ protein (e.g., CasZa) has a length in a range of from 450-550 amino acids. In some cases, a subject CasZ protein (e.g., CasZa) has a length in a range of from 350-550 amino acids.

In some cases, a subject CasZ protein (e.g., CasZb) has a length in a range of from 350-700 amino acids (e.g., 350-650, or 350-620 amino acids). In some cases, a subject CasZ protein (e.g., CasZb) has a length in a range of from 450-700 amino acids (e.g., 450-650, 500-650 or 500-620 amino acids). In some cases, a subject CasZ protein (e.g., CasZb) has a length in a range of from 500-650 amino acids (e.g., 500-620 amino acids). In some cases, a subject CasZ protein (e.g., CasZb) has a length in a range of from 500-620 amino acids.

In some cases, a subject CasZ protein (e.g., CasZc) has a length in a range of from 600-800 amino acids (e.g., 600-650 or 700-800 amino acids). In some cases, a subject CasZ protein (e.g., CasZc) has a length in a range of from 600-650 amino acids. In some cases, a subject CasZ protein (e.g., CasZc) has a length in a range of from 700-800 amino acids.

In some cases, a subject CasZ protein (e.g., CasZd) has a length in a range of from 400-650 amino acids (e.g., 400-600, 400-550, 500-650, 500-600 or 500-550 amino acids). In some cases, a subject CasZ protein (e.g., CasZd) has a length in a range of from 500-600 amino acids. In some cases, a subject CasZ protein (e.g., CasZd) has a length in a range of from 500-550 amino acids. In some cases, a subject CasZ protein (e.g., CasZd) has a length in a range of from 400-550 amino acids.

In some cases, a subject CasZ protein (e.g., CasZe) has a length in a range of from 450-700 amino acids (e.g., 450-650, 450-615, 475-700, 475-650, or 475-615 amino acids). In some cases, a subject CasZ protein (e.g., CasZe) has a length in a range of from 450-675 amino acids. In some cases, a subject CasZ protein (e.g., CasZe) has a length in a range of from 475-675 amino acids.

In some cases, a subject CasZ protein (e.g., CasZf) has a length in a range of from 400-550 amino acids (e.g., 400-520, 400-500, 400-475, 415-550, 415-520, 415-500, or 415-475 amino acids). In some cases, a subject CasZ protein (e.g., CasZf) has a length in a range of from 400-475 amino acids (e.g., 400-450 amino acids).

In some cases, a subject CasZ protein (e.g., CasZg) has a length in a range of from 500-750 amino acids (e.g., 550-750 or 500-700 amino acids). In some cases, a subject CasZ protein (e.g., CasZg) has a length in a range of from 700-750 amino acids. In some cases, a subject CasZ protein (e.g., CasZg) has a length in a range of from 550-600 amino acids.

In some cases, a subject CasZ protein (e.g., CasZh) has a length in a range of from 380-450 amino acids (e.g., 380-420, 400-450, or 400-420 amino acids). In some cases, a subject CasZ protein (e.g., CasZh) has a length in a range of from 400-420 amino acids.

In some cases, a subject CasZ protein (e.g., CasZi) has a length in a range of from 700-800 amino acids (e.g., 700-750, 720-800, or 720-750 amino acids). In some cases, a subject CasZ protein (e.g., CasZi) has a length in a range of from 720-780 amino acids.

In some cases, a subject CasZ protein (e.g., CasZj) has a length in a range of from 600-750 amino acids (e.g., 600-700 or 650-700 amino acids). In some cases, a subject CasZ protein (e.g., CasZj) has a length in a range of from 400-420 amino acids.

In some cases, a subject CasZ protein (e.g., CasZk) has a length in a range of from 450-600 amino acids (e.g., 450-580, 480-600, 480-580, or 500-600 amino acids). In some cases, a subject CasZ protein (e.g., CasZk) has a length in a range of from 480-580 amino acids.

In some cases, a subject CasZ protein (e.g., CasZl) has a length in a range of from 350-500 amino acids (e.g., 350-450, 380-450, 350-420, or 380-420 amino acids). In some cases a subject CasZ protein (e.g., CasZl) has a length in a range of from 380-420 amino acids.

In some cases, a subject CasZ protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with a CasZa protein of FIG. 1 or FIG. 7. For example, in some cases, a subject CasZ protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with a CasZa protein of FIG. 1 or FIG. 7. In some cases, a subject CasZ protein includes an amino acid sequence having 80% or more sequence identity (e.g., 85% or more, 90% or more, 95% or more, 97% or more, 98% or more, 99% or more, or 100% sequence identity) with a CasZa protein of FIG. 1 or FIG. 7. In some cases, a subject CasZ protein includes an amino acid sequence having 90% or more sequence identity (e.g., 95% or more, 97% or more, 98% or more, 99% or more, or 100% sequence identity) with a CasZa protein of FIG. 1 or FIG. 7. In some cases, a subject CasZ protein includes a CasZa amino acid sequence of FIG. 1 or FIG. 7. In some cases, a subject CasZ protein includes a CasZa amino acid sequence of FIG. 1 or FIG. 7, with the exception that the sequence includes one or more amino acid substitutions (e.g., 1, 2, or 3 amino acid substitutions) that reduces the naturally occurring catalytic activity of the protein (e.g., such as at one or more catalytic amino acid positions)(e.g., in some cases such that the CasZ protein is a dCasZ). In some cases, a subject CasZ protein includes an amino acid sequence having 90% or more sequence identity (e.g., 95% or more, 97% or more, 98% or more, 99% or more, or 100% sequence identity) with a CasZa protein of FIG. 1 or FIG. 7 and has a length in a range of from 350-800 amino acids (e.g., 350-800, 350-750, 350-700, 350-550, 450-550, 450-750, 450-650, or 450-550 amino acids).

In some cases, a subject CasZ protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with a CasZb protein of FIG. 1 or FIG. 7. For example, in some cases, a subject CasZ protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with a CasZb protein of FIG. 1 or FIG. 7. In some cases, a subject CasZ protein includes an amino acid sequence having 80% or more sequence identity (e.g., 85% or more, 90% or more, 95% or more, 97% or more, 98% or more, 99% or more, or 100% sequence identity) with a CasZb protein of FIG. 1 or FIG. 7. In some cases, a subject CasZ protein includes an amino acid sequence having 90% or more sequence identity (e.g., 95% or more, 97% or more, 98% or more, 99% or more, or 100% sequence identity) with a CasZb protein of FIG. 1 or FIG. 7. In some cases, a subject CasZ protein includes a CasZb amino acid sequence of FIG. 1 or FIG. 7. In some cases, a subject CasZ protein includes a CasZb amino acid sequence of FIG. 1 or FIG. 7, with the exception that the sequence includes an amino acid substitution (e.g., 1, 2, or 3 amino acid substitutions) that reduces the naturally occurring catalytic activity of the protein (e.g., such as at one or more catalytic amino acid positions)(e.g., in some cases such that the CasZ protein is a dCasZ). In some cases, a subject CasZ protein includes an amino acid sequence having 90% or more sequence identity (e.g., 95% or more, 97% or more, 98% or more, 99% or more, or 100% sequence identity) with a CasZb protein of FIG. 1 or FIG. 7 and has a length in a range of from 350-700 amino acids (e.g., 350-650, or 350-620 amino acids).

In some cases, a subject CasZ protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with a CasZc protein of FIG. 1 or FIG. 7. For example, in some cases, a subject CasZ protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with a CasZc protein of FIG. 1 or FIG. 7. In some cases, a subject CasZ protein includes an amino acid sequence having 80% or more sequence identity (e.g., 85% or more, 90% or more, 95% or more, 97% or more, 98% or more, 99% or more, or 100% sequence identity) with a CasZc protein of FIG. 1 or FIG. 7. In some cases, a subject CasZ protein includes an amino acid sequence having 90% or more sequence identity (e.g., 95% or more, 97% or more, 98% or more, 99% or more, or 100% sequence identity) with a CasZc protein of FIG. 1 or FIG. 7. In some cases, a subject CasZ protein includes a CasZc amino acid sequence of FIG. 1 or FIG. 7. In some cases, a subject CasZ protein includes a CasZc amino acid sequence of FIG. 1 or FIG. 7, with the exception that the sequence includes an amino acid substitution (e.g., 1, 2, or 3 amino acid substitutions) that reduces the naturally occurring catalytic activity of the protein (e.g., such as at one or more catalytic amino acid positions)(e.g., in some cases such that the CasZ protein is a dCasZ). In some cases, a subject CasZ protein includes an amino acid sequence having 90% or more sequence identity (e.g., 95% or more, 97% or more, 98% or more, 99% or more, or 100% sequence identity) with a CasZc protein of FIG. 1 or FIG. 7 and has a length in a range of from 600-800 amino acids (e.g., 600-650 or 700-800 amino acids).

In some cases, a subject CasZ protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with a CasZd protein of FIG. 1 or FIG. 7. For example, in some cases, a subject CasZ protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with a CasZd protein of FIG. 1 or FIG. 7. In some cases, a subject CasZ protein includes an amino acid sequence having 80% or more sequence identity (e.g., 85% or more, 90% or more, 95% or more, 97% or more, 98% or more, 99% or more, or 100% sequence identity) with a CasZd protein of FIG. 1 or FIG. 7. In some cases, a subject CasZ protein includes an amino acid sequence having 90% or more sequence identity (e.g., 95% or more, 97% or more, 98% or more, 99% or more, or 100% sequence identity) with a CasZd protein of FIG. 1 or FIG. 7. In some cases, a subject CasZ protein includes a CasZd amino acid sequence of FIG. 1 or FIG. 7. In some cases, a subject CasZ protein includes a CasZd amino acid sequence of FIG. 1 or FIG. 7, with the exception that the sequence includes an amino acid substitution (e.g., 1, 2, or 3 amino acid substitutions) that reduces the naturally occurring catalytic activity of the protein (e.g., such as at one or more catalytic amino acid positions)(e.g., in some cases such that the CasZ protein is a dCasZ). In some cases, a subject CasZ protein includes an amino acid sequence having 90% or more sequence identity (e.g., 95% or more, 97% or more, 98% or more, 99% or more, or 100% sequence identity) with a CasZd protein of FIG. 1 or FIG. 7 and has a length in a range of from 400-650 amino acids (e.g., 400-600, 400-550, 500-650, 500-600 or 500-550 amino acids).

In some cases, a subject CasZ protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with a CasZe protein of FIG. 1 or FIG. 7. For example, in some cases, a subject CasZ protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with a CasZe protein of FIG. 1 or FIG. 7. In some cases, a subject CasZ protein includes an amino acid sequence having 80% or more sequence identity (e.g., 85% or more, 90% or more, 95% or more, 97% or more, 98% or more, 99% or more, or 100% sequence identity) with a CasZe protein of FIG. 1 or FIG. 7. In some cases, a subject CasZ protein includes an amino acid sequence having 90% or more sequence identity (e.g., 95% or more, 97% or more, 98% or more, 99% or more, or 100% sequence identity) with a CasZe protein of FIG. 1 or FIG. 7. In some cases, a subject CasZ protein includes a CasZe amino acid sequence of FIG. 1 or FIG. 7. In some cases, a subject CasZ protein includes a CasZe amino acid sequence of FIG. 1 or FIG. 7, with the exception that the sequence includes an amino acid substitution (e.g., 1, 2, or 3 amino acid substitutions) that reduces the naturally occurring catalytic activity of the protein (e.g., such as at one or more catalytic amino acid positions)(e.g., in some cases such that the CasZ protein is a dCasZ). In some cases, a subject CasZ protein includes an amino acid sequence having 90% or more sequence identity (e.g., 95% or more, 97% or more, 98% or more, 99% or more, or 100% sequence identity) with a CasZe protein of FIG. 1 or FIG. 7 and has a length in a range of from 450-700 amino acids (e.g., 450-650, 450-615, 475-700, 475-650, or 475-615 amino acids).

In some cases, a subject CasZ protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with a CasZf protein of FIG. 1 or FIG. 7. For example, in some cases, a subject CasZ protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with a CasZf protein of FIG. 1 or FIG. 7. In some cases, a subject CasZ protein includes an amino acid sequence having 80% or more sequence identity (e.g., 85% or more, 90% or more, 95% or more, 97% or more, 98% or more, 99% or more, or 100% sequence identity) with a CasZf protein of FIG. 1 or FIG. 7. In some cases, a subject CasZ protein includes an amino acid sequence having 90% or more sequence identity (e.g., 95% or more, 97% or more, 98% or more, 99% or more, or 100% sequence identity) with a CasZf protein of FIG. 1 or FIG. 7. In some cases, a subject CasZ protein includes a CasZf amino acid sequence of FIG. 1 or FIG. 7. In some cases, a subject CasZ protein includes a CasZf amino acid sequence of FIG. 1 or FIG. 7, with the exception that the sequence includes an amino acid substitution (e.g., 1, 2, or 3 amino acid substitutions) that reduces the naturally occurring catalytic activity of the protein (e.g., such as at one or more catalytic amino acid positions)(e.g., in some cases such that the CasZ protein is a dCasZ). In some cases, a subject CasZ protein includes an amino acid sequence having 90% or more sequence identity (e.g., 95% or more, 97% or more, 98% or more, 99% or more, or 100% sequence identity) with a CasZf protein of FIG. 1 or FIG. 7 and has a length in a range of from 400-750 amino acids (e.g., 400-700, 700-650, 400-620, 400-600, 400-550, 400-520, 400-500, 400-475, 415-550, 415-520, 415-500, or 415-475 amino acids).

In some cases, a subject CasZ protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with a CasZg protein of FIG. 1 or FIG. 7. For example, in some cases, a subject CasZ protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with a CasZg protein of FIG. 1 or FIG. 7. In some cases, a subject CasZ protein includes an amino acid sequence having 80% or more sequence identity (e.g., 85% or more, 90% or more, 95% or more, 97% or more, 98% or more, 99% or more, or 100% sequence identity) with a CasZg protein of FIG. 1 or FIG. 7. In some cases, a subject CasZ protein includes an amino acid sequence having 90% or more sequence identity (e.g., 95% or more, 97% or more, 98% or more, 99% or more, or 100% sequence identity) with a CasZg protein of FIG. 1 or FIG. 7. In some cases, a subject CasZ protein includes a CasZg amino acid sequence of FIG. 1 or FIG. 7. In some cases, a subject CasZ protein includes a CasZg amino acid sequence of FIG. 1 or FIG. 7, with the exception that the sequence includes an amino acid substitution (e.g., 1, 2, or 3 amino acid substitutions) that reduces the naturally occurring catalytic activity of the protein (e.g., such as at one or more catalytic amino acid positions)(e.g., in some cases such that the CasZ protein is a dCasZ). In some cases, a subject CasZ protein includes an amino acid sequence having 90% or more sequence identity (e.g., 95% or more, 97% or more, 98% or more, 99% or more, or 100% sequence identity) with a CasZg protein of FIG. 1 or FIG. 7 and has a length in a range of from 500-750 amino acids (e.g., 500-750 amino acids (e.g., 550-750 amino acids)).

In some cases, a subject CasZ protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with a CasZh protein of FIG. 1 or FIG. 7. For example, in some cases, a subject CasZ protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with a CasZh protein of FIG. 1 or FIG. 7. In some cases, a subject CasZ protein includes an amino acid sequence having 80% or more sequence identity (e.g., 85% or more, 90% or more, 95% or more, 97% or more, 98% or more, 99% or more, or 100% sequence identity) with a CasZh protein of FIG. 1 or FIG. 7. In some cases, a subject CasZ protein includes an amino acid sequence having 90% or more sequence identity (e.g., 95% or more, 97% or more, 98% or more, 99% or more, or 100% sequence identity) with a CasZh protein of FIG. 1 or FIG. 7. In some cases, a subject CasZ protein includes a CasZh amino acid sequence of FIG. 1 or FIG. 7. In some cases, a subject CasZ protein includes a CasZh amino acid sequence of FIG. 1 or FIG. 7, with the exception that the sequence includes an amino acid substitution (e.g., 1, 2, or 3 amino acid substitutions) that reduces the naturally occurring catalytic activity of the protein (e.g., such as at one or more catalytic amino acid positions)(e.g., in some cases such that the CasZ protein is a dCasZ). In some cases, a subject CasZ protein includes an amino acid sequence having 90% or more sequence identity (e.g., 95% or more, 97% or more, 98% or more, 99% or more, or 100% sequence identity) with a CasZh protein of FIG. 1 or FIG. 7 and has a length in a range of from 380-450 amino acids (e.g., 380-420, 400-450, or 400-420 amino acids).

In some cases, a subject CasZ protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with a CasZi protein of FIG. 1 or FIG. 7. For example, in some cases, a subject CasZ protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with a CasZi protein of FIG. 1 or FIG. 7. In some cases, a subject CasZ protein includes an amino acid sequence having 80% or more sequence identity (e.g., 85% or more, 90% or more, 95% or more, 97% or more, 98% or more, 99% or more, or 100% sequence identity) with a CasZi protein of FIG. 1 or FIG. 7. In some cases, a subject CasZ protein includes an amino acid sequence having 90% or more sequence identity (e.g., 95% or more, 97% or more, 98% or more, 99% or more, or 100% sequence identity) with a CasZi protein of FIG. 1 or FIG. 7. In some cases, a subject CasZ protein includes a CasZi amino acid sequence of FIG. 1 or FIG. 7. In some cases, a subject CasZ protein includes a CasZi amino acid sequence of FIG. 1 or FIG. 7, with the exception that the sequence includes an amino acid substitution (e.g., 1, 2, or 3 amino acid substitutions) that reduces the naturally occurring catalytic activity of the protein (e.g., such as at one or more catalytic amino acid positions)(e.g., in some cases such that the CasZ protein is a dCasZ). In some cases, a subject CasZ protein includes an amino acid sequence having 90% or more sequence identity (e.g., 95% or more, 97% or more, 98% or more, 99% or more, or 100% sequence identity) with a CasZi protein of FIG. 1 or FIG. 7 and has a length in a range of from 700-800 amino acids (e.g., 700-750, 720-800, or 720-750 amino acids).

In some cases, a subject CasZ protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with a CasZj protein of FIG. 1 or FIG. 7. For example, in some cases, a subject CasZ protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with a CasZj protein of FIG. 1 or FIG. 7. In some cases, a subject CasZ protein includes an amino acid sequence having 80% or more sequence identity (e.g., 85% or more, 90% or more, 95% or more, 97% or more, 98% or more, 99% or more, or 100% sequence identity) with a CasZj protein of FIG. 1 or FIG. 7. In some cases, a subject CasZ protein includes an amino acid sequence having 90% or more sequence identity (e.g., 95% or more, 97% or more, 98% or more, 99% or more, or 100% sequence identity) with a CasZj protein of FIG. 1 or FIG. 7. In some cases, a subject CasZ protein includes a CasZj amino acid sequence of FIG. 1 or FIG. 7. In some cases, a subject CasZ protein includes a CasZj amino acid sequence of FIG. 1 or FIG. 7, with the exception that the sequence includes an amino acid substitution (e.g., 1, 2, or 3 amino acid substitutions) that reduces the naturally occurring catalytic activity of the protein (e.g., such as at one or more catalytic amino acid positions)(e.g., in some cases such that the CasZ protein is a dCasZ). In some cases, a subject CasZ protein includes an amino acid sequence having 90% or more sequence identity (e.g., 95% or more, 97% or more, 98% or more, 99% or more, or 100% sequence identity) with a CasZj protein of FIG. 1 or FIG. 7 and has a length in a range of from 600-750 amino acids (e.g., 600-700 or 650-700 amino acids).

In some cases, a subject CasZ protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with a CasZk protein of FIG. 1 or FIG. 7. For example, in some cases, a subject CasZ protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with a CasZk protein of FIG. 1 or FIG. 7. In some cases, a subject CasZ protein includes an amino acid sequence having 80% or more sequence identity (e.g., 85% or more, 90% or more, 95% or more, 97% or more, 98% or more, 99% or more, or 100% sequence identity) with a CasZk protein of FIG. 1 or FIG. 7. In some cases, a subject CasZ protein includes an amino acid sequence having 90% or more sequence identity (e.g., 95% or more, 97% or more, 98% or more, 99% or more, or 100% sequence identity) with a CasZk protein of FIG. 1 or FIG. 7. In some cases, a subject CasZ protein includes a CasZk amino acid sequence of FIG. 1 or FIG. 7. In some cases, a subject CasZ protein includes a CasZk amino acid sequence of FIG. 1 or FIG. 7, with the exception that the sequence includes an amino acid substitution (e.g., 1, 2, or 3 amino acid substitutions) that reduces the naturally occurring catalytic activity of the protein (e.g., such as at one or more catalytic amino acid positions)(e.g., in some cases such that the CasZ protein is a dCasZ). In some cases, a subject CasZ protein includes an amino acid sequence having 90% or more sequence identity (e.g., 95% or more, 97% or more, 98% or more, 99% or more, or 100% sequence identity) with a CasZk protein of FIG. 1 or FIG. 7 and has a length in a range of from 450-600 amino acids (e.g., 450-580, 480-600, 480-580, or 500-600 amino acids).

In some cases, a subject CasZ protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with a CasZl protein of FIG. 1 or FIG. 7. For example, in some cases, a subject CasZ protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with a CasZl protein of FIG. 1 or FIG. 7. In some cases, a subject CasZ protein includes an amino acid sequence having 80% or more sequence identity (e.g., 85% or more, 90% or more, 95% or more, 97% or more, 98% or more, 99% or more, or 100% sequence identity) with a CasZl protein of FIG. 1 or FIG. 7. In some cases, a subject CasZ protein includes an amino acid sequence having 90% or more sequence identity (e.g., 95% or more, 97% or more, 98% or more, 99% or more, or 100% sequence identity) with a CasZl protein of FIG. 1 or FIG. 7. In some cases, a subject CasZ protein includes a CasZl amino acid sequence of FIG. 1 or FIG. 7. In some cases, a subject CasZ protein includes a CasZl amino acid sequence of FIG. 1 or FIG. 7, with the exception that the sequence includes an amino acid substitution (e.g., 1, 2, or 3 amino acid substitutions) that reduces the naturally occurring catalytic activity of the protein (e.g., such as at one or more catalytic amino acid positions)(e.g., in some cases such that the CasZ protein is a dCasZ). In some cases, a subject CasZ protein includes an amino acid sequence having 90% or more sequence identity (e.g., 95% or more, 97% or more, 98% or more, 99% or more, or 100% sequence identity) with a CasZl protein of FIG. 1 or FIG. 7 and has a length in a range of from 450-600 amino acids (e.g., 450-580, 480-600, 480-580, or 500-600 amino acids).

In some cases, a subject CasZ protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with a CasZe, CasZf, CasZg, or CasZh protein of FIG. 1 or FIG. 7. For example, in some cases, a subject CasZ protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with a CasZe, CasZf, CasZg, or CasZh protein of FIG. 1 or FIG. 7. In some cases, a subject CasZ protein includes an amino acid sequence having 80% or more sequence identity (e.g., 85% or more, 90% or more, 95% or more, 97% or more, 98% or more, 99% or more, or 100% sequence identity) with a CasZe, CasZf, CasZg, or CasZh protein of FIG. 1 or FIG. 7. In some cases, a subject CasZ protein includes an amino acid sequence having 90% or more sequence identity (e.g., 95% or more, 97% or more, 98% or more, 99% or more, or 100% sequence identity) with a CasZe, CasZf, CasZg, or CasZh protein of FIG. 1 or FIG. 7. In some cases, a subject CasZ protein includes an amino acid sequence having a CasZe, CasZf, CasZg, or CasZh protein sequence of FIG. 1 or FIG. 7. In some cases, a subject CasZ protein includes an amino acid sequence having a CasZe, CasZf, CasZg, or CasZh protein sequence of FIG. 1 or FIG. 7, with the exception that the sequence includes an amino acid substitution (e.g., 1, 2, or 3 amino acid substitutions) that reduces the naturally occurring catalytic activity of the protein (e.g., such as at one or more catalytic amino acid positions). In some cases, a subject CasZ protein includes an amino acid sequence having 90% or more sequence identity (e.g., 95% or more, 97% or more, 98% or more, 99% or more, or 100% sequence identity) with a CasZe, CasZf, CasZg, or CasZh protein of FIG. 1 or FIG. 7 and has a length in a range of from 350-900 amino acids (e.g., 350-850, 350-800, 400-900, 400-850, or 400-800 amino acids).

In some cases, a subject CasZ protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with a CasZa, CasZb, CasZc, CasZd, CasZe, CasZf, CasZg, CasZh, CasZi, CasZj, CasZK, or CasZl protein of FIG. 1 or FIG. 7. For example, in some cases, a subject CasZ protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with a CasZa, CasZb, CasZc, CasZd, CasZe, CasZf, CasZg, CasZh, CasZi, CasZj, CasZK, or CasZl protein of FIG. 1 or FIG. 7. In some cases, a subject CasZ protein includes an amino acid sequence having 80% or more sequence identity (e.g., 85% or more, 90% or more, 95% or more, 97% or more, 98% or more, 99% or more, or 100% sequence identity) with a CasZa, CasZb, CasZc, CasZd, CasZe, CasZf, CasZg, CasZh, CasZi, CasZj, CasZK, or CasZl protein of FIG. 1 or FIG. 7. In some cases, a subject CasZ protein includes an amino acid sequence having 90% or more sequence identity (e.g., 95% or more, 97% or more, 98% or more, 99% or more, or 100% sequence identity) with a CasZa, CasZb, CasZc, CasZd, CasZe, CasZf, CasZg, CasZh, CasZi, CasZj, CasZK, or CasZl protein of FIG. 1 or FIG. 7. In some cases, a subject CasZ protein includes an amino acid sequence having a CasZa, CasZb, CasZc, CasZd, CasZe, CasZf, CasZg, CasZh, CasZi, CasZj, CasZK, or CasZl protein sequence of FIG. 1 or FIG. 7. In some cases, a subject CasZ protein includes an amino acid sequence having a CasZa, CasZb, CasZc, CasZd, CasZe, CasZf, CasZg, CasZh, CasZi, CasZj, CasZK, or CasZl protein sequence of FIG. 1 or FIG. 7, with the exception that the sequence includes an amino acid substitution (e.g., 1, 2, or 3 amino acid substitutions) that reduces the naturally occurring catalytic activity of the protein (e.g., such as at one or more catalytic amino acid positions). In some cases, a subject CasZ protein includes an amino acid sequence having 90% or more sequence identity (e.g., 95% or more, 97% or more, 98% or more, 99% or more, or 100% sequence identity) with a CasZa, CasZb, CasZc, CasZd, CasZe, CasZf, CasZg, CasZh, CasZi, CasZj, CasZK, or CasZl protein of FIG. 1 or FIG. 7 and has a length in a range of from 350-900 amino acids (e.g., 350-850, 350-800, 400-900, 400-850, or 400-800 amino acids).

CasZ Variants

A variant CasZ protein has an amino acid sequence that is different by at least one amino acid (e.g., has a deletion, insertion, substitution, fusion) when compared to the amino acid sequence of the corresponding wild type CasZ protein. A CasZ protein that cleaves one strand but not the other of a double stranded target nucleic acid is referred to herein as a "nickase" (e.g., a "nickase CasZ"). A CasZ protein that has substantially no nuclease activity is referred to herein as a dead CasZ protein ("dCasZ") (with the caveat that nuclease activity can be provided by a heterologous polypeptide—a fusion partner—in the case of a chimeric CasZ protein, which is described in more detail below). For any of the CasZ variant proteins described herein (e.g., nickase CasZ, dCasZ, chimeric CasZ), the CasZ variant can include a CasZ protein sequence with the same parameters described above (e.g., domains that are present, percent identity, length, and the like).

Variants—Catalytic Activity

In some cases, the CasZ protein is a variant CasZ protein, e.g., mutated relative to the naturally occurring catalytically active sequence, and exhibits reduced cleavage activity (e.g., exhibits 90%, or less, 80% or less, 70% or less, 60% or less, 50% or less, 40% or less, or 30% or less cleavage activity) when compared to the corresponding naturally occurring sequence. In some cases, such a variant CasZ protein is a catalytically 'dead' protein (has substantially no cleavage activity) and can be referred to as a 'dCasZ.' In some cases, the variant CasZ protein is a nickase (cleaves only one strand of a double stranded target nucleic acid, e.g., a double stranded target DNA). As described in more detail herein, in some cases, a CasZ protein (in some case a CasZ protein with wild type cleavage activity and in some cases a variant CasZ with reduced cleavage activity, e.g., a dCasZ or a nickase CasZ) is fused (conjugated) to a heterologous polypeptide that has an activity of interest (e.g., a catalytic activity of interest) to form a fusion protein (a chimeric CasZ protein).

Catalytic residues of CasZ include D405, E586 and D684 when numbered according to CasZi.1 (e.g., see FIG. 1). Thus, in some cases, the CasZ protein has reduced activity and one or more of the above described amino acids (or one or more corresponding amino acids of any CasZ protein) are mutated (e.g., substituted with an alanine). In some cases, the variant CasZ protein is a catalytically 'dead' protein (is catalytically inactive) and is referred to as 'dCasZ.' A dCasZ protein can be fused to a fusion partner that provides an activity, and in some cases, the dCasZ (e.g., one without a fusion partner that provides catalytic activity—but which can have an NLS when expressed in a eukaryotic cell) can bind to target DNA and can be used for imaging (e.g., the protein can be tagged/labeled) and/or can block RNA polymerase from transcribing from a target DNA. In some cases, the variant CasZ protein is a nickase (cleaves only one strand of a double stranded target nucleic acid, e.g., a double stranded target DNA).

Variants—Chimeric CasZ (i.e., Fusion Proteins)

As noted above, in some cases, a CasZ protein (in some cases a CasZ protein with wild type cleavage activity and in some cases a variant CasZ with reduced cleavage activity, e.g., a dCasZ or a nickase CasZ) is fused (conjugated) to a heterologous polypeptide that has an activity of interest (e.g., a catalytic activity of interest) to form a fusion protein (a chimeric CasZ protein). A heterologous polypeptide to which a CasZ protein can be fused is referred to herein as a 'fusion partner.'

In some cases, the fusion partner can modulate transcription (e.g., inhibit transcription, increase transcription) of a target DNA. For example, in some cases the fusion partner is a protein (or a domain from a protein) that inhibits transcription (e.g., a transcriptional repressor, a protein that functions via recruitment of transcription inhibitor proteins, modification of target DNA such as methylation, recruitment of a DNA modifier, modulation of histones associated with target DNA, recruitment of a histone modifier such as those that modify acetylation and/or methylation of histones, and the like). In some cases the fusion partner is a protein (or a domain from a protein) that increases transcription (e.g., a transcription activator, a protein that acts via recruitment of transcription activator proteins, modification of target DNA such as demethylation, recruitment of a DNA modifier, modulation of histones associated with target DNA, recruitment of a histone modifier such as those that modify acetylation and/or methylation of histones, and the like).

In some cases, a chimeric CasZ protein includes a heterologous polypeptide that has enzymatic activity that modifies a target nucleic acid (e.g., nuclease activity such as FokI nuclease activity, methyltransferase activity, demethylase activity, DNA repair activity, DNA damage activity, deamination activity, dismutase activity, alkylation activity, depurination activity, oxidation activity, pyrimidine dimer forming activity, integrase activity, transposase activity, recombinase activity, polymerase activity, ligase activity, helicase activity, photolyase activity or glycosylase activity).

In some cases, a chimeric CasZ protein includes a heterologous polypeptide that has enzymatic activity that modifies a polypeptide (e.g., a histone) associated with a target nucleic acid (e.g., methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity or demyristoylation activity).

Examples of proteins (or fragments thereof) that can be used in increase transcription include but are not limited to: transcriptional activators such as VP16, VP64, VP48, VP160, p65 subdomain (e.g., from NFkB), and activation domain of EDLL and/or TAL activation domain (e.g., for activity in plants); histone lysine methyltransferases such as SET1A, SET1B, MLL1 to 5, ASH1, SYMD2, NSD1, and the like; histone lysine demethylases such as JHDM2a/b, UTX, JMJD3, and the like; histone acetyltransferases such as GCN5, PCAF, CBP, p300, TAF1, TIP60/PLIP, MOZ/MYST3, MORF/MYST4, SRC1, ACTR, P160, CLOCK, and the like; and DNA demethylases such as Ten-Eleven Translocation (TET) dioxygenase 1 (TET1CD), TET1, DME, DML1, DML2, ROS1, and the like.

Examples of proteins (or fragments thereof) that can be used in decrease transcription include but are not limited to: transcriptional repressors such as the Krüppel associated box (KRAB or SKD); KOX1 repression domain; the Mad mSIN3 interaction domain (SID); the ERF repressor domain (ERD), the SRDX repression domain (e.g., for repression in plants), and the like; histone lysine methyltransferases such as Pr-SET7/8, SUV4-20H1, RIZ1, and the like; histone lysine demethylases such as JMJD2A/JHDM3A, JMJD2B, JMJD2C/GASC1, JMJD2D, JARID1A/RBP2, JARID1B/PLU-1, JARID1C/SMCX, JARID1D/SMCY, and the like; histone lysine deacetylases such as HDAC1, HDAC2, HDAC3, HDAC8, HDAC4, HDAC5, HDAC7, HDAC9, SIRT1, SIRT2, HDAC11, and the like; DNA methylases such as HhaI DNA m5c-methyltransferase (M.HhaI), DNA methyltransferase 1 (DNMT1), DNA methyltransferase 3a (DNMT3a), DNA methyltransferase 3b (DNMT3b), METI, DRM3 (plants), ZMET2, CMT1, CMT2 (plants), and the like; and periphery recruitment elements such as Lamin A, Lamin B, and the like.

In some cases, the fusion partner has enzymatic activity that modifies the target nucleic acid (e.g., ssRNA, dsRNA, ssDNA, dsDNA). Examples of enzymatic activity that can be provided by the fusion partner include but are not limited to: nuclease activity such as that provided by a restriction enzyme (e.g., FokI nuclease), methyltransferase activity such as that provided by a methyltransferase (e.g., HhaI DNA m5c-methyltransferase (M.HhaI), DNA methyltransferase 1 (DNMT1), DNA methyltransferase 3a (DNMT3a), DNA methyltransferase 3b (DNMT3b), METI, DRM3 (plants), ZMET2, CMT1, CMT2 (plants), and the like); demethylase activity such as that provided by a demethylase (e.g., Ten-Eleven Translocation (TET) dioxygenase 1 (TET1CD), TET1, DME, DML1, DML2, ROS1, and the like), DNA repair activity, DNA damage activity, deamination activity such as that provided by a deaminase (e.g., a cytosine deaminase enzyme such as rat APOBEC1), dismutase activity, alkylation activity, depurination activity, oxidation activity, pyrimidine dimer forming activity, integrase activity such as that provided by an integrase and/or resolvase (e.g., Gin invertase such as the hyperactive mutant of the Gin invertase, GinH106Y; human immunodeficiency virus type 1 integrase (IN); Tn3 resolvase; and the like), transposase activity, recombinase activity such as that provided by a recombinase (e.g., catalytic domain of Gin recombinase), polymerase activity, ligase activity, helicase activity, photolyase activity, and glycosylase activity).

In some cases, the fusion partner has enzymatic activity that modifies a protein associated with the target nucleic acid (e.g., ssRNA, dsRNA, ssDNA, dsDNA) (e.g., a histone, an RNA binding protein, a DNA binding protein, and the like). Examples of enzymatic activity (that modifies a protein associated with a target nucleic acid) that can be provided by the fusion partner include but are not limited to: methyltransferase activity such as that provided by a histone methyltransferase (HMT) (e.g., suppressor of variegation 3-9 homolog 1 (SUV39H1, also known as KMT1A), euchromatic histone lysine methyltransferase 2 (G9A, also known as KMT1C and EHMT2), SUV39H2, ESET/SETDB1, and the like), SET1A, SET1B, MLL1 to 5, ASH1, SYMD2, NSD1, DOT1L, Pr-SET7/8, SUV4-20H1, EZH2, RIZ1), demethylase activity such as that provided by a histone demethylase (e.g., Lysine Demethylase 1A (KDM1A also known as LSD1), JHDM2a/b, JMJD2A/JHDM3A, JMJD2B, JMJD2C/GASC1, JMJD2D, JARID1A/RBP2, JARID1B/PLU-1, JARID1C/SMCX, JARID1D/SMCY, UTX, JMJD3, and the like), acetyltransferase activity such as that provided by a histone acetylase transferase (e.g., catalytic core/fragment of the human acetyltransferase p300, GCN5, PCAF, CBP, TAF1, TIP60/PLIP, MOZ/MYST3, MORF/MYST4, HBO1/MYST2, HMOF/MYST1, SRC1, ACTR, P160, CLOCK, and the like), deacetylase activity such as that provided by a histone deacetylase (e.g., HDAC1, HDAC2, HDAC3, HDAC8, HDAC4, HDAC5, HDAC7, HDAC9, SIRT1, SIRT2, HDAC11, and the like), kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, and demyristoylation activity.

Additional examples of a suitable fusion partners are dihydrofolate reductase (DHFR) destabilization domain (e.g., to generate a chemically controllable chimeric CasZ protein), and a chloroplast transit peptide. Suitable chloroplast transit peptides include, but are not limited to:

```
                                      (SEQ ID NO: 101)
MASMISSSAVTTVSRASRGQSAAMAPFGGLKSMTGFPVRKVNTDITSITSN

GGRVKCMQVWPPIGKKKFETLSYLPPLTRDSRA;

(SEQ ID NO: 102)
MASMISSSAVTTVSRASRGQSAAMAPFGGLKSMTGFPVRKVNTDITSITSN

GGRVKS;

(SEQ ID NO: 103)
MASSMLSSATMVASPAQATMVAPFNGLKSSAAFPATRKANNDITSITSNGG

RVNCMQVWPPIEKKKFETLSYLPDLTDSGGRVNC;

(SEQ ID NO: 104)
MAQVSRICNGVQNPSLISNLSKSSQRKSPLSVSLKTQQHPRAYPISSSWGL

KKSGMTLIGSELRPLKVMSSVSTAC;

(SEQ ID NO: 105)
MAQVSRICNGVWNPSLISNLSKSSQRKSPLSVSLKTQQHPRAYPISSSWGL

KKSGMTLIGSELRPLKVMSSVSTAC;
```

```
                                      (SEQ ID NO: 106)
MAQINNMAQGIQTLNPNSNFHKPQVPKSSSFLVFGSKKLKNSANSMLVLKK

DSIFMQLFCSFRISASVATAC;

(SEQ ID NO: 107)
MAALVTSQLATSGTVLSVTDRFRRPGFQGLRPRNPADAALGMRTVGASAAP

KQSRKPHRFDRRCLSMVV;

(SEQ ID NO: 108)
MAALTTSQLATSATGFGIADRSAPSSLLRHGFQGLKPRSPAGGDATSLSVT

TSARATPKQQRSVQRGSRRFPSVVVC;

(SEQ ID NO: 109)
MASSVLSSAAVATRSNVAQANMVAPFTGLKSAASFPVSRKQNLDITSIASN

GGRVQC;

(SEQ ID NO: 110)
MESLAATSVFAPSRVAVPAARALVRAGTVVPTRRTSSTSGTSGVKCSAAVT

PQASPVISRSAAAA;
and
                                      (SEQ ID NO: 111)
MGAAATSMQSLKFSNRLVPPSRRLSPVPNNVTCNNLPKSAAPVRTVKCCAS

SWNSTINGAAATTNGASAASS.
```

In some case, a CasZ fusion polypeptide of the present disclosure comprises: a) a CasZ polypeptide of the present disclosure; and b) a chloroplast transit peptide. Thus, for example, a CRISPR-CasZ complex can be targeted to the chloroplast. In some cases, this targeting may be achieved by the presence of an N-terminal extension, called a chloroplast transit peptide (CTP) or plastid transit peptide. Chromosomal transgenes from bacterial sources must have a sequence encoding a CTP sequence fused to a sequence encoding an expressed polypeptide if the expressed polypeptide is to be compartmentalized in the plant plastid (e.g. chloroplast). Accordingly, localization of an exogenous polypeptide to a chloroplast is often 1 accomplished by means of operably linking a polynucleotide sequence encoding a CTP sequence to the 5' region of a polynucleotide encoding the exogenous polypeptide. The CTP is removed in a processing step during translocation into the plastid. Processing efficiency may, however, be affected by the amino acid sequence of the CTP and nearby sequences at the NH 2 terminus of the peptide. Other options for targeting to the chloroplast which have been described are the maize cab-m7 signal sequence (U.S. Pat. No. 7,022,896, WO 97/41228) a pea glutathione reductase signal sequence (WO 97/41228) and the CTP described in US2009029861.

In some cases, a CasZ fusion polypeptide of the present disclosure can comprise: a) a CasZ polypeptide of the present disclosure; and b) an endosomal escape peptide. In some cases, an endosomal escape polypeptide comprises the amino acid sequence GLFXALLXLLXSLWXLLLXA (SEQ ID NO: 112), wherein each X is independently selected from lysine, histidine, and arginine. In some cases, an endosomal escape polypeptide comprises the amino acid sequence GLFHALLHLLHSLWHLLLHA (SEQ ID NO: 113).

For examples of some of the above fusion partners (and more) used in the context of fusions with Cas9, Zinc Finger, and/or TALE proteins (for site specific target nucleic modification, modulation of transcription, and/or target protein modification, e.g., histone modification), see, e.g.: Nomura et al, J Am Chem Soc. 2007 Jul. 18; 129(28):8676-7; Rivenbark et al., Epigenetics. 2012 April; 7(4):350-60; Nucleic Acids Res. 2016 Jul. 8; 44(12):5615-28; Gilbert et al., Cell. 2013 Jul. 18; 154(2):442-51; Kearns et al., Nat Methods. 2015 May; 12(5):401-3; Mendenhall et al., Nat Biotechnol. 2013 December; 31(12):1133-6; Hilton et al., Nat Biotechnol. 2015 May; 33(5):510-7; Gordley et al., Proc Natl Acad Sci USA. 2009 Mar. 31; 106(13):5053-8; Akopian et al., Proc Natl Acad Sci USA. 2003 Jul. 22; 100(15):8688-91; Tan et., al., J Virol. 2006 February; 80(4):1939-48; Tan et al., Proc Natl Acad Sci USA. 2003 Oct. 14; 100(21): 11997-2002; Papworth et al., Proc Natl Acad Sci USA. 2003 Feb. 18; 100(4):1621-6; Sanjana et al., Nat Protoc. 2012 Jan. 5; 7(1):171-92; Beerli et al., Proc Natl Acad Sci USA. 1998 Dec. 8; 95(25):14628-33; Snowden et al., Curr Biol. 2002 Dec. 23; 12(24):2159-66; Xu et. al., Xu et al., Cell Discov. 2016 May 3; 2:16009; Komor et al., Nature. 2016 Apr. 20; 533(7603):420-4; Chaikind et al., Nucleic Acids Res. 2016 Aug. 11; Choudhury at. al., Oncotarget. 2016 Jun. 23; Du et al., Cold Spring Harb Protoc. 2016 Jan. 4; Pham et al., Methods Mol Biol. 2016; 1358:43-57; Balboa et al., Stem Cell Reports. 2015 Sep. 8; 5(3):448-59; Hara et al., Sci Rep. 2015 Jun. 9; 5:11221; Piatek et al., Plant Biotechnol J. 2015 May; 13(4):578-89; Hu et al., Nucleic Acids Res. 2014 April; 42(7):4375-90; Cheng et al., Cell Res. 2013 October; 23(10):1163-71; and Maeder et al., Nat Methods. 2013 October; 10(10):977-9.

Additional suitable heterologous polypeptides include, but are not limited to, a polypeptide that directly and/or indirectly provides for increased transcription and/or translation of a target nucleic acid (e.g., a transcription activator or a fragment thereof, a protein or fragment thereof that recruits a transcription activator, a small molecule/drug-responsive transcription and/or translation regulator, a translation-regulating protein, etc.). Non-limiting examples of heterologous polypeptides to accomplish increased or decreased transcription include transcription activator and transcription repressor domains. In some such cases, a chimeric CasZ polypeptide is targeted by the guide nucleic acid (guide RNA) to a specific location (i.e., sequence) in the target nucleic acid and exerts locus-specific regulation such as blocking RNA polymerase binding to a promoter (which selectively inhibits transcription activator function), and/or modifying the local chromatin status (e.g., when a fusion sequence is used that modifies the target nucleic acid or modifies a polypeptide associated with the target nucleic acid). In some cases, the changes are transient (e.g., transcription repression or activation). In some cases, the changes are inheritable (e.g., when epigenetic modifications are made to the target nucleic acid or to proteins associated with the target nucleic acid, e.g., nucleosomal histones).

Non-limiting examples of heterologous polypeptides for use when targeting ssRNA target nucleic acids include (but are not limited to): splicing factors (e.g., RS domains); protein translation components (e.g., translation initiation, elongation, and/or release factors; e.g., eIF4G); RNA methylases; RNA editing enzymes (e.g., RNA deaminases, e.g., adenosine deaminase acting on RNA (ADAR), including A to I and/or C to U editing enzymes); helicases; RNA-binding proteins; and the like. It is understood that a heterologous polypeptide can include the entire protein or in some cases can include a fragment of the protein (e.g., a functional domain).

The heterologous polypeptide of a subject chimeric CasZ polypeptide can be any domain capable of interacting with ssRNA (which, for the purposes of this disclosure, includes intramolecular and/or intermolecular secondary structures, e.g., double-stranded RNA duplexes such as hairpins, stem-loops, etc.), whether transiently or irreversibly, directly or indirectly, including but not limited to an effector domain selected from the group comprising; Endonucleases (for example RNase III, the CRR22 DYW domain, Dicer, and PIN (PilT N-terminus) domains from proteins such as SMG5 and SMG6); proteins and protein domains responsible for stimulating RNA cleavage (for example CPSF, CstF, CFIm and CFIIm); Exonucleases (for example XRN-1 or Exonuclease T); Deadenylases (for example HNT3); proteins and protein domains responsible for nonsense mediated RNA decay (for example UPF1, UPF2, UPF3, UPF3b, RNP S1, Y14, DEK, REF2, and SRm160); proteins and protein domains responsible for stabilizing RNA (for example PABP); proteins and protein domains responsible for repressing translation (for example Ago2 and Ago4); proteins and protein domains responsible for stimulating translation (for example Staufen); proteins and protein domains responsible for (e.g., capable of) modulating translation (e.g., translation factors such as initiation factors, elongation factors, release factors, etc., e.g., eIF4G); proteins and protein domains responsible for polyadenylation of RNA (for example PAP1, GLD-2, and Star-PAP); proteins and protein domains responsible for polyuridinylation of RNA (for example CI D1 and terminal uridylate transferase); proteins and protein domains responsible for RNA localization (for example from IMP1, ZBP1, She2p, She3p, and Bicaudal-D); proteins and protein domains responsible for nuclear retention of RNA (for example Rrp6); proteins and protein domains responsible for nuclear export of RNA (for example TAP, NXF1, THO, TREX, REF, and Aly); proteins and protein domains responsible for repression of RNA splicing (for example PTB, Sam68, and hnRNP A1); proteins and protein domains responsible for stimulation of RNA splicing (for example Serine/Arginine-rich (SR) domains); proteins and protein domains responsible for reducing the efficiency of transcription (for example FUS (TLS)); and proteins and protein domains responsible for stimulating transcription (for example CDK7 and HIV Tat). Alternatively, the effector domain may be selected from the group comprising Endonucleases; proteins and protein domains capable of stimulating RNA cleavage; Exonucleases; Deadenylases; proteins and protein domains having nonsense mediated RNA decay activity; proteins and protein domains capable of stabilizing RNA; proteins and protein domains capable of repressing translation; proteins and protein domains capable of stimulating translation; proteins and protein domains capable of modulating translation (e.g., translation factors such as initiation factors, elongation factors, release factors, etc., e.g., eIF4G); proteins and protein domains capable of polyadenylation of RNA; proteins and protein domains capable of polyuridinylation of RNA; proteins and protein domains having RNA localization activity; proteins and protein domains capable of nuclear retention of RNA; proteins and protein domains having RNA nuclear export activity; proteins and protein domains capable of repression of RNA splicing; proteins and protein domains capable of stimulation of RNA splicing; proteins and protein domains capable of reducing the efficiency of transcription; and proteins and protein domains capable of stimulating transcription. Another suitable heterologous polypeptide is a PUF RNA-binding domain, which is described in more detail in WO2012068627, which is hereby incorporated by reference in its entirety.

Some RNA splicing factors that can be used (in whole or as fragments thereof) as heterologous polypeptides for a chimeric CasZ polypeptide have modular organization, with separate sequence-specific RNA binding modules and splicing effector domains. For example, members of the Serine/Arginine-rich (SR) protein family contain N-terminal RNA recognition motifs (RRMs) that bind to exonic splicing enhancers (ESEs) in pre-mRNAs and C-terminal RS domains that promote exon inclusion. As another example, the hnRNP protein hnRNP A1 binds to exonic splicing silencers (ESSs) through its RRM domains and inhibits exon inclusion through a C-terminal Glycine-rich domain. Some splicing factors can regulate alternative use of splice site (ss) by binding to regulatory sequences between the two alternative sites. For example, ASF/SF2 can recognize ESEs and promote the use of intron proximal sites, whereas hnRNP A1 can bind to ESSs and shift splicing towards the use of intron distal sites. One application for such factors is to generate ESFs that modulate alternative splicing of endogenous genes, particularly disease associated genes. For example, Bcl-x pre-mRNA produces two splicing isoforms with two alternative 5' splice sites to encode proteins of opposite functions. The long splicing isoform Bcl-xL is a potent apoptosis inhibitor expressed in long-lived postmitotic cells and is up-regulated in many cancer cells, protecting cells against apoptotic signals. The short isoform Bcl-xS is a pro-apoptotic isoform and expressed at high levels in cells with a high turnover rate (e.g., developing lymphocytes). The ratio of the two Bcl-x splicing isoforms is regulated by multiple cω-elements that are located in either the core exon region or the exon extension region (i.e., between the two alternative 5' splice sites). For more examples, see WO2010075303, which is hereby incorporated by reference in its entirety.

Further suitable fusion partners include, but are not limited to, proteins (or fragments thereof) that are boundary elements (e.g., CTCF), proteins and fragments thereof that provide periphery recruitment (e.g., Lamin A, Lamin B, etc.), protein docking elements (e.g., FKBP/FRB, Pil1/Aby1, etc.).

Examples of various additional suitable heterologous polypeptide (or fragments thereof) for a subject chimeric CasZ polypeptide include, but are not limited to those described in the following applications (which publications are related to other CRISPR endonucleases such as Cas9, but the described fusion partners can also be used with CasZ instead): PCT patent applications: WO2010075303, WO2012068627, and WO2013155555, and can be found, for example, in U.S. patents and patent applications: U.S. Pat. Nos. 8,906,616; 8,895,308; 8,889,418; 8,889,356; 8,871,445; 8,865,406; 8,795,965; 8,771,945; 8,697,359; 20140068797; 20140170753; 20140179006; 20140179770; 20140186843; 20140186919; 20140186958; 20140189896; 20140227787; 20140234972; 20140242664; 20140242699; 20140242700; 20140242702; 20140248702; 20140256046; 20140273037; 20140273226; 20140273230; 20140273231; 20140273232; 20140273233; 20140273234; 20140273235; 20140287938; 20140295556; 20140295557; 20140298547; 20140304853; 20140309487; 20140310828; 20140310830; 20140315985; 20140335063; 20140335620; 20140342456; 20140342457; 20140342458; 20140349400; 20140349405; 20140356867; 20140356956; 20140356958; 20140356959; 20140357523; 20140357530; 20140364333; and 20140377868; all of which are hereby incorporated by reference in their entirety.

In some cases, a heterologous polypeptide (a fusion partner) provides for subcellular localization, i.e., the heterologous polypeptide contains a subcellular localization sequence (e.g., a nuclear localization signal (NLS) for targeting to the nucleus, a sequence to keep the fusion protein out of the nucleus, e.g., a nuclear export sequence (NES), a sequence to keep the fusion protein retained in the cytoplasm, a mitochondrial localization signal for targeting to the mitochondria, a chloroplast localization signal for targeting to a chloroplast, an ER retention signal, and the like). In some embodiments, a CasZ fusion polypeptide does not include a NLS so that the protein is not targeted to the nucleus (which can be advantageous, e.g., when the target nucleic acid is an RNA that is present in the cyosol). In some embodiments, the heterologous polypeptide can provide a tag (i.e., the heterologous polypeptide is a detectable label) for ease of tracking and/or purification (e.g., a fluorescent protein, e.g., green fluorescent protein (GFP), YFP, RFP, CFP, mCherry, tdTomato, and the like; a histidine tag, e.g., a 6×His tag; a hemagglutinin (HA) tag; a FLAG tag; a Myc tag; and the like).

In some cases a CasZ protein (e.g., a wild type CasZ protein, a variant CasZ protein, a chimeric CasZ protein, a dCasZ protein, a chimeric CasZ protein where the CasZ portion has reduced nuclease activity—such as a dCasZ protein fused to a fusion partner, and the like) includes (is fused to) a nuclear localization signal (NLS) (e.g, in some cases 2 or more, 3 or more, 4 or more, or 5 or more NLSs). Thus, in some cases, a CasZ polypeptide includes one or more NLSs (e.g., 2 or more, 3 or more, 4 or more, or 5 or more NLSs). In some cases, one or more NLSs (2 or more, 3 or more, 4 or more, or 5 or more NLSs) are positioned at or near (e.g., within 50 amino acids of) the N-terminus and/or the C-terminus. In some cases, one or more NLSs (2 or more, 3 or more, 4 or more, or 5 or more NLSs) are positioned at or near (e.g., within 50 amino acids of) the N-terminus. In some cases, one or more NLSs (2 or more, 3 or more, 4 or more, or 5 or more NLSs) are positioned at or near (e.g., within 50 amino acids of) the C-terminus. In some cases, one or more NLSs (3 or more, 4 or more, or 5 or more NLSs) are positioned at or near (e.g., within 50 amino acids of) both the N-terminus and the C-terminus. In some cases, an NLS is positioned at the N-terminus and an NLS is positioned at the C-terminus.

In some cases a CasZ protein (e.g., a wild type CasZ protein, a variant CasZ protein, a chimeric CasZ protein, a dCasZ protein, a chimeric CasZ protein where the CasZ portion has reduced nuclease activity—such as a dCasZ protein fused to a fusion partner, and the like) includes (is fused to) between 1 and 10 NLSs (e.g., 1-9, 1-8, 1-7, 1-6, 1-5, 2-10, 2-9, 2-8, 2-7, 2-6, or 2-5 NLSs). In some cases a CasZ protein (e.g., a wild type CasZ protein, a variant CasZ protein, a chimeric CasZ protein, a dCasZ protein, a chimeric CasZ protein where the CasZ portion has reduced nuclease activity—such as a dCasZ protein fused to a fusion partner, and the like) includes (is fused to) between 2 and 5 NLSs (e.g., 2-4, or 2-3 NLSs).

Non-limiting examples of NLSs include an NLS sequence derived from: the NLS of the SV40 virus large T-antigen, having the amino acid sequence PKKKRKV (SEQ ID NO: 114); the NLS from nucleoplasmin (e.g., the nucleoplasmin bipartite NLS with the sequence KRPAATKKAGQAKKKK (SEQ ID NO: 115)); the c-myc NLS having the amino acid sequence PAAKRVKLD (SEQ ID NO: 116) or RQRRNELKRSP (SEQ ID NO: 117); the hRNPA1 M9 NLS having the sequence NQSSNFGPMKGGNFG-GRSSGPYGGGGQYFAKPRNQGGY (SEQ ID NO: 118); the sequence RMRIZFKNKGKDTAELRRRRVEVS-VELRKAKKDEQILKRRNV (SEQ ID NO: 119) of the IBB domain from importin-alpha; the sequences VSRKRPRP (SEQ ID NO: 120) and PPKKARED (SEQ ID NO: 121) of the myoma T protein; the sequence PQPKKKPL (SEQ ID NO: 122) of human p53; the sequence SALIKKKKKMAP (SEQ ID NO: 123) of mouse c-abl IV; the sequences DRLRR (SEQ ID NO: 124) and PKQKKRK (SEQ ID NO: 125) of the influenza virus NS1; the sequence RKLKK-KIKKL (SEQ ID NO: 126) of the Hepatitis virus delta antigen; the sequence REKKKFLKRR (SEQ ID NO: 127) of the mouse Mx1 protein; the sequence KRKGDEVDGVDEVAKKKSKK (SEQ ID NO: 128) of the human poly(ADP-ribose) polymerase; and the sequence RKCLQAGMNLEARKTKK (SEQ ID NO: 129) of the steroid hormone receptors (human) glucocorticoid. In general, NLS (or multiple NLSs) are of sufficient strength to drive accumulation of the CasZ protein in a detectable amount in the nucleus of a eukaryotic cell. Detection of accumulation in the nucleus may be performed by any suitable technique. For example, a detectable marker may be fused to the CasZ protein such that location within a cell may be visualized. Cell nuclei may also be isolated from cells, the contents of which may then be analyzed by any suitable process for detecting protein, such as immunohistochemistry, Western blot, or enzyme activity assay. Accumulation in the nucleus may also be determined indirectly.

In some cases, a CasZ fusion polypeptide includes a "Protein Transduction Domain" or PTD (also known as a CPP—cell penetrating peptide), which refers to a polypeptide, polynucleotide, carbohydrate, or organic or inorganic compound that facilitates traversing a lipid bilayer, micelle, cell membrane, organelle membrane, or vesicle membrane. A PTD attached to another molecule, which can range from a small polar molecule to a large macromolecule and/or a nanoparticle, facilitates the molecule traversing a membrane, for example going from extracellular space to intracellular space, or cytosol to within an organelle. In some embodiments, a PTD is covalently linked to the amino terminus a polypeptide (e.g., linked to a wild type CasZ to generate a fusino protein, or linked to a variant CasZ protein such as a dCasZ, nickase CasZ, or chimeric CasZ protein to generate a fusion protein). In some embodiments, a PTD is covalently linked to the carboxyl terminus of a polypeptide (e.g., linked to a wild type CasZ to generate a fusino protein, or linked to a variant CasZ protein such as a dCasZ, nickase CasZ, or chimeric CasZ protein to generate a fusion protein). In some cases, the PTD is inserted internally in the CasZ fusion polypeptide (i.e., is not at the N- or C-terminus of the CasZ fusion polypeptide) at a suitable insertion site. In some cases, a subject CasZ fusion polypeptide includes (is conjugated to, is fused to) one or more PTDs (e.g., two or more, three or more, four or more PTDs). In some cases, a PTD includes a nuclear localization signal (NLS) (e.g, in some cases 2 or more, 3 or more, 4 or more, or 5 or more NLSs). Thus, in some cases, a CasZ fusion polypeptide includes one or more NLSs (e.g., 2 or more, 3 or more, 4 or more, or 5 or more NLSs). In some cases, a PTD is covalently linked to a nucleic acid (e.g., a CasZ guide nucleic acid, a polynucleotide encoding a CasZ guide nucleic acid, a polynucleotide encoding a CasZ fusion polypeptide, a donor polynucleotide, etc.). Examples of PTDs include but are not limited to a minimal undecapeptide protein transduction domain (corresponding to residues 47-57 of HIV-1 TAT comprising YGRKKRRQRRR; SEQ ID NO: 130); a polyarginine sequence comprising a number of arginines sufficient to direct entry into a cell (e.g., 3, 4, 5, 6, 7, 8, 9, 10, or 10-50 arginines); a VP22 domain (Zender et al. (2002) *Cancer Gene Ther.* 9(6):489-96); an Drosophila Antennapedia protein transduction domain (Noguchi et al. (2003) *Diabetes* 52(7):1732-1737); a truncated human calcitonin peptide (Trehin et al. (2004) *Pharm. Research* 21:1248-1256); polylysine (Wender et al. (2000) *Proc. Natl. Acad. Sci. USA* 97:13003-13008); RRQRRTSKLMKR (SEQ ID NO: 131); Transportan GWTLNSAGYLLGKINLKA-LAALAKKIL (SEQ ID NO: 132); KALAWEAKLAKA-LAKALAKHLAKALAKALKCEA (SEQ ID NO: 133); and RQIKIWFQNRRMKWKK (SEQ ID NO: 134). Exemplary PTDs include but are not limited to, YGRKKRRQRRR (SEQ ID NO: 130), RKKRRQRRR (SEQ ID NO: 135); an arginine homopolymer of from 3 arginine residues to 50 arginine residues; Exemplary PTD domain amino acid sequences include, but are not limited to, any of the following: YGRKKRRQRRR (SEQ ID NO: 130); RKKRRQRR (SEQ ID NO: 136); YARAAARQARA (SEQ ID NO: 137); THRLPRRRRRR (SEQ ID NO: 138); and GGR-RARRRRRR (SEQ ID NO: 139). In some embodiments, the PTD is an activatable CPP (ACPP) (Aguilera et al. (2009) *Integr Biol (Camb)* June; 1(5-6): 371-381). ACPPs comprise a polycationic CPP (e.g., Arg9 or "R9") connected via a cleavable linker to a matching polyanion (e.g., Glu9 or "E9"), which reduces the net charge to nearly zero and thereby inhibits adhesion and uptake into cells. Upon cleavage of the linker, the polyanion is released, locally unmasking the polyarginine and its inherent adhesiveness, thus "activating" the ACPP to traverse the membrane.

Linkers (e.g., for Fusion Partners)

In some instances, a subject CasZ protein is fused to a fusion partner via a linker polypeptide (e.g., one or more linker polypeptides). The linker polypeptide may have any of a variety of amino acid sequences. Proteins can be joined by a spacer peptide, generally of a flexible nature, although other chemical linkages are not excluded. Suitable linkers include polypeptides of between 4 amino acids and 40 amino acids in length, or between 4 amino acids and 25 amino acids in length. These linkers can be produced by using synthetic, linker-encoding oligonucleotides to couple the proteins, or can be encoded by a nucleic acid sequence encoding the fusion protein. Peptide linkers with a degree of flexibility can be used. The linking peptides may have virtually any amino acid sequence, bearing in mind that the preferred linkers will have a sequence that results in a generally flexible peptide. The use of small amino acids, such as glycine and alanine, are of use in creating a flexible peptide. The creation of such sequences is routine to those of skill in the art. A variety of different linkers are commercially available and are considered suitable for use.

Examples of linker polypeptides include glycine polymers $(G)_n$, glycine-serine polymers (including, for example, $(GS)_n$, $GSGGS_n$ (SEQ ID NO: 140), $GGSGGS_n$ (SEQ ID NO: 141), and $GGGS_n$ (SEQ ID NO: 142), where n is an integer of at least one), glycine-alanine polymers, alanine-serine polymers. Exemplary linkers can comprise amino acid sequences including, but not limited to, GGSG (SEQ ID NO: 143), GGSGG (SEQ ID NO: 144), GSGSG (SEQ ID NO: 145), GSGGG (SEQ ID NO: 146), GGGSG (SEQ ID NO: 147), GSSSG (SEQ ID NO: 148), and the like. The ordinarily skilled artisan will recognize that design of a peptide conjugated to any desired element can include linkers that are all or partially flexible, such that the linker can include a flexible linker as well as one or more portions that confer less flexible structure.

Detectable Labels

In some cases, a CasZ polypeptide of the present disclosure comprises (e.g., can be attached/fused to) a detectable label. Suitable detectable labels and/or moieties that can provide a detectable signal can include, but are not limited to, an enzyme, a radioisotope, a member of a specific binding pair; a fluorophore; a fluorescent protein; a quantum dot; and the like.

Suitable fluorescent proteins include, but are not limited to, green fluorescent protein (GFP) or variants thereof, blue fluorescent variant of GFP (BFP), cyan fluorescent variant of GFP (CFP), yellow fluorescent variant of GFP (YFP), enhanced GFP (EGFP), enhanced CFP (ECFP), enhanced YFP (EYFP), GFPS65T, Emerald, Topaz (TYFP), Venus, Citrine, mCitrine, GFPuv, destabilised EGFP (dEGFP), destabilised ECFP (dECFP), destabilised EYFP (dEYFP), mCFPm, Cerulean, T-Sapphire, CyPet, YPet, mKO, HcRed, t-HcRed, DsRed, DsRed2, DsRed-monomer, J-Red, dimer2, t-dimer2(12), mRFP1, pocilloporin, Renilla GFP, Monster GFP, paGFP, Kaede protein and kindling protein, Phycobiliproteins and Phycobiliprotein conjugates including B-Phycoerythrin, R-Phycoerythrin and Allophycocyanin. Other examples of fluorescent proteins include mHoneydew, mBanana, mOrange, dTomato, tdTomato, mTangerine, mStrawberry, mCherry, mGrape1, mRaspberry, mGrape2, mPlum (Shaner et al. (2005) Nat. Methods 2:905-909), and the like. Any of a variety of fluorescent and colored proteins from Anthozoan species, as described in, e.g., Matz et al. (1999) Nature Biotechnol. 17:969-973, is suitable for use.

Suitable enzymes include, but are not limited to, horse radish peroxidase (HRP), alkaline phosphatase (AP), beta-galactosidase (GAL), glucose-6-phosphate dehydrogenase, beta-N-acetylglucosaminidase, 0-glucuronidase, invertase, Xanthine Oxidase, firefly luciferase, glucose oxidase (GO), and the like.

Protospacer Adjacent Motif (PAM)

A natural CasZ protein binds to target DNA at a target sequence defined by the region of complementarity between the DNA-targeting RNA and the target DNA. As is the case for many CRISPR endonucleases, site-specific binding (and/or cleavage) of a double stranded target DNA occurs at locations determined by both (i) base-pairing complementarity between the guide RNA and the target DNA; and (ii) a short motif [referred to as the protospacer adjacent motif (PAM)] in the target DNA.

In some cases, the PAM for a CasZ protein is immediately 5' of the target sequence of the non-complementary strand of the target DNA (also referred to as the non-target strand; the complementary strand hybridizes to the guide sequence of the guide RNA while the non-complementary strand does not directly hybridize with the guide RNA and is the reverse complement of the non-complementary strand). In some cases (e.g., for CasZc), the PAM sequence of the non-complementary strand is 5'-TTA-3'. In some cases (e.g., for CasZb), the PAM sequence of the non-complementary strand is 5'-TTTN-3'. In some cases (e.g., for CasZb), the PAM sequence of the non-complementary strand is 5'-TTTA-3'.

In some cases, different CasZ proteins (i.e., CasZ proteins from various species) may be advantageous to use in the various provided methods in order to capitalize on various enzymatic characteristics of the different CasZ proteins (e.g., for different PAM sequence preferences; for increased or decreased enzymatic activity; for an increased or decreased level of cellular toxicity; to change the balance between NHEJ, homology-directed repair, single strand breaks, double strand breaks, etc.; to take advantage of a short total sequence; and the like). CasZ proteins from different species may require different PAM sequences in the target DNA. Thus, for a particular CasZ protein of choice, the PAM sequence preference may be different than the sequence(s) described above. Various methods (including in silico and/or wet lab methods) for identification of the appropriate PAM sequence are known in the art and are routine, and any convenient method can be used.

CasZ Guide RNA

A nucleic acid molecule that binds to a CasZ protein, forming a ribonucleoprotein complex (RNP), and targets the complex to a specific location within a target nucleic acid (e.g., a target DNA) is referred to herein as a "CasZ guide RNA" or simply as a "guide RNA." It is to be understood that in some cases, a hybrid DNA/RNA can be made such that a CasZ guide RNA includes DNA bases in addition to RNA bases, but the term "CasZ guide RNA" is still used to encompass such a molecule herein.

A CasZ guide RNA can be said to include two segments, a targeting segment and a protein-binding segment. The targeting segment of a CasZ guide RNA includes a nucleotide sequence (a guide sequence) that is complementary to (and therefore hybridizes with) a specific sequence (a target site) within a target nucleic acid (e.g., a target ssRNA, a target ssDNA, the complementary strand of a double stranded target DNA, etc.). The protein-binding segment (or "protein-binding sequence") interacts with (binds to) a CasZ polypeptide. The protein-binding segment of a subject CasZ guide RNA includes two complementary stretches of nucleotides that hybridize to one another to form a double stranded RNA duplex (dsRNA duplex). Site-specific binding and/or cleavage of a target nucleic acid (e.g., genomic DNA) can occur at locations (e.g., target sequence of a target locus) determined by base-pairing complementarity between the CasZ guide RNA (the guide sequence of the CasZ guide RNA) and the target nucleic acid.

A CasZ guide RNA and a CasZ protein, e.g., a fusion CasZ polypeptide, form a complex (e.g., bind via non-covalent interactions). The CasZ guide RNA provides target specificity to the complex by including a targeting segment, which includes a guide sequence (a nucleotide sequence that is complementary to a sequence of a target nucleic acid). The CasZ protein of the complex provides the site-specific activity (e.g., cleavage activity provided by the CasZ protein and/or an activity provided by the fusion partner in the case of a chimeric CasZ protein). In other words, the CasZ protein is guided to a target nucleic acid sequence (e.g. a target sequence) by virtue of its association with the CasZ guide RNA.

The "guide sequence" also referred to as the "targeting sequence" of a CasZ guide RNA can be modified so that the CasZ guide RNA can target a CasZ protein (e.g., a naturally occurring CasZ protein, a fusion CasZ polypeptide (chimeric CasZ), and the like) to any desired sequence of any desired target nucleic acid, with the exception (e.g., as described herein) that the PAM sequence can be taken into account. Thus, for example, a CasZ guide RNA can have a guide sequence with complementarity to (e.g., can hybridize to) a sequence in a nucleic acid in a eukaryotic cell, e.g., a viral nucleic acid, a eukaryotic nucleic acid (e.g., a eukaryotic chromosome, chromosomal sequence, a eukaryotic RNA, etc.), and the like.

In some cases, a CasZ guide RNA has a length of 30 nucleotides (nt) or more (e.g., 35 nt or more, 40 nt or more, 45 nt or more, 50 nt or more, 55 nt or more, or 60 nt or more). In some embodiments, a CasZ guide RNA has a length of 40 nucleotides (nt) or more (e.g., 45 nt or more, 50 nt or more, 55 nt or more, or 60 nt or more). In some cases, a CasZ guide RNA has a length of from 30 nucleotides (nt) to 100 nt (e.g., 30-90, 30-80, 30-75, 30-70, 30-65, 40-100, 40-90, 40-80, 40-75, 40-70, or 40-65). In some cases, a CasZ guide RNA has a length of from 40 nucleotides (nt) to 100 nt (e.g., 40-90, 40-80, 40-75, 40-70, or 40-65 nt).

Guide Sequence of a CasZ Guide RNA

A subject CasZ guide RNA includes a guide sequence (i.e., a targeting sequence), which is a nucleotide sequence that is complementary to a sequence (a target site) in a target nucleic acid. In other words, the guide sequence of a CasZ guide RNA can interact with a target nucleic acid (e.g., double stranded DNA (dsDNA), single stranded DNA (ssDNA), single stranded RNA (ssRNA), or double stranded RNA (dsRNA)) in a sequence-specific manner via hybridization (i.e., base pairing). The guide sequence of a CasZ guide RNA can be modified (e.g., by genetic engineering)/designed to hybridize to any desired target sequence (e.g., while taking the PAM into account, e.g., when targeting a dsDNA target) within a target nucleic acid (e.g., a eukaryotic target nucleic acid such as genomic DNA).

In some cases, the percent complementarity between the guide sequence and the target site of the target nucleic acid is 60% or more (e.g., 65% or more, 70% or more, 75% or more, 80% or more, 85% or more, 90% or more, 95% or more, 97% or more, 98% or more, 99% or more, or 100%). In some cases, the percent complementarity between the guide sequence and the target site of the target nucleic acid is 80% or more (e.g., 85% or more, 90% or more, 95% or more, 97% or more, 98% or more, 99% or more, or 100%). In some cases, the percent complementarity between the guide sequence and the target site of the target nucleic acid is 90% or more (e.g., 95% or more, 97% or more, 98% or more, 99% or more, or 100%). In some cases, the percent complementarity between the guide sequence and the target site of the target nucleic acid is 100%.

In some cases, the percent complementarity between the guide sequence and the target site of the target nucleic acid is 100% over the seven contiguous 3'-most nucleotides of the target site of the target nucleic acid.

In some cases, the percent complementarity between the guide sequence and the target site of the target nucleic acid is 60% or more (e.g., 70% or more, 75% or more, 80% or more, 85% or more, 90% or more, 95% or more, 97% or more, 98% or more, 99% or more, or 100%) over 17 or more (e.g., 18 or more, 19 or more, 20 or more, 21 or more, 22 or more) contiguous nucleotides. In some cases, the percent complementarity between the guide sequence and the target site of the target nucleic acid is 80% or more (e.g., 85% or more, 90% or more, 95% or more, 97% or more, 98% or more, 99% or more, or 100%) over 17 or more (e.g., 18 or more, 19 or more, 20 or more, 21 or more, 22 or more) contiguous nucleotides. In some cases, the percent complementarity between the guide sequence and the target site of the target nucleic acid is 90% or more (e.g., 95% or more, 97% or more, 98% or more, 99% or more, or 100%) over 17 or more (e.g., 18 or more, 19 or more, 20 or more, 21 or more, 22 or more) contiguous nucleotides. In some cases, the percent complementarity between the guide sequence and the target site of the target nucleic acid is 100% over 17 or more (e.g., 18 or more, 19 or more, 20 or more, 21 or more, 22 or more) contiguous nucleotides.

In some cases, the percent complementarity between the guide sequence and the target site of the target nucleic acid is 60% or more (e.g., 70% or more, 75% or more, 80% or more, 85% or more, 90% or more, 95% or more, 97% or more, 98% or more, 99% or more, or 100%) over 19 or more (e.g., 20 or more, 21 or more, 22 or more) contiguous nucleotides. In some cases, the percent complementarity between the guide sequence and the target site of the target nucleic acid is 80% or more (e.g., 85% or more, 90% or more, 95% or more, 97% or more, 98% or more, 99% or more, or 100%) over 19 or more (e.g., 20 or more, 21 or more, 22 or more) contiguous nucleotides. In some cases, the percent complementarity between the guide sequence and the target site of the target nucleic acid is 90% or more (e.g., 95% or more, 97% or more, 98% or more, 99% or more, or 100%) over 19 or more (e.g., 20 or more, 21 or more, 22 or more) contiguous nucleotides. In some cases, the percent complementarity between the guide sequence and the target site of the target nucleic acid is 100% over 19 or more (e.g., 20 or more, 21 or more, 22 or more) contiguous nucleotides.

In some cases, the percent complementarity between the guide sequence and the target site of the target nucleic acid is 60% or more (e.g., 70% or more, 75% or more, 80% or more, 85% or more, 90% or more, 95% or more, 97% or more, 98% or more, 99% or more, or 100%) over 17-25 contiguous nucleotides. In some cases, the percent complementarity between the guide sequence and the target site of the target nucleic acid is 80% or more (e.g., 85% or more, 90% or more, 95% or more, 97% or more, 98% or more, 99% or more, or 100%) over 17-25 contiguous nucleotides. In some cases, the percent complementarity between the guide sequence and the target site of the target nucleic acid is 90% or more (e.g., 95% or more, 97% or more, 98% or more, 99% or more, or 100%) over 17-25 contiguous nucleotides. In some cases, the percent complementarity between the guide sequence and the target site of the target nucleic acid is 100% over 17-25 contiguous nucleotides.

In some cases, the percent complementarity between the guide sequence and the target site of the target nucleic acid is 60% or more (e.g., 70% or more, 75% or more, 80% or more, 85% or more, 90% or more, 95% or more, 97% or more, 98% or more, 99% or more, or 100%) over 19-25 contiguous nucleotides. In some cases, the percent complementarity between the guide sequence and the target site of the target nucleic acid is 80% or more (e.g., 85% or more, 90% or more, 95% or more, 97% or more, 98% or more, 99% or more, or 100%) over 19-25 contiguous nucleotides. In some cases, the percent complementarity between the guide sequence and the target site of the target nucleic acid is 90% or more (e.g., 95% or more, 97% or more, 98% or more, 99% or more, or 100%) over 19-25 contiguous nucleotides. In some cases, the percent complementarity between the guide sequence and the target site of the target nucleic acid is 100% over 19-25 contiguous nucleotides.

In some cases, the guide sequence has a length in a range of from 17-30 nucleotides (nt) (e.g., from 17-25, 17-22, 17-20, 19-30, 19-25, 19-22, 19-20, 20-30, 20-25, or 20-22 nt). In some cases, the guide sequence has a length in a range of from 17-25 nucleotides (nt) (e.g., from 17-22, 17-20, 19-25, 19-22, 19-20, 20-25, or 20-22 nt). In some cases, the guide sequence has a length of 17 or more nt (e.g., 18 or more, 19 or more, 20 or more, 21 or more, or 22 or more nt; 19 nt, 20 nt, 21 nt, 22 nt, 23 nt, 24 nt, 25 nt, etc.). In some cases, the guide sequence has a length of 19 or more nt (e.g., 20 or more, 21 or more, or 22 or more nt; 19 nt, 20 nt, 21 nt, 22 nt, 23 nt, 24 nt, 25 nt, etc.). In some cases, the guide sequence has a length of 17 nt. In some cases, the guide sequence has a length of 18 nt. In some cases, the guide sequence has a length of 19 nt. In some cases, the guide sequence has a length of 20 nt. In some cases, the guide sequence has a length of 21 nt. In some cases, the guide sequence has a length of 22 nt. In some cases, the guide sequence has a length of 23 nt.

Protein-Binding Segment of a CasZ Guide RNA

The protein-binding segment of a subject CasZ guide RNA interacts with a CasZ protein. The CasZ guide RNA guides the bound CasZ protein to a specific nucleotide sequence within target nucleic acid via the above-mentioned guide sequence. The protein-binding segment of a CasZ guide RNA comprises two stretches of nucleotides that are complementary to one another and hybridize to form a double stranded RNA duplex (dsRNA duplex). Thus, the protein-binding segment includes a dsRNA duplex.

In some cases, the dsRNA duplex region includes a range of from 5-25 base pairs (bp) (e.g., from 5-22, 5-20, 5-18, 5-15, 5-12, 5-10, 5-8, 8-25, 8-22, 8-18, 8-15, 8-12, 12-25, 12-22, 12-18, 12-15, 13-25, 13-22, 13-18, 13-15, 14-25, 14-22, 14-18, 14-15, 15-25, 15-22, 15-18, 17-25, 17-22, or 17-18 bp, e.g., 5 bp, 6 bp, 7 bp, 8 bp, 9 bp, 10 bp, etc.). In some cases, the dsRNA duplex region includes a range of from 6-15 base pairs (bp) (e.g., from 6-12, 6-10, or 6-8 bp, e.g., 6 bp, 7 bp, 8 bp, 9 bp, 10 bp, etc.). In some cases, the duplex region includes 5 or more bp (e.g., 6 or more, 7 or more, or 8 or more bp). In some cases, the duplex region includes 6 or more bp (e.g., 7 or more, or 8 or more bp). In some cases, not all nucleotides of the duplex region are paired, and therefore the duplex forming region can include a bulge. The term "bulge" herein is used to mean a stretch of nucleotides (which can be one nucleotide or multiple nucleotides) that do not contribute to a double stranded duplex, but which are surround 5' and 3' by nucleotides that do contribute, and as such a bulge is considered part of the duplex region. In some cases, the dsRNA includes 1 or more bulges (e.g., 2 or more, 3 or more, 4 or more bulges). In some cases, the dsRNA duplex includes 2 or more bulges (e.g., 3 or more, 4 or more bulges). In some cases, the dsRNA duplex includes 1-5 bulges (e.g., 1-4, 1-3, 2-5, 2-4, or 2-3 bulges).

Thus, in some cases, the stretches of nucleotides that hybridize to one another to form the dsRNA duplex have 70%-100% complementarity (e.g., 75%-100%, 80%-10%, 85%-100%, 90%-100%, 95%-100% complementarity) with one another. In some cases, the stretches of nucleotides that hybridize to one another to form the dsRNA duplex have 70%-100% complementarity (e.g., 75%-100%, 80%-10%, 85%-100%, 90%-100%, 95%-100% complementarity) with one another. In some cases, the stretches of nucleotides that hybridize to one another to form the dsRNA duplex have 85%-100% complementarity (e.g., 90%-100%, 95%-100% complementarity) with one another. In some cases, the stretches of nucleotides that hybridize to one another to form the dsRNA duplex have 70%-95% complementarity (e.g., 75%-95%, 80%-95%, 85%-95%, 90%-95% complementarity) with one another.

In other words, in some embodiments, the dsRNA duplex includes two stretches of nucleotides that have 70%-100% complementarity (e.g., 75%-100%, 80%-10%, 85%-100%, 90%-100%, 95%-100% complementarity) with one another. In some cases, the dsRNA duplex includes two stretches of nucleotides that have 85%-100% complementarity (e.g., 90%-100%, 95%-100% complementarity) with one another. In some cases, the dsRNA duplex includes two stretches of nucleotides that have 70%-95% complementarity (e.g., 75%-95%, 80%-95%, 85%-95%, 90%-95% complementarity) with one another.

The duplex region of a subject CasZ guide RNA can include one or more (1, 2, 3, 4, 5, etc) mutations relative to a naturally occurring duplex region. For example, in some cases a base pair can be maintained while the nucleotides contributing to the base pair from each segment can be different. In some cases, the duplex region of a subject CasZ guide RNA includes more paired bases, less paired bases, a smaller bulge, a larger bulge, fewer bulges, more bulges, or any convenient combination thereof, as compared to a naturally occurring duplex region (of a naturally occurring CasZ guide RNA).

Examples of various Cas9 guide RNAs and cpf1 guide RNAs can be found in the art, and in some cases variations similar to those introduced into Cas9 guide RNAs can also be introduced into CasZ guide RNAs of the present disclosure (e.g., mutations to the dsRNA duplex region, extension of the 5' or 3' end for added stability for to provide for interaction with another protein, and the like). For example, see Jinek et al., Science. 2012 Aug. 17; 337(6096):816-21; Chylinski et al., RNA Biol. 2013 May; 10(5):726-37; Ma et al., Biomed Res Int. 2013; 2013:270805; Hou et al., Proc Natl Acad Sci USA. 2013 Sep. 24; 110(39):15644-9; Jinek et al., Elife. 2013; 2:e00471; Pattanayak et al., Nat Biotechnol. 2013 September; 31(9):839-43; Qi et al, Cell. 2013 Feb. 28; 152(5):1173-83; Wang et al., Cell. 2013 May 9; 153(4):910-8; Auer et al., Genome Res. 2013 Oct. 31; Chen et al., Nucleic Acids Res. 2013 Nov. 1; 41(20):e19; Cheng et al., Cell Res. 2013 October; 23(10):1163-71; Cho et al., Genetics. 2013 November; 195(3):1177-80; DiCarlo et al., Nucleic Acids Res. 2013 April; 41(7):4336-43; Dickinson et al., Nat Methods. 2013 October; 10(10):1028-34; Ebina et al., Sci Rep. 2013; 3:2510; Fujii et. al, Nucleic Acids Res. 2013 Nov. 1; 41(20):e187; Hu et al., Cell Res. 2013 November; 23(11):1322-5; Jiang et al., Nucleic Acids Res. 2013 Nov. 1; 41(20):e188; Larson et al., Nat Protoc. 2013 November; 8(11):2180-96; Mali et. at., Nat Methods. 2013 October; 10(10):957-63; Nakayama et al., Genesis. 2013 December; 51(12):835-43; Ran et al., Nat Protoc. 2013 November; 8(11):2281-308; Ran et al., Cell. 2013 Sep. 12; 154(6):1380-9; Upadhyay et al., G3 (Bethesda). 2013 Dec. 9; 3(12):2233-8; Walsh et al., Proc Natl Acad Sci USA. 2013 Sep. 24; 110(39):15514-5; Xie et al., Mol Plant. 2013 Oct. 9; Yang et al., Cell. 2013 Sep. 12; 154(6):1370-9; Briner et al., Mol Cell. 2014 Oct. 23; 56(2):333-9; and U.S. patents and patent applications: U.S. Pat. Nos. 8,906,616; 8,895,308; 8,889,418; 8,889,356; 8,871,445; 8,865,406; 8,795,965; 8,771,945; 8,697,359; 20140068797; 20140170753; 20140179006; 20140179770; 20140186843; 20140186919; 20140186958; 20140189896; 20140227787; 20140234972; 20140242664; 20140242699; 20140242700; 20140242702; 20140248702; 20140256046; 20140273037; 20140273226; 20140273230; 20140273231; 20140273232; 20140273233; 20140273234; 20140273235; 20140287938; 20140295556; 20140295557; 20140298547; 20140304853; 20140309487; 20140310828; 20140310830; 20140315985; 20140335063; 20140335620; 20140342456; 20140342457; 20140342458; 20140349400; 20140349405; 20140356867; 20140356956; 20140356958; 20140356959; 20140357523; 20140357530; 20140364333; and 20140377868; all of which are hereby incorporated by reference in their entirety.

A CasZ guide RNA comprises both the guide sequence and two stretches ("duplex-forming segments") of nucleotides that hybridize to form the dsRNA duplex of the protein-binding segment. The particular sequence of a given CasZ guide RNA can be characteristic of the species in which a crRNA is found. Examples of suitable CasZ guide RNAs are provided herein.

Example Guide RNA Sequences

Repeat sequences (non-guide sequence portion of a CasZ guide RNA) of crRNAs for naturally existing CasZ proteins (e.g., see FIG. 1 and FIG. 7) are shown in Table 1 and Table 3.

TABLE 1 crRNA repeat sequences for CasZ proteins

| CasZ Protein | Repeat sequence | SEQ ID NO: |
|---|---|---|
| Za.1 | GTTGCATTCCTTCATTCGTCTATTCGGGTTCTGCAAC | 51 |
| Za.2 | GTTGCATTCCTTCATTCGTCTATCCGGGTTCTGCAAG | 52 |
| Za.3 | GTTGCAGAACCCGAATAGACGAATGAAGGAATGCAAC | 53 |
| Za.4 | CTATCATATTCAGAACAAAGGGATTAAGGAATGCAAC | 54 |
| Za.5 | CTTTCATACTCAGAACAAAGGGATTAAGGAATGCAAC | 55 |
| Za.6 | GTCTACAACTCATTGATAGAAATCAATGAGTTAGACA | 56 |
| Za.7 | GTTATAAAGGCGGGATCGCGACCGAGCGATTGAAAG | 57 |
| Zb.1 | GTTGCATTCCTTAATTCATTTTCTCAATATCGGAAAC | 58 |
| Zb.2 | GTTGCAGAAATAGAATAAAGGAATTAAGGAATGCAAC | 59 |
| Zb.3 | CTTTCATACTCAGAACAAAGGGATTAAGGAATGCAAC | 55 |
| Zb.4 | ATTTCATACTCAGAACAAAGGGATTAAGGAATGCAAC | 61 |
| Zb.5 | GTTTCAGCGCACGAATTAACGAGATGAGAGATGCAACT | 62 |
| Zb.6 | CTTGCAGAAGCTGAATAGACGAATCAAGGAATGCAAC | 63 |
| Zb.7 | CACTTGCAGGCCTTGAATAGAGGAGTTAAGGAATGCAAC | 64 |
| Zb.8 | GTCTCCATGACTGAAAAGTCGTGGCCGAATTGAAAC | 65 |
| Zb.9 | GTTGCAGCGCCCGAACTGACGAGACGAGAGATGCAAC | 66 |
| Zb.10 | GTTGCGCGAATAGAATAAAGGAATTAAGGAATGCAAC | 67 |
| Zb.11 | AGTTGCATTCCTTAATCCCTCTGTTCAGTTTGTGCAAT | 68 |
| Zc.1 | GTTGCATTCCTAGTTTCTCTAATTAGCACTGTGCAAC | 69 |
| Zc.2 | GTTGCGGCGCGCGAATAAACGAGACTAGGAATGCAAC | 70 |
| Zc.3 | ACTAGTTGCATTCCTTAATCCCTTTGTTCTGAATATGCTAG | 71 |
| Zc.4 | CTTTCATATTCAGAACAAAGGGATTAAGGAATGCAAC | 72 |
| Zc.5 | GTTGCAGTCCTTAACCCCTAGTTTCTGAATATGAAAGAT | 73 |
| Zc.6 | GTTGCAGCCCCGAACTAACGAGATGAGAGATGCAAC | 74 |
| Zc.7 | CTTGCAGAACAATCATATATGACTAATCAGACTGCAAC | 75 |
| Zd.1 | GTTGCACTCACCGGTGCTCACGACGTAGGGATGCAAC | 76 |
| Zd.2 | GTCCCTACTCGCTAGGGAAACTAATTGAATGGAAAC | 77 |
| Ze.1 | GTTGCATTCGGGTGCAAAACAGGGAGTAGAGTGTAAC | 78 |
| Ze.2 | CTTCCAAACTCGAGCCAGTGGGGAGAGAAGTGGCA | 79 |
| Ze.3 | CCTGTAGACCGGTCTCATTCTGAGAGGGGTATGCAACT | 80 |
| Ze.4 | GTCTCGAGACCCTACAGATTTTGGAGAGGGGTGGGAC | 81 |
| Ze.4b | GTCCCACCCCTCTCCAAAATCTGTAGGGTCTCGAGAC | 82 |
| Zf.1 | GTAGCAGGACTCTCCTCGAGAGAAACAGGGGTATGCT | 83 |
| Zf.2 | GTACAATACCTCTCCTTTAAGAGAGGGAGGGGTACGCTAC | 84 |

TABLE 1-continued crRNA repeat sequences for CasZ proteins

| CasZ Protein | Repeat sequence | SEQ ID NO: |
|---|---|---|
| Zf.3 | CCCCCTCGTTTCCTTCAGGGGATTCCTTTCC | 85 |
| Zg.1 | GGTTCCCCCGGGCGCGGGTGGGGTGGCG | 86 |
| Zg.2 | GGCTGCTCCGGGTGCGCGTGGAGCGAGG | 87 |
| Zh.1 | GTTTTATACCCTTTAGAATTTAAACTGTCTAAAAG | 88 |
| Zi.1 | ATTGCACCGGCCAACGCAAATCTGATTGATGGACAC | 89 |
| Zi.2 | GCCGCAGCGGCCGACGCGGCCCTGATCGATGGACAC | 90 |
| Zj.1 | GTCGAAATGCCCGCGCGGGGCGTCGTACCCGCGAC | 91 |
| Zk.1 | GGCTAGCCCGTGCGCGCAGGGACGAGTGG | 92 |
| Zk.2 | GCCCGTGCGCGCAGGGACGAGTGG | 93 |
| Zk.3 | GTTGCAGCGGCCGACGGAGCGCGAGCGTGGATGCCAC | 94 |
| Zk.4 | CCATCGCCCCGCGCGCACGTGGATGAGCC | 95 |
| Zl.1 | CTTTAGACTTCTCCGGAAGTCGAATTAATGGAAAC | 96 |
| Zl.2 | GGGCGCCCCGCGCGAGCGGGGGTTGAAG | 97 |
| Za.8 | CTTGCAGAACCCGGATAGACGAATGAAGGAATGCAAC | 295 |
| Zb.12 | CTTGCAGGCCTTGAATAGAGGAGTTAAGGAATGCAAC | 296 |
| Zb.13 | GTTGCACAGTGCTAATTAGAGAAACTAGGAATGCAAC | 297 |
| Zb.14 | CTAGCATATTCAGAACAAAGGGATTAAGGAATGCAAC | 298 |
| Zb.15 | CTTTCATATTCAGAAACTAGGGGTTAAGGACTGCAAC | 299 |
| Zc.8 | GTTGCATCCCTACGTCGTGAGCACCGGTGAGTGCAAC | 300 |
| Ze.5 | GGAAAGGAATCCCCTGAAGGAAACGAGGGGG | 301 |
| Zg.3 | GTGTCCATCAATCAGATTTGCGTTGGCCGGTGCAAT | 302 |
| Zb.16 | GTTTCAGCGCACGAATTAACGAGATGAGAGATGCAAC | 303 |
| Zj.2 | CTTTTAGACAGTTTAAATTCTAAAGGGTATAAAAC | 307 |

In some cases, a subject CasZ guide RNA comprises (e.g., in addition to a guide sequence, e.g., as part of the protein-binding region) a crRNA sequence of Table 1 or Table 3. In some cases, a subject CasZ guide RNA comprises a nucleotide sequence having 70% or more identity (e.g., 75% or more, 80% or more, 85% or more, 90% or more, 93% or more, 95% or more, 97% or more, 98% or more, or 100% identity) with a crRNA sequence of Table 1 or Table 3. In some cases, a subject CasZ guide RNA comprises a nucleotide sequence having 80% or more identity (e.g., 85% or more, 90% or more, 93% or more, 95% or more, 97% or more, 98% or more, or 100% identity) with a crRNA sequence of Table 1 or Table 3. In some cases, a subject CasZ guide RNA comprises a nucleotide sequence having 90% or more identity (e.g., 93% or more, 95% or more, 97% or more, 98% or more, or 100% identity) with a crRNA sequence of Table 1 or Table 3.

In some cases, a subject CasZ guide RNA comprises (e.g., in addition to a guide sequence, e.g., as part of the protein-binding region) a CasZa, CasZb, CasZc, CasZd, CasZe, CasZf, CasZg, CasZh, or CasZi crRNA sequence of Table 1 or Table 3. In some cases, a subject CasZ guide RNA comprises a nucleotide sequence having 70% or more identity (e.g., 75% or more, 80% or more, 85% or more, 90% or more, 93% or more, 95% or more, 97% or more, 98% or more, or 100% identity) with a CasZa, CasZb, CasZc, CasZd, CasZe, CasZf, CasZg, CasZh, or CasZi crRNA sequence of Table 1 or Table 3. In some cases, a subject CasZ guide RNA comprises a nucleotide sequence having 80% or more identity (e.g., 85% or more, 90% or more, 93% or more, 95% or more, 97% or more, 98% or more, or 100% identity) with a CasZa, CasZb, CasZc, CasZd, CasZe, CasZf, CasZg, CasZh, or CasZi crRNA sequence of Table 1 or Table 3. In some cases, a subject CasZ guide RNA comprises a nucleotide sequence having 90% or more identity (e.g., 93% or more, 95% or more, 97% or more, 98% or more, or 100% identity) with a CasZa, CasZb, CasZc, CasZd, CasZe, CasZf, CasZg, CasZh, or CasZi crRNA sequence of Table 1 or Table 3.

In some cases, a subject CasZ guide RNA comprises (e.g., in addition to a guide sequence, e.g., as part of the protein-binding region) a CasZa crRNA sequence of Table 1 or Table 3. In some cases, a subject CasZ guide RNA comprises a nucleotide sequence having 70% or more identity (e.g., 75% or more, 80% or more, 85% or more, 90% or more, 93% or more, 95% or more, 97% or more, 98% or more, or 100% identity) with a CasZa crRNA sequence of Table 1 or Table 3. In some cases, a subject CasZ guide RNA comprises a nucleotide sequence having 80% or more identity (e.g., 85% or more, 90% or more, 93% or more, 95% or more, 97% or more, 98% or more, or 100% identity) with a CasZa crRNA sequence of Table 1 or Table 3. In some cases, a subject CasZ guide RNA comprises a nucleotide sequence having 90% or more identity (e.g., 93% or more, 95% or more, 97% or more, 98% or more, or 100% identity) with a CasZa crRNA sequence of Table 1 or Table 3.

In some cases, a subject CasZ guide RNA comprises (e.g., in addition to a guide sequence, e.g., as part of the protein-binding region) a CasZb crRNA sequence of Table 1 or Table 3. In some cases, a subject CasZ guide RNA comprises a nucleotide sequence having 70% or more identity (e.g., 75% or more, 80% or more, 85% or more, 90% or more, 93% or more, 95% or more, 97% or more, 98% or more, or 100% identity) with a CasZb crRNA sequence of Table 1 or Table 3. In some cases, a subject CasZ guide RNA comprises a nucleotide sequence having 80% or more identity (e.g., 85% or more, 90% or more, 93% or more, 95% or more, 97% or more, 98% or more, or 100% identity) with a CasZb crRNA sequence of Table 1 or Table 3. In some cases, a subject CasZ guide RNA comprises a nucleotide sequence having 90% or more identity (e.g., 93% or more, 95% or more, 97% or more, 98% or more, or 100% identity) with a CasZb crRNA sequence of Table 1 or Table 3.

In some cases, a subject CasZ guide RNA comprises (e.g., in addition to a guide sequence, e.g., as part of the protein-binding region) a CasZc crRNA sequence of Table 1 or Table 3. In some cases, a subject CasZ guide RNA comprises a nucleotide sequence having 70% or more identity (e.g., 75% or more, 80% or more, 85% or more, 90% or more, 93% or more, 95% or more, 97% or more, 98% or more, or 100% identity) with a CasZc crRNA sequence of Table 1 or Table 3. In some cases, a subject CasZ guide RNA comprises a nucleotide sequence having 80% or more identity (e.g., 85% or more, 90% or more, 93% or more, 95% or more, 97% or more, 98% or more, or 100% identity) with a CasZc crRNA sequence of Table 1 or Table 3. In some cases, a subject CasZ guide RNA comprises a nucleotide sequence having 90% or more identity (e.g., 93% or more, 95% or more, 97% or more, 98% or more, or 100% identity) with a CasZc crRNA sequence of Table 1 or Table 3.

In some cases, a subject CasZ guide RNA comprises (e.g., in addition to a guide sequence, e.g., as part of the protein-binding region) a CasZd crRNA sequence of Table 1 or Table 3. In some cases, a subject CasZ guide RNA comprises a nucleotide sequence having 70% or more identity (e.g., 75% or more, 80% or more, 85% or more, 90% or more, 93% or more, 95% or more, 97% or more, 98% or more, or 100% identity) with a CasZd crRNA sequence of Table 1 or Table 3. In some cases, a subject CasZ guide RNA comprises a nucleotide sequence having 80% or more identity (e.g., 85% or more, 90% or more, 93% or more, 95% or more, 97% or more, 98% or more, or 100% identity) with a CasZd crRNA sequence of Table 1 or Table 3. In some cases, a subject CasZ guide RNA comprises a nucleotide sequence having 90% or more identity (e.g., 93% or more, 95% or more, 97% or more, 98% or more, or 100% identity) with a CasZd crRNA sequence of Table 1 or Table 3.

In some cases, a subject CasZ guide RNA comprises (e.g., in addition to a guide sequence, e.g., as part of the protein-binding region) a CasZe crRNA sequence of Table 1 or Table 3. In some cases, a subject CasZ guide RNA comprises a nucleotide sequence having 70% or more identity (e.g., 75% or more, 80% or more, 85% or more, 90% or more, 93% or more, 95% or more, 97% or more, 98% or more, or 100% identity) with a CasZe crRNA sequence of Table 1 or Table 3. In some cases, a subject CasZ guide RNA comprises a nucleotide sequence having 80% or more identity (e.g., 85% or more, 90% or more, 93% or more, 95% or more, 97% or more, 98% or more, or 100% identity) with a CasZe crRNA sequence of Table 1 or Table 3. In some cases, a subject CasZ guide RNA comprises a nucleotide sequence having 90% or more identity (e.g., 93% or more, 95% or more, 97% or more, 98% or more, or 100% identity) with a CasZe crRNA sequence of Table 1 or Table 3.

In some cases, a subject CasZ guide RNA comprises (e.g., in addition to a guide sequence, e.g., as part of the protein-binding region) a CasZf crRNA sequence of Table 1 or Table 3. In some cases, a subject CasZ guide RNA comprises a nucleotide sequence having 70% or more identity (e.g., 75% or more, 80% or more, 85% or more, 90% or more, 93% or more, 95% or more, 97% or more, 98% or more, or 100% identity) with a CasZf crRNA sequence of Table 1 or Table 3. In some cases, a subject CasZ guide RNA comprises a nucleotide sequence having 80% or more identity (e.g., 85% or more, 90% or more, 93% or more, 95% or more, 97% or more, 98% or more, or 100% identity) with a CasZf crRNA sequence of Table 1 or Table 3. In some cases, a subject CasZ guide RNA comprises a nucleotide sequence having 90% or more identity (e.g., 93% or more, 95% or more, 97% or more, 98% or more, or 100% identity) with a CasZf crRNA sequence of Table 1 or Table 3.

In some cases, a subject CasZ guide RNA comprises (e.g., in addition to a guide sequence, e.g., as part of the protein-binding region) a CasZg crRNA sequence of Table 1 or Table 3. In some cases, a subject CasZ guide RNA comprises a nucleotide sequence having 70% or more identity (e.g., 75% or more, 80% or more, 85% or more, 90% or more, 93% or more, 95% or more, 97% or more, 98% or more, or 100% identity) with a CasZg crRNA sequence of Table 1 or Table 3. In some cases, a subject CasZ guide RNA comprises a nucleotide sequence having 80% or more identity (e.g., 85% or more, 90% or more, 93% or more, 95% or more, 97% or more, 98% or more, or 100% identity) with a CasZg crRNA sequence of Table 1 or Table 3. In some cases, a subject CasZ guide RNA comprises a nucleotide sequence having 90% or more identity (e.g., 93% or more, 95% or more, 97% or more, 98% or more, or 100% identity) with a CasZg crRNA sequence of Table 1 or Table 3.

In some cases, a subject CasZ guide RNA comprises (e.g., in addition to a guide sequence, e.g., as part of the protein-binding region) a CasZh crRNA sequence of Table 1 or Table 3. In some cases, a subject CasZ guide RNA comprises a nucleotide sequence having 70% or more identity (e.g., 75% or more, 80% or more, 85% or more, 90% or more, 93% or more, 95% or more, 97% or more, 98% or more, or 100% identity) with a CasZh crRNA sequence of Table 1 or Table 3. In some cases, a subject CasZ guide RNA comprises a nucleotide sequence having 80% or more identity (e.g., 85% or more, 90% or more, 93% or more, 95% or more, 97% or more, 98% or more, or 100% identity) with a CasZh crRNA sequence of Table 1 or Table 3. In some cases, a subject CasZ guide RNA comprises a nucleotide sequence having 90% or more identity (e.g., 93% or more, 95% or more, 97% or more, 98% or more, or 100% identity) with a CasZh crRNA sequence of Table 1 or Table 3.

In some cases, a subject CasZ guide RNA comprises (e.g., in addition to a guide sequence, e.g., as part of the protein-binding region) a CasZi crRNA sequence of Table 1 or Table 3. In some cases, a subject CasZ guide RNA comprises a nucleotide sequence having 70% or more identity (e.g., 75% or more, 80% or more, 85% or more, 90% or more, 93% or more, 95% or more, 97% or more, 98% or more, or 100% identity) with a CasZi crRNA sequence of Table 1 or Table 3. In some cases, a subject CasZ guide RNA comprises a nucleotide sequence having 80% or more identity (e.g., 85% or more, 90% or more, 93% or more, 95% or more, 97% or more, 98% or more, or 100% identity) with a CasZi crRNA sequence of Table 1 or Table 3. In some cases, a subject CasZ guide RNA comprises a nucleotide sequence having 90% or more identity (e.g., 93% or more, 95% or more, 97% or more, 98% or more, or 100% identity) with a CasZi crRNA sequence of Table 1 or Table 3.

In some cases, a subject CasZ guide RNA comprises (e.g., in addition to a guide sequence, e.g., as part of the protein-binding region) a CasZj crRNA sequence of Table 1 or Table 3. In some cases, a subject CasZ guide RNA comprises a nucleotide sequence having 70% or more identity (e.g., 75% or more, 80% or more, 85% or more, 90% or more, 93% or more, 95% or more, 97% or more, 98% or more, or 100% identity) with a CasZj crRNA sequence of Table 1 or Table 3. In some cases, a subject CasZ guide RNA comprises a nucleotide sequence having 80% or more identity (e.g., 85% or more, 90% or more, 93% or more, 95% or more, 97% or more, 98% or more, or 100% identity) with a CasZj crRNA sequence of Table 1 or Table 3. In some cases, a subject CasZ guide RNA comprises a nucleotide sequence having 90% or more identity (e.g., 93% or more, 95% or more, 97% or more, 98% or more, or 100% identity) with a CasZj crRNA sequence of Table 1 or Table 3.

In some cases, a subject CasZ guide RNA comprises (e.g., in addition to a guide sequence, e.g., as part of the protein-binding region) a CasZk crRNA sequence of Table 1 or Table 3. In some cases, a subject CasZ guide RNA comprises a nucleotide sequence having 70% or more identity (e.g., 75% or more, 80% or more, 85% or more, 90% or more, 93% or more, 95% or more, 97% or more, 98% or more, or 100% identity) with a CasZk crRNA sequence of Table 1 or Table 3. In some cases, a subject CasZ guide RNA comprises a nucleotide sequence having 80% or more identity (e.g., 85% or more, 90% or more, 93% or more, 95% or more, 97% or more, 98% or more, or 100% identity) with a CasZk crRNA sequence of Table 1 or Table 3. In some cases, a subject CasZ guide RNA comprises a nucleotide sequence having 90% or more identity (e.g., 93% or more, 95% or more, 97% or more, 98% or more, or 100% identity) with a CasZk crRNA sequence of Table 1 or Table 3.

In some cases, a subject CasZ guide RNA comprises (e.g., in addition to a guide sequence, e.g., as part of the protein-binding region) a CasZl crRNA sequence of Table 1 or Table 3. In some cases, a subject CasZ guide RNA comprises a nucleotide sequence having 70% or more identity (e.g., 75% or more, 80% or more, 85% or more, 90% or more, 93% or more, 95% or more, 97% or more, 98% or more, or 100% identity) with a CasZl crRNA sequence of Table 1 or Table 3. In some cases, a subject CasZ guide RNA comprises a nucleotide sequence having 80% or more identity (e.g., 85% or more, 90% or more, 93% or more, 95% or more, 97% or more, 98% or more, or 100% identity) with a CasZl crRNA sequence of Table 1 or Table 3. In some cases, a subject CasZ guide RNA comprises a nucleotide sequence having 90% or more identity (e.g., 93% or more, 95% or more, 97% or more, 98% or more, or 100% identity) with a CasZl crRNA sequence of Table 1 or Table 3.

In some cases, a subject CasZ guide RNA comprises (e.g., in addition to a guide sequence, e.g., as part of the protein-binding region) a CasZj, CasZl, or CasZk crRNA sequence of Table 1 or Table 3. In some cases, a subject CasZ guide RNA comprises a nucleotide sequence having 70% or more identity (e.g., 75% or more, 80% or more, 85% or more, 90% or more, 93% or more, 95% or more, 97% or more, 98% or more, or 100% identity) with a CasZj, CasZl, or CasZk crRNA sequence of Table 1 or Table 3. In some cases, a subject CasZ guide RNA comprises a nucleotide sequence having 80% or more identity (e.g., 85% or more, 90% or more, 93% or more, 95% or more, 97% or more, 98% or more, or 100% identity) with a CasZj, CasZl, or CasZk crRNA sequence of Table 1 or Table 3. In some cases, a subject CasZ guide RNA comprises a nucleotide sequence having 90% or more identity (e.g., 93% or more, 95% or more, 97% or more, 98% or more, or 100% identity) with a CasZj, CasZl, or CasZk crRNA sequence of Table 1 or Table 3.

CasZ Transactivating Noncoding RNA (trancRNA)

Compositions and methods of the present disclosure include a CasZ transactivating noncoding RNA ("trancRNA"; also referred to herein as a "CasZ trancRNA"). In some cases, a trancRNA forms a complex with a CasZ polypeptide of the present disclosure and a CasZ guide RNA. A trancRNA can be identified as a highly transcribed RNA encoded by a nucleotide sequence present in a CasZ locus. The sequence encoding a trancRNA is usually located between the cas genes and the array of the CasZ locus (the repeats) (e.g., can be located adjacent to the repeat sequences). Examples below demonstrate detection of a CasZ trancRNA. In some cases, a CasZ trancRNA co-immunoprecipitates (forms a complex with) with a CasZ polypeptide. In some cases, the presence of a CasZ trancRNA is required for function of the system. Data related to trancRNAs (e.g., their expression and their location on naturally occurring arrays) is presented in the examples section below.

In some cases, a CasZ trancRNA has a length of from 60 nucleotides (nt) to 270 nt (e.g., 60-260, 70-270, 70-260, or 75-255 nt). In some cases, a CasZ trancRNA (e.g., a CasZa trancRNA) has a length of from 60-150 nt (e.g., 60-140, 60-130, 65-150, 65-140, 65-130, 70-150, 70-140, or 70-130 nt). In some cases, a CasZ trancRNA (e.g., a CasZa trancRNA) has a length of from 70-130 nt. In some cases, a CasZ trancRNA (e.g., a CasZa trancRNA) has a length of about 80 nt. In some cases, a CasZ trancRNA (e.g., a CasZa trancRNA) has a length of about 90 nt. In some cases, a CasZ trancRNA (e.g., a CasZa trancRNA) has a length of about 120 nt.

In some cases, a CasZ trancRNA (e.g., a CasZb trancRNA) has a length of from 85-240 nt (e.g., 85-230, 85-220, 85-150, 85-130, 95-240, 95-230, 95-220, 95-150, or 95-130 nt). In some cases, a CasZ trancRNA (e.g., a CasZb trancRNA) has a length of from 95-120 nt. In some cases, a CasZ trancRNA (e.g., a CasZb trancRNA) has a length of about 105 nt. In some cases, a CasZ trancRNA (e.g., a CasZb trancRNA) has a length of about 115 nt. In some cases, a CasZ trancRNA (e.g., a CasZb trancRNA) has a length of about 215 nt.

In some cases, a CasZ trancRNA (e.g., a CasZc trancRNA) has a length of from 80-275 nt (e.g., 85-260 nt). In some cases, a CasZ trancRNA (e.g., a CasZc trancRNA) has a length of from 80-110 nt (e.g., 85-105 nt). In some cases, a CasZ trancRNA (e.g., a CasZc trancRNA) has a length of from 235-270 nt (e.g., 240-260 nt). In some cases, a CasZ trancRNA (e.g., a CasZc trancRNA) has a length of about 95 nt. In some cases, a CasZ trancRNA (e.g., a CasZc trancRNA) has a length of about 250 nt.

Example trancRNA Sequences

Examples of trancRNA sequences for naturally existing CasZ proteins are shown in Table 2.

TABLE 2

CasZ trancRNA sequences

| CasZ Protein | trancRNA sequence | SEQ ID NO |
|---|---|---|
| Za.1 | CGATTCCTCCCTACAGTAGTTAGGTATAGCCGAAAGGTAGAGACTAAATCTGTAGTTGGAGTGGGCCGCTTGCATCGGCC | 151 |
| Za.2 | TCGTCTCGAGGGTTACCAAAATTGGCACTTCTCGACTTTAGGCCGATGCAAGCGGCCCACTCCACTACAGATTTAGTCTCTACCTTGCGGCTATACCTAACTTACTGTAGGGAGGAATCGTG | 152 |
| Za.3 | CTTCACTGATAAAGTGGAGAACCGCTTCACCAAAAGCTGTCCCTTAGGGGATTAGAACTTGAGTGAAGGTGGGCTGCTTGCATCAGCCTAA | 153 |
| Zb.2 | CAGAATAATACTGACTTACTAAGATATCTTGAGGGTATACCCGAAAAGATTGGCGTTGTTGCAACGCAATAAGATGTAAATCTGAAAAGGTTTGGAATCATATAAATAATTTTA | 154 |
| Zb.4 | AAGCCAAGATATGGAATGCCATTGTAATATTATGGTGTTGACTTAGTTTAGATTTAAACAATCTTCGATGGCTATATGCGGAAGGTTTGGCGTCGTTGTAACGC | 155 |
| Zb.6 | CAGTGTGCATAGCTATAACACTACGCAAAGACTGCTAAAGAGCGATGTGCTCTATCGCAGTCTCACCTTTAATGGACTTACGGATCTTTTGGAGCACTAAGCTCCGCTGCGGTGCAACACCGCCCTTTTCTTGCCTCTGCTTGCCCTTTCCGGTTATTATAGCCGGGAGAGTGCGGAAGATTACCGCTCTAGCTCGCAGCATGTTACTGAGTC | 156 |
| Zc.3 | GCAAGTCATTCGGGGACACTTTTTGTTATTTAAAGTGTTTTAGATAAATCAGTGTCATGCTGAATAACGACCCGACCTATAAATAACATAATCC | 157 |
| Zc.5 | GTCCTTAAGGTACTACACATTACATGTGAACGTGGAGCTAATAATAGAAATATTATTAGACTACACCTTATTAATAACGGTAGGAGATCTATATGGTCTTGAATGGAATAGTAATTGTGAAATTATAATTTCTGTTCTTAGCTACTTAAGATGGCTCGTTGCAAGCCACTCGGGGCTCTCTTGAAGTCAAAGAGCTTTAGACAAATCAGTGTCAAACTGAATAACGACCCGACCATGACTTCATAATCCCG | 158 |

In some cases, a subject CasZ trancRNA comprises a CasZa trancRNA sequence above. In some cases, a subject CasZ trancRNA comprises a nucleotide sequence having 70% or more identity (e.g., 75% or more, 80% or more, 85% or more, 90% or more, 93% or more, 95% or more, 97% or more, 98% or more, or 100% identity) with a CasZa trancRNA sequence above. In some cases, a subject CasZ trancRNA comprises a nucleotide sequence having 80% or more identity (e.g., 85% or more, 90% or more, 93% or more, 95% or more, 97% or more, 98% or more, or 100% identity) with a CasZa trancRNA sequence above. In some cases, a subject CasZ trancRNA comprises a nucleotide sequence having 90% or more identity (e.g., 93% or more, 95% or more, 97% or more, 98% or more, or 100% identity) with a CasZa trancRNA sequence above. In some cases, a subject CasZ trancRNA comprises a nucleotide sequence having 80% or more identity (e.g., 85% or more, 90% or more, 93% or more, 95% or more, 97% or more, 98% or more, or 100% identity) with a CasZa trancRNA sequence above, and has a length of from 60-150 nt (e.g., 60-140, 60-130, 65-150, 65-140, 65-130, 70-150, 70-140, or 70-130 nt).

In some cases, a subject CasZ trancRNA comprises a CasZb trancRNA sequence above. In some cases, a subject CasZ trancRNA comprises a nucleotide sequence having 70% or more identity (e.g., 75% or more, 80% or more, 85% or more, 90% or more, 93% or more, 95% or more, 97% or more, 98% or more, or 100% identity) with a CasZb trancRNA sequence above. In some cases, a subject CasZ trancRNA comprises a nucleotide sequence having 80% or more identity (e.g., 85% or more, 90% or more, 93% or more, 95% or more, 97% or more, 98% or more, or 100% identity) with a CasZb trancRNA sequence above. In some cases, a subject CasZ trancRNA comprises a nucleotide sequence having 90% or more identity (e.g., 93% or more, 95% or more, 97% or more, 98% or more, or 100% identity) with a CasZb trancRNA sequence above. In some cases, a subject CasZ trancRNA comprises a nucleotide sequence having 80% or more identity (e.g., 85% or more, 90% or more, 93% or more, 95% or more, 97% or more, 98% or more, or 100% identity) with a CasZb trancRNA sequence above, and has a length of from 85-240 nt (e.g., 85-230, 85-220, 85-150, 85-130, 95-240, 95-230, 95-220, 95-150, or 95-130 nt).

In some cases, a subject CasZ trancRNA comprises a CasZc trancRNA sequence above. In some cases, a subject CasZ trancRNA comprises a nucleotide sequence having 70% or more identity (e.g., 75% or more, 80% or more, 85% or more, 90% or more, 93% or more, 95% or more, 97% or more, 98% or more, or 100% identity) with a CasZc trancRNA sequence above. In some cases, a subject CasZ trancRNA comprises a nucleotide sequence having 80% or more identity (e.g., 85% or more, 90% or more, 93% or more, 95% or more, 97% or more, 98% or more, or 100% identity) with a CasZc trancRNA sequence above. In some cases, a subject CasZ trancRNA comprises a nucleotide sequence having 90% or more identity (e.g., 93% or more, 95% or more, 97% or more, 98% or more, or 100% identity) with a CasZc trancRNA sequence above. In some cases, a subject CasZ trancRNA comprises a nucleotide sequence having 80% or more identity (e.g., 85% or more, 90% or more, 93% or more, 95% or more, 97% or more, 98% or more, or 100% identity) with a CasZc trancRNA sequence above, and has a length of from 80-110 nt (e.g., 85-105 nt) or from 235-270 nt (e.g., 240-260 nt).

In some cases, a subject CasZ trancRNA comprises a CasZa, CasZb, or CasZc trancRNA sequence above. In some cases, a subject CasZ trancRNA comprises a nucleotide sequence having 70% or more identity (e.g., 75% or more, 80% or more, 85% or more, 90% or more, 93% or more, 95% or more, 97% or more, 98% or more, or 100% identity) with a CasZa, CasZb, or CasZc trancRNA sequence above. In some cases, a subject CasZ trancRNA comprises a nucleotide sequence having 80% or more identity (e.g., 85% or more, 90% or more, 93% or more, 95% or more, 97% or more, 98% or more, or 100% identity) with a CasZa, CasZb, or CasZc trancRNA sequence above. In some cases, a subject CasZ trancRNA comprises a nucleotide sequence having 90% or more identity (e.g., 93% or more, 95% or more, 97% or more, 98% or more, or 100% identity) with a CasZa, CasZb, or CasZc trancRNA sequence above. In some cases, a subject CasZ trancRNA comprises a nucleotide sequence having 80% or more identity (e.g., 85% or more, 90% or more, 93% or more, 95% or more, 97% or more, 98% or more, or 100% identity) with a CasZa, CasZb, or CasZc trancRNA sequence above, and has a length of from 60 nucleotides (nt) to 270 nt (e.g., 60-260, 70-270, 70-260, or 75-255 nt).

In some cases, a CasZ trancRNA comprises a modified nucleotide (e.g., methylated). In some cases, a CasZ trancRNA comprises one or more of: i) a base modification or substitution; ii) a backbone modification; iii) a modified internucleoside linkage; and iv) a modified sugar moiety. Possible nucleic acid modifications are described below.

CasZ Systems

The present disclosure provides a CasZ system. A CasZ system of the present disclosure can comprise one or more of: (1) a CasZ transactivating noncoding RNA (trancRNA) (referred to herein as a "CasZ trancRNA") or a nucleic acid encoding the CasZ trancRNA (e.g., an expression vector); (2) a CasZ protein (e.g., a wild type protein, a variant, a catalytically compromised variant, a CasZ fusion protein, and the like) or a nucleic acid encoding the CasZ protein (e.g., an RNA, an expression vector, and the like); and (3) a CasZ guide RNA (that binds to and provides sequence specificity to the CasZ protein, e.g., a guide RNA that can bind to a target sequence of a eukaryotic genome) or a nucleic acid encoding the CasZ guide RNA) (e.g., an expression vector). A CasZ system can include a host cell (e.g., a eukaryotic cell, a plant cell, a mammalian cell, a human cell) that comprises one or more of (1), (2), and (3) (in any combination), e.g., in some cases the host cell comprises a trancRNA and/or a nucleic acid encoding the trancRNA. In some cases, a CasZ system includes (e.g., in addition to the above) a donor template nucleic acid. In some cases, the CasZ system is a system of one or more nucleic acids (e.g., one or more expression vectors encoding any combination of the above).

Nucleic Acids

The present disclosure provides one or more nucleic acids comprising one or more of: a CasZ trancRNA sequence, a nucleotide sequence encoding a CasZ trancRNA, a nucleotide sequence encoding a CasZ polypeptide (e.g., a wild type CasZ protein, a nickase CasZ protein, a dCasZ protein, chimeric CasZ protein/CasZ fusion protein, and the like), a CasZ guide RNA sequence, a nucleotide sequence encoding a CasZ guide RNA, and a donor polynucleotide (donor template, donor DNA) sequence. In some cases, a subject nucleic acid (e.g., the one or more nucleic acids) is a recombinant expression vector (e.g., plasmid, viral vector, minicircle DNA, and the like). In some cases, the nucleotide sequence encoding the CasZ trancRNA, the nucleotide sequence encoding the CasZ protein, and/or the nucleotide sequence encoding the CasZ guide RNA is (are) operably linked to a promoter (e.g., an inducible promoter), e.g., one that is operable in a cell type of choice (e.g., a prokaryotic cell, a eukaryotic cell, a plant cell, an animal cell, a mammalian cell, a primate cell, a rodent cell, a human cell, etc.).

In some cases, a nucleotide sequence encoding a CasZ polypeptide of the present disclosure is codon optimized. This type of optimization can entail a mutation of a CasZ-encoding nucleotide sequence to mimic the codon preferences of the intended host organism or cell while encoding the same protein. Thus, the codons can be changed, but the encoded protein remains unchanged. For example, if the intended target cell was a human cell, a human codon-optimized CasZ-encoding nucleotide sequence could be used. As another non-limiting example, if the intended host cell were a mouse cell, then a mouse codon-optimized CasZ-encoding nucleotide sequence could be generated. As another non-limiting example, if the intended host cell were a plant cell, then a plant codon-optimized CasZ-encoding nucleotide sequence could be generated. As another non-limiting example, if the intended host cell were an insect cell, then an insect codon-optimized CasZ-encoding nucleotide sequence could be generated.

The present disclosure provides one or more recombinant expression vectors that include (in different recombinant expression vectors in some cases, and in the same recombinant expression vector in some cases): a CasZ trancRNA sequence, a nucleotide sequence encoding a CasZ trancRNA, a nucleotide sequence encoding a CasZ polypeptide (e.g., a wild type CasZ protein, a nickase CasZ protein, a dCasZ protein, chimeric CasZ protein/CasZ fusion protein, and the like), a CasZ guide RNA sequence, a nucleotide sequence encoding a CasZ guide RNA, and a donor polynucleotide (donor template, donor DNA) sequence. In some cases, a subject nucleic acid (e.g., the one or more nucleic acids) is a recombinant expression vector (e.g., plasmid, viral vector, minicircle DNA, and the like). In some cases, the nucleotide sequence encoding the CasZ trancRNA, the nucleotide sequence encoding the CasZ protein, and/or the nucleotide sequence encoding the CasZ guide RNA is (are) operably linked to a promoter (e.g., an inducible promoter), e.g., one that is operable in a cell type of choice (e.g., a prokaryotic cell, a eukaryotic cell, a plant cell, an animal cell, a mammalian cell, a primate cell, a rodent cell, a human cell, etc.).

Suitable expression vectors include viral expression vectors (e.g. viral vectors based on vaccinia virus; poliovirus; adenovirus (see, e.g., Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., H Gene Ther 5:1088 1097, 1999; WO 94/12649, WO 93/03769; WO 93/19191; WO 94/28938; WO 95/11984 and WO 95/00655); adeno-associated virus (AAV) (see, e.g., Ali et al., Hum Gene Ther 9:81 86, 1998, Flannery et al., PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641 648, 1999; Ali et al., Hum Mol Genet 5:591 594, 1996; Srivastava in WO 93/09239, Samulski et al., J. Vir. (1989) 63:3822-3828; Mendelson et al., Virol. (1988) 166:154-165; and Flotte et al., PNAS (1993) 90:10613-10617); SV40; herpes simplex virus; human immunodeficiency virus (see, e.g., Miyoshi et al., PNAS 94:10319 23, 1997; Takahashi et al., J Virol 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus); and the like. In some cases, a recombinant expression vector of the present disclosure is a recombinant adeno-associated virus (AAV) vector. In some cases, a recombinant expression vector of the present disclosure is a recombinant lentivirus vector. In some cases, a recombinant expression vector of the present disclosure is a recombinant retroviral vector.

Depending on the host/vector system utilized, any of a number of suitable transcription and translation control elements, including constitutive and inducible promoters, transcription enhancer elements, transcription terminators, etc. may be used in the expression vector.

In some embodiments, a nucleotide sequence encoding a CasZ guide RNA is operably linked to a control element, e.g., a transcriptional control element, such as a promoter. In some embodiments, a nucleotide sequence encoding a CasZ protein or a CasZ fusion polypeptide is operably linked to a control element, e.g., a transcriptional control element, such as a promoter.

The transcriptional control element can be a promoter. In some cases, the promoter is a constitutively active promoter. In some cases, the promoter is a regulatable promoter. In some cases, the promoter is an inducible promoter. In some cases, the promoter is a tissue-specific promoter. In some cases, the promoter is a cell type-specific promoter. In some cases, the transcriptional control element (e.g., the promoter) is functional in a targeted cell type or targeted cell population. For example, in some cases, the transcriptional control element can be functional in eukaryotic cells, e.g., hematopoietic stem cells (e.g., mobilized peripheral blood (mPB) CD34(+) cell, bone marrow (BM) CD34(+) cell, etc.).

Non-limiting examples of eukaryotic promoters (promoters functional in a eukaryotic cell) include EF1α, those from cytomegalovirus (CMV) immediate early, herpes simplex virus (HSV) thymidine kinase, early and late SV40, long terminal repeats (LTRs) from retrovirus, and mouse metallothionein-I. Selection of the appropriate vector and promoter is well within the level of ordinary skill in the art. The expression vector may also contain a ribosome binding site for translation initiation and a transcription terminator. The expression vector may also include appropriate sequences for amplifying expression. The expression vector may also include nucleotide sequences encoding protein tags (e.g., 6xHis tag, hemagglutinin tag, fluorescent protein, etc.) that can be fused to the CasZ protein, thus resulting in a chimeric CasZ polypeptide.

In some cases, a nucleotide sequence encoding a CasZ guide RNA and/or a CasZ fusion polypeptide is operably linked to an inducible promoter. In some cases, a nucleotide sequence encoding a CasZ guide RNA and/or a CasZ fusion protein is operably linked to a constitutive promoter.

A promoter can be a constitutively active promoter (i.e., a promoter that is constitutively in an active/"ON" state), it may be an inducible promoter (i.e., a promoter whose state, active/"ON" or inactive/"OFF", is controlled by an external stimulus, e.g., the presence of a particular temperature, compound, or protein.), it may be a spatially restricted promoter (i.e., transcriptional control element, enhancer, etc.)(e.g., tissue specific promoter, cell type specific promoter, etc.), and it may be a temporally restricted promoter (i.e., the promoter is in the "ON" state or "OFF" state during specific stages of embryonic development or during specific stages of a biological process, e.g., hair follicle cycle in mice).

Suitable promoters can be derived from viruses and can therefore be referred to as viral promoters, or they can be derived from any organism, including prokaryotic or eukaryotic organisms. Suitable promoters can be used to drive expression by any RNA polymerase (e.g., pol I, pol II, pol III). Exemplary promoters include, but are not limited to the SV40 early promoter, mouse mammary tumor virus long terminal repeat (LTR) promoter; adenovirus major late promoter (Ad MLP); a herpes simplex virus (HSV) promoter, a cytomegalovirus (CMV) promoter such as the CMV immediate early promoter region (CMVIE), a rous sarcoma virus (RSV) promoter, a human U6 small nuclear promoter (U6) (Miyagishi et al., Nature Biotechnology 20, 497-500 (2002)), an enhanced U6 promoter (e.g., Xia et al., Nucleic Acids Res. 2003 Sep. 1; 31(17)), a human H1 promoter (H1), and the like.

In some cases, a nucleotide sequence encoding a CasZ guide RNA is operably linked to (under the control of) a promoter operable in a eukaryotic cell (e.g., a U6 promoter, an enhanced U6 promoter, an H1 promoter, and the like). As would be understood by one of ordinary skill in the art, when expressing an RNA (e.g., a guide RNA) from a nucleic acid (e.g., an expression vector) using a U6 promoter (e.g., in a eukaryotic cell), or another PolIII promoter, the RNA may need to be mutated if there are several Ts in a row (coding for Us in the RNA). This is because a string of Ts (e.g., 5 Ts) in DNA can act as a terminator for polymerase III (PolIII). Thus, in order to ensure transcription of a guide RNA in a eukaryotic cell it may sometimes be necessary to modify the sequence encoding the guide RNA to eliminate runs of Ts. In some cases, a nucleotide sequence encoding a CasZ protein (e.g., a wild type CasZ protein, a nickase CasZ protein, a dCasZ protein, a chimeric CasZ protein and the like) is operably linked to a promoter operable in a eukaryotic cell (e.g., a CMV promoter, an EF1α promoter, an estrogen receptor-regulated promoter, and the like).

Examples of inducible promoters include, but are not limited to T7 RNA polymerase promoter, T3 RNA polymerase promoter, Isopropyl-beta-D-thiogalactopyranoside (IPTG)-regulated promoter, lactose induced promoter, heat shock promoter, Tetracycline-regulated promoter, Steroid-regulated promoter, Metal-regulated promoter, estrogen receptor-regulated promoter, etc. Inducible promoters can therefore be regulated by molecules including, but not limited to, doxycycline; estrogen and/or an estrogen analog; IPTG; etc.

Inducible promoters suitable for use include any inducible promoter described herein or known to one of ordinary skill in the art. Examples of inducible promoters include, without limitation, chemically/biochemically-regulated and physically-regulated promoters such as alcohol-regulated promoters, tetracycline-regulated promoters (e.g., anhydrotetracycline (aTc)-responsive promoters and other tetracycline-responsive promoter systems, which include a tetracycline repressor protein (tetR), a tetracycline operator sequence (tetO) and a tetracycline transactivator fusion protein (tTA)), steroid-regulated promoters (e.g., promoters based on the rat glucocorticoid receptor, human estrogen receptor, moth ecdysone receptors, and promoters from the steroid/retinoid/thyroid receptor superfamily), metal-regulated promoters (e.g., promoters derived from metallothionein (proteins that bind and sequester metal ions) genes from yeast, mouse and human), pathogenesis-regulated promoters (e.g., induced by salicylic acid, ethylene or benzothiadiazole (BTH)), temperature/heat-inducible promoters (e.g., heat shock promoters), and light-regulated promoters (e.g., light responsive promoters from plant cells).

In some cases, the promoter is a spatially restricted promoter (i.e., cell type specific promoter, tissue specific promoter, etc.) such that in a multi-cellular organism, the promoter is active (i.e., "ON") in a subset of specific cells. Spatially restricted promoters may also be referred to as enhancers, transcriptional control elements, control sequences, etc. Any convenient spatially restricted promoter may be used as long as the promoter is functional in the targeted host cell (e.g., eukaryotic cell; prokaryotic cell).

In some cases, the promoter is a reversible promoter. Suitable reversible promoters, including reversible inducible promoters are known in the art. Such reversible promoters may be isolated and derived from many organisms, e.g., eukaryotes and prokaryotes. Modification of reversible promoters derived from a first organism for use in a second organism, e.g., a first prokaryote and a second a eukaryote, a first eukaryote and a second a prokaryote, etc., is well known in the art. Such reversible promoters, and systems based on such reversible promoters but also comprising additional control proteins, include, but are not limited to, alcohol regulated promoters (e.g., alcohol dehydrogenase I (alcA) gene promoter, promoters responsive to alcohol transactivator proteins (AlcR), etc.), tetracycline regulated promoters, (e.g., promoter systems including TetActivators, TetON, TetOFF, etc.), steroid regulated promoters (e.g., rat glucocorticoid receptor promoter systems, human estrogen receptor promoter systems, retinoid promoter systems, thyroid promoter systems, ecdysone promoter systems, mifepristone promoter systems, etc.), metal regulated promoters (e.g., metallothionein promoter systems, etc.), pathogenesis-related regulated promoters (e.g., salicylic acid regulated promoters, ethylene regulated promoters, benzothiadiazole regulated promoters, etc.), temperature regulated promoters (e.g., heat shock inducible promoters (e.g., HSP-70, HSP-90, soybean heat shock promoter, etc.), light regulated promoters, synthetic inducible promoters, and the like.

Methods of introducing a nucleic acid (e.g., DNA or RNA) (e.g., a nucleic acid comprising a donor polynucleotide sequence, one or more nucleic acids encoding a CasZ protein and/or a CasZ guide RNA and/or a CasZ trancRNA, and the like) into a host cell are known in the art, and any convenient method can be used to introduce a nucleic acid (e.g., an expression construct) into a cell. Suitable methods include e.g., viral infection, transfection, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct microinjection, nanoparticle-mediated nucleic acid delivery, and the like.

Introducing the recombinant expression vector into cells can occur in any culture media and under any culture conditions that promote the survival of the cells. Introducing the recombinant expression vector into a target cell can be carried out in vivo or ex vivo. Introducing the recombinant expression vector into a target cell can be carried out in vitro.

In some cases, a CasZ protein can be provided as RNA. The RNA can be provided by direct chemical synthesis or may be transcribed in vitro from a DNA (e.g., encoding the CasZ protein). Once synthesized, the RNA may be introduced into a cell by any of the well-known techniques for introducing nucleic acids into cells (e.g., microinjection, electroporation, transfection, etc.).

Nucleic acids may be provided to the cells using well-developed transfection techniques; see, e.g. Angel and Yanik (2010) PLoS ONE 5(7): e11756, and the commercially available TransMessenger® reagents from Qiagen, Stemfect™ RNA Transfection Kit from Stemgent, and TransIT®-mRNA Transfection Kit from Mirus Bio LLC. See also Beumer et al. (2008) PNAS 105(50):19821-19826.

Vectors may be provided directly to a target host cell. In other words, the cells are contacted with vectors comprising the subject nucleic acids (e.g., recombinant expression vectors having the donor template sequence and encoding the CasZ guide RNA; recombinant expression vectors encoding the CasZ protein; etc.) such that the vectors are taken up by the cells. Methods for contacting cells with nucleic acid vectors that are plasmids, include electroporation, calcium chloride transfection, microinjection, and lipofection are well known in the art. For viral vector delivery, cells can be contacted with viral particles comprising the subject viral expression vectors.

Retroviruses, for example, lentiviruses, are suitable for use in methods of the present disclosure. Commonly used retroviral vectors are "defective", i.e. unable to produce viral proteins required for productive infection. Rather, replication of the vector requires growth in a packaging cell line. To generate viral particles comprising nucleic acids of interest, the retroviral nucleic acids comprising the nucleic acid are packaged into viral capsids by a packaging cell line. Different packaging cell lines provide a different envelope protein (ecotropic, amphotropic or xenotropic) to be incorporated into the capsid, this envelope protein determining the specificity of the viral particle for the cells (ecotropic for murine and rat; amphotropic for most mammalian cell types including human, dog and mouse; and xenotropic for most mammalian cell types except murine cells). The appropriate packaging cell line may be used to ensure that the cells are targeted by the packaged viral particles. Methods of introducing subject vector expression vectors into packaging cell lines and of collecting the viral particles that are generated by the packaging lines are well known in the art. Nucleic acids can also introduced by direct micro-injection (e.g., injection of RNA).

Vectors used for providing the nucleic acids encoding CasZ guide RNA and/or a CasZ polypeptide to a target host cell can include suitable promoters for driving the expression, that is, transcriptional activation, of the nucleic acid of interest. In other words, in some cases, the nucleic acid of interest will be operably linked to a promoter. This may include ubiquitously acting promoters, for example, the CMV-3-actin promoter, or inducible promoters, such as promoters that are active in particular cell populations or that respond to the presence of drugs such as tetracycline. By transcriptional activation, it is intended that transcription will be increased above basal levels in the target cell by 10 fold, by 100 fold, more usually by 1000 fold. In addition, vectors used for providing a nucleic acid encoding a CasZ guide RNA and/or a CasZ protein to a cell may include nucleic acid sequences that encode for selectable markers in the target cells, so as to identify cells that have taken up the CasZ guide RNA and/or CasZ protein.

A nucleic acid comprising a nucleotide sequence encoding a CasZ polypeptide, or a CasZ fusion polypeptide, is in some cases an RNA. Thus, a CasZ fusion protein can be introduced into cells as RNA. Methods of introducing RNA into cells are known in the art and may include, for example, direct injection, transfection, or any other method used for the introduction of DNA. A CasZ protein may instead be provided to cells as a polypeptide. Such a polypeptide may optionally be fused to a polypeptide domain that increases solubility of the product. The domain may be linked to the polypeptide through a defined protease cleavage site, e.g. a TEV sequence, which is cleaved by TEV protease. The linker may also include one or more flexible sequences, e.g. from 1 to 10 glycine residues. In some embodiments, the cleavage of the fusion protein is performed in a buffer that maintains solubility of the product, e.g. in the presence of from 0.5 to 2 M urea, in the presence of polypeptides and/or polynucleotides that increase solubility, and the like. Domains of interest include endosomolytic domains, e.g. influenza HA domain; and other polypeptides that aid in production, e.g. IF2 domain, GST domain, GRPE domain, and the like. The polypeptide may be formulated for improved stability. For example, the peptides may be PEGylated, where the polyethyleneoxy group provides for enhanced lifetime in the blood stream.

Additionally, or alternatively, a CasZ polypeptide of the present disclosure may be fused to a polypeptide permeant domain to promote uptake by the cell. A number of permeant domains are known in the art and may be used in the non-integrating polypeptides of the present disclosure, including peptides, peptidomimetics, and non-peptide carriers. For example, a permeant peptide may be derived from the third alpha helix of Drosophila melanogaster transcription factor Antennapaedia, referred to as penetratin, which comprises the amino acid sequence RQIKIWFQNRRMKWKK (SEQ ID NO: 134). As another example, the permeant peptide comprises the HIV-1 tat basic region amino acid sequence, which may include, for example, amino acids 49-57 of naturally-occurring tat protein. Other permeant domains include poly-arginine motifs, for example, the region of amino acids 34-56 of HIV-1 rev protein, nona-arginine, octa-arginine, and the like. (See, for example, Futaki et al. (2003) Curr Protein Pept Sci. 2003 April; 4(2): 87-9 and 446; and Wender et al. (2000) Proc. Natl. Acad. Sci. U.S.A 2000 Nov. 21; 97(24):13003-8; published U.S. Patent applications 20030220334; 20030083256; 20030032593; and 20030022831, herein specifically incorporated by reference for the teachings of translocation peptides and peptoids). The nona-arginine (R9) sequence is one of the more efficient PTDs that have been characterized (Wender et al. 2000; Uemura et al. 2002). The site at which the fusion is made may be selected in order to optimize the biological activity, secretion or binding characteristics of the polypeptide. The optimal site will be determined by routine experimentation.

A CasZ polypeptide of the present disclosure may be produced in vitro or by eukaryotic cells or by prokaryotic cells, and it may be further processed by unfolding, e.g. heat denaturation, dithiothreitol reduction, etc. and may be further refolded, using methods known in the art.

Modifications of interest that do not alter primary sequence include chemical derivatization of polypeptides, e.g., acylation, acetylation, carboxylation, amidation, etc. Also included are modifications of glycosylation, e.g. those made by modifying the glycosylation patterns of a polypeptide during its synthesis and processing or in further processing steps; e.g. by exposing the polypeptide to enzymes which affect glycosylation, such as mammalian glycosylating or deglycosylating enzymes. Also embraced are sequences that have phosphorylated amino acid residues, e.g. phosphotyrosine, phosphoserine, or phosphothreonine.

Also suitable for inclusion in embodiments of the present disclosure are nucleic acids (e.g., encoding a CasZ guide RNA, encoding a CasZ fusion protein, etc.) and proteins (e.g., a CasZ fusion protein derived from a wild type protein or a variant protein) that have been modified using ordinary molecular biological techniques and synthetic chemistry so as to improve their resistance to proteolytic degradation, to change the target sequence specificity, to optimize solubility properties, to alter protein activity (e.g., transcription modulatory activity, enzymatic activity, etc.) or to render them more suitable. Analogs of such polypeptides include those containing residues other than naturally occurring L-amino acids, e.g. D-amino acids or non-naturally occurring synthetic amino acids. D-amino acids may be substituted for some or all of the amino acid residues.

A CasZ polypeptide of the present disclosure may be prepared by in vitro synthesis, using conventional methods as known in the art. Various commercial synthetic apparatuses are available, for example, automated synthesizers by Applied Biosystems, Inc., Beckman, etc. By using synthesizers, naturally occurring amino acids may be substituted with unnatural amino acids. The particular sequence and the manner of preparation will be determined by convenience, economics, purity required, and the like.

If desired, various groups may be introduced into the peptide during synthesis or during expression, which allow for linking to other molecules or to a surface. Thus cysteines can be used to make thioethers, histidines for linking to a metal ion complex, carboxyl groups for forming amides or esters, amino groups for forming amides, and the like.

A CasZ polypeptide of the present disclosure may also be isolated and purified in accordance with conventional methods of recombinant synthesis. A lysate may be prepared of the expression host and the lysate purified using high performance liquid chromatography (HPLC), exclusion chromatography, gel electrophoresis, affinity chromatography, or other purification technique. For the most part, the compositions which are used will comprise 20% or more by weight of the desired product, more usually 75% or more by weight, preferably 95% or more by weight, and for therapeutic purposes, usually 99.5% or more by weight, in relation to contaminants related to the method of preparation of the product and its purification. Usually, the percentages will be based upon total protein. Thus, in some cases, a CasZ polypeptide, or a CasZ fusion polypeptide, of the present disclosure is at least 80% pure, at least 85% pure, at least 90% pure, at least 95% pure, at least 98% pure, or at least 99% pure (e.g., free of contaminants, non-CasZ proteins or other macromolecules, etc.).

To induce cleavage or any desired modification to a target nucleic acid (e.g., genomic DNA), or any desired modification to a polypeptide associated with target nucleic acid, the CasZ guide RNA and/or the CasZ polypeptide and/or the CasZ trancRNA, and/or the donor template sequence, whether they be introduced as nucleic acids or polypeptides, can be provided to the cells for about 30 minutes to about 24 hours, e.g., 1 hour, 1.5 hours, 2 hours, 2.5 hours, 3 hours, 3.5 hours 4 hours, 5 hours, 6 hours, 7 hours, 8 hours, 12 hours, 16 hours, 18 hours, 20 hours, or any other period from about 30 minutes to about 24 hours, which may be repeated with a frequency of about every day to about every 4 days, e.g., every 1.5 days, every 2 days, every 3 days, or any other frequency from about every day to about every four days. The agent(s) may be provided to the subject cells one or more times, e.g. one time, twice, three times, or more than three times, and the cells allowed to incubate with the agent(s) for some amount of time following each contacting event e.g. 16-24 hours, after which time the media is replaced with fresh media and the cells are cultured further.

In cases in which two or more different targeting complexes are provided to the cell (e.g., two different CasZ guide RNAs that are complementary to different sequences within the same or different target nucleic acid), the complexes may be provided simultaneously (e.g. as two polypeptides and/or nucleic acids), or delivered simultaneously. Alternatively, they may be provided consecutively, e.g. the targeting complex being provided first, followed by the second targeting complex, etc. or vice versa.

To improve the delivery of a DNA vector into a target cell, the DNA can be protected from damage and its entry into the cell facilitated, for example, by using lipoplexes and polyplexes. Thus, in some cases, a nucleic acid of the present disclosure (e.g., a recombinant expression vector of the present disclosure) can be covered with lipids in an organized structure like a micelle or a liposome. When the organized structure is complexed with DNA it is called a lipoplex. There are three types of lipids, anionic (negatively-charged), neutral, or cationic (positively-charged). Lipoplexes that utilize cationic lipids have proven utility for gene transfer. Cationic lipids, due to their positive charge, naturally complex with the negatively charged DNA. Also as a result of their charge, they interact with the cell membrane. Endocytosis of the lipoplex then occurs, and the DNA is released into the cytoplasm. The cationic lipids also protect against degradation of the DNA by the cell.

Complexes of polymers with DNA are called polyplexes. Most polyplexes consist of cationic polymers and their production is regulated by ionic interactions. One large difference between the methods of action of polyplexes and lipoplexes is that polyplexes cannot release their DNA load into the cytoplasm, so to this end, co-transfection with endosome-lytic agents (to lyse the endosome that is made during endocytosis) such as inactivated adenovirus must occur. However, this is not always the case; polymers such as polyethylenimine have their own method of endosome disruption as does chitosan and trimethylchitosan.

Dendrimers, a highly branched macromolecule with a spherical shape, may be also be used to genetically modify stem cells. The surface of the dendrimer particle may be functionalized to alter its properties. In particular, it is possible to construct a cationic dendrimer (i.e., one with a positive surface charge). When in the presence of genetic material such as a DNA plasmid, charge complementarity leads to a temporary association of the nucleic acid with the cationic dendrimer. On reaching its destination, the dendrimer-nucleic acid complex can be taken up into a cell by endocytosis.

In some cases, a nucleic acid of the disclosure (e.g., an expression vector) includes an insertion site for a guide sequence of interest. For example, a nucleic acid can include an insertion site for a guide sequence of interest, where the insertion site is immediately adjacent to a nucleotide sequence encoding the portion of a CasZ guide RNA that does not change when the guide sequence is changed to hybrized to a desired target sequence (e.g., sequences that contribute to the CasZ binding aspect of the guide RNA, e.g, the sequences that contribute to the dsRNA duplex(es) of the CasZ guide RNA—this portion of the guide RNA can also be referred to as the 'scaffold' or 'constant region' of the guide RNA). Thus, in some cases, a subject nucleic acid (e.g., an expression vector) includes a nucleotide sequence encoding a CasZ guide RNA, except that the portion encoding the guide sequence portion of the guide RNA is an insertion sequence (an insertion site). An insertion site is any nucleotide sequence used for the insertion of a desired sequence. "Insertion sites" for use with various technologies are known to those of ordinary skill in the art and any convenient insertion site can be used. An insertion site can be for any method for manipulating nucleic acid sequences. For example, in some cases the insertion site is a multiple cloning site (MCS) (e.g., a site including one or more restriction enzyme recognition sequences), a site for ligation independent cloning, a site for recombination-based cloning (e.g., recombination based on att sites), a nucleotide sequence recognized by a CRISPR/Cas (e.g. Cas9) based technology, and the like.

An insertion site can be any desirable length, and can depend on the type of insertion site (e.g., can depend on whether (and how many) the site includes one or more restriction enzyme recognition sequences, whether the site includes a target site for a CRISPR/Cas protein, etc.). In some cases, an insertion site of a subject nucleic acid is 3 or more nucleotides (nt) in length (e.g., 5 or more, 8 or more, 10 or more, 15 or more, 17 or more, 18 or more, 19 or more, 20 or more or 25 or more, or 30 or more nt in length). In some cases, the length of an insertion site of a subject nucleic acid has a length in a range of from 2 to 50 nucleotides (nt) (e.g., from 2 to 40 nt, from 2 to 30 nt, from 2 to 25 nt, from 2 to 20 nt, from 5 to 50 nt, from 5 to 40 nt, from 5 to 30 nt, from 5 to 25 nt, from 5 to 20 nt, from 10 to 50 nt, from 10 to 40 nt, from 10 to 30 nt, from 10 to 25 nt, from 10 to 20 nt, from 17 to 50 nt, from 17 to 40 nt, from 17 to 30 nt, from 17 to 25 nt). In some cases, the length of an insertion site of a subject nucleic acid has a length in a range of from 5 to 40 nt.

Nucleic Acid Modifications

In some embodiments, a subject nucleic acid (e.g., a CasZ guide RNA or trancRNA) has one or more modifications, e.g., a base modification, a backbone modification, etc., to provide the nucleic acid with a new or enhanced feature (e.g., improved stability). A nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to the 2', the 3', or the 5' hydroxyl moiety of the sugar. In forming oligonucleotides, the phosphate groups covalently link adjacent nucleosides to one another to form a linear polymeric compound. In turn, the respective ends of this linear polymeric compound can be further joined to form a circular compound, however, linear compounds are suitable. In addition, linear compounds may have internal nucleotide base complementarity and may therefore fold in a manner as to produce a fully or partially double-stranded compound. Within oligonucleotides, the phosphate groups are commonly referred to as forming the internucleoside backbone of the oligonucleotide. The normal linkage or backbone of RNA and DNA is a 3' to 5' phosphodiester linkage.

Suitable nucleic acid modifications include, but are not limited to: 2'Omethyl modified nucleotides, 2' Fluoro modified nucleotides, locked nucleic acid (LNA) modified nucleotides, peptide nucleic acid (PNA) modified nucleotides, nucleotides with phosphorothioate linkages, and a 5' cap (e.g., a 7-methylguanylate cap (m7G)). Additional details and additional modifications are described below.

A 2'-O-Methyl modified nucleotide (also referred to as 2'-O-Methyl RNA) is a naturally occurring modification of RNA found in tRNA and other small RNAs that arises as a post-transcriptional modification. Oligonucleotides can be directly synthesized that contain 2'-O-Methyl RNA. This modification increases Tm of RNA:RNA duplexes but results in only small changes in RNA:DNA stability. It is stabile with respect to attack by single-stranded ribonucleases and is typically 5 to 10-fold less susceptible to DNases than DNA. It is commonly used in antisense oligos as a means to increase stability and binding affinity to the target message.

2' Fluoro modified nucleotides (e.g., 2' Fluoro bases) have a fluorine modified ribose which increases binding affinity (Tm) and also confers some relative nuclease resistance when compared to native RNA. These modifications are commonly employed in ribozymes and siRNAs to improve stability in serum or other biological fluids.

LNA bases have a modification to the ribose backbone that locks the base in the C3'-endo position, which favors RNA A-type helix duplex geometry. This modification significantly increases Tm and is also very nuclease resistant. Multiple LNA insertions can be placed in an oligo at any position except the 3'-end. Applications have been described ranging from antisense oligos to hybridization probes to SNP detection and allele specific PCR. Due to the large increase in Tm conferred by LNAs, they also can cause an increase in primer dimer formation as well as self-hairpin formation. In some cases, the number of LNAs incorporated into a single oligo is 10 bases or less.

The phosphorothioate (PS) bond (i.e., a phosphorothioate linkage) substitutes a sulfur atom for a non-bridging oxygen in the phosphate backbone of a nucleic acid (e.g., an oligo). This modification renders the internucleotide linkage resistant to nuclease degradation. Phosphorothioate bonds can be introduced between the last 3-5 nucleotides at the 5'- or 3'-end of the oligo to inhibit exonuclease degradation. Including phosphorothioate bonds within the oligo (e.g., throughout the entire oligo) can help reduce attack by endonucleases as well.

In some embodiments, a subject nucleic acid has one or more nucleotides that are 2'-O-Methyl modified nucleotides. In some embodiments, a subject nucleic acid (e.g., a guide RNA, a tranc RNA, etc.) has one or more 2' Fluoro modified nucleotides. In some embodiments, a subject nucleic acid (e.g., a dsRNA, a siNA, etc.) has one or more LNA bases. In some embodiments, a subject nucleic acid (e.g., a dsRNA, a siNA, etc.) has one or more nucleotides that are linked by a phosphorothioate bond (i.e., the subject nucleic acid has one or more phosphorothioate linkages). In some embodiments, a subject nucleic acid (e.g., a dsRNA, a siNA, etc.) has a 5' cap (e.g., a 7-methylguanylate cap (m7G)). In some embodiments, a subject nucleic acid (e.g., a guide RNA, a tranc RNA, etc.) has a combination of modified nucleotides. For example, a subject nucleic acid (e.g., a guide RNA, a tranc RNA, etc.) can have a 5' cap (e.g., a 7-methylguanylate cap (m7G)) in addition to having one or more nucleotides with other modifications (e.g., a 2'-O-Methyl nucleotide and/or a 2' Fluoro modified nucleotide and/or a LNA base and/or a phosphorothioate linkage).

Modified Backbones and Modified Internucleoside Linkages

Examples of suitable nucleic acids (e.g., a CasZ guide RNA and/or CasZ trancRNA) containing modifications include nucleic acids containing modified backbones or non-natural internucleoside linkages. Nucleic acids having modified backbones include those that retain a phosphorus atom in the backbone and those that do not have a phosphorus atom in the backbone.

Suitable modified oligonucleotide backbones containing a phosphorus atom therein include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, phosphorodiamidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Suitable oligonucleotides having inverted polarity comprise a single 3' to 3' linkage at the 3'-most internucleotide linkage i.e. a single inverted nucleoside residue which may be a basic (the nucleobase is missing or has a hydroxyl group in place thereof). Various salts (such as, for example, potassium or sodium), mixed salts and free acid forms are also included.

In some embodiments, a subject nucleic acid comprises one or more phosphorothioate and/or heteroatom internucleoside linkages, in particular —CH$_2$—NHO—CH$_2$—, —CH$_2$—N(CH$_3$)—O—CH$_2$— (known as a methylene (methylimino) or MMI backbone), —CH$_2$—O—N(CH$_3$)—CH$_2$—, —CH$_2$—N(CH$_3$)—N(CH$_3$)—CH$_2$— and —O—N(CH$_3$)—CH$_2$—CH$_2$— (wherein the native phosphodiester internucleotide linkage is represented as —O—P(═O)(OH)—O—CH$_2$—). MMI type internucleoside linkages are disclosed in the above referenced U.S. Pat. No. 5,489,677, the disclosure of which is incorporated herein by reference in its entirety. Suitable amide internucleoside linkages are disclosed in U.S. Pat. No. 5,602,240, the disclosure of which is incorporated herein by reference in its entirety.

Also suitable are nucleic acids having morpholino backbone structures as described in, e.g., U.S. Pat. No. 5,034,506. For example, in some embodiments, a subject nucleic acid comprises a 6-membered morpholino ring in place of a ribose ring. In some of these embodiments, a phosphorodiamidate or other non-phosphodiester internucleoside linkage replaces a phosphodiester linkage.

Suitable modified polynucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and CH$_2$ component parts.

Mimetics

A subject nucleic acid can be a nucleic acid mimetic. The term "mimetic" as it is applied to polynucleotides is intended to include polynucleotides wherein only the furanose ring or both the furanose ring and the internucleotide linkage are replaced with non-furanose groups, replacement of only the furanose ring is also referred to in the art as being a sugar surrogate. The heterocyclic base moiety or a modified heterocyclic base moiety is maintained for hybridization with an appropriate target nucleic acid. One such nucleic acid, a polynucleotide mimetic that has been shown to have excellent hybridization properties, is referred to as a peptide nucleic acid (PNA). In PNA, the sugar-backbone of a polynucleotide is replaced with an amide containing backbone, in particular an aminoethylglycine backbone. The nucleotides are retained and are bound directly or indirectly to aza nitrogen atoms of the amide portion of the backbone.

One polynucleotide mimetic that has been reported to have excellent hybridization properties is a peptide nucleic acid (PNA). The backbone in PNA compounds is two or more linked aminoethylglycine units which gives PNA an amide containing backbone. The heterocyclic base moieties are bound directly or indirectly to aza nitrogen atoms of the amide portion of the backbone. Representative U.S. patents that describe the preparation of PNA compounds include, but are not limited to: U.S. Pat. Nos. 5,539,082; 5,714,331; and 5,719,262, the disclosures of which are incorporated herein by reference in their entirety.

Another class of polynucleotide mimetic that has been studied is based on linked morpholino units (morpholino nucleic acid) having heterocyclic bases attached to the morpholino ring. A number of linking groups have been reported that link the morpholino monomeric units in a morpholino nucleic acid. One class of linking groups has been selected to give a non-ionic oligomeric compound. The non-ionic morpholino-based oligomeric compounds are less likely to have undesired interactions with cellular proteins. Morpholino-based polynucleotides are non-ionic mimics of oligonucleotides which are less likely to form undesired interactions with cellular proteins (Dwaine A. Braasch and David R. Corey, Biochemistry, 2002, 41(14), 4503-4510). Morpholino-based polynucleotides are disclosed in U.S. Pat. No. 5,034,506, the disclosure of which is incorporated herein by reference in its entirety. A variety of compounds within the morpholino class of polynucleotides have been prepared, having a variety of different linking groups joining the monomeric subunits.

A further class of polynucleotide mimetic is referred to as cyclohexenyl nucleic acids (CeNA). The furanose ring normally present in a DNA/RNA molecule is replaced with a cyclohexenyl ring. CeNA DMT protected phosphoramidite monomers have been prepared and used for oligomeric compound synthesis following classical phosphoramidite chemistry. Fully modified CeNA oligomeric compounds and oligonucleotides having specific positions modified with CeNA have been prepared and studied (see Wang et al., *J. Am. Chem. Soc.*, 2000, 122, 8595-8602, the disclosure of which is incorporated herein by reference in its entirety). In general, the incorporation of CeNA monomers into a DNA chain increases its stability of a DNA/RNA hybrid. CeNA oligoadenylates formed complexes with RNA and DNA complements with similar stability to the native complexes. The study of incorporating CeNA structures into natural nucleic acid structures was shown by NMR and circular dichroism to proceed with easy conformational adaptation.

A further modification includes Locked Nucleic Acids (LNAs) in which the 2'-hydroxyl group is linked to the 4' carbon atom of the sugar ring thereby forming a 2'-C,4'-C-oxymethylene linkage thereby forming a bicyclic sugar moiety. The linkage can be a methylene ($-CH_2-$), group bridging the 2' oxygen atom and the 4' carbon atom wherein n is 1 or 2 (Singh et al., *Chem. Commun.*, 1998, 4, 455-456, the disclosure of which is incorporated herein by reference in its entirety). LNA and LNA analogs display very high duplex thermal stabilities with complementary DNA and RNA (Tm=+3 to +10° C.), stability towards 3'-exonucleolytic degradation and good solubility properties. Potent and nontoxic antisense oligonucleotides containing LNAs have been described (e.g., Wahlestedt et al., *Proc. Natl. Acad. Sci. U.S.A.*, 2000, 97, 5633-5638, the disclosure of which is incorporated herein by reference in its entirety).

The synthesis and preparation of the LNA monomers adenine, cytosine, guanine, 5-methyl-cytosine, thymine and uracil, along with their oligomerization, and nucleic acid recognition properties have been described (e.g., Koshkin et al., *Tetrahedron*, 1998, 54, 3607-3630, the disclosure of which is incorporated herein by reference in its entirety). LNAs and preparation thereof are also described in WO 98/39352 and WO 99/14226, as well as U.S. applications 20120165514, 20100216983, 20090041809, 20060117410, 20040014959, 20020094555, and 20020086998, the disclosures of which are incorporated herein by reference in their entirety.

Modified Sugar Moieties

A subject nucleic acid can also include one or more substituted sugar moieties. Suitable polynucleotides comprise a sugar substituent group selected from: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted C.sub.1 to $C_{10}$ alkyl or $C_2$ to $C_{10}$ alkenyl and alkynyl. Particularly suitable are $O((CH_2)_nO)_mCH_3$, $O(CH_2)_nOCH_3$, $O(CH_2)_nNH_2$, $O(CH_2)_nCH_3$, $O(CH_2)_nONH_2$, and $O(CH_2)_nON((CH_2)_nCH_3)_2$, where n and m are from 1 to about 10. Other suitable polynucleotides comprise a sugar substituent group selected from: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A suitable modification includes 2'-methoxyethoxy (2'-O—$CH_2CH_2OCH_3$, also known as 2'-O-(2-methoxyethyl) or 2'-MOE) (Martin et al., *Helv. Chim. Acta*, 1995, 78, 486-504, the disclosure of which is incorporated herein by reference in its entirety) i.e., an alkoxyalkoxy group. A further suitable modification includes 2'-dimethylaminooxyethoxy, i.e., a $O(CH_2)_2ON(CH_3)_2$ group, also known as 2'-DMAOE, as described in examples hereinbelow, and 2'-dimethylaminoethoxyethoxy (also known in the art as 2'-O-dimethyl-amino-ethoxy-ethyl or 2'-DMAEOE), i.e., 2'-O—$CH_2$—O—$CH_2$—$N(CH_3)_2$.

Other suitable sugar substituent groups include methoxy (—O—$CH_3$), aminopropoxy (—$OCH_2CH_2CH_2NH_2$), allyl (—$CH_2$—CH=$CH_2$), —O-allyl (—O—$CH_2$—CH=$CH_2$) and fluoro (F). 2'-sugar substituent groups may be in the arabino (up) position or ribo (down) position. A suitable 2'-arabino modification is 2'-F. Similar modifications may also be made at other positions on the oligomeric compound, particularly the 3' position of the sugar on the 3' terminal nucleoside or in 2'-5' linked oligonucleotides and the 5' position of 5' terminal nucleotide. Oligomeric compounds may also have sugar mimetics such as cyclobutyl moieties in place of the pentofuranosyl sugar.

Base Modifications and Substitutions

A subject nucleic acid may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido(5,4-b)(1,4)benzoxazin-2 (3H)-one), phenothiazine cytidine (1H-pyrimido(5,4-b)(1,4) benzothiazin-2(3H)-one), G-clamps such as a substituted phenoxazine cytidine (e.g. 9-(2-aminoethoxy)-H-pyrimido (5,4-(b) (1,4)benzoxazin-2(3H)-one), carbazole cytidine (2H-pyrimido(4,5-b)indol-2-one), pyridoindole cytidine (H-pyrido(3', 2': 4,5)pyrrolo(2,3-d)pyrimidin-2-one).

Heterocyclic base moieties may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, pages 858-859, Kroschwitz, J. I., ed. John Wiley & Sons, 1990, those disclosed by Englisch et al., *Angewandte Chemie, International Edition*, 1991, 30, 613, and those disclosed by Sanghvi, Y. S., Chapter 15, *Antisense Research and Applications*, pages 289-302, Crooke, S. T. and Lebleu, B., ed., CRC Press, 1993; the disclosures of which are incorporated herein by reference in their entirety. Certain of these nucleobases are useful for increasing the binding affinity of an oligomeric compound. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi et al., eds., Antisense Research and Applications, CRC Press, Boca Raton, 1993, pp. 276-278; the disclosure of which is incorporated herein by reference in its entirety) and are suitable base substitutions, e.g., when combined with 2'-O-methoxyethyl sugar modifications.

Conjugates

Another possible modification of a subject nucleic acid involves chemically linking to the polynucleotide one or more moieties or conjugates which enhance the activity, cellular distribution or cellular uptake of the oligonucleotide. These moieties or conjugates can include conjugate groups covalently bound to functional groups such as primary or secondary hydroxyl groups. Conjugate groups include, but are not limited to, intercalators, reporter molecules, polyamines, polyamides, polyethylene glycols, polyethers, groups that enhance the pharmacodynamic properties of oligomers, and groups that enhance the pharmacokinetic properties of oligomers. Suitable conjugate groups include, but are not limited to, cholesterols, lipids, phospholipids, biotin, phenazine, folate, phenanthridine, anthraquinone, acridine, fluoresceins, rhodamines, coumarins, and dyes. Groups that enhance the pharmacodynamic properties include groups that improve uptake, enhance resistance to degradation, and/or strengthen sequence-specific hybridization with the target nucleic acid. Groups that enhance the pharmacokinetic properties include groups that improve uptake, distribution, metabolism or excretion of a subject nucleic acid.

Conjugate moieties include but are not limited to lipid moieties such as a cholesterol moiety (Letsinger et al., *Proc. Natl. Acad. Sci. USA*, 1989, 86, 6553-6556), cholic acid (Manoharan et al., *Bioorg. Med. Chem. Let.*, 1994, 4, 1053-1060), a thioether, e.g., hexyl-S-tritylthiol (Manoharan et al., *Ann. N.Y Acad. Sci.*, 1992, 660, 306-309; Manoharan et al., *Bioorg. Med. Chem. Let.*, 1993, 3, 2765-2770), a thiocholesterol (Oberhauser et al., *Nucl. Acids Res.*, 1992, 20, 533-538), an aliphatic chain, e.g., dodecandiol or undecyl residues (Saison-Behmoaras et al., *EMBO J.*, 1991, 10, 1111-1118; Kabanov et al., *FEBS Lett.*, 1990, 259, 327-330; Svinarchuk et al., *Biochimie*, 1993, 75, 49-54), a phospholipid, e.g., di-hexadecyl-rac-glycerol or triethylammonium 1,2-di-O-hexadecyl-rac-glycero-3-H-phosphonate (Manoharan et al., *Tetrahedron Lett.*, 1995, 36, 3651-3654; Shea et al., *Nucl. Acids Res.*, 1990, 18, 3777-3783), a polyamine or a polyethylene glycol chain (Manoharan et al., *Nucleosides & Nucleotides*, 1995, 14, 969-973), or adamantane acetic acid (Manoharan et al., *Tetrahedron Lett.*, 1995, 36, 3651-3654), a palmityl moiety (Mishra et al., *Biochim. Biophys. Acta*, 1995, 1264, 229-237), or an octadecylamine or hexylamino-carbonyl-oxycholesterol moiety (Crooke et al., *J. Pharmacol. Exp. Ther.*, 1996, 277, 923-937).

A conjugate may include a "Protein Transduction Domain" or PTD (also known as a CPP—cell penetrating peptide), which may refer to a polypeptide, polynucleotide, carbohydrate, or organic or inorganic compound that facilitates traversing a lipid bilayer, micelle, cell membrane, organelle membrane, or vesicle membrane. A PTD attached to another molecule, which can range from a small polar molecule to a large macromolecule and/or a nanoparticle, facilitates the molecule traversing a membrane, for example going from extracellular space to intracellular space, or cytosol to within an organelle (e.g., the nucleus). In some cases, a PTD is covalently linked to the 3' end of an exogenous polynucleotide. In some cases, a PTD is covalently linked to the 5' end of an exogenous polynucleotide. Exemplary PTDs include but are not limited to a minimal undecapeptide protein transduction domain (corresponding to residues 47-57 of HIV-1 TAT comprising YGRKKRRQRRR; SEQ ID NO: 130); a polyarginine sequence comprising a number of arginines sufficient to direct entry into a cell (e.g., 3, 4, 5, 6, 7, 8, 9, 10, or 10-50 arginines); a VP22 domain (Zender et al. (2002) *Cancer Gene Ther.* 9(6):489-96); an *Drosophila* Antennapedia protein transduction domain (Noguchi et al. (2003) *Diabetes* 52(7):1732-1737); a truncated human calcitonin peptide (Trehin et al. (2004) *Pharm. Research* 21:1248-1256); polylysine (Wender et al. (2000) *Proc. Natl. Acad. Sci. USA* 97:13003-13008); RRQRRTSKLMKR SEQ ID NO: 131); Transportan GWTLNSAGYLLGKINLKALAALAKKIL SEQ ID NO: 132); KALAWEAKLAKALAKA-LAKHLAKALAKALKCEA SEQ ID NO: 133); and RQIKIWFQNRRMKWKK SEQ ID NO: 134). Exemplary PTDs include but are not limited to, YGRKKRRQRRR SEQ ID NO: 130), RKKRRQRRR SEQ ID NO: 135); an arginine homopolymer of from 3 arginine residues to 50 arginine residues; Exemplary PTD domain amino acid sequences include, but are not limited to, any of the following: YGRKKRRQRRR SEQ ID NO: 130); RKKRRQRR SEQ ID NO: 136); YARAAARQARA SEQ ID NO: 137); THRL-PRRRRRR SEQ ID NO: 138); and GGRRARRRRRR SEQ ID NO: 139). In some cases, the PTD is an activatable CPP (ACPP) (Aguilera et al. (2009) *Integr Biol (Camb) June;* 1(5-6): 371-381). ACPPs comprise a polycationic CPP (e.g., Arg9 or "R9") connected via a cleavable linker to a matching polyanion (e.g., Glu9 or "E9"), which reduces the net charge to nearly zero and thereby inhibits adhesion and uptake into cells. Upon cleavage of the linker, the polyanion is released, locally unmasking the polyarginine and its inherent adhesiveness, thus "activating" the ACPP to traverse the membrane.

Introducing Components into a Target Cell

A CasZ guide RNA (or a nucleic acid comprising a nucleotide sequence encoding same) and/or a CasZ polypeptide (or a nucleic acid comprising a nucleotide sequence encoding same) and/or a CasZ trancRNA (or a nucleic acid that includes a nucleotide sequence encoding same) and/or a donor polynucleotide (donor template) can be introduced into a host cell by any of a variety of well-known methods.

Any of a variety of compounds and methods can be used to deliver to a target cell a CasZ system of the present disclosure. As a non-limiting example, a CasZ system of the present disclosure can be combined with a lipid. As another non-limiting example, a CasZ system of the present disclosure can be combined with a particle, or formulated into a particle.

Methods of introducing a nucleic acid into a host cell are known in the art, and any convenient method can be used to introduce a subject nucleic acid (e.g., an expression construct/vector) into a target cell (e.g., prokaryotic cell, eukaryotic cell, plant cell, animal cell, mammalian cell, human cell, and the like). Suitable methods include, e.g., viral infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro injection, nanoparticle-mediated nucleic acid delivery (see, e.g., Panyam et., al Adv Drug Deliv Rev. 2012 Sep. 13. pii: 50169-409X(12)00283-9. doi: 10.1016/j.addr.2012.09.023), and the like.

In some cases, a CasZ polypeptide of the present disclosure (e.g., wild type protein, variant protein, chimeric/fusion protein, dCasZ, etc.) is provided as a nucleic acid (e.g., an mRNA, a DNA, a plasmid, an expression vector, a viral vector, etc.) that encodes the CasZ polypeptide. In some cases, the CasZ polypeptide of the present disclosure is provided directly as a protein (e.g., without an associated guide RNA or with an associate guide RNA, i.e., as a ribonucleoprotein complex). A CasZ polypeptide of the present disclosure can be introduced into a cell (provided to the cell) by any convenient method; such methods are known to those of ordinary skill in the art. As an illustrative example, a CasZ polypeptide of the present disclosure can be injected directly into a cell (e.g., with or without a CasZ guide RNA or nucleic acid encoding a CasZ guide RNA, and with or without a donor polynucleotide and with or without a CasZ trancRNA). As another example, a preformed complex of a CasZ polypeptide of the present disclosure and a CasZ guide RNA (an RNP) can be introduced into a cell (e.g, eukaryotic cell) (e.g., via injection, via nucleofection; via a protein transduction domain (PTD) conjugated to one or more components, e.g., conjugated to the CasZ protein, conjugated to a guide RNA, conjugated to a CasZ trancRNA, conjugated to a CasZ polypeptide of the present disclosure and a guide RNA; etc.).

In some cases, a nucleic acid (e.g., a CasZ guide RNA and/or a nucleic acid encoding it, a nucleic acid encoding a CasZ protein, a CasZ trancRNA and/or a nucleic acid encoding it, and the like) and/or a polypeptide (e.g., a CasZ polypeptide; a CasZ fusion polypeptide) is delivered to a cell (e.g., a target host cell) in a particle, or associated with a particle. In some cases, a CasZ system of the present disclosure is delivered to a cell in a particle, or associated with a particle. The terms "particle" and nanoparticle" can be used interchangeable, as appropriate. For example, a recombinant expression vector comprising a nucleotide sequence encoding a CasZ polypeptide of the present disclosure and/or a CasZ guide RNA, an mRNA comprising a nucleotide sequence encoding a CasZ polypeptide of the present disclosure, and guide RNA may be delivered simultaneously using particles or lipid envelopes; for instance, a CasZ polypeptide and/or a CasZ guide RNA and/or a trancRNA, e.g., as a complex (e.g., a ribonucleoprotein (RNP) complex), can be delivered via a particle, e.g., a delivery particle comprising lipid or lipidoid and hydrophilic polymer, e.g., a cationic lipid and a hydrophilic polymer, for instance wherein the cationic lipid comprises 1,2-dioleoyl-3-trimethylammonium-propane (DOTAP) or 1,2-ditetradecanoyl-sn-glycero-3-phosphocholine (DMPC) and/or wherein the hydrophilic polymer comprises ethylene glycol or polyethylene glycol (PEG); and/or wherein the particle further comprises cholesterol (e.g., particle from formulation 1=DOTAP 100, DMPC 0, PEG 0, Cholesterol 0; formulation number 2=DOTAP 90, DMPC 0, PEG 10, Cholesterol 0; formulation number 3=DOTAP 90, DMPC 0, PEG 5, Cholesterol 5). For example, a particle can be formed using a multistep process in which a CasZ polypepide and a CasZ guideRNA are mixed together, e.g., at a 1:1 molar ratio, e.g., at room temperature, e.g., for 30 minutes, e.g., in sterile, nuclease free 1×phosphate-buffered saline (PBS); and separately, DOTAP, DMPC, PEG, and cholesterol as applicable for the formulation are dissolved in alcohol, e.g., 100% ethanol; and, the two solutions are mixed together to form particles containing the complexes).

A CasZ polypeptide of the present disclosure (or an mRNA comprising a nucleotide sequence encoding a CasZ polypeptide of the present disclosure; or a recombinant expression vector comprising a nucleotide sequence encoding a CasZ polypeptide of the present disclosure) and/or CasZ guide RNA (or a nucleic acid such as one or more expression vectors encoding the CasZ guide RNA) may be delivered simultaneously using particles or lipid envelopes. For example, a biodegradable core-shell structured nanoparticle with a poly (β-amino ester) (PBAE) core enveloped by a phospholipid bilayer shell can be used. In some cases, particles/nanoparticles based on self assembling bioadhesive polymers are used; such particles/nanoparticles may be applied to oral delivery of peptides, intravenous delivery of peptides and nasal delivery of peptides, e.g., to the brain. Other embodiments, such as oral absorption and ocular delivery of hydrophobic drugs are also contemplated. A molecular envelope technology, which involves an engineered polymer envelope which is protected and delivered to the site of the disease, can be used. Doses of about 5 mg/kg can be used, with single or multiple doses, depending on various factors, e.g., the target tissue.

Lipidoid compounds (e.g., as described in US patent application 20110293703) are also useful in the administration of polynucleotides, and can be used to deliver a CasZ polypeptide of the present disclosure, a CasZ fusion polypeptide of the present disclosure, an RNP of the present disclosure, a nucleic acid of the present disclosure, or a CasZ system of the present disclosure. In one aspect, the aminoalcohol lipidoid compounds are combined with an agent to be delivered to a cell or a subject to form microparticles, nanoparticles, liposomes, or micelles. The aminoalcohol lipidoid compounds may be combined with other aminoalcohol lipidoid compounds, polymers (synthetic or natural), surfactants, cholesterol, carbohydrates, proteins, lipids, etc. to form the particles. These particles may then optionally be combined with a pharmaceutical excipient to form a pharmaceutical composition.

A poly(beta-amino alcohol) (PBAA) can be used to deliver a CasZ polypeptide of the present disclosure, a CasZ fusion polypeptide of the present disclosure, an RNP of the present disclosure, a nucleic acid of the present disclosure (e.g., a CasZ guide RNA and/or a CasZ trancRNA), or a CasZ system of the present disclosure, to a target cell. US Patent Publication No. 20130302401 relates to a class of poly(beta-amino alcohols) (PBAAs) that has been prepared using combinatorial polymerization.

Sugar-based particles may be used, for example GalNAc, as described with reference to WO2014118272 (incorporated herein by reference) and Nair, J K et al., 2014, Journal of the American Chemical Society 136 (49), 16958-16961) can be used to deliver a CasZ polypeptide of the present disclosure, a CasZ fusion polypeptide of the present disclosure, an RNP of the present disclosure, a nucleic acid of the present disclosure, or a CasZ system of the present disclosure, to a target cell.

In some cases, lipid nanoparticles (LNPs) are used to deliver a CasZ polypeptide of the present disclosure, a CasZ fusion polypeptide of the present disclosure, an RNP of the present disclosure, a nucleic acid of the present disclosure (e.g., a CasZ guide RNA and/or a CasZ trancRNA), or a CasZ system of the present disclosure, to a target cell. Negatively charged polymers such as RNA may be loaded into LNPs at low pH values (e.g., pH 4) where the ionizable lipids display a positive charge. However, at physiological pH values, the LNPs exhibit a low surface charge compatible with longer circulation times. Four species of ionizable cationic lipids have been focused upon, namely 1,2-dilineoyl-3-dimethylammonium-propane (DLinDAP), 1,2-dilinoleyloxy-3-N,N-dimethylaminopropane (DLinDMA), 1,2-dilinoleyloxy-keto-N,N-dimethyl-3-aminopropane (DLinKDMA), and 1,2-dilinoleyl-4-(2-dimethylaminoethyl)-[1,3]-dioxolane (DLinKC2-DMA). Preparation of LNPs and is described in, e.g., Rosin et al. (2011) Molecular Therapy 19:1286-2200). The cationic lipids 1,2-dilineoyl-3-dimethylammonium-propane (DLinDAP), 1,2-dilinoleyloxy-3-N,N-dimethylaminopropane (DLinDMA), 1,2-dilinoleyloxyketo-N,N-dimethyl-3-aminopropane (DLinK-DMA), 1,2-dilinoleyl-4-(2-dimethylaminoethyl)-[1,3]-dioxolane (DLinKC2-DMA), (3-o-[2"-(methoxypolyethyleneglycol 2000) succinoyl]-1,2-dimyristoyl-sn-glycol (PEG-S-DMG), and R-3-[.omega.-methoxy-poly(ethylene glycol) 2000) carbamoyl]-1,2-dimyristyloxlpropyl-3-amine (PEG-C-DOMG) may be used. A nucleic acid (e.g., a CasZ guide RNA; a nucleic acid of the present disclosure; etc.) may be encapsulated in LNPs containing DLinDAP, DLinDMA, DLinK-DMA, and DLinKC2-DMA (cationic lipid:DSPC:CHOL:PEGS-DMG or PEG-C-DOMG at 40:10:40:10 molar ratios). In some cases, 0.2% SP-DiOC18 is incorporated.

Spherical Nucleic Acid (SNA™) constructs and other nanoparticles (particularly gold nanoparticles) can be used to deliver a CasZ polypeptide of the present disclosure, a CasZ fusion polypeptide of the present disclosure, an RNP of the present disclosure, a nucleic acid of the present disclosure (e.g., a CasZ guide RNA and/or a CasZ trancRNA), or a CasZ system of the present disclosure, to a target cell. See, e.g., Cutler et al., J. Am. Chem. Soc. 2011 133:9254-9257, Hao et al., Small. 2011 7:3158-3162, Zhang et al., ACS Nano. 2011 5:6962-6970, Cutler et al., J. Am. Chem. Soc. 2012 134:1376-1391, Young et al., Nano Lett. 2012 12:3867-71, Zheng et al., Proc. Natl. Acad. Sci. USA. 2012 109:11975-80, Mirkin, Nanomedicine 2012 7:635-638 Zhang et al., J. Am. Chem. Soc. 2012 134:16488-1691, Weintraub, Nature 2013 495:S14-S16, Choi et al., Proc. Natl. Acad. Sci. USA. 2013 110(19): 7625-7630, Jensen et al., Sci. Transl. Med. 5, 209ra152 (2013) and Mirkin, et al., Small, 10:186-192.

Self-assembling nanoparticles with RNA may be constructed with polyethyleneimine (PEI) that is PEGylated with an Arg-Gly-Asp (RGD) peptide ligand attached at the distal end of the polyethylene glycol (PEG).

In general, a "nanoparticle" refers to any particle having a diameter of less than 1000 nm. In some cases, nanoparticles suitable for use in delivering a CasZ polypeptide of the present disclosure, a CasZ fusion polypeptide of the present disclosure, an RNP of the present disclosure, a nucleic acid of the present disclosure (e.g., a CasZ guide RNA and/or a CasZ trancRNA), or a CasZ system of the present disclosure, to a target cell have a diameter of 500 nm or less, e.g., from 25 nm to 35 nm, from 35 nm to 50 nm, from 50 nm to 75 nm, from 75 nm to 100 nm, from 100 nm to 150 nm, from 150 nm to 200 nm, from 200 nm to 300 nm, from 300 nm to 400 nm, or from 400 nm to 500 nm. In some cases, nanoparticles suitable for use in delivering a CasZ polypeptide of the present disclosure, a CasZ fusion polypeptide of the present disclosure, an RNP of the present disclosure, a nucleic acid of the present disclosure, or a CasZ system of the present disclosure, to a target cell have a diameter of from 25 nm to 200 nm. In some cases, nanoparticles suitable for use in delivering a CasZ polypeptide of the present disclosure, a CasZ fusion polypeptide of the present disclosure, an RNP of the present disclosure, a nucleic acid of the present disclosure, or a CasZ system of the present disclosure, to a target cell have a diameter of 100 nm or less In some cases, nanoparticles suitable for use in delivering a CasZ polypeptide of the present disclosure, a CasZ fusion polypeptide of the present disclosure, an RNP of the present disclosure, a nucleic acid of the present disclosure, or a CasZ system of the present disclosure, to a target cell have a diameter of from 35 nm to 60 nm.

Nanoparticles suitable for use in delivering a CasZ polypeptide of the present disclosure, a CasZ fusion polypeptide of the present disclosure, an RNP of the present disclosure, a nucleic acid of the present disclosure (e.g., a CasZ guide RNA and/or a CasZ trancRNA), or a CasZ system of the present disclosure, to a target cell may be provided in different forms, e.g., as solid nanoparticles (e.g., metal such as silver, gold, iron, titanium), non-metal, lipid-based solids, polymers), suspensions of nanoparticles, or combinations thereof. Metal, dielectric, and semiconductor nanoparticles may be prepared, as well as hybrid structures (e.g., core-shell nanoparticles). Nanoparticles made of semiconducting material may also be labeled quantum dots if they are small enough (typically below 10 nm) that quantization of electronic energy levels occurs. Such nanoscale particles are used in biomedical applications as drug carriers or imaging agents and may be adapted for similar purposes in the present disclosure.

Semi-solid and soft nanoparticles are also suitable for use in delivering a CasZ polypeptide of the present disclosure, a CasZ fusion polypeptide of the present disclosure, an RNP of the present disclosure, a nucleic acid of the present disclosure (e.g., a CasZ guide RNA and/or a CasZ trancRNA), or a CasZ system of the present disclosure, to a target cell. A prototype nanoparticle of semi-solid nature is the liposome.

In some cases, an exosome is used to deliver a CasZ polypeptide of the present disclosure, a CasZ fusion polypeptide of the present disclosure, an RNP of the present disclosure, a nucleic acid of the present disclosure (e.g., a CasZ guide RNA and/or a CasZ trancRNA), or a CasZ system of the present disclosure, to a target cell. Exosomes are endogenous nano-vesicles that transport RNAs and proteins, and which can deliver RNA to the brain and other target organs.

In some cases, a liposome is used to deliver a CasZ polypeptide of the present disclosure, a CasZ fusion polypeptide of the present disclosure, an RNP of the present disclosure, a nucleic acid of the present disclosure (e.g., a CasZ guide RNA and/or a CasZ trancRNA), or a CasZ system of the present disclosure, to a target cell. Liposomes are spherical vesicle structures composed of a uni- or multilamellar lipid bilayer surrounding internal aqueous compartments and a relatively impermeable outer lipophilic phospholipid bilayer. Liposomes can be made from several different types of lipids; however, phospholipids are most commonly used to generate liposomes. Although liposome formation is spontaneous when a lipid film is mixed with an aqueous solution, it can also be expedited by applying force in the form of shaking by using a homogenizer, sonicator, or an extrusion apparatus. Several other additives may be added to liposomes in order to modify their structure and properties. For instance, either cholesterol or sphingomyelin may be added to the liposomal mixture in order to help stabilize the liposomal structure and to prevent the leakage of the liposomal inner cargo. A liposome formulation may be mainly comprised of natural phospholipids and lipids such as 1,2-distearoyl-sn-glycero-3-phosphatidyl choline (DSPC), sphingomyelin, egg phosphatidylcholines and monosialoganglioside.

A stable nucleic-acid-lipid particle (SNALP) can be used to deliver a CasZ polypeptide of the present disclosure, a CasZ fusion polypeptide of the present disclosure, an RNP of the present disclosure, a nucleic acid of the present disclosure (e.g., a CasZ guide RNA and/or a CasZ trancRNA), or a CasZ system of the present disclosure, to a target cell. The SNALP formulation may contain the lipids 3-N-[(methoxypoly(ethylene glycol) 2000) carbamoyl]-1,2-dimyristyloxy-propylamine (PEG-C-DMA), 1,2-dilinoleyloxy-N,N-dimethyl-3-aminopropane (DLinDMA), 1,2-distearoyl-sn-glycero-3-phosphocholine (DSPC) and cholesterol, in a 2:40:10:48 molar percent ratio. The SNALP liposomes may be prepared by formulating D-Lin-DMA and PEG-C-DMA with distearoylphosphatidylcholine (DSPC), Cholesterol and siRNA using a 25:1 lipid/siRNA ratio and a 48/40/10/2 molar ratio of Cholesterol/D-Lin-DMA/DSPC/PEG-C-DMA. The resulting SNALP liposomes can be about 80-100 nm in size. A SNALP may comprise synthetic cholesterol (Sigma-Aldrich, St Louis, Mo., USA), dipalmitoylphosphatidylcholine (Avanti Polar Lipids, Alabaster, Ala., USA), 3-N-[(w-methoxy poly(ethylene glycol)2000) carbamoyl]-1,2-dimyrestyloxypropylamine, and cationic 1,2-dilinoleyloxy-3-N,Ndimethylaminopropane. A SNALP may comprise synthetic cholesterol (Sigma-Aldrich), 1,2-distearoyl-sn-glycero-3-phosphocholine (DSPC; Avanti Polar Lipids Inc.), PEG-cDMA, and 1,2-dilinoleyloxy-3-(N; N-dimethyl)aminopropane (DLinDMA).

Other cationic lipids, such as amino lipid 2,2-dilinoleyl-4-dimethylaminoethyl-[1,3]-dioxolane (DLin-KC2-DMA) can be used to deliver a CasZ polypeptide of the present disclosure, a CasZ fusion polypeptide of the present disclosure, an RNP of the present disclosure, a nucleic acid of the present disclosure (e.g., a CasZ guide RNA and/or a CasZ trancRNA), or a CasZ system of the present disclosure, to a target cell. A preformed vesicle with the following lipid composition may be contemplated: amino lipid, distearoylphosphatidylcholine (DSPC), cholesterol and (R)-2,3-bis(octadecyloxy) propyl-1-(methoxy poly(ethylene glycol)2000)propylcarbamate (PEG-lipid) in the molar ratio 40/10/40/10, respectively, and a FVII siRNA/total lipid ratio of approximately 0.05 (w/w). To ensure a narrow particle size distribution in the range of 70-90 nm and a low polydispersity index of 0.11.+−.0.04 (n=56), the particles may be extruded up to three times through 80 nm membranes prior to adding the guide RNA. Particles containing the highly potent amino lipid 16 may be used, in which the molar ratio of the four lipid components 16, DSPC, cholesterol and PEG-lipid (50/10/38.5/1.5) which may be further optimized to enhance in vivo activity.

Lipids may be formulated with a CasZ system of the present disclosure or component(s) thereof or nucleic acids encoding the same to form lipid nanoparticles (LNPs). Suitable lipids include, but are not limited to, DLin-KC2-DMA4, C12-200 and colipids disteroylphosphatidyl choline, cholesterol, and PEG-DMG may be formulated with a CasZ system, or component thereof, of the present disclosure, using a spontaneous vesicle formation procedure. The component molar ratio may be about 50/10/38.5/1.5 (DLin-KC2-DMA or C12-200/disteroylphosphatidyl choline/cholesterol/PEG-DMG).

A CasZ system of the present disclosure, or a component thereof, may be delivered encapsulated in PLGA microspheres such as that further described in US published applications 20130252281 and 20130245107 and 20130244279.

Supercharged proteins can be used to deliver a CasZ polypeptide of the present disclosure, a CasZ fusion polypeptide of the present disclosure, an RNP of the present disclosure, a nucleic acid of the present disclosure (e.g., a CasZ guide RNA and/or a CasZ trancRNA), or a CasZ system of the present disclosure, to a target cell. Supercharged proteins are a class of engineered or naturally occurring proteins with unusually high positive or negative net theoretical charge. Both supernegatively and superpositively charged proteins exhibit the ability to withstand thermally or chemically induced aggregation. Superpositively charged proteins are also able to penetrate mammalian cells. Associating cargo with these proteins, such as plasmid DNA, RNA, or other proteins, can enable the functional delivery of these macromolecules into mammalian cells both in vitro and in vivo.

Cell Penetrating Peptides (CPPs) can be used to deliver a CasZ polypeptide of the present disclosure, a CasZ fusion polypeptide of the present disclosure, an RNP of the present disclosure, a nucleic acid of the present disclosure (e.g., a CasZ guide RNA and/or a CasZ trancRNA), or a CasZ system of the present disclosure, to a target cell. CPPs typically have an amino acid composition that either contains a high relative abundance of positively charged amino acids such as lysine or arginine or has sequences that contain an alternating pattern of polar/charged amino acids and non-polar, hydrophobic amino acids.

An implantable device can be used to deliver a CasZ polypeptide of the present disclosure, a CasZ fusion polypeptide of the present disclosure, an RNP of the present disclosure, a nucleic acid of the present disclosure (e.g., a CasZ guide RNA and/or a CasZ trancRNA) (e.g., a CasZ guide RNA, a nucleic acid encoding a CasZ guide RNA, a nucleic acid encoding CasZ polypeptide, a donor template, and the like), or a CasZ system of the present disclosure, to a target cell (e.g., a target cell in vivo, where the target cell is a target cell in circulation, a target cell in a tissue, a target cell in an organ, etc.). An implantable device suitable for use in delivering a CasZ polypeptide of the present disclosure, a CasZ fusion polypeptide of the present disclosure, an RNP of the present disclosure, a nucleic acid of the present disclosure (e.g., a CasZ guide RNA and/or a CasZ trancRNA), or a CasZ system of the present disclosure, to a target cell (e.g., a target cell in vivo, where the target cell is a target cell in circulation, a target cell in a tissue, a target cell in an organ, etc.) can include a container (e.g., a reservoir, a matrix, etc.) that comprises the CasZ polypeptide, the CasZ fusion polypeptide, the RNP, or the CasZ system (or component thereof, e.g., a nucleic acid of the present disclosure).

A suitable implantable device can comprise a polymeric substrate, such as a matrix for example, that is used as the device body, and in some cases additional scaffolding materials, such as metals or additional polymers, and materials to enhance visibility and imaging. An implantable delivery device can be advantageous in providing release locally and over a prolonged period, where the polypeptide and/or nucleic acid to be delivered is released directly to a target site, e.g., the extracellular matrix (ECM), the vasculature surrounding a tumor, a diseased tissue, etc. Suitable implantable delivery devices include devices suitable for use in delivering to a cavity such as the abdominal cavity and/or any other type of administration in which the drug delivery system is not anchored or attached, comprising a biostable and/or degradable and/or bioabsorbable polymeric substrate, which may for example optionally be a matrix. In some cases, a suitable implantable drug delivery device comprises degradable polymers, wherein the main release mechanism is bulk erosion. In some cases, a suitable implantable drug delivery device comprises non degradable, or slowly degraded polymers, wherein the main release mechanism is diffusion rather than bulk erosion, so that the outer part functions as membrane, and its internal part functions as a drug reservoir, which practically is not affected by the surroundings for an extended period (for example from about a week to about a few months). Combinations of different polymers with different release mechanisms may also optionally be used. The concentration gradient at the can be maintained effectively constant during a significant period of the total releasing period, and therefore the diffusion rate is effectively constant (termed "zero mode" diffusion). By the term "constant" it is meant a diffusion rate that is maintained above the lower threshold of therapeutic effectiveness, but which may still optionally feature an initial burst and/or may fluctuate, for example increasing and decreasing to a certain degree. The diffusion rate can be so maintained for a prolonged period, and it can be considered constant to a certain level to optimize the therapeutically effective period, for example the effective silencing period.

In some cases, the implantable delivery system is designed to shield the nucleotide based therapeutic agent from degradation, whether chemical in nature or due to attack from enzymes and other factors in the body of the subject.

The site for implantation of the device, or target site, can be selected for maximum therapeutic efficacy. For example, a delivery device can be implanted within or in the proximity of a tumor environment, or the blood supply associated with a tumor. The target location can be, e.g.: 1) the brain at degenerative sites like in Parkinson or Alzheimer disease at the basal ganglia, white and gray matter; 2) the spine, as in the case of amyotrophic lateral sclerosis (ALS); 3) uterine cervix; 4) active and chronic inflammatory joints; 5) dermis as in the case of psoriasis; 7) sympathetic and sensoric nervous sites for analgesic effect; 7) a bone; 8) a site of acute or chronic infection; 9) Intra vaginal; 10) Inner ear—auditory system, labyrinth of the inner ear, vestibular system; 11) Intra tracheal; 12) Intra-cardiac; coronary, epicardiac; 13) urinary tract or bladder; 14) biliary system; 15) parenchymal tissue including and not limited to the kidney, liver, spleen; 16) lymph nodes; 17) salivary glands; 18) dental gums; 19) Intra-articular (into joints); 20) Intraocular; 21) Brain tissue; 22) Brain ventricles; 23) Cavities, including abdominal cavity (for example but without limitation, for ovary cancer); 24) Intra esophageal; and 25) Intra rectal; and 26) into the vasculature.

The method of insertion, such as implantation, may optionally already be used for other types of tissue implantation and/or for insertions and/or for sampling tissues, optionally without modifications, or alternatively optionally only with non-major modifications in such methods. Such methods optionally include but are not limited to brachytherapy methods, biopsy, endoscopy with and/or without ultrasound, such as stereotactic methods into the brain tissue, laparoscopy, including implantation with a laparoscope into joints, abdominal organs, the bladder wall and body cavities.

Modified Host Cells

The present disclosure provides a modified cell comprising a CasZ polypeptide of the present disclosure and/or a nucleic acid comprising a nucleotide sequence encoding a CasZ polypeptide of the present disclosure. The present disclosure provides a modified cell comprising a CasZ polypeptide of the present disclosure, where the modified cell is a cell that does not normally comprise a CasZ polypeptide of the present disclosure. The present disclosure provides a modified cell (e.g., a genetically modified cell) comprising nucleic acid comprising a nucleotide sequence encoding a CasZ polypeptide of the present disclosure. The present disclosure provides a genetically modified cell that is genetically modified with an mRNA comprising a nucleotide sequence encoding a CasZ polypeptide of the present disclosure. The present disclosure provides a genetically modified cell that is genetically modified with a recombinant expression vector comprising a nucleotide sequence encoding a CasZ polypeptide of the present disclosure. The present disclosure provides a genetically modified cell that is genetically modified with a recombinant expression vector comprising: a) a nucleotide sequence encoding a CasZ polypeptide of the present disclosure; and b) a nucleotide sequence encoding a CasZ guide RNA of the present disclosure. The present disclosure provides a genetically modified cell that is genetically modified with a recombinant expression vector comprising: a) a nucleotide sequence encoding a CasZ polypeptide of the present disclosure; b) a nucleotide sequence encoding a CasZ guide RNA of the present disclosure; and c) a nucleotide sequence encoding a donor template.

A cell that serves as a recipient for a CasZ polypeptide of the present disclosure and/or a nucleic acid comprising a nucleotide sequence encoding a CasZ polypeptide of the present disclosure and/or a CasZ guide RNA of the present disclosure (or a nucleic acid encoding it) and/or a CasZ trancRNA (or a nucleic acid encoding it), can be any of a variety of cells, including, e.g., in vitro cells; in vivo cells; ex vivo cells; primary cells; cancer cells; animal cells; plant cells; algal cells; fungal cells; etc. A cell that serves as a recipient for a CasZ polypeptide of the present disclosure and/or a nucleic acid comprising a nucleotide sequence encoding a CasZ polypeptide of the present disclosure and/or a CasZ guide RNA of the present disclosure is referred to as a "host cell" or a "target cell." A host cell or a target cell can be a recipient of a CasZ system of the present disclosure. A host cell or a target cell can be a recipient of a CasZ RNP of the present disclosure. A host cell or a target cell can be a recipient of a single component of a CasZ system of the present disclosure.

Non-limiting examples of cells (target cells) include: a prokaryotic cell, eukaryotic cell, a bacterial cell, an archaeal cell, a cell of a single-cell eukaryotic organism, a protozoa cell, a cell from a plant (e.g., cells from plant crops, fruits, vegetables, grains, soy bean, corn, maize, wheat, seeds, tomatos, rice, cassava, sugarcane, pumpkin, hay, potatos, cotton, cannabis, tobacco, flowering plants, conifers, gymnosperms, angiosperms, ferns, clubmosses, hornworts, liverworts, mosses, dicotyledons, monocotyledons, etc.), an algal cell, (e.g., *Botryococcus braunii, Chlamydomonas reinhardtii, Nannochloropsis gaditana, Chlorella pyrenoidosa, Sargassum patens, C. agardh*, and the like), seaweeds (e.g. kelp) a fungal cell (e.g., a yeast cell, a cell from a mushroom), an animal cell, a cell from an invertebrate animal (e.g., fruit fly, cnidarian, echinoderm, nematode, etc.), a cell from a vertebrate animal (e.g., fish, amphibian, reptile, bird, mammal), a cell from a mammal (e.g., an ungulate (e.g., a pig, a cow, a goat, a sheep); a rodent (e.g., a rat, a mouse); a non-human primate; a human; a feline (e.g., a cat); a canine (e.g., a dog); etc.), and the like. In some cases, the cell is a cell that does not originate from a natural organism (e.g., the cell can be a synthetically made cell; also referred to as an artificial cell).

A cell can be an in vitro cell (e.g., a cell in culture, e.g., an established cultured cell line). A cell can be an ex vivo cell (cultured cell from an individual). A cell can be and in vivo cell (e.g., a cell in an individual). A cell can be an isolated cell. A cell can be a cell inside of an organism. A cell can be an organism. A cell can be a cell in a cell culture (e.g., in vitro cell culture). A cell can be one of a collection of cells. A cell can be a prokaryotic cell or derived from a prokaryotic cell. A cell can be a bacterial cell or can be derived from a bacterial cell. A cell can be an archaeal cell or derived from an archaeal cell. A cell can be a eukaryotic cell or derived from a eukaryotic cell. A cell can be a plant cell or derived from a plant cell. A cell can be an animal cell or derived from an animal cell. A cell can be an invertebrate cell or derived from an invertebrate cell. A cell can be a vertebrate cell or derived from a vertebrate cell. A cell can be a mammalian cell or derived from a mammalian cell. A cell can be a rodent cell or derived from a rodent cell. A cell can be a human cell or derived from a human cell. A cell can be a microbe cell or derived from a microbe cell. A cell can be a fungi cell or derived from a fungi cell. A cell can be an insect cell. A cell can be an arthropod cell. A cell can be a protozoan cell. A cell can be a helminth cell.

Suitable cells include a stem cell (e.g. an embryonic stem (ES) cell, an induced pluripotent stem (iPS) cell; a germ cell (e.g., an oocyte, a sperm, an oogonia, a spermatogonia, etc.); a somatic cell, e.g. a fibroblast, an oligodendrocyte, a glial cell, a hematopoietic cell, a neuron, a muscle cell, a bone cell, a hepatocyte, a pancreatic cell, etc.

Suitable cells include human embryonic stem cells, fetal cardiomyocytes, myofibroblasts, mesenchymal stem cells, autotransplated expanded cardiomyocytes, adipocytes, totipotent cells, pluripotent cells, blood stem cells, myoblasts, adult stem cells, bone marrow cells, mesenchymal cells, embryonic stem cells, parenchymal cells, epithelial cells, endothelial cells, mesothelial cells, fibroblasts, osteoblasts, chondrocytes, exogenous cells, endogenous cells, stem cells, hematopoietic stem cells, bone-marrow derived progenitor cells, myocardial cells, skeletal cells, fetal cells, undifferentiated cells, multi-potent progenitor cells, unipotent progenitor cells, monocytes, cardiac myoblasts, skeletal myoblasts, macrophages, capillary endothelial cells, xenogenic cells, allogenic cells, and post-natal stem cells.

In some cases, the cell is an immune cell, a neuron, an epithelial cell, and endothelial cell, or a stem cell. In some cases, the immune cell is a T cell, a B cell, a monocyte, a natural killer cell, a dendritic cell, or a macrophage. In some cases, the immune cell is a cytotoxic T cell. In some cases, the immune cell is a helper T cell. In some cases, the immune cell is a regulatory T cell (Treg).

In some cases, the cell is a stem cell. Stem cells include adult stem cells. Adult stem cells are also referred to as somatic stem cells.

Adult stem cells are resident in differentiated tissue, but retain the properties of self-renewal and ability to give rise to multiple cell types, usually cell types typical of the tissue in which the stem cells are found. Numerous examples of somatic stem cells are known to those of skill in the art, including muscle stem cells; hematopoietic stem cells; epithelial stem cells; neural stem cells; mesenchymal stem cells; mammary stem cells; intestinal stem cells; mesodermal stem cells; endothelial stem cells; olfactory stem cells; neural crest stem cells; and the like.

Stem cells of interest include mammalian stem cells, where the term "mammalian" refers to any animal classified as a mammal, including humans; non-human primates; domestic and farm animals; and zoo, laboratory, sports, or pet animals, such as dogs, horses, cats, cows, mice, rats, rabbits, etc. In some cases, the stem cell is a human stem cell. In some cases, the stem cell is a rodent (e.g., a mouse; a rat) stem cell. In some cases, the stem cell is a non-human primate stem cell.

Stem cells can express one or more stem cell markers, e.g., SOX9, KRT19, KRT7, LGR5, CA9, FXYD2, CDH6, CLDN18, TSPAN8, BPIFB1, OLFM4, CDH17, and PPARGC1A.

In some cases, the stem cell is a hematopoietic stem cell (HSC). HSCs are mesoderm-derived cells that can be isolated from bone marrow, blood, cord blood, fetal liver and yolk sac. HSCs are characterized as $CD34^+$ and $CD3^-$. HSCs can repopulate the erythroid, neutrophil-macrophage, megakaryocyte and lymphoid hematopoietic cell lineages in vivo. In vitro, HSCs can be induced to undergo at least some self-renewing cell divisions and can be induced to differentiate to the same lineages as is seen in vivo. As such, HSCs can be induced to differentiate into one or more of erythroid cells, megakaryocytes, neutrophils, macrophages, and lymphoid cells.

In other cases, the stem cell is a neural stem cell (NSC). Neural stem cells (NSCs) are capable of differentiating into neurons, and glia (including oligodendrocytes, and astrocytes). A neural stem cell is a multipotent stem cell which is capable of multiple divisions, and under specific conditions can produce daughter cells which are neural stem cells, or neural progenitor cells that can be neuroblasts or glioblasts, e.g., cells committed to become one or more types of neurons and glial cells respectively. Methods of obtaining NSCs are known in the art.

In other cases, the stem cell is a mesenchymal stem cell (MSC). MSCs originally derived from the embryonal mesoderm and isolated from adult bone marrow, can differentiate to form muscle, bone, cartilage, fat, marrow stroma, and tendon. Methods of isolating MSC are known in the art; and any known method can be used to obtain MSC. See, e.g., U.S. Pat. No. 5,736,396, which describes isolation of human MSC.

A cell is in some cases a plant cell. A plant cell can be a cell of a monocotyledon. A cell can be a cell of a dicotyledon.

In some cases, the cell is a plant cell. For example, the cell can be a cell of a major agricultural plant, e.g., Barley, Beans (Dry Edible), Canola, Corn, Cotton (Pima), Cotton (Upland), Flaxseed, Hay (Alfalfa), Hay (Non-Alfalfa), Oats, Peanuts, Rice, Sorghum, Soybeans, Sugarbeets, Sugarcane, Sunflowers (Oil), Sunflowers (Non-Oil), Sweet Potatoes, Tobacco (Burley), Tobacco (Flue-cured), Tomatoes, Wheat (Durum), Wheat (Spring), Wheat (Winter), and the like. As another example, the cell is a cell of a vegetable crops which include but are not limited to, e.g., alfalfa sprouts, aloe leaves, arrow root, arrowhead, artichokes, asparagus, bamboo shoots, banana flowers, bean sprouts, beans, beet tops, beets, bittermelon, bok choy, broccoli, broccoli rabe (rappini), brussels sprouts, cabbage, cabbage sprouts, cactus leaf (nopales), calabaza, cardoon, carrots, cauliflower, celery, chayote, chinese artichoke (crosnes), chinese cabbage, chinese celery, chinese chives, choy sum, chrysanthemum leaves (tung ho), collard greens, corn stalks, corn-sweet, cucumbers, daikon, dandelion greens, dasheen, dau mue (pea tips), donqua (winter melon), eggplant, endive, escarole, fiddle head ferns, field cress, frisee, gai choy (chinese mustard), gailon, galanga (siam, thai ginger), garlic, ginger root, gobo, greens, hanover salad greens, huauzontle, jerusalem artichokes, jicama, kale greens, kohlrabi, lamb's quarters (quilete), lettuce (bibb), lettuce (boston), lettuce (boston red), lettuce (green leaf), lettuce (iceberg), lettuce (lolla rossa), lettuce (oak leaf—green), lettuce (oak leaf—red), lettuce (processed), lettuce (red leaf), lettuce (romaine), lettuce (ruby romaine), lettuce (russian red mustard), linkok, lo bok, long beans, lotus root, mache, maguey (agave) leaves, malanga, mesculin mix, mizuna, moap (smooth luffa), moo, moqua (fuzzy squash), mushrooms, mustard, nagaimo, okra, ong choy, onions green, opo (long squash), ornamental corn, ornamental gourds, parsley, parsnips, peas, peppers (bell type), peppers, pumpkins, radicchio, radish sprouts, radishes, rape greens, rape greens, rhubarb, romaine (baby red), rutabagas, salicornia (sea bean), sinqua (angled/ridged luffa), spinach, squash, straw bales, sugarcane, sweet potatoes, swiss chard, tamarindo, taro, taro leaf, taro shoots, tatsoi, tepeguaje (guaje), tindora, tomatillos, tomatoes, tomatoes (cherry), tomatoes (grape type), tomatoes (plum type), tumeric, turnip tops greens, turnips, water chestnuts, yampi, yams (names), yu choy, yuca (cassava), and the like.

A cell is in some cases an arthropod cell. For example, the cell can be a cell of a sub-order, a family, a sub-family, a group, a sub-group, or a species of, e.g., *Chelicerata*, Myriapodia, Hexipodia, Arachnida, *Insecta*, Archaeognatha, *Thysanura*, Palaeoptera, Ephemeroptera, *Odonata, Anisoptera, Zygoptera*, Neoptera, Exopterygota, *Plecoptera*, Embioptera, *Orthoptera, Zoraptera, Dermaptera, Dictyoptera, Notoptera*, Grylloblattidae, Mantophasmatidae, Phasmatodea, *Blattaria, Isoptera*, Mantodea, Parapneuroptera, Psocoptera, Thysanoptera, Phthiraptera, *Hemiptera*, Endopterygota or Holometabola, *Hymenoptera, Coleoptera*, Strepsiptera, Raphidioptera, *Megaloptera, Neuroptera*, Mecoptera, *Siphonaptera, Diptera, Trichoptera*, or *Lepidoptera*.

A cell is in some cases an insect cell. For example, in some cases, the cell is a cell of a mosquito, a grasshopper, a true bug, a fly, a flea, a bee, a wasp, an ant, a louse, a moth, or a beetle.

Kits

The present disclosure provides a kit comprising a CasZ system of the present disclosure, or a component of a CasZ system of the present disclosure.

A kit of the present disclosure can comprise any combination as listed for a CasZ system (e.g., see above). A kit of the present disclosure can comprise: a) a component, as described above, of a CasZ system of the present disclosure, or can comprise a CasZ system of the present disclosure; and b) one or more additional reagents, e.g., i) a buffer; ii) a protease inhibitor; iii) a nuclease inhibitor; iv) a reagent required to develop or visualize a detectable label; v) a positive and/or negative control target DNA; vi) a positive and/or negative control CasZ guide RNA; vii) a CasZ trancRNA; and the like. A kit of the present disclosure can comprise: a) a component, as described above, of a CasZ system of the present disclosure, or can comprise a CasZ system of the present disclosure; and b) a therapeutic agent.

A kit of the present disclosure can comprise a recombinant expression vector comprising: a) an insertion site for inserting a nucleic acid comprising a nucleotide sequence encoding a portion of a CasZ guide RNA that hybridizes to a target nucleotide sequence in a target nucleic acid; and b) a nucleotide sequence encoding the CasZ-binding portion of a CasZ guide RNA. A kit of the present disclosure can comprise a recombinant expression vector comprising: a) an insertion site for inserting a nucleic acid comprising a nucleotide sequence encoding a portion of a CasZ guide RNA that hybridizes to a target nucleotide sequence in a target nucleic acid; b) a nucleotide sequence encoding the CasZ-binding portion of a CasZ guide RNA; and c) a nucleotide sequence encoding a CasZ polypeptide of the present disclosure. A kit of the present disclosure can comprise a recombinant expression vector comprising a nucleotide sequence encoding a CasZ trancRNA.

Detection of ssDNA

A CasZ (Cas14) polypeptide of the present disclosure, once activated by detection of a target DNA (double or single stranded), can promiscuously cleave non-targeted single stranded DNA (ssDNA). Once a CasZ (Cas14) is activated by a guide RNA, which occurs when the guide RNA hybridizes to a target sequence of a target DNA (i.e., the sample includes the target DNA, e.g., target ssDNA), the protein becomes a nuclease that promiscuously cleaves ssDNAs (i.e., the nuclease cleaves non-target ssDNAs, i.e., ssDNAs to which the guide sequence of the guide RNA does not hybridize). Thus, when the target DNA is present in the sample (e.g., in some cases above a threshold amount), the result is cleavage of ssDNAs in the sample, which can be detected using any convenient detection method (e.g., using a labeled single stranded detector DNA). In some cases, a CasZ polypeptide requires, in addition to a CasZ guide RNA, a tranc RNA for activation.

Provided are compositions and methods for detecting a target DNA (double stranded or single stranded) in a sample. In some cases, a detector DNA is used that is single stranded (ssDNA) and does not hybridize with the guide sequence of the guide RNA (i.e., the detector ssDNA is a non-target ssDNA). Such methods can include (a) contacting the sample with: (i) a CasZ polypeptide; (ii) a guide RNA comprising: a region that binds to the CasZ polypeptide, and a guide sequence that hybridizes with the target DNA; and (iii) a detector DNA that is single stranded and does not hybridize with the guide sequence of the guide RNA; and (b) measuring a detectable signal produced by cleavage of the single stranded detector DNA by the CasZ polypeptide, thereby detecting the target DNA. In some cases, the methods include can include (a) contacting the sample with: (i) a CasZ polypeptide; (ii) a guide RNA comprising: a region that binds to the CasZ polypeptide, and a guide sequence that hybridizes with the target DNA; (iii) a CasZ tranc RNA; and (iv) a detector DNA that is single stranded and does not hybridize with the guide sequence of the guide RNA; and (b)

measuring a detectable signal produced by cleavage of the single stranded detector DNA by the CasZ polypeptide, thereby detecting the target DNA. As noted above, once a subject CasZ polypeptide protein is activated by a guide RNA, which occurs when the sample includes a target DNA to which the guide RNA hybridizes (i.e., the sample includes the targeted target DNA), the CasZ polypeptide is activated and functions as an endoribonuclease that non-specifically cleaves ssDNAs (including non-target ssDNAs) present in the sample. Thus, when the targeted target DNA is present in the sample (e.g., in some cases above a threshold amount), the result is cleavage of ssDNA (including non-target ssDNA) in the sample, which can be detected using any convenient detection method (e.g., using a labeled detector ssDNA).

Also provided are compositions and methods for cleaving single stranded DNAs (ssDNAs) (e.g., non-target ssDNAs). Such methods can include contacting a population of nucleic acids, wherein said population comprises a target DNA and a plurality of non-target ssDNAs, with: (i) a CasZ polypeptide; and (ii) a guide RNA comprising: a region that binds to the CasZ polypeptide, and a guide sequence that hybridizes with the target DNA, wherein the CasZ polypeptide cleaves non-target ssDNAs of said plurality. Such methods can include contacting a population of nucleic acids, wherein said population comprises a target DNA and a plurality of non-target ssDNAs, with: (i) a CasZ polypeptide; (ii) a guide RNA comprising: a region that binds to the CasZ polypeptide, and a guide sequence that hybridizes with the target DNA, and (iii) a CasZ tranc RNA, wherein the CasZ polypeptide cleaves non-target ssDNAs of said plurality. Such methods can be used, e.g., to cleave foreign ssDNAs (e.g., viral DNAs) in a cell.

The contacting step of a subject method can be carried out in a composition comprising divalent metal ions. The contacting step can be carried out in an acellular environment, e.g., outside of a cell. The contacting step can be carried out inside a cell. The contacting step can be carried out in a cell in vitro. The contacting step can be carried out in a cell ex vivo. The contacting step can be carried out in a cell in vivo.

The guide RNA can be provided as RNA or as a nucleic acid encoding the guide RNA (e.g., a DNA such as a recombinant expression vector). The tranc RNA can be provided as RNA or as a nucleic acid encoding the guide RNA (e.g., a DNA such as a recombinant expression vector). The CasZ polypeptide can be provided as a protein per se or as a nucleic acid encoding the protein (e.g., an mRNA, a DNA such as a recombinant expression vector). In some cases, two or more (e.g., 3 or more, 4 or more, 5 or more, or 6 or more) guide RNAs can be provided. In some cases, a single-molecule RNA comprising: i) a CasZ guide RNA; and ii) a tranc RNA (or a nucleic acid comprising a nucleotide sequence encoding the single-molecule RNA) is used.

In some cases (e.g., when contacting a sample with a guide RNA and a CasZ polypeptide; or when contacting a sample with a guide RNA, a CasZ polypeptide, and a tranc RNA), the sample is contacted for 2 hours or less (e.g., 1.5 hours or less, 1 hour or less, 40 minutes or less, 30 minutes or less, 20 minutes or less, 10 minutes or less, or 5 minutes or less, or 1 minute or less) prior to the measuring step. For example, in some cases the sample is contacted for 40 minutes or less prior to the measuring step. In some cases, the sample is contacted for 20 minutes or less prior to the measuring step. In some cases, the sample is contacted for 10 minutes or less prior to the measuring step. In some cases, the sample is contacted for 5 minutes or less prior to the measuring step. In some cases, the sample is contacted for 1 minute or less prior to the measuring step. In some cases, the sample is contacted for from 50 seconds to 60 seconds prior to the measuring step. In some cases, the sample is contacted for from 40 seconds to 50 seconds prior to the measuring step. In some cases, the sample is contacted for from 30 seconds to 40 seconds prior to the measuring step. In some cases, the sample is contacted for from 20 seconds to 30 seconds prior to the measuring step. In some cases, the sample is contacted for from 10 seconds to 20 seconds prior to the measuring step.

In some cases, a method of the present disclosure for detecting a target DNA comprises: a) contacting a sample with a guide RNA, a CasZ polypeptide, and a detector DNA), where the sample is contacted for 2 hours or less (e.g., 1.5 hours or less, 1 hour or less, 40 minutes or less, 30 minutes or less, 20 minutes or less, 10 minutes or less, or 5 minutes or less, or 1 minute or less), under conditions that provide for trans cleavage of the detector DNA; b) maintaining the sample from step (a) for a period of time under conditions that do not provide for trans cleavage of the detector RNA; and c) after the time period of step (b), measuring a detectable signal produced by cleavage of the single stranded detector DNA by the CasZ polypeptide, thereby detecting the target DNA. Conditions that provide for trans cleavage of the detector DNA include temperature conditions such as from 17° C. to about 39° C. (e.g., about 37° C.). Conditions that do not provide for trans cleavage of the detector DNA include temperatures of 10° C. or less, 5° C. or less, 4° C. or less, or 0° C.

In some cases, a method of the present disclosure for detecting a target DNA comprises: a) contacting a sample with a guide RNA, a tranc RNA, a CasZ polypeptide, and a detector DNA (or contacting a sample with: i) a single-molecule RNA comprising a guide RNA and a tranc RNA; i) a CasZ polypeptide; and iii) a detector DNA), where the sample is contacted for 2 hours or less (e.g., 1.5 hours or less, 1 hour or less, 40 minutes or less, 30 minutes or less, 20 minutes or less, 10 minutes or less, or 5 minutes or less, or 1 minute or less), under conditions that provide for trans cleavage of the detector DNA; b) maintaining the sample from step (a) for a period of time under conditions that do not provide for trans cleavage of the detector RNA; and c) after the time period of step (b), measuring a detectable signal produced by cleavage of the single stranded detector DNA by the CasZ polypeptide, thereby detecting the target DNA. Conditions that provide for trans cleavage of the detector DNA include temperature conditions such as from 17° C. to about 39° C. (e.g., about 37° C.). Conditions that do not provide for trans cleavage of the detector DNA include temperatures of 10° C. or less, 5° C. or less, 4° C. or less, or 0° C.

In some cases, a detectable signal produced by cleavage of a single-stranded detector DNA is produced for no more than 60 minutes. For example, in some cases, a detectable signal produced by cleavage of a single-stranded detector DNA is produced for no more than 60 minutes, no more than 45 minutes, no more than 30 minutes, no more than 15 minutes, no more than 10 minutes, or no more than 5 minutes. For example, in some cases, a detectable signal produced by cleavage of a single-stranded detector DNA is produced for a period of time of from 1 minute to 60 minutes, e.g., from 1 minute to 5 minutes, from 5 minutes to 10 minutes, from 10 minutes to 15 minutes, from 15 minutes to 30 minutes, from 30 minutes to 45 minutes, or from 45 minutes to 60 minutes. In some cases, after the detectable signal is produced (e.g., produced for no more than 60 minutes), production of the detectable signal can be stopped, e.g., by lowering the temperature of the sample (e.g., lowering the temperature to 10° C. or less, 5° C. or less, 4° C. or less, or 0° C.), by adding an inhibitor to the sample, by lyophilizing the sample, by heating the sample to over 40° C., and the like. The measuring step can occur at any time after production of the detectable signal has been stopped. For example, the measuring step can occur from 5 minutes to 48 hours after production of the detectable signal has been stopped. For example, the measuring step can occur from 5 minutes to 15 minutes, from 15 minutes to 30 minutes, from 30 minutes to 60 minutes, from 1 hour to 4 hours, from 4 hours to 8 hours, from 8 hours to 12 hours, from 12 hours to 24 hours, from 24 hours to 36 hours, or from 36 hours to 48 hours, after production of the detectable signal has been stopped. The measuring step can occur more than 48 hours after production of the detectable signal has been stopped.

A method of the present disclosure for detecting a target DNA (single-stranded or double-stranded) in a sample can detect a target DNA with a high degree of sensitivity. In some cases, a method of the present disclosure can be used to detect a target DNA present in a sample comprising a plurality of DNAs (including the target DNA and a plurality of non-target DNAs), where the target DNA is present at one or more copies per $10^7$ non-target DNAs (e.g., one or more copies per $10^6$ non-target DNAs, one or more copies per $10^5$ non-target DNAs, one or more copies per $10^4$ non-target DNAs, one or more copies per $10^3$ non-target DNAs, one or more copies per $10^2$ non-target DNAs, one or more copies per 50 non-target DNAs, one or more copies per 20 non-target DNAs, one or more copies per 10 non-target DNAs, or one or more copies per 5 non-target DNAs). In some cases, a method of the present disclosure can be used to detect a target DNA present in a sample comprising a plurality of DNAs (including the target DNA and a plurality of non-target DNAs), where the target DNA is present at one or more copies per $10^{18}$ non-target DNAs (e.g., one or more copies per $10^{15}$ non-target DNAs, one or more copies per $10^{12}$ non-target DNAs, one or more copies per $10^9$ non-target DNAs, one or more copies per $10^6$ non-target DNAs, one or more copies per $10^5$ non-target DNAs, one or more copies per $10^4$ non-target DNAs, one or more copies per $10^3$ non-target DNAs, one or more copies per $10^2$ non-target DNAs, one or more copies per 50 non-target DNAs, one or more copies per 20 non-target DNAs, one or more copies per 10 non-target DNAs, or one or more copies per 5 non-target DNAs).

In some cases, a method of the present disclosure can detect a target DNA present in a sample, where the target DNA is present at from one copy per $10^7$ non-target DNAs to one copy per 10 non-target DNAs (e.g., from 1 copy per $10^7$ non-target DNAs to 1 copy per $10^2$ non-target DNAs, from 1 copy per $10^7$ non-target DNAs to 1 copy per $10^3$ non-target DNAs, from 1 copy per $10^7$ non-target DNAs to 1 copy per $10^4$ non-target DNAs, from 1 copy per $10^7$ non-target DNAs to 1 copy per $10^5$ non-target DNAs, from 1 copy per $10^7$ non-target DNAs to 1 copy per $10^6$ non-target DNAs, from 1 copy per $10^6$ non-target DNAs to 1 copy per 10 non-target DNAs, from 1 copy per $10^6$ non-target DNAs to 1 copy per $10^2$ non-target DNAs, from 1 copy per $10^6$ non-target DNAs to 1 copy per $10^3$ non-target DNAs, from 1 copy per $10^6$ non-target DNAs to 1 copy per $10^4$ non-target DNAs, from 1 copy per $10^6$ non-target DNAs to 1 copy per $10^5$ non-target DNAs, from 1 copy per $10^5$ non-target DNAs to 1 copy per 10 non-target DNAs, from 1 copy per $10^5$ non-target DNAs to 1 copy per $10^2$ non-target DNAs, from 1 copy per $10^5$ non-target DNAs to 1 copy per $10^3$ non-target DNAs, or from 1 copy per $10^5$ non-target DNAs to 1 copy per $10^4$ non-target DNAs).

In some cases, a method of the present disclosure can detect a target DNA present in a sample, where the target DNA is present at from one copy per $10^{18}$ non-target DNAs to one copy per 10 non-target DNAs (e.g., from 1 copy per $10^{18}$ non-target DNAs to 1 copy per $10^2$ non-target DNAs, from 1 copy per $10^{15}$ non-target DNAs to 1 copy per $10^2$ non-target DNAs, from 1 copy per $10^{12}$ non-target DNAs to 1 copy per $10^2$ non-target DNAs, from 1 copy per $10^9$ non-target DNAs to 1 copy per $10^2$ non-target DNAs, from 1 copy per $10^7$ non-target DNAs to 1 copy per $10^2$ non-target DNAs, from 1 copy per $10^7$ non-target DNAs to 1 copy per $10^3$ non-target DNAs, from 1 copy per $10^7$ non-target DNAs to 1 copy per $10^4$ non-target DNAs, from 1 copy per $10^7$ non-target DNAs to 1 copy per $10^5$ non-target DNAs, from 1 copy per $10^7$ non-target DNAs to 1 copy per $10^6$ non-target DNAs, from 1 copy per $10^6$ non-target DNAs to 1 copy per 10 non-target DNAs, from 1 copy per $10^6$ non-target DNAs to 1 copy per $10^2$ non-target DNAs, from 1 copy per $10^6$ non-target DNAs to 1 copy per $10^3$ non-target DNAs, from 1 copy per $10^6$ non-target DNAs to 1 copy per $10^4$ non-target DNAs, from 1 copy per $10^6$ non-target DNAs to 1 copy per $10^5$ non-target DNAs, from 1 copy per $10^5$ non-target DNAs to 1 copy per 10 non-target DNAs, from 1 copy per $10^5$ non-target DNAs to 1 copy per $10^2$ non-target DNAs, from 1 copy per 105 non-target DNAs to 1 copy per $10^3$ non-target DNAs, or from 1 copy per $10^5$ non-target DNAs to 1 copy per $10^4$ non-target DNAs).

In some cases, a method of the present disclosure can detect a target DNA present in a sample, where the target DNA is present at from one copy per $10^7$ non-target DNAs to one copy per 100 non-target DNAs (e.g., from 1 copy per $10^7$ non-target DNAs to 1 copy per $10^2$ non-target DNAs, from 1 copy per $10^7$ non-target DNAs to 1 copy per $10^3$ non-target DNAs, from 1 copy per $10^7$ non-target DNAs to 1 copy per $10^4$ non-target DNAs, from 1 copy per $10^7$ non-target DNAs to 1 copy per $10^5$ non-target DNAs, from 1 copy per $10^7$ non-target DNAs to 1 copy per $10^6$ non-target DNAs, from 1 copy per $10^6$ non-target DNAs to 1 copy per 100 non-target DNAs, from 1 copy per $10^6$ non-target DNAs to 1 copy per $10^2$ non-target DNAs, from 1 copy per $10^6$ non-target DNAs to 1 copy per $10^3$ non-target DNAs, from 1 copy per $10^6$ non-target DNAs to 1 copy per $10^4$ non-target DNAs, from 1 copy per $10^6$ non-target DNAs to 1 copy per $10^5$ non-target DNAs, from 1 copy per $10^5$ non-target DNAs to 1 copy per 100 non-target DNAs, from 1 copy per $10^5$ non-target DNAs to 1 copy per $10^2$ non-target DNAs, from 1 copy per $10^5$ non-target DNAs to 1 copy per $10^3$ non-target DNAs, or from 1 copy per $10^5$ non-target DNAs to 1 copy per $10^4$ non-target DNAs).

In some cases, the threshold of detection, for a subject method of detecting a target DNA in a sample, is 10 nM or less. Thus, e.g., the target DNA can be present in the sample in a concentration of 10 nM or less. The term "threshold of detection" is used herein to describe the minimal amount of target DNA that must be present in a sample in order for detection to occur. Thus, as an illustrative example, when a threshold of detection is 10 nM, then a signal can be detected when a target DNA is present in the sample at a concentration of 10 nM or more. In some cases, a method of the present disclosure has a threshold of detection of 5 nM or less. In some cases, a method of the present disclosure has a threshold of detection of 1 nM or less. In some cases, a method of the present disclosure has a threshold of detection of 0.5 nM or less. In some cases, a method of the present disclosure has a threshold of detection of 0.1 nM or less. In some cases, a method of the present disclosure has a threshold of detection of 0.05 nM or less. In some cases, a method of the present disclosure has a threshold of detection of 0.01 nM or less. In some cases, a method of the present disclosure has a threshold of detection of 0.005 nM or less. In some cases, a method of the present disclosure has a threshold of detection of 0.001 nM or less. In some cases, a method of the present disclosure has a threshold of detection of 0.0005 nM or less. In some cases, a method of the present disclosure has a threshold of detection of 0.0001 nM or less. In some cases, a method of the present disclosure has a threshold of detection of 0.00005 nM or less. In some cases, a method of the present disclosure has a threshold of detection of 0.00001 nM or less. In some cases, a method of the present disclosure has a threshold of detection of 10 pM or less. In some cases, a method of the present disclosure has a threshold of detection of 1 pM or less. In some cases, a method of the present disclosure has a threshold of detection of 500 fM or less. In some cases, a method of the present disclosure has a threshold of detection of 250 fM or less. In some cases, a method of the present disclosure has a threshold of detection of 100 fM or less. In some cases, a method of the present disclosure has a threshold of detection of 50 fM or less. In some cases, a method of the present disclosure has a threshold of detection of 500 aM (attomolar) or less. In some cases, a method of the present disclosure has a threshold of detection of 250 aM or less. In some cases, a method of the present disclosure has a threshold of detection of 100 aM or less. In some cases, a method of the present disclosure has a threshold of detection of 50 aM or less. In some cases, a method of the present disclosure has a threshold of detection of 10 aM or less. In some cases, a method of the present disclosure has a threshold of detection of 1 aM or less.

In some cases, the threshold of detection (for detecting the target DNA in a subject method), is in a range of from 500 fM to 1 nM (e.g., from 500 fM to 500 pM, from 500 fM to 200 pM, from 500 fM to 100 pM, from 500 fM to 10 pM, from 500 fM to 1 pM, from 800 fM to 1 nM, from 800 fM to 500 pM, from 800 fM to 200 pM, from 800 fM to 100 pM, from 800 fM to 10 pM, from 800 fM to 1 pM, from 1 pM to 1 nM, from 1 pM to 500 pM, from 1 pM to 200 pM, from 1 pM to 100 pM, or from 1 pM to 10 pM) (where the concentration refers to the threshold concentration of target DNA at which the target DNA can be detected). In some cases, a method of the present disclosure has a threshold of detection in a range of from 800 fM to 100 pM. In some cases, a method of the present disclosure has a threshold of detection in a range of from 1 pM to 10 pM. In some cases, a method of the present disclosure has a threshold of detection in a range of from 10 fM to 500 fM, e.g., from 10 fM to 50 fM, from 50 fM to 100 fM, from 100 fM to 250 fM, or from 250 fM to 500 fM.

In some cases, the minimum concentration at which a target DNA can be detected in a sample is in a range of from 500 fM to 1 nM (e.g., from 500 fM to 500 pM, from 500 fM to 200 pM, from 500 fM to 100 pM, from 500 fM to 10 pM, from 500 fM to 1 pM, from 800 fM to 1 nM, from 800 fM to 500 pM, from 800 fM to 200 pM, from 800 fM to 100 pM, from 800 fM to 10 pM, from 800 fM to 1 pM, from 1 pM to 1 nM, from 1 pM to 500 pM, from 1 pM to 200 pM, from 1 pM to 100 pM, or from 1 pM to 10 pM). In some cases, the minimum concentration at which a target DNA can be detected in a sample is in a range of from 800 fM to 100 pM. In some cases, the minimum concentration at which a target DNA can be detected in a sample is in a range of from 1 pM to 10 pM.

In some cases, the threshold of detection (for detecting the target DNA in a subject method), is in a range of from 1 aM to 1 nM (e.g., from 1 aM to 500 pM, from 1 aM to 200 pM, from 1 aM to 100 pM, from 1 aM to 10 pM, from 1 aM to 1 pM, from 100 aM to 1 nM, from 100 aM to 500 pM, from 100 aM to 200 pM, from 100 aM to 100 pM, from 100 aM to 10 pM, from 100 aM to 1 pM, from 250 aM to 1 nM, from 250 aM to 500 pM, from 250 aM to 200 pM, from 250 aM to 100 pM, from 250 aM to 10 pM, from 250 aM to 1 pM, from 500 aM to 1 nM, from 500 aM to 500 pM, from 500 aM to 200 pM, from 500 aM to 100 pM, from 500 aM to 10 pM, from 500 aM to 1 pM, from 750 aM to 1 nM, from 750 aM to 500 pM, from 750 aM to 200 pM, from 750 aM to 100 pM, from 750 aM to 10 pM, from 750 aM to 1 pM, from 1 fM to 1 nM, from 1 fM to 500 pM, from 1 fM to 200 pM, from 1 fM to 100 pM, from 1 fM to 10 pM, from 1 fM to 1 pM, from 500 fM to 500 pM, from 500 fM to 200 pM, from 500 fM to 100 pM, from 500 fM to 10 pM, from 500 fM to 1 pM, from 800 fM to 1 nM, from 800 fM to 500 pM, from 800 fM to 200 pM, from 800 fM to 100 pM, from 800 fM to 10 pM, from 800 fM to 1 pM, from 1 pM to 1 nM, from 1 pM to 500 pM, from 1 pM to 200 pM, from 1 pM to 100 pM, or from 1 pM to 10 pM) (where the concentration refers to the threshold concentration of target DNA at which the target DNA can be detected). In some cases, a method of the present disclosure has a threshold of detection in a range of from 1 aM to 800 aM. In some cases, a method of the present disclosure has a threshold of detection in a range of from 50 aM to 1 pM. In some cases, a method of the present disclosure has a threshold of detection in a range of from 50 aM to 500 fM.

In some cases, a target DNA is present in a sample in a range of from 1 aM to 1 nM (e.g., from 1 aM to 500 pM, from 1 aM to 200 pM, from 1 aM to 100 pM, from 1 aM to 10 pM, from 1 aM to 1 pM, from 100 aM to 1 nM, from 100 aM to 500 pM, from 100 aM to 200 pM, from 100 aM to 100 pM, from 100 aM to 10 pM, from 100 aM to 1 pM, from 250 aM to 1 nM, from 250 aM to 500 pM, from 250 aM to 200 pM, from 250 aM to 100 pM, from 250 aM to 10 pM, from 250 aM to 1 pM, from 500 aM to 1 nM, from 500 aM to 500 pM, from 500 aM to 200 pM, from 500 aM to 100 pM, from 500 aM to 10 pM, from 500 aM to 1 pM, from 750 aM to 1 nM, from 750 aM to 500 pM, from 750 aM to 200 pM, from 750 aM to 100 pM, from 750 aM to 10 pM, from 750 aM to 1 pM, from 1 fM to 1 nM, from 1 fM to 500 pM, from 1 fM to 200 pM, from 1 fM to 100 pM, from 1 fM to 10 pM, from 1 fM to 1 pM, from 500 fM to 500 pM, from 500 fM to 200 pM, from 500 fM to 100 pM, from 500 fM to 10 pM, from 500 fM to 1 pM, from 800 fM to 1 nM, from 800 fM to 500 pM, from 800 fM to 200 pM, from 800 fM to 100 pM, from 800 fM to 10 pM, from 800 fM to 1 pM, from 1 pM to 1 nM, from 1 pM to 500 pM, from 1 pM to 200 pM, from 1 pM to 100 pM, or from 1 pM to 10 pM). In some cases, a target DNA is present in a sample in a range of from 1 aM to 800 aM. In some cases, a target DNA is present in a sample in a range of from 50 aM to 1 pM. In some cases, a target DNA is present in a sample in a range of from 50 aM to 500 fM.

In some cases, the minimum concentration at which a target DNA can be detected in a sample is in a range of from 1 aM to 1 nM (e.g., from 1 aM to 500 pM, from 1 aM to 200 pM, from 1 aM to 100 pM, from 1 aM to 10 pM, from 1 aM to 1 pM, from 100 aM to 1 nM, from 100 aM to 500 pM, from 100 aM to 200 pM, from 100 aM to 100 pM, from 100 aM to 10 pM, from 100 aM to 1 pM, from 250 aM to 1 nM, from 250 aM to 500 pM, from 250 aM to 200 pM, from 250 aM to 100 pM, from 250 aM to 10 pM, from 250 aM to 1 pM, from 500 aM to 1 nM, from 500 aM to 500 pM, from 500 aM to 200 pM, from 500 aM to 100 pM, from 500 aM to 10 pM, from 500 aM to 1 pM, from 750 aM to 1 nM, from 750 aM to 500 pM, from 750 aM to 200 pM, from 750 aM to 100 pM, from 750 aM to 10 pM, from 750 aM to 1 pM, from 1 fM to 1 nM, from 1 fM to 500 pM, from 1 fM to 200 pM, from 1 fM to 100 pM, from 1 fM to 10 pM, from 1 fM to 1 pM, from 500 fM to 500 pM, from 500 fM to 200 pM, from 500 fM to 100 pM, from 500 fM to 10 pM, from 500 fM to 1 pM, from 800 fM to 1 nM, from 800 fM to 500 pM, from 800 fM to 200 pM, from 800 fM to 100 pM, from 800 fM to 10 pM, from 800 fM to 1 pM, from 1 pM to 1 nM, from 1 pM to 500 pM, from 1 pM to 200 pM, from 1 pM to 100 pM, or from 1 pM to 10 pM). In some cases, the minimum concentration at which a target DNA can be detected in a sample is in a range of from 1 aM to 500 pM. In some cases, the minimum concentration at which a target DNA can be detected in a sample is in a range of from 100 aM to 500 pM.

In some cases, a target DNA is present in a sample in a range of from 1 aM to 1 nM (e.g., from 1 aM to 500 pM, from 1 aM to 200 pM, from 1 aM to 100 pM, from 1 aM to 10 pM, from 1 aM to 1 pM, from 100 aM to 1 nM, from 100 aM to 500 pM, from 100 aM to 200 pM, from 100 aM to 100 pM, from 100 aM to 10 pM, from 100 aM to 1 pM, from 250 aM to 1 nM, from 250 aM to 500 pM, from 250 aM to 200 pM, from 250 aM to 100 pM, from 250 aM to 10 pM, from 250 aM to 1 pM, from 500 aM to 1 nM, from 500 aM to 500 pM, from 500 aM to 200 pM, from 500 aM to 100 pM, from 500 aM to 10 pM, from 500 aM to 1 pM, from 750 aM to 1 nM, from 750 aM to 500 pM, from 750 aM to 200 pM, from 750 aM to 100 pM, from 750 aM to 10 pM, from 750 aM to 1 pM, from 1 fM to 1 nM, from 1 fM to 500 pM, from 1 fM to 200 pM, from 1 fM to 100 pM, from 1 fM to 10 pM, from 1 fM to 1 pM, from 500 fM to 500 pM, from 500 fM to 200 pM, from 500 fM to 100 pM, from 500 fM to 10 pM, from 500 fM to 1 pM, from 800 fM to 1 nM, from 800 fM to 500 pM, from 800 fM to 200 pM, from 800 fM to 100 pM, from 800 fM to 10 pM, from 800 fM to 1 pM, from 1 pM to 1 nM, from 1 pM to 500 pM, from 1 pM to 200 pM, from 1 pM to 100 pM, or from 1 pM to 10 pM). In some cases, a target DNA is present in a sample in a range of from 1 aM to 500 pM. In some cases, a target DNA is present in a sample in a range of from 100 aM to 500 pM.

In some cases, a subject composition or method exhibits an attomolar (aM) sensitivity of detection. In some cases, a subject composition or method exhibits a femtomolar (fM) sensitivity of detection. In some cases, a subject composition or method exhibits a picomolar (pM) sensitivity of detection. In some cases, a subject composition or method exhibits a nanomolar (nM) sensitivity of detection.

Target DNA

A target DNA can be single stranded (ssDNA) or double stranded (dsDNA). When the target DNA is single stranded, there is no preference or requirement for a PAM sequence in the target DNA. However, when the target DNA is dsDNA, a PAM is usually present adjacent to the target sequence of the target DNA (e.g., see discussion of the PAM elsewhere herein). The source of the target DNA can be the same as the source of the sample, e.g., as described below.

The source of the target DNA can be any source. In some cases, the target DNA is a viral DNA (e.g., a genomic DNA of a DNA virus). As such, subject method can be for detecting the presence of a viral DNA amongst a population of nucleic acids (e.g., in a sample). A subject method can also be used for the cleavage of non-target ssDNAs in the present of a target DNA. For example, if a method takes place in a cell, a subject method can be used to promiscuously cleave non-target ssDNAs in the cell (ssDNAs that do not hybridize with the guide sequence of the guide RNA) when a particular target DNA is present in the cell (e.g., when the cell is infected with a virus and viral target DNA is detected).

Examples of possible target DNAs include, but are not limited to, viral DNAs such as: a papovavirus (e.g., human papillomavirus (HPV), polyomavirus); a hepadnavirus (e.g., Hepatitis B Virus (HBV)); a herpesvirus (e.g., herpes simplex virus (HSV), varicella zoster virus (VZV), Epstein-Barr virus (EBV), cytomegalovirus (CMV), herpes lymphotropic virus, *Pityriasis Rosea*, kaposi's sarcoma-associated herpesvirus); an adenovirus (e.g., atadenovirus, aviadenovirus, ichtadenovirus, mastadenovirus, siadenovirus); a poxvirus (e.g., smallpox, vaccinia virus, cowpox virus, monkeypox virus, orf virus, pseudocowpox, bovine papular stomatitis virus; tanapox virus, yaba monkey tumor virus; molluscum contagiosum virus (MCV)); a parvovirus (e.g., adeno-associated virus (AAV), Parvovirus B19, human bocavirus, bufavirus, human parv4 G1); Geminiviridae; Nanoviridae; Phycodnaviridae; and the like. In some cases, the target DNA is parasite DNA. In some cases, the target DNA is bacterial DNA, e.g., DNA of a pathogenic bacterium.

Samples

A subject sample includes nucleic acid (e.g., a plurality of nucleic acids). The term "plurality" is used herein to mean two or more. Thus, in some cases a sample includes two or more (e.g., 3 or more, 5 or more, 10 or more, 20 or more, 50 or more, 100 or more, 500 or more, 1,000 or more, or 5,000 or more) nucleic acids (e.g., DNAs). A subject method can be used as a very sensitive way to detect a target DNA present in a sample (e.g., in a complex mixture of nucleic acids such as DNAs). In some cases, the sample includes 5 or more DNAs (e.g., 10 or more, 20 or more, 50 or more, 100 or more, 500 or more, 1,000 or more, or 5,000 or more DNAs) that differ from one another in sequence. In some cases, the sample includes 10 or more, 20 or more, 50 or more, 100 or more, 500 or more, $10^3$ or more, $5 \times 10^3$ or more, $10^4$ or more, $5 \times 10^4$ or more, $10^5$ or more, $5 \times 10^5$ or more, $10^6$ or more $5 \times 10^6$ or more, or $10^7$ or more, DNAs. In some cases, the sample comprises from 10 to 20, from 20 to 50, from 50 to 100, from 100 to 500, from 500 to $10^3$, from $10^3$ to $5 \times 10^3$, from $5 \times 10^3$ to $10^4$, from $10^4$ to $5 \times 10^4$, from $5 \times 10^4$ to $10^5$, from $10^5$ to $5 \times 10^5$, from $5 \times 10^5$ to $10^6$, from $10^6$ to $5 \times 10^6$, or from $5 \times 10^6$ to $10^7$, or more than $10^7$, DNAs. In some cases, the sample comprises from 5 to $10^7$ DNAs (e.g., that differ from one another in sequence)(e.g., from 5 to $10^6$, from 5 to $10^5$, from 5 to 50,000, from 5 to 30,000, from 10 to $10^6$, from 10 to $10^5$, from 10 to 50,000, from 10 to 30,000, from 20 to $10^6$, from 20 to 105, from 20 to 50,000, or from 20 to 30,000 DNAs). In some cases, the sample includes 20 or more DNAs that differ from one another in sequence. In some cases, the sample includes DNAs from a cell lysate (e.g., a eukaryotic cell lysate, a mammalian cell lysate, a human cell lysate, a prokaryotic cell lysate, a plant cell lysate, and the like). For example, in some cases the sample includes DNA from a cell such as a eukaryotic cell, e.g., a mammalian cell such as a human cell.

The term "sample" is used herein to mean any sample that includes DNA (e.g., in order to determine whether a target DNA is present among a population of DNAs). The sample can be derived from any source, e.g., the sample can be a synthetic combination of purified DNAs; the sample can be a cell lysate, an DNA-enriched cell lysate, or DNAs isolated and/or purified from a cell lysate. The sample can be from a patient (e.g., for the purpose of diagnosis). The sample can be from permeabilized cells. The sample can be from crosslinked cells. The sample can be in tissue sections. The sample can be from tissues prepared by crosslinking followed by delipidation and adjustment to make a uniform refractive index. Examples of tissue preparation by crosslinking followed by delipidation and adjustment to make a uniform refractive index have been described in, for example, Shah et al., Development (2016) 143, 2862-2867 doi:10.1242/dev.138560.

A "sample" can include a target DNA and a plurality of non-target DNAs. In some cases, the target DNA is present in the sample at one copy per 10 non-target DNAs, one copy per 20 non-target DNAs, one copy per 25 non-target DNAs, one copy per 50 non-target DNAs, one copy per 100 non-target DNAs, one copy per 500 non-target DNAs, one copy per $10^3$ non-target DNAs, one copy per $5 \times 10^3$ non-target DNAs, one copy per $10^4$ non-target DNAs, one copy per $5 \times 10^4$ non-target DNAs, one copy per $10^5$ non-target DNAs, one copy per $5 \times 10^5$ non-target DNAs, one copy per $10^6$ non-target DNAs, or less than one copy per $10^6$ non-target DNAs. In some cases, the target DNA is present in the sample at from one copy per 10 non-target DNAs to 1 copy per 20 non-target DNAs, from 1 copy per 20 non-target DNAs to 1 copy per 50 non-target DNAs, from 1 copy per 50 non-target DNAs to 1 copy per 100 non-target DNAs, from 1 copy per 100 non-target DNAs to 1 copy per 500 non-target DNAs, from 1 copy per 500 non-target DNAs to 1 copy per $10^3$ non-target DNAs, from 1 copy per $10^3$ non-target DNAs to 1 copy per $5 \times 10^3$ non-target DNAs, from 1 copy per $5 \times 10^3$ non-target DNAs to 1 copy per $10^4$ non-target DNAs, from 1 copy per $10^4$ non-target DNAs to 1 copy per $10^5$ non-target DNAs, from 1 copy per $10^5$ non-target DNAs to 1 copy per $10^6$ non-target DNAs, or from 1 copy per $10^6$ non-target DNAs to 1 copy per $10^7$ non-target DNAs.

Suitable samples include but are not limited to saliva, blood, serum, plasma, urine, aspirate, and biopsy samples. Thus, the term "sample" with respect to a patient encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents; washed; or enrichment for certain cell populations, such as cancer cells. The definition also includes sample that have been enriched for particular types of molecules, e.g., DNAs. The term "sample" encompasses biological samples such as a clinical sample such as blood, plasma, serum, aspirate, cerebral spinal fluid (CSF), and also includes tissue obtained by surgical resection, tissue obtained by biopsy, cells in culture, cell supernatants, cell lysates, tissue samples, organs, bone marrow, and the like. A "biological sample" includes biological fluids derived therefrom (e.g., cancerous cell, infected cell, etc.), e.g., a sample comprising DNAs that is obtained from such cells (e.g., a cell lysate or other cell extract comprising DNAs).

A sample can comprise, or can be obtained from, any of a variety of cells, tissues, organs, or acellular fluids. Suitable sample sources include eukaryotic cells, bacterial cells, and archaeal cells. Suitable sample sources include single-celled organisms and multi-cellular organisms. Suitable sample sources include single-cell eukaryotic organisms; a plant or a plant cell; an algal cell, e.g., *Botryococcus braunii, Chlamydomonas reinhardtii, Nannochloropsis gaditana, Sargassum patens, C. agardh*, and the like; a fungal cell (e.g., a yeast cell); an animal cell, tissue, or organ; a cell, tissue, or organ from an invertebrate animal (e.g. fruit fly, cnidarian, echinoderm, nematode, an insect, an arachnid, etc.); a cell, tissue, fluid, or organ from a vertebrate animal (e.g., fish, amphibian, reptile, bird, mammal); a cell, tissue, fluid, or organ from a mammal (e.g., a human; a non-human primate; an ungulate; a feline; a bovine; an ovine; a caprine; etc.). Suitable sample sources include nematodes, protozoans, and the like. Suitable sample sources include parasites such as helminths, malarial parasites, etc.

Suitable sample sources include a cell, tissue, or organism of any of the six kingdoms, e.g., Bacteria (e.g., Eubacteria); Archaebacteria; Protista; Fungi; Plantae; and Animalia. Suitable sample sources include plant-like members of the kingdom Protista, including, but not limited to, algae (e.g., green algae, red algae, glaucophytes, cyanobacteria); fungus-like members of Protista, e.g., slime molds, water molds, etc.; animal-like members of Protista, e.g., flagellates (e.g., *Euglena*), amoeboids (e.g., amoeba), sporozoans (e.g., Apicomplexa, Myxozoa, Microsporidia), and ciliates (e.g., Paramecium). Suitable sample sources include members of the kingdom Fungi, including, but not limited to, members of any of the phyla: Basidiomycota (club fungi; e.g., members of *Agaricus, Amanita, Boletus*, Cantherellus, etc.); Ascomycota (sac fungi, including, e.g., *Saccharomyces*); Mycophycophyta (lichens); Zygomycota (conjugation fungi); and Deuteromycota. Suitable sample sources include include members of the kingdom Plantae, including, but not limited to, members of any of the following divisions: Bryophyta (e.g., mosses), Anthocerotophyta (e.g., hornworts), Hepaticophyta (e.g., liverworts), Lycophyta (e.g., club mosses), Sphenophyta (e.g., horsetails), Psilophyta (e.g., whisk ferns), Ophioglossophyta, Pterophyta (e.g., ferns), Cycadophyta, Gingkophyta, Pinophyta, Gnetophyta, and Magnoliophyta (e.g., flowering plants). Suitable sample sources include include members of the kingdom Animalia, including, but not limited to, members of any of the following phyla: Porifera (sponges); Placozoa; Orthonectida (parasites of marine invertebrates); Rhombozoa; Cnidaria (corals, anemones, jellyfish, sea pens, sea pansies, sea wasps); Ctenophora (comb jellies); Platyhelminthes (flatworms); Nemertina (ribbon worms); Ngathostomulida (jawed worms)p Gastrotricha; Rotifera; Priapulida; Kinorhyncha; Loricifera; Acanthocephala; Entoprocta; Nemotoda; Nematomorpha; Cycliophora; Mollusca (mollusks); Sipuncula (peanut worms); Annelida (segmented worms); Tardigrada (water bears); Onychophora (velvet worms); Arthropoda (including the subphyla: *Chelicerata*, Myriapoda, Hexapoda, and Crustacea, where the *Chelicerata* include, e.g., arachnids, Merostomata, and Pycnogonida, where the Myriapoda include, e.g., Chilopoda (centipedes), Diplopoda (millipedes), Paropoda, and Symphyla, where the Hexapoda include insects, and where the Crustacea include shrimp, krill, barnacles, etc.; Phoronida; Ectoprocta (moss animals); Brachiopoda; Echinodermata (e.g. starfish, sea daisies, feather stars, sea urchins, sea cucumbers, brittle stars, brittle baskets, etc.); Chaetognatha (arrow worms); Hemichordata (acorn worms); and Chordata. Suitable members of Chordata include any member of the following subphyla: Urochordata (sea squirts; including Ascidiacea, Thaliacea, and Larvacea); Cephalochordata (lancelets); Myxini (hagfish); and Vertebrata, where members of Vertebrata include, e.g., members of Petromyzontida (lampreys), Chondrichthyces (cartilaginous fish), Actinopterygii (ray-finned fish), Actinista (coelocanths), Dipnoi (lungfish), Reptilia (reptiles, e.g., snakes, alligators, crocodiles, lizards, etc.), Aves (birds); and Mammalian (mammals). Suitable plants include any monocotyledon and any dicotyledon.

Suitable sources of a sample include cells, fluid, tissue, or organ taken from an organism; from a particular cell or group of cells isolated from an organism; etc. For example, where the organism is a plant, suitable sources include xylem, the phloem, the cambium layer, leaves, roots, etc. Where the organism is an animal, suitable sources include particular tissues (e.g., lung, liver, heart, kidney, brain, spleen, skin, fetal tissue, etc.), or a particular cell type (e.g., neuronal cells, epithelial cells, endothelial cells, astrocytes, macrophages, glial cells, islet cells, T lymphocytes, B lymphocytes, etc.).

In some cases, the source of the sample is a (or is suspected of being a diseased cell, fluid, tissue, or organ. In some cases, the source of the sample is a normal (non-diseased) cell, fluid, tissue, or organ. In some cases, the source of the sample is a (or is suspected of being a pathogen-infected cell, tissue, or organ. For example, the source of a sample can be an individual who may or may not be infected—and the sample could be any biological sample (e.g., blood, saliva, biopsy, plasma, serum, bronchoalveolar lavage, sputum, a fecal sample, cerebrospinal fluid, a fine needle aspirate, a swab sample (e.g., a buccal swab, a cervical swab, a nasal swab), interstitial fluid, synovial fluid, nasal discharge, tears, buffy coat, a mucous membrane sample, an epithelial cell sample (e.g., epithelial cell scraping), etc.) collected from the individual. In some cases, the sample is a cell-free liquid sample. In some cases, the sample is a liquid sample that can comprise cells. Pathogens include viruses, fungi, helminths, protozoa, malarial parasites, *Plasmodium* parasites, *Toxoplasma* parasites, *Schistosoma* parasites, and the like. "Helminths" include roundworms, heartworms, and phytophagous nematodes (Nematoda), flukes (Tematoda), Acanthocephala, and tapeworms (Cestoda). Protozoan infections include infections from Giardia spp., *Trichomonas* spp., African trypanosomiasis, amoebic dysentery, babesiosis, balantidial dysentery, Chaga's disease, coccidiosis, malaria and toxoplasmosis. Examples of pathogens such as parasitic/protozoan pathogens include, but are not limited to: *Plasmodium falciparum, Plasmodium vivax, Trypanosoma cruzi* and *Toxoplasma gondii*. Fungal pathogens include, but are not limited to: *Cryptococcus neoformans, Histoplasma capsulatum, Coccidioides immitis, Blastomyces dermatitidis, Chlamydia trachomatis,* and *Candida albicans*. Pathogenic viruses include, e.g., immunodeficiency virus (e.g., HIV); influenza virus; dengue; West Nile virus; herpes virus; yellow fever virus; Hepatitis Virus C; Hepatitis Virus A; Hepatitis Virus B; papillomavirus; and the like. Pathogenic viruses can include DNA viruses such as: a papovavirus (e.g., human papillomavirus (HPV), polyomavirus); a hepadnavirus (e.g., Hepatitis B Virus (HBV)); a herpesvirus (e.g., herpes simplex virus (HSV), varicella zoster virus (VZV), epstein-barr virus (EBV), cytomegalovirus (CMV), herpes lymphotropic virus, *Pityriasis Rosea*, kaposi's sarcoma-associated herpesvirus); an adenovirus (e.g., atadenovirus, aviadenovirus, ichtadenovirus, mastadenovirus, siadenovirus); a poxvirus (e.g., smallpox, vaccinia virus, cowpox virus, monkeypox virus, orf virus, pseudocowpox, bovine papular stomatitis virus; tanapox virus, yaba monkey tumor virus; molluscum contagiosum virus (MCV)); a parvovirus (e.g., adeno-associated virus (AAV), Parvovirus B19, human bocavirus, bufavirus, human parv4 G1); Geminiviridae; Nanoviridae; Phycodnaviridae; and the like. Pathogens can include, e.g., DNA viruses [e.g.: a papovavirus (e.g., human papillomavirus (HPV), polyomavirus); a hepadnavirus (e.g., Hepatitis B Virus (HBV)); a herpesvirus (e.g., herpes simplex virus (HSV), varicella zoster virus (VZV), Epstein-barr virus (EBV), cytomegalovirus (CMV), herpes lymphotropic virus, *Pityriasis Rosea*, kaposi's sarcoma-associated herpesvirus); an adenovirus (e.g., atadenovirus, aviadenovirus, ichtadenovirus, mastadenovirus, siadenovirus); a poxvirus (e.g., smallpox, vaccinia virus, cowpox virus, monkeypox virus, orf virus, pseudocowpox, bovine papular stomatitis virus; tanapox virus, yaba monkey tumor virus; molluscum contagiosum virus (MCV)); a parvovirus (e.g., adeno-associated virus (AAV), Parvovirus B19, human bocavirus, bufavirus, human parv4 G1); Geminiviridae; Nanoviridae; Phycodnaviridae; and the like], *Mycobacterium tuberculosis, Streptococcus agalactiae*, methicillin-resistant *Staphylococcus aureus, Legionella pneumophila, Streptococcus pyogenes, Escherichia coli, Neisseria gonorrhoeae, Neisseria meningitidis*, Pneumococcus, *Cryptococcus neoformans, Histoplasma capsulatum, Hemophilus influenzae* B, *Treponema pallidum*, Lyme disease spirochetes, *Pseudomonas aeruginosa, Mycobacterium leprae, Brucella abortus*, rabies virus, influenza virus, cytomegalovirus, herpes simplex virus I, herpes simplex virus II, human serum parvo-like virus, respiratory syncytial virus, varicella-zoster virus, hepatitis B virus, hepatitis C virus, measles virus, adenovirus, human T-cell leukemia viruses, Epstein-Barr virus, murine leukemia virus, mumps virus, vesicular stomatitis virus, Sindbis virus, lymphocytic choriomeningitis virus, wart virus, blue tongue virus, Sendai virus, feline leukemia virus, Reovirus, polio virus, simian virus 40, mouse mammary tumor virus, dengue virus, rubella virus, West Nile virus, *Plasmodium falciparum, Plasmodium vivax, Toxoplasma gondii, Trypanosoma rangeli, Trypanosoma cruzi, Trypanosoma rhodesiense, Trypanosoma brucei, Schistosoma mansoni, Schistosoma japonicum, Babesia bovis, Eimeria tenella, Onchocerca volvulus, Leishmania tropica, Mycobacterium tuberculosis, Trichinella spiralis, Theileria parva, Taenia hydatigena, Taenia ovis, Taenia saginata, Echinococcus granulosus, Mesocestoides corti, Mycoplasma arthritidis, M. hyorhinis, M. orale, M. arginini, Acholeplasma laidlawii, M. salivarium* and *M. pneumoniae*.

Measuring a Detectable Signal

In some cases, a subject method includes a step of measuring (e.g., measuring a detectable signal produced by CasZ-mediated ssDNA cleavage). Because a CasZ polypeptide cleaves non-targeted ssDNA once activated, which occurs when a guide RNA hybridizes with a target DNA in the presence of a CasZ polypeptide (and, in some cases, also including a tranc RNA), a detectable signal can be any signal that is produced when ssDNA is cleaved. For example, in some cases the step of measuring can include one or more of: gold nanoparticle based detection (e.g., see Xu et al., Angew Chem Int Ed Engl. 2007; 46(19):3468-70; and Xia et al., Proc Natl Acad Sci USA. 2010 Jun. 15; 107(24): 10837-41), fluorescence polarization, colloid phase transition/dispersion (e.g., Baksh et al., Nature. 2004 Jan. 8; 427(6970):139-41), electrochemical detection, semiconductor-based sensing (e.g., Rothberg et al., Nature. 2011 Jul. 20; 475(7356):348-52; e.g., one could use a phosphatase to generate a pH change after ssDNA cleavage reactions, by opening 2'-3' cyclic phosphates, and by releasing inorganic phosphate into solution), and detection of a labeled detector ssDNA (see elsewhere herein for more details). The readout of such detection methods can be any convenient readout. Examples of possible readouts include but are not limited to: a measured amount of detectable fluorescent signal; a visual analysis of bands on a gel (e.g., bands that represent cleaved product versus uncleaved substrate), a visual or sensor based detection of the presence or absence of a color (i.e., color detection method), and the presence or absence of (or a particular amount of) an electrical signal.

The measuring can in some cases be quantitative, e.g., in the sense that the amount of signal detected can be used to determine the amount of target DNA present in the sample. The measuring can in some cases be qualitative, e.g., in the sense that the presence or absence of detectable signal can indicate the presence or absence of targeted DNA (e.g., virus, SNP, etc.). In some cases, a detectable signal will not be present (e.g., above a given threshold level) unless the targeted DNA(s) (e.g., virus, SNP, etc.) is present above a particular threshold concentration. In some cases, the threshold of detection can be titrated by modifying the amount of CasZ polypeptide, guide RNA, sample volume, and/or detector ssDNA (if one is used). As such, for example, as would be understood by one of ordinary skill in the art, a number of controls can be used if desired in order to set up one or more reactions, each set up to detect a different threshold level of target DNA, and thus such a series of reactions could be used to determine the amount of target DNA present in a sample (e.g., one could use such a series of reactions to determine that a target DNA is present in the sample 'at a concentration of at least X'). Non-limiting examples of applications of/uses for the compositions and methods of the disclosure include single-nucleotide polymorphism (SNP) detection, cancer screening, detection of bacterial infection, detection of antibiotic resistance, detection of viral infection, and the like. The compositions and methods of this disclosure can be used to detect any DNA target. For example, any virus that integrates nucleic acid material into the genome can be detected because a subject sample can include cellular genomic DNA—and the guide RNA can be designed to detect integrated nucleotide sequence. A method of the present disclosure in some cases does not include an amplification step. A method of the present disclosure in some cases includes an amplification step.

In some cases, a method of the present disclosure can be used to determine the amount of a target DNA in a sample (e.g., a sample comprising the target DNA and a plurality of non-target DNAs). Determining the amount of a target DNA in a sample can comprise comparing the amount of detectable signal generated from a test sample to the amount of detectable signal generated from a reference sample. Determining the amount of a target DNA in a sample can comprise: measuring the detectable signal to generate a test measurement; measuring a detectable signal produced by a reference sample to generate a reference measurement; and comparing the test measurement to the reference measurement to determine an amount of target DNA present in the sample.

For example, in some cases, a method of the present disclosure for determining the amount of a target DNA in a sample comprises: a) contacting the sample (e.g., a sample comprising the target DNA and a plurality of non-target DNAs) with: (i) a guide RNA that hybridizes with the target DNA, (ii) a CasZ polypeptide that cleaves DNAs present in the sample, and (iii) a detector ssDNA; b) measuring a detectable signal produced by CasZ polypeptide-mediated ssDNA cleavage (e.g., cleavage of the detector ssDNA), generating a test measurement; c) measuring a detectable signal produced by a reference sample to generate a reference measurement; and d) comparing the test measurement to the reference measurement to determine an amount of target DNA present in the sample.

As another example, in some cases, a method of the present disclosure for determining the amount of a target DNA in a sample comprises: a) contacting the sample (e.g., a sample comprising the target DNA and a plurality of non-target DNAs) with: (i) a guide RNA that hybridizes with the target DNA, (ii) a CasZ polypeptide that cleaves DNAs present in the sample, (iii) a tranc RNA; (iv) a detector ssDNA; b) measuring a detectable signal produced by CasZ polypeptide-mediated ssDNA cleavage (e.g., cleavage of the detector ssDNA), generating a test measurement; c) measuring a detectable signal produced by a reference sample to generate a reference measurement; and d) comparing the test measurement to the reference measurement to determine an amount of target DNA present in the sample.

Amplification of Nucleic Acids in the Sample

In some embodiments, sensitivity of a subject composition and/or method (e.g., for detecting the presence of a target DNA, such as viral DNA or a SNP, in cellular genomic DNA) can be increased by coupling detection with nucleic acid amplification. In some cases, the nucleic acids in a sample are amplified prior to contact with a CasZ polypeptide that cleaves ssDNA (e.g., amplification of nucleic acids in the sample can begin prior to contact with a CasZ polypeptide). In some cases, the nucleic acids in a sample are amplified simultaneous with contact with a CasZ polypeptide. For example, in some cases a subject method includes amplifying nucleic acids of a sample (e.g., by contacting the sample with amplification components) prior to contacting the amplified sample with a CasZ polypeptide. In some cases, a subject method includes contacting a sample with amplification components at the same time (simultaneous with) that the sample is contacted with a CasZ polypeptide. If all components are added simultaneously (amplification components and detection components such as a CasZ polypeptide, a guide RNA, and a detector DNA), it is possible that the trans-cleavage activity of the CasZ polypeptide, will begin to degrade the nucleic acids of the sample at the same time the nucleic acids are undergoing amplification. However, even if this is the case, amplifying and detecting simultaneously can still increase sensitivity compared to performing the method without amplification.

In some cases, specific sequences (e.g., sequences of a virus, sequences that include a SNP of interest) are amplified from the sample, e.g., using primers. As such, a sequence to which the guide RNA will hybridize can be amplified in order to increase sensitivity of a subject detection method—this could achieve biased amplification of a desired sequence in order to increase the number of copies of the sequence of interest present in the sample relative to other sequences present in the sample. As one illustrative example, if a subject method is being used to determine whether a given sample includes a particular virus (or a particular SNP), a desired region of viral sequence (or non-viral genomic sequence) can be amplified, and the region amplified will include the sequence that would hybridize to the guide RNA if the viral sequence (or SNP) were in fact present in the sample.

As noted, in some cases the nucleic acids are amplified (e.g., by contact with amplification components) prior to contacting the amplified nucleic acids with a CasZ polypeptide. In some cases, amplification occurs for 10 seconds or more, (e.g., 30 seconds or more, 45 seconds or more, 1 minute or more, 2 minutes or more, 3 minutes or more, 4 minutes or more, 5 minutes or more, 7.5 minutes or more, 10 minutes or more, etc.) prior to contact with an enzymatically active CasZ polypeptide. In some cases, amplification occurs for 2 minutes or more (e.g., 3 minutes or more, 4 minutes or more, 5 minutes or more, 7.5 minutes or more, 10 minutes or more, etc.) prior to contact with an active CasZ polypeptide. In some cases, amplification occurs for a period of time in a range of from 10 seconds to 60 minutes (e.g., 10 seconds to 40 minutes, 10 seconds to 30 minutes, 10 seconds to 20 minutes, 10 seconds to 15 minutes, 10 seconds to 10 minutes, 10 seconds to 5 minutes, 30 seconds to 40 minutes, 30 seconds to 30 minutes, 30 seconds to 20 minutes, 30 seconds to 15 minutes, 30 seconds to 10 minutes, 30 seconds to 5 minutes, 1 minute to 40 minutes, 1 minute to 30 minutes, 1 minute to 20 minutes, 1 minute to 15 minutes, 1 minute to 10 minutes, 1 minute to 5 minutes, 2 minutes to 40 minutes, 2 minutes to 30 minutes, 2 minutes to 20 minutes, 2 minutes to 15 minutes, 2 minutes to 10 minutes, 2 minutes to 5 minutes, 5 minutes to 40 minutes, 5 minutes to 30 minutes, 5 minutes to 20 minutes, 5 minutes to 15 minutes, or 5 minutes to 10 minutes). In some cases, amplification occurs for a period of time in a range of from 5 minutes to 15 minutes. In some cases, amplification occurs for a period of time in a range of from 7 minutes to 12 minutes.

In some cases, a sample is contacted with amplification components at the same time as contact with a CasZ polypeptide. In some such cases, the CasZ polypeptide is inactive at the time of contact and is activated once nucleic acids in the sample have been amplified.

Various amplification methods and components will be known to one of ordinary skill in the art and any convenient method can be used (see, e.g., Zanoli and Spoto, Biosensors (Basel). 2013 March; 3(1): 18-43; Gill and Ghaemi, Nucleosides, Nucleotides, and Nucleic Acids, 2008, 27: 224-243; Craw and Balachandrana, Lab Chip, 2012, 12, 2469-2486; which are herein incorporated by reference in their entirety). Nucleic acid amplification can comprise polymerase chain reaction (PCR), reverse transcription PCR (RT-PCR), quantitative PCR (qPCR), reverse transcription qPCR (RT-qPCR), nested PCR, multiplex PCR, asymmetric PCR, touchdown PCR, random primer PCR, hemi-nested PCR, polymerase cycling assembly (PCA), colony PCR, ligase chain reaction (LCR), digital PCR, methylation specific-PCR (MSP), co-amplification at lower denaturation temperature-PCR (COLD-PCR), allele-specific PCR, intersequence-specific PCR (ISS-PCR), whole genome amplification (WGA), inverse PCR, and thermal asymmetric interlaced PCR (TAIL-PCR).

In some cases, the amplification is isothermal amplification. The term "isothermal amplification" indicates a method of nucleic acid (e.g., DNA) amplification (e.g., using enzymatic chain reaction) that can use a single temperature incubation thereby obviating the need for a thermal cycler. Isothermal amplification is a form of nucleic acid amplification which does not rely on the thermal denaturation of the target nucleic acid during the amplification reaction and hence may not require multiple rapid changes in temperature. Isothermal nucleic acid amplification methods can therefore be carried out inside or outside of a laboratory environment. By combining with a reverse transcription step, these amplification methods can be used to isothermally amplify RNA.

Examples of isothermal amplification methods include but are not limited to: loop-mediated isothermal Amplification (LAMP), helicase-dependent Amplification (HDA), recombinase polymerase amplification (RPA), strand displacement amplification (SDA), nucleic acid sequence-based amplification (NASBA), transcription mediated amplification (TMA), nicking enzyme amplification reaction (NEAR), rolling circle amplification (RCA), multiple displacement amplification (MDA), Ramification (RAM), circular helicase-dependent amplification (cHDA), single primer isothermal amplification (SPIA), signal mediated amplification of RNA technology (SMART), self-sustained sequence replication (3SR), genome exponential amplification reaction (GEAR) and isothermal multiple displacement amplification (IMDA).

In some cases, the amplification is recombinase polymerase amplification (RPA) (see, e.g., U.S. Pat. Nos. 8,030,000; 8,426,134; 8,945,845; 9,309,502; and 9,663,820, which are hereby incorporated by reference in their entirety). Recombinase polymerase amplification (RPA) uses two opposing primers (much like PCR) and employs three enzymes—a recombinase, a single-stranded DNA-binding protein (SSB) and a strand-displacing polymerase. The recombinase pairs oligonucleotide primers with homologous sequence in duplex DNA, SSB binds to displaced strands of DNA to prevent the primers from being displaced, and the strand displacing polymerase begins DNA synthesis where the primer has bound to the target DNA. Adding a reverse transcriptase enzyme to an RPA reaction can facilitate detection RNA as well as DNA, without the need for a separate step to produce cDNA. One example of components for an RPA reaction is as follows (see, e.g., U.S. Pat. Nos. 8,030,000; 8,426,134; 8,945,845; 9,309,502; 9,663,820): 50 mM Tris pH 8.4, 80 mM Potassium acetate, 10 mM Magnesium acetate, 2 mM DTT, 5% PEG compound (Carbowax-20M), 3 mM ATP, 30 mM Phosphocreatine, 100 ng/µl creatine kinase, 420 ng/µl gp32, 140 ng/µl UvsX, 35 ng/µl UvsY, 2000M dNTPs, 300 nM each oligonucleotide, 35 ng/µl Bsu polymerase, and a nucleic acid-containing sample).

In a transcription mediated amplification (TMA), an RNA polymerase is used to make RNA from a promoter engineered in the primer region, and then a reverse transcriptase synthesizes cDNA from the primer. A third enzyme, e.g., Rnase H can then be used to degrade the RNA target from cDNA without the heat-denatured step. This amplification technique is similar to Self-Sustained Sequence Replication (3SR) and Nucleic Acid Sequence Based Amplification (NASBA), but varies in the enzymes employed. For another example, helicase-dependent amplification (HDA) utilizes a thermostable helicase (Tte-UvrD) rather than heat to unwind dsDNA to create single-strands that are then available for hybridization and extension of primers by polymerase. For yet another example, a loop mediated amplification (LAMP) employs a thermostable polymerase with strand displacement capabilities and a set of four or more specific designed primers. Each primer is designed to have hairpin ends that, once displaced, snap into a hairpin to facilitate self-priming and further polymerase extension. In a LAMP reaction, though the reaction proceeds under isothermal conditions, an initial heat denaturation step is required for double-stranded targets. In addition, amplification yields a ladder pattern of various length products. For yet another example, a strand displacement amplification (SDA) combines the ability of a restriction endonuclease to nick the unmodified strand of its target DNA and an exonuclease-deficient DNA polymerase to extend the 3' end at the nick and displace the downstream DNA strand.

Detector DNA

In some cases, a subject method includes contacting a sample (e.g., a sample comprising a target DNA and a plurality of non-target ssDNAs) with: i) a CasZ polypeptide; ii) a guide RNA; and iii) a detector DNA that is single stranded and does not hybridize with the guide sequence of the guide RNA.

A suitable single-stranded detector DNA has a length of from 7 nucleotides to 25 nucleotides. For example, a suitable single-stranded detector DNA has a length of from 7 nucleotides to 10 nucleotides, from 11 nucleotides to 15 nucleotides, from 15 nucleotides to 20 nucleotides, or from 20 nucleotides to 25 nucleotides. In some cases, a suitable single-stranded detector DNA has a length of from 10 nucleotides to 15 nucleotides. In some cases, a suitable single-stranded detector DNA has a length of 10 nucleotides. In some cases, a suitable single-stranded detector DNA has a length of 11 nucleotides. In some cases, a suitable single-stranded detector DNA has a length of 12 nucleotides. In some cases, a suitable single-stranded detector DNA has a length of 13 nucleotides. In some cases, a suitable single-stranded detector DNA has a length of 14 nucleotides. In some cases, a suitable single-stranded detector DNA has a length of 15 nucleotides.

In some cases, a subject method includes: a) contacting a sample with a labeled single stranded detector DNA (detector ssDNA) that includes a fluorescence-emitting dye pair; a CasZ polypeptide that cleaves the labeled detector ssDNA after it is activated (by binding to the guide RNA in the context of the guide RNA hybridizing to a target DNA); and b) measuring the detectable signal that is produced by the fluorescence-emitting dye pair. For example, in some cases, a subject method includes contacting a sample with a labeled detector ssDNA comprising a fluorescence resonance energy transfer (FRET) pair or a quencher/fluor pair, or both. In some cases, a subject method includes contacting a sample with a labeled detector ssDNA comprising a FRET pair. In some cases, a subject method includes contacting a sample with a labeled detector ssDNA comprising a fluor/quencher pair.

Fluorescence-emitting dye pairs comprise a FRET pair or a quencher/fluor pair. In both cases of a FRET pair and a quencher/fluor pair, the emission spectrum of one of the dyes overlaps a region of the absorption spectrum of the other dye in the pair. As used herein, the term "fluorescence-emitting dye pair" is a generic term used to encompass both a "fluorescence resonance energy transfer (FRET) pair" and a "quencher/fluor pair," both of which terms are discussed in more detail below. The term "fluorescence-emitting dye pair" is used interchangeably with the phrase "a FRET pair and/or a quencher/fluor pair."

In some cases (e.g., when the detector ssDNA includes a FRET pair) the labeled detector ssDNA produces an amount of detectable signal prior to being cleaved, and the amount of detectable signal that is measured is reduced when the labeled detector ssDNA is cleaved. In some cases, the labeled detector ssDNA produces a first detectable signal prior to being cleaved (e.g., from a FRET pair) and a second detectable signal when the labeled detector ssDNA is cleaved (e.g., from a quencher/fluor pair). As such, in some cases, the labeled detector ssDNA comprises a FRET pair and a quencher/fluor pair.

In some cases, the labeled detector ssDNA comprises a FRET pair. FRET is a process by which radiationless transfer of energy occurs from an excited state fluorophore to a second chromophore in close proximity. The range over which the energy transfer can take place is limited to approximately 10 nanometers (100 angstroms), and the efficiency of transfer is extremely sensitive to the separation distance between fluorophores. Thus, as used herein, the term "FRET" ("fluorescence resonance energy transfer"; also known as "Förster resonance energy transfer") refers to a physical phenomenon involving a donor fluorophore and a matching acceptor fluorophore selected so that the emission spectrum of the donor overlaps the excitation spectrum of the acceptor, and further selected so that when donor and acceptor are in close proximity (usually 10 nm or less) to one another, excitation of the donor will cause excitation of and emission from the acceptor, as some of the energy passes from donor to acceptor via a quantum coupling effect. Thus, a FRET signal serves as a proximity gauge of the donor and acceptor; only when they are in close proximity to one another is a signal generated. The FRET donor moiety (e.g., donor fluorophore) and FRET acceptor moiety (e.g., acceptor fluorophore) are collectively referred to herein as a "FRET pair".

The donor-acceptor pair (a FRET donor moiety and a FRET acceptor moiety) is referred to herein as a "FRET pair" or a "signal FRET pair." Thus, in some cases, a subject labeled detector ssDNA includes two signal partners (a signal pair), when one signal partner is a FRET donor moiety and the other signal partner is a FRET acceptor moiety. A subject labeled detector ssDNA that includes such a FRET pair (a FRET donor moiety and a FRET acceptor moiety) will thus exhibit a detectable signal (a FRET signal) when the signal partners are in close proximity (e.g., while on the same RNA molecule), but the signal will be reduced (or absent) when the partners are separated (e.g., after cleavage of the RNA molecule by a CasZ polypeptide).

FRET donor and acceptor moieties (FRET pairs) will be known to one of ordinary skill in the art and any convenient FRET pair (e.g., any convenient donor and acceptor moiety pair) can be used. Examples of suitable FRET pairs include but are not limited to those presented in Table 1. See also: Bajar et al. Sensors (Basel). 2016 Sep. 14; 16(9); and Abraham et al. PLoS One. 2015 Aug. 3; 10(8):e0134436.

TABLE 6

Examples of FRET pairs (donor and acceptor FRET moieties)

| Donor | Acceptor |
|---|---|
| Tryptophan | Dansyl |
| IAEDANS (1) | DDPM (2) |
| BFP | DsRFP |
| Dansyl | Fluorescein isothiocyanate (FITC) |
| Dansyl | Octadecylrhodamine |
| Cyan fluorescent protein (CFP) | Green fluorescent protein (GFP) |
| CF (3) | Texas Red |
| Fluorescein | Tetramethylrhodamine |
| Cy3 | Cy5 |
| GFP | Yellow fluorescent protein (YFP) |
| BODIPY FL (4) | BODIPY FL (4) |
| Rhodamine 110 | Cy3 |
| Rhodamine 6G | Malachite Green |
| FITC | Eosin Thiosemicarbazide |
| B-Phycoerythrin | Cy5 |
| Cy5 | Cy5.5 |

(1) 5-(2-iodoacetylaminoethyl)aminonaphthalene-1-sulfonic acid
(2) N-(4-dimethylamino-3,5-dinitrophenyl)maleimide
(3) carboxyfluorescein succinimidyl ester
(4) 4,4-difluoro-4-bora-3a,4a-diaza-s-indacene In some cases, a detectable signal is produced when the labeled detector ssDNA is cleaved (e.g., in some cases, the labeled detector ssDNA comprises a quencher/fluor pair). One signal partner of a signal quenching pair produces a detectable signal and the other signal partner is a quencher moiety that quenches the detectable signal of the first signal partner (i.e., the quencher moiety quenches the signal of the signal moiety such that the signal from the signal moiety is reduced (quenched) when the signal partners are in proximity to one another, e.g., when the signal partners of the signal pair are in close proximity).

For example, in some cases, an amount of detectable signal increases when the labeled detector ssDNA is cleaved. For example, in some cases, the signal exhibited by one signal partner (a signal moiety) is quenched by the other signal partner (a quencher signal moiety), e.g., when both are present on the same ssDNA molecule prior to cleavage by a CasZ polypeptide. Such a signal pair is referred to herein as a "quencher/fluor pair", "quenching pair", or "signal quenching pair." For example, in some cases, one signal partner (e.g., the first signal partner) is a signal moiety that produces a detectable signal that is quenched by the second signal partner (e.g., a quencher moiety). The signal partners of such a quencher/fluor pair will thus produce a detectable signal when the partners are separated (e.g., after cleavage of the detector ssDNA by a CasZ polypeptide), but the signal will be quenched when the partners are in close proximity (e.g., prior to cleavage of the detector ssDNA by a CasZ polypeptide).

A quencher moiety can quench a signal from the signal moiety (e.g., prior to cleavage of the detector ssDNA by a CasZ polypeptide) to various degrees. In some cases, a quencher moiety quenches the signal from the signal moiety where the signal detected in the presence of the quencher moiety (when the signal partners are in proximity to one another) is 95% or less of the signal detected in the absence of the quencher moiety (when the signal partners are separated). For example, in some cases, the signal detected in the presence of the quencher moiety can be 90% or less, 80% or less, 70% or less, 60% or less, 50% or less, 40% or less, 30% or less, 20% or less, 15% or less, 10% or less, or 5% or less of the signal detected in the absence of the quencher moiety. In some cases, no signal (e.g., above background) is detected in the presence of the quencher moiety.

In some cases, the signal detected in the absence of the quencher moiety (when the signal partners are separated) is at least 1.2 fold greater (e.g., at least 1.3 fold, at least 1.5 fold, at least 1.7 fold, at least 2 fold, at least 2.5 fold, at least 3 fold, at least 3.5 fold, at least 4 fold, at least 5 fold, at least 7 fold, at least 10 fold, at least 20 fold, or at least 50 fold greater) than the signal detected in the presence of the quencher moiety (when the signal partners are in proximity to one another).

In some cases, the signal moiety is a fluorescent label. In some such cases, the quencher moiety quenches the signal (the light signal) from the fluorescent label (e.g., by absorbing energy in the emission spectra of the label). Thus, when the quencher moiety is not in proximity with the signal moiety, the emission (the signal) from the fluorescent label is detectable because the signal is not absorbed by the quencher moiety. Any convenient donor acceptor pair (signal moiety/quencher moiety pair) can be used and many suitable pairs are known in the art.

In some cases, the quencher moiety absorbs energy from the signal moiety (also referred to herein as a "detectable label") and then emits a signal (e.g., light at a different wavelength). Thus, in some cases, the quencher moiety is itself a signal moiety (e.g., a signal moiety can be 6-carboxyfluorescein while the quencher moiety can be 6-carboxy-tetramethylrhodamine), and in some such cases, the pair could also be a FRET pair. In some cases, a quencher moiety is a dark quencher. A dark quencher can absorb excitation energy and dissipate the energy in a different way (e.g., as heat). Thus, a dark quencher has minimal to no fluorescence of its own (does not emit fluorescence). Examples of dark quenchers are further described in U.S. Pat. Nos. 8,822,673 and 8,586,718; U.S. patent publications 20140378330, 20140349295, and 20140194611; and international patent applications: WO200142505 and WO200186001, all if which are hereby incorporated by reference in their entirety.

Examples of fluorescent labels include, but are not limited to: an Alexa Fluor® dye, an ATTO dye (e.g., ATTO 390, ATTO 425, ATTO 465, ATTO 488, ATTO 495, ATTO 514, ATTO 520, ATTO 532, ATTO Rho6G, ATTO 542, ATTO 550, ATTO 565, ATTO Rho3B, ATTO Rho11, ATTO Rho12, ATTO Thio12, ATTO Rho101, ATTO 590, ATTO 594, ATTO Rho13, ATTO 610, ATTO 620, ATTO Rho14, ATTO 633, ATTO 647, ATTO 647N, ATTO 655, ATTO Oxa12, ATTO 665, ATTO 680, ATTO 700, ATTO 725, ATTO 740), a DyLight dye, a cyanine dye (e.g., Cy2, Cy3, Cy3.5, Cy3b, Cy5, Cy5.5, Cy7, Cy7.5), a FluoProbes dye, a Sulfo Cy dye, a Seta dye, an IRIS Dye, a SeTau dye, an SRfluor dye, a Square dye, fluorescein isothiocyanate (FITC), tetramethylrhodamine (TRITC), Texas Red, Oregon Green, Pacific Blue, Pacific Green, Pacific Orange, quantum dots, and a tethered fluorescent protein.

In some cases, a detectable label is a fluorescent label selected from: an Alexa Fluor® dye, an ATTO dye (e.g., ATTO 390, ATTO 425, ATTO 465, ATTO 488, ATTO 495, ATTO 514, ATTO 520, ATTO 532, ATTO Rho6G, ATTO 542, ATTO 550, ATTO 565, ATTO Rho3B, ATTO Rho11, ATTO Rho12, ATTO Thio12, ATTO Rho101, ATTO 590, ATTO 594, ATTO Rho13, ATTO 610, ATTO 620, ATTO Rho14, ATTO 633, ATTO 647, ATTO 647N, ATTO 655, ATTO Oxa12, ATTO 665, ATTO 680, ATTO 700, ATTO 725, ATTO 740), a DyLight dye, a cyanine dye (e.g., Cy2, Cy3, Cy3.5, Cy3b, Cy5, Cy5.5, Cy7, Cy7.5), a FluoProbes dye, a Sulfo Cy dye, a Seta dye, an IRIS Dye, a SeTau dye, an SRfluor dye, a Square dye, fluorescein (FITC), tetramethylrhodamine (TRITC), Texas Red, Oregon Green, Pacific Blue, Pacific Green, and Pacific Orange.

In some cases, a detectable label is a fluorescent label selected from: an Alexa Fluor® dye, an ATTO dye (e.g., ATTO 390, ATTO 425, ATTO 465, ATTO 488, ATTO 495, ATTO 514, ATTO 520, ATTO 532, ATTO Rho6G, ATTO 542, ATTO 550, ATTO 565, ATTO Rho3B, ATTO Rho11, ATTO Rho12, ATTO Thio12, ATTO Rho101, ATTO 590, ATTO 594, ATTO Rho13, ATTO 610, ATTO 620, ATTO Rho14, ATTO 633, ATTO 647, ATTO 647N, ATTO 655, ATTO Oxa12, ATTO 665, ATTO 680, ATTO 700, ATTO 725, ATTO 740), a DyLight dye, a cyanine dye (e.g., Cy2, Cy3, Cy3.5, Cy3b, Cy5, Cy5.5, Cy7, Cy7.5), a FluoProbes dye, a Sulfo Cy dye, a Seta dye, an IRIS Dye, a SeTau dye, an SRfluor dye, a Square dye, fluorescein (FITC), tetramethylrhodamine (TRITC), Texas Red, Oregon Green, Pacific Blue, Pacific Green, Pacific Orange, a quantum dot, and a tethered fluorescent protein.

Examples of ATTO dyes include, but are not limited to: ATTO 390, ATTO 425, ATTO 465, ATTO 488, ATTO 495, ATTO 514, ATTO 520, ATTO 532, ATTO Rho6G, ATTO 542, ATTO 550, ATTO 565, ATTO Rho3B, ATTO Rho11, ATTO Rho12, ATTO Thio12, ATTO Rho101, ATTO 590, ATTO 594, ATTO Rho13, ATTO 610, ATTO 620, ATTO Rho14, ATTO 633, ATTO 647, ATTO 647N, ATTO 655, ATTO Oxa12, ATTO 665, ATTO 680, ATTO 700, ATTO 725, and ATTO 740.

Examples of AlexaFluor dyes include, but are not limited to: Alexa Fluor®350, Alexa Fluor®405, Alexa Fluor®430, Alexa Fluor®488, Alexa Fluor®500, Alexa Fluor®514, Alexa Fluor® 532, Alexa Fluor®546, Alexa Fluor®555, Alexa Fluor®568, Alexa Fluor®594, Alexa Fluor®610, Alexa Fluor®633, Alexa Fluor®635, Alexa Fluor®647, Alexa Fluor®660, Alexa Fluor®680, Alexa Fluor®700, Alexa Fluor®750, Alexa Fluor®790, and the like.

Examples of quencher moieties include, but are not limited to: a dark quencher, a Black Hole Quencher® (BHQ®) (e.g., BHQ-0, BHQ-1, BHQ-2, BHQ-3), a Qxl quencher, an ATTO quencher (e.g., ATTO 540Q, ATTO 580Q, and ATTO 612Q), dimethylaminoazobenzenesulfonic acid (Dabsyl), Iowa Black RQ, Iowa Black FQ, IRDye QC-1, a QSY dye (e.g., QSY 7, QSY 9, QSY 21), AbsoluteQuencher, Eclipse, and metal clusters such as gold nanoparticles, and the like.

In some cases, a quencher moiety is selected from: a dark quencher, a Black Hole Quencher® (BHQ®) (e.g., BHQ-0, BHQ-1, BHQ-2, BHQ-3), a Qxl quencher, an ATTO quencher (e.g., ATTO 540Q, ATTO 580Q, and ATTO 612Q), dimethylaminoazobenzenesulfonic acid (Dabsyl), Iowa Black RQ, Iowa Black FQ, IRDye QC-1, a QSY dye (e.g., QSY 7, QSY 9, QSY 21), AbsoluteQuencher, Eclipse, and a metal cluster.

Examples of an ATTO quencher include, but are not limited to: ATTO 540Q, ATTO 580Q, and ATTO 612Q. Examples of a Black Hole Quencher® (BHQ®) include, but are not limited to: BHQ-0 (493 nm), BHQ-1 (534 nm), BHQ-2 (579 nm) and BHQ-3 (672 nm).

For examples of some detectable labels (e.g., fluorescent dyes) and/or quencher moieties, see, e.g., Bao et al., Annu Rev Biomed Eng. 2009; 11:25-47; as well as U.S. Pat. Nos. 8,822,673 and 8,586,718; U.S. patent publications 20140378330, 20140349295, 20140194611, 20130323851, 20130224871, 20110223677, 20110190486, 20110172420, 20060179585 and 20030003486; and international patent applications: WO200142505 and WO200186001, all of which are hereby incorporated by reference in their entirety.

In some cases, cleavage of a labeled detector ssDNA can be detected by measuring a colorimetric read-out. For example, the liberation of a fluorophore (e.g., liberation from a FRET pair, liberation from a quencher/fluor pair, and the like) can result in a wavelength shift (and thus color shift) of a detectable signal. Thus, in some cases, cleavage of a subject labeled detector ssDNA can be detected by a color-shift. Such a shift can be expressed as a loss of an amount of signal of one color (wavelength), a gain in the amount of another color, a change in the ration of one color to another, and the like.

Kits for Detecting Target DNA

The present disclosure provides a kit for detecting a target DNA, e.g., in a sample comprising a plurality of DNAs. In some cases, the kit comprises: (a) a labeled detector ssDNA (e.g., a labeled detector ssDNA comprising a fluorescence-emitting dye pair, e.g., a FRET pair and/or a quencher/fluor pair); and (b) one or more of: (i) a guide RNA, and/or a nucleic acid encoding said guide RNA; and ii) a CasZ polypeptide, and/or a nucleic acid encoding said CasZ polypeptide. In some cases, a nucleic acid encoding a guide RNA includes sequence insertion sites for the insertion of guide sequences by a user.

In some cases, the kit comprises: (a) a labeled detector ssDNA (e.g., a labeled detector ssDNA comprising a fluorescence-emitting dye pair, e.g., a FRET pair and/or a quencher/fluor pair); and (b) one or more of: (i) a guide RNA, and/or a nucleic acid encoding said guide RNA; ii) a tranc RNA and/or a nucleic acid encoding said guide RNA; and iii) a CasZ polypeptide, and/or a nucleic acid encoding said CasZ polypeptide. In some cases, a nucleic acid encoding a guide RNA includes sequence insertion sites for the insertion of guide sequences by a user.

In some cases, the kit comprises: (a) a labeled detector ssDNA (e.g., a labeled detector ssDNA comprising a fluorescence-emitting dye pair, e.g., a FRET pair and/or a quencher/fluor pair); and (b) one or more of: (i) a single-molecule RNA comprising a guide RNA and a tranc RNA, and/or a nucleic acid encoding single-molecule RNA; and iii) a CasZ polypeptide, and/or a nucleic acid encoding said CasZ polypeptide. In some cases, a nucleic acid encoding a single-molecule RNA includes sequence insertion sites for the insertion of guide sequences by a user.

In some cases, a subject kit comprises: (a) a labeled detector ssDNA comprising a fluorescence-emitting dye pair, e.g., a FRET pair and/or a quencher/fluor pair; and (b) one or more of: (i) a guide RNA, and/or a nucleic acid encoding said guide RNA; and/or i) a CasZ polypeptide.

Positive Controls

A kit of the present disclosure (e.g., one that comprises a labeled detector ssDNA and a CasZ polypeptide) can also include a positive control target DNA. In some cases, the kit also includes a positive control guide RNA that comprises a nucleotide sequence that hybridizes to the control target DNA. In some cases, the positive control target DNA is provided in various amounts, in separate containers. In some cases, the positive control target DNA is provided in various known concentrations, in separate containers, along with control non-target DNAs.

Nucleic Acids

While the RNAs of the disclosure (e.g., guide RNAs, tranc RNAs, single-molecule RNAs comprising a guide RNA and a tranc RNA) can be synthesized using any convenient method (e.g., chemical synthesis, in vitro using an RNA polymerase enzyme, e.g., T7 polymerase, T3 polymerase, SP6 polymerase, etc.), nucleic acids encoding such RNAs are also envisioned. Additionally, while a CasZ polypeptide of the disclosure can be provided (e.g., as part of a kit) in protein form, nucleic acids (such as mRNA and/or DNA) encoding the CasZ polypeptide can also be provided.

In some cases, a kit of the present disclosure comprises a nucleic acid (e.g., a DNA, e.g., a recombinant expression vector) that comprises a nucleotide sequence encoding a single-molecule RNA comprising: i) a guide RNA; and ii) a tranc RNA. In some cases, the nucleotide sequence encodes the guide RNA portion of the single-molecule RNA without a guide sequence. For example, in some cases, the nucleic acid comprises a nucleotide sequence encoding: i) a constant region of a guide RNA (a guide RNA without a guide sequence), and comprises an insertion site for a nucleic acid encoding a guide sequence; and ii) a tranc RNA.

For example, in some cases, a kit of the present disclosure comprises a nucleic acid (e.g., a DNA, e.g., a recombinant expression vector) that comprises a nucleotide sequence encoding a guide RNA. In some cases, the nucleotide sequence encodes a guide RNA without a guide sequence. For example, in some cases, the nucleic acid comprises a nucleotide sequence encoding a constant region of a guide RNA (a guide RNA without a guide sequence), and comprises an insertion site for a nucleic acid encoding a guide sequence. In some cases, a kit of the present disclosure comprises a nucleic acid (e.g., an mRNA, a DNA, e.g., a recombinant expression vector) that comprises a nucleotide sequence encoding a CasZ polypeptide.

In some cases, the guide RNA-encoding nucleotide sequence is operably linked to a promoter, e.g., a promoter that is functional in a prokaryotic cell, a promoter that is functional in a eukaryotic cell, a promoter that is functional in a mammalian cell, a promoter that is functional in a human cell, and the like. In some cases, a nucleotide sequence encoding a CasZ polypeptide is operably linked to a promoter, e.g., a promoter that is functional in a prokaryotic cell, a promoter that is functional in a eukaryotic cell, a promoter that is functional in a mammalian cell, a promoter that is functional in a human cell, a cell type-specific promoter, a regulatable promoter, a tissue-specific promoter, and the like. UTILITY CasZ compositions (e.g., expression vectors, kits, compositions, nucleic acids, and the like) find use in a variety of methods. For example, a CasZ compositions of the present disclosure can be used to (i) modify (e.g., cleave, e.g., nick; methylate; etc.) target nucleic acid (DNA or RNA; single stranded or double stranded); (ii) modulate transcription of a target nucleic acid; (iii) label a target nucleic acid; (iv) bind a target nucleic acid (e.g., for purposes of isolation, labeling, imaging, tracking, etc.); (v) modify a polypeptide (e.g., a histone) associated with a target nucleic acid; and the like. Thus, the present disclosure provides a method of modifying a target nucleic acid. In some cases, a method of the present disclosure for modifying a target nucleic acid comprises contacting the target nucleic acid with: a) a CasZ polypeptide of the present disclosure; and b) one or more (e.g., two) CasZ guide RNAs. In some cases, a method of the present disclosure for modifying a target nucleic acid comprises contacting the target nucleic acid with: a) a CasZ polypeptide, and b) one or more (e.g., two) CasZ guide RNAs, and c) a CasZ trancRNA. In some cases, a method of the present disclosure for modifying a target nucleic acid comprises contacting the target nucleic acid with: a) a CasZ polypeptide of the present disclosure; b) a CasZ guide RNA; and c) a donor nucleic acid (e.g, a donor template). In some cases, a method of the present disclosure for modifying a target nucleic acid comprises contacting the target nucleic acid with: a) a CasZ polypeptide; b) a CasZ guide RNA; c) a CasZ trancRNA, and d) a donor nucleic acid (e.g, a donor template). In some cases, the contacting step is carried out in a cell in vitro. In some cases, the contacting step is carried out in a cell in vivo. In some cases, the contacting step is carried out in a cell ex vivo.

Because a method that uses a CasZ polypeptide includes binding of the CasZ polypeptide to a particular region in a target nucleic acid (by virtue of being targeted there by an associated CasZ guide RNA), the methods are generally referred to herein as methods of binding (e.g., a method of binding a target nucleic acid). However, it is to be understood that in some cases, while a method of binding may result in nothing more than binding of the target nucleic acid, in other cases, the method can have different final results (e.g., the method can result in modification of the target nucleic acid, e.g., cleavage/methylation/etc., modulation of transcription from the target nucleic acid; modulation of translation of the target nucleic acid; genome editing; modulation of a protein associated with the target nucleic acid; isolation of the target nucleic acid; etc.).

For examples of suitable methods (e.g., that are used with CRISPR/Cas9 systems), see, for example, Jinek et al., Science. 2012 Aug. 17; 337(6096):816-21; Chylinski et al., RNA Biol. 2013 May; 10(5):726-37; Ma et al., Biomed Res Int. 2013; 2013:270805; Hou et al., Proc Natl Acad Sci USA. 2013 Sep. 24; 110(39):15644-9; Jinek et al., Elife. 2013; 2:e00471; Pattanayak et al., Nat Biotechnol. 2013 September; 31(9):839-43; Qi et al, Cell. 2013 Feb. 28; 152(5):1173-83; Wang et al., Cell. 2013 May 9; 153(4):910-8; Auer et al., Genome Res. 2013 Oct. 31; Chen et al., Nucleic Acids Res. 2013 Nov. 1; 41(20):e19; Cheng et al., Cell Res. 2013 October; 23(10):1163-71; Cho et al., Genetics. 2013 November; 195(3):1177-80; DiCarlo et al., Nucleic Acids Res. 2013 April; 41(7):4336-43; Dickinson et al., Nat Methods. 2013 October; 10(10):1028-34; Ebina et al., Sci Rep. 2013; 3:2510; Fujii et al, Nucleic Acids Res. 2013 Nov. 1; 41(20):e187; Hu et al., Cell Res. 2013 November; 23(11): 1322-5; Jiang et al., Nucleic Acids Res. 2013 Nov. 1; 41(20):e188; Larson et al., Nat Protoc. 2013 November; 8(11):2180-96; Mali et. at., Nat Methods. 2013 October; 10(10):957-63; Nakayama et al., Genesis. 2013 December; 51(12):835-43; Ran et al., Nat Protoc. 2013 November; 8(11):2281-308; Ran et al., Cell. 2013 Sep. 12; 154(6):1380-9; Upadhyay et al., G3 (Bethesda). 2013 Dec. 9; 3(12):2233-8; Walsh et al., Proc Natl Acad Sci USA. 2013 Sep. 24; 110(39):15514-5; Xie et al., Mol Plant. 2013 Oct. 9; Yang et al., Cell. 2013 Sep. 12; 154(6):1370-9; and U.S. patents and patent applications: U.S. Pat. Nos. 8,906,616; 8,895,308; 8,889,418; 8,889,356; 8,871,445; 8,865,406; 8,795,965; 8,771,945; 8,697,359; 20140068797; 20140170753; 20140179006; 20140179770; 20140186843; 20140186919; 20140186958; 20140189896; 20140227787; 20140234972; 20140242664; 20140242699; 20140242700; 20140242702; 20140248702; 20140256046; 20140273037; 20140273226; 20140273230; 20140273231; 20140273232; 20140273233; 20140273234; 20140273235; 20140287938; 20140295556; 20140295557; 20140298547; 20140304853; 20140309487; 20140310828; 20140310830; 20140315985; 20140335063; 20140335620; 20140342456; 20140342457; 20140342458; 20140349400; 20140349405; 20140356867; 20140356956; 20140356958; 20140356959; 20140357523; 20140357530; 20140364333; and 20140377868; each of which is hereby incorporated by reference in its entirety.

For example, the present disclosure provides (but is not limited to) methods of cleaving a target nucleic acid; methods of editing a target nucleic acid; methods of modulating transcription from a target nucleic acid; methods of isolating a target nucleic acid, methods of binding a target nucleic acid, methods of imaging a target nucleic acid, methods of modifying a target nucleic acid, and the like.

As used herein, the terms/phrases "contact a target nucleic acid" and "contacting a target nucleic acid", for example, with a CasZ polypeptide or with a CasZ fusion polypeptide, etc., encompass all methods for contacting the target nucleic acid. For example, a CasZ polypeptide can be provided to a cell as protein, RNA (encoding the CasZ polypeptide), or DNA (encoding the CasZ polypeptide); while a CasZ guide RNA can be provided as a guide RNA or as a nucleic acid encoding the guide RNA and a CasZ trancRNA can be provided as a trancRNA or as a nucleic acid encoding the trancRNA. As such, when, for example, performing a method in a cell (e.g., inside of a cell in vitro, inside of a cell in vivo, inside of a cell ex vivo), a method that includes contacting the target nucleic acid encompasses the introduction into the cell of any or all of the components in their active/final state (e.g., in the form of a protein(s) for CasZ polypeptide; in the form of a protein for a CasZ fusion polypeptide; in the form of an RNA in some cases for the guide RNA), and also encompasses the introduction into the cell of one or more nucleic acids encoding one or more of the components (e.g., nucleic acid(s) comprising nucleotide sequence(s) encoding a CasZ polypeptide or a CasZ fusion polypeptide, nucleic acid(s) comprising nucleotide sequence(s) encoding guide RNA(s), nucleic acid comprising a nucleotide sequence encoding a donor template, and the like). Because the methods can also be performed in vitro outside of a cell, a method that includes contacting a target nucleic acid, (unless otherwise specified) encompasses contacting outside of a cell in vitro, inside of a cell in vitro, inside of a cell in vivo, inside of a cell ex vivo, etc.

In some cases, a method of the present disclosure for modifying a target nucleic acid comprises introducing into a target cell a CasZ locus, e.g., a nucleic acid comprising a nucleotide sequence encoding a CasZ polypeptide as well as nucleotide sequences of about 1 kilobase (kb) to 5 kb in length surrounding the CasZ-encoding nucleotide sequence from a cell (e.g., in some cases a cell that in its natural state (the state in which it occurs in nature) comprises a CasZ locus) comprising a CasZ locus, where the target cell does not normally (in its natural state) comprise a CasZ locus (e.g., in some cases the locus includes a CasZ trancRNA. However, one or more spacer sequences, encoding guide sequences for the encoded crRNA(s), can be modified such that one or more target sequences of interest are targeted. Thus, for example, in some cases, a method of the present disclosure for modifying a target nucleic acid comprises introducing into a target cell a CasZ locus, e.g., a nucleic acid obtained from a source cell (e.g., in some cases a cell that in its natural state (the state in which it occurs in nature) comprises a CasZ locus), where the nucleic acid has a length of from 100 nucleotides (nt) to 5 kb in length (e.g., from 100 nt to 500 nt, from 500 nt to 1 kb, from 1 kb to 1.5 kb, from 1.5 kb to 2 kb, from 2 kb to 2.5 kb, from 2.5 kb to 3 kb, from 3 kb to 3.5 kb, from 3.5 kb to 4 kb, or from 4 kb to 5 kb in length) and comprises a nucleotide sequence encoding a CasZ polypeptide. As noted above, in some such cases, one or more spacer sequences, encoding guide sequences for the encoded crRNA(s), can be modified such that one or more target sequences of interest are targeted. In some cases, the method comprises introducing into a target cell: i) a CasZ locus; and ii) a donor DNA template. In some cases, the target nucleic acid is in a cell-free composition in vitro. In some cases, the target nucleic acid is present in a target cell. In some cases, the target nucleic acid is present in a target cell, where the target cell is a prokaryotic cell. In some cases, the target nucleic acid is present in a target cell, where the target cell is a eukaryotic cell. In some cases, the target nucleic acid is present in a target cell, where the target cell is a mammalian cell. In some cases, the target nucleic acid is present in a target cell, where the target cell is a plant cell.

In some cases, a method of the present disclosure for modifying a target nucleic acid comprises contacting a target nucleic acid with a CasZ polypeptide of the present disclosure, or with a CasZ fusion polypeptide of the present disclosure. In some cases, abmethod of the present disclosure for modifying a target nucleic acid comprises contacting a target nucleic acid with a CasZ polypeptide and a CasZ guide RNA. In some cases, abmethod of the present disclosure for modifying a target nucleic acid comprises contacting a target nucleic acid with a CasZ polypeptide, a CasZ guide RNA, and a CasZ trancRNA. In some cases, abmethod of the present disclosure for modifying a target nucleic acid comprises contacting a target nucleic acid with a CasZ polypeptide, a first CasZ guide RNA, and a second CasZ guide RNA (and in some cases a CasZ trancRNA). In some cases, a method of the present disclosure for modifying a target nucleic acid comprises contacting a target nucleic acid with a CasZ polypeptide of the present disclosure and a CasZ guide RNA and a donor DNA template. In some cases, a method of the present disclosure for modifying a target nucleic acid comprises contacting a target nucleic acid with a CasZ polypeptide of the present disclosure and a CasZ guide RNA and a CasZ trancRNA and a donor DNA template.

In some cases, the target nucleic acid is in a cell-free composition in vitro. In some cases, the target nucleic acid is present in a target cell. In some cases, the target nucleic acid is present in a target cell, where the target cell is a prokaryotic cell. In some cases, the target nucleic acid is present in a target cell, where the target cell is a eukaryotic cell. In some cases, the target nucleic acid is present in a target cell, where the target cell is a mammalian cell. In some cases, the target nucleic acid is present in a target cell, where the target cell is a plant cell.

Target Nucleic Acids and Target Cells of Interest

A target nucleic acid can be any nucleic acid (e.g., DNA, RNA), can be double stranded or single stranded, can be any type of nucleic acid (e.g., a chromosome (genomic DNA), derived from a chromosome, chromosomal DNA, plasmid, viral, extracellular, intracellular, mitochondrial, chloroplast, linear, circular, etc.) and can be from any organism (e.g., as long as the CasZ guide RNA comprises a nucleotide sequence that hybridizes to a target sequence in a target nucleic acid, such that the target nucleic acid can be targeted).

A target nucleic acid can be DNA or RNA. A target nucleic acid can be double stranded (e.g., dsDNA, dsRNA) or single stranded (e.g., ssRNA, ssDNA). In some cases, a target nucleic acid is single stranded. In some cases, a target nucleic acid is a single stranded RNA (ssRNA). In some cases, a target ssRNA (e.g., a target cell ssRNA, a viral ssRNA, etc.) is selected from: mRNA, rRNA, tRNA, non-coding RNA (ncRNA), long non-coding RNA (lncRNA), and microRNA (miRNA). In some cases, a target nucleic acid is a single stranded DNA (ssDNA) (e.g., a viral DNA). As noted above, in some cases, a target nucleic acid is single stranded.

A target nucleic acid can be located anywhere, for example, outside of a cell in vitro, inside of a cell in vitro, inside of a cell in vivo, inside of a cell ex vivo. Suitable target cells (which can comprise target nucleic acids such as genomic DNA) include, but are not limited to: a bacterial cell; an archaeal cell; a cell of a single-cell eukaryotic organism; a plant cell; an algal cell, e.g., *Botryococcus braunii, Chlamydomonas reinhardtii, Nannochloropsis gaditana, Chlorella pyrenoidosa, Sargassum patens, C. agardh*, and the like; a fungal cell (e.g., a yeast cell); an animal cell; a cell from an invertebrate animal (e.g. fruit fly, a cnidarian, an echinoderm, a nematode, etc.); a cell of an insect (e.g., a mosquito; a bee; an agricultural pest; etc.); a cell of an arachnid (e.g., a spider; a tick; etc.); a cell from a vertebrate animal (e.g., a fish, an amphibian, a reptile, a bird, a mammal); a cell from a mammal (e.g., a cell from a rodent; a cell from a human; a cell of a non-human mammal; a cell of a rodent (e.g., a mouse, a rat); a cell of a lagomorph (e.g., a rabbit); a cell of an ungulate (e.g., a cow, a horse, a camel, a llama, a vicuna, a sheep, a goat, etc.); a cell of a marine mammal (e.g., a whale, a seal, an elephant seal, a dolphin, a sea lion; etc.) and the like. Any type of cell may be of interest (e.g. a stem cell, e.g. an embryonic stem (ES) cell, an induced pluripotent stem (iPS) cell, a germ cell (e.g., an oocyte, a sperm, an oogonia, a spermatogonia, etc.), an adult stem cell, a somatic cell, e.g. a fibroblast, a hematopoietic cell, a neuron, a muscle cell, a bone cell, a hepatocyte, a pancreatic cell; an in vitro or in vivo embryonic cell of an embryo at any stage, e.g., a 1-cell, 2-cell, 4-cell, 8-cell, etc. stage zebrafish embryo; etc.).

Cells may be from established cell lines or they may be primary cells, where "primary cells", "primary cell lines", and "primary cultures" are used interchangeably herein to refer to cells and cells cultures that have been derived from a subject and allowed to grow in vitro for a limited number of passages, i.e. splittings, of the culture. For example, primary cultures are cultures that may have been passaged 0 times, 1 time, 2 times, 4 times, 5 times, 10 times, or 15 times, but not enough times go through the crisis stage. Typically, the primary cell lines are maintained for fewer than 10 passages in vitro. Target cells can be unicellular organisms and/or can be grown in culture. If the cells are primary cells, they may be harvest from an individual by any convenient method. For example, leukocytes may be conveniently harvested by apheresis, leukocytapheresis, density gradient separation, etc., while cells from tissues such as skin, muscle, bone marrow, spleen, liver, pancreas, lung, intestine, stomach, etc. can be conveniently harvested by biopsy.

In some of the above applications, the subject methods may be employed to induce target nucleic acid cleavage, target nucleic acid modification, and/or to bind target nucleic acids (e.g., for visualization, for collecting and/or analyzing, etc.) in mitotic or post-mitotic cells in vivo and/or ex vivo and/or in vitro (e.g., to disrupt production of a protein encoded by a targeted mRNA, to cleave or otherwise modify target DNA, to genetically modify a target cell, and the like). Because the guide RNA provides specificity by hybridizing to target nucleic acid, a mitotic and/or post-mitotic cell of interest in the disclosed methods may include a cell from any organism (e.g. a bacterial cell, an archaeal cell, a cell of a single-cell eukaryotic organism, a plant cell, an algal cell, e.g., *Botryococcus braunii, Chlamydomonas reinhardtii, Nannochloropsis gaditana, Chlorella pyrenoidosa, Sargassum patens, C. agardh*, and the like, a fungal cell (e.g., a yeast cell), an animal cell, a cell from an invertebrate animal (e.g. fruit fly, cnidarian, echinoderm, nematode, etc.), a cell from a vertebrate animal (e.g., fish, amphibian, reptile, bird, mammal), a cell from a mammal, a cell from a rodent, a cell from a human, etc.). In some cases, a subject CasZ protein (and/or nucleic acid encoding the protein such as DNA and/or RNA), and/or CasZ guide RNA (and/or a DNA encoding the guide RNA), and/or donor template, and/or RNP can be introduced into an individual (i.e., the target cell can be in vivo) (e.g., a mammal, a rat, a mouse, a pig, a primate, a non-human primate, a human, etc.). In some cases, such an administration can be for the purpose of treating and/or preventing a disease, e.g., by editing the genome of targeted cells.

Plant cells include cells of a monocotyledon, and cells of a dicotyledon. The cells can be root cells, leaf cells, cells of the xylem, cells of the phloem, cells of the cambium, apical meristem cells, parenchyma cells, collenchyma cells, sclerenchyma cells, and the like. Plant cells include cells of agricultural crops such as wheat, corn, rice, sorghum, millet, soybean, etc. Plant cells include cells of agricultural fruit and nut plants, e.g., plant that produce apricots, oranges, lemons, apples, plums, pears, almonds, etc.

Additional examples of target cells are listed above in the section titled "Modified cells." Non-limiting examples of cells (target cells) include: a prokaryotic cell, eukaryotic cell, a bacterial cell, an archaeal cell, a cell of a single-cell eukaryotic organism, a protozoa cell, a cell from a plant (e.g., cells from plant crops, fruits, vegetables, grains, soy bean, corn, maize, wheat, seeds, tomatos, rice, cassava, sugarcane, pumpkin, hay, potatos, cotton, cannabis, tobacco, flowering plants, conifers, gymnosperms, angiosperms, ferns, clubmosses, hornworts, liverworts, mosses, dicotyledons, monocotyledons, etc.), an algal cell, (e.g., *Botryococcus braunii, Chlamydomonas reinhardtii, Nannochloropsis gaditana, Chlorella pyrenoidosa, Sargassum patens, C. agardh*, and the like), seaweeds (e.g. kelp) a fungal cell (e.g., a yeast cell, a cell from a mushroom), an animal cell, a cell from an invertebrate animal (e.g., fruit fly, cnidarian, echinoderm, nematode, etc.), a cell from a vertebrate animal (e.g., fish, amphibian, reptile, bird, mammal), a cell from a mammal (e.g., an ungulate (e.g., a pig, a cow, a goat, a sheep); a rodent (e.g., a rat, a mouse); a non-human primate; a human; a feline (e.g., a cat); a canine (e.g., a dog); etc.), and the like. In some cases, the cell is a cell that does not originate from a natural organism (e.g., the cell can be a synthetically made cell; also referred to as an artificial cell).

A cell can be an in vitro cell (e.g., established cultured cell line). A cell can be an ex vivo cell (cultured cell from an individual). A cell can be and in vivo cell (e.g., a cell in an individual). A cell can be an isolated cell. A cell can be a cell inside of an organism. A cell can be an organism. A cell can be a cell in a cell culture (e.g., in vitro cell culture). A cell can be one of a collection of cells. A cell can be a prokaryotic cell or derived from a prokaryotic cell. A cell can be a bacterial cell or can be derived from a bacterial cell. A cell can be an archaeal cell or derived from an archaeal cell. A cell can be a eukaryotic cell or derived from a eukaryotic cell. A cell can be a plant cell or derived from a plant cell. A cell can be an animal cell or derived from an animal cell. A cell can be an invertebrate cell or derived from an invertebrate cell. A cell can be a vertebrate cell or derived from a vertebrate cell. A cell can be a mammalian cell or derived from a mammalian cell. A cell can be a rodent cell or derived from a rodent cell. A cell can be a human cell or derived from a human cell. A cell can be a microbe cell or derived from a microbe cell. A cell can be a fungi cell or derived from a fungi cell. A cell can be an insect cell. A cell can be an arthropod cell. A cell can be a protozoan cell. A cell can be a helminth cell.

Suitable cells include a stem cell (e.g. an embryonic stem (ES) cell, an induced pluripotent stem (iPS) cell; a germ cell (e.g., an oocyte, a sperm, an oogonia, a spermatogonia, etc.); a somatic cell, e.g. a fibroblast, an oligodendrocyte, a glial cell, a hematopoietic cell, a neuron, a muscle cell, a bone cell, a hepatocyte, a pancreatic cell, etc.

Suitable cells include human embryonic stem cells, fetal cardiomyocytes, myofibroblasts, mesenchymal stem cells, autotransplated expanded cardiomyocytes, adipocytes, totipotent cells, pluripotent cells, blood stem cells, myoblasts, adult stem cells, bone marrow cells, mesenchymal cells, embryonic stem cells, parenchymal cells, epithelial cells, endothelial cells, mesothelial cells, fibroblasts, osteoblasts, chondrocytes, exogenous cells, endogenous cells, stem cells, hematopoietic stem cells, bone-marrow derived progenitor cells, myocardial cells, skeletal cells, fetal cells, undifferentiated cells, multi-potent progenitor cells, unipotent progenitor cells, monocytes, cardiac myoblasts, skeletal myoblasts, macrophages, capillary endothelial cells, xenogenic cells, allogenic cells, and post-natal stem cells.

In some cases, the cell is an immune cell, a neuron, an epithelial cell, and endothelial cell, or a stem cell. In some cases, the immune cell is a T cell, a B cell, a monocyte, a natural killer cell, a dendritic cell, or a macrophage. In some cases, the immune cell is a cytotoxic T cell. In some cases, the immune cell is a helper T cell. In some cases, the immune cell is a regulatory T cell (Treg).

In some cases, the cell is a stem cell. Stem cells include adult stem cells. Adult stem cells are also referred to as somatic stem cells.

Adult stem cells are resident in differentiated tissue, but retain the properties of self-renewal and ability to give rise to multiple cell types, usually cell types typical of the tissue in which the stem cells are found. Numerous examples of somatic stem cells are known to those of skill in the art, including muscle stem cells; hematopoietic stem cells; epithelial stem cells; neural stem cells; mesenchymal stem cells; mammary stem cells; intestinal stem cells; mesodermal stem cells; endothelial stem cells; olfactory stem cells; neural crest stem cells; and the like.

Stem cells of interest include mammalian stem cells, where the term "mammalian" refers to any animal classified as a mammal, including humans; non-human primates; domestic and farm animals; and zoo, laboratory, sports, or pet animals, such as dogs, horses, cats, cows, mice, rats, rabbits, etc. In some cases, the stem cell is a human stem cell. In some cases, the stem cell is a rodent (e.g., a mouse; a rat) stem cell. In some cases, the stem cell is a non-human primate stem cell.

Stem cells can express one or more stem cell markers, e.g., SOX9, KRT19, KRT7, LGR5, CA9, FXYD2, CDH6, CLDN18, TSPAN8, BPIFB1, OLFM4, CDH17, and PPARGC1A.

In some cases, the stem cell is a hematopoietic stem cell (HSC). HSCs are mesoderm-derived cells that can be isolated from bone marrow, blood, cord blood, fetal liver and yolk sac. HSCs are characterized as $CD34^+$ and $CD3^-$. HSCs can repopulate the erythroid, neutrophil-macrophage, megakaryocyte and lymphoid hematopoietic cell lineages in vivo. In vitro, HSCs can be induced to undergo at least some self-renewing cell divisions and can be induced to differentiate to the same lineages as is seen in vivo. As such, HSCs can be induced to differentiate into one or more of erythroid cells, megakaryocytes, neutrophils, macrophages, and lymphoid cells.

In other cases, the stem cell is a neural stem cell (NSC). Neural stem cells (NSCs) are capable of differentiating into neurons, and glia (including oligodendrocytes, and astrocytes). A neural stem cell is a multipotent stem cell which is capable of multiple divisions, and under specific conditions can produce daughter cells which are neural stem cells, or neural progenitor cells that can be neuroblasts or glioblasts, e.g., cells committed to become one or more types of neurons and glial cells respectively. Methods of obtaining NSCs are known in the art.

In other cases, the stem cell is a mesenchymal stem cell (MSC). MSCs originally derived from the embryonal mesoderm and isolated from adult bone marrow, can differentiate to form muscle, bone, cartilage, fat, marrow stroma, and tendon. Methods of isolating MSC are known in the art; and any known method can be used to obtain MSC. See, e.g., U.S. Pat. No. 5,736,396, which describes isolation of human MSC.

A cell is in some cases a plant cell. A plant cell can be a cell of a monocotyledon. A cell can be a cell of a dicotyledon.

In some cases, the cell is a plant cell. For example, the cell can be a cell of a major agricultural plant, e.g., Barley, Beans (Dry Edible), Canola, Corn, Cotton (Pima), Cotton (Upland), Flaxseed, Hay (Alfalfa), Hay (Non-Alfalfa), Oats, Peanuts, Rice, Sorghum, Soybeans, Sugarbeets, Sugarcane, Sunflowers (Oil), Sunflowers (Non-Oil), Sweet Potatoes, Tobacco (Burley), Tobacco (Flue-cured), Tomatoes, Wheat (Durum), Wheat (Spring), Wheat (Winter), and the like. As another example, the cell is a cell of a vegetable crops which include but are not limited to, e.g., alfalfa sprouts, aloe leaves, arrow root, arrowhead, artichokes, asparagus, bamboo shoots, banana flowers, bean sprouts, beans, beet tops, beets, bittermelon, bok choy, broccoli, broccoli rabe (rappini), brussels sprouts, cabbage, cabbage sprouts, cactus leaf (nopales), calabaza, cardoon, carrots, cauliflower, celery, chayote, chinese artichoke (crosnes), chinese cabbage, chinese celery, chinese chives, choy sum, chrysanthemum leaves (tung ho), collard greens, corn stalks, corn-sweet, cucumbers, daikon, dandelion greens, dasheen, dau mue (pea tips), donqua (winter melon), eggplant, endive, escarole, fiddle head ferns, field cress, frisee, gai choy (chinese mustard), gailon, galanga (siam, thai ginger), garlic, ginger root, gobo, greens, hanover salad greens, huauzontle, jerusalem artichokes, jicama, kale greens, kohlrabi, lamb's quarters (quilete), lettuce (bibb), lettuce (boston), lettuce (boston red), lettuce (green leaf), lettuce (iceberg), lettuce (lolla rossa), lettuce (oak leaf—green), lettuce (oak leaf—red), lettuce (processed), lettuce (red leaf), lettuce (romaine), lettuce (ruby romaine), lettuce (russian red mustard), linkok, lo bok, long beans, lotus root, mache, maguey (agave) leaves, malanga, mesculin mix, mizuna, moap (smooth luffa), moo, moqua (fuzzy squash), mushrooms, mustard, nagaimo, okra, ong choy, onions green, opo (long squash), ornamental corn, ornamental gourds, parsley, parsnips, peas, peppers (bell type), peppers, pumpkins, radicchio, radish sprouts, radishes, rape greens, rape greens, rhubarb, romaine (baby red), rutabagas, salicornia (sea bean), sinqua (angled/ridged luffa), spinach, squash, straw bales, sugarcane, sweet potatoes, swiss chard, tamarindo, taro, taro leaf, taro shoots, tatsoi, tepeguaje (guaje), tindora, tomatillos, tomatoes, tomatoes (cherry), tomatoes (grape type), tomatoes (plum type), tumeric, turnip tops greens, turnips, water chestnuts, yampi, yams (names), yu choy, yuca (cassava), and the like.

A cell is in some cases an arthropod cell. For example, the cell can be a cell of a sub-order, a family, a sub-family, a group, a sub-group, or a species of, e.g., *Chelicerata*, Myriapodia, Hexipodia, Arachnida, *Insecta*, Archaeognatha, *Thysanura*, Palaeoptera, Ephemeroptera, *Odonata, Anisoptera, Zygoptera*, Neoptera, Exopterygota, *Plecoptera*, Embioptera, *Orthoptera, Zoraptera, Dermaptera, Dictyoptera, Notoptera*, Grylloblattidae, Mantophasmatidae, Phasmatodea, *Blattaria, Isoptera*, Mantodea, Parapneuroptera, Psocoptera, Thysanoptera, Phthiraptera, *Hemiptera*, Endopterygota or Holometabola, *Hymenoptera, Coleoptera*, Strepsiptera, Raphidioptera, *Megaloptera, Neuroptera*, Mecoptera, *Siphonaptera, Diptera, Trichoptera*, or *Lepidoptera*.

A cell is in some cases an insect cell. For example, in some cases, the cell is a cell of a mosquito, a grasshopper, a true bug, a fly, a flea, a bee, a wasp, an ant, a louse, a moth, or a beetle.

Donor Polynucleotide (Donor Template)

Guided by a CasZ guide RNA, a CasZ protein in some cases generates site-specific double strand breaks (DSBs) or single strand breaks (SSBs) (e.g., when the CasZ protein is a nickase variant) within double-stranded DNA (dsDNA) target nucleic acids, which are repaired either by non-homologous end joining (NHEJ) or homology-directed recombination (HDR).

In some cases, contacting a target DNA (with a CasZ protein and a CasZ guide RNA) occurs under conditions that are permissive for nonhomologous end joining or homology-directed repair. Thus, in some cases, a subject method includes contacting the target DNA with a donor polynucleotide (e.g., by introducing the donor polynucleotide into a cell), wherein the donor polynucleotide, a portion of the donor polynucleotide, a copy of the donor polynucleotide, or a portion of a copy of the donor polynucleotide integrates into the target DNA. In some cases, the method does not comprise contacting a cell with a donor polynucleotide, and the target DNA is modified such that nucleotides within the target DNA are deleted.

In some cases, a CasZ trancRNA (or nucleic acid encoding same), a CasZ guide RNA (or nucleic acid encoding same), and/or a CasZ protein (or a nucleic acid encoding same, such as an RNA or a DNA, e.g, one or more expression vectors) are coadministered (e.g., contacted with a target nucleic acid, administered to cells, etc.) with a donor polynucleotide sequence that includes at least a segment with homology to the target DNA sequence, the subject methods may be used to add, i.e. insert or replace, nucleic acid material to a target DNA sequence (e.g. to "knock in" a nucleic acid, e.g., one that encodes for a protein, an siRNA, an miRNA, etc.), to add a tag (e.g., 6×His, a fluorescent protein (e.g., a green fluorescent protein; a yellow fluorescent protein, etc.), hemagglutinin (HA), FLAG, etc.), to add a regulatory sequence to a gene (e.g. promoter, polyadenylation signal, internal ribosome entry sequence (IRES), 2A peptide, start codon, stop codon, splice signal, localization signal, etc.), to modify a nucleic acid sequence (e.g., introduce a mutation, remove a disease causing mutation by introducing a correct sequence), and the like. As such, a complex comprising a CasZ guide RNA and CasZ protein (or CasZ guide RNA and CasZ trancRNA and CasZ protein) is useful in any in vitro or in vivo application in which it is desirable to modify DNA in a site-specific, i.e. "targeted", way, for example gene knock-out, gene knock-in, gene editing, gene tagging, etc., as used in, for example, gene therapy, e.g. to treat a disease or as an antiviral, antipathogenic, or anticancer therapeutic, the production of genetically modified organisms in agriculture, the large scale production of proteins by cells for therapeutic, diagnostic, or research purposes, the induction of iPS cells, biological research, the targeting of genes of pathogens for deletion or replacement, etc.

In applications in which it is desirable to insert a polynucleotide sequence into he genome where a target sequence is cleaved, a donor polynucleotide (a nucleic acid comprising a donor sequence) can also be provided to the cell. By a "donor sequence" or "donor polynucleotide" or "donor template" it is meant a nucleic acid sequence to be inserted at the site cleaved by the CasZ protein (e.g., after dsDNA cleavage, after nicking a target DNA, after dual nicking a target DNA, and the like). The donor polynucleotide can contain sufficient homology to a genomic sequence at the target site, e.g. 70%, 80%, 85%, 90%, 95%, or 100% homology with the nucleotide sequences flanking the target site, e.g. within about 50 bases or less of the target site, e.g. within about 30 bases, within about 15 bases, within about 10 bases, within about 5 bases, or immediately flanking the target site, to support homology-directed repair between it and the genomic sequence to which it bears homology. Approximately 25, 50, 100, or 200 nucleotides, or more than 200 nucleotides, of sequence homology between a donor and a genomic sequence (or any integral value between 10 and 200 nucleotides, or more) can support homology-directed repair. Donor polynucleotides can be of any length, e.g. 10 nucleotides or more, 50 nucleotides or more, 100 nucleotides or more, 250 nucleotides or more, 500 nucleotides or more, 1000 nucleotides or more, 5000 nucleotides or more, etc.

The donor sequence is typically not identical to the genomic sequence that it replaces. Rather, the donor sequence may contain at least one or more single base changes, insertions, deletions, inversions or rearrangements with respect to the genomic sequence, so long as sufficient homology is present to support homology-directed repair (e.g., for gene correction, e.g., to convert a disease-causing base pair ot a non disease-causing base pair). In some embodiments, the donor sequence comprises a non-homologous sequence flanked by two regions of homology, such that homology-directed repair between the target DNA region and the two flanking sequences results in insertion of the non-homologous sequence at the target region. Donor sequences may also comprise a vector backbone containing sequences that are not homologous to the DNA region of interest and that are not intended for insertion into the DNA region of interest. Generally, the homologous region(s) of a donor sequence will have at least 50% sequence identity to a genomic sequence with which recombination is desired. In certain embodiments, 60%, 70%, 80%, 90%, 95%, 98%, 99%, or 99.9% sequence identity is present. Any value between 1% and 100% sequence identity can be present, depending upon the length of the donor polynucleotide.

The donor sequence may comprise certain sequence differences as compared to the genomic sequence, e.g. restriction sites, nucleotide polymorphisms, selectable markers (e.g., drug resistance genes, fluorescent proteins, enzymes etc.), etc., which may be used to assess for successful insertion of the donor sequence at the cleavage site or in some cases may be used for other purposes (e.g., to signify expression at the targeted genomic locus). In some cases, if located in a coding region, such nucleotide sequence differences will not change the amino acid sequence, or will make silent amino acid changes (i.e., changes which do not affect the structure or function of the protein). Alternatively, these sequences differences may include flanking recombination sequences such as FLPs, loxP sequences, or the like, that can be activated at a later time for removal of the marker sequence.

In some cases, the donor sequence is provided to the cell as single-stranded DNA. In some cases, the donor sequence is provided to the cell as double-stranded DNA. It may be introduced into a cell in linear or circular form. If introduced in linear form, the ends of the donor sequence may be protected (e.g., from exonucleolytic degradation) by any convenient method and such methods are known to those of skill in the art. For example, one or more dideoxynucleotide residues can be added to the 3' terminus of a linear molecule and/or self-complementary oligonucleotides can be ligated to one or both ends. See, for example, Chang et al. (1987) Proc. Natl. Acad Sci USA 84:4959-4963; Nehls et al. (1996) Science 272:886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues. As an alternative to protecting the termini of a linear donor sequence, additional lengths of sequence may be included outside of the regions of homology that can be degraded without impacting recombination. A donor sequence can be introduced into a cell as part of a vector molecule having additional sequences such as, for example, replication origins, promoters and genes encoding antibiotic resistance. Moreover, donor sequences can be introduced as naked nucleic acid, as nucleic acid complexed with an agent such as a liposome or poloxamer, or can be delivered by viruses (e.g., adenovirus, AAV), as described elsewhere herein for nucleic acids encoding a CasZ guide RNA and/or a CasZ fusion polypeptide and/or donor polynucleotide.

Transgenic, Non-Human Organisms

As described above, in some cases, a nucleic acid (e.g., a recombinant expression vector) of the present disclosure (e.g., a nucleic acid comprising a nucleotide sequence encoding a CasZ polypeptide; a nucleic acid comprising a nucleotide sequence encoding a CasZ fusion polypeptide; etc.), is used as a transgene to generate a transgenic non-human organism that produces a CasZ polypeptide, or a CasZ fusion polypeptide, of the present disclosure. The present disclosure provides a transgenic-non-human organism comprising a nucleotide sequence encoding a CasZ polypeptide, or a CasZ fusion polypeptide, of the present disclosure.

Transgenic, Non-Human Animals

The present disclosure provides a transgenic non-human animal, which animal comprises a transgene comprising a nucleic acid comprising a nucleotide sequence encoding a CasZ polypeptide or a CasZ fusion polypeptide. In some embodiments, the genome of the transgenic non-human animal comprises a nucleotide sequence encoding a CasZ polypeptide, or a CasZ fusion polypeptide, of the present disclosure. In some cases, the transgenic non-human animal is homozygous for the genetic modification. In some cases, the transgenic non-human animal is heterozygous for the genetic modification. In some embodiments, the transgenic non-human animal is a vertebrate, for example, a fish (e.g., salmon, trout, zebra fish, gold fish, puffer fish, cave fish, etc.), an amphibian (frog, newt, salamander, etc.), a bird (e.g., chicken, turkey, etc.), a reptile (e.g., snake, lizard, etc.), a non-human mammal (e.g., an ungulate, e.g., a pig, a cow, a goat, a sheep, etc.; a lagomorph (e.g., a rabbit); a rodent (e.g., a rat, a mouse); a non-human primate; etc.), etc. In some cases, the transgenic non-human animal is an invertebrate. In some cases, the transgenic non-human animal is an insect (e.g., a mosquito; an agricultural pest; etc.). In some cases, the transgenic non-human animal is an arachnid.

Nucleotide sequences encoding a CasZ polypeptide, or a CasZ fusion polypeptide, of the present disclosure can be under the control of (i.e., operably linked to) an unknown promoter (e.g., when the nucleic acid randomly integrates into a host cell genome) or can be under the control of (i.e., operably linked to) a known promoter. Suitable known promoters can be any known promoter and include constitutively active promoters (e.g., CMV promoter), inducible promoters (e.g., heat shock promoter, tetracycline-regulated promoter, steroid-regulated promoter, metal-regulated promoter, estrogen receptor-regulated promoter, etc.), spatially restricted and/or temporally restricted promoters (e.g., a tissue specific promoter, a cell type specific promoter, etc.), etc.

Transgenic Plants

As described above, in some cases, a nucleic acid (e.g., a recombinant expression vector) of the present disclosure (e.g., a nucleic acid comprising a nucleotide sequence encoding a CasZ polypeptide of the present disclosure; a nucleic acid comprising a nucleotide sequence encoding a CasZ fusion polypeptide of the present disclosure; etc.), is used as a transgene to generate a transgenic plant that produces a CasZ polypeptide, or a CasZ fusion polypeptide, of the present disclosure. The present disclosure provides a transgenic plant comprising a nucleotide sequence encoding a CasZ polypeptide, or a CasZ fusion polypeptide, of the present disclosure. In some embodiments, the genome of the transgenic plant comprises a subject nucleic acid. In some embodiments, the transgenic plant is homozygous for the genetic modification. In some embodiments, the transgenic plant is heterozygous for the genetic modification.

Methods of introducing exogenous nucleic acids into plant cells are well known in the art. Such plant cells are considered "transformed," as defined above. Suitable methods include viral infection (such as double stranded DNA viruses), transfection, conjugation, protoplast fusion, electroporation, particle gun technology, calcium phosphate precipitation, direct microinjection, silicon carbide whiskers technology, Agrobacterium-mediated transformation and the like. The choice of method is generally dependent on the type of cell being transformed and the circumstances under which the transformation is taking place (i.e. in vitro, ex vivo, or in vivo).

Transformation methods based upon the soil bacterium *Agrobacterium tumefaciens* are particularly useful for introducing an exogenous nucleic acid molecule into a vascular plant. The wild type form of *Agrobacterium* contains a Ti (tumor-inducing) plasmid that directs production of tumorigenic crown gall growth on host plants. Transfer of the tumor-inducing T-DNA region of the Ti plasmid to a plant genome requires the Ti plasmid-encoded virulence genes as well as T-DNA borders, which are a set of direct DNA repeats that delineate the region to be transferred. An *Agrobacterium*-based vector is a modified form of a Ti plasmid, in which the tumor inducing functions are replaced by the nucleic acid sequence of interest to be introduced into the plant host.

*Agrobacterium*-mediated transformation generally employs cointegrate vectors or binary vector systems, in which the components of the Ti plasmid are divided between a helper vector, which resides permanently in the *Agrobacterium* host and carries the virulence genes, and a shuttle vector, which contains the gene of interest bounded by T-DNA sequences. A variety of binary vectors is well known in the art and are commercially available, for example, from Clontech (Palo Alto, Calif.). Methods of coculturing *Agrobacterium* with cultured plant cells or wounded tissue such as leaf tissue, root explants, hypocotyledons, stem pieces or tubers, for example, also are well known in the art. See, e.g., Glick and Thompson, (eds.), Methods in Plant Molecular Biology and Biotechnology, Boca Raton, Fla.: CRC Press (1993).

Microprojectile-mediated transformation also can be used to produce a subject transgenic plant. This method, first described by Klein et al. (Nature 327:70-73 (1987)), relies on microprojectiles such as gold or tungsten that are coated with the desired nucleic acid molecule by precipitation with calcium chloride, spermidine or polyethylene glycol. The microprojectile particles are accelerated at high speed into an angiosperm tissue using a device such as the BIOLISTIC PD-1000 (Biorad; Hercules Calif.).

A nucleic acid of the present disclosure (e.g., a nucleic acid (e.g., a recombinant expression vector) comprising a nucleotide sequence encoding a CasZ polypeptide, or a CasZ fusion polypeptide, of the present disclosure) may be introduced into a plant in a manner such that the nucleic acid is able to enter a plant cell(s), e.g., via an in vivo or ex vivo protocol. By "in vivo," it is meant in the nucleic acid is administered to a living body of a plant e.g. infiltration. By "ex vivo" it is meant that cells or explants are modified outside of the plant, and then such cells or organs are regenerated to a plant. A number of vectors suitable for stable transformation of plant cells or for the establishment of transgenic plants have been described, including those described in Weissbach and Weissbach, (1989) Methods for Plant Molecular Biology Academic Press, and Gelvin et al., (1990) Plant Molecular Biology Manual, Kluwer Academic Publishers. Specific examples include those derived from a Ti plasmid of *Agrobacterium tumefaciens*, as well as those disclosed by Herrera-Estrella et al. (1983) Nature 303: 209, Bevan (1984) Nucl Acid Res. 12: 8711-8721, Klee (1985) Bio/Technolo 3: 637-642. Alternatively, non-Ti vectors can be used to transfer the DNA into plants and cells by using free DNA delivery techniques. By using these methods transgenic plants such as wheat, rice (Christou (1991) Bio/Technology 9:957-9 and 4462) and corn (Gordon-Kamm (1990) Plant Cell 2: 603-618) can be produced. An immature embryo can also be a good target tissue for monocots for direct DNA delivery techniques by using the particle gun (Weeks et al. (1993) Plant Physiol 102: 1077-1084; Vasil (1993) Bio/Technolo 10: 667-674; Wan and Lemeaux (1994) Plant Physiol 104: 37-48 and for *Agrobacterium*-mediated DNA transfer (Ishida et al. (1996) Nature Biotech 14: 745-750). Exemplary methods for introduction of DNA into chloroplasts are biolistic bombardment, polyethylene glycol transformation of protoplasts, and microinjection (Danieli et al Nat. Biotechnol 16:345-348, 1998; Staub et al Nat. Biotechnol 18: 333-338, 2000; O'Neill et al Plant J. 3:729-738, 1993; Knoblauch et al Nat. Biotechnol 17: 906-909; U.S. Pat. Nos. 5,451,513, 5,545,817, 5,545,818, and 5,576, 198; in Intl. Application No. WO 95/16783; and in Boynton et al., Methods in Enzymology 217: 510-536 (1993), Svab et al., Proc. Natl. Acad. Sci. USA 90: 913-917 (1993), and McBride et al., Proc. Natl. Acad. Sci. USA 91: 7301-7305 (1994)). Any vector suitable for the methods of biolistic bombardment, polyethylene glycol transformation of protoplasts and microinjection will be suitable as a targeting vector for chloroplast transformation. Any double stranded DNA vector may be used as a transformation vector, especially when the method of introduction does not utilize *Agrobacterium*.

Plants which can be genetically modified include grains, forage crops, fruits, vegetables, oil seed crops, palms, forestry, and vines. Specific examples of plants which can be modified follow: maize, banana, peanut, field peas, sunflower, tomato, canola, tobacco, wheat, barley, oats, potato, soybeans, cotton, carnations, sorghum, lupin and rice.

The present disclosure provides transformed plant cells, tissues, plants and products that contain the transformed plant cells. A feature of the subject transformed cells, and tissues and products that include the same is the presence of a subject nucleic acid integrated into the genome, and production by plant cells of a CasZ polypeptide, or a CasZ fusion polypeptide, of the present disclosure. Recombinant plant cells of the present invention are useful as populations of recombinant cells, or as a tissue, seed, whole plant, stem, fruit, leaf, root, flower, stem, tuber, grain, animal feed, a field of plants, and the like.

Nucleotide sequences encoding a CasZ polypeptide, or a CasZ fusion polypeptide, of the present disclosure can be under the control of (i.e., operably linked to) an unknown promoter (e.g., when the nucleic acid randomly integrates into a host cell genome) or can be under the control of (i.e., operably linked to) a known promoter. Suitable known promoters can be any known promoter and include constitutively active promoters, inducible promoters, spatially restricted and/or temporally restricted promoters, etc.

Examples of Non-Limiting Aspects of the Disclosure

Aspects, including embodiments, of the present subject matter described above may be beneficial alone or in combination, with one or more other aspects or embodiments. Without limiting the foregoing description, certain non-limiting aspects of the disclosure, numbered 1-36 are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

Aspects

Aspect 1. A method of guiding a CasZ polypeptide to a target sequence of a target nucleic acid, the method comprising contacting the target nucleic acid with an engineered and/or non-naturally occurring complex comprising: (a) a CasZ polypeptide; and (b) a CasZ guide RNA that comprises a guide sequence that hybridizes to a target sequence of the target nucleic acid, and comprises a region that binds to the CasZ polypeptide.

Aspect 2. The method of aspect 1, wherein the method results in modification of the target nucleic acid, modulation of transcription from the target nucleic acid, or modification of a polypeptide associated with a target nucleic acid.

Aspect 3. The method of aspect 2, wherein the target nucleic acid is modified by being cleaved.

Aspect 4. The method of any one of aspects 1-3, wherein the target nucleic acid is selected from: double stranded DNA, single stranded DNA, RNA, genomic DNA, and extrachromosomal DNA.

Aspect 5. The method of any one of aspects 1-4, wherein the guide sequence and the region that binds to the CasZ polypeptide are heterologous to one another.

Aspect 6. The method of any one of aspects 1-5, wherein said contacting results in genome editing.

Aspect 7. The method of any one of aspects 1-5, wherein said contacting takes place outside of a bacterial cell and outside of an archaeal cell.

Aspect 8. The method of any one of aspects 1-5, wherein said contacting takes place in vitro outside of a cell.

Aspect 9. The method of any one of aspects 1-7, wherein said contacting takes place inside of a target cell.

Aspect 10. The method of aspect 9, wherein said contacting comprises: introducing into the target cell at least one of: (a) the CasZ polypeptide, or a nucleic acid encoding the CasZ polypeptide; and (b) the CasZ guide RNA, or a nucleic acid encoding the CasZ guide RNA.

Aspect 11. The method of aspect 10, wherein the nucleic acid encoding the CasZ polypeptide is a non-naturally sequence that is codon optimized for expression in the target cell.

Aspect 12. The method of any one of aspects 9-11, wherein the target cell is a eukaryotic cell.

Aspect 13. The method of any one of aspects 9-12, wherein the target cell is in culture in vitro.

Aspect 14. The method of any one of aspects 9-12, wherein the target cell is in vivo.

Aspect 15. The method of any one of aspects 9-12, wherein the target cell is ex vivo.

Aspect 16. The method of aspect 12, wherein the eukaryotic cell is selected from the group consisting of: a plant cell, a fungal cell, a single cell eukaryotic organism, a mammalian cell, a reptile cell, an insect cell, an avian cell, a fish cell, a parasite cell, an arthropod cell, an arachnid cell, a cell of an invertebrate, a cell of a vertebrate, a rodent cell, a mouse cell, a rat cell, a primate cell, a non-human primate cell, and a human cell.

Aspect 17. The method of any one of aspects 9-16, wherein said contacting further comprises: introducing a DNA donor template into the target cell.

Aspect 18. The method of any one of aspects 1-17, wherein the method comprises contacting the target nucleic acid with a CasZ transactivating noncoding RNA (trancRNA).

Aspect 19. The method of any one of aspects 9-17, wherein said contacting comprises: introducing a CasZ transactivating noncoding RNA (trancRNA) and/or a nucleic acid encoding the CasZ trancRNA into the target cell.

Aspect 20. The method of aspect 18 or aspect 19, wherein the trancRNA comprises a nucleotide sequence having 70% or more (at least 70%, at least 75%, at least 80%, at least 85%, at least 90%, at least 95%, at least 98%, at least 99%, or 100%) nucleotide sequence identity with a trancRNA sequence of Table 2.

Aspect 21. A composition comprising an engineered and/or non-naturally occurring complex comprising: (a) a CasZ polypeptide, or a nucleic acid encoding said CasZ polypeptide; and (b) a CasZ guide RNA, or a nucleic acid encoding said CasZ guide RNA, wherein said CasZ guide RNA comprises a guide sequence that is complementary to a target sequence of a target nucleic acid, and comprises a region that can bind to the CasZ polypeptide.

Aspect 22. The composition of aspect 21, further comprising a CasZ transactivating noncoding RNA (trancRNA), or a nucleic acid encoding said CasZ trancRNA.

Aspect 23. A kit comprising an engineered and/or non-naturally occurring complex comprising: (a) a CasZ polypeptide, or a nucleic acid encoding said CasZ polypeptide; (b) a CasZ guide RNA, or a nucleic acid encoding said CasZ guide RNA, wherein said CasZ guide RNA comprises a guide sequence that is complementary to a target sequence of a target nucleic acid, and comprises a region that can bind to the CasZ polypeptide.

Aspect 24. The kit of aspect 23, further comprising a CasZ transactivating noncoding RNA (trancRNA), or a nucleic acid encoding said CasZ trancRNA.

Aspect 25. A genetically modified eukaryotic cell, comprising at least one of: (a) a CasZ polypeptide, or a nucleic acid encoding said CasZ polypeptide; (b) a CasZ guide RNA, or a nucleic acid encoding said CasZ guide RNA, wherein said CasZ guide RNA comprises a guide sequence that is complementary to a target sequence of a target nucleic acid, and comprises a region that can bind to the CasZ polypeptide; and (c) a CasZ transactivating noncoding RNA (trancRNA), or a nucleic acid encoding said CasZ trancRNA.

Aspect 26. The composition, kit, or eukaryotic cell of any one of the preceding aspects, characterized by at least one of: (a) the nucleic acid encoding said CasZ polypeptide comprises a nucleotide sequence that: (i) encodes the CasZ polypeptide and, (ii) is operably linked to a heterologous promoter; (b) the nucleic acid encoding said CasZ guide RNA comprises a nucleotide sequence that: (i) encodes the CasZ guide RNA and, (ii) is operably linked to a heterologous promoter; and (c) the nucleic acid encoding said CasZ trancRNA comprises a nucleotide sequence that: (i) encodes the CasZ trancRNA and, (ii) is operably linked to a heterologous promoter.

Aspect 27. The composition, kit, or eukaryotic cell of any one of the preceding aspects, for use in a method of therapeutic treatment of a patient.

Aspect 28. The method, composition, kit, or eukaryotic cell of any one of the preceding aspects, wherein at least one of: the nucleic acid encoding said CasZ polypeptide, the nucleic acid encoding said CasZ guide RNA, and the nucleic acid encoding said CasZ trancRNA, is a recombinant expression vector.

Aspect 29. The method, composition, kit, or eukaryotic cell of any one of the preceding aspects, wherein the CasZ guide RNA and/or the CasZ trancRNA comprises one or more of: a modified nucleobase, a modified backbone or non-natural internucleoside linkage, a modified sugar moiety, a Locked Nucleic Acid, a Peptide Nucleic Acid, and a deoxyribonucleotide.

Aspect 30. The method, composition, kit, or eukaryotic cell of any one of the preceding aspects, wherein the CasZ polypeptide is a variant CasZ polypeptide with reduced nuclease activity compared to a corresponding wild type CasZ protein.

Aspect 31. The method, composition, kit, or eukaryotic cell of any one of the preceding aspects, wherein at least one of: the CasZ polypeptide, the nucleic acid encoding the CasZ polypeptide, the CasZ guide RNA, the nucleic acid encoding the CasZ guide RNA, the CasZ trancRNA, and the nucleic acid encoding the CasZ trancRNA; is conjugated to a heterologous moiety.

Aspect 32. The method, composition, kit, or eukaryotic cell of aspect 31, wherein the heterologous moiety is a heterologous polypeptide.

Aspect 33. The method, composition, kit, or eukaryotic cell of any one of the preceding aspects, wherein the CasZ polypeptide has reduced nuclease activity compared to a corresponding wild type CasZ protein, and is fused to a heterologous polypeptide.

Aspect 34. The method, composition, kit, or eukaryotic cell of aspect 33, wherein the heterologous polypeptide: (i) has DNA modifying activity, (ii) exhibits the ability to increase or decrease transcription, and/or (iii) has enzymatic activity that modifies a polypeptide associated with DNA.

Aspect 35. The method, composition, kit, or eukaryotic cell of any one of the preceding aspects, wherein the CasZ polypeptide comprises an amino acid sequence having 70% or more (at least 70%, at least 75%, at least 80%, at least 85%, at least 90%, at least 95%, at least 98%, at least 99%, or 100%) amino acid sequence identity with a CasZ protein of FIG. 1 or FIG. 7.

Aspect 36. The method, composition, kit, or eukaryotic cell of any one of the preceding aspects, wherein the guide sequence and the region that binds to the CasZ polypeptide are heterologous to one another.

Aspect 37. A method of detecting a target DNA in a sample, the method comprising: (a) contacting the sample with: (i) a CasZ polypeptide; (ii) a guide RNA comprising: a region that binds to the CasZ polypeptide, and a guide sequence that hybridizes with the target DNA; and (iii) a detector DNA that is single stranded and does not hybridize with the guide sequence of the guide RNA; and (b) measuring a detectable signal produced by cleavage of the single stranded detector DNA by the CasZ, thereby detecting the target DNA.

Aspect 38. The method of aspect 37, wherein the target DNA is single stranded.

Aspect 39. The method of aspect 37 or 38, wherein the target DNA is double stranded.

Aspect 40. The method of any one of aspects 37-39, wherein the target DNA is viral DNA.

Aspect 41. The method of any one of aspects 37-40, wherein the target DNA is papovavirus, hepdnavirus, herpesvirus, adenovirus, poxvirus, or parvovirus DNA.

Aspect 42. The method of any one of aspects 37-41, wherein the CasZ polypeptide comprises an amino acid sequence having at least 85% amino acid sequence identity to the CasZ amino acid sequence set forth in any one of FIGS. 1 and 7.

Aspect 43. The method of any one of aspects 37-41, wherein the CasZ polypeptide is a Cas14a polypeptide.

Aspect 44. The method according to any one of aspects 37-43, wherein the sample comprises DNA molecules from a cell lysate.

Aspect 45. The method according to any one of aspects 37-44, wherein the sample comprises cells.

Aspect 46. The method according to any one of aspects 37-45, wherein said contacting is carried out inside of a cell in vitro, ex vivo, or in vivo.

Aspect 47. The method according to aspect 46, wherein the cell is a eukaryotic cell.

Aspect 48. The method according to any one of aspects 37-47, wherein the target DNA can be detected at a concentration as low as 10 aM.

Aspect 49. The method according to any one of aspects 37-48, comprising determining an amount of the target DNA present in the sample.

Aspect 50. The method according to aspect 49, wherein said determining comprises: measuring the detectable signal to generate a test measurement; measuring a detectable signal produced by a reference sample or cell to generate a reference measurement; and comparing the test measurement to the reference measurement to determine an amount of target DNA present in the sample.

Aspect 51. The method according to any one of aspects 37-50, wherein measuring a detectable signal comprises one or more of: gold nanoparticle based detection, fluorescence polarization, colloid phase transition/dispersion, electrochemical detection, and semiconductor-based sensing.

Aspect 52. The method according to any one of aspects 37-51, wherein the single stranded detector DNA comprises a fluorescence-emitting dye pair.

Aspect 53. The method according to aspect 52, wherein the fluorescence-emitting dye pair produces an amount of detectable signal prior to cleavage of the single stranded detector DNA, and the amount of detectable signal is reduced after cleavage of the single stranded detector DNA.

Aspect 54. The method according to aspect 52, wherein the single stranded detector DNA produces a first detectable signal prior to being cleaved and a second detectable signal after cleavage of the single stranded detector DNA.

Aspect 55. The method according to any one of aspects 52-54, wherein the fluorescence-emitting dye pair is a fluorescence resonance energy transfer (FRET) pair.

Aspect 56. The method according to aspect 18, wherein an amount of detectable signal increases after cleavage of the single stranded detector DNA.

Aspect 57. The method according to aspect 52 or aspect 56, wherein the fluorescence-emitting dye pair is a quencher/fluor pair.

Aspect 58. The method according to any one of aspects 52-57, wherein the single stranded detector DNA comprises two or more fluorescence-emitting dye pairs.

Aspect 59. The method according to aspect 58, wherein said two or more fluorescence-emitting dye pairs include a fluorescence resonance energy transfer (FRET) pair and a quencher/fluor pair.

Aspect 60. The method according to any one of aspects 37-59, wherein the single stranded detector DNA comprises a modified nucleobase, a modified sugar moiety, and/or a modified nucleic acid linkage.

Aspect 61. The method according to any one of aspects 37-60, wherein the method comprises amplifying nucleic acids in the sample.

Aspect 62. The method according to aspect 61, wherein said amplifying comprises isothermal amplification.

Aspect 63. The method according to aspect 62, wherein the isothermal amplification comprises recombinase polymerase amplification (RPA).

Aspect 64. The method according to any one of aspects 61-63, wherein said amplifying begins prior to the contacting of step (a).

Aspect 65. The method according to any one of aspects 61-63, wherein said amplifying begins together with the contacting of step (a).

Aspect 66. A kit for detecting a target DNA in a sample, the kit comprising: (a) a guide RNA, or a nucleic acid encoding the guide RNA; wherein the guide RNA comprises: a region that binds to a CasZ polypeptide, and a guide sequence that is complementary to a target DNA; and (b) a labeled detector DNA that is single stranded and does not hybridize with the guide sequence of the guide RNA.

Aspect 67. The kit of aspect 66, further comprising a CasZ polypeptide.

Aspect 68. The kit of aspect 67, wherein the CasZ polypeptide comprises an amino acid sequence having at least 85% amino acid sequence identity to the CasZ amino acid sequence set forth in any one of FIGS. 1 and 7.

Aspect 69. The kit of aspect 67, wherein the CasZ polypeptide is a Cas14a polypeptide.

Aspect 70. The kit of any one of aspects 66-69, wherein the single stranded detector DNA comprises a fluorescence-emitting dye pair.

Aspect 71. The kit of aspect 70, wherein the fluorescence-emitting dye pair is a FRET pair.

Aspect 72. The kit of aspect 70, wherein the fluorescence-emitting dye pair is a quencher/fluor pair.

Aspect 73. The kit of any one of aspects 70-72, wherein the single stranded detector DNA comprises two or more fluorescence-emitting dye pairs.

Aspect 74. The kit of aspect 73, wherein said two or more fluorescence-emitting dye pairs include a first fluorescence-emitting dye pair that produces a first detectable signal and a second fluorescence-emitting dye pair that produces a second detectable signal.

Aspect 75. The kit of any one of aspects 66-74, further comprising nucleic acid amplification components.

Aspect 76. The kit of aspect 75, wherein the nucleic acid amplification components are components for recombinase polymerase amplification (RPA).

Aspect 77. A method of cleaving single stranded DNAs (ssDNAs), the method comprising: contacting a population of nucleic acids, wherein said population comprises a target DNA and a plurality of non-target ssDNAs, with: (i) a CasZ polypeptide; and (ii) a guide RNA comprising: a region that binds to the CasZ polypeptide, and a guide sequence that hybridizes with the target DNA, wherein the CasZ polypeptide cleaves non-target ssDNAs of said plurality.

Aspect 78. The method of aspect 77, wherein said contacting is inside of a cell in vitro, ex vivo, or in vivo.

Aspect 79. The method of aspect 78, wherein the cell is a eukaryotic cell.

Aspect 80. The method of aspect 79, wherein the eukaryotic cell is a plant cell.

Aspect 81. The method of any one of aspects 78-80, wherein the non-target ssDNAs are foreign to the cell.

Aspect 82. The method of aspect 81, wherein the non-target ssDNAs are viral DNAs.

Aspect 83. The method of any one of aspects 77-82, wherein the target DNA is single stranded.

Aspect 84. The method of any one of aspects 77-82, wherein the target DNA is double stranded.

Aspect 85. The method of any one of aspects 77-84, wherein the target DNA is viral DNA.

Aspect 86. The method of any one of aspects 77-84, wherein the target DNA is papovavirus, hepdnavirus, herpesvirus, adenovirus, poxvirus, or parvovirus DNA.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Materials and Methods

The following materials and methods generally apply to the results presented in the Examples described herein except where noted otherwise.

Metagenomics and Metatranscriptomics

The initial analysis was performed on previously assembled and binned metagenomes from two sites: the Rifle Integrated Field Research (IFRC) site, adjacent to the Colorado River near Rifle, Colorado and Crystal Geyser, a cold, $CO_2$-driven geyser on the Colorado Plateau in Utah. Metatranscriptomic data from IFRC site was used to detect transcription of non-coding elements in nature. Further mining of CRISPR-Cas14 systems was then performed on public metagenomes from IMG/M.

CRISPR-Cas Computation Analysis

The assembled contigs from the various samples were scanned with the HMMer suite for known Cas proteins using Hidden Markov Model (HMMs) profiles. Additional HMMs were constructed for Cas14 proteins based on the MAFFT alignments of putative type V effectors that contained less than 800 aa, and were adjacent to acquisition cas genes and CRISPR arrays. These HMMs were iteratively refined by augmenting them with manually selected novel putative Cas14 sequences that were found using the existing Cas14 HMM models. The sequence of Cas14 repeat sequences are provided in Table 3. CRISPR arrays were identified using a local version of the CrisprFinder software and CRISPRDetect. Phylogenetic trees of Cas1 and type V effector proteins were constructed using RAxML with PROTGAMMALG as the substitution model and 100 bootstrap samplings. Trees were visualized using FigTree 1.4.1 (http://tree.bio.ed.ac.uk/software/figtree/). Metatranscriptomic reads were mapped to assembled contigs using Bowtie2. RNase presence analysis was based on HMMs that were built from alignment of KEGG orthologous groups (KOs) downloaded from KEGG database.

TABLE 3

Repeat sequences (non-guide sequence portion of a Cas14 guide RNA) of all Cas14 proteins used herein (e.g., see FIG. 7) are shown in Table 3.

| Cas14 Protein | Repeat sequence | SEQ ID NO: | Scaffold Accession No: |
|---|---|---|---|
| Cas14a.1 (CasZa.3) | GTTGCAGAACCCGAATAGACGAATGAAGGAATGCAAC | 53 | NCBI: MK005734 |
| Cas14a.2 (Za.8) | CTTGCAGAACCCGGATAGACGAATGAAGGAATGCAAC | 295 | NCBI: MK005733 |
| Cas14a.3 (CasZa.3) | GTTGCAGAACCCGAATAGACGAATGAAGGAATGCAAC | 53 | NCBI: MK005732 |
| Cas14a.4 (CasZa.4) | CTATCATATTCAGAACAAAGGGATTAAGGAATGCAAC | 54 | NCBI: MK005735 |
| Cas14a.5 (CasZa.5, CasZb.3) | CTTTCATACTCAGAACAAAGGGATTAAGGAATGCAAC | 55 | NCBI: MK005736 |
| Cas14a.6 (CasZa.6) | GTCTACAACTCATTGATAGAAATCAATGAGTTAGACA | 56 | IMG/M: Ga0137385_10000156 |
| Cas14b.1 (Cas Zb.2) | GTTGCAGAAATAGAATAAAGGAATTAAGGAATGCAAC | 59 | NCBI: MK005737 |
| Cas14b.2 (CasZa.5, CasZb.3) | CTTTCATACTCAGAACAAAGGGATTAAGGAATGCAAC | 55 | NCBI: MK005738 |
| Cas14b.3 (CasZb.4) | ATTTCATACTCAGAACAAAGGGATTAAGGAATGCAAC | 61 | NCBI: MK005739 |
| Cas14b.4 (CasZb.16) | GTTTCAGCGCACGAATTAACGAGATGAGAGATGCAAC | 303 | NCBI: MK005740 |
| Cas14b.5 (CasZb.6) | CTTGCAGAAGCTGAATAGACGAATCAAGGAATGCAAC | 63 | NCBI: MK005741 |

TABLE 3-continued

Repeat sequences (non-guide sequence portion of a
Cas14 guide RNA) of all Cas14 proteins used herein
(e.g., see FIG. 7) are shown in Table 3.

| Cas14 Protein | Repeat sequence | SEQ ID NO: | Scaffold Accession No: |
|---|---|---|---|
| Cas14b.6 (Za.12) | CTTGCAGGCCTTGAATAGAGGAGTTAAGGAATGCAAC | 296 | NCBI: MK005742 |
| Cas14b.7 (CasZb.9) | GTTGCAGCGCCCGAACTGACGAGACGAGAGATGCAAC | 66 | IMG/M: Ga0172369_10000737 |
| Cas14b.8 (CasZb.10) | GTTGCGCGAATAGAATAAAGGAATTAAGGAATGCAAC | 67 | IMG/M: Ga0172369_10010464 |
| Cas14b.9 (CasZb.11) | AGTTGCATTCCTTAATCCCTCTGTTCAGTTTGTGCAAT | 68 | IMG/M: Ga0172365_10004421 |
| Cas14b.10 (Zb.13) | GTTGCACAGTGCTAATTAGAGAAACTAGGAATGCAAC | 297 | NCBI: MK005743 |
| Cas14b.11 (CasZc.2) | GTTGCGGCGCGCGAATAAACGAGACTAGGAATGCAAC | 70 | NCBI: MK005744 |
| Cas14b.12 (Zb.14) | CTAGCATATTCAGAACAAAGGGATTAAGGAATGCAAC | 298 | NCBI: MK005745 |
| Cas14b.13 (CasZc.4) | CTTTCATATTCAGAACAAAGGGATTAAGGAATGCAAC | 72 | NCBI: MK005746 |
| Cas14b.14 (Zb.15) | CTTTCATATTCAGAAACTAGGGGTTAAGGACTGCAAC | 299 | NCBI: MK005747 |
| Cas14b.15 (CasZc.6) | GTTGCAGCCCCCGAACTAACGAGATGAGAGATGCAAC | 74 | IMG/M: Ga0116204_1008574 |
| Cas14b.16 (casZc.7) | CTTGCAGAACAATCATATATGACTAATCAGACTGCAAC | 75 | IMG/M: Ga0078972_1001015a |
| Cas14c.1 (Zb.8) | GTTGCATCCCTACGTCGTGAGCACCGGTGAGTGCAAC | 300 | NCBI: MK005748 |
| Cas14c.2 (CasZd.2) | GTCCCTACTCGCTAGGGAAACTAATTGAATGGAAAC | 77 | IMG/M: JGI12048J13642_10201286 |
| Cas14d.1 (CasZe.2) | CTTCCAAACTCGAGCCAGTGGGGAGAGAAGTGGCA | 79 | NCBI: MK005750 |
| Cas14d.2 (CasZe.3) | CCTGTAGACCGGTCTCATTCTGAGAGGGGTATGCAACT | 80 | NCBI: MK005751 |
| Cas14d.3 (CasZe.4) | GTCTCGAGACCCTACAGATTTTGGAGAGGGGTGGGAC | 81 | NCBI: MK005752 |
| Cas14e.1 (CasZf.1) | GTAGCAGGACTCTCCTCGAGAGAAACAGGGGTATGCT | 83 | NCBI: MK005753 |
| Cas14e.2 (CasZf.2) | GTACAATACCTCTCCTTTAAGAGAGGGAGGGGTACGCTAC | 84 | NCBI: MK005754 |
| Cas14e.3 (Zc.5) | GGAAAGGAATCCCCTGAAGGAAACGAGGGGG | 301 | NCBI: MK005755 |
| Cas14f.1 (CasZg.1) | GGTTCCCCCGGGCGCGGGTGGGGTGGCG | 86 | NCBI: MK005756 |
| Cas14f.2 (CasZg.2) | GGCTGCTCCGGGTGCGCGTGGAGCGAGG | 87 | IMG/M: Ga0105042_100140 |

TABLE 3-continued

Repeat sequences (non-guide sequence portion of a Cas14 guide RNA) of all Cas14 proteins used herein (e.g., see FIG. 7) are shown in Table 3.

| Cas14 Protein | Repeat sequence | SEQ ID NO: | Scaffold Accession No: |
|---|---|---|---|
| Cas14g.1 (Ze.3) | GTGTCCATCAATCAGATTTGCGTTGGCCGGTGCAAT | 302 | NCBI: MK005758 |
| Cas14g.2 (CasZi.2) | GCCGCAGCGGCCGACGCGGCCCTGATCGATGGACAC | 90 | IMG/M: Ga0123330_1010394 |
| Cas14h.1 (CasZk.1) | GGCTAGCCCGTGCGCGCAGGGACGAGTGG | 92 | IMG/M: Ga0070762_10001740 |
| Cas14h.2 (CasZk.2) | GCCCGTGCGCGCAGGGACGAGTGG | 93 | IMG/M: Ga0070766_10011912 |
| Cas14h.3 (CasZk.4) | CCATCGCCCCGCGCGCACGTGGATGAGCC | 95 | IMG/M: Ga0116216_10000905 |
| Cas14u.1 (CasZa.7) | GTTATAAAGGCGGGGATCGCGACCGAGCGATTGAAAG | 57 | IMG/M: Ga0066793_10010091 |
| Cas14u.2 (CasZb.8) | GTCTCCATGACTGAAAAGTCGTGGCCGAATTGAAAC | 65 | IMG/M: JGI24730J26740_1002785 |
| Cas14u.3 (CasZe.1) | GTTGCATTCGGGTGCAAAACAGGGAGTAGAGTGTAAC | 78 | NCBI: MK005749 |
| Cas14u.4 (CasZj.2) | CTTTTAGACAGTTTAAATTCTAAAGGGTATAAAAC | 307 | NCBI: MK005757 |
| Cas14u.5 (CasZj.1) | GTCGAAATGCCCGCGCGGGGCGTCGTACCCGCGAC | 308 | IMG/M: Ga0137373_10000316 |
| Cas14u.6 (CasZk.3) | GTTGCAGCGGCCGACGGAGCGCGAGCGTGGATGCCAC | 309 | IMG/M: Ga0070717_10000077 |
| Cas14u.7 (CasZl.1) | CTTTAGACTTCTCCGGAAGTCGAATTAATGGAAAC | 310 | IMG/M: JGI12210 IMG/M: J13797_10004690 |
| Cas14u.8 (CasZl.2) | GGGCGCCCCGCGCGAGCGGGGTTGAAG | 311 | IMG/M: Ga0073904_10021651 |

Generation of Expression Plasmids, RNA and DNA Substrates

Minimal CRISPR loci for putative systems were designed by removing acquisition proteins and generating minimal arrays with a single spacer. These minimal loci were ordered as gBlocks (IDT) and assembled into a plasmid with a tetracycline inducible promoter driving expression of the locus. Plasmid maps were available on Addgene and in the figures. All RNA was in vitro transcribed using T7 polymerase and PCR products as dsDNA template. Resulting IVTs were gel extracted and ethanol precipitated. DNA substrates were obtained from IDT and their sequences are available in Table 4. For radiolabeled cleavage assays DNA oligos were gel extracted from a PAGE gel before radiolabeling. For FQ assays, DNA substrates were used without further purification.

E. coli RNAseq

Small RNA sequencing was conducted as described previously with modification in Harrington et al. (2017). E. coli NEB Stable3 was transformed with a plasmid expressing Cas14a1 system with a tetracycline inducible promoter upstream of the Cas14a1 ORF or the same plasmid with an N-terminal 10x-histidine tag fused to Cas14. Starters were grown up overnight in SOB, diluted 1:100 in 5 mL fresh SOB containing 214 nM anhydrotetracycline and grown up overnight at 25° C. For sequencing of RNA pulled down with Cas14a, the plasmid containing an N-terminal His-tag fused to Cas14a1 was grown up at 18° C. before lysis and purification as described in "Protein purification", stopping after the Ni-NTA elution. Cells were pelleted and RNA was extracted using hot phenol as previously described. Total nucleic acids were treated with TURBO DNase and phenol extracted. The resulting RNA was treated with rSAP which was heat inactivated before addition of T4 PNK. Adapters were ligated onto the small RNA using the NEBnext small RNA kit and gel-extracted on an 8% native PAGE gel. RNA was sequenced on a MiSeq with single end 300 bp reads. For analysis, the resulting reads were trimmed using Cutadapt, discarding sequences<8 nt and mapped to the plasmid reference using Bowtie2.

PAM Depletion Assays

PAM depletion assays were conducted as previously described in Burstein et al. (2017). Randomized plasmid libraries were generated using a primer containing a randomized PAM region adjacent to the target sequence. The randomized primers were hybridized with a primer that was complementary to the 3' end of the primer and the duplex was extended using Klenow Fragment (NEB). The dsDNA containing the target and were digested with EcoRI and NcoI, ligated into pUC19 backbone and transformed into *E. coli* DH5α and >107 cells were harvested. Next *E. coli* NEBstable was transformed with either a CRISPR plasmid or an empty vector control and these transformed *E. coli* were made electrocompetent by repeated washing with 10% glycerol. These electrocompetent cells were transformed with 200 ng of the target library and plated on bioassay dishes containing selection for the target (carbenicillin, 100 mg 1-1) and CRISPR plasmid (chloramphenicol, 30 mg 1-1). Cells were harvested and prepared for amplicon sequencing on an Illumina MiSeq. The PAM region was extracted using Cutadapt and depletion values were calculated in python. PAMs were visualized using WebLogo.

Transcriptomic RNA Mapping

RNA was extracted from 0.2 mm filters using the Invitrogen TRIzol reagent, followed by genomic DNA removal and cleaning using the Qiagen RNase-Free DNase Set kit and the Qiagen Mini RNeasy kit. An Agilent 2100 Bioanalyzer (Agilent Technologies) was used to assess the integrity of the RNA samples. The Applied Biosystems SOLiD Total RNA-Seq kit was used to generate the cDNA template library. The SOLiD EZ Bead system (Life Technologies) was used to perform emulsion clonal bead amplification to generate bead templates for SOLiD platform sequencing. Samples were sequenced at Pacific Northwest National Laboratory on the 5500XL SOLiD platform. The 50 bp single reads were trimmed using Sickle as in Brown et al. (2015).

Protein Purification

Cas14a1 was purified as described previously with modification. *E. coli* BL21(DE3) RIL were transformed with 10×His-MBP-Cas14a1 expression plasmid and grown up to OD600=0.5 in Terrific Broth (TB) and induced with 0.5 mM IPTG. Cells were grown overnight at 18° C., collected by centrifugation, resuspended in Lysis Buffer (50 mM Tris-HCl, pH 7.5, 20 mM imidazole, 0.5 mM TCEP, 500 mM NaCl) and broken by sonication. Lysate was batch loaded on to Ni-NTA resin, washed with the above buffer before elution with Elution Buffer (50 mM Tris-HCl, pH 7.5, 300 mM imidazole, 0.5 mM TCEP, 500 mM NaCl). The MBP and His-tag were removed by overnight incubation with TEV at 4° C. The resulting protein exchanged into Buffer A (20 mM HEPES, pH 7.5, 0.5 mM TCEP, 150 mM NaCl) and loaded over tandem MBP, heparin columns (GE, Hi-Trap) and eluted with a linear gradient from Buffer A to Buffer B (20 mM HEPES, pH 7.5, 0.5 mM TCEP, 1250 mM NaCl). The resulting fractions containing Cas14a1 were loaded onto an 5200 gel filtration column, flash frozen and stored at −80° C. until use.

In Vitro Cleavage Assays

Radiolabeled

Radiolabeled cleavage assays were conducted in 1× Cleavage Buffer (25 mM NaCl, 20 mM HEPES, pH 7.5, 1 mM DTT, 5% glycerol). 100 nM Cas14a1 was complexed with 125 nM crRNA and 125 nM tracrRNA for 10 min at RT. ~1 nM radiolabeled DNA or RNA substrate was added and allowed to react for 30 min at 37° C. The reaction was stopped by adding 2× Quench Buffer (90% formamide, 25 mM EDTA and trace bromophenol blue), heated to 95° C. for 2 min and run on a 10% polyacrylamide gel containing 7M Urea and 0.5×TBE. Products were visualized by phosphorimaging.

M13 DNA Cleavage

M13 DNA cleavage assays were conducted in 100 mM NaCl, 20 mM HEPES, pH 7.5, 1 mM DTT, 5% glycerol. 250 nM Cas14a1 was complexed with 250 nM crRNA and 250 nM tracrRNA and 250 nM ssDNA activator. The reaction was initiated by addition of 5 nM M13 ssDNA plasmid and was quenched by addition of loading buffer supplemented with 10 mM EDTA. Products were separated on a 1.5% agarose TAE gel prestained with SYBR gold (Thermofisher).

FQ Detection of Trans-Cleavage

FQ detection was conducted as previously described in Chen et al. (2018) with modification. 100 nM Cas14a1 was complexed with 125 nM crRNA, 125 nM tracrRNA, 50 nM FQ probe and 2 nM ssDNA activator in 1× Cleavage Buffer at 37° C. for 10 min. The reaction was then initiated by addition of activator DNA when for all reactions except for the RNA optimization experiments where the variable RNA component was used to initiate. The reaction was monitored in a fluorescence plate reader for up to 120 minutes at 37° C. with fluorescence measurements taken every 1 min (λex: 485 nm; λem: 535 nm). The resulting data were background subtracted using the readings taken in the absence of activator and fit using a single exponential decay curve.

Data Availability

Plasmids used herein are available on Addgene (plasmid numbers 112500, 112501, 112502, 112503, 112504, 112505, 112506). Oligonucleotides used herein are provided in Table 4 and Table 5. The plasmids used herein are provided in FIG. 24. The Cas14 protein sequences used herein are provided in FIG. 7.

TABLE 4

Oligonucleotides and plasmids used herein.

| DNA Name | Sequence | SEQ ID NO: |
|---|---|---|
| Radiolabeld DNA activator 1 T strand | cTACGCCGattatcttctgacaactttcgcaagcggtgtaaggtaAAAAAtgCGGGCAC | 220 |

TABLE 4-continued

Oligonucleotides and plasmids used herein.

| DNA Name | Sequence | SEQ ID NO: |
| --- | --- | --- |
| Radiolabeld DNA activator 1 NT strand | GTGCCCGcaTTTTTtaccttacaccgcttgcgaaagttgtcagaagataatCGGCGTAg | 221 |
| Radiolabeld DNA activator 2 T strand | tttatatgtttctcctggagataacgcaatcgtgacaactttcgcaagcggtgtaaggtaGCAGGCTTCcgaattccgcgttttttacggc | 222 |
| Radiolabeld DNA activator 2 NT strand | gccgtaaaaacgcggaattcgGAAGCCTGCtaccttacaccgcttgcgaaagttgtcacgattgcgttatctccaggagaaacatataaa | 223 |
| Radiolabeld Activator 3 | gatcttcagcTATACATTATTGCACCAACACTAAGGCAGAGTATGtttacctggac | 224 |
| Radiolabeld Activator 4 | gatcttcagcTTTGTATTACTGGAAGGATGCTTGCTTGAGGTGTAaaaacctggac | 225 |
| F-Q 5 nt | /56-FAM/TTTTT/3IABkFQ/ | 226 |
| F-Q 6 nt | /56-FAM/TTTTTT/3IABkFQ/ | 227 |
| F-Q 7 nt | /56-FAM/TTTTTTT/3IABkFQ/ | 228 |
| F-Q 8 nt | /56-FAM/TTTTTTTT/3IABkFQ/ | 229 |
| F-Q 9 nt | /56-FAM/TTTTTTTTT/3IABkFQ/ | 230 |
| F-Q 10 nt | /56-FAM/TTTTTTTTTT/3IABkFQ/ | 231 |
| F-Q 11 nt | /56-FAM/TTTTTTTTTTT/3IABkFQ/ | 232 |
| F-Q 12 nt | /56-FAM/TTTTTTTTTTTT/3IABkFQ/ | 233 |
| F-Q 10 nt A/T | /56-FAM/TATATATATA/3IABkFQ/ | 371 |
| F-Q 6 nt A/T | /56-FAM/TATATA/3IABkFQ/ | 372 |
| F-Q 5 nt A/T | /56-FAM/TATAT/3IABkFQ/ | 373 |
| Target 2, Perfect AAAT 3' | GCCGGGGTGGTGCCCATCCTGGTCGAGCTGGACGGCGACGTAAACGGCCACAAGC | 234 |
| Target 2, Perfect TCGT 3' | GCCGGGGTGGTGCCCATCCTGGTCGAGCTGGACGGCGACGTGCTCGGCCACAAGC | 235 |
| Target 2, 1-2MM | GCCGGGGTGGTGCCCATCCTGGTCGAGCTGGACGGCGAGCTAAACGGCCACAAGC | 236 |
| Target 2, 3-4MM | GCCGGGGTGGTGCCCATCCTGGTCGAGCTGGACGGCCTCGTAAACGGCCACAAGC | 237 |
| Target 2, 5-6MM | GCCGGGGTGGTGCCCATCCTGGTCGAGCTGGACGCGGACGTAAACGGCCACAAGC | 238 |
| Target 2, 7-8MM | GCCGGGGTGGTGCCCATCCTGGTCGAGCTGGAGCGCGACGTAAACGGCCACAAGC | 239 |
| Target 2, 9-10MM | GCCGGGGTGGTGCCCATCCTGGTCGAGCTGCTCGGCGACGTAAACGGCCACAAGC | 240 |
| Target 2, 11-12MM | GCCGGGGTGGTGCCCATCCTGGTCGAGCACGACGGCGACGTAAACGGCCACAAGC | 241 |
| Target 2, 13-14MM | GCCGGGGTGGTGCCCATCCTGGTCGACGTGGACGGCGACGTAAACGGCCACAAGC | 242 |

TABLE 4-continued

Oligonucleotides and plasmids used herein.

| DNA Name | Sequence | SEQ ID NO: |
|---|---|---|
| Target 2, 15-16MM | GCCGGGGTGGTGCCCATCCTGGTCCTGCTGGACGGCGACGTAAACGGCCACAAGC | 243 |
| Target 2, 17-18MM | GCCGGGGTGGTGCCCATCCTGGAGGAGCTGGACGGCGACGTAAACGGCCACAAGC | 244 |
| Target 2, 19-20MM | GCCGGGGTGGTGCCCATCCTCCTCGAGCTGGACGGCGACGTAAACGGCCACAAGC | 245 |
| HERC2 Amp Fwd | G*T*G*T*TAATACAAAGGTACAGGAACAAAGAATTTG | 246 |
| HERC2 Amp Rev | CAAAGAGAAGCCTCGGCC | 247 |
| Target 1, Perfect AAAT 3' | TTTATTCAAGGCAATCACTATCAGCTGTGGAACACCCAGGTAAACTAACACAACT | 248 |
| Target 1, Perfect TCGT 3' | TTTATTCAAGGCAATCACTATCAGCTGTGGAACACCCAGGTGCTCTAACACAACT | 249 |
| Target 1, 1-2MM | TTTATTCAAGGCAATCACTATCAGCTGTGGAACACCCACCTAAACTAACACAACT | 250 |
| Target 1, 3-4MM | TTTATTCAAGGCAATCACTATCAGCTGTGGAACACCGTGGTAAACTAACACAACT | 251 |
| Target 1, 5-6MM | TTTATTCAAGGCAATCACTATCAGCTGTGGAACAGGCAGGTAAACTAACACAACT | 252 |
| Target 1, 7-8MM | TTTATTCAAGGCAATCACTATCAGCTGTGGAAGTCCCAGGTAAACTAACACAACT | 253 |
| Target 1, 9-10MM | TTTATTCAAGGCAATCACTATCAGCTGTGGTTCACCCAGGTAAACTAACACAACT | 254 |
| Target 1, 11-12MM | TTTATTCAAGGCAATCACTATCAGCTGTCCAACACCCAGGTAAACTAACACAACT | 255 |
| Target 1, 13-14MM | TTTATTCAAGGCAATCACTATCAGCTCAGGAACACCCAGGTAAACTAACACAACT | 256 |
| Target 1, 15-16MM | TTTATTCAAGGCAATCACTATCAGGAGTGGAACACCCAGGTAAACTAACACAACT | 257 |
| Target 1, 17-18MM | TTTATTCAAGGCAATCACTATCTCCTGTGGAACACCCAGGTAAACTAACACAACT | 258 |
| Target 1, 19-20MM | TTTATTCAAGGCAATCACTAAGAGCTGTGGAACACCCAGGTAAACTAACACAACT | 259 |
| Target 3, Perfect | cTACGCCGattatcttctgacaactttcgcaagcggtgtaaggtaAAAAAtgCGGGCAC | 220 |
| Target 3, 1-2MM | cTACGCCGattatcttctgacaactttcgcaagcggtgtaaggCGAAAAAtgCGGGCAC | 260 |
| Target 3, 3-4MM | cTACGCCGattatcttctgacaactttcgcaagcggtgtaaAAtaAAAAAtgCGGGCAC | 261 |
| Target 3, 5-6MM | cTACGCCGattatcttctgacaactttcgcaagcggtgtGGgtaAAAAAtgCGGGCAC | 262 |
| Target 3, 7-8MM | cTACGCCGattatcttctgacaactttcgcaagcggtACaaggtaAAAAAtgCGGGCAC | 263 |
| Target 3, 9-10MM | cTACGCCGattatcttctgacaactttcgcaagcgACgtaaggtaAAAAAtgCGGGCAC | 264 |
| Target 3, 11-12MM | cTACGCCGattatcttctgacaactttcgcaagTAgtgtaaggtaAAAAAtgCGGGCAC | 265 |

TABLE 4-continued

Oligonucleotides and plasmids used herein.

| DNA Name | Sequence | SEQ ID NO: |
|---|---|---|
| Target 3, 13-14MM | cTACGCCGattatcttctgacaactttcgcaGAcggtgtaaggtaAAAAAtgCGGGCAC | 266 |
| Target 3, 15-16MM | cTACGCCGattatcttctgacaactttcgTGagcggtgtaaggtaAAAAAtgCGGGCAC | 267 |
| Target 3, 17-18MM | cTACGCCGattatcttctgacaactttTAcaagcggtgtaaggtaAAAAAtgCGGGCAC | 268 |
| Target 3, 19-20MM | cTACGCCGattatcttctgacaactCCcgcaagcggtgtaaggtaAAAAAtgCGGGCAC | 269 |
| Target 3, 21-22MM | cTACGCCGattatcttctgacaaTCttcgcaagcggtgtaaggtaAAAAAtgCGGGCAC | 270 |
| Target 3, 23-24MM | cTACGCCGattatcttctgacGGctttcgcaagcggtgtaaggtaAAAAAtgCGGGCAC | 271 |
| Target 3, 25-26MM | cTACGCCGattatcttctgGTaactttcgcaagcggtgtaaggtaAAAAAtgCGGGCAC | 272 |
| Full Length Activator | cTACGCCGattatcttctgacaactttcgcaagcggtgtaaggtaAAAAAtgCGGGCAC | 220 |
| -20 5' activator target | tatcttctgacaactttcgcaagcggtgtaaggtaAAAAAtgCGGGCAC | 273 |
| -25 5' activator target | tctgacaactttcgcaagcggtgtaaggtaAAAAAtgCGGGCAC | 274 |
| -30 5' activator target | caactttcgcaagcggtgtaaggtaAAAAAtgCGGGCAC | 275 |
| -35 5' activator target | ttcgcaagcggtgtaaggtaAAAAAtgCGGGCAC | 276 |
| -5 3' activator target | cTACGCCGattatcttctgacaactttcgcaagcggtgtaaggtaAAAAAtgCG | 277 |
| -9 3' activator target | cTACGCCGattatcttctgacaactttcgcaagcggtgtaaggtaAAAA | 278 |
| -14 3' activator target | cTACGCCGattatcttctgacaactttcgcaagcggtgta | 279 |
| -19 3' activator target | cTACGCCGattatcttctgacaactttcgcaagcg | 280 |
| -24 3' activator target | cTACGCCGattatcttctgacaactttcgc | 281 |
| -29 3' activator target | cTACGCCGattatcttctgacaact | 282 |
| -34 3' activator target | cTACGCCGattatcttctga | 283 |
| No loop | caactttcgcaagcggtgtaaggtaAAAAAtgCG | 284 |
| 0 nt SL | atggaatgtggcgaacgctttcaacGAAcaactttcgcaagcggtgtaaggtaAAAAAtgCG | 285 |
| 5 nt SL | atggaatgtggcgaacgcttagttgGAAAcaactttcgcaagcggtgtaaggtaAAAAAtgCG | 286 |

TABLE 4-continued

Oligonucleotides and plasmids used herein.

| DNA Name | Sequence | SEQ ID NO: |
|---|---|---|
| 10 nt SL | atggaatgtggcgaagcgaaagttgGAAAcaactttcgcaagcggtgtaaggtaAAAAAtgCG | 287 |
| 15 nt SL | atggaatgtgcgcttgcgaaagttgGAAAcaactttcgcaagcggtgtaaggtaAAAAAtgCG | 288 |
| 20 nt SL | atggatacaccgcttgcgaaagttgGAAAcaactttcgcaagcggtgtaaggtaAAAAAtgCG | 289 |
| 25 nt SL | taccttacaccgcttgcgaaagttgGAAAcaactttcgcaagcggtgtaaggtaAAAAAtgCG | 290 |
| M13_1 Oligo | GTTTTATCTTCTGCTGGTGGTTCGTTCGGTATTTTTAATG | 291 |
| M13_2 Oligo | CATTAAAAATACCGAACGAACCACCAGCAGAAGATAAAAC | 292 |
| M13_3 Oligo | GACCATTTGCGAAATGTATCTAATGGTCAAACTAAATCTACTC | 293 |
| M13_4 Oligo | GAGTAGATTTAGTTTGACCATTAGATACATTTCGCAAATGGTC | 294 |

TABLE 5

RNA Oligonucleotides.

| RNA Name | Sequence | SEQ ID NO: |
|---|---|---|
| ssRNA target | cTACGCCGattatcttctgacaactttcgcaagcggtgtaaggtaAAAAAtgCGGGCACcc | 332 |
| crRNA | GGAATGCAACtaccttacaccgcttgcgaa | 333 |
| tracrRNA | CTTCACTGATAAAGTGGAGAACCGCTTCACCAAAAGCTGTCCCTTAGGGGATTAGAACTTGAGTGAAGGTGGGCTGCTTGCATCAGCCTAATGTCGAGAAGTGCTTTCTTCGGAAAGTAACCCTCGAAACAAATTCATTT | 334 |
| crRNA 1 | GACGAATGAAGGAATGCAACtaccttacaccgcttgcgaa | 335 |
| crRNA 2 | GACGAATGAAGGAATGCAACccttacaccgcttgcgaaag | 336 |
| crRNA 3 | GACGAATGAAGGAATGCAACttacaccgcttgcgaaagtt | 337 |
| crRNA 4 | GACGAATGAAGGAATGCAACacaccgcttgcgaaagttgt | 338 |
| crRNA MM target 2 | GACGAATGAAGGAATGCAACCGTCGCCGTCCAGCTCGACCA | 339 |
| crRNA MM target 3 | GACGAATGAAGGAATGCAACGATCGTTACGCTAACTATGA | 340 |
| HERC2A sgRNA | TTCACTGATAAAGTGGAGAACCGCTTCACCAAAAGCTGTCCCTTAGGGGATTAGAACTTGAGTGAAGGTGGGCTGCTTGCATCAGCCTAATGTCGAGAAGTGCTTTCTTCGGAAAGTAACCCTCGAAACAAATTCATTTgaaaGAATGAAGGAATGCAACacttgacacttaatgctcaa | 341 |
| LbCas12a HERC2 crRNA | GGGTAATTTCTACTAAGTGTAGATacttgacacttaatgctcaa | 342 |
| 25 nt spacer crRNA target 4 | GACGAATGAAGGAATGCAACtaccttacaccgcttgcgaaagttg | 343 |
| 20 nt spacer crRNA target 4 | GACGAATGAAGGAATGCAACtaccttacaccgcttgcgaa | 335 |

TABLE 5-continued

RNA Oligonucleotides.

| RNA Name | Sequence | SEQ ID NO: |
|---|---|---|
| 18 nt spacer crRNA target 4 | GACGAATGAAGGAATGCAACtaccttacaccgcttgcg | 344 |
| 16 nt spacer crRNA target 4 | GACGAATGAAGGAATGCAACtaccttacaccgcttg | 345 |
| 14 nt spacer crRNA target 4 | GACGAATGAAGGAATGCAACtaccttacaccgct | 346 |
| 12 nt spacer crRNA target 4 | GACGAATGAAGGAATGCAACtaccttacaccg | 347 |
| 10 nt spacer crRNA target 4 | GACGAATGAAGGAATGCAACtaccttacac | 348 |
| Full repeat crRNA target 4 | GTTGCAGAACCCGAATAGACGAATGAAGGAATGCAACtaccttacaccgcttgcgaa | 349 |
| 20 nt repeat crRNA target 4 | GACGAATGAAGGAATGCAACtaccttacaccgcttgcgaa | 335 |
| 17 nt repeat crRNA target 4 | GAATGAAGGAATGCAACtaccttacaccgcttgcgaa | 350 |
| 15 nt repeat crRNA target 4 | ATGAAGGAATGCAACtaccttacaccgcttgcgaa | 351 |
| 10 nt repeat crRNA target 4 | GGAATGCAACtaccttacaccgcttgcgaa | 333 |
| tracrRNA +41 nt | CTTCACTGATAAAGTGGAGAACCGCTTCACCAAAAGCTGTCCCTTAGGGGATTAGAACTTGAGTGAAGGTGGGCTGCTTGCATCAGCCTAATGTCGAGAAGTGCTTTCTTCGGAAAGTAACCCTCGAAACAAATTCATTTTTCCTCTCCAATTCTGCACAAAAAAGGTGAGTCCTTAT | 352 |
| tracrRNA +3 nt | CTTCACTGATAAAGTGGAGAACCGCTTCACCAAAAGCTGTCCCTTAGGGGATTAGAACTTGAGTGAAGGTGGGCTGCTTGCATCAGCCTAATGTCGAGAAGTGCTTTCTTCGGAAAGTAACCCTCGAAACAAATTCATTT | 334 |
| tracrRNA -26 | CTTCACTGATAAAGTGGAGAACCGCTTCACCAAAAGCTGTCCCTTAGGGGATTAGAACTTGAGTGAAGGTGGGCTGCTTGCATCAGCCTAATGTCGAGAAGTGCTTTCTT | 353 |
| tracrRNA -65 | CTTCACTGATAAAGTGGAGAACCGCTTCACCAAAAGCTGTCCCTTAGGGGATTAGAACTTGAGTGAAGGTGG | 354 |
| tracrRNA +0 | TTCACTGATAAAGTGGAGAACCGCTTCACCAAAAGCTGTCCCTTAGGGGATTAGAACTTGAGTGAAGGTGGGCTGCTTGCATCAGCCTAATGTCGAGAAGTGCTTTCTTCGGAAAGTAACCCTCGAAACAAATTCA | 355 |
| tracrRNA +90 nt | ttcacacTTCACTGATAAAGTGGAGAACCGCTTCACCAAAAGCTGTCCCTTAGGGGATTAGAACTTGAGTGAAGGTGGGCTGCTTGCATCAGCCTAATGTCGAGAAGTGCTTTCTTCGGAAAGTAACCCTCGAAACAAATTCAttttcctctccaattctgcacaaaaaaaggtgagtcctttataaaccggcgtgcagaacgccggctcaccttttttcttcattcgattta | 356 |

TABLE 5-continued

RNA Oligonucleotides.

| RNA Name | Sequence | SEQ ID NO: |
|---|---|---|
| sgRNA 1 | CTTCACTGATAAAGTGGGAGAACCGCTTCACCAAAAGCTGTC CCTTAGGGGATTAGAACTTGAGTGAAGGTGGGCTGCTTGCA TCAGCCTAATGTCGAGAAGTGCTTTCTTCGGAAAGTAACCCT CGAAACAAATTCATTTgaaaGAATGAAGGAATGCAACtaccttaca ccgcttgcgaa | 357 |
| sgRNA 2 | CTTCACTGATAAAGTGGGAGAACCGCTTCACCAAAAGCTGTC CCTTAGGGGATTAGAACTTGAGTGAAGGTGGGCTGCTTGCA TCAGCCTAATGTCGAGAAGTGCTTTCTTCGGAAAGTAACCCT CGAAACAAATTCATTTTTCCTCTCCAATTCTGCACAAgaaaGT TGCAGAACCCGAATAGACGAATGAAGGAATGCAACtaccttacac cgcttgcgaa | 358 |
| M13 target 1 crRNA | GACGAATGAAGGAATGCAACTACCGAACGAACCACCAGCA GAAGA | 359 |
| M13 target 2 crRNA | GACGAATGAAGGAATGCAACTCTTCTGCTGGTGGTTCGTTC GGTA | 360 |
| M13 target 3 crRNA | GACGAATGAAGGAATGCAACGTTTGACCATTAGATACATTT CG | 361 |
| M13 target 4 crRNA | GACGAATGAAGGAATGCAACCGAAATGTATCTAATGGTCAA AC | 362 |

Example 1

FIG. 1 depicts examples of naturally occurring CasZ protein sequences.

FIG. 2 depicts schematic representations of CasZ loci, which include a Cas1 protein in addition to the CasZ protein.

FIG. 3 depicts a phylogenetic tree of CasZ sequences in relation to other Class 2 CRISPR/Cas effector protein sequences.

Figure 4:
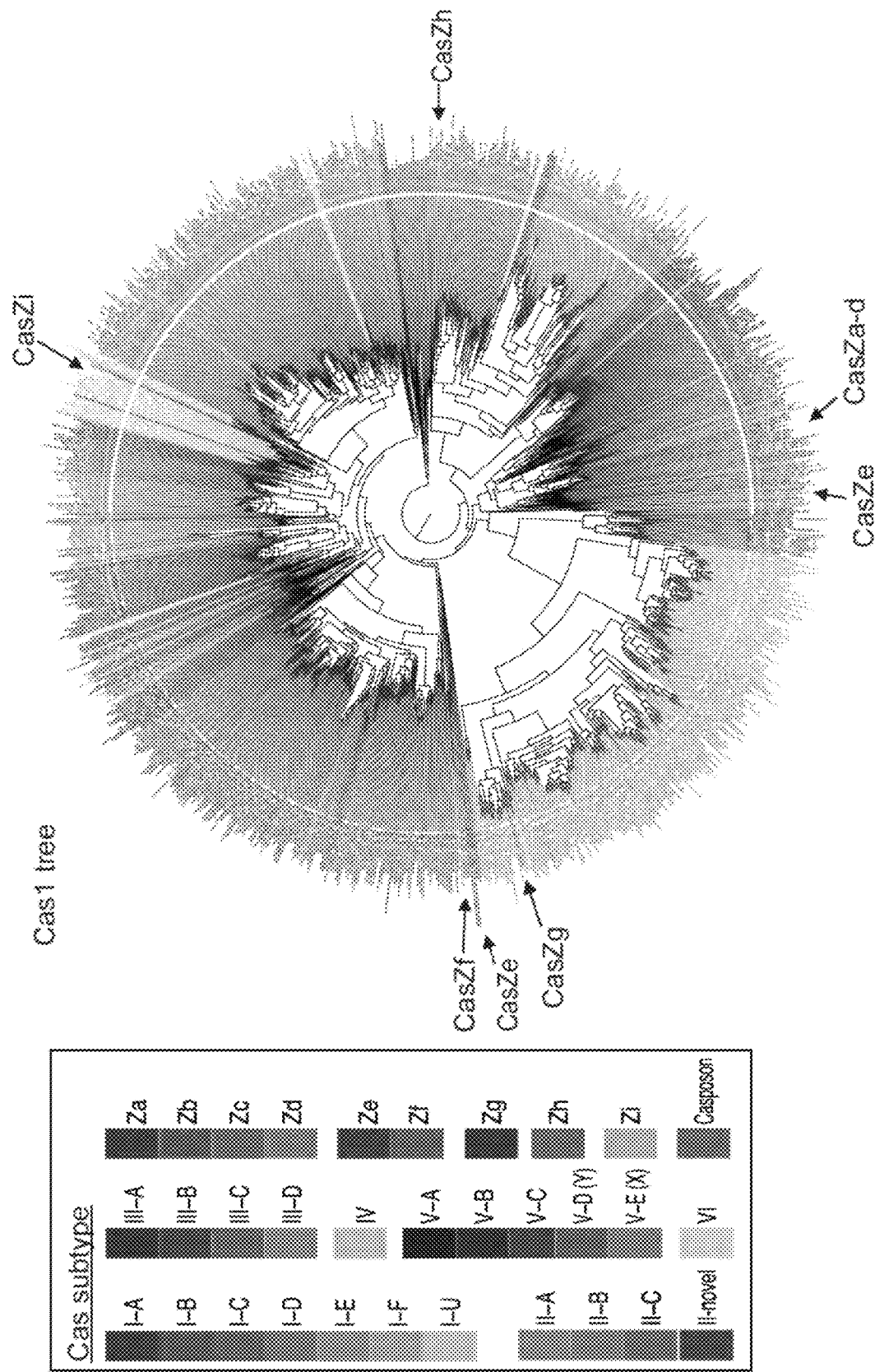
FIG. 4 depicts a phylogenetic tree of Cas1 sequences from CasZ loci in relation to Cas1 sequences from other Class 2 CRISPR/Cas loci.
Figure 5A:
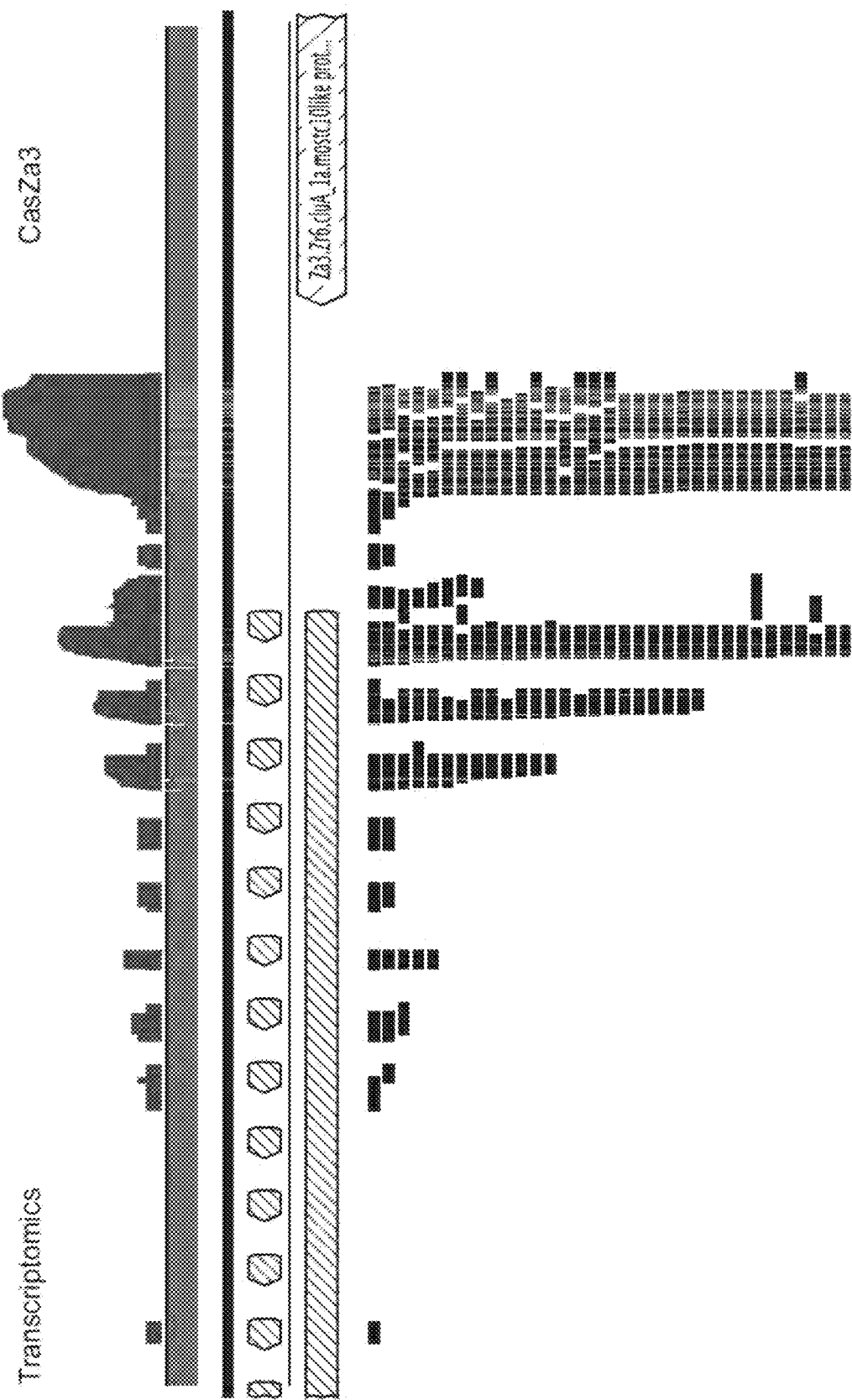
Figure 5B:
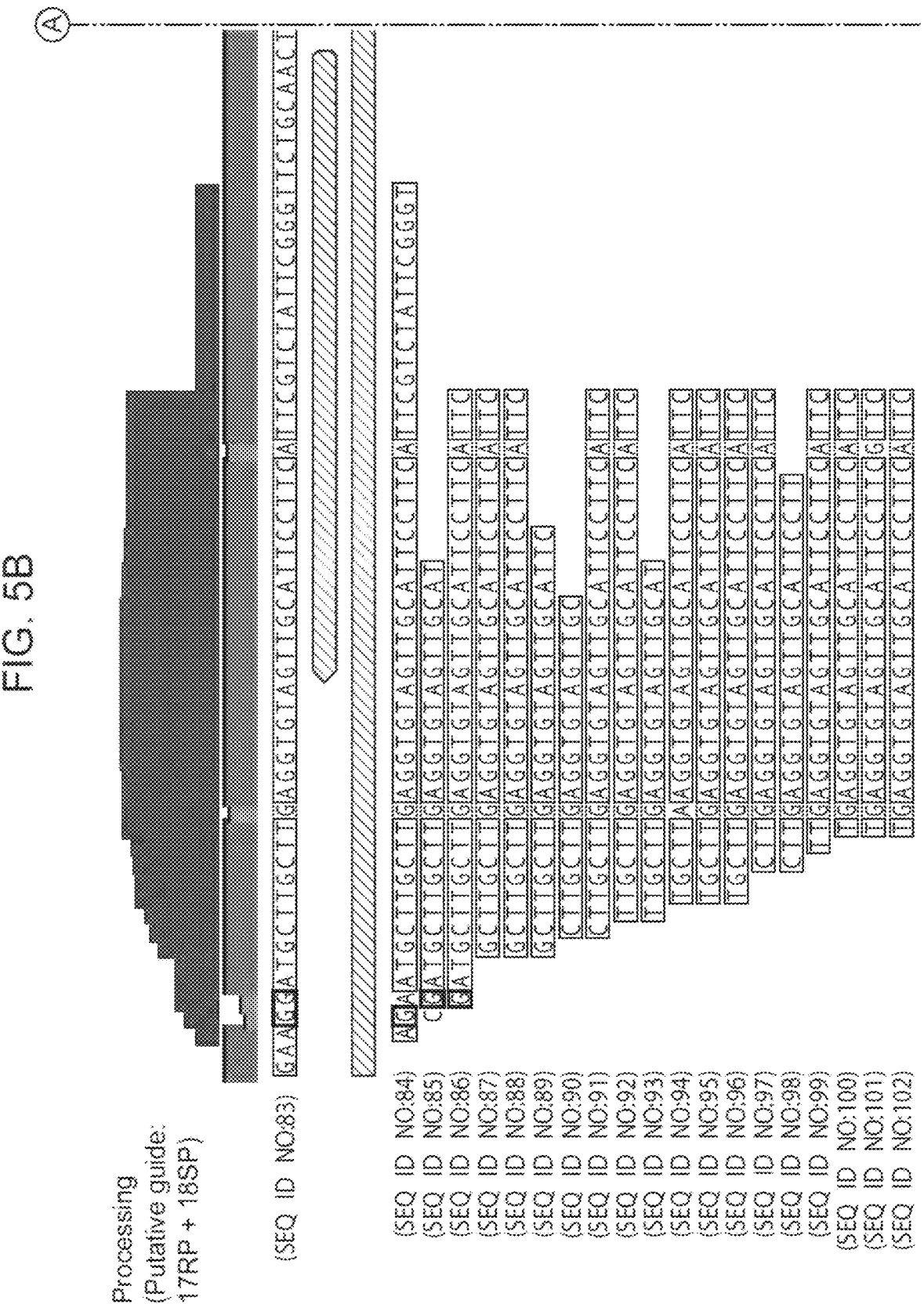
Figure 5C:
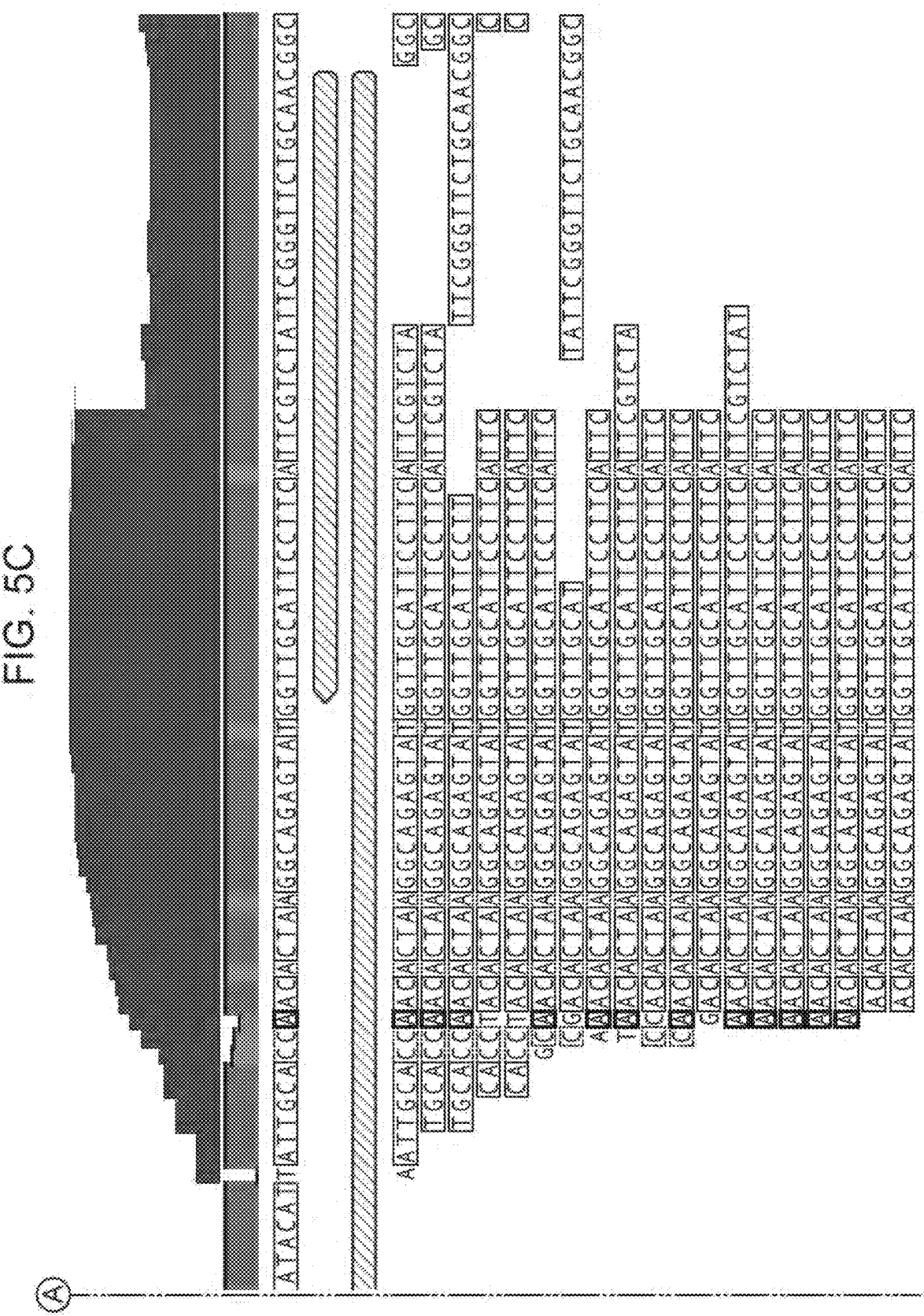
Figure 5D:
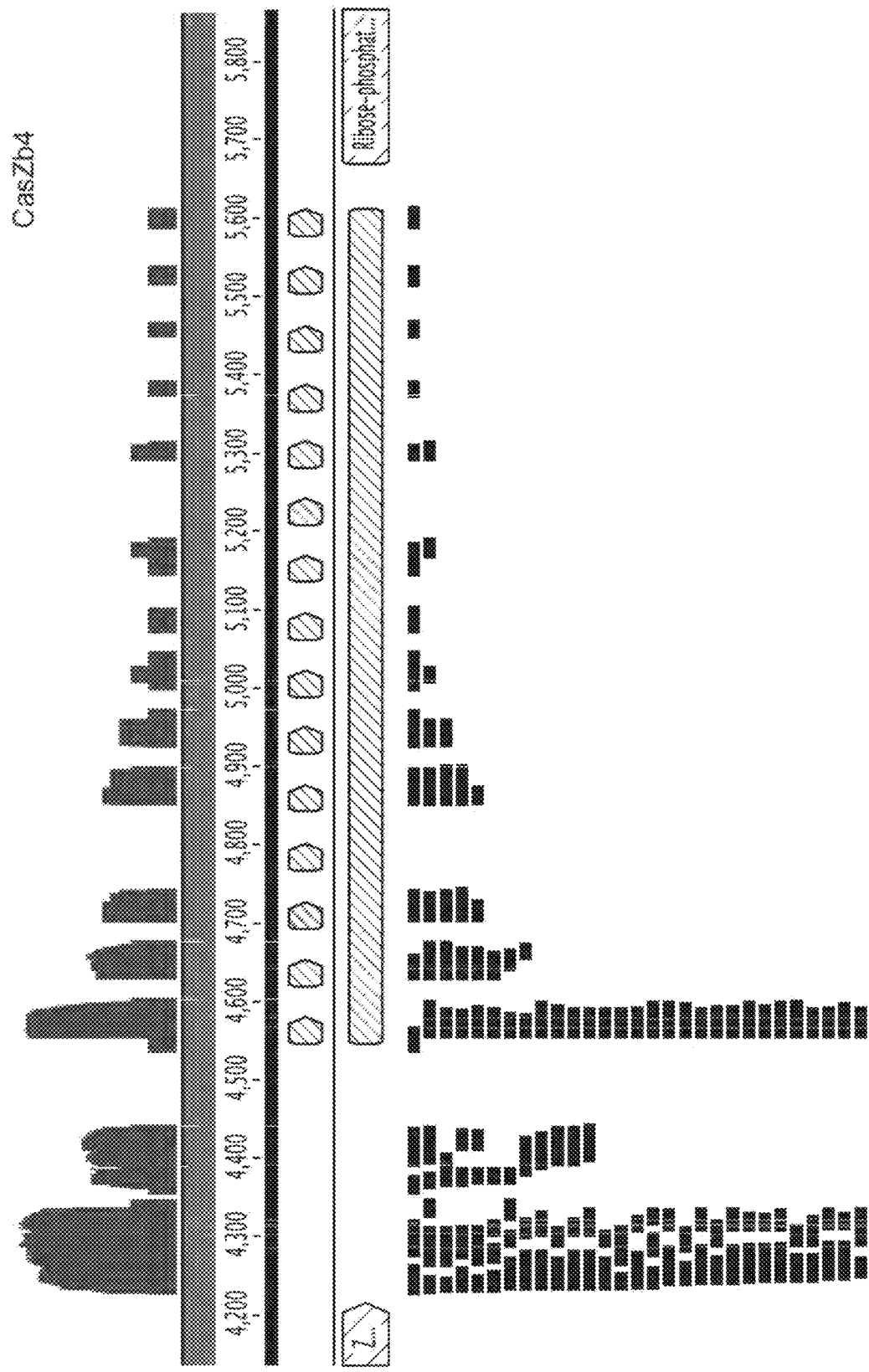
Figure 5E:
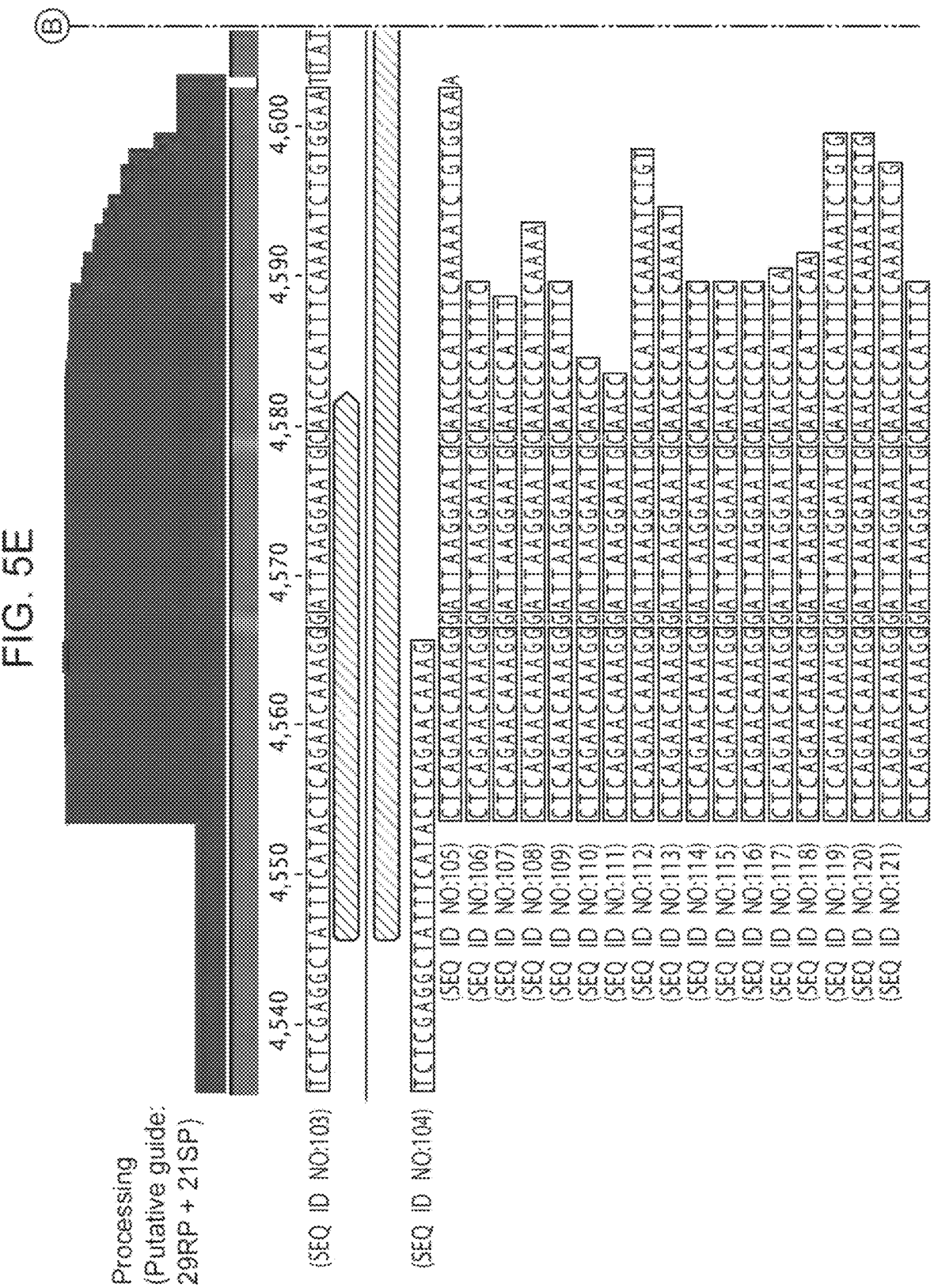
Figure 5F:
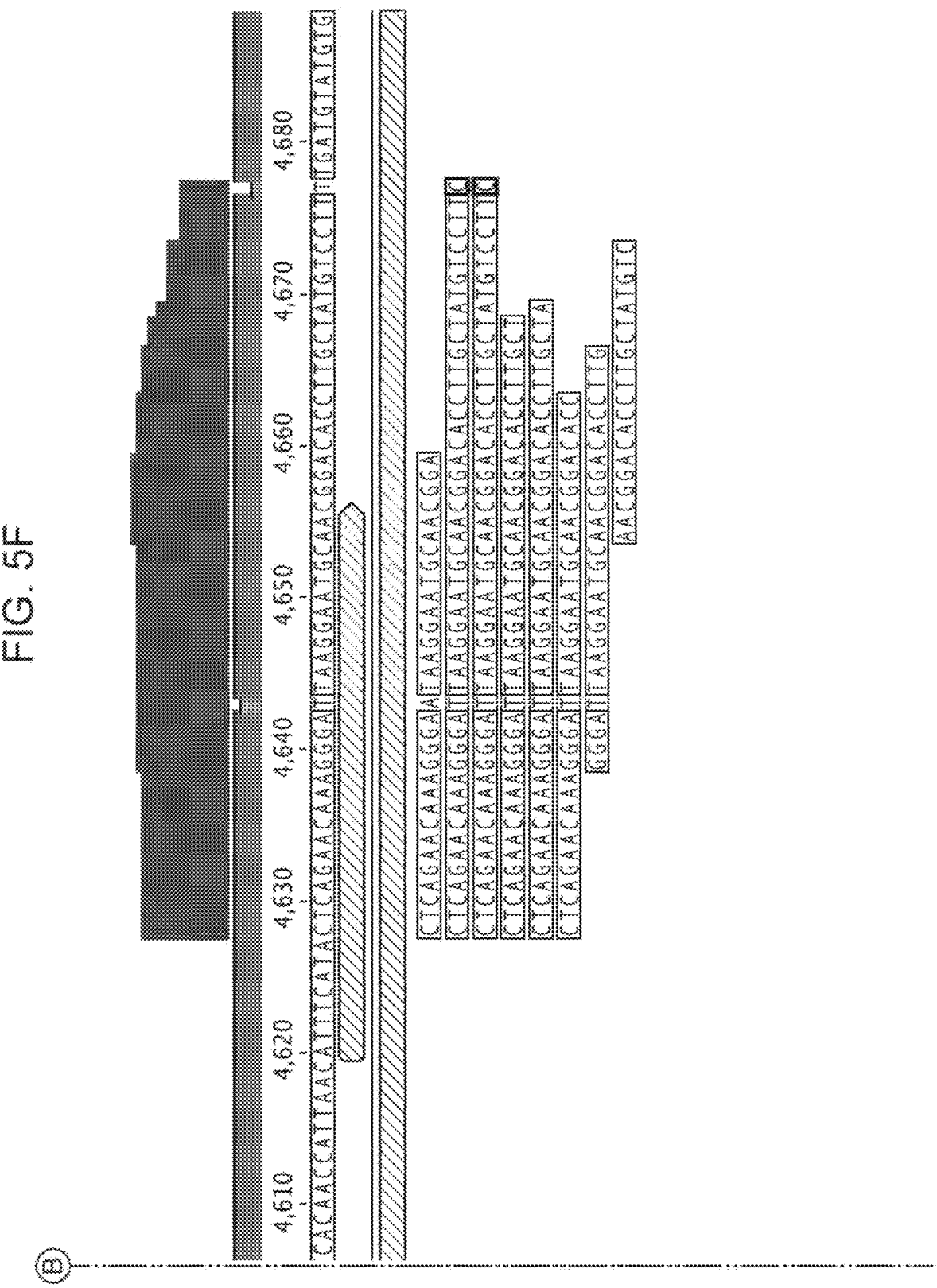
Figure 5G:
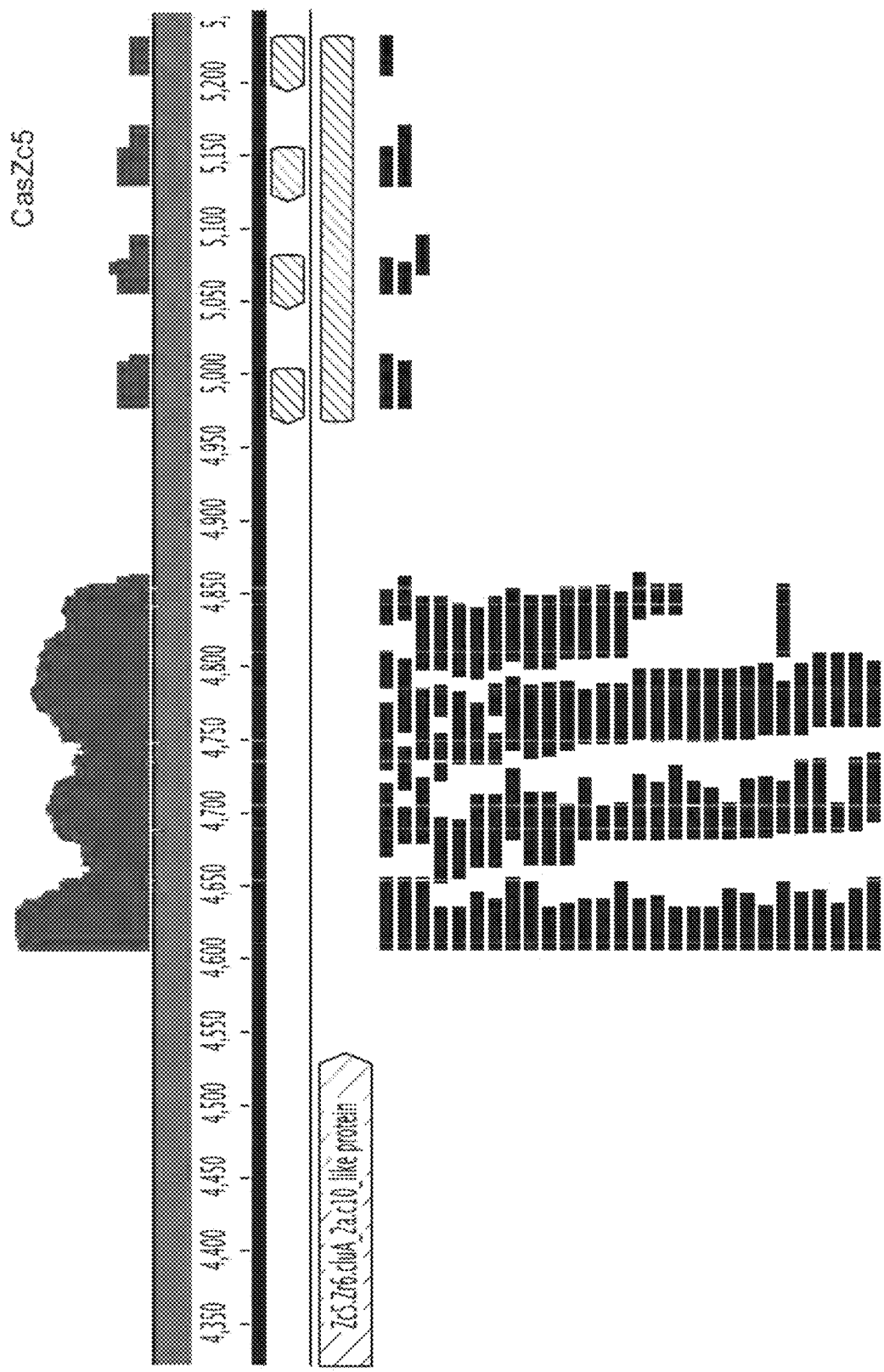
Figure 5H:
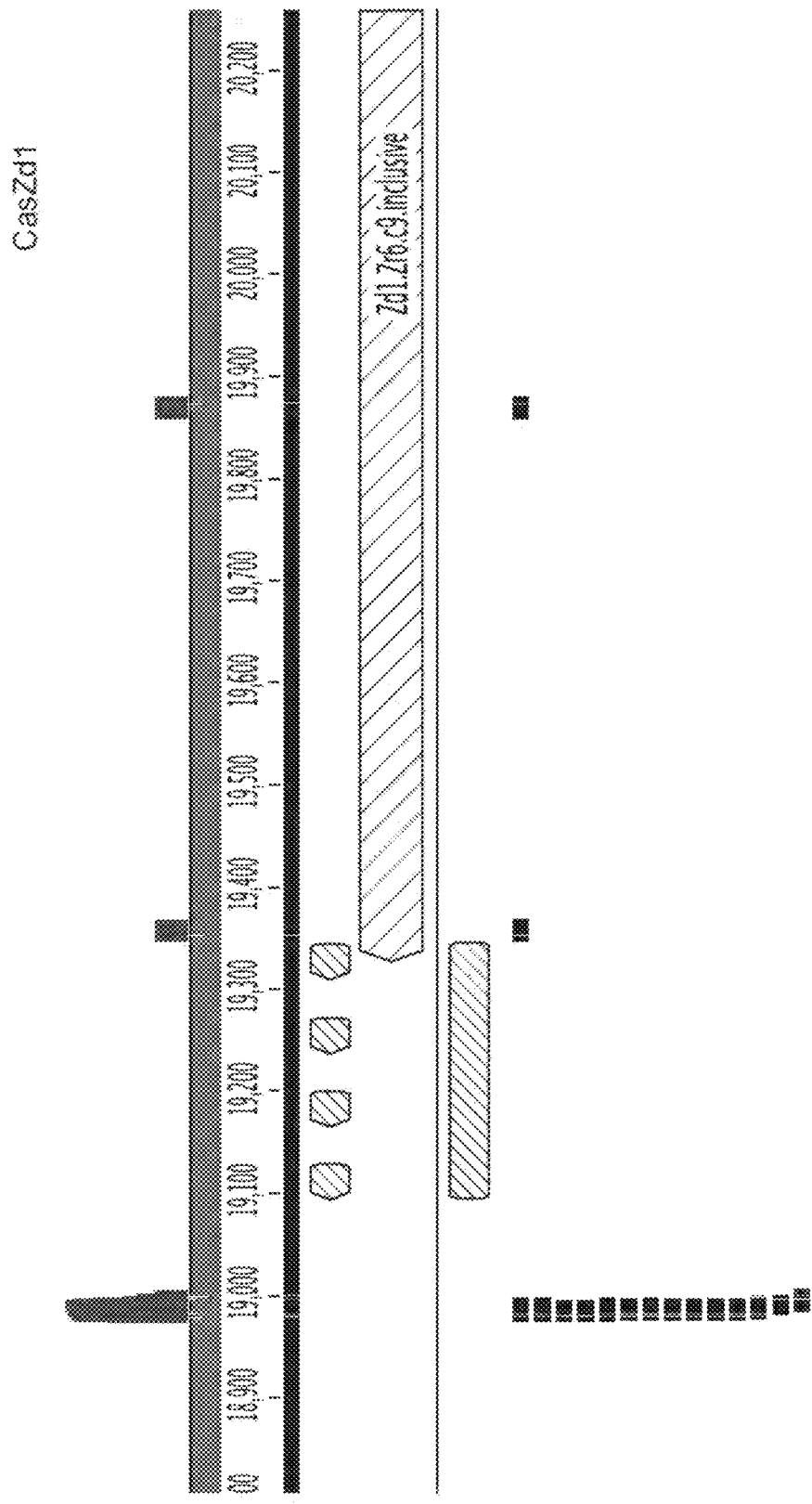
Figure 51:
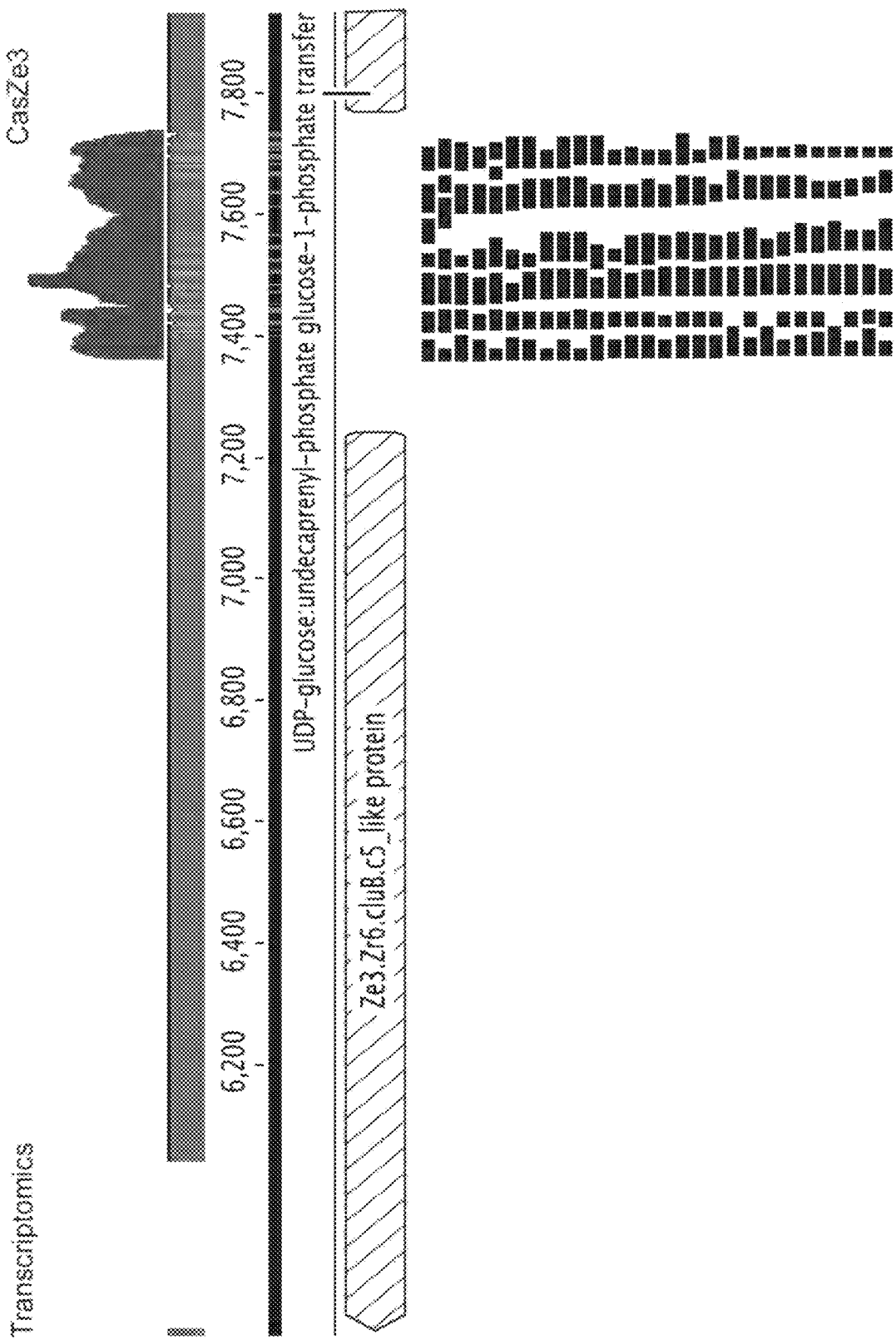
Figure 6:
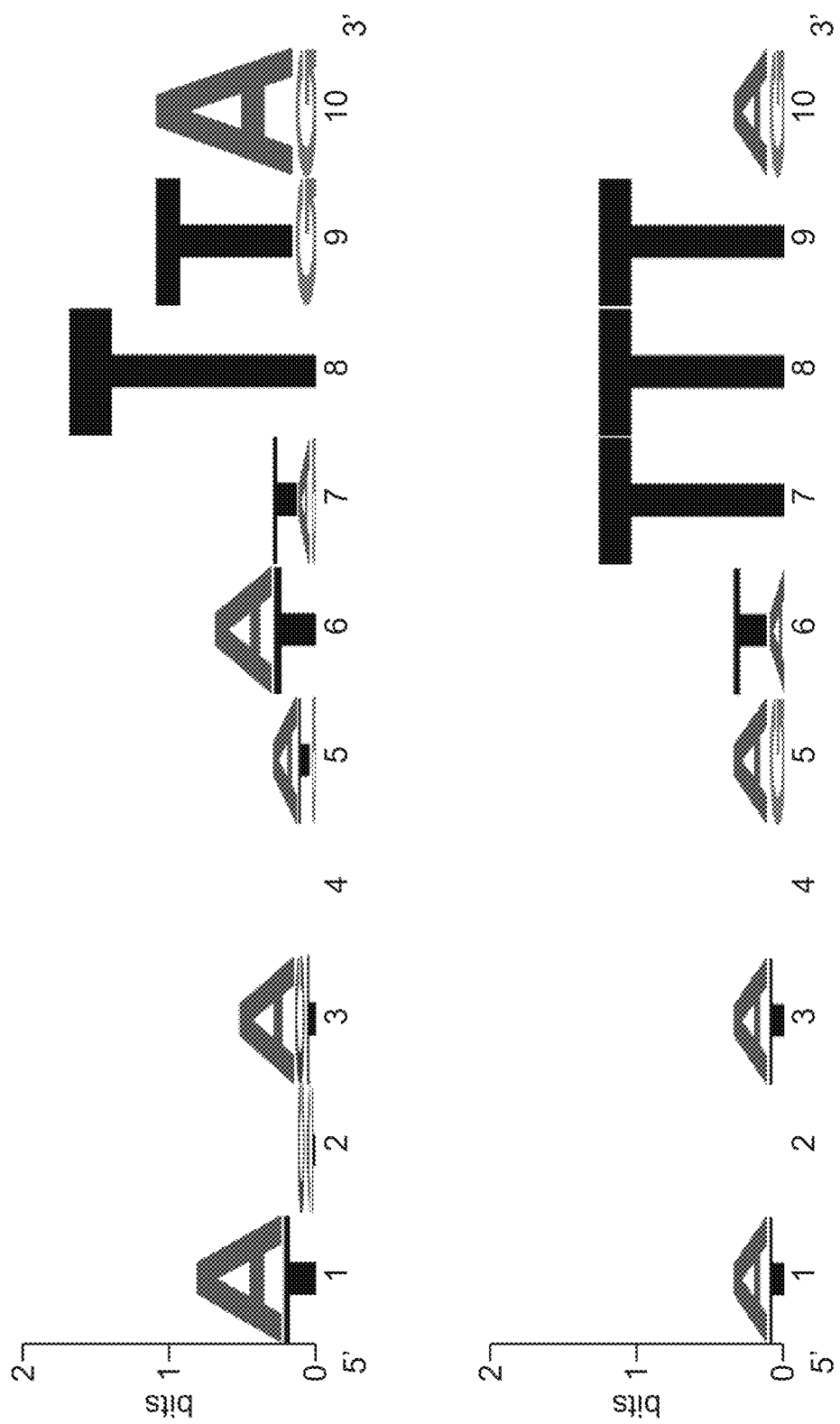
FIG. 6 depicts results for PAM preferences as assayed using PAM depletion assays for CasZc (top) and CasZb (bottom).
Figure 8A:
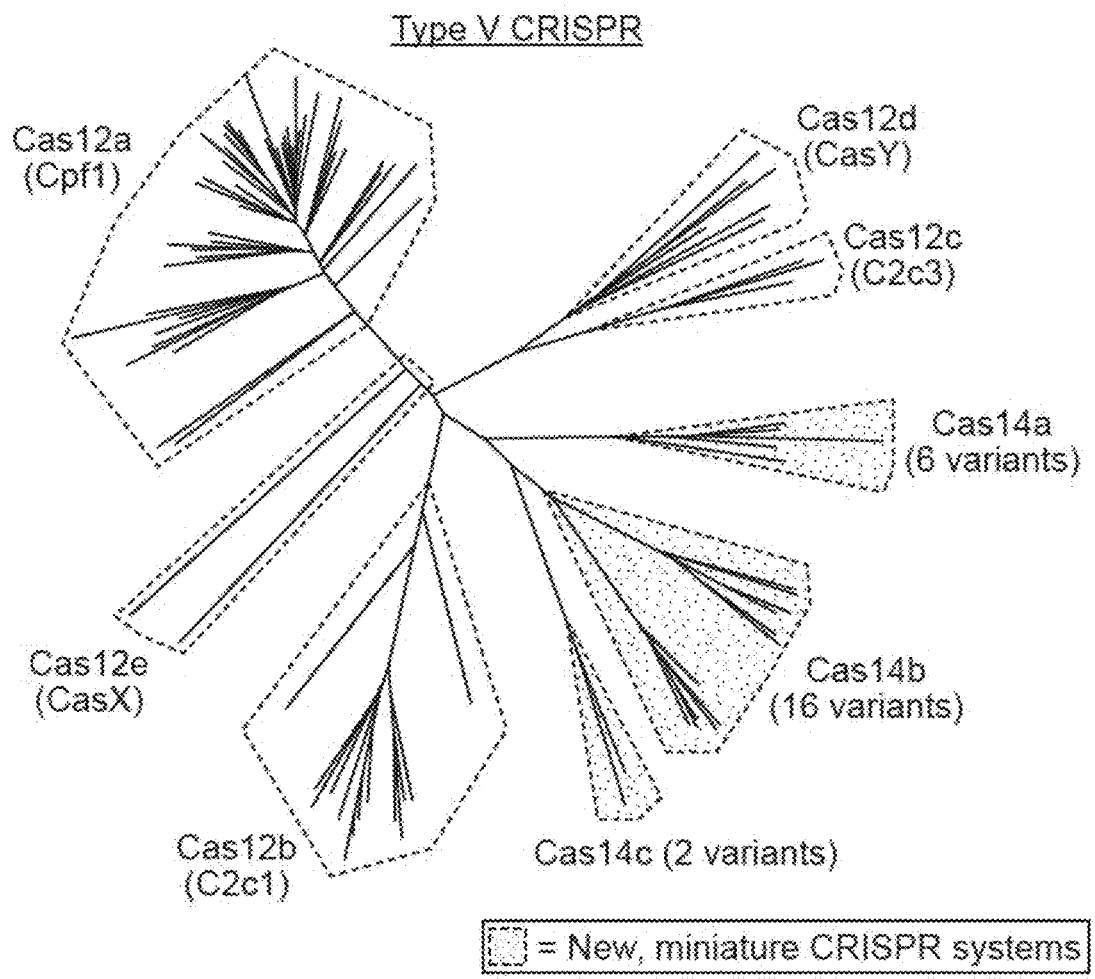
FIGS. 8A-8D depict the architecture and phylogeny of CRISPR-Cas14 genomic loci.
Figure 8B:
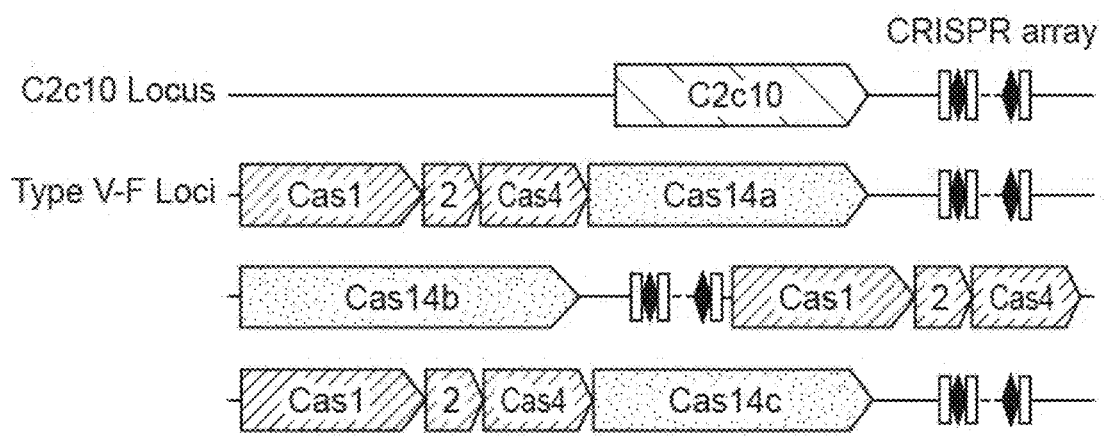
Figure 8C:
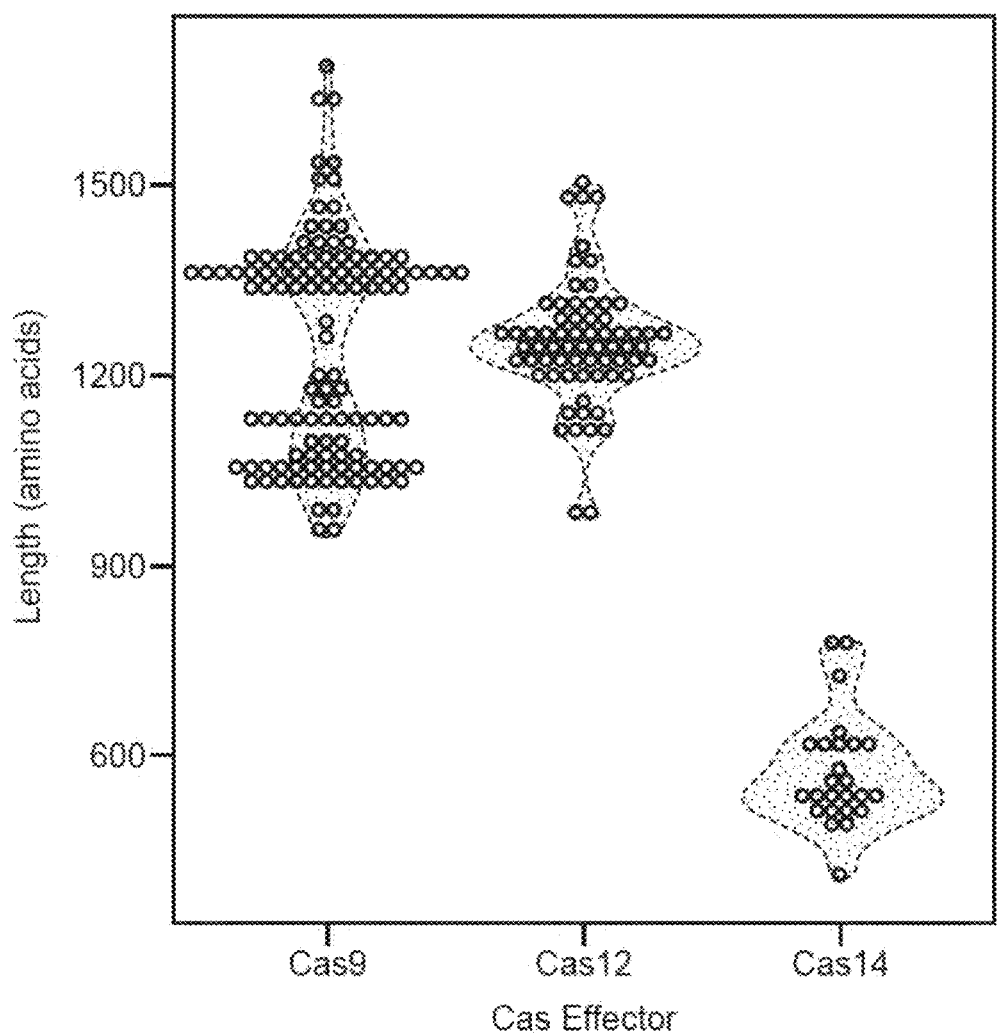
Figure 8D:
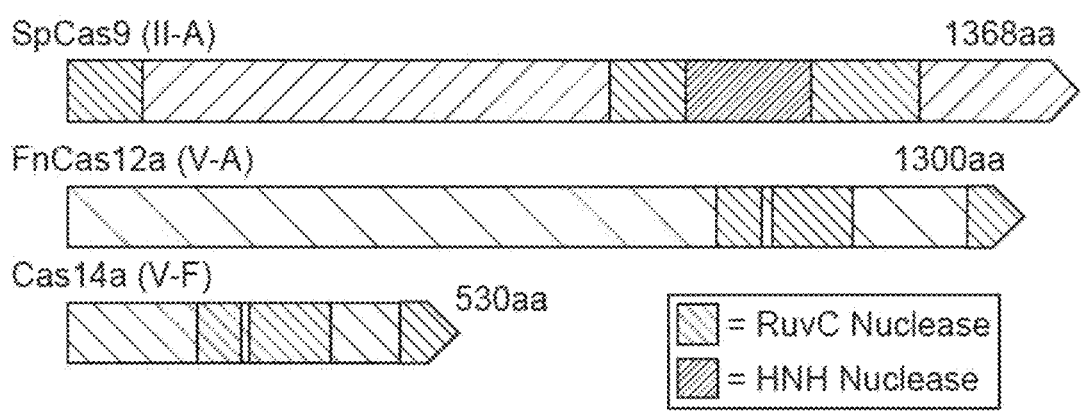

FIG. 4 depicts a phylogenetic tree of Cas1 sequences from CasZ loci in relation to Cas1 sequences from other Class 2 CRISPR/Cas loci.

FIG. 5 depicts transcriptomic RNA mapping data demonstrating expression of trancRNA from CasZ loci. The trancRNAs are adjacent to the CasZ repeat array, but do not include the repeat sequence and are not complementary to the repeat sequence. Shown are RNA mapping data for the following loci: CasZa3, CasZb4, CasZc5, CasZd1, and CasZe3. Small repeating aligned arrows represent the repeats of the CRISPR array (indicating the presence of guide RNA-encoding sequence); the peaks outside and adjacent to the repeat arrays represent highly transcribed trancRNAs.

This metatranscriptomic data was not 16S depleted, and hence large portions of the data were mapped to 16S, and mRNA, for example, was almost not represented at all in these reads. Nonetheless, RNA mapping to the predicted trancRNA regions was observed.

Example 2

A set of CRISPR-Cas systems from uncultivated archaea that contained Cas14, a family of exceptionally compact RNA-guided nucleases of just 400-700 amino acids were disclosed herein, including Cas1 and Cas2 proteins that are responsible for integrating DNA into CRISPR genomic loci and showed evidence of actively adapting their CRISPR arrays to new infections. Despite their small size, Cas14 proteins were capable of RNA-guided single-stranded DNA (ssDNA) cleavage without restrictive sequence requirements. Moreover, target recognition by Cas14 triggered non-specific cutting of ssDNA molecules. Metagenomic data showed that multiple CRISPR-Cas14 systems evolved independently and suggested a potential evolutionary origin of single-effector CRISPR-based adaptive immunity.

Figure 9:
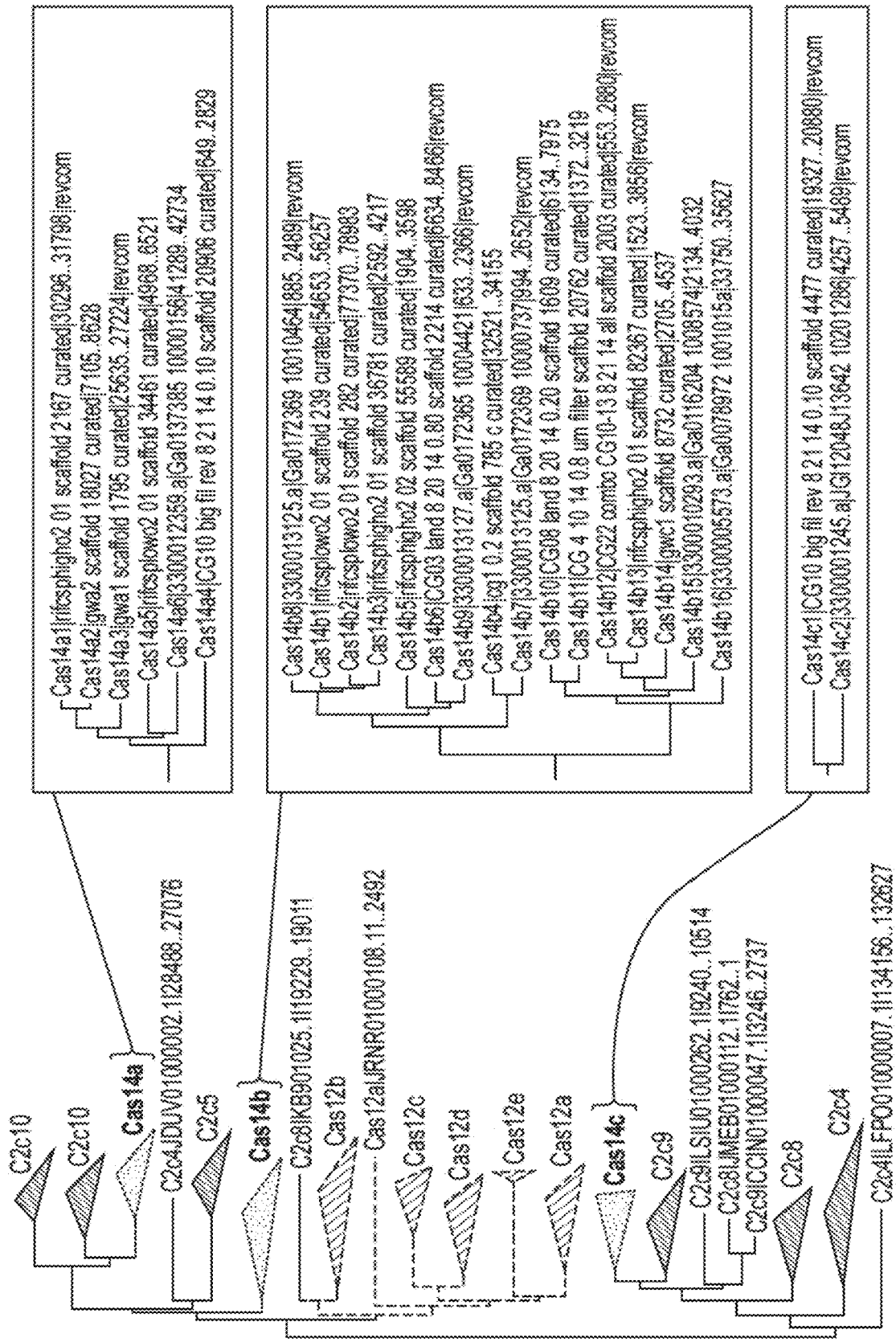
FIG. 9 depicts a phylogenetic analysis of Cas14 orthologs.
Figure 11A:
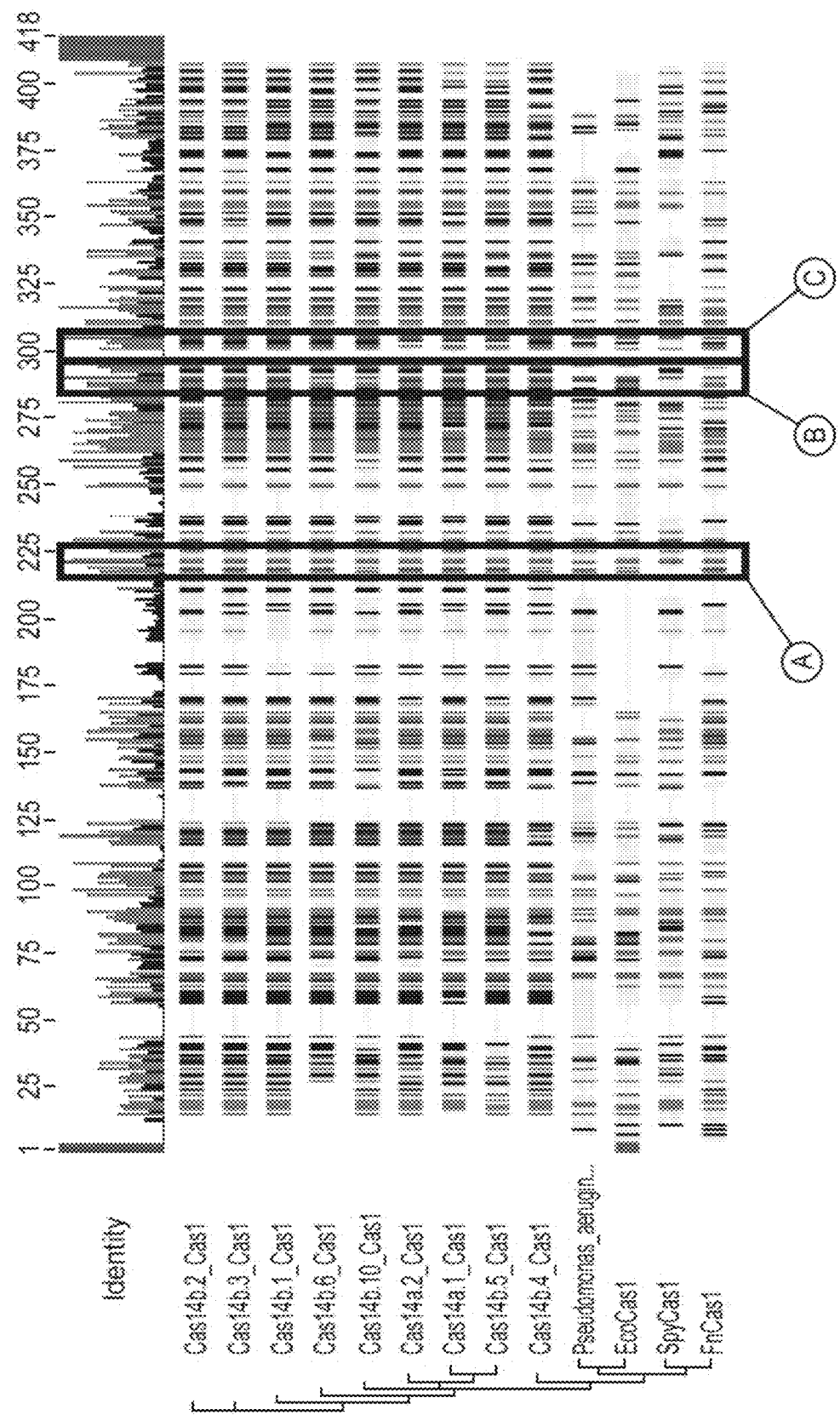
FIGS. 11A-11D depict the acquisition of new spacers by CRISPR-Cas14 systems.
Figure 11B:
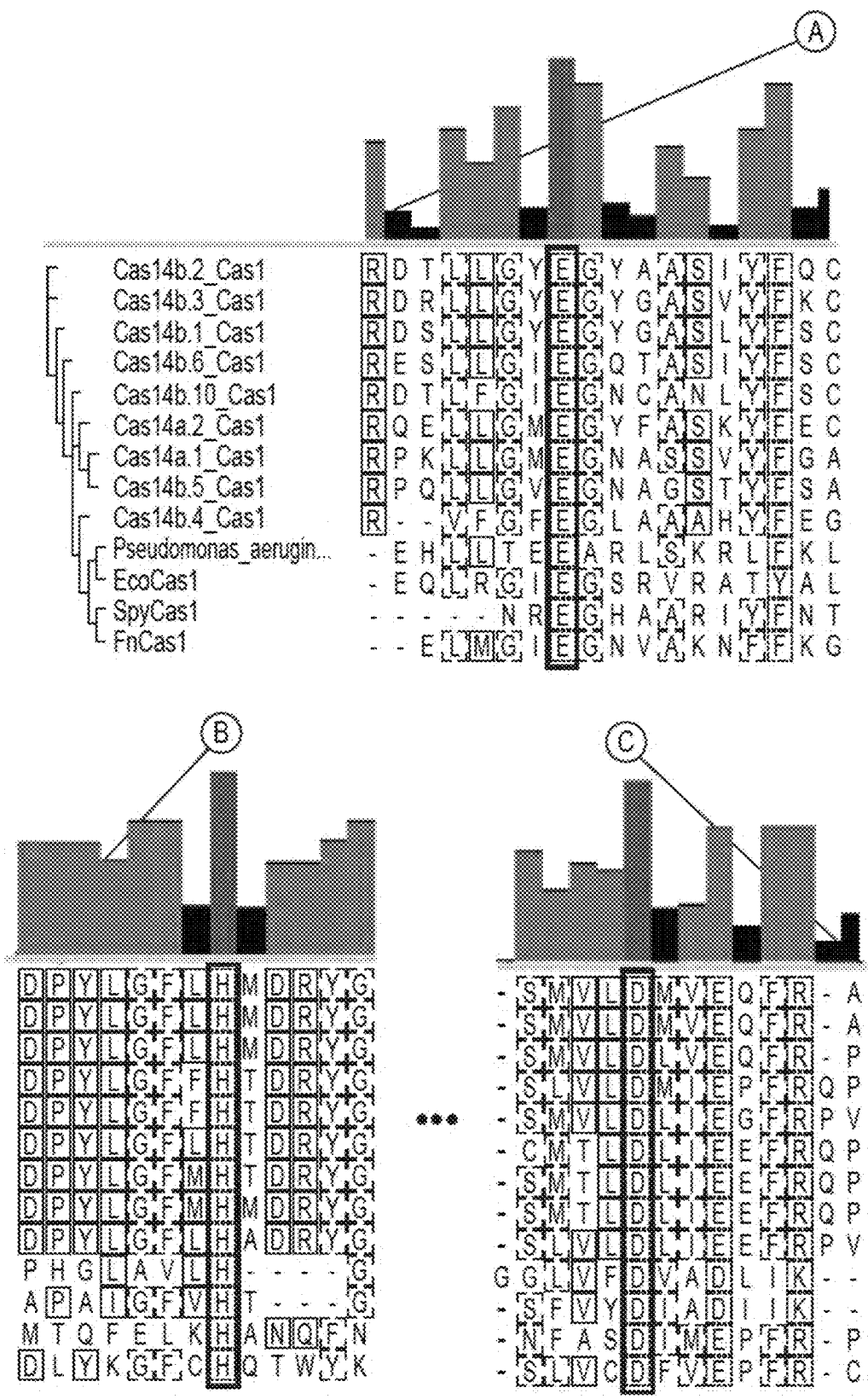
Figure 11C:
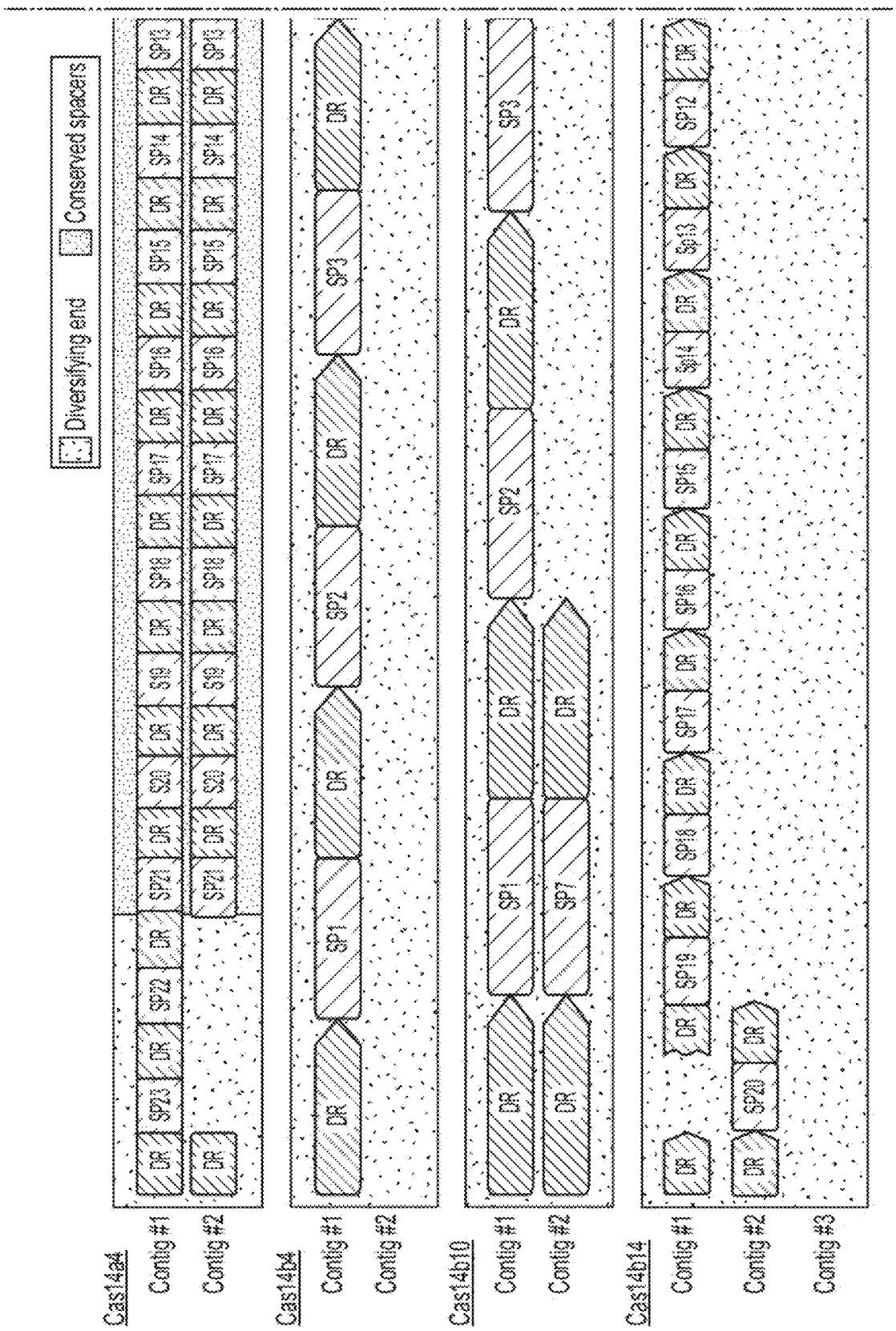
Figure 11D:
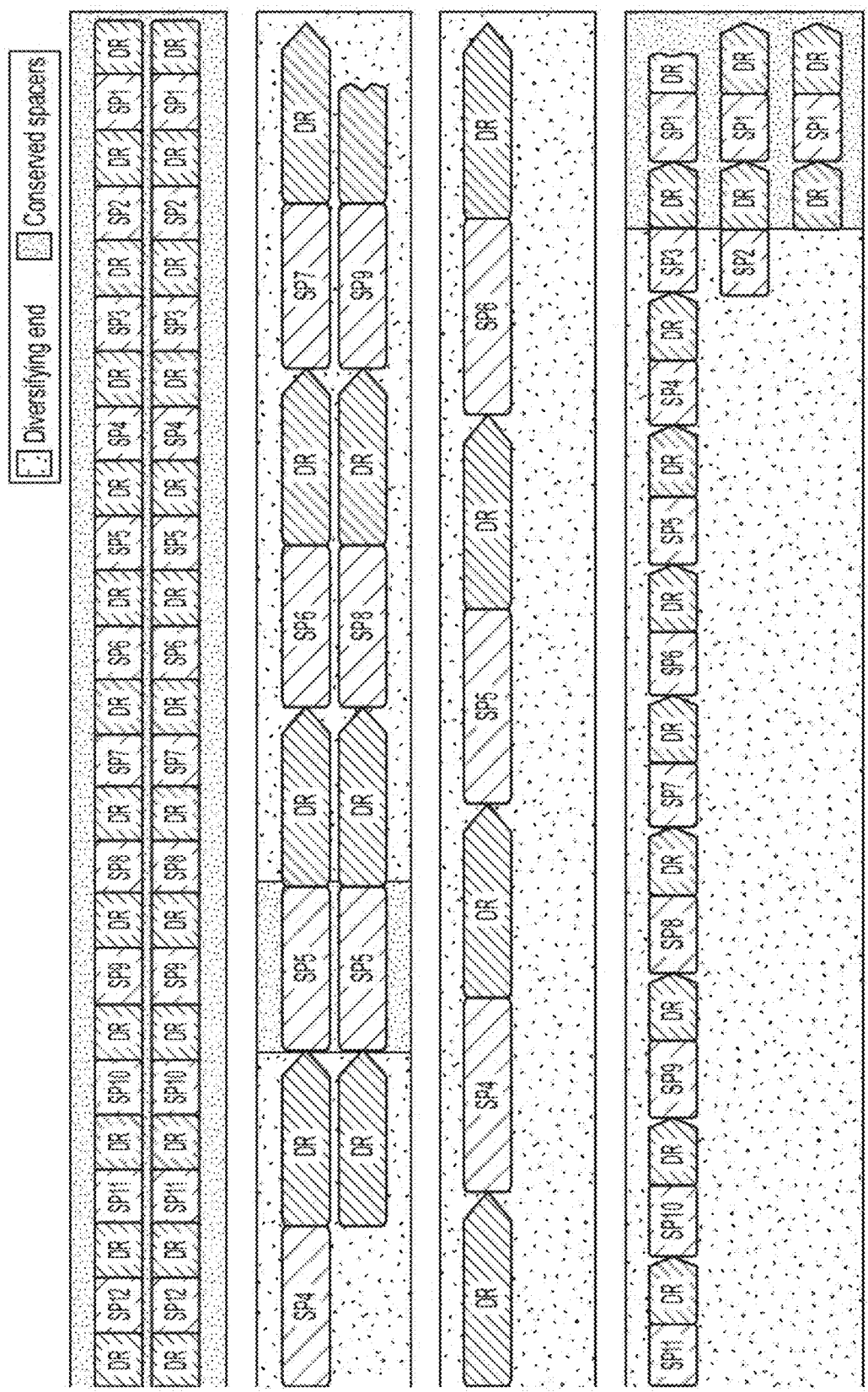
Figure 12A:
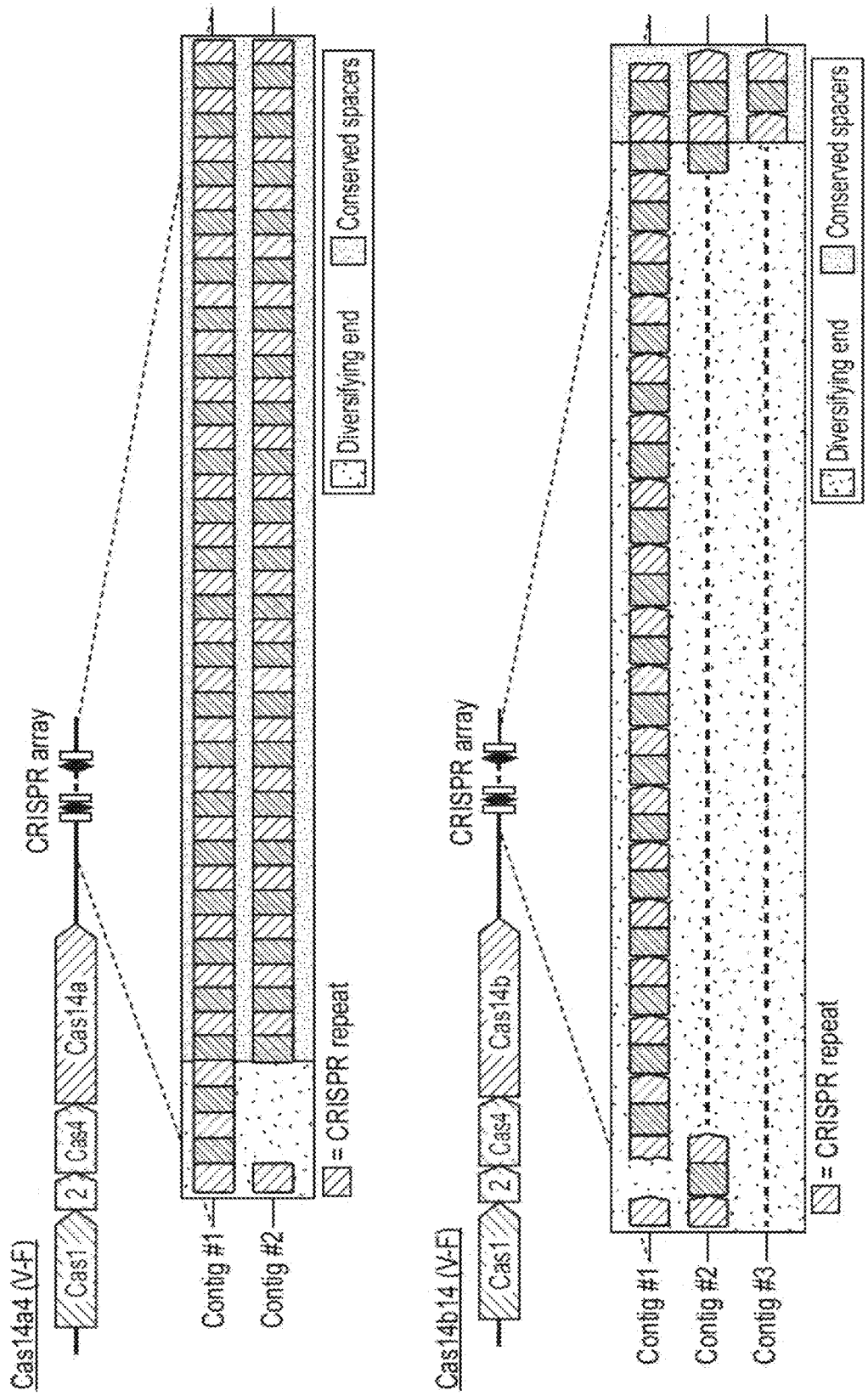
FIGS. 12A-12D depict that CRISPR-Cas14a actively adapts and encodes a tracrRNA.
Figure 12B:
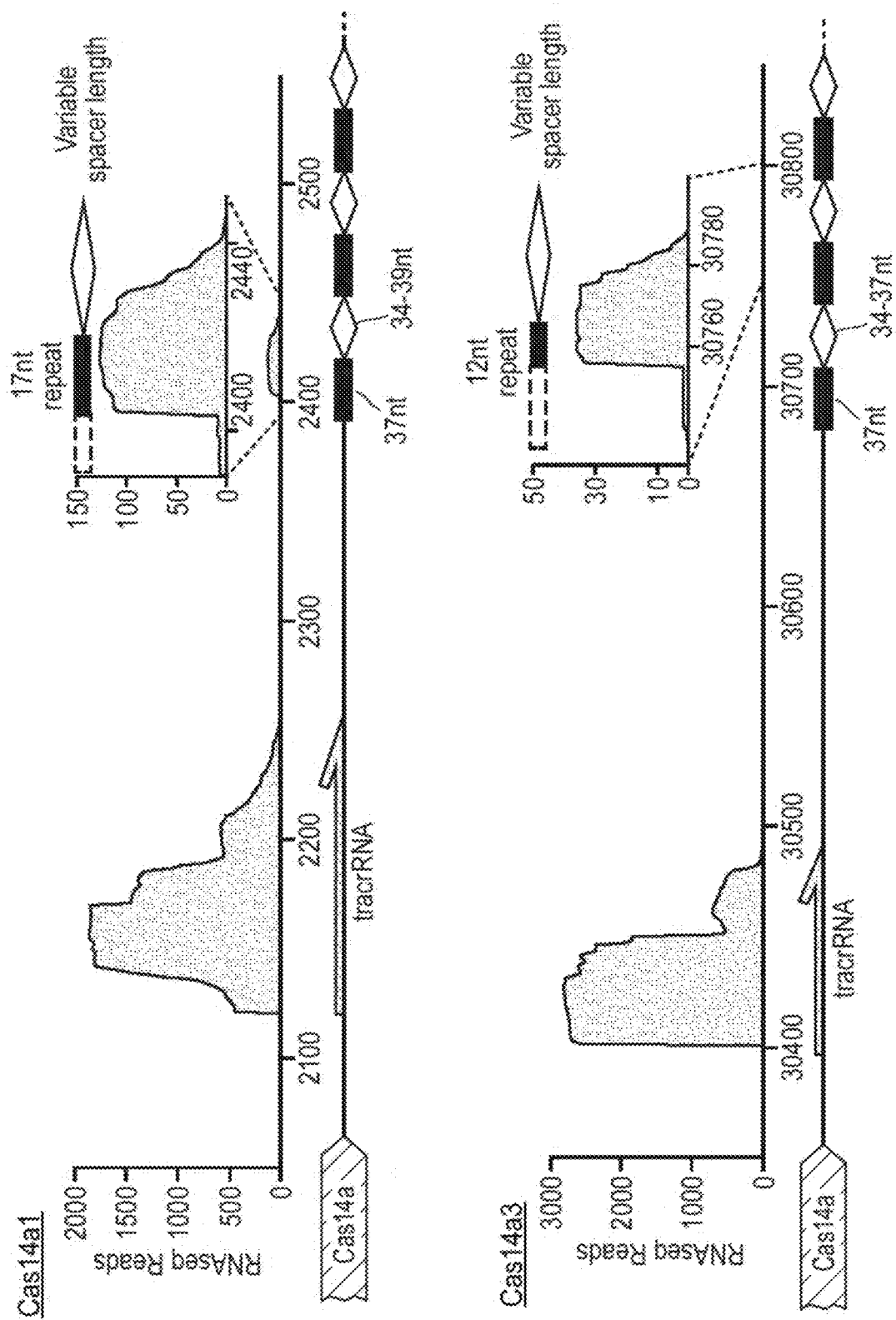
Figure 12C:
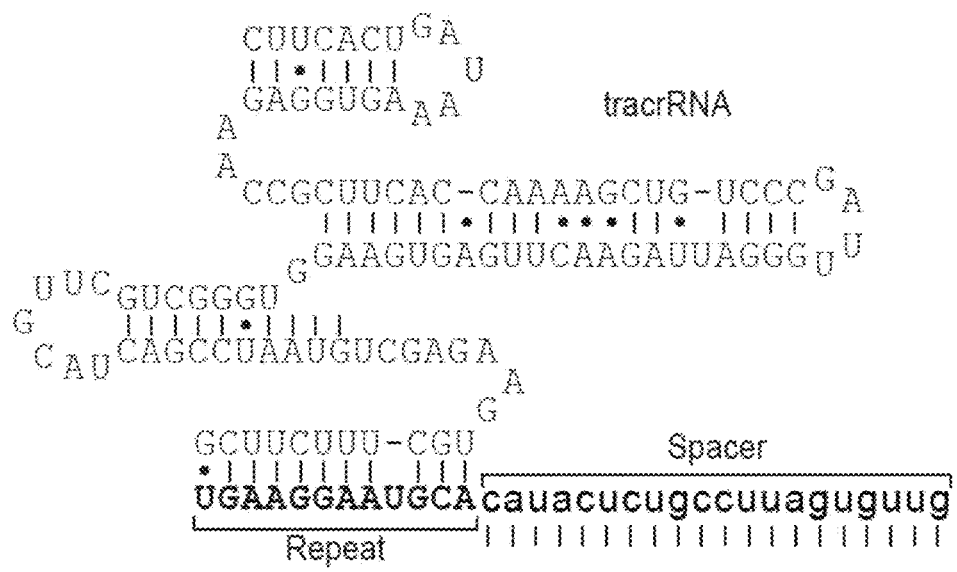
Figure 12D:
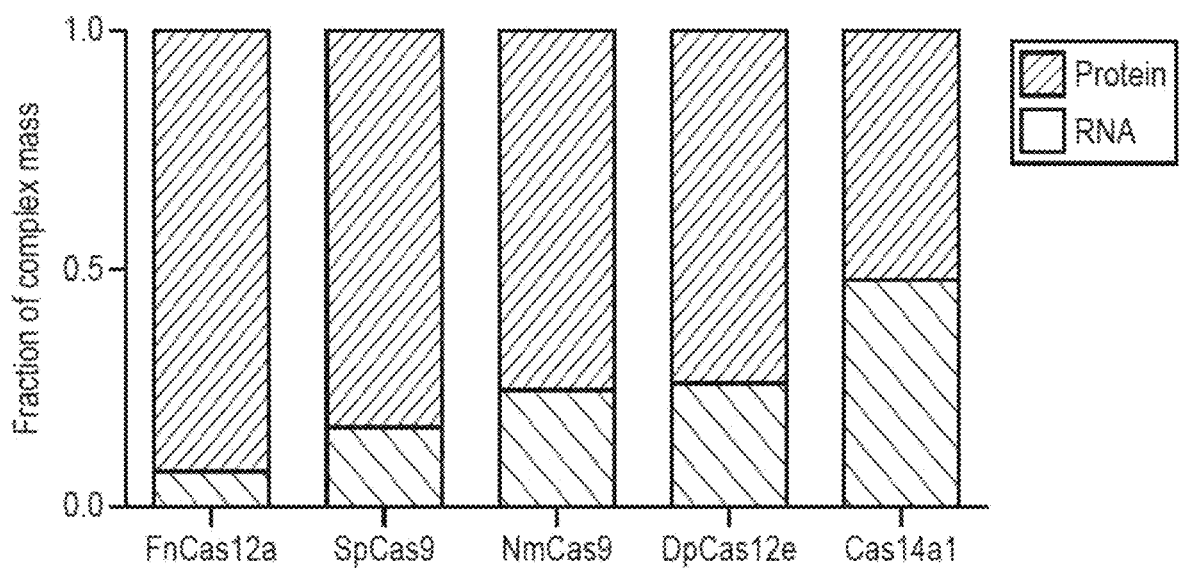
Figure 13A:
Figure 13B:
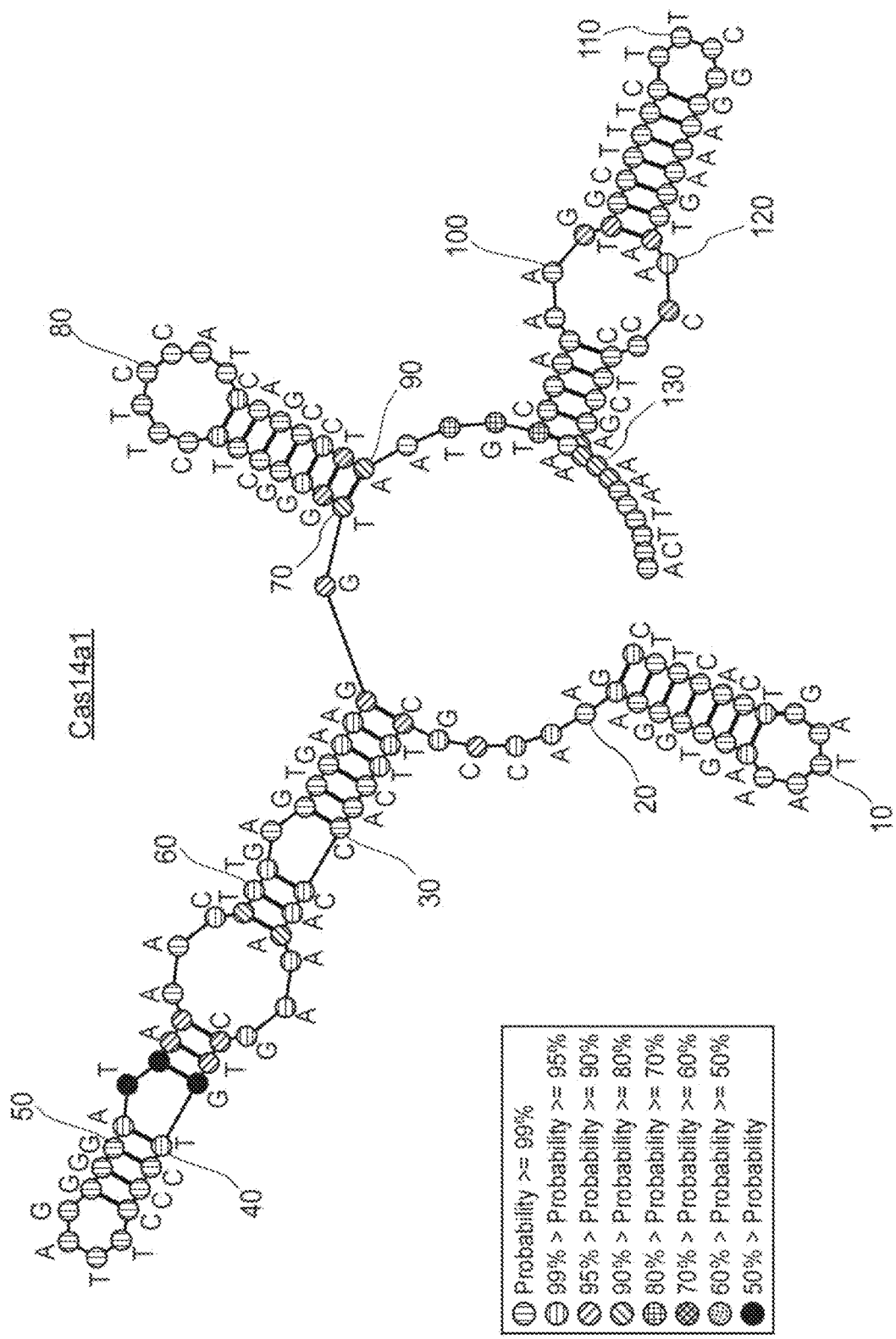
Figure 13D:
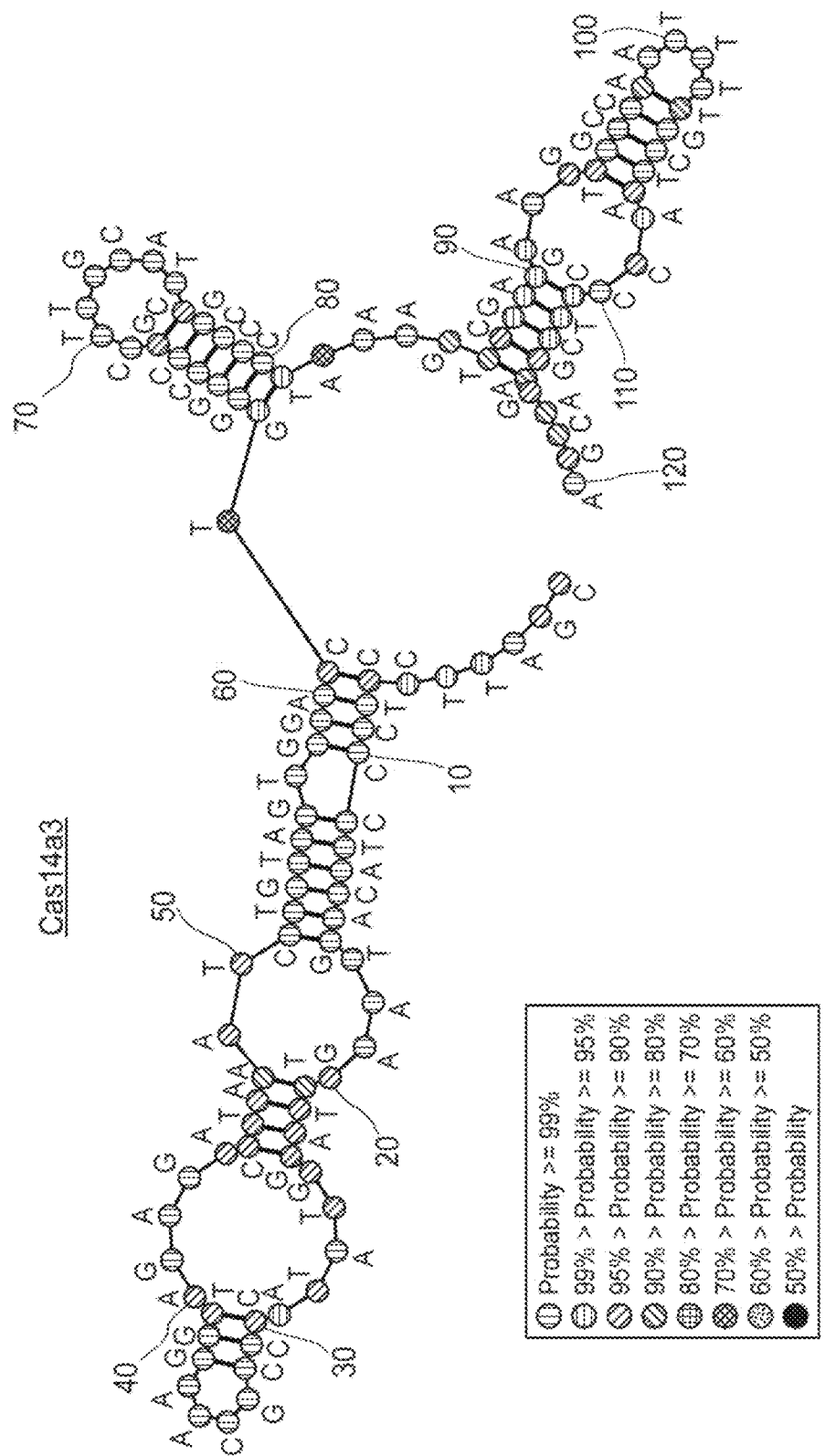
Figure 13E:
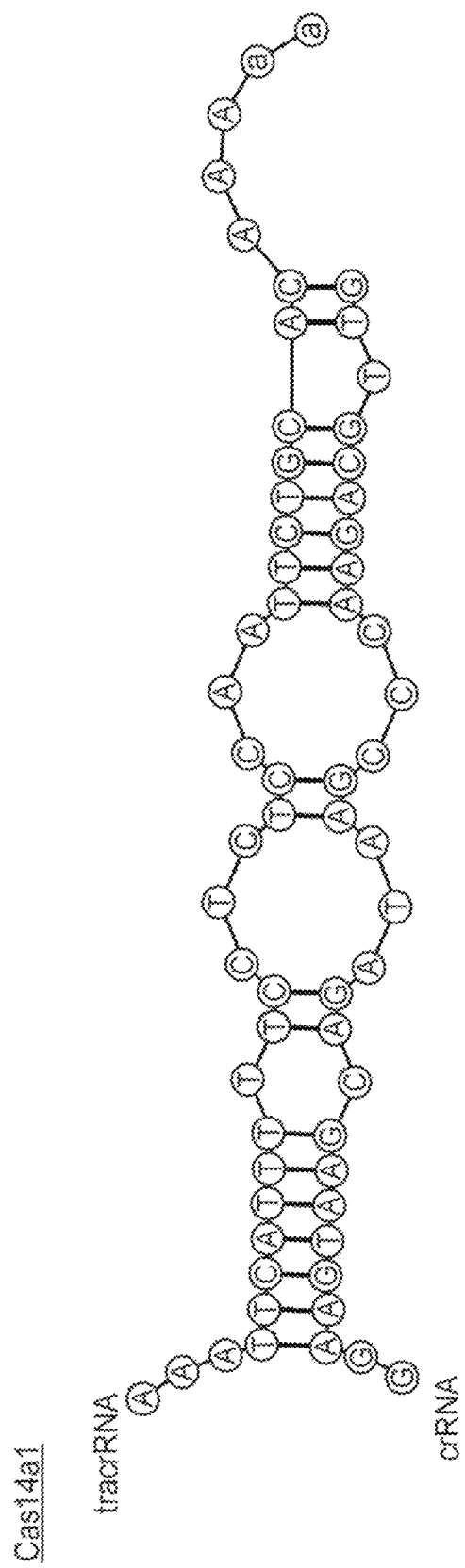

Competition between microbes and viruses stimulated the evolution of CRISPR-based adaptive immunity to provide protection against infectious agents. In class 2 CRISPR-Cas systems, a single 100-200 kilodalton (kD) CRISPR-associated (Cas) protein with multiple functional domains carried out RNA-guided binding and cutting of DNA or RNA substrates. To determine whether simpler, smaller RNA-guided proteins occurred in nature, terabase-scale metagenomic datasets were queried for uncharacterized genes proximal to both a CRISPR array and cas1, the gene that encoded the universal CRISPR integrase. This analysis identified a diverse family of CRISPR-Cas systems that contain cas1, cas2, cas4, and cas14, described herein, encoding a 40-70 kD polypeptide (FIG. 8, Panel A). Twenty-four (24) different cas14 gene variants have been identified that cluster into three subgroups (Cas14a-c) based on comparative sequence analysis (FIG. 8, Panels A-B, FIG. 9, FIG. 10). Cas14 proteins were ~400-700 amino acids (aa), about half the size of previously known class 2 CRISPR RNA-guided enzymes (FIG. 8, Panels C-D). While the identified Cas14 proteins exhibited considerable sequence diversity, all were united by the presence of a predicted RuvC nuclease domain, whose organization was characteristic of Type V CRISPR-Cas DNA-targeting enzymes (FIG. 8, Panel D).

The identified Cas14 proteins occurred almost exclusively within DPANN, a super-phylum of symbiotic archaea characterized by small cell and genome sizes. Phylogenetic comparisons showed that Cas14 proteins were widely diverse with similarities to C2c10 and C2c9, families of bacterial RuvC-domain-containing proteins that were sometimes found near a CRISPR array but never together with other cas genes (FIG. 8, Panel B and FIG. 9). This observation and the small size of c2c10 and cas14 genes made it improbable that these systems could function as standalone CRISPR effectors.

FIG. 8, Panels A-D depict architecture and phylogeny of CRISPR-Cas14 genomic loci. FIG. 8, Panel A depicts a phylogenetic tree of Type V CRISPR systems. Newly identified miniature CRISPR systems are highlighted in orange. FIG. 8, Panel B depicts representative loci architectures for C2c10 and CRISPR-Cas14 systems. FIG. 8, Panel C depicts the length distribution of Cas14a-c systems compared to Cas12a-e and Cas9. FIG. 8, Panel D depicts the domain organization of Cas14a compared to Cas9 and Cas12a. Protein lengths are drawn to scale.

FIG. 9 depicts the maximum likelihood tree for known Type V CRISPR effectors and class 2 candidates containing a RuvC domain. Inset shows individual orthologs for each newly identified subtype. FIG. 10 depicts a maximum likelihood tree for Cas1 from known CRISPR systems.

Example 3

Figure 14A:
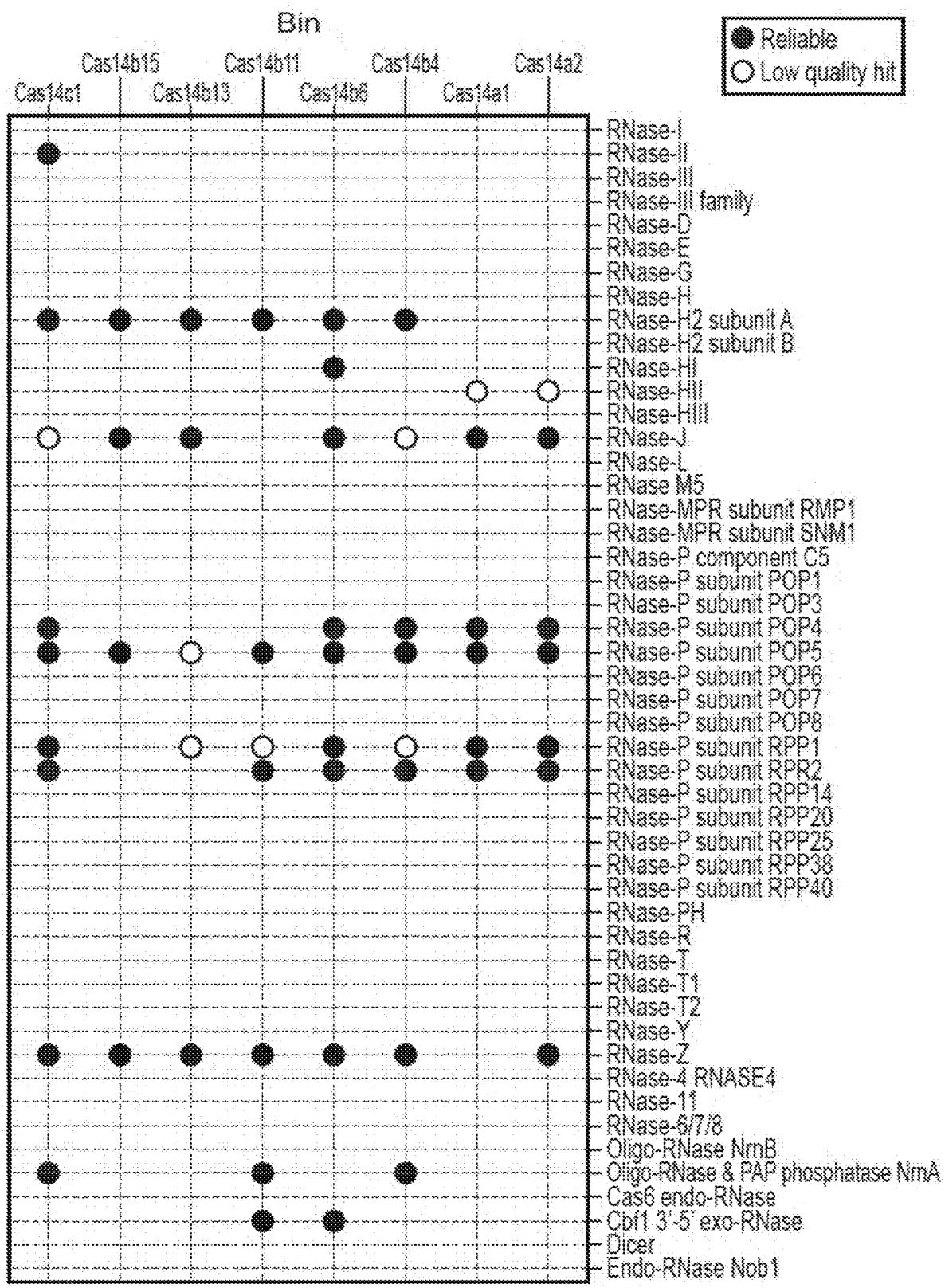
FIGS. 14A-14B depict RNA processing and heterologous expression by CRISPR-Cas14.
Figure 14B:
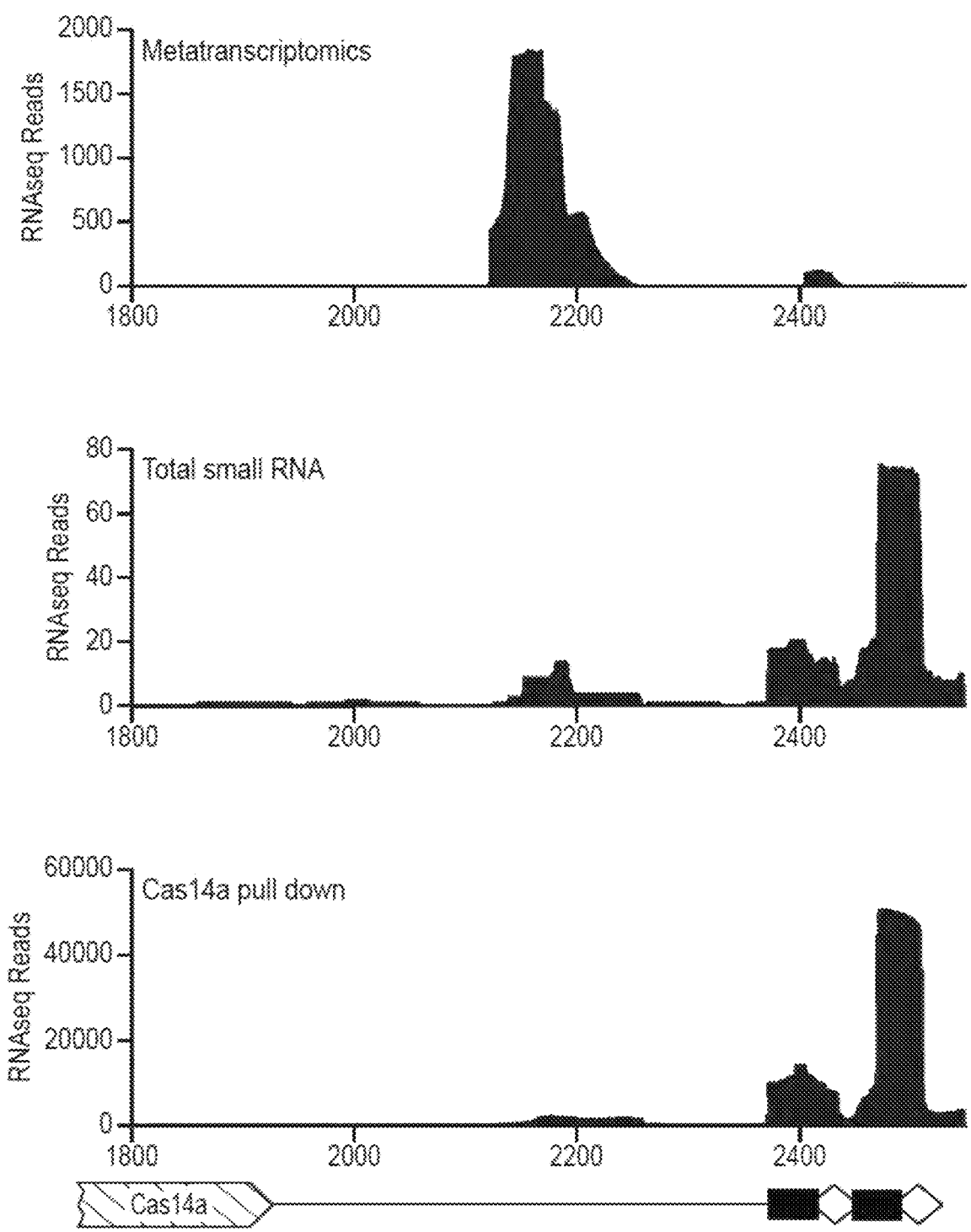

Based on their proximity to conserved genes responsible for creating genetic memory of infection (cas1, cas2, cas4) (FIG. 11, Panel A), it was explored whether CRISPR-Cas14 systems actively acquired DNA sequences into their CRISPR arrays. Assembled metagenomic contiguous DNA sequences (contigs) for multiple CRISPR-Cas14 loci revealed that otherwise identical CRISPR systems showed diversity in their CRISPR arrays, suggesting active adaptation to new infections (FIG. 11, Panel B and FIG. 12, Panel A). Without intending to be bound by any particular theory, it is proposed that the active acquisition of new DNA sequences indicated that these CRISPR-Cas14 loci encoded functional enzymes with nucleic acid targeting activity despite their small size. To test this possibility, it was investigated whether RNA components were produced from CRISPR-Cas14 loci. Environmental metatranscriptomic sequencing data were analyzed for the presence of RNA from the native archaeal host that contains CRISPR-Cas14a (FIG. 12, Panel B and FIG. 13, Panel A). In addition to CRISPR RNAs (crRNAs), a highly abundant non-coding RNA was mapped to about a 130-base pair sequence located between cas14a and the adjacent CRISPR array. The 20 nucleotides (nts) at the 3' end of this transcript were mostly complementary to the repeat segment of the crRNA (FIG. 12, Panel C and FIG. 13, Panel B), as observed for trans-activating CRISPR RNAs (tracrRNAs) found in association with Cas9, Cas12b and Cas12e CRISPR systems. In these previously studied systems, the double-stranded-RNA-cutting enzyme Ribonuclease III (RNase III) generated mature tracrRNAs and crRNAs, but no genes encoding RNase III were present in cas14-containing reconstructed genomes (FIG. 14, Panel A). This observation implied that an alternative mechanism for CRISPR-associated RNA processing existed in these hosts.

Figure 15A:
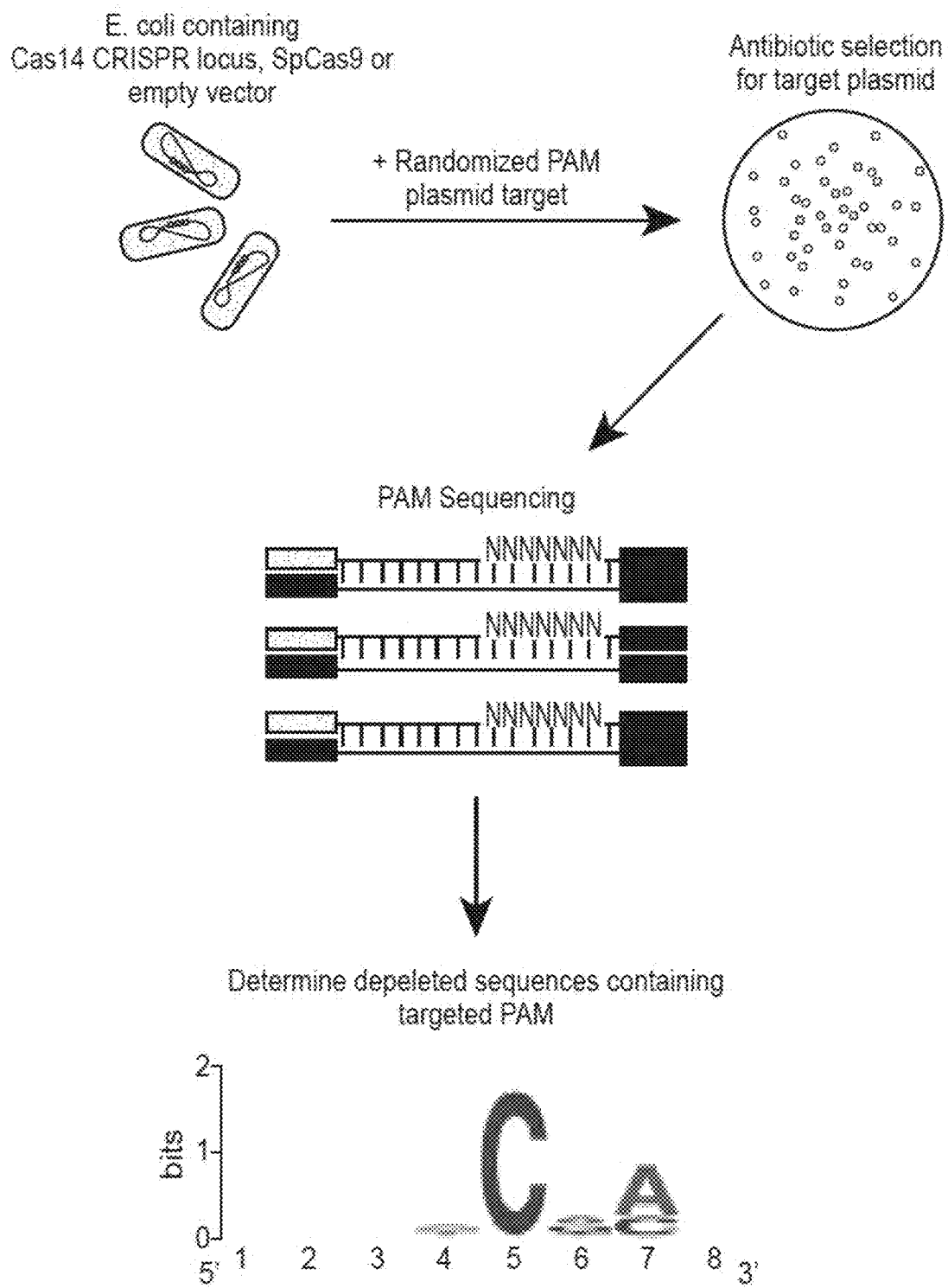
Figure 15D:
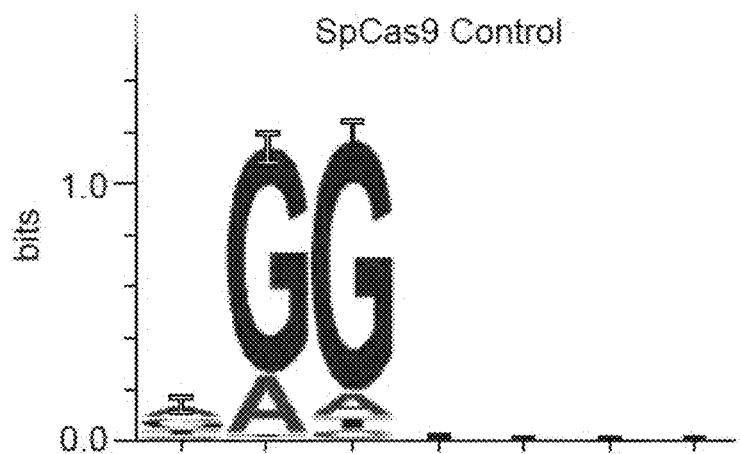

To test whether the Cas14a proteins and associated RNA components could assemble in a heterologous organism, a plasmid was introduced into E. coli containing a minimal CRISPR-Cas14a locus that included the Cas14 gene, the CRISPR array and intergenic regions containing the putative tracrRNA. Affinity purification of the Cas14a protein from cell lysate and sequencing of co-purifying RNA revealed a highly abundant mature crRNA as well as the putative tracrRNA, suggesting that Cas14 associated with both crRNA and tracrRNA (FIG. 14, Panel B). The calculated mass of the assembled Cas14a protein-tracrRNA-crRNA particle was 48% RNA by weight compared to just 17% for S. pyogenes Cas9 (SpCas9) (FIG. 12, Panel D) and 8% for F. novicida Cas12a (FnCas12a), hinting at a central role of the RNA in the architecture of the Cas14a complex. Known class 2 CRISPR systems required a short sequence called a protospacer adjacent motif (PAM) to target double-stranded DNA (dsDNA). To test whether Cas14a required a PAM and could conduct dsDNA interference, E. coli was transformed expressing a minimal Cas14a locus with a dsDNA plasmid containing a randomized PAM region next to a sequence matching the target-encoding sequence (spacer) in the Cas14 array. No depletion of a PAM sequence was detected among E. coli transformants, suggesting that the CRISPR-Cas14a system was either unable to target dsDNA, could do so without requiring a PAM, or was inactive in this heterologous host (FIG. 15, Panels A-D).

FIG. 11, Panels A-B depict acquisition of new spacers by CRISPR-Cas14 systems. FIG. 11, Panel A depicts alignment of Cas14 Cas1 orthologs. Expansion shows conservation of previously implicated active site residues highlighted in red boxes. FIG. 11, Panel B depicts multiple CRISPR arrays assembled for various CRISPR-Cas14 systems revealing spacer diversity for these CRISPR systems. Orange arrows indicate repeats while variously colored boxes indicate unique spacers.

FIG. 12, Panels A-D depict that CRISPR-Cas14a actively adapts and encodes a tracrRNA. FIG. 12, Panel A depicts pacer diversity for Cas14a and Cas14b with CRISPR repeats diagramed in orange and unique spacers shown in different colors. FIG. 12, Panel B depicts metatranscriptomics reads mapped to Cas14a1 and Cas14a3. Inset shows expansion of most abundant repeat and spacer sequence. FIG. 12, Panel C depicts in silico predicted structure of Cas14a1 crRNA and tracrRNA. RNase III orthologs were not identified in host genomes (FIG. 14, Panel A). FIG. 12, Panel D depicts fraction of various CRISPR complexes mass made up of by RNA and protein.

FIG. 13, Panels A-B depict metatranscriptomics for CRISPR-Cas14 loci. FIG. 13, Panel A depicts environmental RNA sequencing reads for Cas14a orthologs. Location of Cas14 and the CRISPR array indicated below. RNA structures to the right show the in silico predicted structure of the tracrRNA identified from metatranscriptomics. FIG. 13, Panel B depicts predicted hybridization for Cas14a1 crRNA:tracrRNA duplex.

FIG. 14, Panels A-B depict RNA processing and heterologous expression by CRISPR-Cas14. FIG. 14, Panel A depicts the presence of common RNase orthologs in Cas14 containing genomes. Light purple represents hits that were significantly shorter than the expected length for the given RNase. Note that RNase III is absent in all investigated genomes. FIG. 14, Panel B depicts small RNAseq reads from heterologous expression of Cas14a1 locus in E. coli (FIG. 14, Panel B, bottom two graphs) compared to metatranscriptomic reads (FIG. 14, Panel B, top graph). Pull down refers to RNA that copurified with Ni-NTA affinity purified Cas14a1.

FIG. 15, Panels A-D depict plasmid depletion by Cas14a1 and SpCas9. FIG. 15, Panel A depicts a diagram outlining a PAM discovery experiment. E. coli expressing the CRISPR system of interest was challenged with a plasmid containing a randomized PAM sequence flanking the target. The surviving (transformed) cells were harvested and sequenced along with a control harboring an empty vector. The depleted sequences were then sequenced and PAMs depleted more than the PAM Depletion Value Threshold (PDVT) were used to generate a Weblogo. FIG. 15, Panels B-D depict PAM sequences depleted by heterologously expressed Cas14a1 transformed with a target plasmid containing a randomized PAM sequence 5' (FIG. 15, Panel B) or 3' (FIG. 15, Panel C) of the target. "No sequences" indicated that no sequences were found to be depleted at or above the given PDVT.

Example 4

Figure 16A:
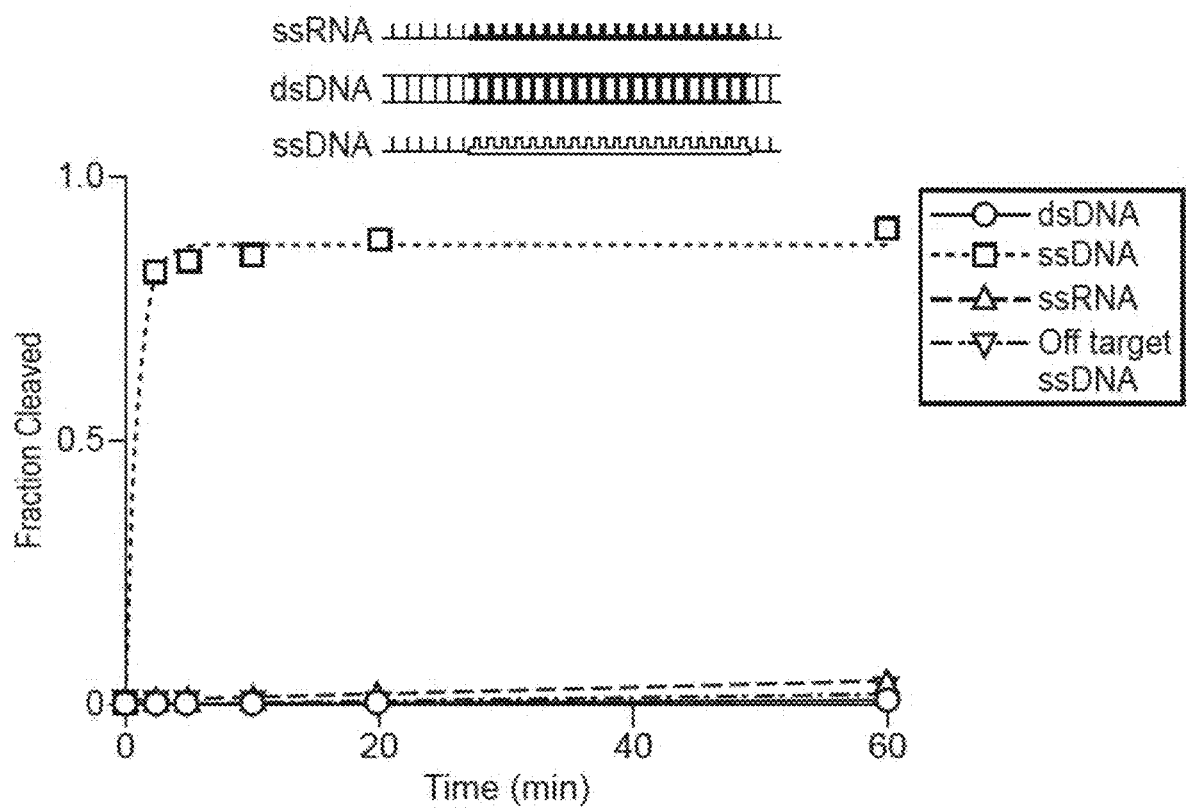
Figure 16D:
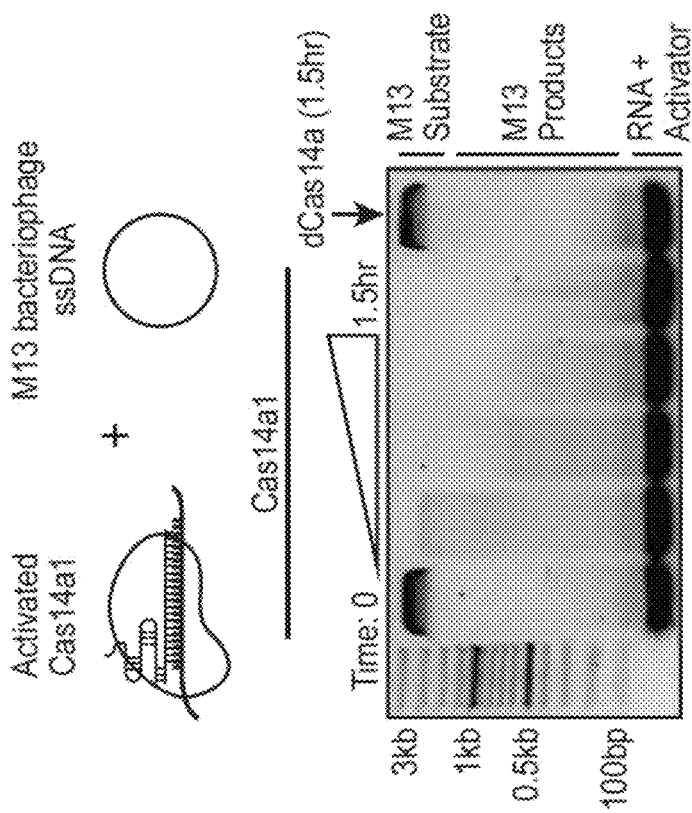
Figure 16C:
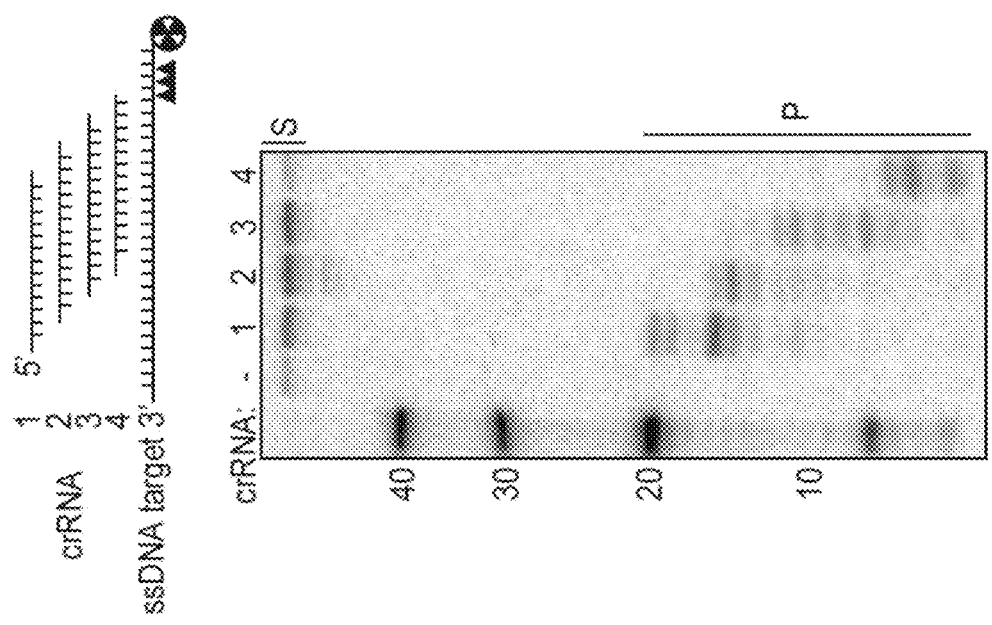
Figure 17A:
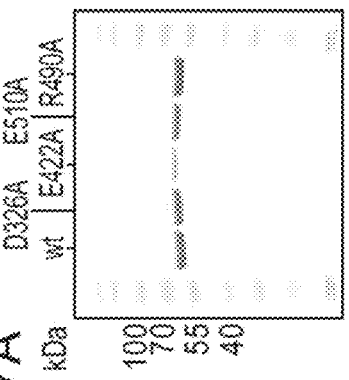
Figure 17B:
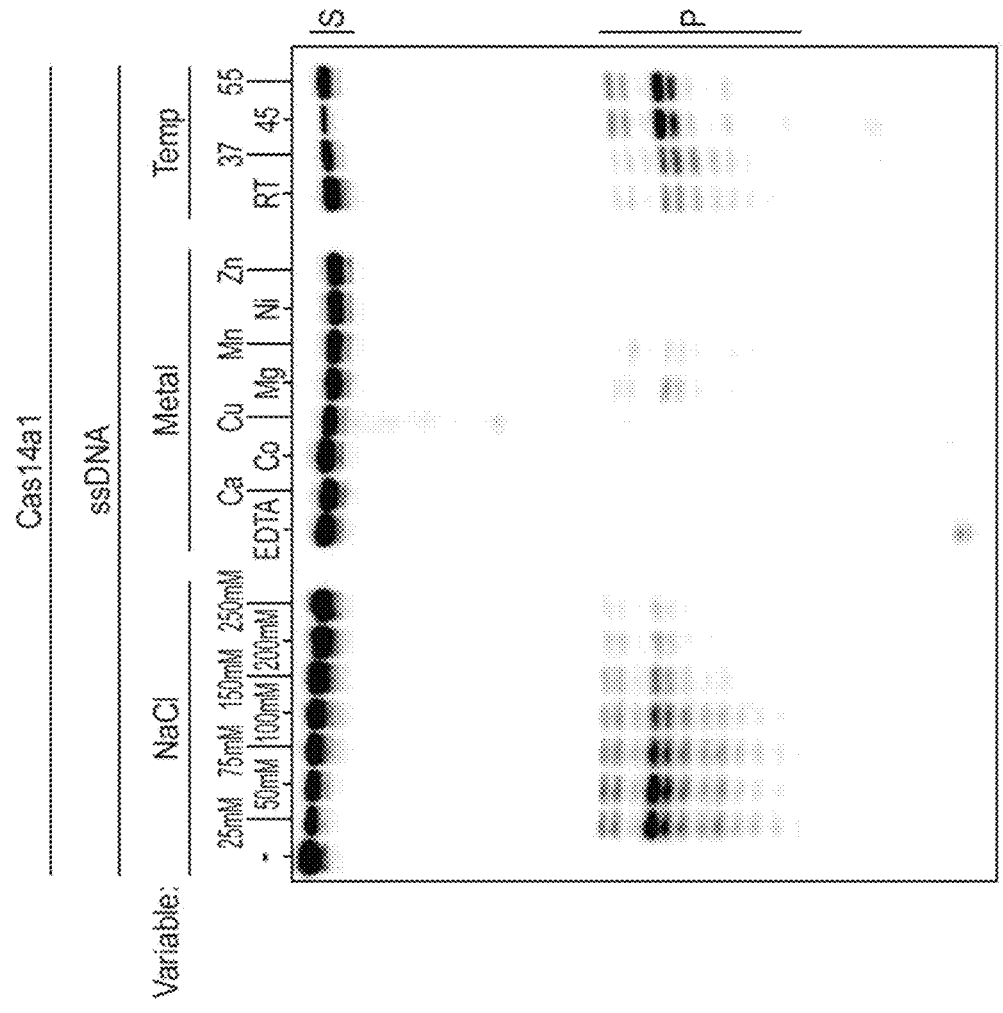
Figure 17C:
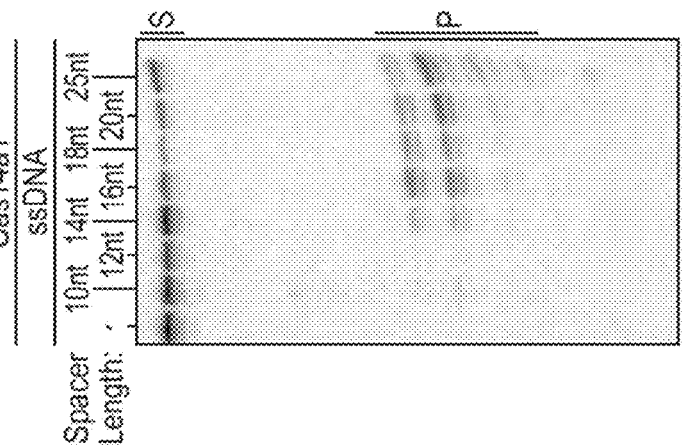
Figure 17D:
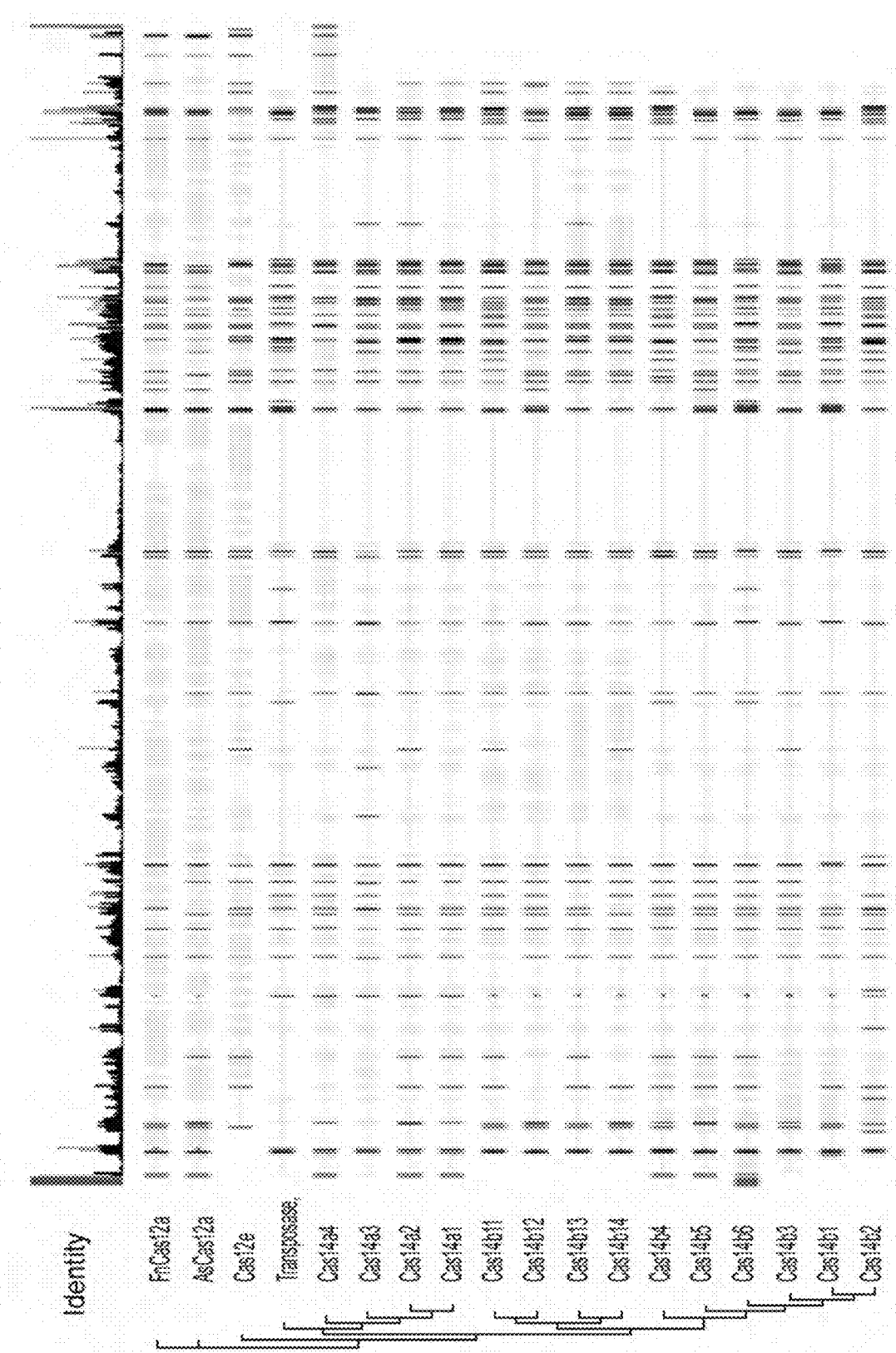
Figure 17E:
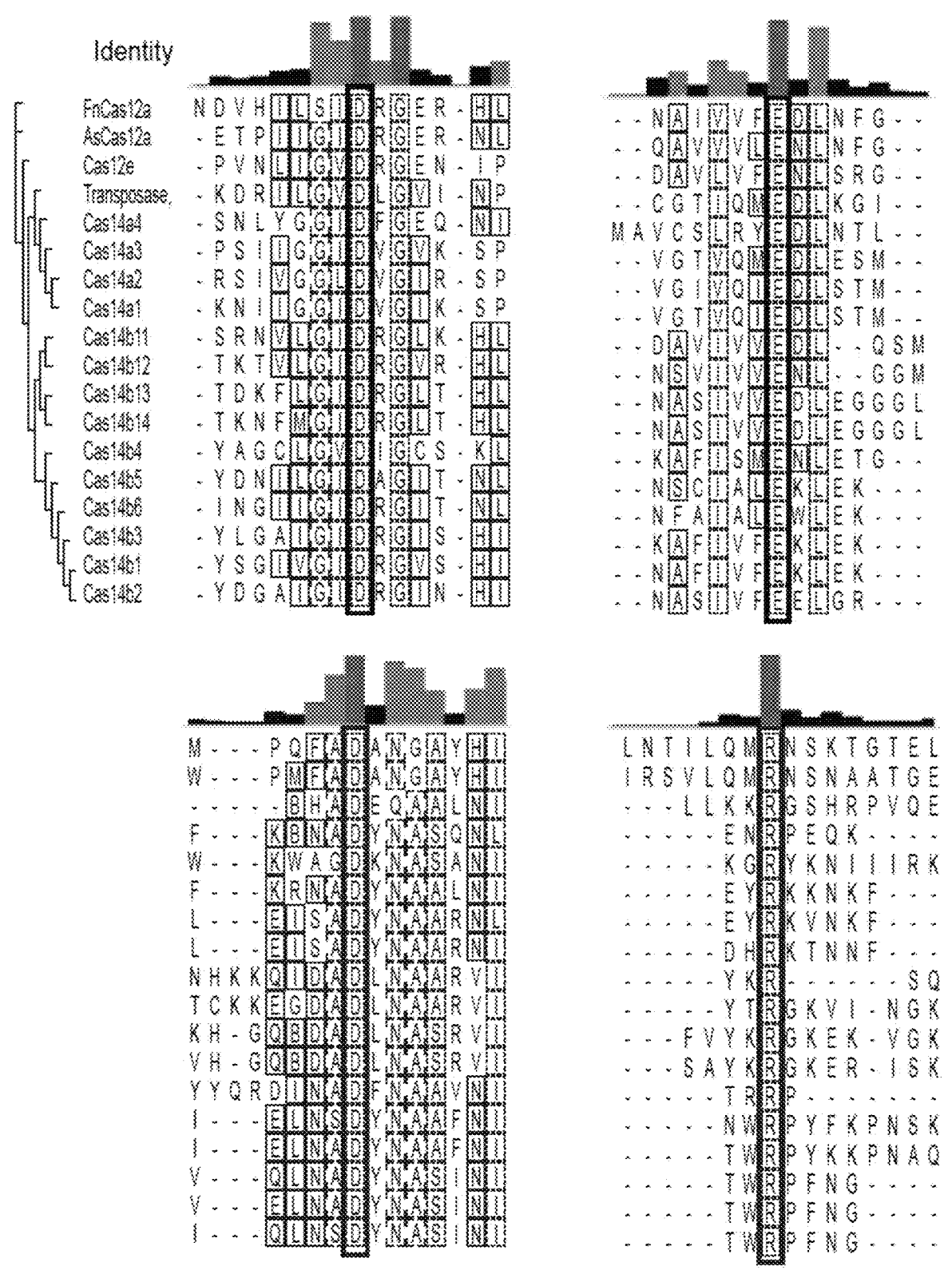
Figure 18:
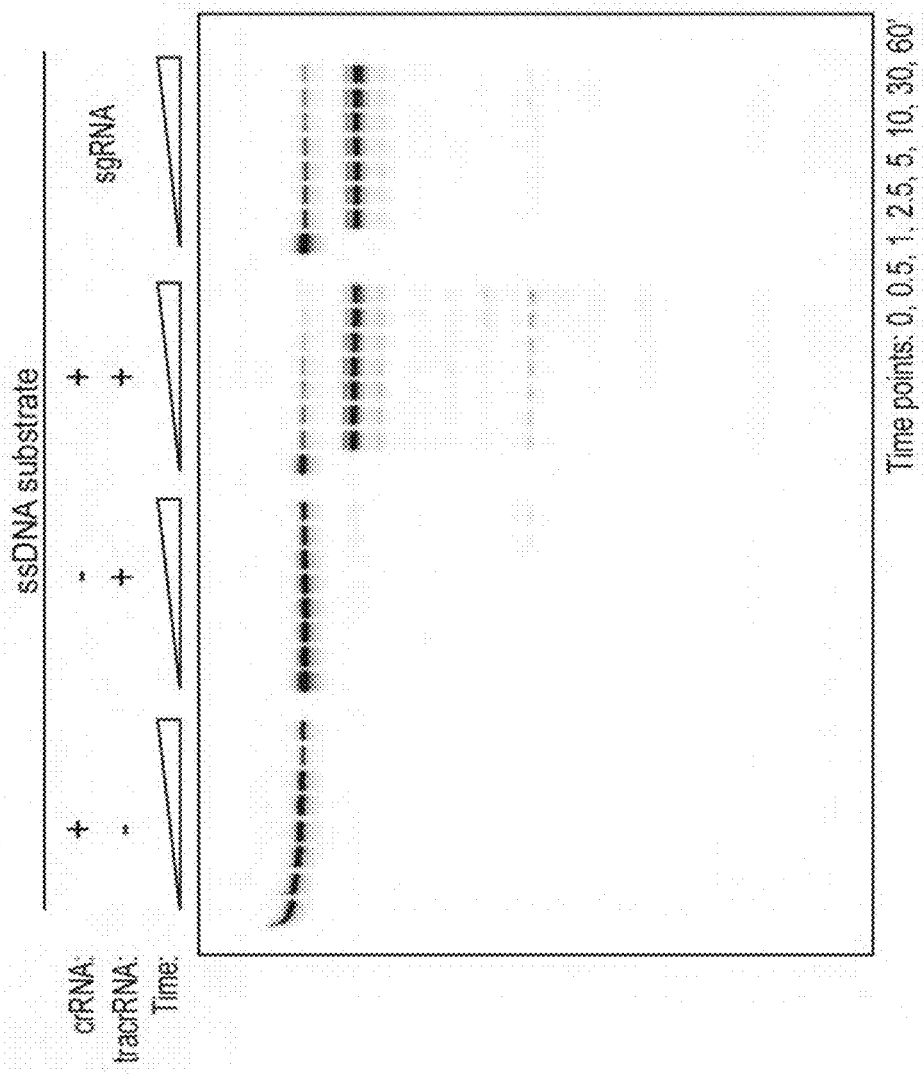
FIG. 18 depicts kinetics of Cas14a1 cleavage of ssDNA with various guide RNA components.
Figure 17F:
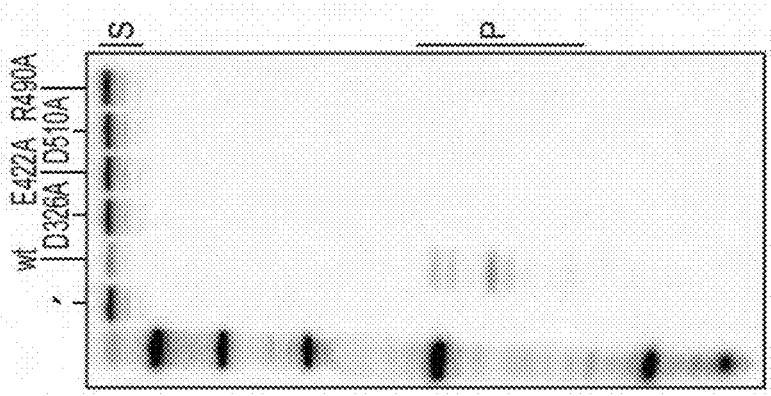
Figure 19E:
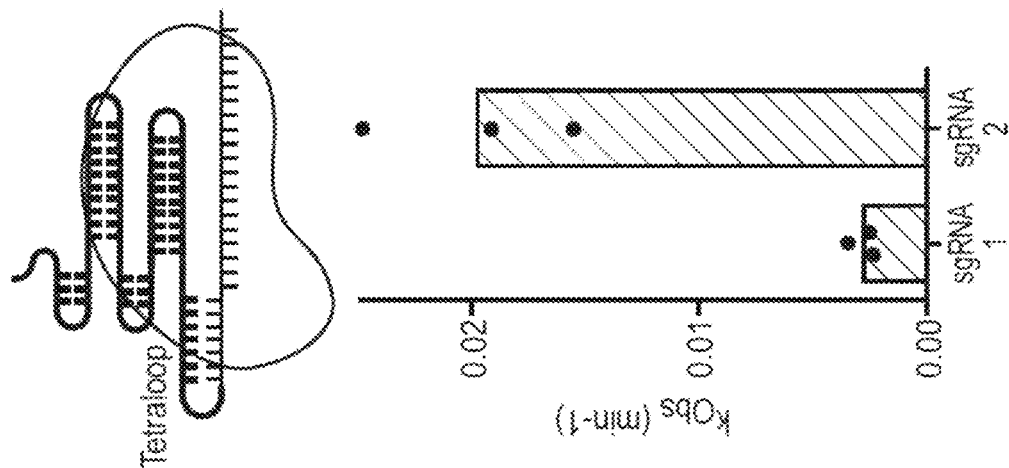
Figure 19D:
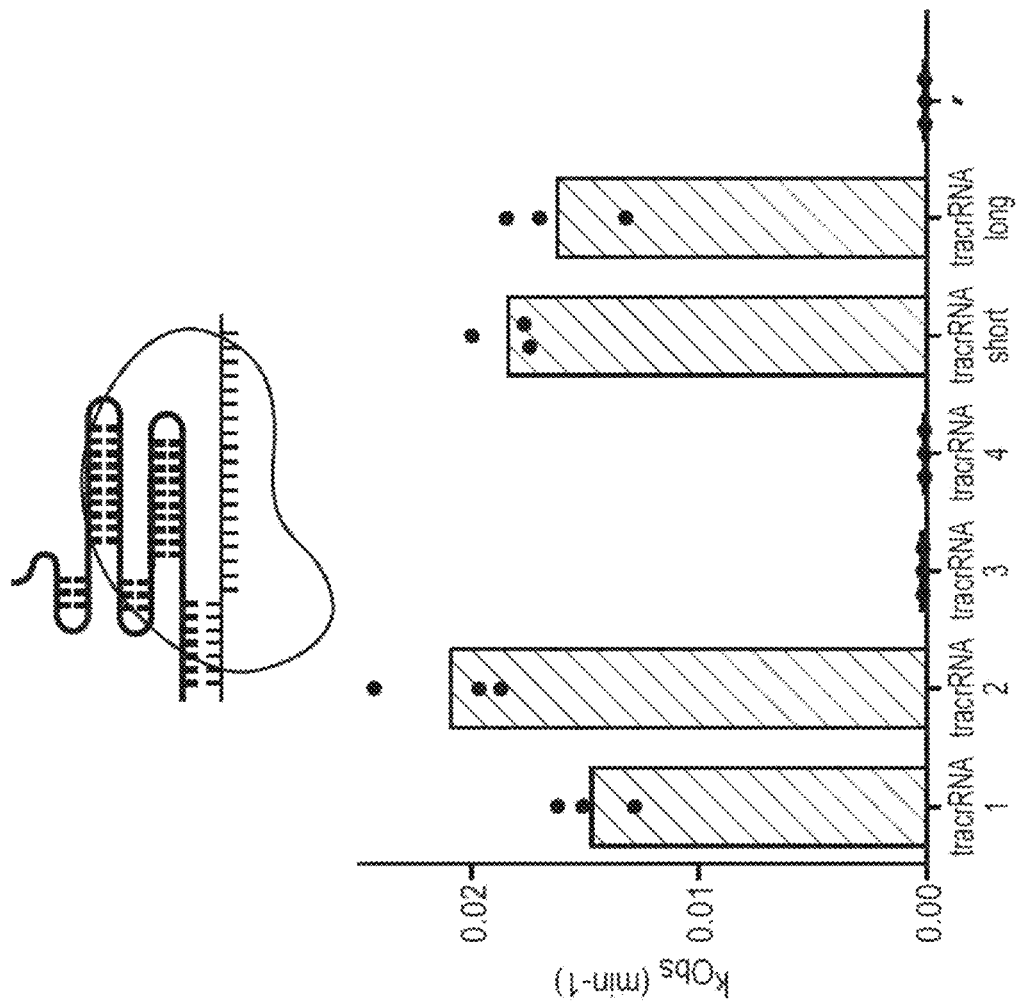
Figure 20B:
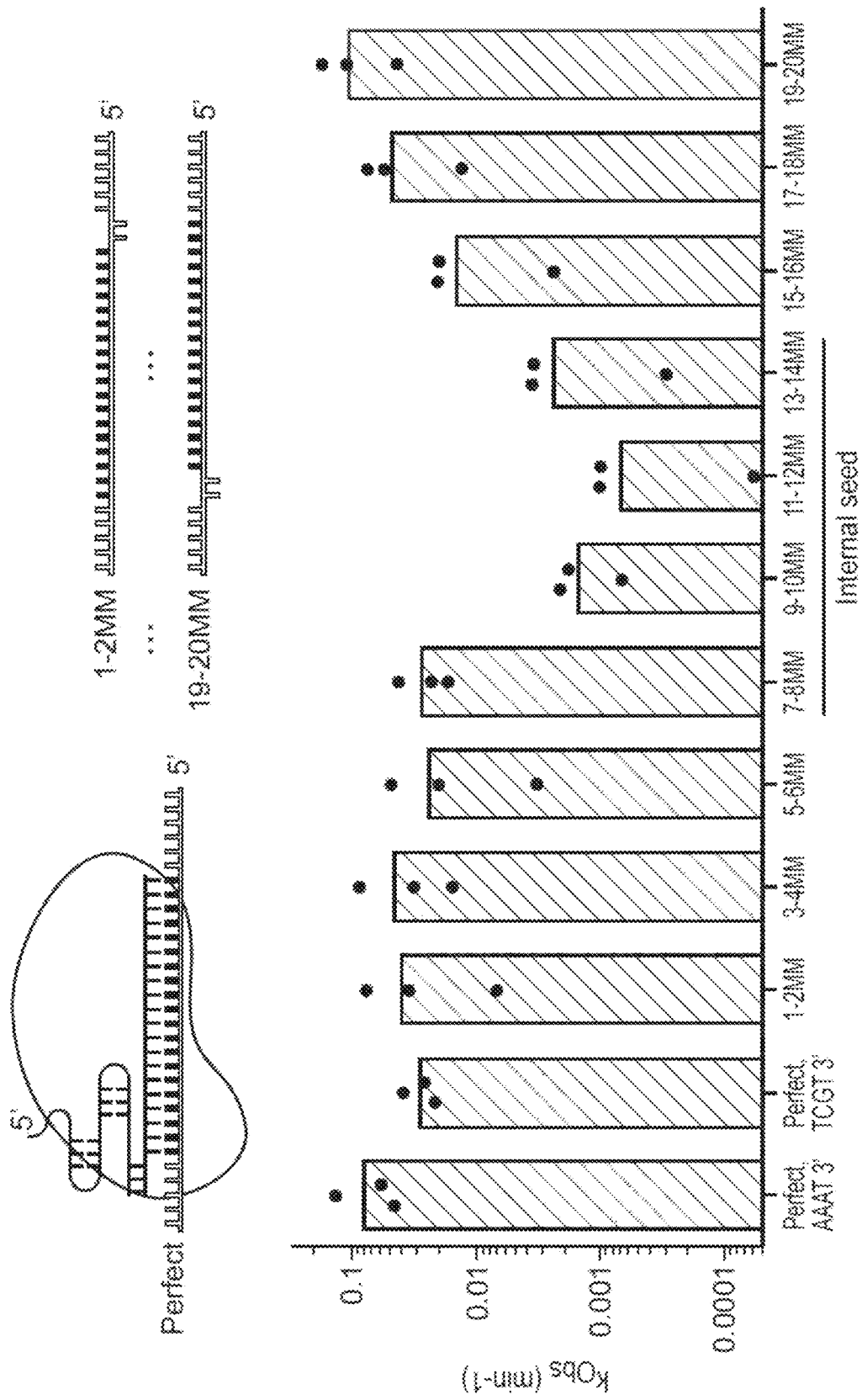
Figure 20C:
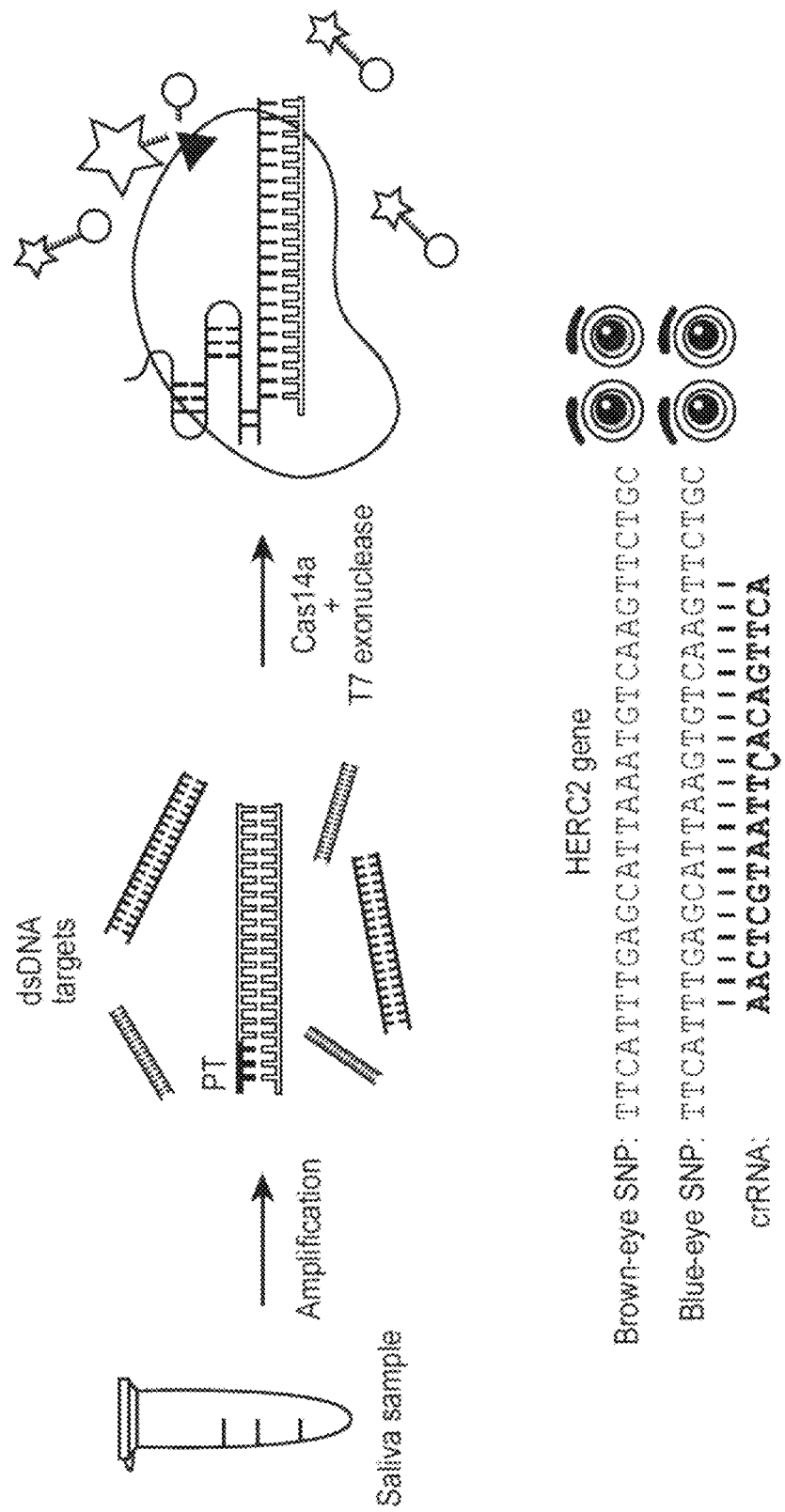
Figure 20E:
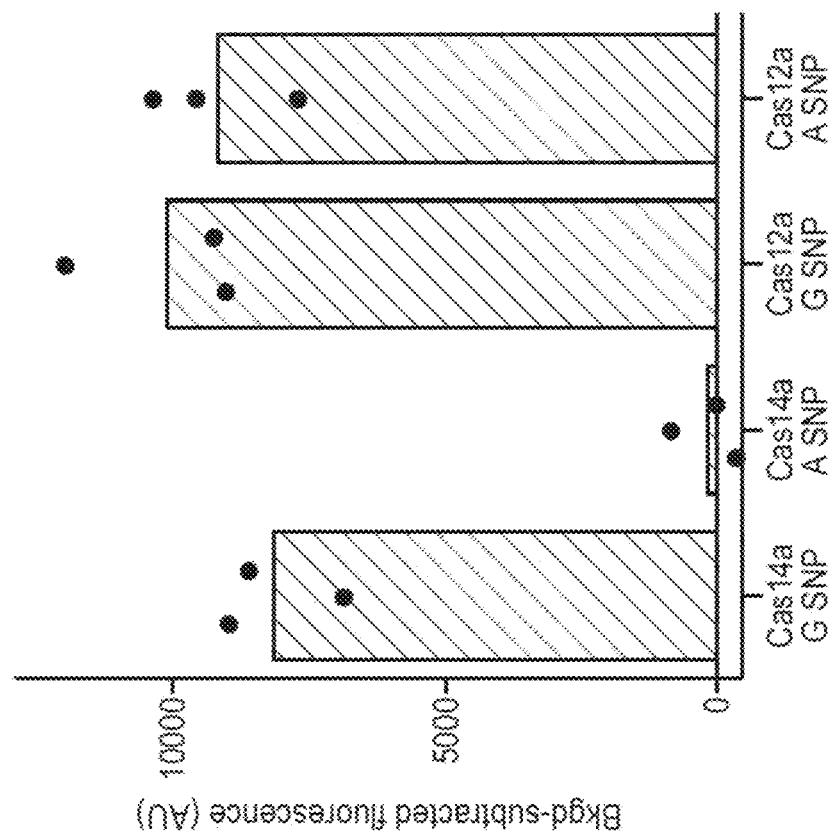
Figure 20D:
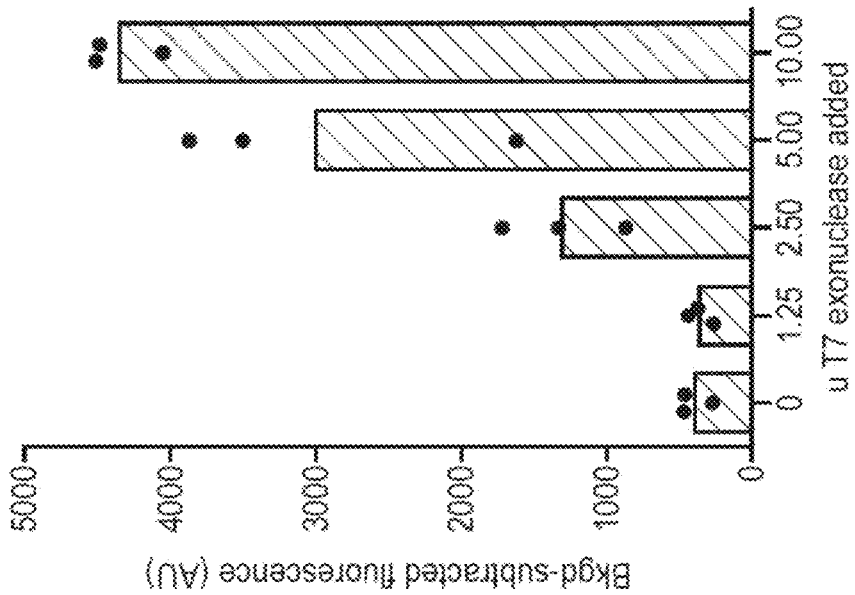
Figure 21B:
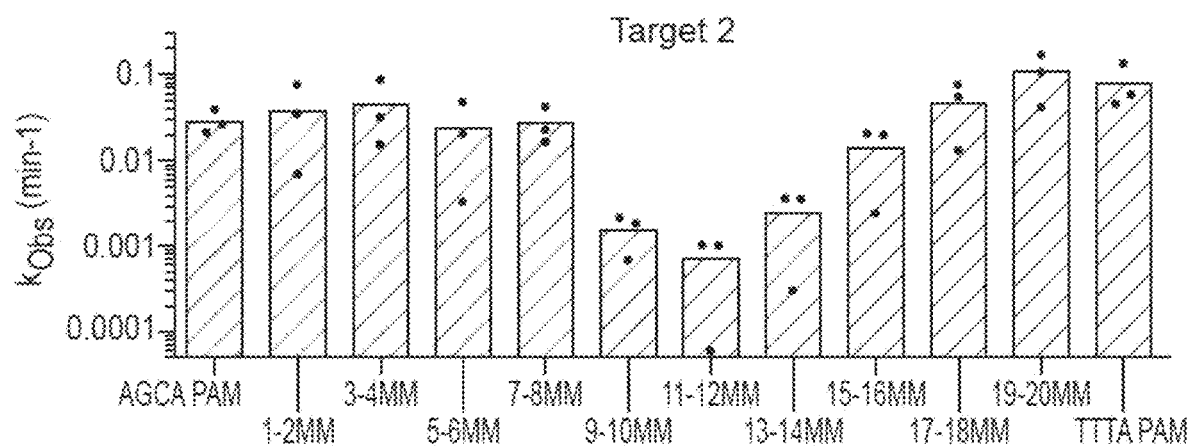
Figure 21C:
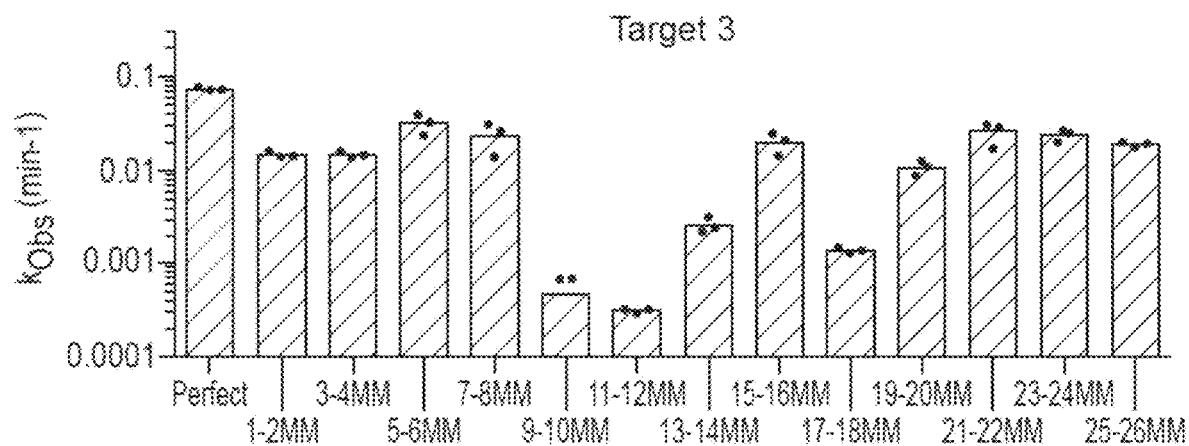
Figure 21D:
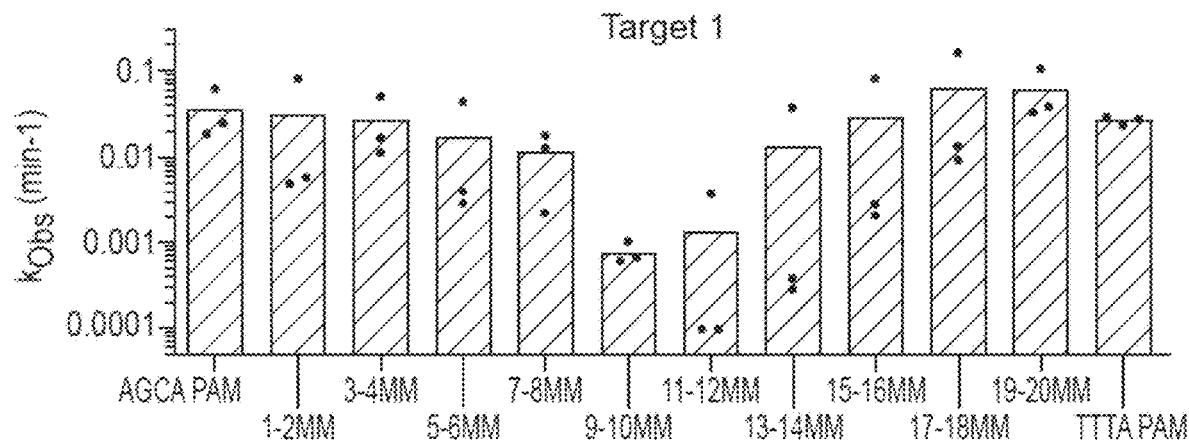
Figure 21E:
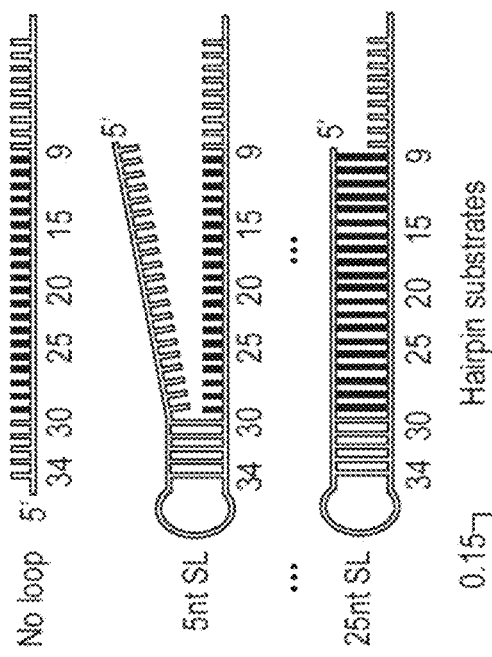
Figure 21F:
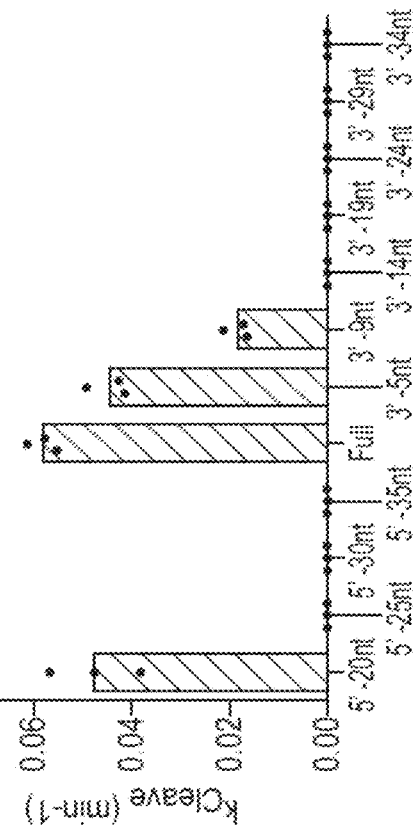

It was tested whether purified Cas14a-tracrRNA-crRNA complexes were capable of RNA-guided nucleic acid cleavage in vitro. All currently reconstituted DNA-targeting class 2 interference complexes were able to recognize both dsDNA and ssDNA substrates. Purified Cas14a-tracrRNA-crRNA complexes were incubated with radiolabeled target oligonucleotides (ssDNA, dsDNA, and ssRNA) bearing 20-nucleotide sequence complementary to the crRNA guide sequence, or a non-complementary ssDNA, and these substrates were analyzed for Cas14a-mediated cleavage. Only in the presence of a complementary ssDNA substrate was any cleavage product detected (FIG. 16, Panel A and FIG. 17, Panels A-C), and cleavage was dependent on the presence of both tracrRNA and crRNA, which could also be combined into a single-guide RNA (sgRNA) (FIG. 16, Panel B and FIG. 18). The lack of detectable dsDNA cleavage suggested that Cas14a targeted ssDNA selectively, although it was possible that some other factor or sequence requirement could enable dsDNA recognition in the native host. Mutation of the conserved active site residues in the Cas14a RuvC domain eliminated cleavage activity (FIG. 17, Panel A), implicating RuvC as the domain responsible for DNA cutting. Moreover, Cas14a DNA cleavage was sensitive to truncation of the RNA components to lengths shorter than the naturally produced sequences (FIG. 16, Panel B and FIG. 19, Panels A-D). These results established Cas14a as the smallest class 2 CRISPR effector demonstrated to conduct programmable RNA-guided DNA cleavage.

It was tested whether Cas14a required a PAM for ssDNA cleavage in vitro by tiling Cas14a guides across a ssDNA substrate (FIG. 16, Panel C). Despite sequence variation adjacent to the targets of these different guides, cleavage was observed for all four sequences. The cleavage sites occurred beyond the guide-complementary region of the ssDNA and shifted in response to guide binding position (FIG. 16, Panel C). These data demonstrated Cas14a was an ssDNA-targeting CRISPR endonuclease that did not require a PAM for activation.

Based on the observation that Cas14a cut outside of the crRNA/DNA targeting heteroduplex, it was proposed that Cas14a may possess target-activated non-specific ssDNA cleavage activity, similar to the RuvC-containing enzyme Cas12a. To test this possibility, Cas14a-tracrRNA-crRNA was incubated with a complementary activator DNA and an aliquot of M13 bacteriophage ssDNA bearing no sequence complementarity to the Cas14a crRNA or activator (FIG. 16, Panel D). The M13 ssDNA was rapidly degraded to small fragments, an activity that was eliminated by mutation of the conserved Cas14a RuvC active site, suggesting that activation of Cas14a resulted in non-specific ssDNA degradation.

To investigate the specificity of target-dependent non-specific DNA cutting activity by Cas14a, a fluorophore-quencher (FQ) assay was adapted in which cleavage of dye-labeled ssDNA generates a fluorescent signal (FIG. 20, Panel A). When Cas14a was incubated with various guide RNA-target ssDNA pairs, a fluorescent signal was observed only in the presence of the cognate target and showed strong preference for longer FQ-containing substrates (FIG. 19, Panel F and FIG. 20, Panel A). Cas14a mismatch tolerance was tested by tiling 2-nt mismatches across the targeted region in various ssDNA substrates. Mismatches near the middle of the ssDNA target strongly inhibited Cas14a activity, revealing an internal seed sequence that was distinct from the PAM-proximal seed region observed for dsDNA-targeting CRISPR-Cas systems (FIG. 20, Panel B and FIG. 21, Panels A-D). Moreover, DNA substrates containing strong secondary structure resulted in reduced activation of Cas14a (FIG. 21, Panel E). Truncation of ssDNA substrates also resulted in reduced or undetectable trans cleavage (FIG. 21, Panel F). These results suggested a mechanism of fidelity distinct from dsDNA-targeting class 2 CRISPR systems, possibly utilizing a preordered region of the crRNA to gate cleavage activity similarly to the RNA-targeting Cas13a enzymes.

Further investigation of compact Type V systems in metagenomic data revealed a large diversity of systems that, like Cas14a-c, include a gene encoding a short RuvC-containing protein adjacent to acquisition-associated cas genes and a CRISPR array. Twenty (20) additional such systems were found that cluster into five main families (Cas14d-h). These families seemed to have evolved from independent domestication events of TnpB, the transposase-associated protein implicated as the evolutionary parent of type V CRISPR effectors. Excluding cas14g, which was related to cas12b, the cas14-like genes formed separate clades on the type V effector phylogeny (FIG. 22, Panels A-B), and their cas1 genes had different origins (FIG. 10, Panel A). Altogether 38 CRISPR-Cas14 systems belonging to eight families (Cas14a-h) were identified and eight additional systems that could not be clustered with the analysis (termed Cas14u, Table 3).

The small size of the Cas14 proteins described herein and their resemblance to type V effector proteins suggested that RNA-guided ssDNA cleavage may have existed as an ancestral class 2 CRISPR system. In this scenario, a small, domesticated TnpB-like ssDNA interference complex may have gained additional domains over time, gradually improving dsDNA recognition and cleavage. Smaller Cas9 orthologs exhibited weaker dsDNA-targeting activity than their larger counterparts but retained the ability to robustly cleave ssDNA. Aside from the evolutionary implications, the ability of Cas14 to specifically target ssDNA suggested a role in defense against ssDNA viruses or mobile genetic elements (MGEs) that propagated through ssDNA intermediates. Without intending to be bound by any particular theory, an ssDNA-targeting CRISPR system may be particularly advantageous in certain marine environments where ssDNA viruses comprised the vast majority of viral abundance.

FIG. 16, Panels A-D depict CRISPR-Cas14a as an RNA-guided DNA-endonuclease. FIG. 16, Panel A depicts cleavage kinetics of Cas14a1 targeting ssDNA, dsDNA, ssRNA and off-target ssDNA. FIG. 16, Panel B depicts a diagram of Cas14a RNP bound to target ssDNA and Cas14a1 cleavage kinetics of radiolabeled ssDNA in the presence of various RNA components. FIG. 16, Panel C depicts tiling of a ssDNA substrate by Cas14a1 guide sequences. FIG. 16, Panel D depicts cleavage of the ssDNA viral M13 genome with activated Cas14a1.

FIG. 17, Panels A-E depict degradation of ssDNA by Cas14a1. FIG. 17, Panel A depicts SDS-PAGE of purified Cas14a1 and Cas14a1 point mutants. FIG. 17, Panel B depicts optimization of salt, cation and temperature for Cas14a1 cleavage of ssDNA targets. FIG. 17, Panel C depicts radiolabeled cleavage of ssDNA by Cas14a1 with spacer sequences of various lengths. FIG. 17, Panel D depicts alignment of Cas14 with previously studied Cas12 proteins to identify RuvC active site residues and FIG. 17, Panel E depicts cleavage of ssDNA by purified Cas14a1 RuvC point mutants.

FIG. 18 depicts the kinetics of Cas14a1 cleavage of ssDNA with various guide RNA components.

FIG. 19, Panels A-F depict optimization of Cas14a1 guide RNA components. FIG. 19, Panel A depicts a diagram of Cas14a1 targeting ssDNA. Impact on Cas14a1 cleavage of an FQ ssDNA substrate by varying the spacer length (FIG. 19, Panel B), repeat length (FIG. 19, Panel C), tracrRNA (FIG. 19, Panel D), and fusing the crRNA and tracrRNA together (FIG. 19, Panel E). FIG. 19, Panel F depicts a heat map showing the background subtracted fluorescence resulting from cleavage of an ssDNA FQ reporter in the presence of various guide and target combinations.

FIG. 20, Panels A-E depict high fidelity ssDNA SNP detection by CRISPR-Cas14a. FIG. 20, Panel A depicts a fluorescent-quencher (FQ) assay for detection of ssDNA by Cas14a1 and the cleavage kinetics for various length FQ substrates. FIG. 20, Panel B depicts cleavage kinetics for Cas14a1 with mismatches tiled across the substrate (individual points represent replicate measurements). FIG. 20, panel C depicts a diagram of Cas14-DETECTR strategy and HERC2 eye color SNP. FIG. 20, panel D depicts titration of T7 exonuclease and impact on Cas14a-DETECTR. FIG. 20, panel E, depicts SNP detection using Cas14a-DETECTR with a blue-eye targeting guide for a blue-eyed and brown-eyed saliva sample compared to ssDNA detection using Cas12a.

FIG. 21, Panels A-F depict the impact of various activators on Cas14a1 cleavage rate FIG. 21, Panel A depicts a diagram of Cas14a1 targeting of ssDNA with position of mismatches used in panels A-D and raw rates for representative replicates of mismatch (MM) position for Target 1. Cleavage rates for Cas14a targeting substrates with mutations tiled across three different substrates (FIG. 21, Panels B-D). FIG. 21, Panel E depicts trans cleavage rates for substrates with increasing amounts of secondary structure. FIG. 21, Panel F depicts trans leavage rates with truncated substrates. Points represent individual measurements.

Figure 22A:
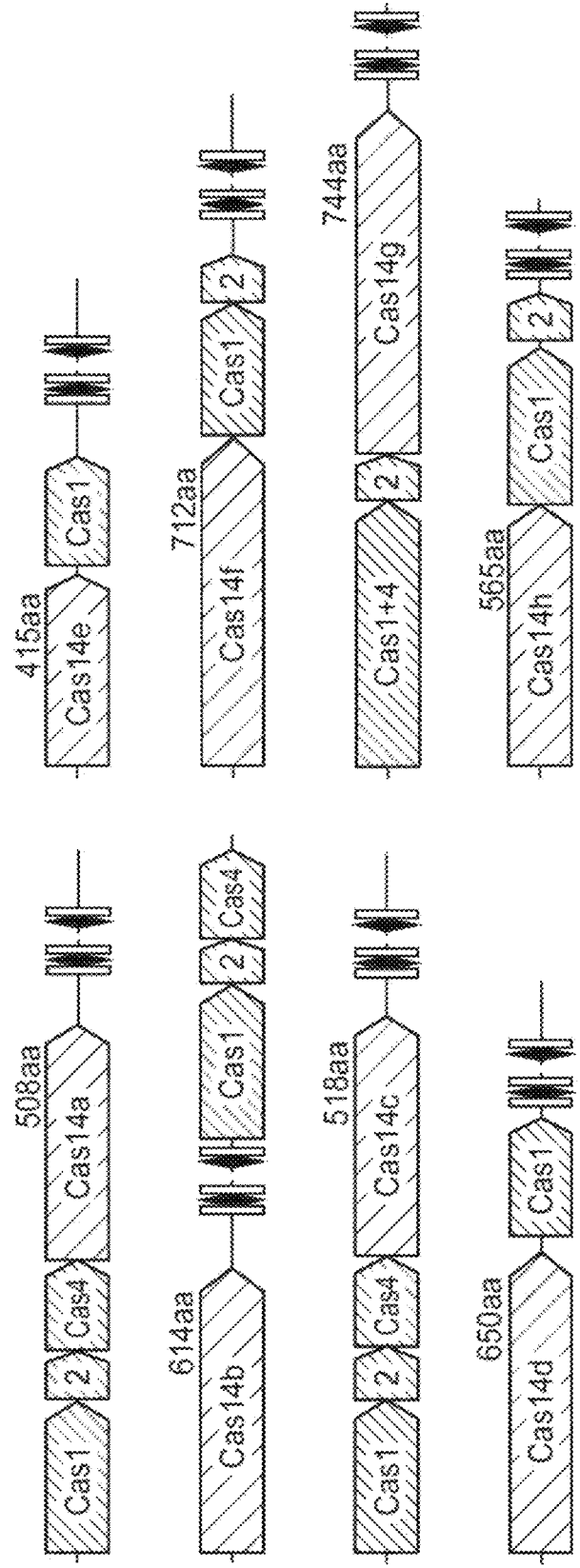
FIGS. 22A-22B depict diversity of CRISPR-Cas14 systems.
Figure 22B:
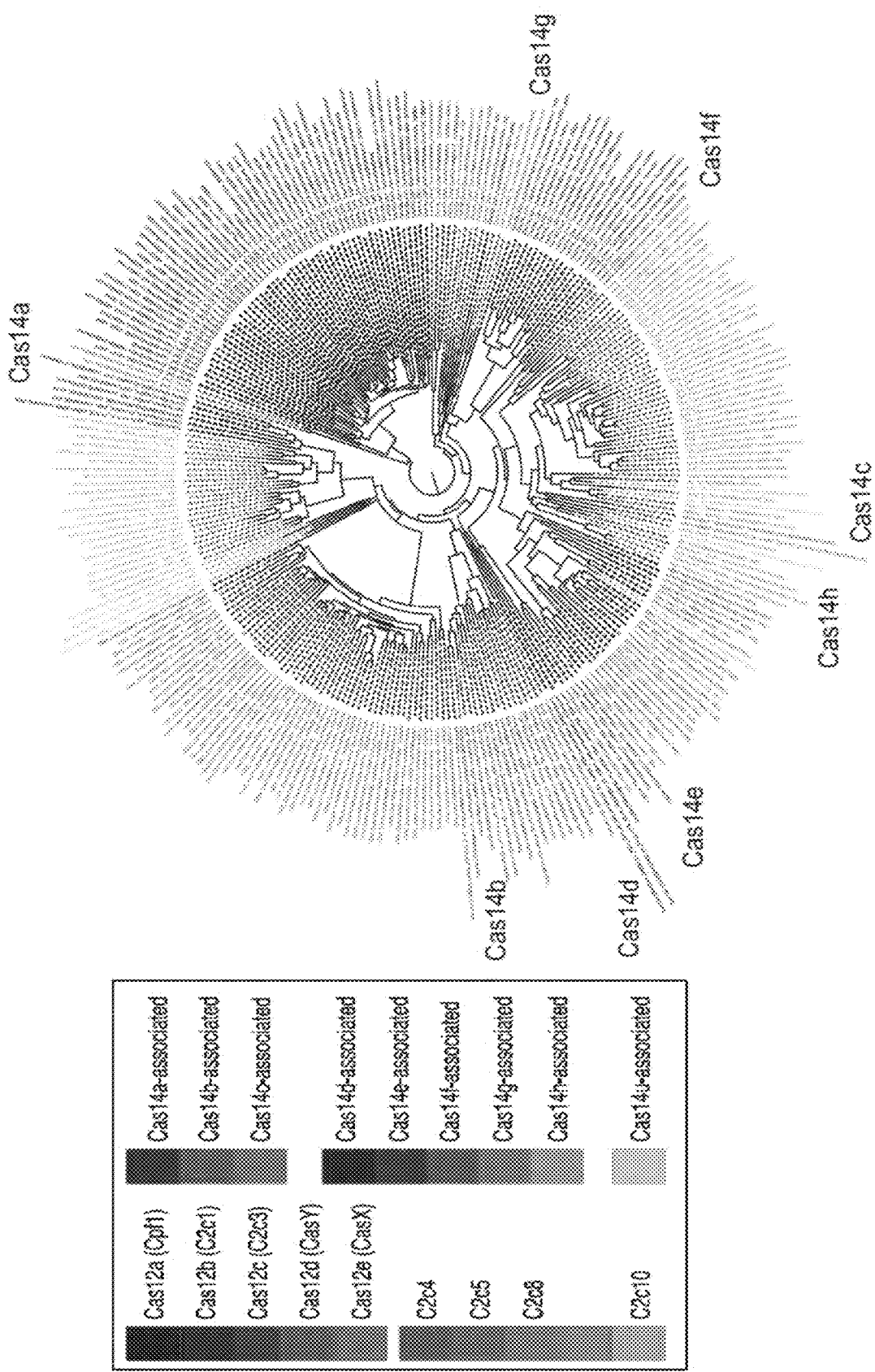

FIG. 22, Panels A-B depict diversity of CRISPR-Cas14 systems. FIG. 22, Panel A depicts representative locus architecture for indicated Cas14 systems. Protein lengths are drawn to scale. FIG. 22, Panel B depicts a maximum likelihood tree for Type V effectors including all eight identified subtypes of Cas14.

Figure 23A:
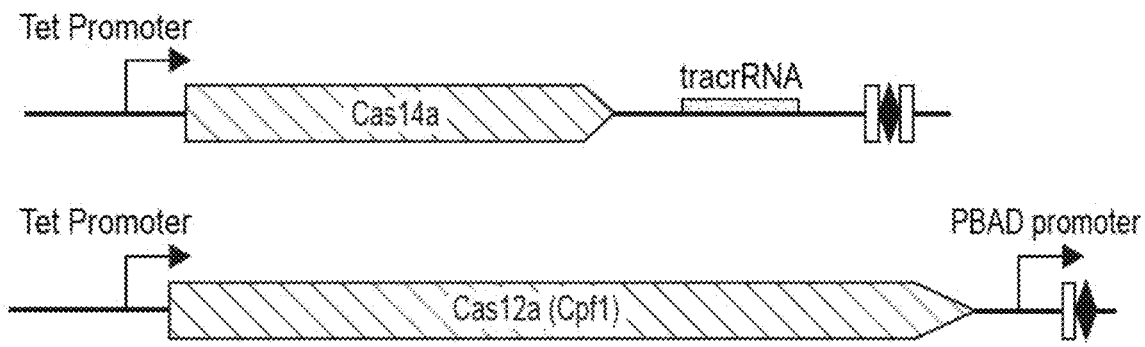
FIGS. 23A-23C depict a test of Cas14a1 mediated interference in a heterologous host. Diagram of Cas14a1 and LbCas12a constructs to test interference in E. coli.
Figure 23B:
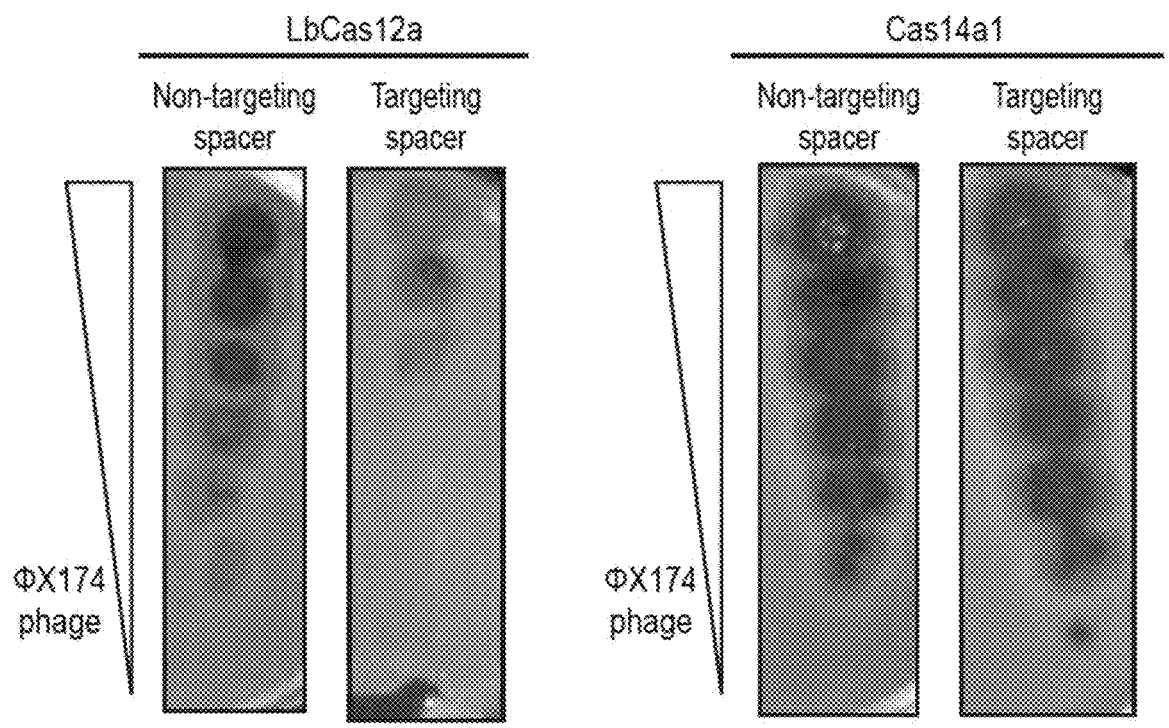
Figure 23C:
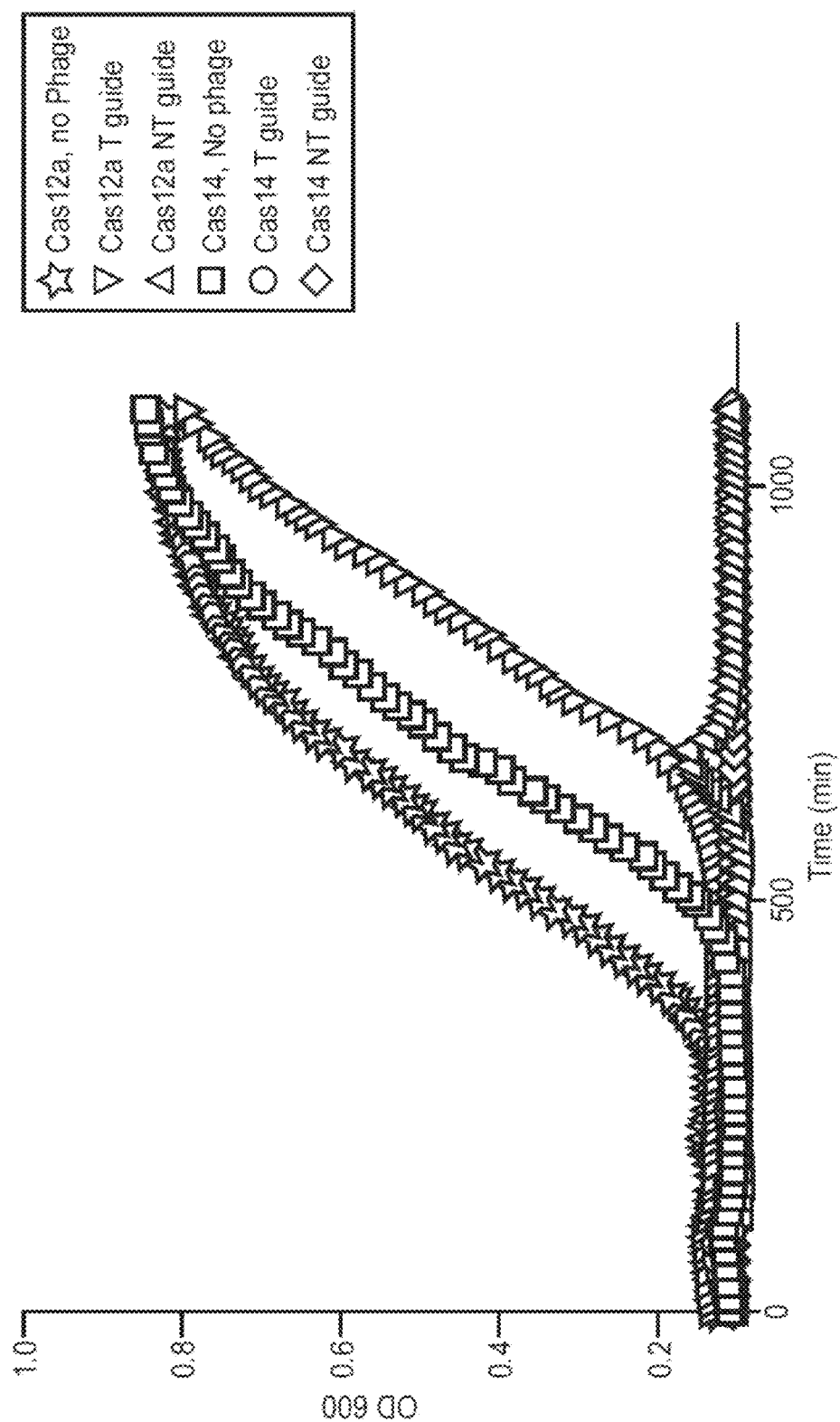
Figure 25A:
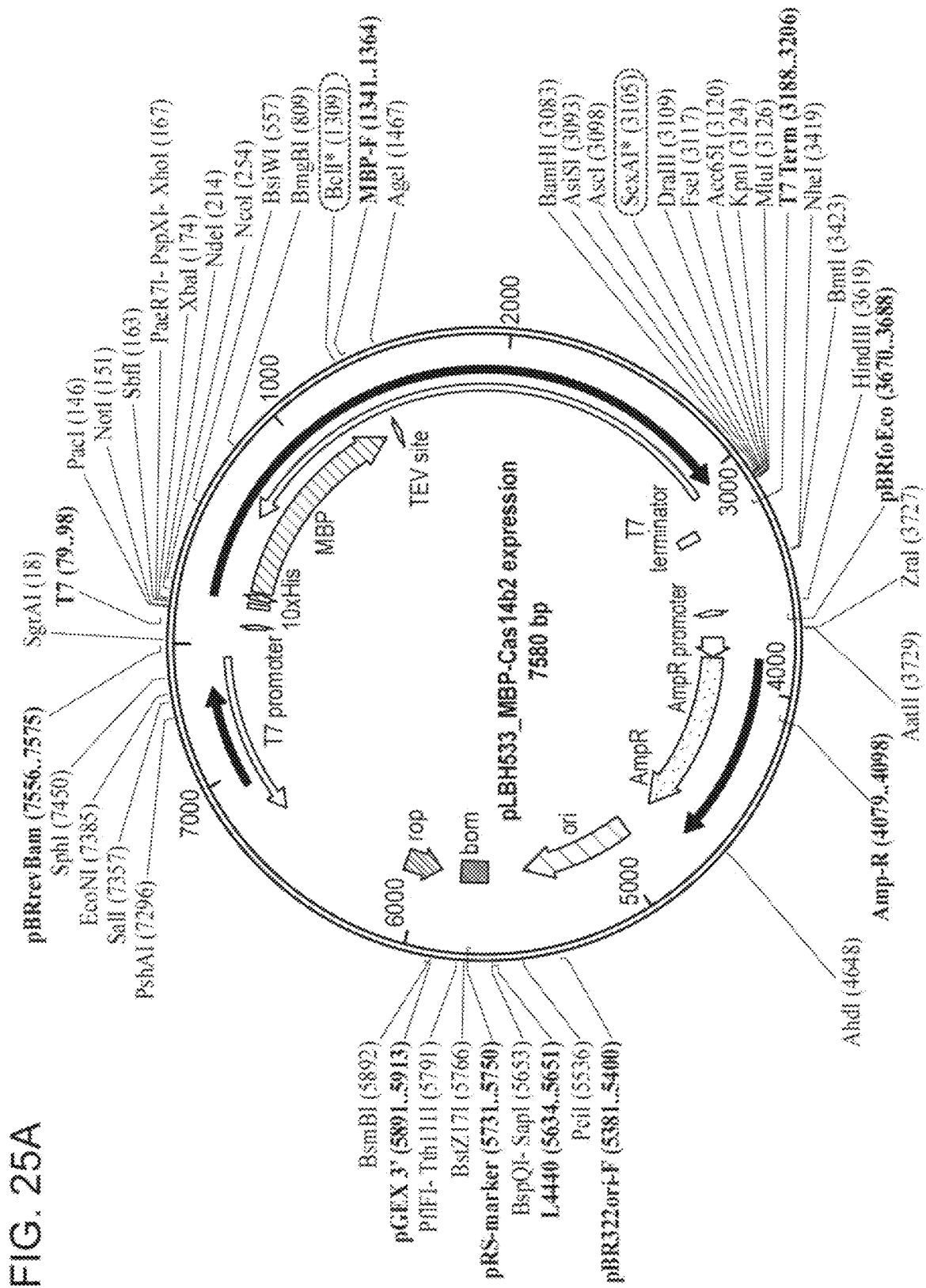
FIGS. 25A-25E depict a sequence map of each of the plasmids disclosed in FIG. 24.
Figure 25B:
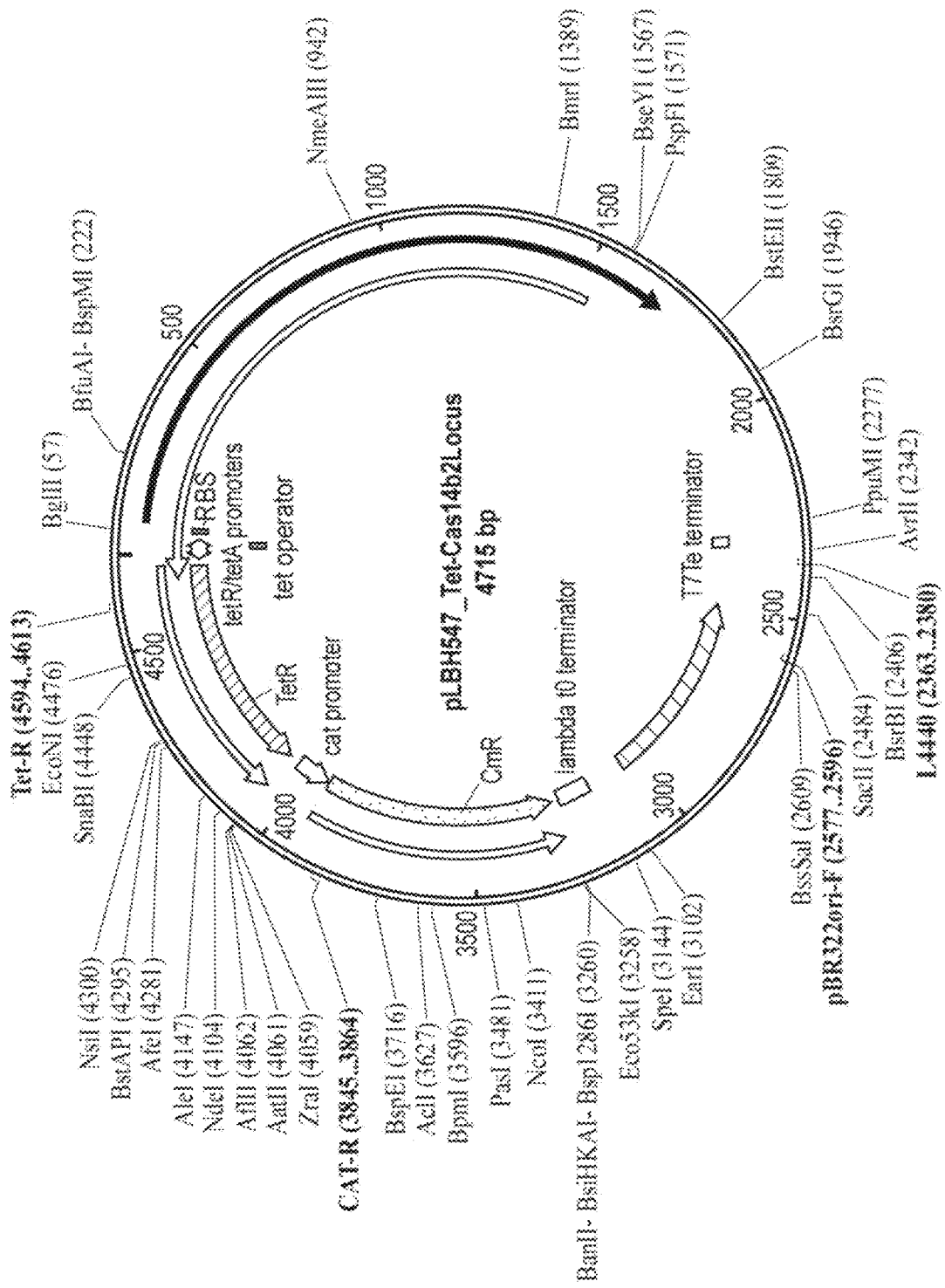
Figure 25C:
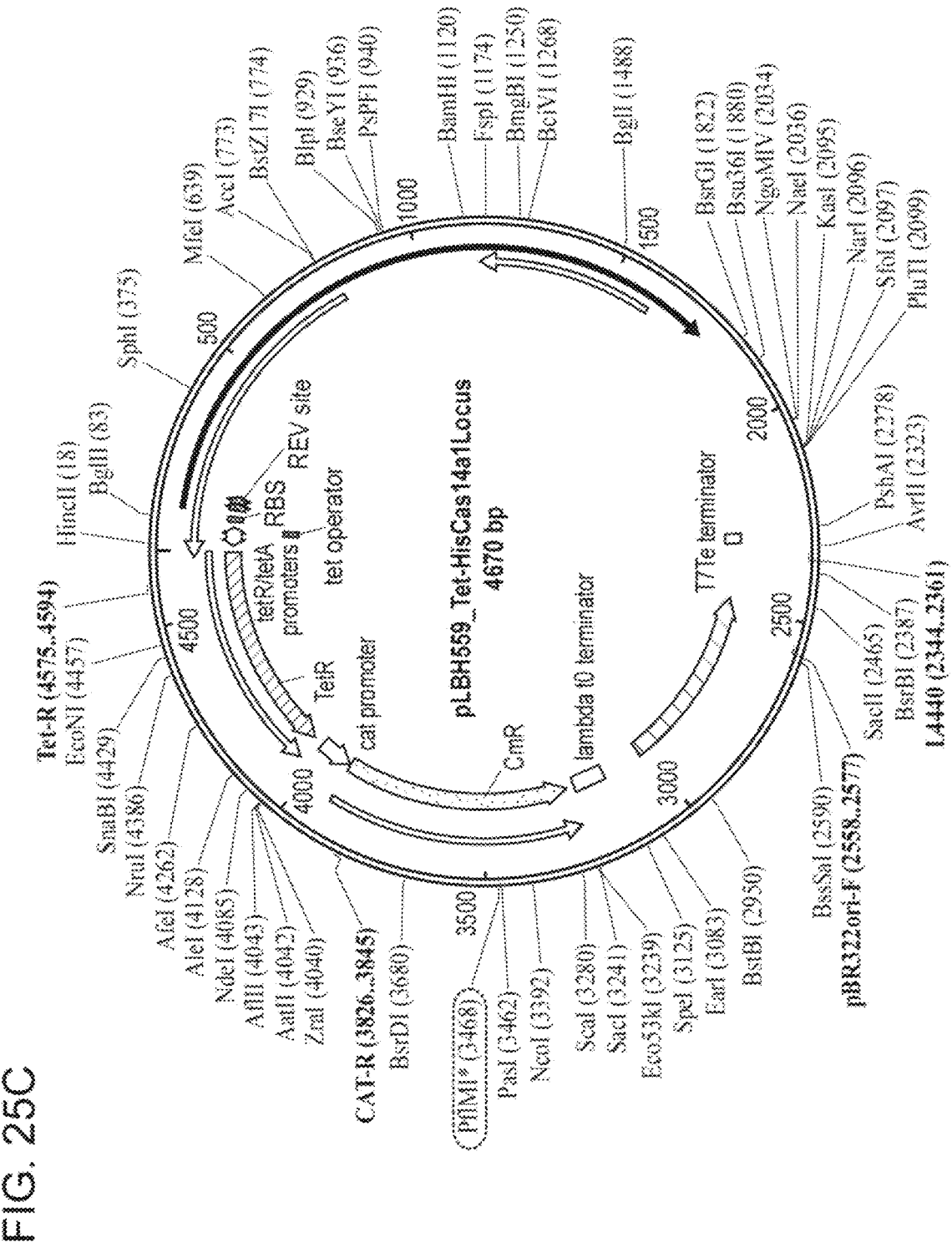
Figure 25D:
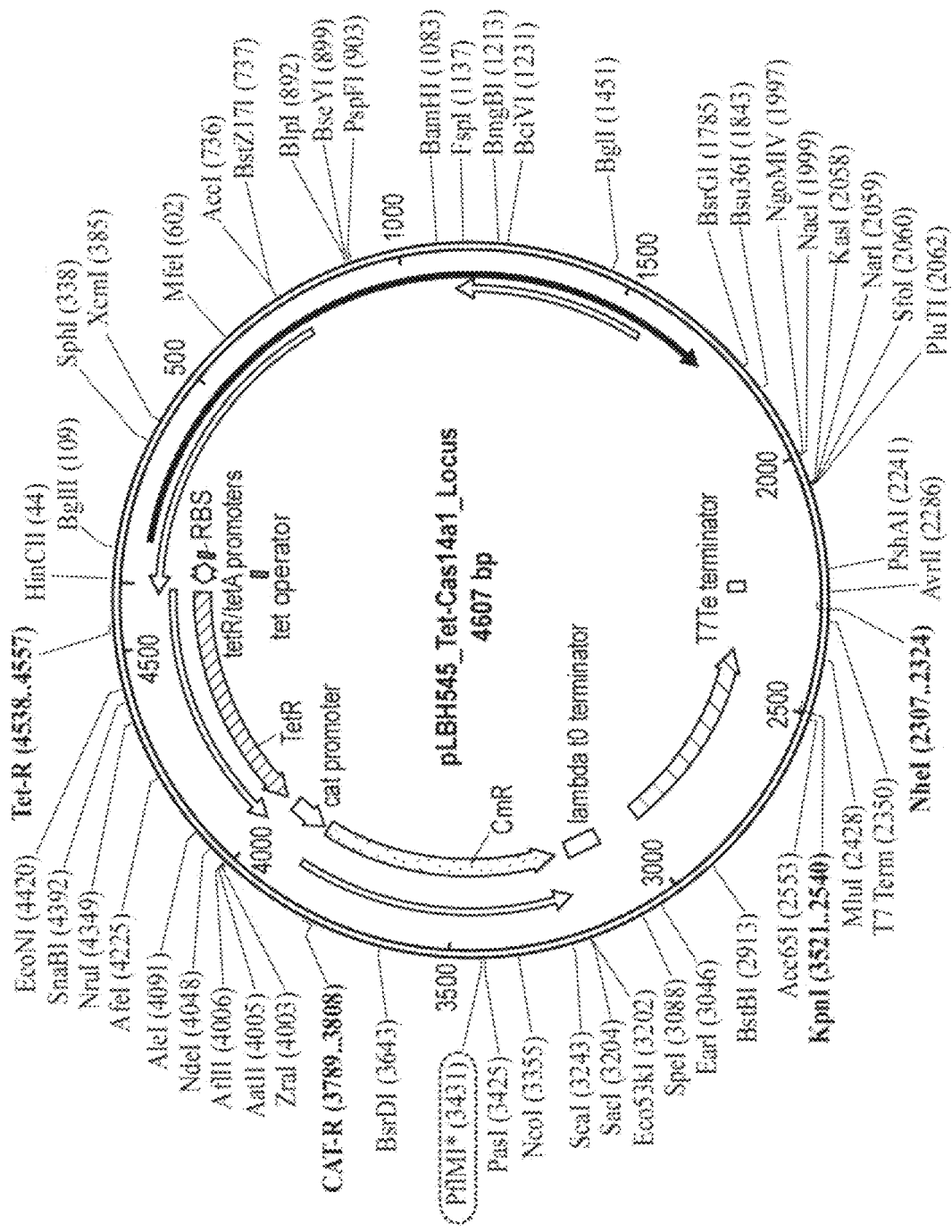
Figure 25E:
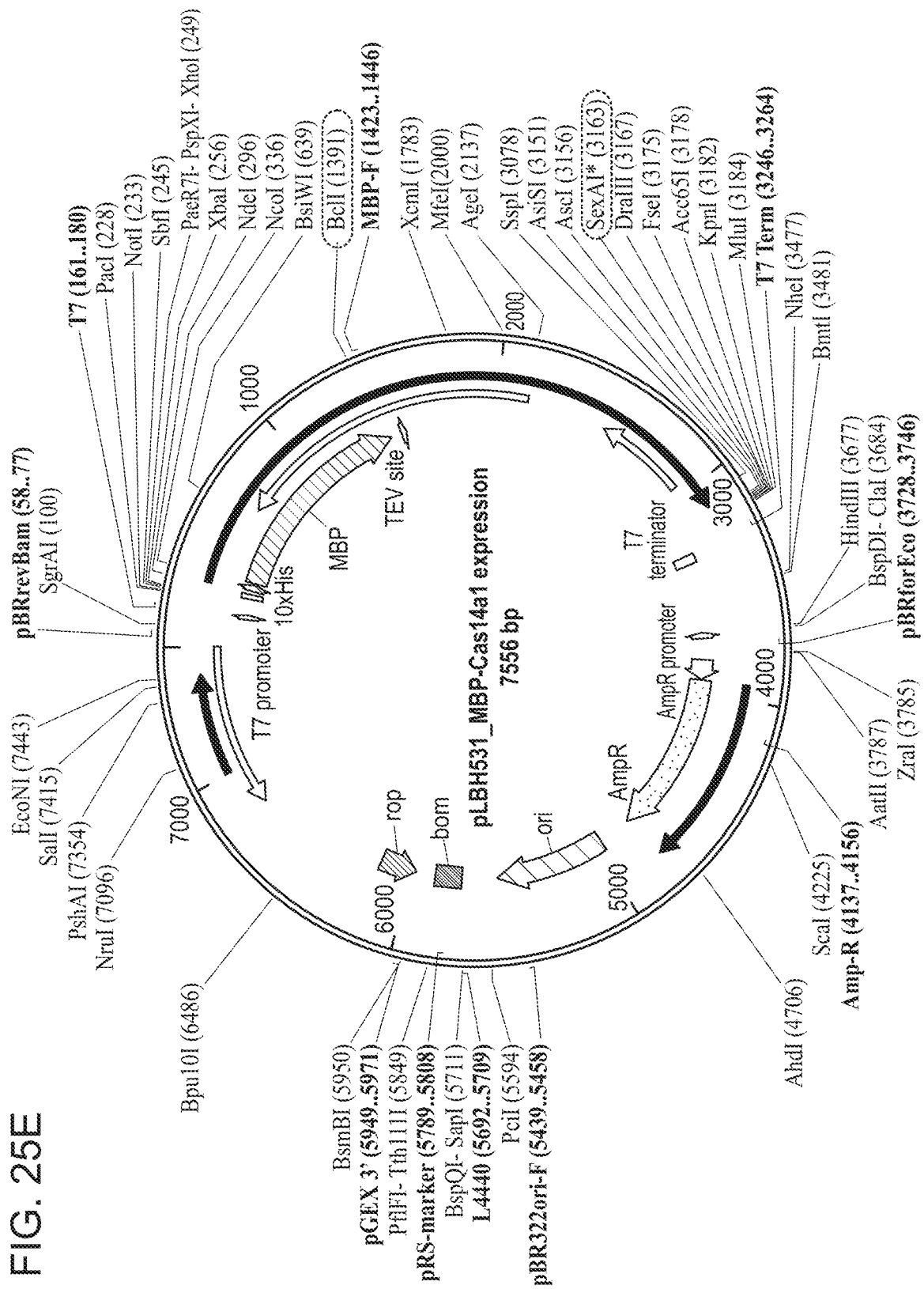

FIG. 23, Panels A-C depict a test of Cas14a1 mediated interference in a heterologous host. Diagram of Cas14a1 and LbCas12a constructs to test interference in *E. coli*. (B) Plaques of ΟΧ174 spotted on *E. coli* revealing Cas12a- but not Cas14a1-mediated interference. Each spot represents a 10-fold dilution of the ΟΧ174 stock. (C) Growth curves of *E. coli* expressing Cas14a1 or LbCas12a infected with ΟΧ174 (T, targeting; NT, non-targeting). FIG. 19, Panel F shows a heat map showing the background-subtracted fluorescence resulting from cleavage of a ssDNA FQ reporter in the presence of various guide and target combinations after a 30-minute incubation.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

REFERENCES

1. R. Barrangou et al., CRISPR provides acquired resistance against viruses in prokaryotes. *Science*. 315, 1709-12 (2007).
2. S. A. Jackson et al., CRISPR-Cas: Adapting to change. *Science*. 356 (6333), pp. 1-9 (2017).
3. S. Shmakov et al., Diversity and evolution of class 2 CRISPR-Cas systems. *Nat. Rev. Microbiol.* 15, 169-182 (2017).
4. J. S. Chen, J. A. Doudna, The chemistry of Cas9 and its CRISPR colleagues. *Nat. Rev. Chem.* 1, 0078 (2017).
5. C. T. Brown et al., Unusual biology across a group comprising more than 15% of domain Bacteria. *Nature*. 523, 208-211 (2015).
6. K. Anantharaman et al., Thousands of microbial genomes shed light on interconnected biogeochemical processes in an aquifer system. *Nat. Commun.* 7, 13219 (2016).
7. V. M. Markowitz et al., IMG/M 4 version of the integrated metagenome comparative analysis system. *Nucleic Acids Res.* 42, 568-573 (2014).
8. V. M. Markowitz et al., IMG: The integrated microbial genomes database and comparative analysis system. *Nucleic Acids Res.* 40, 115-122 (2012).
9. A. J. Probst et al., Genomic resolution of a cold subsurface aquifer community provides metabolic insights for novel microbes adapted to high $CO_2$ concentrations. *Environ. Microbiol.* 19, 459-474 (2017).
10. I. Yosef, M. G. Goren, U. Qimron, Proteins and DNA elements essential for the CRISPR adaptation process in *Escherichia coli*. *Nucleic Acids Res.* 40, 5569-5576 (2012).
11. J. K. Nunez, A. S. Y. Lee, A. Engelman, J. a. Doudna, Integrase-mediated spacer acquisition during CRISPR-Cas adaptive immunity. *Nature*. 519, 193-198 (2015).
12. S. Shmakov et al., Discovery and Functional Characterization of Diverse Class 2 CRISPR-Cas Systems. *Mol. Cell.* 60, 385-397 (2015).
13. D. Burstein et al., New CRISPR-Cas systems from uncultivated microbes. *Nature*. 542, 237-241 (2017).
14. C. Rinke et al., Insights into the phylogeny and coding potential of microbial dark matter. *Nature*. 499, 431-437 (2013).
15. C. J. Castelle et al., Genomic expansion of domain archaea highlights roles for organisms from new phyla in anaerobic carbon cycling. *Curr. Biol.* 25, 690-701 (2015).
16. E. Deltcheva et al., CRISPR RNA maturation by trans-encoded small RNA and host factor RNase III. *Nature*. 471, 602-607 (2011).
17. K. E. Savell, J. J. Day, Applications of CRISPR/CAS9 in the mammalian central nervous system. *Yale J. Biol. Med.* 90 (2017), pp. 567-581.
18. F. J. M. Mojica, C. Diez-Villasenor, J. Garcia-Martinez, C. Almendros, Short motif sequences determine the targets of the prokaryotic CRISPR defence system. *Microbiology*. 155, 733-740 (2009).
19. Y. Zhang, R. Rajan, H. S. Seifert, A. Mondragón, E. J. Sontheimer, DNase H Activity of *Neisseria meningitidis* Cas9. *Mol. Cell.* 60, 242-255 (2015).
20. E. Ma, L. B. Harrington, M. R. O'Connell, K. Zhou, J. A. Doudna, Single-Stranded DNA Cleavage by Divergent CRISPR-Cas9 Enzymes. *Mol. Cell.* 60, 398-407 (2015).

21. J. S. Chen et al., CRISPR-Cas12a target binding unleashes indiscriminate single-stranded DNase activity. *Science.* 360, 436-439 (2018).
22. B. Zetsche et al., Cpf1 Is a Single RNA-Guided Endonuclease of a Class 2 CRISPR-Cas System. *Cell.* 163, 759-771 (2015).
23. A. East-Seletsky et al., Two distinct RNase activities of CRISPR-C2c2 enable guide-RNA processing and RNA detection. *Nature.* 538, 270-273 (2016).
24. L. Liu et al., The Molecular Architecture for RNA-Guided RNA Cleavage by Cas13a. *Cell.* 170, 714-726.e10 (2017).
25. O. O. Abudayyeh et al., C2c2 is a single-component programmable RNA-guided RNA-targeting CRISPR effector. *Science (80-.).* 353, 1-9 (2016).
26. G. J. Knott et al., Guide-bound structures of an RNA-targeting A-cleaving CRISPR-Cas13a enzyme. *Nat. Struct. Mol. Biol.* 24, 825-833 (2017).
27. S. Y. Li et al., CRISPR-Cas12a has both cis- and trans-cleavage activities on single-stranded DNA. *Cell Res.* 28, 491-493 (2018).
28. H. Eiberg et al., Blue eye color in humans may be caused by a perfectly associated founder mutation in a regulatory element located within the HERC2 gene inhibiting OCA2 expression. *Hum. Genet.* 123, 177-187 (2008).
29. S. Shmakov et al., Diversity and evolution of class 2 CRISPR-Cas systems. *Nat. Rev. Microbiol.* 15, 169-182 (2017).
30. E. V Koonin, K. S. Makarova, F. Zhang, Diversity, classification and evolution of CRISPR-Cas systems. *Curr. Opin. Microbiol.* 37, 67-78 (2017).
31. K. S. Makarova et al., An updated evolutionary classification of CRISPR-Cas systems. *Nat Rev Microbiol,* 1-15 (2015).
32. O. Barabas et al., Mechanism of IS 200/IS 605 Family DNA Transposases: Activation and Transposon-Directed Target Site Selection, 208-220 (2008).
33. M. Yoshida et al., Quantitative viral community DNA analysis reveals the dominance of single-stranded DNA viruses in offshore upper bathyal sediment from Tohoku, Japan. *Front. Microbiol.* 9, 1-10 (2018).
34. C. T. Brown et al., Unusual biology across a group comprising more than 15% of domain Bacteria. *Nature.* 523, 208-211 (2015).
35. K. Anantharaman et al., Thousands of microbial genomes shed light on interconnected biogeochemical processes in an aquifer system. *Nat. Commun.* 7, 13219 (2016).
36. A. J. Probst et al., Genomic resolution of a cold subsurface aquifer community provides metabolic insights for novel microbes adapted to high $CO_2$ concentrations. *Environ. Microbiol.* 19, 459-474 (2017).
37. V. M. Markowitz et al., IMG/M 4 version of the integrated metagenome comparative analysis system. *Nucleic Acids Res.* 42, 568-573 (2014).
38. V. M. Markowitz et al., IMG: The integrated microbial genomes database and comparative analysis system. *Nucleic Acids Res.* 40, 115-122 (2012).
39. R. D. Finn, J. Clements, S. R. Eddy, HMMER web server: interactive sequence similarity searching. *Nucleic Acids Res.* 39, W29-W37 (2011).
40. D. Burstein et al., New CRISPR-Cas systems from uncultivated microbes. *Nature.* 542, 237-241 (2017).
41. I. Grissa, G. Vergnaud, C. Pourcel, CRISPRFinder: a web tool to identify clustered regularly interspaced short palindromic repeats. *Nucleic Acids Res.* 35, W52-W57 (2007).
42. A. Biswas, R. H. J. Staals, S. E. Morales, P. C. Fineran, C. M. Brown, CRISPRDetect: A flexible algorithm to define CRISPR arrays. *BMC Genomics.* 17, 1-14 (2016).
43. A. Stamatakis, RAxML version 8: A tool for phylogenetic analysis and post-analysis of large phylogenies. *Bioinformatics.* 30, 1312-1313 (2014).
44. B. Langmead, S. L. Salzberg, Fast gapped-read alignment with Bowtie 2. *Nat Methods.* 9, 357-359 (2012).
45. H. Ogata et al., KEGG: Kyoto encyclopedia of genes and genomes. *Nucleic Acids Res.* 27, 29-34 (1999).
46. L. B. Harrington et al., A thermostable Cas9 with increased lifetime in human plasma. *Nat. Commun.* 8, 1-7 (2017).
47. G. Crooks, G. Hon, J. Chandonia, S. Brenner, NCBI GenBank FTP Site\unWebLogo: a sequence logo generator. *Genome Res.* 14, 1188-1190 (2004).
48. L. B. Harrington et al., A Broad-Spectrum Inhibitor of CRISPR-Cas9. *Cell.* 170, 1224-1233.e15 (2017).
49. J. S. Chen et al., CRISPR-Cas12a target binding unleashes indiscriminate single-stranded DNase activity. *Science.* 360, 436-439 (2018).
50. Brown et al., Unusual biology across a group comprising more than 15% of domain Bacteria. *Nature.* 523, 208-211 (2015), doi:10.1038/nature14486.

The invention claimed is:

1. A method of modifying a target locus of interest comprising delivering to said locus:

a) an engineered polypeptide or a nucleic acid encoding the engineered polypeptide, wherein the engineered polypeptide is a variant of the polypeptide according to SEQ ID NO: 3, wherein the variant has reduced nucleic acid cleavage activity relative to the polypeptide according to SEQ ID NO: 3, wherein the variant comprises an amino acid sequence at least 80% identical to SEQ ID NO: 3, and wherein the variant comprises at least one amino acid substitution at a position selected from a group consisting of D326, E422, R490, and D510 of SEQ ID NO: 3; and b) a guide nucleic acid or DNA molecule encoding the guide nucleic acid, the guide nucleic acid comprising:

i) a first sequence that is bound by the polypeptide, wherein the first sequence comprises a nucleotide sequence that is at least 90% identical to residues 28-37 of SEQ ID NO: 53, and ii) a second sequence that hybridizes to a target sequence of a target nucleic acid, wherein the first sequence is located 5' of the second sequence.

2. The method of claim 1, wherein the engineered polypeptide recognizes a PAM of 5'-TTTN-3', wherein T is thymine and N is any nucleotide.

3. The method of claim 1, wherein the engineered polypeptide recognizes a PAM of 5'-TTTR-3', wherein T is thymine and R is selected from guanine and adenine.

4. The method of claim 1, wherein the engineered polypeptide is at least 90% identical to SEQ ID NO: 3.

5. The method of claim 1, wherein the engineered polypeptide is fused to a heterologous protein, and wherein modifying the target locus comprises introducing, removing, or altering an epigenetic modification of the target locus.

6. The method of claim 1, wherein the engineered polypeptide is linked to a methyltransferase.

7. The method of claim 1, wherein the engineered polypeptide is catalytically inactive.

8. The method of claim 1, wherein the engineered polypeptide comprises at least one amino acid substitution at an aspartic acid residue or a glutamic acid residue relative to a protein that is 100% identical to SEQ ID NO: 3.

9. The method of claim 8, wherein the at least one amino acid substitution is located in a RuvC domain.

10. The method of claim 1, wherein the engineered polypeptide comprises at least one amino acid substitution that is selected from an amino acid corresponding to D326A, E422A, D510A, and R490A of SEQ ID NO: 3, or any combination thereof.

11. The method of claim 1, comprising modifying the target locus in a cell.

12. The method of claim 11, wherein the cell is a eukaryotic cell.

13. The method of claim 12, wherein the eukaryotic cell is selected from a stem cell, a germ cell, a fibroblast, an oligodendrocyte, a glial cell, a hematopoietic cell, a neuron, a muscle cell, a bone cell, a hepatocyte, a pancreatic cell, a myofibroblast, a cardiac myoblast, a skeletal myoblast, and a T cell.

14. The method of claim 1, comprising modifying the target locus in a human subject.

15. The method of claim 14, comprising delivering the nucleic acid encoding the engineered polypeptide and the guide nucleic acid to the human subject via a lipid nanoparticle.

16. The method of claim 15, wherein the nucleic acid encoding the engineered polypeptide comprises a messenger RNA.

17. The method of claim 14, comprising delivering the nucleic acid encoding the engineered polypeptide and the DNA molecule encoding the guide nucleic acid to the human subject via an adeno-associated viral vector.

18. The method of claim 1, comprising delivering a donor nucleic acid to said locus.

19. A composition comprising:
a) an engineered polypeptide or a nucleic acid encoding the engineered polypeptide, wherein the engineered polypeptide is a variant of the polypeptide according to SEQ ID NO: 3, wherein the variant has reduced nucleic acid cleavage activity relative to the polypeptide according to SEQ ID NO: 3, wherein the variant comprises an amino acid sequence at least 80% identical to SEQ ID NO: 3, and wherein the variant comprises at least one amino acid substitution at a position selected from a group consisting of D326, E422, R490, and D510 of SEQ ID NO: 3; and
b) a guide nucleic acid or DNA molecule encoding the guide nucleic acid, the guide nucleic acid comprising:
i) a first sequence that is bound by the polypeptide, wherein the first sequence comprises a nucleotide sequence that is at least 90% identical to residues 28-37 of SEQ ID NO: 53, and
ii) a second sequence that hybridizes to a target sequence of a target nucleic acid, wherein
the first sequence is located 5' of the second sequence.

20. The composition of claim 19, wherein the engineered polypeptide recognizes a PAM of 5'-TTTN-3', wherein T is thymine and N is any nucleotide.

21. The composition of claim 19, wherein the engineered polypeptide recognizes a PAM of 5'-TTTR-3', wherein T is thymine and R is selected from guanine and adenine.

22. The composition of claim 19, wherein the engineered polypeptide is at least 90% identical to SEQ ID NO: 3.

23. The composition of claim 19, wherein the engineered polypeptide is fused to a heterologous protein.

24. The composition of claim 19, wherein the engineered polypeptide is linked to a methyltransferase.

25. The composition of claim 19, wherein the engineered polypeptide is catalytically inactive.

26. The composition of claim 19, wherein the engineered polypeptide further comprises at least one amino acid substitution at an aspartic acid residue or a glutamic acid residue relative to a protein that is 100% identical to SEQ ID NO: 3.

27. The composition of claim 19, wherein the engineered polypeptide comprises at least one amino acid substitution that is selected from an amino acid corresponding to D326A, E422A, D510A, and R490A of SEQ ID NO: 3, or any combination thereof.

28. The composition of claim 19, further comprising a lipid nanoparticle or an adeno-associated viral vector.

29. The composition of claim 19, wherein the nucleic acid encoding the engineered polypeptide comprises a messenger RNA.

30. The composition of claim 19, further comprising a donor nucleic acid.

* * * * *

UNITED STATES PATENT AND TRADEMARK OFFICE
CERTIFICATE OF CORRECTION

| | | |
|---|---|---|
| PATENT NO. | : 12,264,314 B1 | Page 1 of 1 |
| APPLICATION NO. | : 18/392905 | |
| DATED | : April 1, 2025 | |
| INVENTOR(S) | : Jennifer A. Doudna et al. | |

It is certified that error appears in the above-identified patent and that said Letters Patent is hereby corrected as shown below:

In the Specification

Please insert the following paragraph in Column 1, after Line 21:
-- Statement Regarding Federally Sponsored Research
This invention was made with government support under Grant Number DE-AC02-05CH11231 awarded by the U.S. Department of Energy and under Grant Number 1244557 awarded by the National Science Foundation. The government has certain rights in the invention. --

Signed and Sealed this
Twenty-seventh Day of May, 2025

Coke Morgan Stewart
*Acting Director of the United States Patent and Trademark Office*